(12) United States Patent
Holstege et al.

(10) Patent No.: US 6,653,071 B1
(45) Date of Patent: Nov. 25, 2003

(54) DISSECTING THE REGULATORY CIRCUITRY OF A EUKARYOTIC GENOMEI

(75) Inventors: Frank C. P. Holstege, Houten (NL); Richard A. Young, Weston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 379 days.

(21) Appl. No.: 09/326,137

(22) Filed: Jun. 4, 1999

Related U.S. Application Data

(60) Provisional application No. 60/110,051, filed on Nov. 25, 1998, provisional application No. 60/109,534, filed on Nov. 23, 1998, provisional application No. 60/097,498, filed on Aug. 21, 1998, and provisional application No. 60/087,909, filed on Jun. 4, 1998.

(51) Int. Cl.[7] ............................ C12Q 1/68; C12N 9/12; C07H 21/02; C07H 21/04; C07K 1/00
(52) U.S. Cl. ......................... 435/6; 435/194; 435/196; 536/23.1; 536/24.3; 530/350
(58) Field of Search .............................. 435/6, 255.1, 4, 435/194, 7.4, 196; 536/23.1, 24.3; 530/350

(56) References Cited

U.S. PATENT DOCUMENTS 5,919,666 A * 7/1999 Young et al. ............... 435/91.2

OTHER PUBLICATIONS

Côté, J., et al., "Stimulation of GAL4 Derivative Binding to Nucleosomal DNA by the Yeast SWI/SNF Complex", *Science*, 265: 53–60 (1994).

Greenblatt, J., "RNA Polymerase II Holoenzyme and Transcriptional Regulation", *Current Opinion in Cell Biology*, 9: 310–319 (1997).

Hampsey, M., "Molecular Genetics of the RNA Polymerase II General Transcriptional Machinery", *Microbiology and Molecular Biology Reviews*, 62(2): 465–503 (1998).

Hengartner, C. J., et al., "Association of an Activator with an RNA Polymerase II Holoenzyme", *Genes & Development*, 9(8): 897–910 (1995).

Kim, Y–J., et al., "A Multiprotein Mediator of Transcriptional Activation and Its Interaction with the C–Terminal Repeat Domain of RNA Polymerase II", *Cell*, 77: 599–608 (1994).

Koh, S. S., et al., "An Activator Target in the RNA Polymerase II Holoenzyme", *Cell*, 1: 895–904 (1998).

Koleske, A.J. and Young, R. A., "An RNA Polymerase II Holoenzyme Responsive to Activators", *Nature*, 368: 466–469 (1994).

Laurent, B.C, et al., "The Yeast SNF2/SW12 Protein has DNA–Stimulated ATPase Activity Required for Transcriptional Activation", *Genes & Development*, 7: 583–91 (1993).

Li, Y., "Yeast Global Transcriptional Regulators Sin4 and Rgr 1 are Components of Mediator Complex/RNA Polymerase II Holoenzyme", *Proc. Natl. Acad. Sci. USA*, 92: 10864–10868 (1995).

Myer, V. E. and Young, R. A., "RNA Polymerase II Holoenzymes and Subcomplexes", *J. Biol. Chem.*, 273(43): 27757–27760 (1998).

Myers, L. C. et al., "The Med Proteins of Yeast and Their Function Through the RNA Polymerase II Carboxy–terminal Domain", *Genes& Development*, 12: 45–54 (1998).

Orphanides, G., et al., "The General Transcription Factors of RNA Polymerase II", *Genes & Development*, 10(21): 2657–2683 (1996).

Roeder, R. G., "The Role of General Initiation Factors in Transcription by RNA Polymerase II", *Trends in Biochemical Science*, 21(9): 327–335 (1996).

Schnitzler, G., et al., "Human SWI/SNF Interconverts a Nucleosome Between Its Base State and a Stable Remodeled State", *Cell*, 94: 17–27 (1998).

Sun, X., et al., "NAT, a Human Complex Containing Srb Polypeptides that Functions as a Negative Regulator of Activated Transcription", *Cell*, 2: 213–222 (1998).

Thompson, C. M., et al., "A Multisubunit Complex Associated with the RNA Polymearse II CTD and TATA–Binding Protein in Yeast", *Cell*, 73: 1361–1375 (1993).

Thompson, C. M. and Young, R. A., "General Requirement for RNA Polymerase II Holoenzymes in vivo", *Proc. Natl. Acad. Sci. USA*, 92: 4587–4590 (1995).

Velculescu, V. E., et al., "Characterization of the Yeast Transcriptome", *Cell*, 88: 243–251 (1997).

Wodicka, L et al., Genome–wide expression monitoring in Saccharomyces cerevisiae, Nature Biotechnology, vol. 15, pp. 1359–1367, Dec. 9, 1997.*

* cited by examiner

Primary Examiner—Stephanie W. Zitomer
Assistant Examiner—Cynthia Wilder
(74) Attorney, Agent, or Firm—Hamilton, Brook, Smith & Reynolds, P.C.

(57) ABSTRACT

A method of identifying cellular regulatory circuits which employ at least one component of a subcomplex of regulatory proteins within the RNA II polymerase holoenzyme which behaves as a signal processor for gene-specific regulators (at least one component of a eukaryotic transcription initiation apparatus) and of determining the set of components of the apparatus which are responsible for regulation of each gene and the set of genes which are coordinately controlled by each transcription factor.

11 Claims, 200 Drawing Sheets

(2 of 200 Drawing Sheet(s) Filed in Color)

| Srb5 Up | | | | | | | Average | | |
|---|---|---|---|---|---|---|---|---|---|
| Gene | SRB WT#1 | WT#SRB5#1 | SRE SRB WT#2 | WT#2 SRB5#2 | SRB MT1/WT1 | MT2/WT2 | Fold Up | Corrected? | Confidence |
| AHT1 (YHR093W) | -11 A | 15 A | -19 A | 0 A | -1.3 | 0.0 | 4.5 | Yes | Med |
| BUB1 (YGR188C) | -13 A | 26 A | 3 A | 17 P | -1.9 | 6.3 | 7.1 | Yes | Med |
| HXT10 (YFL011W) | -66 A | 0 A | -11 A | 2 A | 0.0 | -0.2 | 7.9 | Yes | Med |
| HXT17 (YNR072W) | -74 A | 15 A | 7 A | 21 A | -0.2 | 3.2 | 10.5 | Yes | Med |
| HXT5 (YHR096C) | -49 A | 21 A | 0 A | 14 P | -0.4 | #DIV/0! | 8.3 | Yes | Med |
| ORF YAL043C-A | -19 A | 13 A | -19 A | -2 A | -0.7 | 0.1 | 4.9 | Yes | Med |
| ORF YAL045C | -30 A | -9 A | 5 A | 21 A | 0.3 | 4.2 | 4.2 | Yes | Med |
| ORF YBL018C exon 1 | -16 A | 14 A | -13 A | 8 A | -0.9 | -0.6 | 5.1 | Yes | Med |
| ORF YBR008C | 287 A | 638 P | 280 P | 1001 P | 2.2 | 3.6 | 2.9 | | Good |
| ORF YBR124W | -49 A | -23 A | -10 A | 3 A | 0.5 | -0.3 | 3.9 | Yes | Med |
| ORF YBR296C | -44 A | -13 A | -2 P | 9 A | 0.3 | -4.3 | 4.2 | Yes | Med |
| ORF YCR010C | -33 A | -22 A | 5 A | 17 A | 0.7 | 3.5 | 2.9 | Yes | Med |
| ORF YCR056W | -41 A | -20 A | 7 A | 18 A | 0.5 | 2.6 | 3.5 | Yes | Med |
| ORF YDR187C | -2 A | 9 A | -13 A | 0 A | -5.9 | 0.0 | 2.4 | Yes | Med |
| ORF YDR271C | -37 A | 47 P | 3 A | 16 A | -1.3 | 5.2 | 10.9 | Yes | Med |
| ORF YER039C | -64 A | -28 A | -12 A | 29 A | 0.4 | -2.4 | 7.8 | Yes | Med |
| ORF YER081W | 62 A | 288 P | 110 P | 351 P | 4.6 | 3.2 | 3.9 | | Good |
| ORF YER116C | 13 A | 42 A | 14 P | 44 P | 3.1 | 3.2 | 3.2 | | Good |
| ORF YGL090W | -30 A | 13 A | -29 A | 23 P | -0.4 | -0.8 | 9.5 | Yes | Med |
| ORF YGL152C | -28 A | 7 A | -21 A | -10 A | -0.2 | 0.5 | 4.6 | Yes | Med |
| ORF YGR051C | -57 A | -38 A | -23 A | 14 A | 0.7 | -0.6 | 5.7 | Yes | Med |
| ORF YGR203W | -13 A | 15 A | 11 A | 44 A | -1.1 | 4.0 | 4.8 | Yes | Med |
| ORF YGR243W | -34 A | 22 A | 30 A | 74 P | -0.6 | 2.4 | 6.8 | Yes | Med |
| ORF YGR290W | 9 A | 26 A | -14 A | 14 A | 2.7 | -1.0 | 4.1 | Yes | Med |
| ORF YGR291C (_f) | -34 A | -5 A | -16 A | 12 A | 0.1 | -0.7 | 5.7 | Yes | Med |
| ORF YHR140W | -28 A | -9 A | -11 A | 0 A | 0.3 | 0.0 | 3.0 | Yes | Med |
| ORF YIL025C | -21 A | 14 A | -26 A | -11 A | -0.7 | 0.4 | 4.9 | Yes | Med |
| ORF YIL032C | 0 A | 14 A | -23 A | -4 A | #DIV/0! | 0.2 | 3.3 | Yes | Med |
| ORF YIL117C | 9 A | 170 P | 90 P | 232 P | 18.1 | 2.6 | 10.3 | | Good |
| ORF YIL122W | -8 A | 12 A | -7 A | 13 A | -1.6 | -1.9 | 3.9 | Yes | Med |
| ORF YIR043C (_i) | -55 A | -40 A | -32 A | -2 A | 0.7 | 0.1 | 4.4 | Yes | Med |
| ORF YJL032W | 13 A | 28 A | 16 M | 33 P | 2.1 | 2.0 | 2.1 | | Good |
| ORF YJL056C | -28 A | -18 A | -8 A | 5 A | 0.6 | -0.5 | 2.3 | Yes | Med |

Figure 1A

| | | | | | | | | |
|---|---|---|---|---|---|---|---|---|
| ORF YJL064W | -19 | A | -1 | A | -4 | A | 8 | A | 0.1 | -1.8 | 3.0 | Yes | Med |
| ORF YJL066C | -19 | A | 64 | P | 12 | A | 41 | P | -3.4 | 3.4 | 10.0 | Yes | Med |
| ORF YJL077C | -36 | A | -22 | A | -5 | A | 17 | A | 0.6 | -3.2 | 3.7 | Yes | Med |
| ORF YJL107C | 13 | A | 54 | A | 9 | A | 47 | A | 4.1 | 5.1 | 4.6 | | Good |
| ORF YJL135W | 39 | A | 86 | P | 5 | A | 29 | A | 2.2 | 5.6 | 3.9 | | Good |
| ORF YKL097C | -105 | A | -60 | A | -10 | A | 34 | A | 0.6 | -3.3 | 9.0 | Yes | Med |
| ORF YKR102W | 0 | A | 82 | P | 20 | P | 46 | P | #DIV/0! | 2.4 | 9.4 | Yes | Med |
| ORF YML037C | 32 | A | 72 | P | 21 | P | 44 | P | 2.3 | 2.1 | 2.2 | | Good |
| ORF YML048W-A | -47 | A | 16 | A | 6 | A | 19 | A | -0.3 | 3.1 | 7.9 | Yes | Med |
| ORF YML058C-A | -58 | A | -30 | A | 2 | A | 44 | A | 0.5 | 21.4 | 13.5 | Yes | Med |
| ORF YML066C | -34 | A | -9 | A | -10 | A | 9 | P | 0.3 | -0.8 | 4.4 | Yes | Med |
| ORF YML102C-A | -18 | A | 25 | A | -12 | A | -1 | A | -1.3 | 0.1 | 5.4 | Yes | Med |
| ORF YMR244W | -121 | A | 23 | A | 13 | M | 38 | A | -0.2 | 2.9 | 15.9 | Yes | Med |
| ORF YMR254C | -116 | A | 19 | A | 4 | A | 17 | A | -0.2 | 4.0 | 15.5 | Yes | Med |
| ORF YNL195C | -63 | A | 27 | A | 11 | A | 22 | P | -0.4 | 2.0 | 10.0 | Yes | Med |
| ORF YOL037C | 11 | A | 88 | A | -7 | A | 5 | P | 8.4 | -0.8 | 5.4 | Yes | Med |
| ORF YOL099C | -47 | A | -4 | A | 16 | A | 48 | P | 0.1 | 2.9 | 5.8 | Yes | Med |
| ORF YOL134C | -216 | A | -88 | A | 7 | A | 64 | P | 0.4 | 9.8 | 17.7 | Yes | Med |
| ORF YOL155C | 205 | P | 623 | P | 180 | P | 618 | P | 3.0 | 3.4 | 3.2 | | Excl |
| ORF YOR134W | -47 | A | 0 | A | 13 | A | 38 | P | 0.0 | 2.9 | 6.2 | Yes | Med |
| ORF YOR146W | -95 | A | -15 | A | 14 | A | 28 | P | 0.2 | 2.0 | 8.9 | Yes | Med |
| ORF YPL275W (_f) | -63 | A | -31 | A | 7 | A | 24 | P | 0.5 | 3.7 | 5.1 | Yes | Med |
| ORF YPL281C (_f) | -21 | A | 27 | A | 2 | A | 39 | A | -1.3 | 18.0 | 13.8 | Yes | Med |
| ORF YPR151C | -189 | A | -69 | A | 5 | A | 34 | P | 0.4 | 6.2 | 15.1 | Yes | Med |
| OYE3 (YPL171C) | -63 | A | 92 | P | 16 | P | 47 | P | -1.5 | 2.9 | 17.0 | Yes | Med |
| REC104 (YHR157W) | 8 | A | 42 | A | 18 | A | 46 | P | 5.5 | 2.6 | 4.0 | | Good |
| REC114 (YMR133W) | -68 | A | -51 | A | -1 | A | 12 | A | 0.7 | -11.5 | 3.0 | Yes | Med |
| URA3 (YEL021W) | 174 | A | 27 | A | 88 | P | 453 | P | 2.2 | 5.2 | 3.7 | | Good |
| VMA21 (YGR105W) | 447 | P | 1480 | P | 499 | P | 1898 | P | 3.3 | 3.8 | 3.6 | | Excl |
| YCLX05c/ (control?) | -41 | A | -26 | A | -15 | A | -3 | A | 0.6 | 0.2 | 2.7 | Yes | Med |

Figure 1B

| Srb5 Up | | | | | | | | | |
|---|---|---|---|---|---|---|---|---|---|
| Gene | SRB WT#1 | WT#SRB5#1 | SRE SRB WT#2 | WT#2SRB5#2 | SRB:MT1/WT1 | MT2/WT2 | Average Fold Up | Corrected? | Confidence |
| ORF YOL134C | -216 A | -88 A | 7 A | 64 P | 0.4 | 9.8 | 17.7 | Yes | Med |
| OYE3 (YPL171C) | -63 A | 92 P | 16 P | 47 P | -1.5 | 2.9 | 17.0 | Yes | Med |
| ORF YMR244W | -121 A | 23 A | 13 M | 38 A | -0.2 | 2.9 | 15.9 | Yes | Med |
| ORF YMR254C | -116 A | 19 A | 4 A | 17 A | -0.2 | 4.0 | 15.5 | Yes | Med |
| ORF YPR151C | -189 A | -69 A | 5 A | 34 P | 0.4 | 6.2 | 15.1 | Yes | Med |
| ORF YPL281C (_f) | -21 A | 27 A | 2 A | 39 A | -1.3 | 18.0 | 13.8 | Yes | Med |
| ORF YML058C-A | -58 A | -30 A | 2 A | 44 A | 0.5 | 21.4 | 13.5 | Yes | Med |
| ORF YDR271C | -37 A | 47 P | 3 A | 16 A | -1.3 | 5.2 | 10.9 | Yes | Med |
| HXT17 (YNR072W) | -74 A | 15 A | 7 A | 21 A | -0.2 | 3.2 | 10.5 | Yes | Med |
| ORF YIL117C | 9 A | 170 P | 90 P | 232 P | 18.1 | 2.6 | 10.3 | | Good |
| ORF YNL195C | -63 A | 27 A | 11 A | 22 P | -0.4 | 2.0 | 10.0 | Yes | Med |
| ORF YJL066C | -19 A | 64 P | 12 A | 41 P | -3.4 | 3.4 | 10.0 | Yes | Med |
| ORF YGL090W | -30 A | 13 A | -29 A | 23 P | -0.4 | -0.8 | 9.5 | Yes | Med |
| ORF YKR102W | 0 A | 82 P | 20 P | 46 P | #DIV/0! | 2.4 | 9.4 | Yes | Med |
| ORF YKL097C | -105 A | -60 A | -10 A | 34 A | 0.6 | -3.3 | 9.0 | Yes | Med |
| ORF YOR146W | -95 A | -15 A | 14 A | 28 P | 0.2 | 2.0 | 8.9 | Yes | Med |
| HXT5 (YHR096C) | -49 A | 21 A | 0 A | 14 P | -0.4 | #DIV/0! | 8.3 | Yes | Med |
| HXT10 (YFL011W) | -66 A | 0 A | -11 A | 2 A | 0.0 | -0.2 | 7.9 | Yes | Med |
| ORF YML048W-A | -47 A | 16 A | 6 A | 19 A | -0.3 | 3.1 | 7.9 | Yes | Med |
| ORF YER039C | -64 A | -28 A | -12 A | 29 A | 0.4 | -2.4 | 7.8 | Yes | Med |
| BUB1 (YGR188C) | -13 A | 26 A | 3 A | 17 P | -1.9 | 6.3 | 7.1 | Yes | Med |
| ORF YGR243W | -34 A | 22 A | 30 A | 74 P | -0.6 | 2.4 | 6.8 | Yes | Med |
| ORF YOR134W | -47 A | 0 A | 13 A | 38 P | 0.0 | 2.9 | 6.2 | Yes | Med |
| ORF YOL099C | -47 A | -4 A | 16 A | 48 P | 0.1 | 2.9 | 5.8 | Yes | Med |
| ORF YGR291C (_f) | -34 A | -5 A | -16 A | 12 A | 0.1 | -0.7 | 5.7 | Yes | Med |
| ORF YGR051C | -57 A | -38 A | -23 A | 14 A | -0.7 | -0.6 | 5.7 | Yes | Med |
| ORF YML102C-A | -18 A | 25 A | -12 A | -1 A | -1.3 | 0.1 | 5.4 | Yes | Med |
| ORF YOL037C | 11 A | 88 A | -7 A | 5 P | 8.4 | -0.8 | 5.4 | Yes | Med |
| ORF YPL275W (_f) | -63 A | -31 A | 7 A | 24 P | 0.5 | 3.7 | 5.1 | Yes | Med |
| ORF YBL018C exon 1 | -16 A | 14 A | -13 A | 8 A | -0.9 | -0.6 | 5.1 | Yes | Med |
| ORF YIL025C | -21 A | 14 A | -26 A | -11 A | 0.4 | 0.4 | 4.9 | Yes | Med |
| ORF YAL043C-A | -19 A | 13 A | -19 A | -2 A | -0.7 | 0.1 | 4.9 | Yes | Med |
| ORF YGR203W | -13 A | 15 A | 11 A | 44 A | -1.1 | 4.0 | 4.8 | Yes | Med |
| ORF YJL107C | 13 A | 54 A | 9 A | 47 A | 4.1 | 5.1 | 4.6 | | Good |
| ORF YGL152C | -28 A | 7 A | -21 A | -10 A | -0.2 | 0.5 | 4.6 | Yes | Med |
| AHT1 (YHR093W) | -11 A | 15 A | -19 A | 0 A | -1.3 | 0.0 | 4.5 | Yes | Med |
| ORF YIR043C (_i) | -55 A | -40 A | -32 A | -2 A | 0.7 | 0.1 | 4.4 | Yes | Med |
| ORF YML066C | -34 A | -9 A | -10 A | 9 P | 0.3 | -0.8 | 4.4 | Yes | Med |
| ORF YBR296C | -44 A | -13 A | -2 P | 9 A | 0.3 | -4.3 | 4.2 | Yes | Med |

Figure 2A

| | | | | | | | | |
|---|---|---|---|---|---|---|---|---|
| ORF YAL045C | -30 | A | -9 | A | 5 | A | 21 | A | 0.3 | 4.2 | 4.2 | Yes | Med |
| ORF YGR290W | 9 | A | 26 | A | -14 | A | 14 | A | 2.7 | -1.0 | 4.1 | Yes | Med |
| REC104 (YHR157W) | 8 | A | 42 | A | 18 | A | 46 | P | 5.5 | 2.6 | 4.0 | | Good |
| ORF YBR124W | -49 | A | -23 | A | -10 | A | 3 | A | 0.5 | -0.3 | 3.9 | Yes | Med |
| ORF YER081W | 62 | A | 288 | P | 110 | P | 351 | P | 4.6 | 3.2 | 3.9 | | Good |
| ORF YIL122W | -8 | A | 12 | A | -7 | A | 13 | A | -1.6 | -1.9 | 3.9 | Yes | Med |
| ORF YJL135W | 39 | A | 86 | P | 5 | A | 29 | A | 2.2 | 5.6 | 3.9 | | Good |
| URA3 (YEL021W) | 174 | A | 389 | P | 88 | P | 453 | P | 2.2 | 5.2 | 3.7 | | Good |
| ORF YJL077C | -36 | A | -22 | A | -5 | A | 17 | A | 0.6 | -3.2 | 3.7 | Yes | Med |
| VMA21 (YGR105W) | 447 | P | 1480 | P | 499 | P | 1898 | P | 3.3 | 3.8 | 3.6 | | Excl |
| ORF YCR056W | -41 | A | -20 | A | 7 | A | 18 | A | 0.5 | 2.6 | 3.5 | Yes | Med |
| ORF YIL032C | 0 | A | 14 | A | -23 | A | -4 | A | #DIV/0! | 0.2 | 3.3 | Yes | Med |
| ORF YOL155C | 205 | P | 623 | P | 180 | P | 618 | P | 3.0 | 3.4 | 3.2 | | Excl |
| ORF YER116C | 13 | A | 42 | A | 14 | P | 44 | P | 3.1 | 3.2 | 3.2 | | Good |
| REC114 (YMR133W) | -68 | A | -51 | A | -1 | A | 12 | A | 0.7 | -11.5 | 3.0 | Yes | Med |
| ORF YHR140W | -28 | A | -9 | A | -11 | A | 0 | A | 0.3 | 0.0 | 3.0 | Yes | Med |
| ORF YJL064W | -19 | A | -1 | A | -4 | A | 8 | A | 0.1 | -1.8 | 3.0 | Yes | Med |
| ORF YBR008C | 287 | A | 638 | P | 280 | P | 1001 | P | 2.2 | 3.6 | 2.9 | | Good |
| ORF YCR010C | -33 | A | -22 | A | 5 | A | 17 | A | 0.7 | 3.5 | 2.9 | Yes | Med |
| YCLX05c/ (control?) | -41 | A | -26 | A | -15 | A | -3 | A | 0.6 | 0.2 | 2.7 | Yes | Med |
| ORF YDR187C | -2 | A | 9 | A | -13 | A | 0 | A | -5.9 | 0.0 | 2.4 | Yes | Med |
| ORF YJL056C | -28 | A | -18 | A | -8 | A | 5 | A | 0.6 | -0.5 | 2.3 | Yes | Med |
| ORF YML037C | 32 | A | 72 | P | 21 | P | 44 | P | 2.3 | 2.1 | 2.2 | | Good |
| ORF YJL032W | 13 | A | 28 | A | 16 | M | 33 | P | 2.1 | 2.0 | 2.1 | | Good |

Figure 2B

| Srb5 Down | | | | | | | | Average | | |
|---|---|---|---|---|---|---|---|---|---|---|
| Gene | SRB WT#1 | WT# | SRB5#1 | SR | SRB WT#2 | WT#: | SRB5#2 | SRB5 MT1/WT1 | MT2/WT2 | Fold Down | Corrected? | Confidence |
| ACE2 (YLR131C) | 116 A | | 54 A | | 94 P | | 22 P | 0.47 | 0.23 | 3.2 | | Good |
| ACS1 (YAL054C) | 108 A | | 43 A | | 52 P | | 24 A | 0.40 | 0.47 | 2.3 | | Good |
| ACT1 (YFL039C) exc | 3257 P | | 1408 P | | 4368 P | | 1898 P | 0.43 | 0.43 | 2.3 | | Excl |
| ADH4 (YGL256W) | 694 P | | 335 P | | 867 P | | 393 P | 0.48 | 0.45 | 2.1 | | Excl |
| AGA1 (YNR044W) | 863 P | | 212 P | | 609 P | | 85 P | 0.25 | 0.14 | 5.6 | | Excl |
| AGA2 (YGL032C) | 381 P | | 62 P | | 408 P | | 83 P | 0.16 | 0.20 | 5.5 | | Excl |
| ALD5 (YMR170C) | 32 A | | 2 A | | 36 P | | 6 P | 0.06 | 0.18 | 11.8 | | Good |
| ALR2 (YFL050C) | 74 P | | 20 A | | 64 P | | 26 P | 0.27 | 0.40 | 3.1 | | Good |
| AMD1 (YML035C) | 224 P | | 82 P | | 399 P | | 147 P | 0.37 | 0.37 | 2.7 | | Excl |
| ASP3 (YLR155C) | 124 A | | 40 A | | 110 P | | 45 A | 0.33 | 0.41 | 2.8 | | Good |
| ASP3 (YLR160C) | 158 A | | -11 A | | 99 P | | 44 A | -0.07 | 0.45 | 18.0 | Yes | Med |
| ATF2 (YGR177C) | 74 A | | 31 M | | 132 P | | 41 P | 0.42 | 0.31 | 2.8 | | Good |
| ATR1 (YML116W) | 468 P | | 95 A | | 224 P | | 111 P | 0.20 | 0.50 | 3.5 | | Good |
| BAR1 (YIL015W) | 453 P | | 50 P | | 466 P | | 43 P | 0.11 | 0.09 | 10.0 | | Excl |
| BIO2 (YGR286C) | 140 P | | 49 P | | 242 P | | 44 P | 0.35 | 0.18 | 4.2 | | Excl |
| BUD2 (YKL092C) | 121 A | | 60 P | | 52 P | | 24 P | 0.49 | 0.46 | 2.1 | | Good |
| CBF2 (YGR140W) | 166 P | | 54 A | | 95 P | | 47 P | 0.33 | 0.49 | 2.5 | | Good |
| CBS1 (YDL069C) | 110 P | | 36 P | | 65 P | | 30 P | 0.33 | 0.45 | 2.6 | | Excl |
| CCE1 (YKL011C) | 34 A | | 12 A | | 78 P | | 19 P | 0.36 | 0.25 | 3.4 | | Good |
| CCR4 (YAL021C) | 170 A | | 47 A | | 299 P | | 84 P | 0.27 | 0.28 | 3.6 | | Good |
| CDC24 (YAL041W) | 94 A | | 35 A | | 135 P | | 64 P | 0.37 | 0.48 | 2.4 | | Good |
| CDC7 (YDL017W) | 92 P | | 40 A | | 69 P | | 34 P | 0.43 | 0.49 | 2.2 | | Good |
| CEM1 (YER061C) | 128 A | | 41 P | | 73 P | | 32 P | 0.32 | 0.43 | 2.7 | | Good |
| CEP3 (YMR168C) | 82 P | | 11 A | | 36 P | | 14 A | 0.13 | 0.39 | 5.2 | | Good |
| CHA1 (YCL064C) | 763 P | | 13 A | | 910 P | | 31 P | 0.02 | 0.03 | 44.4 | | Good |
| CHS2 (YBR038W) | 94 P | | 47 P | | 250 P | | 108 P | 0.50 | 0.43 | 2.2 | | Excl |
| CIN8 (YEL061C) | 47 A | | 18 A | | 27 P | | 8 A | 0.38 | 0.27 | 3.1 | | Good |
| CLA4 (YNL298W) | 179 A | | 46 A | | 126 P | | 62 P | 0.26 | 0.49 | 3.0 | | Good |
| CLB1 (YGR108W) | 219 P | | 104 P | | 216 P | | 91 P | 0.47 | 0.42 | 2.2 | | Excl |
| CLN2 (YPL256C) | 263 P | | 131 A | | 332 P | | 107 P | 0.50 | 0.32 | 2.6 | | Good |
| CLN3 (YAL040C) | 190 P | | 94 P | | 265 P | | 84 P | 0.49 | 0.32 | 2.6 | | Good |
| COQ1 (YBR003W) | 113 P | | 19 A | | 170 P | | 63 P | 0.17 | 0.37 | 4.4 | | Good |
| CTR1 (YPR124W) | 779 P | | 300 P | | 676 P | | 297 P | 0.39 | 0.44 | 2.4 | | Excl |
| CTS1 (YLR286C) | 2605 P | | 804 P | | 2211 P | | 847 P | 0.31 | 0.38 | 2.9 | | Excl |
| CYB2 (YML054C) | 84 A | | 33 A | | 77 P | | 37 P | 0.40 | 0.47 | 2.3 | | Good |
| DAL3 (YIR032C) | 98 A | | -3 A | | 23 P | | 10 A | -0.03 | 0.42 | 11.3 | Yes | Med |
| DAL82 (YNL314W) | 268 A | | 8 A | | 39 P | | 14 A | 0.03 | 0.36 | 18.9 | | Good |
| DAT1 (YML113W) | 697 P | | 161 P | | 452 P | | 181 P | 0.23 | 0.40 | 3.4 | | Excl |
| DBP2 (YNL112W) ex | 2421 P | | 704 P | | 1893 P | | 550 P | 0.29 | 0.29 | 3.4 | | Excl |

Figure 3A

| | 2242 P | 719 P | 3087 P | 1414 P | | | | | |
|---|---|---|---|---|---|---|---|---|---|
| DBP2 (YNL112W) ex | | | | | | 0.32 | 0.46 | 2.7 | Excl |
| DCD1 (YHR144C) | 183 P | 56 A | 189 P | 63 P | | 0.31 | 0.33 | 3.1 | Good |
| DCG1 (YIR030C) | 15 A | -23 A | 30 P | -2 A | | -1.51 | -0.05 | 7.0 Yes | Med |
| DED1 (YOR204W) | 1074 P | 296 P | 672 P | 203 P | | 0.28 | 0.30 | 3.5 | Excl |
| DIP1 (YKL017C) | 45 A | 7 A | 54 P | 14 P | | 0.16 | 0.26 | 5.1 | Good |
| DIT1 (YDR403W) | 21 A | 9 A | 25 P | -3 A | | 0.45 | -0.14 | 4.0 Yes | Med |
| DLD1 (YDL174C) | 365 P | 131 P | 423 P | 142 P | | 0.36 | 0.34 | 2.9 | Excl |
| DOA4 (YDR069C) | 51 P | 10 A | 58 P | 25 P | | 0.21 | 0.43 | 3.6 | Good |
| DOG1 (YHR044C) | 13 A | -8 A | 21 A | 2 A | | -0.60 | 0.11 | 6.7 Yes | Med |
| DRS1 (YLL008W) | 716 P | 240 P | 747 P | 337 P | | 0.34 | 0.45 | 2.6 | Excl |
| DRS2 (YAL026C) | 81 A | 33 A | 132 P | 55 P | | 0.40 | 0.42 | 2.4 | Good |
| DSK2 (YOR035C) | 95 A | 23 A | 49 P | 21 P | | 0.24 | 0.43 | 3.2 | Good |
| EFB1 (YAL003W) ex | 5059 P | 2513 P | 5538 P | 2563 P | | 0.50 | 0.46 | 2.1 | Excl |
| EMP70 (YLR083C) | 295 P | 126 P | 654 P | 281 P | | 0.43 | 0.43 | 2.3 | Excl |
| ENO1 (YGR254W) | 1842 P | 896 P | 3066 P | 1385 P | | 0.49 | 0.45 | 2.1 | Excl |
| ERG5 (YMR015C) | 245 P | 105 A | 433 P | 194 P | | 0.43 | 0.45 | 2.3 | Good |
| FAA3 (YIL009W) | 151 P | 21 A | 159 P | 64 P | | 0.14 | 0.40 | 4.9 | Good |
| FAR1 (YJL157C) | 679 P | 74 M | 541 P | 74 P | | 0.11 | 0.14 | 8.3 | Good |
| FAT2 (YBR222C) | 135 P | 47 P | 140 P | 63 P | | 0.34 | 0.45 | 2.6 | Excl |
| FCY21 (YER060W) l | 85 A | 27 A | 77 P | 16 M | | 0.31 | 0.21 | 4.0 | Good |
| FCY22 (YER060W-A | 98 P | -16 A | 81 P | 22 P | | -0.16 | 0.27 | 13.2 Yes | Med |
| FIG2 (YCR089W) | 71 A | 34 P | 98 P | 27 P | | 0.47 | 0.28 | 2.9 | Good |
| FKH2 (YNL068C) | -16 A | -27 A | 108 P | 45 P | | 1.71 | 0.42 | 2.3 Yes | Med |
| FLO1 (YAR050W) | 46 A | 22 A | 51 P | 24 A | | 0.48 | 0.48 | 2.1 | Good |
| FSP2 (YJL221C) (_f | 74 A | 12 A | 44 P | 10 A | | 0.17 | 0.22 | 5.3 | Good |
| FUR1 (YHR128W) | 936 P | 389 P | 1112 P | 531 P | | 0.42 | 0.48 | 2.3 | Excl |

Figure 3B

| | | | | | | | |
|---|---|---|---|---|---|---|---|
| FUR4 (YBR021W) | 133 P | 52 A | 146 P | 57 P | 0.39 | 0.39 | 2.5 | Good |
| FUS1 (YCL027W) | 146 P | 41 M | 97 P | 27 P | 0.28 | 0.28 | 3.6 | Good |
| FUS2 (YMR232W) | 263 A | 58 A | 14 A | -23 A | 0.22 | -1.64 | 6.0 Yes | Med |
| FUS3 (YBL016W) | 116 A | 42 A | 170 P | 43 P | 0.36 | 0.26 | 3.3 | Good |
| GAL7 (YBR018C) | 44 A | 15 A | 20 P | 2 A | 0.34 | 0.09 | 7.2 | Good |
| GDH3 (YAL062W) | 24 A | -6 A | 32 P | 16 A | -0.24 | 0.49 | 4.0 Yes | Med |
| GDS1 (YOR355W) | 405 P | 192 P | 665 P | 323 P | 0.47 | 0.48 | 2.1 | Excl |
| GEF1 (YJR040W) | 139 P | 53 P | 97 P | 44 P | 0.38 | 0.45 | 2.4 | Excl |
| GLS1 (YLR342W) | 1008 P | 488 P | 1668 P | 722 P | 0.48 | 0.43 | 2.2 | Excl |
| GLT1 (YDL171C) | 887 P | 431 P | 729 P | 363 P | 0.49 | 0.50 | 2.0 | Excl |
| GLY1 (YEL046C) | 1102 P | 387 P | 986 P | 447 P | 0.35 | 0.45 | 2.5 | Excl |
| GND1 (YHR183W) | 1868 P | 868 P | 3359 P | 1347 P | 0.46 | 0.40 | 2.3 | Excl |
| GNP1 (YDR508C) | 960 P | 416 P | 1420 P | 607 P | 0.43 | 0.43 | 2.3 | Excl |
| GPA1 (YHR005C) | 628 P | 129 P | 375 P | 98 P | 0.20 | 0.26 | 4.4 | Excl |
| GPD2 (YOL059W) | 453 P | 123 A | 265 P | 59 P | 0.27 | 0.22 | 4.1 | Good |
| GRR1 (YJR090C) | 182 A | 23 A | 98 P | 48 P | 0.13 | 0.49 | 5.0 | Good |
| HAC1 (YFL031W) | 1264 P | 468 P | 951 P | 411 P | 0.37 | 0.43 | 2.5 | Excl |
| HAP1 (YLR256W) | 455 P | 158 A | 332 P | 90 P | 0.35 | 0.27 | 3.3 | Good |
| HCM1 (YCR065W) | 141 A | 12 A | 145 P | 11 A | 0.08 | 0.08 | 12.5 | Excl |
| HGH1 (YGR187C) | 408 P | 127 P | 493 P | 163 P | 0.31 | 0.33 | 3.1 | Excl |
| HIR1 (YBL008W) | 54 A | 27 A | 76 P | 15 A | 0.50 | 0.19 | 3.6 | Good |
| HMS1 (YMR070W) | 50 P | 25 A | 123 P | 27 A | 0.49 | 0.22 | 3.3 | Good |
| HMT1 (YBR034C) | 611 P | 248 P | 668 P | 222 P | 0.41 | 0.33 | 2.7 | Excl |
| HOR2 (YER062C) | 260 P | 92 P | 337 P | 111 P | 0.35 | 0.33 | 2.9 | Excl |
| HSL7 (YBR133C) | 227 P | 81 P | 335 P | 132 P | 0.36 | 0.39 | 2.7 | Excl |
| HXK2 (YGL253W) | 3757 P | 1614 P | 3678 P | 1732 P | 0.43 | 0.47 | 2.2 | Excl |
| HXT1 (YHR094C) | 1813 P | 613 P | 2773 P | 1188 P | 0.34 | 0.43 | 2.6 | Excl |
| HXT4 (YHR092C) | 138 P | 53 P | 459 P | 82 P | 0.39 | 0.18 | 4.1 | Excl |
| HXT9 (YJL219W) | 37 A | -51 A | 6 A | -4 A | -1.38 | -0.70 | 9.8 Yes | Med |
| ICL1 (YER065C) | 102 A | -3 A | 36 P | 13 P | -0.03 | 0.36 | 11.9 Yes | Med |
| ILV3 (YJR016C) | 926 P | 272 P | 634 P | 313 P | 0.29 | 0.49 | 2.7 | Excl |
| ILV5 (YLR355C) | 5116 P | 1025 P | 3323 P | 1282 P | 0.20 | 0.39 | 3.8 | Excl |
| IME1 (YJR094C) | 45 A | 19 A | 18 A | 3 A | 0.43 | 0.18 | 3.9 | Good |
| ISC10 (YER180C) | 58 P | 15 A | 45 P | 23 P | 0.25 | 0.50 | 3.0 | Good |
| KAP95 (YLR347C) | 308 P | 102 A | 267 P | 102 P | 0.33 | 0.38 | 2.8 | Good |
| KCS1 (YDR017C) | 235 P | 114 P | 283 P | 128 P | 0.49 | 0.45 | 2.1 | Excl |
| KIP2 (YPL155C) | 74 A | 8 A | 68 P | 34 P | 0.10 | 0.49 | 5.8 | Good |
| KNR4 (YGR229C) | 787 P | 336 P | 704 P | 344 P | 0.43 | 0.49 | 2.2 | Excl |
| LEU2 (YCL018W) | 589 P | 256 P | 674 P | 270 P | 0.43 | 0.40 | 2.4 | Excl |
| LYS14 (YDR034C) | 79 A | 30 P | 121 P | 35 P | 0.38 | 0.29 | 3.1 | Good |
| LYS4 (YDR234W) | 641 P | 293 P | 623 P | 279 P | 0.46 | 0.45 | 2.2 | Good |
| MAG1 (YER142C) | 43 A | 13 A | 48 P | 14 M | 0.30 | 0.30 | 3.4 | Excl |
| MAK16 (YAL025C) | 346 P | 158 P | 446 P | 215 P | 0.46 | 0.48 | 2.1 | Excl |

Figure 3C

| | 37 | 3 | 36 | 7 | 0.10 | 0.19 | 7.8 | |
|---|---|---|---|---|---|---|---|---|
| MAL32 (YBR299W) | P | A | A | A | | | | Good |
| MCM1 (YMR043W) | 792 P | 263 P | 351 P | 117 P | 0.33 | 0.33 | 3.0 | Excl |
| MCM2 (YBL023C) | 51 A | 23 A | 74 P | 30 A | 0.46 | 0.40 | 2.3 | Good |
| MCM3 (YEL032W) | 319 A | 82 A | 140 P | 53 P | 0.26 | 0.38 | 3.3 | Good |
| MDH2 (YOL126C) | 395 P | 0 A | 557 P | 127 P | 0.00 | 0.23 | 41.7 Yes | Med |
| MEI4 (YER044C-A) e | 17 A | -3 A | 5 A | -5 A | -0.17 | -0.96 | 3.1 Yes | Med |
| MEK1 (YOR351C) | 132 A | -8 A | 14 A | 4 A | -0.06 | 0.28 | 15.7 Yes | Med |
| MET22 (YOL064C) | 189 A | 77 A | 257 P | 58 P | 0.41 | 0.22 | 3.5 | Good |
| MET25 (YLR303W) | 550 P | 207 P | 821 P | 240 P | 0.38 | 0.29 | 3.0 | Excl |
| MET6 (YER091C) | 549 P | 187 P | 693 P | 271 P | 0.34 | 0.39 | 2.7 | Excl |
| MFA1 (YDR461W) | 2290 P | 23 A | 1719 P | 104 P | 0.01 | 0.06 | 57.5 | Good |
| MFA2 (YNL145W) | 10468 P | 1100 P | 5137 P | 395 P | 0.11 | 0.08 | 11.3 | Excl |
| MIC1 (YGR100W) | 68 P | 22 A | 74 P | 36 P | 0.32 | 0.49 | 2.6 | Good |
| MIG2 (YGL209W) | 372 P | 173 P | 582 P | 166 P | 0.47 | 0.29 | 2.8 | Excl |
| MIS1 (YBR084W) | 914 P | 415 P | 1093 P | 452 P | 0.45 | 0.41 | 2.3 | Excl |
| MRE11 (YMR224C) | 79 A | -21 A | 33 P | 12 A | -0.27 | 0.36 | 11.4 Yes | Med |
| MRK1 (YDL079C) ex | 101 A | -12 A | 26 P | 8 A | -1.22 | 0.30 | 3.8 Yes | Med |
| MRPL4 (YLR439W) | 147 P | 39 A | 96 P | 33 A | 0.26 | 0.35 | 3.3 | Good |
| MRS2 (YOR333C) | 179 A | 19 A | 17 A | 4 A | 0.11 | 0.23 | 6.8 | Good |
| MSH4 (YFL003C) | 36 A | 0 A | 11 A | 0 A | 0.00 | 0.00 | 4.7 Yes | Med |
| MTR2 (YKL186C) | 316 P | 140 A | 220 P | 102 P | 0.44 | 0.47 | 2.2 | Good |
| NAM8 (YHR086W) | 109 A | 16 A | 153 P | 48 A | 0.14 | 0.31 | 5.0 | Good |
| NCA3 (YJL116C) | 137 P | 19 A | 68 P | 22 A | 0.14 | 0.32 | 5.1 | Good |
| NDI1 (YML120C) | 58 A | 12 A | 93 P | 24 P | 0.21 | 0.25 | 4.3 | Good |
| NDT80 (YHR124W) | 66 P | -1 A | 29 A | 10 A | -0.01 | 0.34 | 8.2 Yes | Med |

Figure 3D

| Name | | | | | | | |
|---|---|---|---|---|---|---|---|
| NIP1 (YMR309C) | 684 P | 200 P | 657 P | 267 P | 0.29 | 0.41 | 2.9 | Excl |
| NOP1 (YDL014W) | 3449 P | 1397 P | 3311 P | 1330 P | 0.40 | 0.40 | 2.5 | Excl |
| NPL3 (YDR432W) | 922 P | 302 P | 819 P | 283 P | 0.33 | 0.35 | 3.0 | Excl |
| NPR2 (YEL062W) | 47 A | 17 A | 36 P | 8 A | 0.36 | 0.23 | 3.6 | Good |
| NSR1 (YGR159C) | 2262 P | 744 P | 2771 P | 835 P | 0.33 | 0.30 | 3.2 | Excl |
| OLE1 (YGL055W) | 874 P | 340 P | 2086 P | 799 P | 0.39 | 0.38 | 2.6 | Excl |
| OM45 (YIL136W) | 143 P | 15 A | 52 M | 21 A | 0.10 | 0.40 | 6.1 | Good |
| ORF YAL060W | 257 A | 93 P | 314 P | 83 P | 0.36 | 0.27 | 3.3 | Good |
| ORF YAR003W | 178 A | 33 A | 206 P | 86 P | 0.18 | 0.42 | 3.9 | Good |
| ORF YAR009C (_f) | 2668 P | 1200 P | 2552 P | 1099 P | 0.45 | 0.43 | 2.3 | Excl |
| ORF YAR009C (_i) | 3900 P | 1944 P | 3427 P | 1051 P | 0.50 | 0.31 | 2.6 | Excl |
| ORF YAR010C (_f) | 1167 P | 216 P | 1705 P | 189 P | 0.19 | 0.11 | 7.2 | Excl |
| ORF YAR075W (_f) | 514 P | 208 P | 744 P | 311 P | 0.40 | 0.42 | 2.4 | Excl |
| ORF YBL011W | 224 P | 80 P | 281 P | 112 P | 0.36 | 0.40 | 2.6 | Excl |
| ORF YBL019W | 78 A | -45 A | 49 P | 18 M | -0.58 | 0.37 | 13.7 Yes | Med |
| ORF YBL024W | 290 P | 78 P | 344 P | 170 P | 0.27 | 0.49 | 2.9 | Excl |
| ORF YBL032W | 271 P | 122 P | 279 P | 115 P | 0.45 | 0.41 | 2.3 | Excl |
| ORF YBL094C | 92 P | 21 A | 113 P | 45 P | 0.23 | 0.40 | 3.4 | Good |
| ORF YBL095W | 111 A | 23 A | 88 P | 29 P | 0.21 | 0.33 | 3.9 | Good |
| ORF YBL098W | 30 A | -14 A | 84 P | 32 P | -0.46 | 0.38 | 5.7 Yes | Med |
| ORF YBL101W-A (_f) | 137 P | 35 A | 152 P | 50 P | 0.26 | 0.33 | 3.5 | Good |
| ORF YBL101W-B exon | 119 M | 26 M | 184 P | 26 P | 0.21 | 0.14 | 5.9 | Med |
| ORF YBL101W-B exon | 163 P | 72 P | 308 P | 78 P | 0.44 | 0.25 | 3.1 | Good |
| ORF YBL107C | 113 A | 40 A | 131 P | 17 M | 0.35 | 0.13 | 5.4 | Excl |
| ORF YBL111C exon | -2 A | -42 A | 71 P | -11 A | 26.37 | -0.16 | 12.3 Yes | Med |
| ORF YBL111C exon | 222 P | 6 A | 333 P | 62 P | 0.03 | 0.19 | 21.8 | Good |
| ORF YBL112C (_f) | 456 P | 2 A | 569 P | 138 P | 0.01 | 0.24 | 100.0 | Good |
| ORF YBL113C (_f) | 1186 P | 162 P | 1234 P | 518 P | 0.14 | 0.42 | 4.9 | Excl |
| ORF YBR012W-A (_f) | 1613 P | 444 P | 1714 P | 221 P | 0.28 | 0.13 | 5.7 | Excl |
| ORF YBR012W-B exon | 1230 P | 249 P | 1643 P | 215 P | 0.20 | 0.13 | 6.3 | Excl |
| ORF YBR016W | 1210 P | 380 P | 763 P | 306 P | 0.31 | 0.40 | 2.8 | Good |
| ORF YBR017C | 111 A | 36 M | 205 P | 101 P | 0.32 | 0.49 | 2.6 | Good |
| ORF YBR028C | 98 A | 21 A | 107 P | 40 P | 0.21 | 0.37 | 3.7 | Good |
| ORF YBR032W | 138 P | 30 A | 66 P | 13 A | 0.22 | 0.20 | 4.8 | Good |
| ORF YBR056W | 84 A | 40 M | 169 P | 48 P | 0.47 | 0.28 | 2.8 | Good |
| ORF YBR075W | 251 P | 86 P | 288 P | 133 P | 0.34 | 0.46 | 2.5 | Excl |
| ORF YBR078W exon | 1141 P | 399 P | 2061 P | 463 P | 0.35 | 0.22 | 3.7 | Excl |
| ORF YBR078W exon | 508 P | 220 P | 1167 P | 237 P | 0.43 | 0.20 | 3.6 | Excl |
| ORF YBR086C | 1192 P | 576 P | 1111 P | 514 P | 0.48 | 0.46 | 2.1 | Excl |
| ORF YBR105C | 186 P | 50 P | 383 P | 109 P | 0.27 | 0.28 | 3.6 | Excl |
| ORF YBR125C | 214 P | 66 P | 242 P | 95 P | 0.31 | 0.39 | 2.9 | Excl |
| ORF YBR158W | 968 P | 395 P | 1064 P | 365 P | 0.41 | 0.34 | 2.7 | Excl |

Figure 3E

| ORF | 1205 | | 572 | | 1473 | | 715 | | | | | |
|---|---|---|---|---|---|---|---|---|---|---|---|---|
| ORF YBR162C | 89 | P | 41 | P | 104 | P | 43 | P | 0.47 | 0.49 | 2.1 | | Excl |
| ORF YBR167C | 57 | P | -10 | A | 64 | P | 21 | A | 0.46 | 0.42 | 2.3 | | Excl |
| ORF YBR168W | 195 | M | 67 | P | 230 | P | 101 | P | -0.18 | 0.33 | 8.3 | Yes | Med |
| ORF YBR177C | 30 | A | -19 | A | 25 | P | 10 | A | 0.35 | 0.44 | 2.6 | | Good |
| ORF YBR184W | 100 | A | -16 | A | 36 | P | 17 | P | -0.62 | 0.38 | 6.2 | Yes | Med |
| ORF YBR190W | 156 | A | 62 | A | 266 | P | 90 | P | -0.16 | 0.48 | 12.7 | Yes | Med |
| ORF YBR220C | 197 | P | 98 | P | 238 | P | 81 | P | 0.40 | 0.34 | 2.7 | | Good |
| ORF YBR230C exon 1 | 137 | A | 12 | A | 175 | P | 44 | P | 0.50 | 0.34 | 2.5 | | Excl |
| ORF YBR238C | 179 | P | 80 | P | 180 | P | 63 | P | 0.09 | 0.25 | 7.8 | | Good |
| ORF YBR241C | 297 | P | 56 | P | 476 | P | 155 | P | 0.45 | 0.35 | 2.5 | | Excl |
| ORF YBR244W | 130 | P | 41 | P | 85 | P | 36 | P | 0.19 | 0.33 | 4.2 | | Excl |
| ORF YBR258C | 63 | P | 23 | P | 48 | P | 15 | P | 0.31 | 0.42 | 2.8 | | Excl |
| ORF YBR259W | 249 | P | 76 | P | 292 | P | 62 | P | 0.37 | 0.31 | 3.0 | | Excl |
| ORF YBR267W | 124 | M | 50 | P | 141 | P | 56 | P | 0.30 | 0.21 | 4.0 | | Excl |
| ORF YCL005W | 1133 | P | 535 | P | 1657 | P | 416 | P | 0.40 | 0.39 | 2.5 | | Good |
| ORF YCL019W | 513 | P | 159 | P | 607 | P | 143 | P | 0.47 | 0.25 | 3.1 | | Excl |
| ORF YCL036W | 78 | A | 28 | A | 67 | P | 27 | P | 0.31 | 0.23 | 3.7 | | Excl |
| ORF YCL042W | 125 | P | 45 | P | 253 | P | 55 | P | 0.36 | 0.40 | 2.6 | | Good |
| ORF YCL055W | 81 | A | 16 | A | 83 | P | 40 | M | 0.36 | 0.22 | 3.7 | | Excl |
| ORF YCL060C | 97 | P | 42 | A | 56 | P | 21 | P | 0.20 | 0.48 | 3.5 | | Good |
| ORF YCL063W | 2 | A | -31 | A | 19 | P | -9 | A | 0.43 | 0.37 | 2.5 | | Good |
| ORF YCR006C | 62 | A | 3 | A | 17 | P | 2 | A | -19.78 | -0.46 | 6.1 | Yes | Med |
| ORF YCR007C | 197 | P | 71 | P | 249 | P | 51 | P | 0.06 | 0.10 | 13.8 | | Good |
| ORF YCR008W | 35 | A | -1 | A | 39 | P | 13 | A | 0.36 | 0.21 | 3.8 | | Excl |
| ORF YCR024C | 63 | A | 20 | A | 69 | P | 16 | M | -0.03 | 0.33 | 5.1 | Yes | Med |
| ORF YCR027C | | | | | | | | | 0.31 | 0.23 | 3.8 | | Good |

Figure 3F

| ORF | | | | | | | | | | |
|---|---|---|---|---|---|---|---|---|---|---|
| ORF YCR035C | 446 | P | 186 | P | 526 | P | 237 | P | 0.42 | 0.45 | 2.3 | | Excl |
| ORF YCR045C | 16 | A | -2 | A | 18 | P | 6 | A | -0.15 | 0.34 | 3.3 | Yes | Med |
| ORF YCR062W | 68 | A | 23 | A | 79 | P | 17 | A | 0.34 | 0.22 | 3.7 | | Good |
| ORF YCR063W | 60 | A | 12 | A | 36 | P | 17 | A | 0.19 | 0.46 | 3.7 | | Good |
| ORF YCR068W | 67 | A | 19 | A | 36 | P | 10 | A | 0.28 | 0.29 | 3.5 | | Good |
| ORF YDL019C | 210 | P | 76 | P | 186 | P | 66 | P | 0.36 | 0.36 | 2.8 | | Excl |
| ORF YDL022W | 1084 | P | 151 | P | 1669 | P | 224 | P | 0.14 | 0.13 | 7.3 | | Excl |
| ORF YDL038C | 232 | P | 70 | A | 423 | P | 21 | P | 0.30 | 0.05 | 11.8 | | Good |
| ORF YDL039C | 365 | P | 95 | P | 857 | P | 60 | P | 0.26 | 0.07 | 9.1 | | Excl |
| ORF YDL044C | 57 | A | 28 | A | 75 | P | 31 | P | 0.49 | 0.42 | 2.2 | | Good |
| ORF YDL109C | 116 | A | 41 | A | 74 | P | 34 | P | 0.35 | 0.46 | 2.5 | | Good |
| ORF YDL119C | 100 | P | -8 | A | 92 | P | 4 | A | -0.08 | 0.05 | 21.4 | Yes | Med |
| ORF YDL129W | 143 | P | 43 | A | 81 | P | 28 | P | 0.30 | 0.34 | 3.1 | | Good |
| ORF YDL179W | 87 | A | 29 | A | 151 | P | 17 | M | 0.33 | 0.12 | 5.8 | | Good |
| ORF YDL248W (_l) | 40 | A | 2 | A | 37 | P | -7 | A | 0.06 | -0.19 | 12.9 | Yes | Med |
| ORF YDL248W (_r) | 37 | M | -9 | A | 32 | P | 1 | A | -0.25 | 0.03 | 23.0 | Yes | Med |
| ORF YDR018C | 38 | A | -13 | A | 6 | A | -9 | A | -0.34 | -1.45 | 6.6 | Yes | Med |
| ORF YDR022C | 51 | A | 21 | A | 38 | P | -2 | A | 0.41 | -0.05 | 5.2 | Yes | Med |
| ORF YDR026C | 86 | M | 35 | M | 61 | P | 28 | P | 0.41 | 0.46 | 2.3 | | Good |
| ORF YDR033W | 5497 | P | 519 | P | 4162 | P | 623 | P | 0.09 | 0.15 | 8.6 | | Excl |
| ORF YDR093W | 141 | P | 42 | P | 167 | P | 43 | P | 0.30 | 0.26 | 3.6 | | Excl |
| ORF YDR094W | 157 | P | 62 | P | 226 | P | 102 | P | 0.39 | 0.45 | 2.4 | | Excl |
| ORF YDR118W | 56 | A | 19 | A | 34 | P | 17 | A | 0.33 | 0.49 | 2.5 | | Good |
| ORF YDR131C | 71 | A | 26 | A | 54 | P | 13 | A | 0.36 | 0.24 | 3.5 | | Good |
| ORF YDR233C | 1722 | P | 574 | P | 2573 | P | 748 | P | 0.33 | 0.29 | 3.2 | | Excl |
| ORF YDR248C | 160 | A | 77 | P | 158 | P | 58 | P | 0.48 | 0.37 | 2.4 | | Good |
| ORF YDR250C | 60 | A | 17 | P | 19 | P | 7 | A | 0.29 | 0.37 | 3.1 | | Good |
| ORF YDR267C | 205 | P | 102 | P | 230 | P | 113 | P | 0.50 | 0.49 | 2.0 | | Excl |
| ORF YDR279W | 92 | P | 38 | P | 60 | P | 19 | P | 0.42 | 0.32 | 2.8 | | Excl |
| ORF YDR281C | 17 | A | -3 | A | 17 | P | 2 | A | -0.20 | 0.10 | 7.0 | Yes | Med |
| ORF YDR282C | 83 | A | 35 | A | 92 | P | 29 | P | 0.42 | 0.31 | 2.8 | | Good |
| ORF YDR286C | 92 | P | 35 | P | 68 | P | 25 | P | 0.38 | 0.37 | 2.7 | | Excl |
| ORF YDR334W | 168 | P | 60 | P | 118 | P | 51 | P | 0.36 | 0.43 | 2.5 | | Excl |
| ORF YDR336W | 89 | A | 6 | A | 80 | P | 33 | P | 0.07 | 0.41 | 8.9 | | Good |
| ORF YDR341C | 1544 | P | 752 | P | 1613 | P | 739 | P | 0.49 | 0.46 | 2.1 | | Excl |
| ORF YDR359C | 130 | A | -17 | A | 43 | P | 12 | A | -0.13 | 0.28 | 16.5 | Yes | Med |
| ORF YDR361C | 298 | P | 143 | P | 318 | P | 158 | P | 0.48 | 0.50 | 2.0 | | Excl |
| ORF YDR374C | 10 | A | -20 | A | 7 | A | -16 | A | -2.08 | -2.24 | 5.2 | Yes | Med |
| ORF YDR395W | 206 | A | 85 | P | 432 | P | 169 | P | 0.41 | 0.39 | 2.5 | | Med |
| ORF YDR400W | 111 | A | 35 | P | 170 | P | 63 | P | 0.31 | 0.37 | 3.0 | | Good |

Figure 3G

| ORF | 40 | | 2 | | 17 | | 5 | | | | | |
|---|---|---|---|---|---|---|---|---|---|---|---|---|
| ORF YDR417C | 40 | A | 2 | A | 17 | A | 5 | A | 0.06 | 0.31 | 10.2 | | Good |
| ORF YDR428C | 95 | A | 7 | P | 94 | P | 24 | P | 0.07 | 0.26 | 8.8 | | Good |
| ORF YDR438W | 29 | A | 7 | A | 63 | P | 13 | A | 0.24 | 0.21 | 4.5 | | Good |
| ORF YDR440W | 54 | A | 15 | A | 102 | P | 50 | P | 0.28 | 0.49 | 2.8 | | Good |
| ORF YDR444W | 138 | P | 55 | A | 86 | P | 42 | P | 0.40 | 0.49 | 2.3 | | Good |
| ORF YDR453C | 44 | A | 15 | A | 52 | P | 17 | P | 0.34 | 0.33 | 3.0 | | Good |
| ORF YDR489W | 79 | A | 35 | A | 90 | P | 24 | A | 0.44 | 0.27 | 3.0 | | Good |
| ORF YDR501W | 60 | A | -24 | A | 30 | P | 13 | A | -0.40 | 0.43 | 9.6 | Yes | Med |
| ORF YDR516C | 106 | A | 15 | A | 216 | P | 56 | P | 0.14 | 0.26 | 5.5 | | Good |
| ORF YDR539W | 13 | A | -34 | A | 189 | P | 26 | P | -2.66 | 0.14 | 8.3 | Yes | Med |
| ORF YDR541C | -19 | A | -42 | A | 55 | P | 11 | A | 2.20 | 0.21 | 4.7 | Yes | Med |
| ORF YEL007W | 475 | P | 151 | A | 337 | P | 83 | P | 0.32 | 0.25 | 3.6 | | Good |
| ORF YEL056W | 364 | P | 159 | P | 223 | P | 108 | P | 0.44 | 0.48 | 2.2 | | Excl |
| ORF YEL067C | 51 | A | 24 | A | 22 | A | -4 | A | 0.47 | -0.17 | 3.6 | Yes | Med |
| ORF YEL076C (_f) | 66 | A | 11 | A | 92 | P | 25 | A | 0.16 | 0.27 | 4.9 | | Good |
| ORF YEL076C-A exd | 60 | A | -35 | A | 42 | M | 10 | A | -0.57 | 0.23 | 11.7 | Yes | Med |
| ORF YEL076C-A exa | 142 | P | 26 | A | 56 | P | 18 | A | 0.18 | 0.32 | 4.3 | | Good |
| ORF YER033C | 23 | A | 7 | A | 25 | A | 4 | A | 0.31 | 0.15 | 4.9 | | Good |
| ORF YER036C | 1038 | P | 414 | P | 1296 | P | 468 | P | 0.40 | 0.36 | 2.6 | | Excl |
| ORF YER037W | 13 | A | -18 | A | 47 | P | 8 | A | -1.35 | 0.18 | 5.9 | Yes | Med |
| ORF YER075C | 72 | M | 32 | A | 70 | P | 20 | P | 0.44 | 0.29 | 2.9 | | Good |
| ORF YER089C | 313 | P | 80 | M | 164 | P | 59 | P | 0.26 | 0.36 | 3.4 | | Good |
| ORF YER093C-A exo | 57 | A | 11 | A | 58 | P | 27 | P | 0.19 | 0.47 | 3.7 | | Good |
| ORF YER110C | 491 | P | 243 | P | 478 | P | 210 | P | 0.49 | 0.44 | 2.2 | | Excl |
| ORF YER124C | 196 | P | 79 | P | 370 | P | 132 | P | 0.40 | 0.36 | 2.6 | | Excl |
| ORF YER138C exon | 1391 | P | 203 | P | 1495 | P | 218 | P | 0.15 | 0.15 | 6.9 | | Excl |
| ORF YER160C exon | 1423 | P | 213 | P | 1795 | P | 235 | P | 0.15 | 0.13 | 7.2 | | Excl |
| ORF YER169W | 126 | P | 35 | A | 141 | P | 65 | P | 0.27 | 0.46 | 2.9 | | Good |

Figure 3H

| ORF | | | | | | | | |
|---|---|---|---|---|---|---|---|---|
| ORF YER186C | 160 P | 77 P | 148 P | 62 P | 0.48 | 0.42 | 2.2 | Excl |
| ORF YER188W | 100 P | -8 A | 21 P | 4 A | -0.08 | 0.18 | 13.5 Yes | Med |
| ORF YFL024C | 91 A | 21 A | 133 P | 46 P | 0.23 | 0.35 | 3.6 | Good |
| ORF YFL027C | 164 P | 76 P | 147 P | 59 P | 0.46 | 0.40 | 2.3 | Excl |
| ORF YFL035C-B exon | 577 P | 244 P | 1110 P | 493 P | 0.42 | 0.44 | 2.3 | Excl |
| ORF YFL051C | 53 A | 6 A | 23 A | 4 A | 0.11 | 0.16 | 7.5 | Good |
| ORF YFL055W | 96 P | 22 A | 74 P | 26 P | 0.23 | 0.35 | 3.7 | Good |
| ORF YFL059W (_f) | 115 P | -3 A | 63 P | 14 A | -0.03 | 0.21 | 14.1 Yes | Med |
| ORF YFL060C (_f) | 9 A | -23 A | 30 P | -2 A | -2.41 | -0.05 | 6.4 Yes | Med |
| ORF YFL063W (_r) | 32 A | -8 A | 34 A | -4 A | -0.25 | -0.11 | 7.8 Yes | Med |
| ORF YFL066C (_f) | 277 P | 12 A | 234 P | 98 P | 0.04 | 0.42 | 12.9 | Good |
| ORF YFR032C | 89 P | -13 A | 25 A | 3 A | -0.15 | 0.12 | 14.3 Yes | Med |
| ORF YGL018C | 77 A | 37 A | 49 P | 10 A | 0.47 | 0.20 | 3.6 | Good |
| ORF YGL028C | 455 P | 91 P | 682 P | 129 P | 0.20 | 0.19 | 5.1 | Excl |
| ORF YGL033W exon | 25 A | -4 A | 12 A | -5 A | -0.16 | -0.43 | 4.6 Yes | Med |
| ORF YGL045W | 134 P | 28 A | 38 P | 19 M | 0.21 | 0.49 | 3.4 | Good |
| ORF YGL051W | -2 A | -23 A | 30 P | 10 A | 12.07 | 0.32 | 3.6 Yes | Med |
| ORF YGL064C | 60 P | 8 A | 56 P | 24 P | 0.13 | 0.43 | 5.0 | Good |
| ORF YGL069C | 30 A | 0 A | -3 A | -19 A | 0.00 | 6.86 | 4.6 Yes | Med |
| ORF YGL072C | 15 A | 3 A | 49 P | 22 A | 0.20 | 0.44 | 3.7 | Good |
| ORF YGL081W | 138 A | 53 A | 23 P | 10 A | 0.39 | 0.42 | 2.5 | Good |
| ORF YGL084C | 153 P | 63 P | 190 P | 95 P | 0.41 | 0.50 | 2.2 | Excl |
| ORF YGL139C | 98 P | -10 A | 25 A | -3 A | -0.10 | -0.12 | 13.6 Yes | Med |
| ORF YGL146C | 42 P | 4 A | 11 A | 0 A | 0.10 | 0.00 | 6.3 Yes | Med |
| ORF YGL159W | 147 P | 64 A | 185 P | 54 P | 0.44 | 0.29 | 2.9 | Good |
| ORF YGL176C | 13 A | 0 A | 42 P | 12 A | 0.00 | 0.28 | 3.1 Yes | Med |
| ORF YGL182C | -6 A | -33 A | 7 A | -4 A | 5.77 | -0.55 | 3.8 Yes | Med |
| ORF YGL184C | 25 A | -16 A | 53 P | 8 P | -0.65 | 0.15 | 7.3 Yes | Med |
| ORF YGL196W | 192 P | 70 P | 175 P | 50 P | 0.37 | 0.29 | 3.1 | Excl |
| ORF YGL204C | 109 P | 20 A | 85 P | 17 A | 0.18 | 0.20 | 5.2 | Good |
| ORF YGL223C | 121 P | 58 P | 119 P | 56 P | 0.48 | 0.47 | 2.1 | Excl |
| ORF YGL227W | 9 A | -15 A | 29 P | 12 A | -1.57 | 0.42 | 3.6 Yes | Med |
| ORF YGL239C | 58 P | 4 A | 29 A | 12 A | 0.07 | 0.42 | 8.6 | Good |
| ORF YGL261C (_f) | 219 P | 91 A | 221 P | 102 P | 0.42 | 0.46 | 2.3 | Good |
| ORF YGR004W | 57 A | 18 A | 105 P | 41 P | 0.31 | 0.38 | 2.9 | Good |
| ORF YGR021W | 45 A | 19 A | 37 P | 11 A | 0.42 | 0.30 | 2.8 | Good |
| ORF YGR023W | 15 A | -1 A | 26 A | 8 P | -0.07 | 0.29 | 3.3 Yes | Med |
| ORF YGR025W | 92 P | 42 A | 78 A | 38 M | 0.45 | 0.48 | 2.2 | Good |
| ORF YGR031W | 174 P | 50 P | 107 P | 53 P | 0.29 | 0.49 | 2.8 | Excl |
| ORF YGR036C | 109 P | 53 P | 319 P | 119 P | 0.49 | 0.37 | 2.4 | Excl |
| ORF YGR045C | 57 P | 21 P | 48 P | 15 A | 0.37 | 0.31 | 3.0 | Good |

Figure 31

| | | | | | | | | |
|---|---|---|---|---|---|---|---|---|
| ORF YGR086C | 794 | P | 204 | P | 932 | P | 271 | P | 0.26 | 0.29 | 3.7 | | Excl |
| ORF YGR111W | 60 | P | 22 | A | 1341 | P | 66 | P | 0.36 | 0.49 | 2.4 | | Good |
| ORF YGR112W | 40 | A | 10 | A | 37 | P | -2 | A | 0.25 | -0.04 | 5.8 | Yes | Med |
| ORF YGR131W | 58 | A | 11 | A | 36 | A | 8 | A | 0.19 | 0.21 | 5.1 | | Good |
| ORF YGR138C | 81 | P | -7 | A | 163 | P | 44 | P | -0.09 | 0.27 | 10.7 | Yes | Med |
| ORF YGR160W | 60 | A | 20 | P | 52 | P | 16 | A | 0.33 | 0.30 | 3.2 | | Good |
| ORF YGR200C | 400 | P | 177 | P | 630 | P | 273 | P | 0.44 | 0.43 | 2.3 | | Excl |
| ORF YGR225W | 21 | A | -16 | A | 18 | A | -4 | A | -0.76 | -0.21 | 5.8 | Yes | Med |
| ORF YGR230W | 75 | P | 32 | A | 60 | P | 20 | A | 0.42 | 0.32 | 2.7 | | Good |
| ORF YGR241C | 362 | P | 161 | P | 207 | P | 77 | P | 0.45 | 0.37 | 2.5 | | Excl |
| ORF YGR245C | 370 | P | 153 | P | 416 | P | 170 | P | 0.41 | 0.41 | 2.4 | | Excl |
| ORF YGR260W | 270 | P | 86 | P | 570 | P | 140 | P | 0.32 | 0.25 | 3.6 | | Excl |
| ORF YGR279C | 1866 | P | 713 | P | 3175 | P | 1282 | P | 0.38 | 0.40 | 2.5 | | Excl |
| ORF YGR287C | 87 | A | 17 | A | 47 | P | 16 | A | 0.19 | 0.34 | 4.1 | | Good |
| ORF YGR294W (_f) | 472 | P | 221 | P | 708 | P | 293 | P | 0.47 | 0.41 | 2.3 | | Excl |
| ORF YGR296W exon | 1543 | P | 203 | P | 1273 | P | 605 | P | 0.13 | 0.48 | 4.9 | | Excl |
| ORF YHL021C | 91 | P | 33 | M | 96 | P | 29 | P | 0.36 | 0.30 | 3.1 | | Good |
| ORF YHL026C | 117 | P | 18 | A | 164 | P | 57 | P | 0.15 | 0.35 | 4.7 | | Good |
| ORF YHL028W | 62 | A | -6 | A | 33 | M | 5 | A | -0.10 | 0.16 | 9.9 | Yes | Med |
| ORF YHL044W | 38 | P | 15 | A | 51 | P | 10 | P | 0.39 | 0.19 | 3.9 | | Good |
| ORF YHL046C (_f) | 217 | P | 87 | P | 268 | P | 86 | P | 0.40 | 0.32 | 2.8 | | Excl |
| ORF YHL047C | 270 | P | 62 | A | 204 | P | 77 | P | 0.23 | 0.38 | 3.5 | | Good |
| ORF YHL048W | 221 | A | 105 | P | 185 | P | 57 | P | 0.48 | 0.31 | 2.7 | | Good |
| ORF YHL050C exon | 364 | P | 32 | A | 366 | P | 105 | P | 0.09 | 0.29 | 7.5 | | Good |
| ORF YHL050C exon | 1970 | P | 203 | P | 1429 | P | 682 | P | 0.10 | 0.48 | 5.9 | | Excl |
| ORF YHR020W | 1468 | P | 709 | P | 1966 | P | 978 | P | 0.48 | 0.50 | 2.0 | | Excl |
| ORF YHR022C | 49 | P | 15 | A | 55 | P | 17 | P | 0.30 | 0.32 | 3.2 | | Good |

Figure 3J

| ORF | | | | | | | | |
|---|---|---|---|---|---|---|---|---|
| ORF YHR029C | 117 | P | 10 | A | 107 | P | 48 | P | 0.08 | 0.45 | 7.0 | | Good |
| ORF YHR032W | 140 | P | 58 | P | 279 | P | 84 | P | 0.42 | 0.30 | 2.9 | | Excl |
| ORF YHR061C | 72 | A | 34 | A | 95 | P | 38 | P | 0.47 | 0.41 | 2.3 | | Good |
| ORF YHR070W | 509 | P | 228 | P | 603 | P | 277 | P | 0.45 | 0.46 | 2.2 | | Excl |
| ORF YHR087W | 40 | A | 0 | A | 221 | P | 44 | P | 0.00 | 0.20 | 6.4 | Yes | Med |
| ORF YHR097C exon | 55 | A | 7 | A | 66 | P | 14 | A | 0.13 | 0.22 | 6.2 | | Good |
| ORF YHR097C exon | 211 | P | 36 | A | 119 | P | 45 | P | 0.17 | 0.38 | 4.3 | | Excl |
| ORF YHR108W | 238 | P | 118 | P | 270 | P | 98 | P | 0.50 | 0.36 | 2.4 | | Excl |
| ORF YHR130C | 91 | P | 42 | A | 182 | P | 70 | P | 0.46 | 0.38 | 2.4 | | Good |
| ORF YHR136C | -2 | A | -19 | A | 23 | P | 8 | A | 9.97 | 0.32 | 3.2 | Yes | Med |
| ORF YHR143W | 1036 | P | 307 | P | 1488 | P | 292 | P | 0.30 | 0.20 | 4.2 | | Excl |
| ORF YHR149C | 257 | P | 88 | P | 163 | P | 77 | P | 0.34 | 0.48 | 2.5 | | Excl |
| ORF YHR169W | 217 | P | 65 | P | 208 | P | 92 | P | 0.30 | 0.44 | 2.8 | | Excl |
| ORF YHR182W | 108 | P | 41 | A | 104 | P | 40 | P | 0.38 | 0.38 | 2.6 | | Good |
| ORF YHR198C | 77 | A | 20 | P | 52 | P | 23 | P | 0.26 | 0.45 | 3.1 | | Good |
| ORF YHR214C-B exa | 2009 | P | 386 | P | 1878 | P | 320 | P | 0.19 | 0.17 | 5.5 | | Excl |
| ORF YHR217C (_f) | 74 | A | -10 | A | 140 | A | 38 | A | -0.13 | 0.27 | 10.2 | Yes | Med |
| ORF YHR218W exon | 42 | A | -17 | A | 64 | P | 8 | A | -0.41 | 0.13 | 9.7 | Yes | Med |
| ORF YHR218W exon | 258 | P | 7 | A | 322 | P | 55 | P | 0.03 | 0.17 | 21.6 | | Good |
| ORF YIL051C | 1804 | P | 605 | P | 3370 | P | 921 | P | 0.34 | 0.27 | 3.3 | | Excl |
| ORF YIL056W | 170 | P | 20 | A | 82 | P | 8 | A | 0.12 | 0.09 | 9.8 | | Good |
| ORF YIL059C | 145 | P | 71 | A | 182 | P | 81 | P | 0.49 | 0.45 | 2.1 | | Good |
| ORF YIL071W | 32 | A | -4 | A | 22 | P | 7 | A | -0.12 | 0.31 | 5.2 | Yes | Med |
| ORF YIL082W-A exa | 36 | A | -11 | A | 38 | P | 10 | A | -0.03 | 0.25 | 5.6 | Yes | Med |
| ORF YIL082W-A exa | 130 | P | 61 | P | 104 | P | 49 | P | 0.47 | 0.47 | 2.1 | | Excl |
| ORF YIL092W | 49 | A | 16 | A | 38 | P | 14 | A | 0.32 | 0.35 | 3.0 | | Good |
| ORF YIL100W | 21 | A | -7 | A | 12 | A | 2 | A | -0.33 | 0.18 | 5.5 | Yes | Med |
| ORF YIL123W | 896 | P | 431 | P | 1453 | P | 631 | P | 0.48 | 0.43 | 2.2 | | Excl |
| ORF YIL132C | 9 | A | -2 | A | 37 | P | -9 | A | -0.21 | -0.24 | 5.7 | Yes | Med |
| ORF YIL164C | 66 | A | 32 | A | 64 | P | 26 | A | 0.48 | 0.41 | 2.3 | | Med |
| ORF YIL176C (_f) | 319 | P | 138 | P | 447 | P | 167 | P | 0.43 | 0.37 | 2.5 | | Excl |
| ORF YIL177C exon | 715 | P | 96 | P | 712 | P | 336 | P | 0.13 | 0.47 | 4.8 | | Good |
| ORF YIR040C (_f) | 6 | A | -15 | A | 4 | A | -13 | A | -2.62 | -3.11 | 3.7 | Yes | Med |
| ORF YIR044C (_f) | 445 | P | 170 | P | 564 | P | 194 | P | 0.38 | 0.34 | 2.8 | | Excl |
| ORF YJL017W | 106 | P | 18 | A | 118 | P | 34 | P | 0.17 | 0.29 | 4.7 | | Good |
| ORF YJL020C | 204 | P | 87 | P | 156 | P | 53 | P | 0.43 | 0.34 | 2.6 | | Excl |
| ORF YJL161W | 24 | A | 7 | A | 8 | A | -24 | A | 0.30 | -2.87 | 4.9 | Yes | Med |
| ORF YJL195C | 13 | A | -5 | A | 3 | A | -12 | A | -0.40 | -3.82 | 3.3 | Yes | Med |
| ORF YJL213W | 87 | A | 37 | M | 76 | P | 23 | A | 0.42 | 0.30 | 2.9 | | Good |
| ORF YJL225C exon | 71 | A | 12 | A | 32 | P | 10 | A | 0.17 | 0.30 | 4.5 | | Good |
| ORF YJR003C | 113 | A | 56 | A | 119 | P | 37 | A | 0.50 | 0.31 | 2.6 | | Good |
| ORF YJR019C | 121 | P | 54 | A | 93 | A | 33 | A | 0.45 | 0.36 | 2.5 | | Good |

Figure 3K

| | 1155 | | 332 | | 1442 | | 249 | | | | | |
|---|---|---|---|---|---|---|---|---|---|---|---|---|
| ORF YJR026W (_f) | 1155 | P | 332 | P | 1442 | P | 249 | P | 0.29 | 0.17 | 4.6 | | Excl |
| ORF YJR027W exon | 1342 | P | 347 | P | 1360 | P | 210 | P | 0.26 | 0.15 | 5.2 | | Excl |
| ORF YJR028W (_f) | 1934 | P | 365 | P | 1594 | P | 248 | P | 0.19 | 0.16 | 5.9 | | Excl |
| ORF YJR029W exon | 1624 | P | 411 | P | 1579 | P | 170 | P | 0.25 | 0.11 | 6.6 | | Excl |
| ORF YJR053W | 34 | A | -5 | A | 24 | P | 5 | A | -0.15 | 0.23 | 6.2 | Yes | Med |
| ORF YJR071W | 16 | A | -28 | A | 16 | P | -2 | A | -1.78 | -0.13 | 6.3 | Yes | Med |
| ORF YJR101W | 150 | A | 40 | A | 239 | P | 117 | P | 0.27 | 0.49 | 2.9 | | Good |
| ORF YJR108W | 45 | A | -25 | A | 14 | P | -14 | A | -0.55 | -0.97 | 9.8 | Yes | Med |
| ORF YJR128W | -18 | A | -53 | A | 12 | A | -6 | A | 2.86 | -0.52 | 5.3 | Yes | Med |
| ORF YJR129C | 68 | A | -21 | A | 41 | P | 13 | P | -0.31 | 0.31 | 10.5 | Yes | Med |
| ORF YJR137C | 84 | A | 18 | A | 47 | P | 3 | A | 0.21 | 0.07 | 9.8 | | Good |
| ORF YKL005C | 118 | A | -30 | A | 82 | P | 33 | P | -0.25 | 0.40 | 16.1 | Yes | Med |
| ORF YKL027W | 203 | A | 49 | A | 129 | P | 55 | P | 0.24 | 0.43 | 3.2 | | Good |
| ORF YKL030W | 26 | A | -21 | A | 4 | A | -20 | A | -0.80 | -4.95 | 7.2 | Yes | Med |
| ORF YKL042W | 74 | A | 9 | A | 26 | P | -5 | A | 0.12 | -0.21 | 7.3 | Yes | Med |
| ORF YKL047W | 66 | P | -2 | A | 73 | P | 9 | A | -0.03 | 0.12 | 11.0 | Yes | Med |
| ORF YKL073W | 179 | P | 77 | P | 173 | P | 58 | P | 0.43 | 0.34 | 2.7 | | Excl |
| ORF YKL075C | 89 | P | 26 | M | 95 | P | 47 | P | 0.29 | 0.50 | 2.7 | | Good |
| ORF YKL115C | 45 | A | 18 | A | 25 | A | 8 | A | 0.39 | 0.30 | 2.9 | | Good |
| ORF YKL134C | 66 | A | 19 | A | 35 | P | 12 | A | 0.29 | 0.34 | 3.2 | | Good |
| ORF YKL171W | 5 | A | -30 | A | 28 | P | -43 | A | -5.67 | -1.55 | 10.6 | Yes | Med |
| ORF YKL198C | 132 | P | 46 | A | 46 | P | 16 | A | 0.35 | 0.35 | 2.9 | | Good |
| ORF YKL218C | 66 | A | 26 | A | 85 | P | 25 | P | 0.40 | 0.29 | 3.0 | | Good |
| ORF YKR015C | 66 | A | -5 | A | 4 | A | -10 | A | -0.08 | -2.35 | 8.5 | Yes | Med |
| ORF YKR017C | 55 | A | 9 | A | 52 | P | 13 | P | 0.16 | 0.25 | 5.1 | | Good |
| ORF YKR038C | 329 | P | 135 | P | 246 | P | 103 | P | 0.41 | 0.42 | 2.4 | | Excl |

Figure 3L

| ORF | | | | | | | | | |
|---|---|---|---|---|---|---|---|---|---|
| ORF YKR090W | 153 M | 70 A | 72 P | 31 A | 0.46 | 0.43 | 2.2 | | Good |
| ORF YKR103W | 42 A | 16 A | 22 P | -2 A | 0.38 | -0.10 | 3.7 | Yes | Med |
| ORF YLL002W | 103 P | 51 A | 73 P | 33 M | 0.50 | 0.46 | 2.1 | | Good |
| ORF YLL010C | 176 P | 42 A | 161 P | 48 P | 0.24 | 0.30 | 3.8 | | Good |
| ORF YLL044W | 21 A | -2 A | 21 P | 10 M | -0.08 | 0.47 | 3.3 | Yes | Med |
| ORF YLL054C | 21 A | -9 A | 42 P | 20 M | -0.42 | 0.48 | 4.0 | Yes | Med |
| ORF YLL057C | 55 A | -32 A | 19 P | 1 A | -0.57 | 0.06 | 17.3 | Yes | Med |
| ORF YLL063C | -24 A | -47 A | 26 P | 3 A | 2.00 | 0.13 | 6.4 | Yes | Med |
| ORF YLL067C exon | 1803 P | 311 P | 1342 P | 649 P | 0.17 | 0.48 | 3.9 | | Excl |
| ORF YLR002C | 103 P | 47 A | 234 P | 112 P | 0.46 | 0.48 | 2.1 | | Good |
| ORF YLR004C | 68 P | -11 A | 21 A | -5 A | -0.15 | -0.26 | 10.5 | Yes | Med |
| ORF YLR024C | 26 P | 12 A | 67 P | 30 P | 0.47 | 0.45 | 2.2 | | Good |
| ORF YLR033W | 97 A | 46 A | 103 P | 49 P | 0.47 | 0.48 | 2.1 | | Good |
| ORF YLR040C | 71 A | 9 A | 90 P | 29 P | 0.12 | 0.32 | 5.6 | | Good |
| ORF YLR042C | 21 A | -35 A | 34 P | -1 A | -1.67 | -0.03 | 9.1 | Yes | Med |
| ORF YLR054C | 26 P | -40 A | 15 P | -3 A | -1.53 | -0.21 | 8.5 | Yes | Med |
| ORF YLR073C | 255 P | 109 A | 199 P | 61 P | 0.43 | 0.31 | 2.8 | | Good |
| ORF YLR080W | 74 P | -9 A | 24 P | 10 M | -0.12 | 0.41 | 9.5 | Yes | Med |
| ORF YLR089C | 247 P | 109 P | 307 P | 133 P | 0.44 | 0.43 | 2.3 | | Excl |
| ORF YLR144C | 55 A | 26 A | 144 P | 54 P | 0.48 | 0.37 | 2.4 | | Med |
| ORF YLR149C | 21 A | -49 A | 38 P | 16 P | -2.33 | 0.42 | 8.2 | Yes | Med |
| ORF YLR164W | 39 A | -9 A | 24 A | 10 A | -0.22 | 0.41 | 6.0 | Yes | Med |
| ORF YLR169W | 145 A | 2 A | -3 A | -17 A | 0.01 | 5.56 | 42.7 | Yes | Med |
| ORF YLR173W | 89 A | 30 A | 53 P | 22 A | 0.33 | 0.41 | 2.7 | | Good |
| ORF YLR176C | 37 A | -16 A | 31 P | 10 A | -0.43 | 0.31 | 6.9 | Yes | Med |
| ORF YLR177W | 205 P | 95 P | 185 P | 77 P | 0.46 | 0.42 | 2.3 | | Excl |
| ORF YLR192C | 1342 P | 286 P | 989 P | 439 P | 0.21 | 0.44 | 3.5 | | Excl |
| ORF YLR206W | 379 P | 168 A | 168 P | 66 M | 0.44 | 0.39 | 2.4 | | Good |
| ORF YLR213C | 58 P | -5 A | 19 P | 4 A | -0.09 | 0.23 | 8.5 | Yes | Med |
| ORF YLR218C | 303 P | 47 A | 80 P | 38 P | 0.16 | 0.47 | 4.3 | | Excl |
| ORF YLR220W | 253 P | 93 P | 263 P | 98 P | 0.37 | 0.37 | 2.7 | | Excl |
| ORF YLR231C | 226 P | 65 A | 122 P | 24 P | 0.29 | 0.19 | 4.3 | | Good |
| ORF YLR254C | 155 P | 35 A | 38 P | -1 A | 0.23 | -0.03 | 6.1 | Yes | Med |
| ORF YLR265C | 153 A | 61 A | 104 P | 51 P | 0.40 | 0.49 | 2.3 | | Good |
| ORF YLR296W | 21 A | -16 A | 12 P | -1 A | -0.75 | -0.09 | 5.0 | Yes | Med |
| ORF YLR312C | 37 A | -4 A | 12 A | -20 A | -0.10 | -1.65 | 7.3 | Yes | Med |
| ORF YLR328W | 103 A | 4 A | 177 P | 35 P | 0.03 | 0.20 | 17.1 | | Med |
| ORF YLR415C | 126 A | 53 A | 14 A | -2 A | 0.42 | -0.15 | 2.9 | Yes | Med |
| ORF YLR424W | 26 A | 2 A | 36 P | 14 P | 0.07 | 0.39 | 8.8 | | Good |
| ORF YLR427W | 200 P | 91 P | 142 P | 67 P | 0.46 | 0.47 | 2.2 | | Good |
| ORF YLR432W | 489 P | 200 P | 932 P | 412 P | 0.41 | 0.44 | 2.4 | | Excl |

Figure 3M

| ORF | | | | | | | | | |
|---|---|---|---|---|---|---|---|---|---|
| ORF YLR436C | 142 | P | 32 | A | 174 | P | 61 | P | 0.22 | 0.35 | 3.7 | | Good |
| ORF YLR440C | 142 | P | 32 | A | 73 | P | 20 | P | 0.22 | 0.28 | 4.0 | | Good |
| ORF YML006C | 218 | A | 109 | P | 248 | P | 105 | P | 0.50 | 0.42 | 2.2 | | Good |
| ORF YML018C | 363 | P | 147 | A | 218 | P | 90 | P | 0.41 | 0.42 | 2.4 | | Good |
| ORF YML039W exon | 1147 | P | 302 | P | 1604 | P | 235 | P | 0.26 | 0.15 | 5.3 | | Excl |
| ORF YML040W (_f) | 1505 | P | 135 | M | 1439 | P | 165 | P | 0.09 | 0.11 | 9.9 | | Good |
| ORF YML045W exon | 1750 | P | 321 | P | 1565 | P | 276 | P | 0.18 | 0.18 | 5.6 | | Excl |
| ORF YML076C | 89 | A | -9 | A | 107 | P | 37 | P | -0.10 | 0.34 | 11.3 | Yes | Med |
| ORF YML079W | 147 | A | 39 | A | 206 | P | 71 | P | 0.26 | 0.34 | 3.4 | | Good |
| ORF YML118W | 32 | A | -26 | A | 14 | A | -6 | A | -0.83 | -0.45 | 7.9 | Yes | Med |
| ORF YML122C | -50 | A | -65 | A | -20 | A | -31 | A | 1.30 | 1.59 | 2.7 | Yes | Med |
| ORF YMR006C | 313 | P | 153 | P | 260 | P | 90 | P | 0.49 | 0.35 | 2.5 | | Excl |
| ORF YMR016C | 134 | P | 9 | A | 105 | P | 24 | P | 0.07 | 0.22 | 9.9 | | Good |
| ORF YMR026C | 124 | A | 21 | A | 87 | P | 35 | P | 0.17 | 0.41 | 4.2 | | Good |
| ORF YMR050C exon | 1118 | P | 291 | P | 1538 | P | 257 | P | 0.26 | 0.17 | 4.9 | | Excl |
| ORF YMR051C (_f) | 1397 | P | 160 | A | 1530 | P | 185 | P | 0.11 | 0.12 | 8.5 | | Good |
| ORF YMR063W | 21 | A | -21 | A | 10 | A | -25 | A | -1.00 | -2.40 | 7.7 | Yes | Med |
| ORF YMR067C | 218 | P | 39 | A | 129 | P | 55 | A | 0.18 | 0.43 | 4.0 | | Good |
| ORF YMR068W | 55 | A | -26 | A | 31 | P | -18 | A | -0.48 | -0.59 | 13.1 | Yes | Med |
| ORF YMR075W | 74 | A | 4 | A | 53 | P | 22 | P | 0.05 | 0.41 | 11.7 | | Good |
| ORF YMR098C | 82 | M | 25 | A | 99 | P | 42 | P | 0.30 | 0.42 | 2.8 | | Good |
| ORF YMR100W | 147 | P | 72 | A | 152 | P | 75 | P | 0.49 | 0.50 | 2.0 | | Good |
| ORF YMR101C | 63 | P | -9 | A | -2 | A | -14 | A | -0.14 | 6.78 | 8.4 | Yes | Med |
| ORF YMR102C | 103 | A | 35 | A | 252 | P | 83 | P | 0.34 | 0.33 | 3.0 | | Good |
| ORF YMR106C | 63 | M | 25 | A | 15 | A | 0 | A | 0.39 | 0.00 | 2.8 | Yes | Med |
| ORF YMR111C | 158 | A | 12 | A | 60 | P | 5 | A | 0.08 | 0.09 | 12.0 | | Good |
| ORF YMR112C | 389 | P | 86 | A | 215 | P | 97 | P | 0.22 | 0.45 | 3.4 | | Good |

Figure 3N

| ORF | | | | | | | | | |
|---|---|---|---|---|---|---|---|---|---|
| ORF YMR118C | 37 | A | -33 | A | 5 | A | -5 | A | -0.90 | -1.04 | 8.1 | Yes | Med |
| ORF YMR130W | 68 | A | 16 | A | 160 | P | 60 | P | 0.23 | 0.38 | 3.5 | | Good |
| ORF YMR141C | 74 | A | -30 | A | 31 | P | 8 | A | -0.40 | 0.24 | 12.4 | Yes | Med |
| ORF YMR153W | 192 | P | 77 | P | 198 | P | 87 | P | 0.40 | 0.44 | 2.4 | | Excl |
| ORF YMR157C | 87 | A | 19 | A | 116 | P | 42 | P | 0.22 | 0.36 | 3.6 | | Good |
| ORF YMR158W | 163 | P | 33 | A | 211 | P | 83 | P | 0.20 | 0.39 | 3.7 | | Good |
| ORF YMR173W | 34 | A | -86 | A | 115 | P | 26 | A | -2.51 | 0.22 | 14.3 | Yes | Med |
| ORF YMR176W | 42 | A | -30 | A | 74 | P | 16 | A | -0.71 | 0.22 | 9.5 | Yes | Med |
| ORF YMR180C | 137 | A | 26 | A | 51 | P | 19 | P | 0.19 | 0.38 | 3.9 | | Good |
| ORF YMR187C | -11 | A | -21 | A | 81 | P | 33 | A | 2.00 | 0.41 | 2.3 | Yes | Med |
| ORF YMR211W | 45 | A | -16 | A | 144 | P | 70 | P | -0.35 | 0.48 | 7.1 | Yes | Med |
| ORF YMR212C | 87 | A | -7 | A | 280 | P | 111 | P | -0.08 | 0.39 | 10.7 | Yes | Med |
| ORF YMR213W | 26 | A | -46 | A | 45 | P | 23 | A | -1.73 | 0.50 | 8.2 | Yes | Med |
| ORF YMR216C | 37 | A | 18 | A | 109 | P | 40 | P | 0.48 | 0.36 | 2.4 | | Good |
| ORF YMR291W | 16 | A | -38 | A | 71 | P | 34 | A | -2.44 | 0.48 | 6.5 | Yes | Good |
| ORF YNL018C (_f) | -58 | A | -100 | A | 21 | A | 3 | A | 1.73 | 0.16 | 7.3 | Yes | Med |
| ORF YNL021W | 126 | A | 54 | A | 192 | P | 68 | P | 0.43 | 0.35 | 2.6 | | Excl |
| ORF YNL024C | 142 | A | -8 | A | 152 | P | 54 | P | -0.05 | 0.36 | 16.4 | Yes | Good |
| ORF YNL042W | 247 | A | 15 | A | 93 | P | 35 | P | 0.06 | 0.38 | 9.4 | | Med |
| ORF YNL065W | 74 | A | 15 | A | 701 | P | 305 | P | 0.21 | 0.43 | 3.5 | | Good |
| ORF YNL078W | 353 | A | 92 | A | 245 | P | 89 | P | 0.26 | 0.37 | 3.3 | | Good |
| ORF YNL092W | 32 | A | -46 | A | 91 | A | -1 | A | -1.46 | -0.15 | 8.8 | Yes | Med |
| ORF YNL096C exon 1 | 2958 | P | 1462 | P | 2373 | P | 1113 | P | 0.49 | 0.47 | 2.1 | | Excl |
| ORF YNL119W | 295 | M | 19 | A | 179 | P | 86 | P | 0.07 | 0.48 | 8.7 | | Good |
| ORF YNL122C | 121 | A | -8 | A | 143 | P | 72 | P | -0.06 | 0.50 | 13.9 | Yes | Med |
| ORF YNL127W | 126 | A | -15 | A | 64 | P | 23 | P | -0.12 | 0.36 | 15.6 | Yes | Med |
| ORF YNL141W | 200 | A | 42 | A | 523 | P | 136 | P | 0.21 | 0.26 | 4.3 | | Good |
| ORF YNL179C | 53 | A | 23 | A | 23 | P | 9 | A | 0.44 | 0.41 | 2.4 | | Good |
| ORF YNL190W | 2189 | P | 454 | P | 2259 | P | 939 | P | 0.21 | 0.42 | 3.6 | | Excl |
| ORF YNL194C | 11 | A | -50 | A | 13 | A | 1 | A | -4.75 | 0.05 | 15.9 | Yes | Med |
| ORF YNL203C | 32 | A | -35 | A | 21 | P | -6 | A | -1.10 | -0.29 | 9.3 | Yes | Med |
| ORF YNL279W | 184 | A | 46 | A | 35 | P | 16 | A | 0.25 | 0.46 | 3.1 | | Good |
| ORF YNL318C | 184 | A | 8 | A | -7 | A | -17 | A | 0.04 | 2.64 | 13.0 | Yes | Med |
| ORF YNL323W | 237 | P | -46 | A | 187 | P | 70 | P | -0.19 | 0.37 | 29.6 | Yes | Med |
| ORF YNL327W | 3221 | P | 1019 | P | 2164 | P | 811 | P | 0.32 | 0.37 | 2.9 | | Excl |
| ORF YNL333W (_f) | 58 | A | -54 | A | 95 | P | 23 | P | -0.93 | 0.25 | 13.2 | Yes | Med |
| ORF YNL334C (_f) | 53 | A | -31 | A | 26 | P | -5 | A | -0.58 | -0.18 | 11.4 | Yes | Med |
| ORF YNR004W | -37 | A | -69 | A | 23 | P | 5 | A | 1.88 | 0.23 | 5.4 | Yes | Med |
| ORF YNR018W | 2058 | P | 842 | P | 817 | P | 369 | P | 0.41 | 0.45 | 2.3 | | Excl |
| ORF YNR048W | 195 | P | 85 | A | 110 | P | 46 | P | 0.43 | 0.42 | 2.3 | | Good |
| ORF YNR053C exon | 568 | P | 181 | P | 629 | P | 254 | P | 0.32 | 0.40 | 2.8 | | Excl |

Figure 3O

| ORF YNR062C | 163 | A | | 31 | A | | 11 | A | | 1 | A | 0.19 | 0.06 | 10.9 | | Good |
|---|---|---|---|---|---|---|---|---|---|---|---|---|---|---|---|---|
| ORF YNR074C | 32 | A | | -150 | A | | 168 | P | | 64 | P | -4.75 | 0.38 | 19.5 | Yes | Med |
| ORF YOL002C | 379 | P | | 96 | M | | 611 | P | | 282 | P | 0.25 | 0.46 | 3.1 | | Good |
| ORF YOL028C | 84 | A | | -35 | A | | 53 | P | | 26 | P | -0.41 | 0.48 | 12.9 | Yes | Med |
| ORF YOL047C exon | 5 | A | | -88 | A | | 18 | A | | -3 | A | -16.81 | -0.14 | 11.5 | Yes | Med |
| ORF YOL061W | 1305 | P | | 619 | P | | 1153 | P | | 570 | P | 0.47 | 0.49 | 2.1 | | Excl |
| ORF YOL084W | 68 | A | | -50 | A | | 18 | A | | 5 | A | -0.73 | 0.25 | 13.8 | Yes | Med |
| ORF YOL089C | 121 | P | | -46 | A | | 87 | P | | 39 | P | -0.38 | 0.45 | 17.8 | Yes | Med |
| ORF YOL101C | 384 | P | | 58 | A | | 191 | P | | 64 | P | 0.15 | 0.33 | 4.8 | | Good |
| ORF YOL105C | 121 | A | | -42 | A | | 88 | P | | 38 | P | -0.35 | 0.43 | 17.5 | Yes | Med |
| ORF YOL109W | 15974 | P | | 7131 | P | | 6496 | P | | 3190 | P | 0.45 | 0.49 | 2.1 | | Excl |
| ORF YOL128C | 111 | A | | -58 | A | | 87 | P | | 23 | P | -0.52 | 0.27 | 18.7 | Yes | Med |
| ORF YOL138C | 95 | A | | -8 | A | | 68 | P | | 8 | A | -0.08 | 0.12 | 14.6 | Yes | Med |
| ORF YOL158C | 274 | P | | 115 | A | | 364 | P | | 140 | P | 0.42 | 0.38 | 2.5 | | Good |
| ORF YOL161C (_f) | 211 | A | | 27 | A | | 105 | P | | 34 | A | 0.13 | 0.33 | 5.4 | | Good |
| ORF YOL162W | 126 | A | | 4 | A | | 30 | P | | -5 | A | 0.03 | -0.17 | 20.0 | Yes | Med |
| ORF YOL164W | 184 | A | | -188 | A | | 58 | P | | 11 | A | -1.02 | 0.20 | 39.8 | Yes | Med |
| ORF YOR001W | 774 | P | | 212 | A | | 346 | P | | 167 | P | 0.27 | 0.48 | 2.9 | | Good |
| ORF YOR009W | 626 | A | | 265 | A | | 353 | P | | 133 | A | 0.42 | 0.38 | 2.5 | | Good |
| ORF YOR032C | 21 | A | | -23 | A | | 11 | A | | 0 | A | -1.10 | 0.00 | 5.5 | Yes | Med |
| ORF YOR050C | -63 | A | | -100 | A | | 2 | A | | -15 | A | 1.58 | -6.70 | 5.4 | Yes | Med |
| ORF YOR060C | 111 | A | | 31 | A | | 67 | P | | 29 | P | 0.28 | 0.43 | 3.0 | | Good |
| ORF YOR066W | 695 | P | | 131 | A | | 110 | P | | 47 | P | 0.19 | 0.43 | 3.8 | | Good |
| ORF YOR071C | 47 | A | | -69 | A | | 87 | P | | 25 | P | -1.46 | 0.28 | 13.4 | Yes | Med |
| ORF YOR083W | 16 | A | | -46 | A | | 22 | P | | -7 | A | -2.92 | -0.30 | 9.0 | Yes | Med |
| ORF YOR084W | 274 | A | | -81 | A | | 132 | P | | 56 | P | -0.30 | 0.42 | 36.6 | Yes | Med |
| ORF YOR095C | 442 | P | | 154 | P | | 610 | P | | 207 | P | 0.35 | 0.34 | 2.9 | | Excl |

Figure 3P

| ORF YOR107W | 0 | A | -112 | A | 62 | P | 23 | A | #DIV/0! | 0.37 | 12.5 | Yes | Med |
|---|---|---|---|---|---|---|---|---|---|---|---|---|---|
| ORF YOR111W | 68 | A | -92 | A | 91 | P | 43 | P | -1.35 | 0.47 | 17.1 | Yes | Med |
| ORF YOR178C | 74 | A | -15 | A | 24 | P | 5 | A | -0.21 | 0.22 | 11.2 | Yes | Med |
| ORF YOR239W | 505 | P | 127 | P | 174 | P | 74 | P | 0.25 | 0.43 | 3.2 | | Excl |
| ORF YOR264W | 195 | A | -42 | A | 147 | P | 72 | P | -0.22 | 0.49 | 24.7 | Yes | Med |
| ORF YOR301W | 47 | A | -23 | A | 125 | P | 52 | P | -0.49 | 0.41 | 8.3 | Yes | Med |
| ORF YOR315W | 400 | P | 65 | A | 195 | P | 69 | P | 0.16 | 0.35 | 4.5 | | Good |
| ORF YOR342C | 368 | P | 73 | A | 449 | P | 172 | P | 0.20 | 0.38 | 3.8 | | Good |
| ORF YOR365C | 732 | A | 4 | A | 8 | A | -13 | A | 0.01 | -1.65 | 97.1 | Yes | Med |
| ORF YOR376W | 521 | P | -46 | A | -15 | A | -30 | A | -0.09 | 1.96 | 58.2 | Yes | Med |
| ORF YOR378W | 889 | P | 4 | A | 7 | A | -7 | A | 0.00 | -1.12 | 117.0 | Yes | Med |
| ORF YOR389W | 453 | A | 15 | A | 50 | P | 23 | P | 0.03 | 0.46 | 15.8 | | Good |
| ORF YOR392W (_f) | 26 | A | 4 | A | 10 | A | -3 | A | 0.15 | -0.34 | 4.7 | Yes | Med |
| ORF YPL032C | 647 | P | 104 | A | 405 | P | 143 | P | 0.16 | 0.35 | 4.5 | | Good |
| ORF YPL049C | 305 | P | 0 | A | 318 | P | 116 | P | 0.00 | 0.36 | 31.9 | Yes | Med |
| ORF YPL067C | 121 | A | -96 | A | 491 | P | -1 | A | -0.79 | -0.01 | 26.7 | Yes | Med |
| ORF YPL068C | 274 | A | -27 | A | 80 | P | 23 | P | -0.10 | 0.28 | 31.8 | Yes | Med |
| ORF YPL076W | -16 | A | -27 | A | 48 | P | 23 | A | 1.71 | 0.48 | 2.1 | Yes | Med |
| ORF YPL077C | 147 | A | -19 | A | 32 | P | 7 | M | -0.13 | 0.23 | 18.8 | Yes | Med |
| ORF YPL133C | -11 | A | -23 | A | 51 | P | 24 | M | 2.19 | 0.47 | 2.3 | Yes | Med |
| ORF YPL141C | 205 | A | -38 | A | 125 | P | 32 | P | -0.19 | 0.25 | 26.3 | Yes | Med |
| ORF YPL194W | -68 | A | -119 | A | 30 | M | 9 | A | 1.74 | 0.28 | 6.8 | Yes | Med |
| ORF YPL205C | 100 | A | -46 | A | -2 | A | -15 | A | -0.46 | 6.70 | 15.9 | Yes | Med |
| ORF YPL222W | -16 | A | -88 | A | 17 | P | 7 | A | 5.60 | 0.38 | 8.6 | Yes | Med |
| ORF YPL247C | 342 | P | 131 | P | 55 | P | 21 | P | 0.38 | 0.38 | 2.6 | | Excl |
| ORF YPL276W (_f) | 16 | A | -69 | A | -1 | A | -23 | A | -4.38 | 21.32 | 10.7 | Yes | Med |
| ORF YPL283C exon | 1142 | P | -54 | A | 1205 | P | 569 | P | -0.05 | 0.47 | 120.7 | Yes | Med |
| ORF YPR008W | 237 | P | 100 | A | 260 | P | 70 | P | 0.42 | 0.27 | 3.1 | | Good |
| ORF YPR010C | 1658 | P | 796 | P | 1568 | P | 759 | P | 0.48 | 0.48 | 2.1 | | Excl |
| ORF YPR016C | 1189 | P | 331 | P | 1220 | P | 586 | P | 0.28 | 0.48 | 2.8 | | Excl |
| ORF YPR039W | 53 | A | -35 | A | 12 | A | -6 | A | -0.66 | -0.50 | 10.5 | Yes | Med |
| ORF YPR053C | 626 | P | 104 | A | 362 | P | 176 | P | 0.17 | 0.49 | 4.0 | | Good |
| ORF YPR074C | 1042 | P | 273 | P | 2709 | P | 1266 | P | 0.26 | 0.47 | 3.0 | | Excl |
| ORF YPR106W | 37 | A | -15 | A | 123 | P | 18 | P | -0.42 | 0.15 | 8.7 | Yes | Med |
| ORF YPR115W | 89 | A | 0 | A | 279 | P | 132 | P | 0.00 | 0.47 | 10.0 | Yes | Med |
| ORF YPR195C | -226 | A | -358 | A | 9 | A | -2 | A | 1.58 | -0.23 | 14.2 | Yes | Med |
| ORF YPR199C | -105 | A | -200 | A | 135 | P | 30 | P | 1.90 | 0.23 | 11.7 | Yes | Med |
| ORF YPR200C | -21 | A | -338 | A | 10 | A | -4 | A | 16.08 | -0.41 | 33.1 | Yes | Med |

Figure 3Q

| ORF YPR202W exon | 5 | A | -177 | A | 48 | P | 7 | A | -33.62 | 0.14 | 21.8 | Yes | Med |
|---|---|---|---|---|---|---|---|---|---|---|---|---|---|
| OSH1 (YAR044W) | 97 | A | 41 | A | 116 | P | 23 | P | 0.42 | 0.19 | 3.8 | | Good |
| PAB1 (YER165W) | 979 | P | 439 | P | 1408 | P | 524 | P | 0.45 | 0.37 | 2.5 | | Excl |
| PAC11 (YDR488C) | 60 | A | 28 | A | 48 | P | 10 | A | 0.46 | 0.22 | 3.4 | | Good |
| PAD1 (YDR538W) | 40 | A | 20 | A | 150 | P | 30 | A | 0.50 | 0.20 | 3.5 | | Good |
| PAN1 (YIR006C) | 466 | P | 174 | P | 566 | P | 219 | P | 0.37 | 0.39 | 2.6 | | Excl |
| PCT1 (YGR202C) | 81 | P | 33 | A | 86 | P | 30 | P | 0.40 | 0.35 | 2.7 | | Good |
| PDR5 (YOR153W) | 1116 | P | 450 | P | 2632 | P | 1271 | P | 0.40 | 0.48 | 2.3 | | Excl |
| PES4 (YFR023W) | 30 | A | -23 | A | 23 | A | -14 | A | -0.75 | -0.58 | 9.0 | Yes | Med |
| PET112 (YBL080C) | 54 | A | 22 | A | 39 | P | 6 | A | 0.41 | 0.16 | 4.4 | | Good |
| PET309 (YLR067C) | 0 | A | -11 | A | 53 | P | 23 | A | #DIV/0! | 0.43 | 2.2 | Yes | Med |
| PFK1 (YGR240C) | 1579 | P | 613 | P | 2342 | P | 626 | P | 0.39 | 0.27 | 3.2 | | Excl |
| PFK2 (YMR205C) | 1487 | P | 656 | P | 1692 | P | 549 | P | 0.44 | 0.32 | 2.7 | | Excl |
| PHO12 (YHR215W) | 100 | P | 24 | A | 111 | P | 44 | P | 0.24 | 0.39 | 3.4 | | Good |
| PHO3 (YBR092C) | 695 | P | 277 | P | 1080 | P | 309 | P | 0.40 | 0.29 | 3.0 | | Excl |
| PHO84 (YML123C) | 234 | P | 70 | A | 449 | P | 60 | M | 0.30 | 0.13 | 5.4 | | Good |
| PIG1 (YLR273C) | 92 | A | 9 | A | 56 | P | 25 | A | 0.10 | 0.44 | 6.4 | | Good |
| PKC1 (YBL105C) | 121 | P | 7 | A | 120 | P | 26 | A | 0.06 | 0.22 | 10.9 | | Good |
| PMP1 (YCR024C-A) | 1852 | P | 850 | P | 3860 | P | 1263 | P | 0.46 | 0.33 | 2.6 | | Excl |
| PMP2 (YEL017C-A) | 860 | P | 364 | P | 2225 | P | 807 | P | 0.42 | 0.36 | 2.6 | | Excl |
| POL12 (YBL035C) | 105 | A | 29 | A | 172 | P | 82 | P | 0.28 | 0.48 | 2.9 | | Good |
| POL30 (YBR088C) | 929 | P | 463 | P | 1014 | P | 430 | P | 0.50 | 0.42 | 2.2 | | Good |
| PPH3 (YDR075W) | 144 | P | 70 | P | 124 | P | 27 | A | 0.48 | 0.22 | 3.3 | | Good |
| PPT1 (YGR123C) | 153 | P | 46 | P | 196 | P | 69 | P | 0.30 | 0.35 | 3.1 | | Excl |
| PPZ2 (YDR436W) | 130 | A | 50 | M | 66 | P | 30 | P | 0.38 | 0.45 | 2.4 | | Good |
| PRK1 (YIL095W) | 74 | P | 35 | P | 84 | P | 20 | P | 0.47 | 0.24 | 3.1 | | Excl |
| PRP19 (YLL036C) | 266 | P | 72 | A | 211 | P | 95 | P | 0.27 | 0.45 | 3.0 | | Good |
| PRP31 (YGR091W) | 26 | P | 13 | A | 40 | P | 5 | A | 0.49 | 0.13 | 4.8 | | Good |
| PRY1 (YJL079C) | 411 | P | 115 | P | 419 | P | 126 | P | 0.28 | 0.30 | 3.5 | | Excl |
| PRY2 (YKR013W) | 1361 | P | 665 | P | 724 | P | 299 | P | 0.49 | 0.41 | 2.2 | | Excl |

Figure 3R

| | 1651 | P | 729 | P | 2501 | P | 1195 | P | | | | | |
|---|---|---|---|---|---|---|---|---|---|---|---|---|---|
| PSA1 (YDL055C) | 1651 | P | 729 | P | 2501 | P | 1195 | P | 0.44 | 0.48 | 2.2 | | Excl |
| PSP1 (YDR505C) | 87 | A | 22 | A | 160 | P | 31 | P | 0.25 | 0.20 | 4.5 | | Good |
| PSP2 (YML017W) | 100 | A | -4 | A | 33 | P | 16 | A | -0.04 | 0.49 | 11.4 | Yes | Med |
| PUR5 (YHR216W) | 121 | P | 2 | A | 174 | P | 42 | P | 0.02 | 0.24 | 32.6 | | Good |
| PWP2 (YCR058C) | 65 | A | 28 | A | 138 | P | 37 | P | 0.43 | 0.27 | 3.0 | | Good |
| PYC2 (YBR218C) | 359 | P | 164 | P | 633 | P | 162 | P | 0.46 | 0.26 | 3.1 | | Excl |
| QRI7 (YDL104C) | 54 | P | 12 | A | 46 | P | 21 | P | 0.22 | 0.45 | 3.4 | | Good |
| RAD7 (YJR052W) | 55 | A | 23 | A | 97 | P | 25 | A | 0.41 | 0.26 | 3.2 | | Good |
| RAS1 (YOR101W) | 195 | A | -15 | A | 228 | P | 93 | P | -0.08 | 0.41 | 22.2 | Yes | Med |
| REV7 (YIL139C) | 42 | A | -7 | A | 38 | P | 18 | P | -0.17 | 0.47 | 5.9 | Yes | Med |
| RFT1 (YBL020W) | 195 | P | 66 | A | 203 | P | 100 | P | 0.34 | 0.49 | 2.5 | | Good |
| RIB1 (YBL033C) | 217 | A | 97 | P | 293 | P | 90 | P | 0.44 | 0.31 | 2.8 | | Good |
| RIB7 (YBR153W) | 141 | P | 47 | M | 175 | P | 81 | P | 0.33 | 0.46 | 2.6 | | Good |
| RME1 (YGR044C) | 511 | P | 166 | P | 379 | P | 134 | P | 0.33 | 0.35 | 3.0 | | Excl |
| RNR1 (YER070W) | 479 | P | 223 | P | 396 | P | 172 | P | 0.46 | 0.43 | 2.2 | | Excl |
| ROK1 (YGL171W) | 257 | P | 111 | P | 323 | P | 155 | P | 0.43 | 0.48 | 2.2 | | Excl |
| RPL27B (YDR471W) | 3563 | P | 1586 | P | 3773 | P | 1363 | P | 0.45 | 0.36 | 2.5 | | Excl |
| RPL4A (YHL033C) | 1543 | P | 696 | P | 4133 | P | 1747 | P | 0.45 | 0.42 | 2.3 | | Excl |
| RPL9A (YGL147C) | 4547 | P | 2234 | P | 5268 | P | 2632 | P | 0.49 | 0.50 | 2.0 | | Excl |
| RRN6 (YBL014C) | 98 | P | 40 | A | 137 | P | 26 | A | 0.40 | 0.19 | 3.9 | | Good |
| SAC2 (YDR484W) | 25 | A | 6 | A | 55 | P | 27 | P | 0.23 | 0.49 | 3.2 | | Good |
| SAH1 (YER043C) | 2628 | P | 1007 | P | 2566 | P | 1037 | P | 0.38 | 0.40 | 2.5 | | Excl |
| SAM1 (YLR180W) | 1200 | P | 321 | P | 1015 | P | 314 | P | 0.27 | 0.31 | 3.5 | | Excl |
| SCA1 (YDR443C) | 32 | A | 14 | A | 55 | P | 11 | A | 0.44 | 0.21 | 3.6 | | Good |
| SCO1 (YBR037C) | 21 | A | 7 | A | 78 | P | 22 | M | 0.34 | 0.28 | 3.3 | | Good |
| SDC25 (YLL016W) | 74 | P | 4 | A | 26 | P | -12 | A | 0.05 | -0.46 | 14.3 | Yes | Med |
| SEO1 (YAL067C) | 11 | A | -2 | A | 11 | P | 1 | A | -0.21 | 0.08 | 7.7 | Yes | Med |
| SFP1 (YLR403W) | 166 | A | 74 | A | 284 | P | 69 | P | 0.44 | 0.24 | 3.2 | | Good |
| SHM2 (YLR058C) | 3216 | P | 1307 | P | 3024 | P | 1101 | P | 0.41 | 0.36 | 2.6 | | Excl |
| SIS2 (YKR072C) | 203 | P | 100 | A | 2331 | P | 112 | P | 0.49 | 0.48 | 2.1 | | Excl |
| SKN1 (YGR143W) | 208 | P | 101 | P | 332 | P | 83 | P | 0.49 | 0.25 | 3.0 | | Excl |
| SKN7 (YHR206W) | 247 | P | 100 | P | 314 | P | 95 | P | 0.40 | 0.30 | 2.9 | | Excl |
| SMK1 (YPR054W) | 153 | A | 54 | A | 7 | A | -5 | A | 0.35 | -0.71 | 2.5 | Yes | Med |
| SMY1 (YKL079W) | 155 | P | 54 | A | 76 | P | 30 | P | 0.35 | 0.39 | 2.7 | | Good |
| SMY2 (YBR172C) | 143 | P | 48 | P | 265 | P | 80 | P | 0.33 | 0.30 | 3.2 | | Excl |
| SNM1 (YDR478W) | 49 | A | 9 | A | 150 | P | 27 | P | 0.19 | 0.18 | 5.4 | | Good |
| SNP1 (YIL061C) | 30 | A | 10 | A | 62 | P | 29 | P | 0.33 | 0.48 | 2.6 | | Excl |
| SPA2 (YLL021W) | 134 | A | 61 | A | 225 | P | 110 | P | 0.46 | 0.49 | 2.1 | | Good |
| SPE2 (YOL052C) | 237 | A | 85 | A | 232 | P | 91 | P | 0.36 | 0.39 | 2.7 | | Good |

Figure 3S

| | | | | | | | | |
|---|---|---|---|---|---|---|---|---|
| SPO1 (YNL012W) | 74 | A | -112 | A | 17 | A | 6 | A | -1.51 | 0.34 | 20.0 | Yes | Med |
| SPT8 (YLR055C) | 34 | A | -7 | A | 112 | P | 54 | P | -0.21 | 0.48 | 5.2 | Yes | Med |
| SRA3 (YJL164C) | 129 | A | 60 | A | 129 | P | 46 | A | 0.46 | 0.36 | 2.5 | | Good |
| SRB5 (YGR104C) | 60 | P | -3 | A | 67 | P | 5 | A | -0.05 | 0.08 | 12.7 | Yes | Med |
| SRD1 (YCR018C) | 68 | A | 15 | A | 60 | P | 7 | A | 0.22 | 0.12 | 6.6 | | Good |
| SRN2 (YLR119W) | 224 | P | 68 | A | 93 | P | 41 | M | 0.31 | 0.44 | 2.8 | | Good |
| SSB1 (YDL229W) | 12479 | P | 5100 | P | 9147 | P | 3757 | P | 0.41 | 0.41 | 2.4 | | Excl |
| SSN3 (YPL042C) | 247 | A | 54 | M | 85 | P | 40 | M | 0.22 | 0.48 | 3.3 | | Good |
| SST2 (YLR452C) | 279 | P | 46 | A | 211 | P | 14 | M | 0.16 | 0.07 | 10.6 | | Good |
| STB1 (YNL309W) | -58 | A | -169 | A | 35 | P | 9 | A | 2.92 | 0.27 | 13.0 | Yes | Med |
| STD1 (YOR047C) | 253 | A | 119 | A | 364 | P | 170 | P | 0.47 | 0.47 | 2.1 | | Good |
| STE12 (YHR084W) | 175 | P | 37 | P | 147 | P | 38 | M | 0.21 | 0.26 | 4.3 | | Good |
| STE13 (YOR219C) | 53 | A | -50 | A | 107 | P | 52 | P | -0.95 | 0.49 | 11.3 | Yes | Med |
| STE2 (YFL026W) | 872 | P | 84 | P | 1273 | P | 94 | P | 0.10 | 0.07 | 11.9 | | Excl |
| STE4 (YOR212W) | 342 | A | 131 | A | 648 | P | 270 | P | 0.38 | 0.42 | 2.5 | | Good |
| STE6 (YKL209C) | 574 | P | 116 | P | 690 | P | 105 | P | 0.20 | 0.15 | 5.7 | | Excl |
| STP4 (YDL048C) | 240 | P | 3 | A | 319 | P | 19 | A | 0.01 | 0.06 | 42.7 | | Good |
| STT4 (YLR305C) | 203 | P | 95 | A | 202 | P | 61 | P | 0.47 | 0.30 | 2.7 | | Good |
| STU2 (YLR045C) | 203 | P | 65 | A | 74 | P | 25 | P | 0.32 | 0.33 | 3.1 | | Good |
| SUC2 (YIL162W) | 87 | P | 35 | P | 103 | P | 32 | P | 0.40 | 0.31 | 2.9 | | Excl |
| SUR1 (YPL057C) | 32 | A | 15 | A | 188 | P | 53 | P | 0.49 | 0.28 | 2.8 | | Good |
| SWH1 (YAR042W) | 106 | A | 12 | A | 91 | P | 20 | A | 0.11 | 0.22 | 6.8 | | Good |
| SWI1 (YPL016W) | 121 | A | -15 | A | 107 | P | 48 | P | -0.13 | 0.45 | 14.7 | Yes | Med |
| SYG1 (YIL047C) | 574 | P | 259 | P | 640 | P | 289 | P | 0.45 | 0.45 | 2.2 | | Excl |
| TAL1 (YLR354C) | 1282 | P | 316 | P | 1122 | P | 354 | P | 0.25 | 0.32 | 3.6 | | Excl |
| TEC1 (YBR083W) | 263 | P | 71 | P | 227 | P | 26 | P | 0.27 | 0.11 | 6.2 | | Excl |
| TEF4 (YKL081W) ex | 416 | P | 179 | P | 741 | P | 261 | P | 0.43 | 0.35 | 2.6 | | Excl |
| THI6 (YPL214C) | 232 | P | -31 | A | 160 | P | 75 | P | -0.13 | 0.47 | 27.3 | Yes | Med |
| TIF4631 (YGR162W) | 570 | P | 237 | P | 896 | P | 302 | P | 0.42 | 0.34 | 2.7 | | Excl |

Figure 3T

| | | | | | | | |
|---|---|---|---|---|---|---|---|
| TIR1 (YER011W) | 1362 P | 458 P | 2171 P | 952 P | 0.34 | 0.44 | 2.6 | Excl |
| TOM70 (YNL121C) | 342 P | 92 A | 474 P | 231 P | 0.27 | 0.49 | 2.9 | Good |
| TOP3 (YLR234W) | 63 A | -25 A | 23 P | 4 A | -0.39 | 0.19 | 11.4 Yes | Med |
| TSL1 (YML100W) | 200 P | 18 A | 322 P | 39 P | 0.09 | 0.12 | 9.9 | Good |
| TUP1 (YCR084C) | 486 P | 183 P | 555 P | 224 P | 0.38 | 0.40 | 2.6 | Excl |
| UBP9 (YER098W) | 42 A | 13 A | 21 A | 6 A | 0.31 | 0.29 | 3.3 | Good |
| URA1 (YKL216W) | 2329 P | 361 P | 2930 P | 567 P | 0.16 | 0.19 | 5.8 | Excl |
| URA4 (YLR420W) | 1026 P | 328 P | 640 P | 245 P | 0.32 | 0.38 | 2.9 | Good |
| YAP3 (YLR120C) | 289 P | 111 A | 274 P | 94 P | 0.38 | 0.34 | 2.8 | Good |
| YCK2 (YNL154C) | 1158 P | 508 P | 464 P | 218 P | 0.44 | 0.47 | 2.2 | Excl |
| YCLX07w/_f (contrc | 25 A | -17 A | 36 P | 1 A | -0.69 | 0.02 | 25.0 Yes | Med |
| YCLX12w/_f (contrc | 33 A | 10 A | 97 P | 27 A | 0.31 | 0.28 | 3.4 | Good |
| YCRX02c/_r (control | 105 A | 28 A | 72 P | -10 A | 0.27 | -0.14 | 10.1 Yes | Med |
| YCRX07w/ (control? | 73 A | 30 A | 85 P | 31 P | 0.41 | 0.37 | 2.6 | Good |
| YFL-TyA/_f (control) | 98 P | 20 A | 208 P | 44 P | 0.20 | 0.21 | 4.8 | Good |
| YGP1 (YNL160W) | 1568 P | 669 P | 2260 P | 945 P | 0.43 | 0.42 | 2.4 | Excl |
| YLF2 (YHL014C) | 64 A | 6 A | 55 P | 23 P | 0.09 | 0.43 | 6.6 | Good |
| YRO2 (YBR054W) | 278 P | 57 P | 642 P | 123 P | 0.21 | 0.19 | 5.1 | Med |
| YSW1 (YBR148W) | 30 A | -9 A | 15 P | -2 A | -0.31 | -0.12 | 5.6 Yes | Med |
| ZDS1 (YMR273C) | 226 A | 96 A | 82 P | 22 A | 0.42 | 0.27 | 3.0 | Good |
| ZRT1 (YGL255W) | 115 P | 47 P | 392 P | 150 P | 0.40 | 0.38 | 2.5 | Excl |

Figure 3U

Srb5 Down

| Gene | SRB WT#1 | WT#SRB5#1 | SRI SRB WT#2 | WT#:SRB5#2 | SRB=MT1/WT1 | MT2/WT2 | Average Fold Down | Corrected? | Confidence |
|---|---|---|---|---|---|---|---|---|---|
| ORF YPL283C exon | 1142 P | -54 A | 1205 P | 569 P | -0.05 | 0.47 | 120.7 | Yes | Med |
| ORF YOR378W | 889 P | 4 A | 7 A | -7 A | 0.00 | -1.12 | 117.0 | Yes | Med |
| ORF YBL112C (_f) | 456 P | 2 A | 569 P | 138 P | 0.01 | 0.24 | 100.0 | | Good |
| ORF YOR365C | 732 A | 4 A | 8 A | -13 A | 0.01 | -1.65 | 97.1 | Yes | Med |
| ORF YOR376W | 521 P | -46 A | -15 A | -30 A | -0.09 | 1.96 | 58.2 | Yes | Med |
| MFA1 (YDR461W) | 2290 P | 231 A | 1719 P | 104 P | 0.01 | 0.06 | 57.5 | | Good |
| CHA1 (YCL064C) | 763 P | 13 A | 910 P | 31 P | 0.02 | 0.03 | 44.4 | | Good |
| STP4 (YDL048C) | 240 P | 3 A | 319 P | 19 A | 0.01 | 0.06 | 42.7 | | Good |
| ORF YLR169W | 145 A | 2 A | -3 A | -17 A | 0.01 | 5.56 | 42.7 | Yes | Med |
| MDH2 (YOL126C) | 395 P | 0 A | 557 P | 127 P | 0.00 | 0.23 | 41.7 | Yes | Med |
| ORF YOL164W | 184 A | -188 A | 58 P | 11 A | -1.02 | 0.20 | 39.8 | Yes | Med |
| ORF YOR084W | 274 A | -81 A | 132 P | 56 P | -0.30 | 0.42 | 36.6 | Yes | Med |
| ORF YPR200C | -21 A | -338 A | 10 A | -4 A | 16.08 | -0.41 | 33.1 | Yes | Med |
| PUR5 (YHR216W) | 121 P | 2 A | 174 P | 42 P | 0.02 | 0.24 | 32.6 | | Good |
| ORF YPL049C | 305 P | 0 A | 318 P | 116 P | 0.00 | 0.36 | 31.9 | Yes | Med |
| ORF YPL068C | 274 A | -27 A | 80 P | 23 P | -0.10 | 0.28 | 31.8 | Yes | Med |
| ORF YNL323W | 237 P | -46 A | 187 P | 70 P | -0.19 | 0.37 | 29.6 | Yes | Med |
| THI6 (YPL214C) | 232 P | -31 A | 160 P | 75 P | -0.13 | 0.47 | 27.3 | Yes | Med |
| ORF YPL067C | 121 A | -96 A | 49 P | -1 A | -0.79 | -0.01 | 26.7 | Yes | Med |
| ORF YPL141C | 205 A | -38 A | 125 P | 32 P | -0.19 | 0.25 | 26.3 | Yes | Med |
| YCLX07w_f (contro | 25 A | -17 A | 36 P | 1 A | -0.69 | 0.02 | 25.0 | Yes | Med |
| ORF YOR264W | 195 A | -42 A | 147 P | 72 P | -0.22 | 0.49 | 24.7 | Yes | Med |
| ORF YDL248W (_r) | 37 M | -9 A | 32 P | 1 A | -0.25 | 0.03 | 23.0 | Yes | Med |
| RAS1 (YOR101W) | 195 A | -15 A | 228 P | 93 P | -0.08 | 0.41 | 22.2 | Yes | Med |
| ORF YPR202W exon | 5 A | -177 A | 48 P | 7 A | -33.62 | 0.14 | 21.8 | Yes | Med |
| ORF YBL111C exon | 222 P | 6 A | 333 P | 62 P | 0.03 | 0.19 | 21.8 | | Good |
| ORF YHR218W exon | 258 P | 7 A | 322 P | 55 P | 0.03 | 0.17 | 21.6 | | Good |
| ORF YDL119C | 100 P | -8 A | 92 P | 4 A | -0.08 | 0.05 | 21.4 | Yes | Med |
| ORF YOL162W | 126 A | 4 A | 30 P | -5 A | 0.03 | -0.17 | 20.0 | Yes | Med |
| SPO1 (YNL012W) | 74 A | -112 A | 17 A | 6 A | -1.51 | 0.34 | 20.0 | Yes | Med |
| ORF YNR074C | 321 A | -150 A | 168 P | 64 P | -4.75 | 0.38 | 19.5 | Yes | Med |
| DAL82 (YNL314W) | 268 A | 8 A | 39 P | 14 A | 0.03 | 0.36 | 18.9 | | Good |
| ORF YPL077C | 147 A | -19 A | 32 P | 7 M | -0.13 | 0.23 | 18.8 | Yes | Med |
| ORF YOL128C | 111 A | -58 A | 87 P | 23 P | -0.52 | 0.27 | 18.7 | Yes | Med |
| ASP3 (YLR160C) (_ | 158 A | -11 A | 99 P | 44 A | -0.07 | 0.45 | 18.0 | Yes | Med |

Figure 4A

| ORF | | | | | | | | |
|---|---|---|---|---|---|---|---|---|
| ORF YOL089C | 121 | P | -46 | A | 87 | P | 39 | P | -0.38 | 0.45 | 17.8 | Yes | Med |
| ORF YOL105C | 121 | A | -42 | A | 88 | P | 38 | P | -0.35 | 0.43 | 17.5 | Yes | Med |
| ORF YLL057C | 55 | A | -32 | A | 19 | P | 1 | A | -0.57 | 0.06 | 17.3 | Yes | Med |
| ORF YOR111W | 68 | A | -92 | A | 91 | P | 43 | P | -1.35 | 0.47 | 17.1 | Yes | Med |
| ORF YLR328W | 103 | A | 4 | A | 177 | P | 35 | P | 0.03 | 0.20 | 17.1 | | Good |
| ORF YDR359C | 130 | A | -17 | A | 43 | P | 12 | A | -0.13 | 0.28 | 16.5 | Yes | Med |
| ORF YNL024C | 142 | A | -8 | A | 152 | P | 54 | P | -0.05 | 0.36 | 16.4 | Yes | Med |
| ORF YKL005C | 118 | A | -30 | A | 82 | P | 33 | P | -0.25 | 0.40 | 16.1 | Yes | Med |
| ORF YNL194C | 11 | A | -50 | A | 13 | A | 1 | A | -4.75 | 0.05 | 15.9 | Yes | Med |
| ORF YPL205C | 100 | A | -46 | A | -2 | A | -15 | A | -0.46 | 6.70 | 15.9 | Yes | Good |
| ORF YOR389W | 453 | A | 15 | A | 50 | P | 23 | P | 0.03 | 0.46 | 15.8 | | Med |
| MEK1 (YOR351C) | 132 | A | -8 | A | 14 | A | 4 | A | -0.06 | 0.28 | 15.7 | Yes | Med |
| ORF YNL127W | 126 | A | -15 | A | 64 | P | 23 | P | -0.12 | 0.36 | 15.6 | Yes | Med |
| SWI1 (YPL016W) | 121 | A | -15 | A | 107 | P | 48 | P | -0.13 | 0.45 | 14.7 | Yes | Med |
| ORF YOL138C | 95 | A | -8 | A | 68 | P | 8 | A | -0.08 | 0.12 | 14.6 | Yes | Med |
| SDC25 (YLL016W) | 74 | P | 4 | A | 26 | P | -12 | A | 0.05 | -0.46 | 14.3 | Yes | Med |
| ORF YMR173W | 34 | A | -86 | A | 115 | P | 26 | A | -2.51 | 0.22 | 14.3 | Yes | Med |
| ORF YFR032C | 89 | P | -13 | A | 25 | A | 3 | A | -0.15 | 0.12 | 14.3 | Yes | Med |
| ORF YPR195C | -226 | A | -358 | A | 9 | A | -2 | A | 1.58 | -0.23 | 14.2 | Yes | Med |
| ORF YFL059W (_f) | 115 | P | -3 | A | 63 | P | 14 | A | -0.03 | 0.21 | 14.1 | Yes | Med |
| ORF YNL122C | 121 | A | -8 | A | 143 | P | 72 | P | -0.06 | 0.50 | 13.9 | Yes | Med |
| ORF YOL084W | 68 | A | -50 | A | 18 | A | 5 | A | -0.73 | 0.25 | 13.8 | Yes | Med |
| ORF YCR007C | 62 | A | 3 | A | 17 | P | 2 | A | 0.06 | 0.10 | 13.8 | | Good |
| ORF YBL019W | 78 | A | -45 | A | 49 | P | 18 | M | -0.58 | 0.37 | 13.7 | Yes | Med |
| ORF YGL138C | 98 | P | -10 | A | 25 | A | -3 | A | -0.10 | -0.12 | 13.6 | Yes | Med |
| ORF YER188W | 100 | P | -8 | A | 21 | P | 4 | A | -0.08 | 0.18 | 13.5 | Yes | Med |
| ORF YOR071C | 47 | A | -69 | A | 87 | P | 25 | P | -1.46 | 0.28 | 13.4 | Yes | Med |
| FCY22 (YER060W-A | 98 | P | -16 | A | 81 | P | 22 | P | -0.16 | 0.27 | 13.2 | Yes | Med |
| ORF YNL333W (_f) | 58 | A | -54 | A | 95 | P | 23 | P | -0.93 | 0.25 | 13.2 | Yes | Med |
| ORF YMR068W | 55 | A | -26 | A | 31 | P | 18 | A | -0.48 | -0.59 | 13.1 | Yes | Med |

Figure 4B

| | | | | | | | |
|---|---|---|---|---|---|---|---|
| ORF YNL318C | 184 A | 8 A | -7 A | -17 A | 0.04 | 2.64 | 13.0 Yes | Med |
| STB1 (YNL309W) | -58 A | -169 A | 35 P | 9 A | 2.92 | 0.27 | 13.0 Yes | Med |
| ORF YDL248W (_j) | 40 A | 2 A | 37 P | -7 A | 0.06 | -0.19 | 12.9 Yes | Med |
| ORF YOL028C | 84 A | -35 A | 53 P | 26 P | -0.41 | 0.48 | 12.9 Yes | Med |
| ORF YFL066C (_f) | 277 P | 12 A | 234 P | 98 P | 0.04 | 0.42 | 12.9 | Good |
| SRB5 (YGR104C) | 60 P | -3 A | 67 P | 5 A | -0.05 | 0.08 | 12.7 Yes | Med |
| YBR190W | 100 A | -16 A | 36 P | 17 P | -0.16 | 0.48 | 12.7 Yes | Med |
| ORF YOR107W | 0 A | -112 A | 62 P | 23 A | #DIV/0! | 0.37 | 12.5 Yes | Med |
| HCM1 (YCR065W) | 141 A | 121 A | 145 P | 11 A | 0.08 | 0.08 | 12.5 | Good |
| ORF YMR141C | 74 A | -30 A | 31 P | 8 A | -0.40 | 0.24 | 12.4 Yes | Med |
| ORF YBL111C exon | -2 A | -42 A | 71 P | -11 A | 26.37 | -0.16 | 12.3 Yes | Med |
| ORF YMR111C | 158 A | 12 A | 60 P | 5 A | 0.08 | 0.09 | 12.0 | Good |
| STE2 (YFL026W) | 872 P | 84 P | 1273 P | 94 P | 0.10 | 0.07 | 11.9 | Excl |
| ICL1 (YER065C) | 102 A | -3 A | 36 P | 13 P | -0.03 | 0.36 | 11.9 Yes | Med |
| ALD5 (YMR170C) | 32 A | 2 A | 36 P | 6 P | 0.06 | 0.18 | 11.8 | Good |
| ORF YDL038C | 232 P | 70 A | 423 P | 21 P | 0.30 | 0.05 | 11.8 | Good |
| ORF YMR075W | 74 A | 4 A | 53 P | 22 P | 0.05 | 0.41 | 11.7 | |
| ORF YPR199C | -105 A | -200 A | 135 P | 30 P | 1.90 | 0.23 | 11.7 Yes | Med |
| ORF YEL076C-A exc | 60 A | -35 A | 42 M | 10 A | -0.57 | 0.23 | 11.7 Yes | Med |
| ORF YOL047C exon | 5 A | -88 A | 181 A | -3 A | -16.81 | -0.14 | 11.5 Yes | Med |
| ORF YNL334C (_f) | 53 A | -31 A | 26 P | -5 A | -0.58 | -0.18 | 11.4 Yes | Med |
| TOP3 (YLR234W) | 63 A | -25 A | 23 P | 4 A | -0.39 | 0.19 | 11.4 Yes | Med |
| MRE11 (YMR224C) | 79 A | -21 A | 33 P | 12 A | -0.27 | 0.36 | 11.4 Yes | Med |
| MFA2 (YNL145W) | 10468 P | 1100 P | 5137 P | 395 P | 0.11 | 0.08 | 11.3 | Excl |
| ORF YOR178C | 74 A | -15 A | 24 P | 5 A | -0.21 | 0.22 | 11.2 Yes | Med |
| ORF YKL047W | 66 P | -2 A | 73 P | 9 A | -0.03 | 0.12 | 11.0 Yes | Med |
| PKC1 (YBL105C) | 121 P | 7 A | 120 P | 26 A | 0.06 | 0.22 | 10.9 | Good |
| ORF YNR062C | 163 A | 31 A | 11 A | 1 A | 0.19 | 0.06 | 10.9 | Good |
| ORF YPL276W (_f) | 16 A | -69 A | -1 A | -23 A | -4.38 | 21.32 | 10.7 Yes | Med |
| ORF YGR138C | 81 P | -7 A | 163 P | 44 P | -0.09 | 0.27 | 10.7 Yes | Med |
| ORF YMR212C | 87 A | -7 A | 280 P | 111 P | -0.08 | 0.39 | 10.7 Yes | Med |

Figure 4C

| SST2 (YLR452C) | 279 | P | 46 | A | 211 | P | 14 | M | 0.16 | 0.07 | 10.6 | | Good |
|---|---|---|---|---|---|---|---|---|---|---|---|---|---|
| ORF YKL171W | 5 | A | -30 | A | 28 | P | -43 | A | -5.67 | -1.55 | 10.6 | Yes | Med |
| ORF YJR129C | 68 | A | -21 | A | 41 | P | 13 | P | -0.31 | 0.31 | 10.5 | Yes | Med |
| ORF YPR039W | 53 | A | -35 | A | 12 | A | -6 | A | -0.66 | -0.50 | 10.5 | Yes | Med |
| ORF YLR004C | 68 | P | -11 | A | 21 | A | -5 | A | -0.15 | -0.26 | 10.5 | Yes | Med |
| ORF YHR217C (_f) | 74 | A | -10 | A | 140 | A | 38 | A | -0.13 | 0.27 | 10.2 | Yes | Med |
| ORF YDR417C | 40 | A | 2 | A | 17 | A | 5 | A | 0.06 | 0.31 | 10.2 | | Good |
| YCR102c/_r (control) | 105 | A | 28 | A | 72 | P | -10 | A | 0.27 | -0.14 | 10.1 | Yes | Med |
| BAR1 (YIL015W) | 453 | P | 50 | P | 466 | P | 43 | P | 0.11 | 0.09 | 10.0 | | Excl |
| ORF YPR115W | 89 | A | 0 | A | 279 | P | 132 | P | 0.00 | 0.47 | 10.0 | Yes | Med |
| ORF YML040W (_f) | 1505 | P | 135 | M | 1439 | P | 165 | P | 0.09 | 0.11 | 9.9 | | Good |
| ORF YHL028W | 62 | A | -6 | A | 33 | M | 5 | A | -0.10 | 0.16 | 9.9 | Yes | Med |
| ORF YMR016C | 134 | P | 9 | A | 105 | P | 24 | P | 0.07 | 0.22 | 9.9 | | Good |
| TSL1 (YML100W) | 200 | P | 18 | A | 322 | P | 39 | P | 0.09 | 0.12 | 9.9 | | Good |
| HXT9 (YJL219W) | 37 | A | -51 | A | 6 | A | -4 | A | -1.38 | -0.70 | 9.8 | | Med |
| ORF YJR108W | 45 | A | -25 | A | 14 | P | -14 | A | -0.55 | -0.97 | 9.8 | Yes | Med |
| ORF YIL056W | 170 | P | 20 | A | 82 | P | 8 | A | 0.12 | 0.09 | 9.8 | Yes | Good |
| ORF YJR137C | 84 | A | 18 | A | 47 | P | 3 | A | 0.21 | 0.07 | 9.8 | | Good |
| ORF YHR218W exon | 42 | A | -17 | A | 64 | P | 8 | A | -0.41 | 0.13 | 9.7 | Yes | Med |
| ORF YDR501W | 60 | A | -24 | A | 30 | P | 13 | A | -0.40 | 0.43 | 9.6 | Yes | Med |
| ORF YMR176W | 42 | A | -30 | A | 74 | P | 16 | A | -0.71 | 0.22 | 9.5 | Yes | Med |
| ORF YLR080W | 74 | P | -9 | A | 24 | P | 10 | M | -0.12 | 0.41 | 9.5 | Yes | Med |
| ORF YNL042W | 247 | A | 15 | A | 93 | P | 35 | P | 0.06 | 0.38 | 9.4 | | Good |
| ORF YNL203C | 32 | A | -35 | A | 21 | P | -6 | A | -1.10 | -0.29 | 9.3 | Yes | Med |
| ORF YLR042C | 21 | A | -35 | A | 34 | P | -1 | A | -1.67 | -0.03 | 9.1 | Yes | Med |
| ORF YDL039C | 365 | P | 95 | P | 857 | P | 60 | P | 0.26 | 0.07 | 9.1 | | Excl |
| ORF YOR083W | 16 | A | -46 | A | 22 | P | -7 | A | -2.92 | -0.30 | 9.0 | Yes | Med |
| PES4 (YFR023W) | 30 | A | -23 | A | 23 | A | -14 | A | -0.75 | -0.58 | 9.0 | Yes | Med |
| ORF YDR336W | 89 | A | 6 | A | 80 | P | 33 | P | 0.07 | 0.41 | 8.9 | | Good |
| ORF YLR424W | 26 | A | 2 | A | 36 | P | 14 | P | 0.07 | 0.39 | 8.8 | | Good |
| ORF YNL092W | 32 | A | -46 | A | 9 | A | -1 | A | -1.46 | -0.15 | 8.8 | Yes | Med |
| ORF YDR428C | 95 | A | 7 | P | 94 | P | 24 | P | 0.07 | 0.26 | 8.8 | | Good |
| ORF YNL119W | 295 | M | 19 | A | 179 | P | 86 | P | 0.07 | 0.48 | 8.7 | | Good |

Figure 4D

| | | | | | | | |
|---|---|---|---|---|---|---|---|
| ORF YPR106W | 37 A | -15 A | 123 P | 18 P | -0.42 | 0.15 | 8.7 Yes | Med |
| ORF YDR033W | 5497 P | 519 P | 4162 P | 623 P | 0.09 | 0.15 | 8.6 | Excl |
| ORF YPL222W | -16 A | -88 A | 17 P | 7 A | 5.60 | 0.38 | 8.6 Yes | Med |
| ORF YGL239C | 58 P | 4 A | 29 A | 12 A | 0.07 | 0.42 | 8.6 | Good |
| ORF YLR054C | 26 P | -40 A | 15 P | -3 A | -1.53 | -0.21 | 8.5 Yes | Med |
| ORF YMR051C (_f) | 1397 P | 160 A | 1530 P | 185 P | 0.11 | 0.12 | 8.5 | Good |
| ORF YKR015C | 66 A | -5 A | 4 A | -10 A | -0.08 | -2.35 | 8.5 Yes | Med |
| ORF YLR213C | 58 P | -5 A | 19 P | 4 A | -0.09 | 0.23 | 8.5 Yes | Med |
| ORF YMR101C | 63 P | -9 A | -2 A | -14 A | -0.14 | 6.78 | 8.4 Yes | Med |
| ORF YBR168W | 57 P | -10 A | 64 P | 21 A | -0.18 | 0.33 | 8.3 Yes | Med |
| ORF YDR539W | 13 A | -34 A | 189 P | 26 P | -2.66 | 0.14 | 8.3 Yes | Med |
| FAR1 (YJL157C) | 679 P | 74 M | 541 P | 74 P | 0.11 | 0.14 | 8.3 | Good |
| ORF YOR301W | 47 A | -23 A | 125 P | 52 P | -0.49 | 0.41 | 8.3 Yes | Med |
| ORF YLR149C | 21 A | -49 A | 38 P | 16 P | -2.33 | 0.42 | 8.2 Yes | Med |
| ORF YMR213W | 26 A | -46 A | 45 P | 23 A | -1.73 | 0.50 | 8.2 Yes | Med |
| NDT80 (YHR124W) | 66 P | -1 A | 29 A | 10 A | -0.01 | 0.34 | 8.2 Yes | Med |
| ORF YMR118C | 37 A | -33 A | 5 A | -5 A | -0.90 | -1.04 | 8.1 Yes | Med |
| ORF YML118W | 32 A | -26 A | 14 A | -6 A | -0.83 | -0.45 | 7.9 Yes | Med |
| ORF YBR238C | 137 A | 12 A | 175 P | 44 P | 0.09 | 0.25 | 7.8 | Good |
| MAL32 (YBR299W) | 37 P | 3 A | 36 A | 7 A | 0.10 | 0.19 | 7.8 | Good |
| ORF YFL063W (_r) | 32 A | -8 A | 34 A | -4 A | -0.25 | -0.11 | 7.8 Yes | Med |
| ORF YMR063W | 21 A | -21 A | 10 A | -25 A | -1.00 | -2.40 | 7.7 Yes | Med |
| SEO1 (YAL067C) | 11 A | -2 A | 11 P | 1 A | -0.21 | 0.08 | 7.7 Yes | Med |
| ORF YFL051C | 53 A | 6 A | 23 A | 4 A | 0.11 | 0.16 | 7.5 | Good |
| ORF YHL050C exon | 364 P | 32 A | 366 P | 105 P | 0.09 | 0.29 | 7.5 | Good |
| ORF YNL018C (_f) | -58 A | -100 A | 21 A | 3 A | 1.73 | 0.16 | 7.3 Yes | Med |
| ORF YLR312C | 37 A | -4 A | 12 A | -20 A | -0.10 | -1.65 | 7.3 Yes | Med |
| ORF YKL042W | 74 A | 9 A | 26 P | -5 A | 0.12 | -0.21 | 7.3 Yes | Med |
| ORF YDL022W | 1084 P | 151 P | 1669 P | 224 P | 0.14 | 0.13 | 7.3 | Excl |
| ORF YGL184C | 25 A | -16 A | 53 P | 8 P | -0.65 | 0.15 | 7.3 Yes | Med |
| GAL7 (YBR018C) | 44 A | 15 A | 201 P | 2 A | 0.34 | 0.09 | 7.2 | Good |
| ORF YAR010C (_f) | 1167 P | 216 P | 1705 P | 189 P | 0.19 | 0.11 | 7.2 Yes | Excl |
| ORF YKL030W | 26 A | -4 A | 4 A | -20 A | -0.80 | -4.95 | 7.2 Yes | Med |
| ORF YER160C exon | 1423 P | 213 P | 1795 P | 235 P | 0.15 | 0.13 | 7.2 | Excl |
| ORF YMR211W | 45 A | -16 A | 144 P | 70 P | -0.35 | 0.48 | 7.1 Yes | Med |
| ORF YHR029C | 117 P | 10 A | 107 P | 48 P | 0.08 | 0.45 | 7.0 | Good |
| ORF YDR281C | 17 A | -3 A | 17 P | 2 A | -0.20 | 0.10 | 7.0 Yes | Med |

Figure 4E

| | | | | | | | |
|---|---|---|---|---|---|---|---|
| DCG1 (YIR030C) | 15 | A | -23 | A | 30 | P | -2 | A | -1.51 | -0.05 | 7.0 | Yes | Med |
| ORF YLR176C | 37 | A | -16 | A | 31 | P | 10 | A | -0.43 | 0.31 | 6.9 | Yes | Med |
| ORF YER138C exon | 1391 | P | 203 | P | 1495 | P | 218 | P | 0.15 | 0.15 | 6.9 | | Excl |
| ORF YPL194W | -68 | A | -119 | A | 30 | M | 9 | A | 1.74 | 0.28 | 6.8 | Yes | Med |
| SWH1 (YAR042W) | 106 | A | 12 | A | 91 | P | 20 | A | 0.11 | 0.22 | 6.8 | | Good |
| MRS2 (YOR333C) | 179 | A | 19 | A | 17 | A | 4 | A | 0.11 | 0.23 | 6.8 | | Good |
| DOG1 (YHR044C) | 13 | A | -8 | A | 21 | A | 2 | A | -0.60 | 0.11 | 6.7 | Yes | Med |
| ORF YJR029W exon | 1624 | P | 411 | P | 1579 | P | 170 | P | 0.25 | 0.11 | 6.6 | | Excl |
| YLF2 (YHL014C) | 64 | A | 6 | A | 55 | P | 23 | P | 0.09 | 0.43 | 6.6 | | Good |
| SRD1 (YCR018C) | 68 | A | 15 | A | 60 | P | 7 | A | 0.22 | 0.12 | 6.6 | | Good |
| ORF YDR018C | 38 | A | -13 | A | 6 | A | -9 | A | -0.34 | -1.45 | 6.6 | Yes | Med |
| ORF YMR291W | 16 | A | -38 | A | 71 | P | 34 | A | -2.44 | 0.48 | 6.5 | Yes | Med |
| ORF YHR087W | 40 | A | 0 | A | 221 | P | 44 | P | 0.00 | 0.20 | 6.4 | Yes | Med |
| ORF YFL060C (_f) | 9 | A | -23 | A | 30 | P | -2 | A | -2.41 | -0.05 | 6.4 | Yes | Med |
| PIG1 (YLR273C) | 92 | A | 9 | A | 56 | P | 25 | A | 0.10 | 0.44 | 6.4 | | Good |
| ORF YLL063C | -24 | A | -47 | A | 26 | P | 3 | A | 2.00 | 0.13 | 6.4 | Yes | Med |
| ORF YGL146C | 42 | P | 4 | A | 11 | A | 0 | A | 0.10 | 0.00 | 6.3 | Yes | Med |
| ORF YBR012W-B ex | 1230 | P | 249 | P | 1643 | P | 215 | P | 0.20 | 0.13 | 6.3 | | Excl |
| ORF YJR071W | 16 | A | -28 | A | 16 | P | -2 | A | -1.78 | -0.13 | 6.3 | Yes | Med |
| ORF YHR097C exon | 55 | A | 7 | A | 66 | P | 14 | A | 0.13 | 0.22 | 6.2 | | Good |
| TEC1 (YBR083W) | 263 | P | 71 | P | 227 | P | 26 | P | 0.27 | 0.11 | 6.2 | | Excl |
| ORF YBR184W | 30 | A | -19 | A | 25 | P | 10 | A | -0.62 | 0.38 | 6.2 | Yes | Med |
| ORF YJR053W | 34 | A | -5 | A | 24 | P | 5 | A | -0.15 | 0.23 | 6.2 | Yes | Med |
| ORF YLR254C | 155 | P | 35 | A | 38 | P | -1 | A | 0.23 | -0.03 | 6.1 | Yes | Med |
| ORF YCR006C | 2 | A | -31 | A | 19 | P | -9 | A | -19.78 | -0.46 | 6.1 | Yes | Med |
| OM45 (YIL136W) | 143 | P | 15 | A | 52 | M | 21 | A | 0.10 | 0.40 | 6.1 | | Good |
| ORF YLR164W | 39 | A | -9 | A | 24 | A | 10 | A | -0.22 | 0.41 | 6.0 | Yes | Med |
| FUS2 (YMR232W) | 263 | A | 58 | A | 14 | A | -23 | A | 0.22 | -1.64 | 6.0 | Yes | Med |
| ORF YER037W | 13 | A | -18 | A | 47 | P | 8 | A | -1.35 | 0.18 | 5.9 | Yes | Med |
| REV7 (YIL139C) | 42 | A | -7 | A | 38 | P | 18 | P | -0.17 | 0.47 | 5.9 | Yes | Med |
| ORF YHL050C exon | 1970 | P | 203 | P | 1429 | P | 682 | P | 0.10 | 0.48 | 5.9 | | Excl |

Figure 4F

| | | | | | | | |
|---|---|---|---|---|---|---|---|
| ORF YJR028W (_f) | 1934 P | 365 P | 1594 P | 248 P | 0.19 | 0.16 | 5.9 | Excl |
| ORF YBL101W-B exc | 119 M | 26 M | 184 P | 26 P | 0.21 | 0.14 | 5.9 | Good |
| ORF YGR112W | 40 A | 10 A | 37 P | -2 A | 0.25 | -0.04 | 5.8 Yes | Med |
| ORF YDL179W | 87 A | 29 A | 151 P | 17 M | 0.33 | 0.12 | 5.8 | Good |
| ORF YGR225W | 21 A | -16 A | 18 A | -4 A | -0.76 | -0.21 | 5.8 Yes | Med |
| URA1 (YKL216W) | 2329 P | 361 P | 2930 P | 567 P | 0.16 | 0.19 | 5.8 | Excl |
| KIP2 (YPL155C) | 74 A | 8 A | 68 P | 34 P | 0.10 | 0.49 | 5.8 | Good |
| STE6 (YKL209C) | 574 P | 116 P | 690 P | 105 P | 0.20 | 0.15 | 5.7 | Excl |
| ORF YIL132C | 9 A | -2 A | 37 P | -9 A | -0.21 | -0.24 | 5.7 Yes | Med |
| ORF YBL098W | 30 A | -14 A | 84 P | 32 P | -0.46 | 0.38 | 5.7 Yes | Med |
| ORF YBR012W-A (_f | 1613 P | 444 P | 1714 P | 221 P | 0.28 | 0.13 | 5.7 | Excl |
| ORF YIL082W-A exa | 36 A | -1 A | 381 P | 10 A | -0.03 | 0.25 | 5.6 Yes | Med |
| YSW1 (YBR148W) | 30 A | -9 A | 15 P | -2 A | -0.31 | -0.12 | 5.6 Yes | Med |
| AGA1 (YNR044W) | 863 P | 212 P | 609 P | 85 P | 0.25 | 0.14 | 5.6 | Excl |
| ORF YLR040C | 71 A | 9 A | 90 P | 29 P | 0.12 | 0.32 | 5.6 | Good |
| ORF YML045W exon | 1750 P | 321 P | 1565 P | 276 P | 0.18 | 0.18 | 5.6 | Excl |
| ORF YHR214C-B exc | 2009 P | 386 P | 1878 P | 320 P | 0.19 | 0.17 | 5.5 | Excl |
| AGA2 (YGL032C) | 381 P | 62 P | 408 P | 83 P | 0.16 | 0.20 | 5.5 | Excl |
| ORF YIL100W | 21 A | -7 A | 12 A | 2 A | -0.33 | 0.18 | 5.5 Yes | Med |
| ORF YOR032C | 21 A | -23 A | 11 A | 0 A | -1.10 | 0.00 | 5.5 Yes | Med |
| ORF YDR516C | 106 A | 15 A | 216 P | 56 P | 0.14 | 0.26 | 5.5 | Good |
| ORF YOL161C (_f) | 211 A | 27 A | 105 A | 34 A | 0.13 | 0.33 | 5.4 | Good |
| SNM1 (YDR478W) | 49 A | 9 A | 150 P | 27 P | 0.19 | 0.18 | 5.4 | Good |
| PHO84 (YML123C) | 234 P | 70 A | 449 P | 60 M | 0.30 | 0.13 | 5.4 | Good |
| ORF YNR004W | -37 A | -69 A | 23 P | 5 A | 1.88 | 0.23 | 5.4 Yes | Med |
| ORF YBL107C | 113 A | 40 A | 131 P | 17 M | 0.35 | 0.13 | 5.4 | Good |
| ORF YOR050C | -63 A | -100 A | 2 A | -15 A | 1.58 | -6.70 | 5.4 Yes | Med |
| ORF YML039W exon | 1147 P | 302 P | 1604 P | 235 P | 0.26 | 0.15 | 5.3 | Excl |
| ORF YJR128W | -18 A | -53 A | 12 A | -6 A | 2.86 | -0.52 | 5.3 Yes | Med |
| FSP2 (YJL221C) (_f | 74 A | 12 A | 44 P | 10 A | 0.17 | 0.22 | 5.3 | Good |
| ORF YIL071W | 32 P | -4 A | 22 P | 7 A | -0.12 | 0.31 | 5.2 Yes | Med |
| ORF YGL204C | 109 P | 20 A | 85 P | 17 A | 0.18 | 0.20 | 5.2 | Good |
| ORF YDR374C | 10 A | -20 A | 7 A | -16 A | -2.08 | -2.24 | 5.2 Yes | Med |
| ORF YDR022C | 51 A | 21 A | 38 P | -2 A | 0.41 | -0.05 | 5.2 Yes | Med |
| ORF YJR027W exon | 1342 P | 347 P | 1360 P | 210 P | 0.26 | 0.15 | 5.2 | Excl |
| SPT8 (YLR055C) | 34 A | -7 A | 112 P | 54 P | -0.21 | 0.48 | 5.2 Yes | Med |
| CEP3 (YMR168C) | 82 P | 11 A | 36 P | 14 A | 0.13 | 0.39 | 5.2 | Good |

Figure 4G

|  | 455 |  | 91 |  | 682 |  | 129 |  |  |  |  |  |
|---|---|---|---|---|---|---|---|---|---|---|---|---|
| ORF YGL028C |  | P |  | P |  | P |  | P | 0.20 | 0.19 | 5.1 |  | Excl |
| ORF YKR017C | 55 | A | 9 | A | 52 | P | 13 | P | 0.16 | 0.25 | 5.1 |  | Good |
| NCA3 (YJL116C) | 137 | P | 19 | A | 68 | P | 22 | A | 0.14 | 0.32 | 5.1 |  | Good |
| DIP1 (YKL017C) | 45 | A | 7 | A | 54 | P | 14 | P | 0.16 | 0.26 | 5.1 |  | Good |
| ORF YCR024C | 35 | A | -1 | A | 39 | P | 13 | A | -0.03 | 0.33 | 5.1 | Yes | Med |
| YRO2 (YBR054W) | 278 | P | 57 | P | 642 | P | 123 | P | 0.21 | 0.19 | 5.1 |  | Excl |
| ORF YGR131W | 58 | A | 11 | A | 36 | A | 8 | A | 0.19 | 0.21 | 5.1 |  | Good |
| NAM8 (YHR086W) | 109 | A | 16 | A | 153 | P | 48 | A | 0.14 | 0.31 | 5.0 |  | Good |
| ORF YLR296W | 21 | A | -16 | A | 12 | P | -1 | A | -0.75 | -0.09 | 5.0 | Yes | Med |
| GRR1 (YJR090C) | 182 | A | 23 | A | 98 | P | 48 | P | 0.13 | 0.49 | 5.0 |  | Good |
| ORF YGL064C | 60 | P | 8 | A | 56 | P | 24 | P | 0.13 | 0.43 | 5.0 |  | Good |
| ORF YER033C | 23 | A | 7 | A | 25 | A | 4 | A | 0.31 | 0.15 | 4.9 |  | Good |
| ORF YMR050C exon | 1118 | P | 291 | P | 1538 | P | 257 | P | 0.26 | 0.17 | 4.9 |  | Excl |
| ORF YEL076C (_f) | 66 | A | 11 | A | 92 | P | 25 | A | 0.16 | 0.27 | 4.9 |  | Good |
| ORF YJL161W | 24 | A | 7 | A | 8 | A | -24 | A | 0.30 | -2.87 | 4.9 | Yes | Med |
| FAA3 (YIL009W) | 151 | P | 21 | A | 159 | P | 64 | P | 0.14 | 0.40 | 4.9 |  | Good |
| ORF YBL113C (_f) | 1186 | P | 162 | P | 1234 | P | 518 | P | 0.14 | 0.42 | 4.9 |  | Excl |
| ORF YGR296W exon | 1543 | P | 203 | P | 1273 | P | 605 | P | 0.13 | 0.48 | 4.9 |  | Excl |
| ORF YOL101C | 384 | P | 58 | A | 191 | P | 64 | P | 0.15 | 0.33 | 4.8 |  | Good |
| YFL-TyA/_f (control) | 98 | P | 20 | A | 208 | P | 44 | P | 0.20 | 0.21 | 4.8 |  | Good |
| ORF YBR032W | 138 | P | 30 | A | 66 | P | 13 | A | 0.22 | 0.20 | 4.8 |  | Good |
| PRP31 (YGR091W) | 26 | P | 13 | A | 40 | P | 5 | A | 0.49 | 0.13 | 4.8 |  | Good |
| ORF YIL177C exon a | 715 | P | 96 | P | 712 | P | 336 | P | 0.13 | 0.47 | 4.8 |  | Excl |
| ORF YOR392W (_f) | 26 | A | 4 | A | 10 | A | -3 | A | 0.15 | -0.34 | 4.7 | Yes | Med |
| ORF YHL026C | 117 | P | 18 | A | 164 | P | 57 | P | 0.15 | 0.35 | 4.7 |  | Good |
| ORF YDR541C | -19 | A | -42 | A | 55 | P | 11 | A | 2.20 | 0.21 | 4.7 | Yes | Med |
| ORF YJL017W | 106 | P | 18 | A | 118 | P | 34 | P | 0.17 | 0.29 | 4.7 |  | Good |
| MSH4 (YFL003C) | 36 | A | 0 | A | 11 | A | 0 | A | 0.00 | 0.00 | 4.7 | Yes | Med |
| ORF YJR026W (_f) | 1155 | P | 332 | P | 1442 | P | 249 | P | 0.29 | 0.17 | 4.6 |  | Excl |
| ORF YGL069C | 30 | A | 0 | A | -3 | A | -19 | A | 0.00 | 6.86 | 4.6 | Yes | Med |
| ORF YGL033W exon | 25 | A | -4 | A | 12 | A | -5 | A | -0.16 | -0.43 | 4.6 | Yes | Med |

Figure 4H

| | | | | | | | |
|---|---|---|---|---|---|---|---|
| ORF YJL225C exon | 71 | A | 12 | A | 32 | P | 10 | A | 0.17 | 0.30 | 4.5 | Good |
| ORF YPL032C | 647 | P | 104 | A | 405 | P | 143 | P | 0.16 | 0.35 | 4.5 | Good |
| PSP1 (YDR505C) | 87 | A | 22 | A | 160 | P | 31 | P | 0.25 | 0.20 | 4.5 | Good |
| ORF YOR315W | 400 | P | 65 | A | 195 | P | 69 | P | 0.16 | 0.35 | 4.5 | Good |
| ORF YDR438W | 29 | A | 7 | A | 63 | P | 13 | A | 0.24 | 0.21 | 4.5 | Good |
| PET112 (YBL080C) | 54 | A | 22 | A | 39 | P | 6 | A | 0.41 | 0.16 | 4.4 | Good |
| COQ1 (YBR003W) | 113 | P | 19 | A | 170 | P | 63 | P | 0.17 | 0.37 | 4.4 | Good |
| GPA1 (YHR005C) | 628 | P | 129 | P | 375 | P | 98 | P | 0.20 | 0.26 | 4.4 | Excl |
| NDI1 (YML120C) | 58 | A | 12 | A | 93 | P | 24 | P | 0.21 | 0.25 | 4.3 | Good |
| ORF YLR231C | 226 | P | 65 | A | 122 | P | 24 | P | 0.29 | 0.19 | 4.3 | Good |
| STE12 (YHR084W) | 175 | P | 37 | P | 147 | P | 38 | M | 0.21 | 0.26 | 4.3 | Good |
| ORF YEL076C-A exon | 142 | P | 26 | A | 56 | P | 18 | A | 0.18 | 0.32 | 4.3 | Good |
| ORF YHR097C exon | 211 | P | 36 | A | 119 | P | 45 | P | 0.17 | 0.38 | 4.3 | Good |
| ORF YNL141W | 200 | A | 42 | A | 523 | P | 136 | P | 0.21 | 0.26 | 4.3 | Good |
| ORF YLR218C | 303 | P | 47 | A | 80 | P | 38 | P | 0.16 | 0.47 | 4.3 | Good |
| ORF YHR143W | 1036 | P | 307 | P | 1488 | P | 292 | P | 0.30 | 0.20 | 4.2 | Excl |
| BIO2 (YGR286C) | 140 | P | 49 | P | 242 | P | 44 | P | 0.35 | 0.18 | 4.2 | Excl |
| ORF YBR244W | 297 | P | 56 | P | 476 | P | 155 | P | 0.19 | 0.33 | 4.2 | Excl |
| ORF YMR026C | 124 | A | 21 | A | 87 | P | 35 | P | 0.17 | 0.41 | 4.2 | Good |
| GPD2 (YOL059W) | 453 | P | 123 | A | 265 | P | 59 | P | 0.27 | 0.22 | 4.2 | Good |
| HXT4 (YHR092C) | 138 | P | 53 | P | 459 | P | 82 | P | 0.39 | 0.18 | 4.1 | Excl |
| ORF YGR287C | 87 | A | 17 | A | 47 | P | 16 | A | 0.19 | 0.34 | 4.1 | Good |
| ORF YPR053C | 626 | P | 104 | A | 362 | P | 176 | P | 0.17 | 0.49 | 4.0 | Good |
| ORF YLR440C | 142 | P | 32 | A | 73 | P | 20 | P | 0.22 | 0.28 | 4.0 | Good |
| FCY21 (YER060W) | 85 | A | 27 | A | 77 | P | 16 | M | 0.31 | 0.21 | 4.0 | Good |
| ORF YLL054C | 21 | A | -9 | A | 42 | P | 20 | M | -0.42 | 0.48 | 4.0 | Med |
| ORF YBR267W | 249 | P | 76 | P | 292 | P | 62 | P | 0.30 | 0.21 | 4.0 | Excl |
| ORF YMR067C | 218 | P | 39 | A | 129 | P | 55 | A | 0.18 | 0.43 | 4.0 | Good |
| GDH3 (YAL062W) | 24 | A | -6 | A | 32 | P | 16 | A | -0.24 | 0.49 | 4.0 | Med |
| DIT1 (YDR403W) | 21 | A | 9 | A | 25 | P | -3 | A | 0.45 | -0.14 | 4.0 | Yes Med |
| ORF YLL067C exon | 1803 | P | 311 | P | 1342 | P | 649 | P | 0.17 | 0.48 | 4.0 | Yes |
| ORF YAR003W | 178 | A | 33 | A | 206 | P | 86 | P | 0.18 | 0.42 | 3.9 | Excl |
| ORF YBL095W | 111 | A | 23 | A | 88 | P | 29 | P | 0.21 | 0.33 | 3.9 | Good |
| ORF YMR180C | 137 | A | 26 | A | 51 | P | 19 | P | 0.19 | 0.38 | 3.9 | Good |
| IME1 (YJR094C) | 45 | A | 19 | A | 18 | A | 3 | A | 0.43 | 0.18 | 3.9 | Good |

Figure 4I

| | | | | | | | |
|---|---|---|---|---|---|---|---|
| RRN6 (YBL014C) | 98 | P | 40 | A | 137 | P | 26 | A | 0.40 | 0.19 | 3.9 | | Good |
| ORF YHL044W | 38 | P | 15 | A | 51 | P | 10 | P | 0.39 | 0.19 | 3.9 | | Good |
| ORF YOR342C | 368 | P | 73 | A | 449 | P | 172 | P | 0.20 | 0.38 | 3.8 | | Good |
| ORF YOR066W | 695 | P | 131 | A | 110 | P | 47 | P | 0.19 | 0.43 | 3.8 | | Good |
| ORF YCR008W | 197 | P | 71 | P | 249 | P | 51 | P | 0.36 | 0.21 | 3.8 | | Excl |
| ORF YCR027C | 63 | A | 20 | A | 69 | P | 16 | M | 0.31 | 0.23 | 3.8 | | Good |
| ILV5 (YLR355C) | 5116 | A | 1025 | P | 3323 | P | 1282 | P | 0.20 | 0.39 | 3.8 | | Excl |
| MRK1 (YDL079C) ex | 10 | A | -12 | A | 26 | P | 8 | A | -1.22 | 0.30 | 3.8 | Yes | Med |
| ORF YGL182C | -6 | A | -33 | A | 7 | A | -4 | A | 5.77 | -0.55 | 3.8 | Yes | Med |
| ORF YLL010C | 176 | P | 42 | A | 161 | P | 48 | P | 0.24 | 0.30 | 3.8 | | Good |
| OSH1 (YAR044W) | 97 | A | 41 | A | 116 | P | 23 | P | 0.42 | 0.19 | 3.8 | | Good |
| ORF YIR040C (_f) | 6 | A | -15 | A | 4 | A | -13 | A | -2.62 | -3.11 | 3.7 | Yes | Med |
| ORF YCR062W | 68 | A | 23 | A | 79 | P | 17 | A | 0.34 | 0.22 | 3.7 | | Good |
| ORF YCL036W | 513 | P | 159 | P | 607 | P | 143 | P | 0.31 | 0.23 | 3.7 | | Excl |
| ORF YMR158W | 163 | P | 33 | A | 211 | P | 83 | P | 0.20 | 0.39 | 3.7 | | Good |
| ORF YKR103W | 42 | A | 16 | A | 22 | P | -2 | A | 0.38 | -0.10 | 3.7 | Yes | Med |
| ORF YCL055W | 125 | P | 45 | P | 253 | P | 55 | P | 0.36 | 0.22 | 3.7 | | Excl |
| ORF YBR028C | 98 | A | 21 | A | 107 | P | 40 | P | 0.21 | 0.37 | 3.7 | | Good |
| ORF YCR063W | 60 | A | 12 | A | 36 | P | 17 | A | 0.19 | 0.46 | 3.7 | | Good |
| ORF YGL072C | 15 | A | 3 | A | 49 | P | 22 | P | 0.20 | 0.44 | 3.7 | | Good |
| ORF YLR436C | 142 | P | 32 | A | 174 | P | 61 | P | 0.22 | 0.35 | 3.7 | | Good |
| ORF YGR086C | 794 | P | 204 | P | 932 | P | 271 | P | 0.26 | 0.29 | 3.7 | | Excl |
| ORF YER093C-A exo | 57 | A | 11 | A | 58 | P | 27 | P | 0.19 | 0.47 | 3.7 | | Good |
| ORF YFL055W | 96 | P | 22 | A | 74 | P | 26 | P | 0.23 | 0.35 | 3.7 | | Good |
| ORF YBR078W exon | 1141 | P | 399 | P | 2061 | P | 463 | P | 0.35 | 0.22 | 3.7 | | Excl |
| ORF YEL067C | 51 | A | 24 | A | 22 | A | -4 | A | 0.47 | -0.17 | 3.6 | Yes | Med |
| ORF YMR157C | 87 | A | 19 | A | 116 | P | 42 | P | 0.22 | 0.36 | 3.6 | | Good |
| ORF YGL051W | -2 | A | -23 | A | 30 | P | 10 | A | 12.07 | 0.32 | 3.6 | Yes | Med |
| ORF YFL024C | 91 | A | 21 | A | 133 | P | 46 | P | 0.23 | 0.35 | 3.6 | | Good |
| ORF YGL227W | 9 | A | -15 | A | 29 | P | 12 | A | -1.57 | 0.42 | 3.6 | Yes | Med |
| ORF YBR105C | 186 | P | 50 | P | 383 | P | 109 | P | 0.27 | 0.28 | 3.6 | | Excl |
| ORF YNL190W | 2189 | P | 454 | P | 2259 | P | 939 | P | 0.21 | 0.42 | 3.6 | | Excl |
| TAL1 (YLR354C) | 1282 | P | 316 | P | 1122 | P | 354 | P | 0.25 | 0.32 | 3.6 | | Excl |

Figure 4J

| | | | | | |
|---|---|---|---|---|---|
| ORF YBR078W exon | 508 P | 220 P | 1167 P | 237 P | 0.43 | 0.20 | 3.6 | Excl |
| ORF YDR093W | 141 P | 42 P | 167 P | 43 P | 0.30 | 0.26 | 3.6 | Excl |
| ORF YGR260W | 270 P | 86 P | 570 P | 140 P | 0.32 | 0.25 | 3.6 | Excl |
| CCR4 (YAL021C) | 170 A | 47 A | 299 P | 84 P | 0.27 | 0.28 | 3.6 | Good |
| FUS1 (YCL027W) | 146 P | 41 M | 97 P | 27 P | 0.28 | 0.28 | 3.6 | Good |
| ORF YEL007W | 475 P | 151 A | 337 P | 83 P | 0.32 | 0.25 | 3.6 | Good |
| HIR1 (YBL008W) | 54 A | 27 A | 76 P | 15 A | 0.50 | 0.19 | 3.6 | Good |
| ORF YGL018C | 77 A | 37 A | 49 P | 10 A | 0.47 | 0.20 | 3.6 | Good |
| DOA4 (YDR069C) | 51 P | 10 A | 58 P | 25 P | 0.21 | 0.43 | 3.6 | Good |
| SCA1 (YDR443C) | 32 A | 14 A | 55 P | 11 A | 0.44 | 0.21 | 3.6 | Good |
| NPR2 (YEL062W) | 47 A | 17 A | 36 P | 8 A | 0.36 | 0.23 | 3.6 | Good |
| ORF YNL065W | 74 A | 15 A | 701 P | 305 P | 0.21 | 0.43 | 3.5 | Good |
| PAD1 (YDR538W) | 40 A | 20 A | 150 P | 301 A | 0.50 | 0.20 | 3.5 | Good |
| ORF YCL060C | 81 A | 16 A | 83 P | 40 M | 0.20 | 0.48 | 3.5 | Good |
| ORF YCR068W | 67 A | 19 A | 36 P | 10 A | 0.28 | 0.29 | 3.5 | Good |
| ORF YMR130W | 68 A | 16 A | 160 P | 60 P | 0.23 | 0.38 | 3.5 | Good |
| ORF YBL101W-A (_ | 137 P | 35 A | 152 P | 50 P | 0.26 | 0.33 | 3.5 | Excl |
| SAM1 (YLR180W) | 1200 P | 321 P | 1015 P | 314 P | 0.27 | 0.31 | 3.5 | Good |
| ATR1 (YML116W) | 468 P | 95 A | 224 P | 111 P | 0.20 | 0.50 | 3.5 | Good |
| ORF YHL047C | 270 P | 62 A | 204 P | 77 P | 0.23 | 0.38 | 3.5 | Excl |
| ORF YLR192C | 1342 P | 286 P | 989 P | 439 P | 0.21 | 0.44 | 3.5 | Good |
| ORF YDR131C | 71 A | 26 A | 54 P | 13 A | 0.36 | 0.24 | 3.5 | Good |
| DED1 (YOR204W) | 1074 P | 296 P | 672 P | 203 P | 0.28 | 0.30 | 3.5 | Excl |
| PRY1 (YJL079C) | 411 P | 115 P | 419 P | 126 P | 0.28 | 0.30 | 3.5 | Excl |
| MET22 (YOL064C) | 189 A | 77 A | 257 P | 58 P | 0.41 | 0.22 | 3.5 | Good |
| ORF YBL094C | 92 P | 21 A | 113 P | 45 P | 0.23 | 0.40 | 3.4 | Good |
| DBP2 (YNL112W) ex | 2421 P | 704 P | 1893 P | 550 P | 0.29 | 0.29 | 3.4 | Excl |
| ORF YGL045W | 134 P | 28 A | 38 P | 19 M | 0.21 | 0.49 | 3.4 | Good |
| QRI7 (YDL104C) | 54 P | 12 A | 46 P | 21 P | 0.22 | 0.45 | 3.4 | Good |
| CCE1 (YKL011C) | 34 A | 12 A | 78 P | 19 P | 0.36 | 0.25 | 3.4 | Good |
| DAT1 (YML113W) | 697 P | 161 P | 452 P | 181 P | 0.23 | 0.40 | 3.4 | Excl |
| YCLX12w_f (contra | 33 A | 10 A | 97 P | 27 P | 0.31 | 0.28 | 3.4 | Good |
| PAC11 (YDR488C) | 60 A | 28 A | 48 P | 10 A | 0.46 | 0.22 | 3.4 | Good |
| ORF YMR112C | 389 P | 86 A | 215 P | 97 P | 0.22 | 0.45 | 3.4 | Good |
| PHO12 (YHR215W) | 100 P | 24 A | 111 P | 44 P | 0.24 | 0.39 | 3.4 | Good |
| MAG1 (YER142C) | 43 A | 13 A | 48 P | 14 M | 0.30 | 0.30 | 3.4 | Good |

Figure 4K

| | | | | | | | | |
|---|---|---|---|---|---|---|---|---|
| ORF YML079W | 147 | A | 39 | A | 206 | P | 71 | P | 0.26 | 0.34 | 3.4 | | Good |
| ORF YER089C | 313 | P | 80 | M | 164 | P | 59 | P | 0.26 | 0.36 | 3.4 | | Good |
| MRPL4 (YLR439W) | 147 | P | 39 | A | 96 | P | 33 | A | 0.26 | 0.35 | 3.3 | | Good |
| SSN3 (YPL042C) | 247 | A | 54 | M | 85 | P | 40 | M | 0.22 | 0.48 | 3.3 | | Good |
| ORF YLL044W | 21 | A | -2 | A | 21 | P | 10 | M | -0.08 | 0.47 | 3.3 | Yes | Med |
| ORF YGR023W | 15 | A | -1 | A | 26 | A | 8 | P | -0.07 | 0.29 | 3.3 | Yes | Med |
| FUS3 (YBL016W) | 116 | A | 42 | A | 170 | P | 43 | P | 0.36 | 0.26 | 3.3 | | Good |
| PPH3 (YDR075W) | 144 | P | 70 | P | 124 | P | 27 | A | 0.48 | 0.22 | 3.3 | | Good |
| ORF YJL195C | 13 | A | -5 | A | 3 | A | -12 | A | -0.40 | -3.82 | 3.3 | Yes | Med |
| UBP9 (YER098W) | 42 | A | 13 | A | 21 | A | 6 | A | 0.31 | 0.29 | 3.3 | | Good |
| ORF YIL051C | 1804 | P | 605 | P | 3370 | P | 921 | P | 0.34 | 0.27 | 3.3 | | Excl |
| HMS1 (YMR070W) | 50 | P | 25 | A | 123 | P | 27 | A | 0.49 | 0.22 | 3.3 | | Good |
| ORF YCR045C | 16 | A | -2 | A | 18 | P | 6 | A | -0.15 | 0.34 | 3.3 | Yes | Med |
| HAP1 (YLR256W) | 455 | P | 158 | A | 332 | P | 90 | P | 0.35 | 0.27 | 3.3 | | Good |
| ORF YNL078W | 353 | A | 92 | A | 245 | P | 89 | P | 0.26 | 0.37 | 3.3 | | Good |
| SCO1 (YBR037C) | 21 | A | 7 | A | 78 | P | 22 | M | 0.34 | 0.28 | 3.3 | | Good |
| MCM3 (YEL032W) | 319 | A | 82 | A | 140 | P | 53 | P | 0.26 | 0.38 | 3.3 | | Good |
| ORF YAL060W | 257 | A | 93 | P | 314 | P | 83 | P | 0.36 | 0.27 | 3.3 | | Good |
| ACE2 (YLR131C) | 116 | A | 54 | A | 94 | P | 22 | P | 0.47 | 0.23 | 3.3 | | Good |
| ORF YHR136C | -2 | A | -19 | A | 23 | P | 8 | A | 9.97 | 0.32 | 3.2 | Yes | Med |
| ORF YKL027W | 203 | A | 49 | A | 129 | P | 55 | P | 0.24 | 0.43 | 3.2 | | Good |
| ORF YHR022C | 49 | P | 15 | A | 55 | P | 17 | P | 0.30 | 0.32 | 3.2 | | Good |
| ORF YDR233C | 1722 | P | 574 | P | 2573 | P | 748 | P | 0.33 | 0.29 | 3.2 | | Excl |
| DSK2 (YOR035C) | 95 | A | 23 | A | 49 | P | 21 | P | 0.24 | 0.43 | 3.2 | | Good |
| SAC2 (YDR484W) | 25 | A | 6 | A | 55 | P | 27 | P | 0.23 | 0.49 | 3.2 | | Good |
| ORF YKL134C | 66 | A | 19 | A | 35 | P | 12 | A | 0.29 | 0.34 | 3.2 | | Good |
| SFP1 (YLR403W) | 166 | A | 74 | A | 284 | P | 69 | P | 0.44 | 0.24 | 3.2 | | Good |
| NSR1 (YGR159C) | 2262 | P | 744 | P | 2771 | P | 835 | P | 0.33 | 0.30 | 3.2 | | Excl |
| ORF YGR160W | 60 | A | 20 | P | 52 | P | 16 | A | 0.33 | 0.30 | 3.2 | | Good |
| RAD7 (YJR052W) | 55 | A | 23 | A | 97 | P | 25 | A | 0.41 | 0.26 | 3.2 | | Good |
| ORF YOR239W | 505 | P | 127 | P | 174 | P | 74 | P | 0.25 | 0.43 | 3.2 | | Excl |
| PFK1 (YGR240C) | 1579 | P | 613 | P | 2342 | P | 626 | P | 0.39 | 0.27 | 3.2 | | Excl |

Figure 4L

| | | | | | | | |
|---|---|---|---|---|---|---|---|
| SMY2 (YBR172C) | 143 P | 48 P | 265 P | 80 P | 0.33 | 0.30 | 3.2 | Excl |
| CIN8 (YEL061C) | 47 A | 18 A | 27 P | 8 A | 0.38 | 0.27 | 3.1 | Good |
| PRK1 (YIL095W) | 74 P | 35 P | 84 P | 20 P | 0.47 | 0.24 | 3.1 | Excl |
| HGH1 (YGR187C) | 408 P | 127 P | 493 P | 163 P | 0.31 | 0.33 | 3.1 | Excl |
| DCD1 (YHR144C) | 183 P | 56 A | 189 P | 63 P | 0.31 | 0.33 | 3.1 | Good |
| ALR2 (YFL050C) | 74 P | 20 A | 64 P | 26 P | 0.27 | 0.40 | 3.1 | Good |
| ORF YDL129W | 143 P | 43 A | 81 P | 28 P | 0.30 | 0.34 | 3.1 | Good |
| ORF YGL196W | 192 P | 70 P | 175 P | 50 P | 0.37 | 0.29 | 3.1 | Excl |
| ORF YBL101W-B exc | 163 P | 72 P | 308 P | 78 P | 0.44 | 0.25 | 3.1 | Excl |
| ORF YDR250C | 60 A | 17 P | 19 P | 7 A | 0.29 | 0.37 | 3.1 | Good |
| PPT1 (YGR123C) | 153 P | 46 P | 196 P | 69 P | 0.30 | 0.35 | 3.1 | Excl |
| ORF YNL279W | 184 A | 46 A | 35 P | 16 A | 0.25 | 0.46 | 3.1 | Good |
| ORF YGL176C | 13 A | 0 A | 42 P | 12 A | 0.00 | 0.28 | 3.1 Yes | Med |
| ORF YHR198C | 77 A | 20 P | 52 P | 23 P | 0.26 | 0.45 | 3.1 | Good |
| MEI4 (YER044C-A) e | 17 A | -3 A | 5 A | -5 A | -0.17 | -0.96 | 3.1 Yes | Med |
| ORF YHL021C | 91 P | 33 M | 96 P | 29 P | 0.36 | 0.30 | 3.1 | Good |
| STU2 (YLR045C) | 203 P | 65 A | 74 P | 25 P | 0.32 | 0.33 | 3.1 | Good |
| ORF YOL002C | 379 P | 96 M | 611 P | 282 P | 0.25 | 0.46 | 3.1 | Excl |
| ORF YCL019W | 1133 P | 535 P | 1657 P | 416 P | 0.47 | 0.25 | 3.1 | Excl |
| ORF YPR008W | 237 P | 100 A | 260 P | 70 P | 0.42 | 0.27 | 3.1 | Good |
| LYS14 (YDR034C) | 79 A | 30 P | 121 P | 35 P | 0.38 | 0.29 | 3.1 | Excl |
| PYC2 (YBR218C) | 359 P | 164 P | 633 P | 162 P | 0.46 | 0.26 | 3.1 | Good |
| ZDS1 (YMR273C) | 226 A | 96 A | 82 P | 22 A | 0.42 | 0.27 | 3.1 | Excl |
| MET25 (YLR303W) | 550 P | 207 P | 821 P | 240 P | 0.38 | 0.29 | 3.0 | Excl |
| SKN1 (YGR143W) | 208 P | 101 P | 332 P | 83 P | 0.49 | 0.25 | 3.0 | Good |
| PWP2 (YCR058C) | 65 A | 28 A | 138 P | 37 P | 0.43 | 0.27 | 3.0 | Excl |
| PHO3 (YBR092C) | 695 P | 277 P | 1080 P | 309 P | 0.40 | 0.29 | 3.0 | Excl |
| MCM1 (YMR043W) | 792 P | 263 P | 351 P | 117 P | 0.33 | 0.33 | 3.0 | Excl |
| ORF YBR259W | 63 P | 23 P | 48 P | 15 P | 0.37 | 0.31 | 3.0 | Excl |
| ORF YDR489W | 79 A | 35 A | 90 P | 24 A | 0.44 | 0.27 | 3.0 | Good |
| ORF YMR102C | 103 A | 35 A | 252 P | 83 P | 0.34 | 0.33 | 3.0 | Good |
| ORF YPR074C | 1042 P | 273 P | 2709 P | 1266 P | 0.26 | 0.47 | 3.0 | Excl |
| ISC10 (YER180C) | 58 P | 15 A | 45 P | 23 P | 0.25 | 0.50 | 3.0 | Good |
| NPL3 (YDR432W) | 922 P | 302 P | 819 P | 283 P | 0.33 | 0.35 | 3.0 | Excl |
| ORF YIL092W | 49 A | 16 A | 38 P | 14 A | 0.32 | 0.35 | 3.0 | Good |
| ORF YDR453C | 44 A | 15 A | 52 P | 17 P | 0.34 | 0.33 | 3.0 | Good |

Figure 4M

| | | | | | | | |
|---|---|---|---|---|---|---|---|
| PRP19 (YLL036C) | 266 P | 72 A | 211 P | 95 P | 0.27 | 0.45 | 3.0 | Good |
| ORF YKL218C | 66 A | 26 A | 85 P | 25 P | 0.40 | 0.29 | 3.0 | Good |
| ORF YGR045C | 57 P | 21 P | 48 P | 15 A | 0.37 | 0.31 | 3.0 | Good |
| RME1 (YGR044C) | 511 P | 166 P | 379 P | 134 P | 0.33 | 0.35 | 3.0 | Excl |
| ORF YOR060C | 111 A | 31 A | 67 P | 29 P | 0.28 | 0.43 | 3.0 | Good |
| CLA4 (YNL298W) | 179 A | 46 A | 126 P | 62 P | 0.26 | 0.49 | 3.0 | Good |
| ORF YDR400W | 111 A | 35 P | 170 P | 63 P | 0.31 | 0.37 | 3.0 | Good |
| NIP1 (YMR309C) | 684 P | 200 P | 657 P | 267 P | 0.29 | 0.41 | 2.9 | Excl |
| HOR2 (YER062C) | 260 P | 92 P | 337 P | 111 P | 0.35 | 0.33 | 2.9 | Excl |
| CTS1 (YLR286C) | 2605 P | 804 P | 2211 P | 847 P | 0.31 | 0.38 | 2.9 | Excl |
| ORF YKL115C | 45 A | 18 A | 25 A | 8 A | 0.39 | 0.30 | 2.9 | Good |
| ORF YNL327W | 3221 P | 1019 P | 2164 P | 811 P | 0.32 | 0.37 | 2.9 | Excl |
| ORF YOR095C | 442 P | 154 P | 610 P | 207 P | 0.35 | 0.34 | 2.9 | Excl |
| ORF YER169W | 126 P | 35 A | 141 P | 65 P | 0.27 | 0.46 | 2.9 | Good |
| ORF YBR125C | 214 P | 66 P | 242 P | 95 P | 0.31 | 0.39 | 2.9 | Excl |
| ORF YGR004W | 57 A | 18 A | 105 P | 41 P | 0.31 | 0.38 | 2.9 | Excl |
| DLD1 (YDL174C) | 365 P | 131 P | 423 P | 142 P | 0.36 | 0.34 | 2.9 | Excl |
| ORF YKL198C | 132 P | 46 A | 46 P | 16 A | 0.35 | 0.35 | 2.9 | Good |
| ORF YJR101W | 150 A | 40 A | 239 P | 117 P | 0.27 | 0.49 | 2.9 | Good |
| SUC2 (YIL162W) | 87 P | 35 P | 103 P | 32 P | 0.40 | 0.31 | 2.9 | Excl |
| ORF YBL024W | 290 P | 78 P | 344 P | 170 P | 0.27 | 0.49 | 2.9 | Excl |
| SKN7 (YHR206W) | 247 P | 100 P | 314 P | 95 P | 0.40 | 0.30 | 2.9 | Excl |
| TOM70 (YNL121C) | 342 P | 92 A | 474 P | 231 P | 0.27 | 0.49 | 2.9 | Good |
| FIG2 (YCR089W) | 71 A | 34 P | 98 P | 27 P | 0.47 | 0.28 | 2.9 | Good |
| URA4 (YLR420W) | 1026 P | 328 P | 640 P | 245 P | 0.32 | 0.38 | 2.9 | Excl |
| ORF YJL213W | 87 A | 37 M | 76 P | 23 A | 0.42 | 0.30 | 2.9 | Good |
| ORF YOR001W | 774 P | 212 A | 346 P | 167 P | 0.27 | 0.48 | 2.9 | Good |
| ORF YLR415C | 126 A | 53 A | 14 A | -2 A | 0.42 | -0.15 | 2.9 Yes | Med |
| ORF YHR032W | 140 P | 58 P | 279 P | 84 P | 0.42 | 0.30 | 2.9 | Excl |
| POL12 (YBL035C) | 105 A | 29 A | 172 P | 82 P | 0.28 | 0.48 | 2.9 | Good |
| ORF YER075C | 72 M | 32 A | 70 P | 20 P | 0.44 | 0.29 | 2.9 | Good |
| ORF YGL159W | 147 P | 64 A | 185 P | 54 P | 0.44 | 0.29 | 2.9 | Good |

Figure 4N

| | | | | | | | | |
|---|---|---|---|---|---|---|---|---|
| ORF YGR021W | 45 | A | 19 | A | 37 | P | 11 | A | 0.42 | 0.30 | 2.8 | | Good |
| ORF YMR098C | 82 | M | 25 | A | 99 | P | 42 | P | 0.30 | 0.42 | 2.8 | | Good |
| ORF YPR016C | 1189 | P | 331 | P | 1220 | P | 586 | P | 0.28 | 0.48 | 2.8 | | Excl |
| ORF YBR016W | 1210 | P | 380 | P | 763 | P | 306 | P | 0.31 | 0.40 | 2.8 | | Excl |
| ORF YMR106C | 63 | M | 25 | A | 15 | A | 0 | A | 0.39 | 0.00 | 2.8 | Yes | Med |
| ORF YBR056W | 84 | A | 40 | M | 169 | P | 48 | P | 0.47 | 0.28 | 2.8 | | Good |
| MIG2 (YGL209W) | 372 | P | 173 | P | 582 | P | 166 | P | 0.47 | 0.29 | 2.8 | | Excl |
| KAP95 (YLR347C) | 308 | P | 102 | A | 267 | P | 102 | P | 0.33 | 0.38 | 2.8 | | Good |
| ATF2 (YGR177C) | 74 | A | 31 | M | 132 | P | 41 | P | 0.42 | 0.31 | 2.8 | | Good |
| ORF YDR440W | 54 | A | 15 | A | 102 | P | 50 | P | 0.28 | 0.49 | 2.8 | | Good |
| ORF YNR053C exon | 568 | P | 181 | P | 629 | P | 254 | P | 0.32 | 0.40 | 2.8 | | Excl |
| SUR1 (YPL057C) | 32 | A | 15 | A | 188 | P | 53 | P | 0.49 | 0.28 | 2.8 | | Good |
| ORF YHL046C (_f) | 217 | P | 87 | P | 268 | P | 86 | P | 0.40 | 0.32 | 2.8 | | Excl |
| ORF YLR073C | 255 | P | 109 | A | 199 | P | 61 | P | 0.43 | 0.31 | 2.8 | | Good |
| ORF YDL019C | 210 | P | 76 | P | 186 | P | 66 | P | 0.36 | 0.36 | 2.8 | | Excl |
| ORF YBR258C | 130 | P | 41 | P | 85 | P | 36 | P | 0.31 | 0.42 | 2.8 | | Excl |
| ORF YDR282C | 83 | A | 35 | A | 92 | P | 29 | P | 0.42 | 0.31 | 2.8 | | Good |
| ORF YHR169W | 217 | P | 65 | P | 208 | P | 92 | P | 0.30 | 0.44 | 2.8 | | Excl |
| YAP3 (YLR120C) | 289 | P | 111 | A | 274 | P | 94 | P | 0.38 | 0.34 | 2.8 | | Good |
| SRN2 (YLR119W) | 224 | P | 68 | A | 93 | P | 41 | M | 0.31 | 0.44 | 2.8 | | Good |
| ORF YGR031W | 174 | P | 50 | P | 107 | P | 53 | P | 0.29 | 0.49 | 2.8 | | Excl |
| ORF YDR279W | 92 | P | 38 | P | 60 | P | 19 | P | 0.42 | 0.32 | 2.8 | | Excl |
| RIB1 (YBL033C) | 217 | A | 97 | P | 293 | P | 90 | P | 0.44 | 0.31 | 2.8 | | Good |
| ORF YIR044C (_f) | 445 | P | 170 | P | 564 | P | 194 | P | 0.38 | 0.34 | 2.8 | | Excl |
| ASP3 (YLR155C) (_ | 124 | A | 40 | A | 110 | P | 45 | A | 0.33 | 0.41 | 2.8 | | Good |
| MET6 (YER091C) | 549 | P | 187 | P | 693 | P | 271 | P | 0.34 | 0.39 | 2.7 | | Excl |
| HMT1 (YBR034C) | 611 | P | 248 | P | 668 | P | 222 | P | 0.41 | 0.33 | 2.7 | | Excl |
| ORF YBR220C | 156 | A | 62 | A | 266 | P | 90 | P | 0.40 | 0.34 | 2.7 | | Good |
| ORF YGR230W | 75 | P | 32 | A | 60 | P | 20 | A | 0.42 | 0.32 | 2.7 | | Good |
| CEM1 (YER061C) | 128 | A | 41 | P | 73 | P | 32 | P | 0.32 | 0.43 | 2.7 | | Good |
| ORF YLR173W | 89 | A | 30 | A | 53 | P | 22 | A | 0.33 | 0.41 | 2.7 | | Good |
| STT4 (YLR305C) | 203 | P | 95 | A | 202 | P | 61 | P | 0.47 | 0.30 | 2.7 | | Good |
| ILV3 (YJR016C) | 926 | P | 272 | P | 634 | P | 313 | P | 0.29 | 0.49 | 2.7 | | Excl |
| AMD1 (YML035C) | 224 | P | 82 | P | 399 | P | 147 | P | 0.37 | 0.37 | 2.7 | | Excl |
| ORF YKL075C | 89 | P | 26 | M | 95 | P | 47 | P | 0.29 | 0.50 | 2.7 | | Good |
| ORF YLR220W | 253 | P | 93 | P | 263 | P | 98 | P | 0.37 | 0.37 | 2.7 | | Excl |

Figure 4O

| | | | | | | | |
|---|---|---|---|---|---|---|---|
| SMY1 (YKL079W) | 155 | P | 54 | A | 76 | P | 30 | P | 0.35 | 0.39 | 2.7 | | Good |
| TIF4631 (YGR162W) | 570 | P | 237 | P | 896 | P | 302 | P | 0.42 | 0.34 | 2.7 | | Excl |
| ORF YBR158W | 968 | P | 395 | P | 1064 | P | 365 | P | 0.41 | 0.34 | 2.7 | | Excl |
| PCT1 (YGR202C) | 81 | P | 33 | A | 86 | P | 30 | P | 0.40 | 0.35 | 2.7 | | Good |
| PFK2 (YMR205C) | 1487 | P | 656 | P | 1692 | P | 549 | P | 0.44 | 0.32 | 2.7 | | Excl |
| ORF YHL048W | 221 | A | 105 | P | 185 | P | 57 | P | 0.48 | 0.31 | 2.7 | | Good |
| ORF YDR286C | 92 | P | 35 | P | 68 | P | 25 | P | 0.38 | 0.37 | 2.7 | | Excl |
| SPE2 (YOL052C) | 237 | A | 85 | A | 232 | P | 91 | P | 0.36 | 0.39 | 2.7 | | Good |
| HSL7 (YBR133C) | 227 | P | 81 | P | 335 | P | 132 | P | 0.36 | 0.39 | 2.7 | | Excl |
| ORF YML122C | -50 | A | -65 | A | -20 | A | -31 | A | 1.30 | 1.59 | 2.7 | Yes | Med |
| ORF YKL073W | 179 | P | 77 | P | 173 | P | 58 | P | 0.43 | 0.34 | 2.7 | | Excl |
| DBP2 (YNL112W) ex | 2242 | P | 7191 | P | 3087 | P | 1414 | P | 0.32 | 0.46 | 2.7 | | Excl |
| ORF YBL011W | 224 | P | 80 | P | 281 | P | 112 | P | 0.36 | 0.40 | 2.6 | | Excl |
| HXT1 (YHR094C) | 1813 | P | 613 | P | 2773 | P | 1188 | P | 0.34 | 0.43 | 2.6 | | Excl |
| ORF YER124C | 196 | P | 79 | P | 370 | P | 132 | P | 0.40 | 0.36 | 2.6 | | Excl |
| ORF YER036C | 1038 | P | 414 | P | 1296 | P | 468 | P | 0.40 | 0.36 | 2.6 | | Excl |
| ORF YCL042W | 78 | A | 28 | A | 67 | P | 27 | P | 0.36 | 0.40 | 2.6 | | Good |
| ORF YAR009C (_i) | 3900 | P | 1944 | P | 3427 | P | 1051 | P | 0.50 | 0.31 | 2.6 | | Excl |
| ORF YJL020C | 204 | P | 87 | P | 156 | P | 53 | P | 0.43 | 0.34 | 2.6 | | Excl |
| ORF YHR182W | 108 | P | 41 | A | 104 | P | 40 | P | 0.38 | 0.38 | 2.6 | | Good |
| PAN1 (YIR006C) | 466 | P | 174 | P | 566 | P | 219 | P | 0.37 | 0.39 | 2.6 | | Excl |
| ORF YJR003C | 113 | A | 56 | A | 119 | P | 37 | A | 0.50 | 0.31 | 2.6 | | Good |
| TIR1 (YER011W) | 1362 | P | 458 | P | 2171 | P | 952 | P | 0.34 | 0.44 | 2.6 | | Excl |
| CBS1 (YDL069C) | 110 | P | 36 | P | 65 | P | 30 | P | 0.33 | 0.45 | 2.6 | | Excl |
| PMP1 (YCR024C-A) | 1852 | P | 850 | P | 3860 | P | 1263 | P | 0.46 | 0.33 | 2.6 | | Excl |
| ORF YPL247C | 342 | P | 131 | P | 55 | P | 21 | P | 0.38 | 0.38 | 2.6 | | Excl |
| SHM2 (YLR058C) | 3216 | P | 1307 | P | 3024 | P | 1101 | P | 0.41 | 0.36 | 2.6 | | Excl |
| RIB7 (YBR153W) | 141 | P | 47 | M | 175 | P | 81 | P | 0.33 | 0.46 | 2.6 | | Good |
| DRS1 (YLL008W) | 716 | P | 240 | P | 747 | P | 337 | P | 0.34 | 0.45 | 2.6 | | Excl |
| ORF YNL021W | 126 | A | 54 | A | 192 | P | 68 | P | 0.43 | 0.35 | 2.6 | | Excl |
| OLE1 (YGL055W) | 874 | P | 340 | P | 2086 | P | 799 | P | 0.39 | 0.38 | 2.6 | | Excl |
| ORF YBR177C | 195 | M | 67 | P | 230 | P | 101 | P | 0.35 | 0.44 | 2.6 | | Good |

Figure 4P

| | | | | | | |
|---|---|---|---|---|---|---|
| MIC1 (YGR100W) | 68 P | 22 A | 74 P | 36 P | 0.32 | 0.49 | Good |
| CLN3 (YAL040C) | 190 P | 94 P | 265 P | 84 P | 0.49 | 0.32 | Excl |
| TEF4 (YKL081W) ex | 416 P | 179 P | 741 P | 261 P | 0.43 | 0.35 | Excl |
| SNP1 (YIL061C) | 30 A | 10 A | 62 P | 29 P | 0.33 | 0.48 | Good |
| TUP1 (YCR084C) | 486 P | 183 P | 555 P | 224 P | 0.38 | 0.40 | Excl |
| YCRX07w/ (control?) | 73 A | 30 A | 85 P | 31 P | 0.41 | 0.37 | Good |
| PMP2 (YEL017C-A) | 860 P | 364 P | 2225 P | 807 P | 0.42 | 0.36 | Excl |
| ORF YBR017C | 111 A | 36 M | 205 P | 101 P | 0.32 | 0.49 | Good |
| FAT2 (YBR222C) | 135 P | 47 P | 140 P | 63 P | 0.34 | 0.45 | Excl |
| CLN2 (YPL256C) | 263 P | 131 A | 332 P | 107 P | 0.50 | 0.32 | Good |
| ORF YGR279C | 1866 P | 713 P | 3175 P | 1282 P | 0.38 | 0.40 | Excl |
| FUR4 (YBR021W) | 133 P | 52 A | 146 P | 57 P | 0.39 | 0.39 | Good |
| SAH1 (YER043C) | 2628 P | 1007 P | 2566 P | 1037 P | 0.38 | 0.40 | Excl |
| ORF YDR334W | 168 P | 60 P | 118 P | 51 P | 0.36 | 0.43 | Excl |
| ORF YBR075W | 251 P | 86 P | 288 P | 133 P | 0.34 | 0.46 | Excl |
| ZRT1 (YGL255W) | 115 P | 47 P | 392 P | 150 P | 0.40 | 0.38 | Excl |
| CBF2 (YGR140W) | 166 P | 54 A | 95 P | 47 P | 0.33 | 0.49 | Excl |
| ORF YBR241C | 179 P | 80 P | 180 P | 63 P | 0.45 | 0.35 | Excl |
| SMK1 (YPR054W) | 153 A | 54 A | 7 A | -5 A | 0.35 | -0.71 | Med |
| GLY1 (YEL046C) | 1102 P | 387 P | 986 P | 447 P | 0.35 | 0.45 | 2.5 Yes Excl |
| ORF YDR118W | 56 A | 191 A | 34 P | 17 A | 0.33 | 0.49 | Good |
| ORF YDL109C | 116 A | 41 A | 74 P | 34 P | 0.35 | 0.46 | Good |
| ORF YHR149C | 257 P | 88 P | 163 P | 77 P | 0.34 | 0.48 | Excl |
| RPL27B (YDR471W) | 3563 P | 1586 P | 3773 P | 1363 P | 0.45 | 0.36 | Excl |
| HAC1 (YFL031W) | 1264 P | 468 P | 951 P | 411 P | 0.37 | 0.43 | Excl |
| ORF YOR009W | 626 A | 265 A | 353 P | 133 A | 0.42 | 0.38 | Good |
| STE4 (YOR212W) | 342 A | 131 A | 648 P | 270 P | 0.38 | 0.42 | Good |
| ORF YCL005W | 124 M | 50 P | 141 P | 56 P | 0.40 | 0.39 | Good |
| ORF YJR019C | 121 P | 54 A | 93 A | 33 A | 0.45 | 0.36 | Excl |
| ORF YCL063W | 97 P | 42 A | 56 P | 21 P | 0.43 | 0.37 | Good |
| ORF YIL176C (_f) | 319 P | 138 P | 447 P | 167 P | 0.43 | 0.37 | Good |
| ORF YDR395W | 206 A | 85 P | 432 P | 169 P | 0.41 | 0.39 | Excl |
| ORF YOL158C | 274 P | 115 A | 364 P | 140 P | 0.42 | 0.38 | Good |
| ORF YBL020W | 195 P | 66 A | 203 P | 100 P | 0.34 | 0.49 | Good |
| NOP1 (YDL014W) | 3449 P | 1397 P | 3311 P | 1330 P | 0.40 | 0.40 | Good |
| ORF YGL081W | 138 A | 53 A | 23 P | 10 A | 0.39 | 0.42 | Excl |
| ORF YBR230C exon | 197 P | 98 P | 238 P | 81 P | 0.50 | 0.34 | Excl |

Figure 4Q

| | | | | | | | |
|---|---|---|---|---|---|---|---|
| SRA3 (YJL164C) | 129 | A | 60 | A | 129 | P | 46 | A | 0.46 | 0.36 | 2.5 | Good |
| ORF YMR006C | 313 | P | 153 | P | 260 | P | 90 | P | 0.49 | 0.35 | 2.5 | Excl |
| PAB1 (YER165W) | 979 | P | 439 | P | 1408 | P | 524 | P | 0.45 | 0.37 | 2.5 | Excl |
| ORF YGR241C | 362 | P | 161 | P | 207 | P | 77 | P | 0.45 | 0.37 | 2.5 | Excl |
| DRS2 (YAL026C) | 81 | A | 33 | A | 132 | P | 55 | P | 0.40 | 0.42 | 2.4 | Good |
| SSB1 (YDL229W) | 12479 | P | 5100 | P | 9147 | P | 3757 | P | 0.41 | 0.41 | 2.4 | Excl |
| CTR1 (YPR124W) | 779 | P | 300 | P | 676 | P | 297 | P | 0.39 | 0.44 | 2.4 | Excl |
| ORF YML018C | 363 | P | 147 | A | 218 | P | 90 | P | 0.41 | 0.42 | 2.4 | Good |
| ORF YAR075W (_f) | 514 | P | 208 | P | 744 | P | 311 | P | 0.40 | 0.42 | 2.4 | Excl |
| ORF YGR245C | 370 | P | 153 | P | 416 | P | 170 | P | 0.41 | 0.41 | 2.4 | Excl |
| GEF1 (YJR040W) | 139 | P | 53 | P | 97 | P | 44 | P | 0.38 | 0.45 | 2.4 | Excl |
| ORF YMR216C | 37 | A | 18 | A | 109 | P | 40 | P | 0.48 | 0.36 | 2.4 | Good |
| PPZ2 (YDR436W) | 130 | A | 50 | M | 66 | P | 30 | P | 0.38 | 0.45 | 2.4 | Good |
| ORF YKR038C | 329 | P | 135 | P | 246 | P | 103 | P | 0.41 | 0.42 | 2.4 | Excl |
| ORF YLR206W | 379 | P | 168 | A | 168 | P | 66 | M | 0.44 | 0.39 | 2.4 | Good |
| ORF YDR248C | 160 | A | 77 | P | 158 | P | 58 | P | 0.48 | 0.37 | 2.4 | Good |
| ORF YGR111W | 60 | P | 22 | A | 134 | P | 66 | P | 0.36 | 0.49 | 2.4 | Good |
| LEU2 (YCL018W) | 589 | P | 256 | P | 674 | P | 270 | P | 0.43 | 0.40 | 2.4 | Excl |
| ORF YLR144C | 55 | A | 26 | A | 144 | P | 54 | P | 0.48 | 0.37 | 2.4 | Good |
| ORF YHR130C | 91 | P | 42 | A | 182 | P | 70 | P | 0.46 | 0.38 | 2.4 | Good |
| CDC24 (YAL041W) | 94 | A | 35 | A | 135 | P | 64 | P | 0.37 | 0.48 | 2.4 | Good |
| ORF YDR094W | 157 | P | 62 | P | 226 | P | 102 | P | 0.39 | 0.45 | 2.4 | Excl |
| ORF YMR153W | 192 | P | 77 | P | 198 | P | 87 | P | 0.40 | 0.44 | 2.4 | Excl |
| ORF YHR108W | 238 | P | 118 | P | 270 | P | 98 | P | 0.50 | 0.36 | 2.4 | Excl |
| ORF YNL179C | 53 | A | 23 | A | 23 | P | 9 | A | 0.44 | 0.41 | 2.4 | Good |
| YGP1 (YNL160W) | 1568 | P | 669 | P | 2260 | P | 945 | P | 0.43 | 0.42 | 2.4 | Excl |
| ORF YGR036C | 109 | P | 53 | P | 319 | P | 119 | P | 0.49 | 0.37 | 2.4 | Excl |
| ORF YLR432W | 489 | P | 200 | P | 932 | P | 412 | P | 0.41 | 0.44 | 2.4 | Excl |
| MCM2 (YBL023C) | 51 | A | 23 | A | 74 | P | 30 | A | 0.46 | 0.40 | 2.3 | Good |
| ORF YNR048W | 195 | P | 85 | A | 110 | P | 46 | P | 0.43 | 0.42 | 2.3 | Good |
| EMP70 (YLR083C) | 295 | P | 126 | P | 654 | P | 281 | P | 0.43 | 0.43 | 2.3 | Excl |

Figure 4R

| | | | | | | | |
|---|---|---|---|---|---|---|---|
| ORF YNR018W | 2058 P | 842 P | 817 P | 369 P | 0.41 | 0.45 | 2.3 | Excl |
| ORF YBL032W | 271 P | 122 P | 279 P | 115 P | 0.45 | 0.41 | 2.3 | Excl |
| ORF YPL133C | -11 A | -23 A | 51 P | 24 M | 2.19 | 0.47 | 2.3 Yes | Med |
| ORF YFL027C | 164 P | 76 P | 147 P | 59 P | 0.46 | 0.40 | 2.3 | Excl |
| ORF YDR026C | 86 M | 35 M | 61 P | 28 P | 0.41 | 0.46 | 2.3 | Good |
| GNP1 (YDR508C) | 960 P | 416 P | 1420 P | 607 P | 0.43 | 0.43 | 2.3 | Excl |
| ACS1 (YAL054C) | 108 A | 43 A | 52 P | 24 A | 0.40 | 0.47 | 2.3 | Good |
| GND1 (YHR183W) | 1868 P | 868 P | 3359 P | 1347 P | 0.46 | 0.40 | 2.3 | Excl |
| CYB2 (YML054C) | 84 A | 33 A | 77 P | 37 P | 0.40 | 0.47 | 2.3 | Good |
| ORF YCR035C | 446 P | 186 P | 526 P | 237 P | 0.42 | 0.45 | 2.3 | Excl |
| ORF YFL035C-B exoı | 577 P | 244 P | 1110 P | 493 P | 0.42 | 0.44 | 2.3 | Excl |
| MIS1 (YBR084W) | 914 P | 415 P | 1093 P | 452 P | 0.45 | 0.41 | 2.3 | Excl |
| FKH2 (YNL068C) | -16 A | -27 A | 108 P | 45 P | 1.71 | 0.42 | 2.3 | Med |
| ACT1 (YFL039C) exc | 3257 P | 1408 P | 4368 P | 1898 P | 0.43 | 0.43 | 2.3 Yes | Excl |
| ORF YHR061C | 72 A | 34 A | 95 P | 38 P | 0.47 | 0.41 | 2.3 | Good |
| ORF YDR444W | 138 P | 55 A | 86 P | 42 P | 0.40 | 0.49 | 2.3 | Good |
| RPL4A (YHL033C) | 1542 P | 696 P | 4133 P | 1747 P | 0.45 | 0.42 | 2.3 | Excl |
| ORF YLR089C | 247 P | 109 P | 307 P | 133 P | 0.44 | 0.43 | 2.3 | Excl |
| ORF YBR167C | 89 P | 41 P | 104 P | 43 P | 0.46 | 0.42 | 2.3 | Excl |
| ORF YGL261C (_f) | 219 P | 91 A | 221 P | 102 P | 0.42 | 0.46 | 2.3 | Excl |
| ORF YGR200C | 400 P | 177 P | 630 P | 273 P | 0.44 | 0.43 | 2.3 | Excl |
| ERG5 (YMR015C) | 245 P | 105 A | 433 P | 194 P | 0.43 | 0.45 | 2.3 | Good |
| ORF YGR294W (_f) | 472 P | 221 P | 708 P | 293 P | 0.47 | 0.41 | 2.3 | Excl |
| ORF YLR177W | 205 P | 95 P | 185 P | 77 P | 0.46 | 0.42 | 2.3 | Excl |
| PDR5 (YOR153W) | 1116 P | 450 P | 2632 P | 1271 P | 0.40 | 0.48 | 2.3 | Excl |
| ORF YMR187C | -11 A | -21 A | 81 P | 33 A | 2.00 | 0.41 | 2.3 Yes | Med |
| ORF YLR265C | 153 A | 61 A | 104 P | 51 P | 0.40 | 0.49 | 2.3 | Good |
| ORF YAR009C (_f) | 2668 P | 1200 P | 2552 P | 1099 P | 0.45 | 0.43 | 2.3 | Excl |
| ORF YIL164C | 66 A | 32 A | 64 P | 26 A | 0.48 | 0.41 | 2.3 | Good |
| FUR1 (YHR128W) | 936 P | 389 P | 1112 P | 531 P | 0.42 | 0.48 | 2.3 | Excl |
| ORF YKR090W | 153 M | 70 A | 72 P | 31 A | 0.46 | 0.43 | 2.2 | Good |
| CLB1 (YGR108W) | 219 P | 104 P | 216 P | 91 P | 0.47 | 0.42 | 2.2 | Excl |
| PRY2 (YKR013W) | 1361 P | 665 P | 724 P | 299 P | 0.49 | 0.41 | 2.2 | Excl |
| HXK2 (YGL253W) | 3757 P | 1614 P | 3678 P | 1732 P | 0.43 | 0.47 | 2.2 | Excl |
| RNR1 (YER070W) | 479 P | 223 P | 396 P | 172 P | 0.46 | 0.43 | 2.2 | Excl |

Figure 4S

| | 160 | P | 77 | P | 148 | P | 62 | P | 0.48 | 0.42 | 2.2 | | Excl |
|---|---|---|---|---|---|---|---|---|---|---|---|---|---|
| ORF YER186C | 160 | P | 77 | P | 148 | P | 62 | P | 0.48 | 0.42 | 2.2 | | Excl |
| ORF YDL044C | 57 | A | 28 | A | 75 | P | 31 | P | 0.49 | 0.42 | 2.2 | | Good |
| PET309 (YLR067C) | 0 | A | -11 | A | 53 | P | 23 | A | #DIV/0! | 0.43 | 2.2 | Yes | Med |
| ORF YGL084C | 153 | P | 63 | P | 190 | P | 95 | P | 0.41 | 0.50 | 2.2 | | Excl |
| SYG1 (YIL047C) | 574 | P | 259 | P | 640 | P | 289 | P | 0.45 | 0.45 | 2.2 | | Excl |
| LYS4 (YDR234W) | 641 | P | 293 | P | 623 | P | 279 | P | 0.46 | 0.45 | 2.2 | | Excl |
| YCK2 (YNL154C) | 1158 | P | 508 | P | 464 | P | 218 | P | 0.44 | 0.47 | 2.2 | | Excl |
| ORF YHR070W | 509 | P | 228 | P | 603 | P | 277 | P | 0.45 | 0.46 | 2.2 | | Excl |
| ROK1 (YGL171W) | 257 | P | 111 | P | 323 | P | 155 | P | 0.43 | 0.48 | 2.2 | | Excl |
| MTR2 (YKL186C) | 316 | P | 140 | A | 220 | P | 102 | P | 0.44 | 0.47 | 2.2 | | Good |
| KNR4 (YGR229C) | 787 | P | 336 | P | 704 | P | 344 | P | 0.43 | 0.49 | 2.2 | | Excl |
| ORF YIL123W | 896 | P | 431 | P | 1453 | P | 631 | P | 0.48 | 0.43 | 2.2 | | Excl |
| GLS1 (YLR342W) | 1008 | P | 488 | P | 1668 | P | 722 | P | 0.48 | 0.43 | 2.2 | | Excl |
| ORF YLR024C | 26 | P | 12 | A | 67 | P | 30 | P | 0.47 | 0.45 | 2.2 | | Good |
| POL30 (YBR088C) | 929 | P | 463 | P | 1014 | P | 430 | P | 0.50 | 0.42 | 2.2 | | Excl |
| ORF YML006C | 218 | A | 109 | P | 248 | P | 105 | P | 0.50 | 0.42 | 2.2 | | Good |
| CDC7 (YDL017W) | 92 | P | 40 | A | 69 | P | 34 | P | 0.43 | 0.49 | 2.2 | | Good |
| ORF YEL056W | 364 | P | 159 | P | 223 | P | 108 | P | 0.44 | 0.48 | 2.2 | | Excl |
| PSA1 (YDL055C) | 1651 | P | 729 | P | 2501 | P | 1195 | P | 0.44 | 0.48 | 2.2 | | Excl |
| CHS2 (YBR038W) | 94 | P | 47 | P | 250 | P | 108 | P | 0.50 | 0.43 | 2.2 | | Excl |
| ORF YLR427W | 200 | P | 91 | A | 142 | P | 67 | P | 0.46 | 0.47 | 2.2 | | Good |
| ORF YER110C | 491 | P | 243 | P | 478 | P | 210 | P | 0.49 | 0.44 | 2.2 | | Excl |
| ORF YGR025W | 92 | P | 42 | A | 78 | A | 38 | M | 0.45 | 0.48 | 2.2 | | Good |
| ORF YPL076W | -16 | A | -27 | A | 48 | P | 23 | A | 1.71 | 0.48 | 2.1 | Yes | Med |
| ORF YIL059C | 145 | P | 71 | A | 182 | P | 81 | P | 0.49 | 0.45 | 2.1 | | Good |
| ADH4 (YGL256W) | 694 | P | 335 | P | 867 | P | 393 | P | 0.48 | 0.45 | 2.1 | | Excl |
| ORF YOL109W | 15974 | P | 7131 | P | 6496 | P | 3190 | P | 0.45 | 0.49 | 2.1 | | Excl |
| KCS1 (YDR017C) | 235 | P | 114 | P | 283 | P | 128 | P | 0.49 | 0.45 | 2.1 | | Excl |
| ENO1 (YGR254W) | 1842 | P | 896 | P | 3066 | P | 1385 | P | 0.49 | 0.45 | 2.1 | | Excl |
| STD1 (YOR047C) | 253 | A | 119 | A | 364 | P | 170 | P | 0.47 | 0.47 | 2.1 | | Good |
| MAK16 (YAL025C) | 346 | P | 158 | P | 446 | P | 215 | P | 0.46 | 0.48 | 2.1 | | Excl |
| ORF YLR002C | 103 | P | 47 | A | 234 | P | 112 | P | 0.46 | 0.48 | 2.1 | | Good |
| ORF YIL082W-A exa | 130 | P | 61 | P | 104 | P | 49 | P | 0.47 | 0.47 | 2.1 | | Excl |

Figure 4T

| | | | | | | |
|---|---|---|---|---|---|---|
| ORF YDR341C | 1544 P | 752 P | 1613 P | 739 P | 0.49 | 0.46 | 2.1 | Excl |
| SPA2 (YLL021W) | 134 A | 61 A | 225 P | 110 P | 0.46 | 0.49 | 2.1 | Good |
| ORF YBR086C | 1192 P | 576 P | 1111 P | 514 P | 0.48 | 0.46 | 2.1 | Excl |
| ORF YLR033W | 97 A | 46 A | 103 P | 49 P | 0.47 | 0.48 | 2.1 | Good |
| ORF YLL002W | 103 P | 51 A | 73 P | 33 M | 0.50 | 0.46 | 2.1 | Good |
| ORF YGL223C | 121 P | 58 P | 119 P | 56 P | 0.48 | 0.47 | 2.1 | Excl |
| BUD2 (YKL092C) | 121 A | 60 P | 52 P | 24 P | 0.49 | 0.46 | 2.1 | Good |
| FLO1 (YAR050W) | 46 A | 22 A | 51 P | 24 A | 0.48 | 0.48 | 2.1 | Good |
| EFB1 (YAL003W) ex | 5059 P | 2513 P | 5538 P | 2563 P | 0.50 | 0.46 | 2.1 | Excl |
| GDS1 (YOR355W) | 405 P | 192 P | 665 P | 323 P | 0.47 | 0.48 | 2.1 | Excl |
| ORF YBR162C | 1205 P | 572 P | 1473 P | 715 P | 0.47 | 0.49 | 2.1 | Excl |
| ORF YNL096C exon | 2958 P | 1462 P | 2373 P | 1113 P | 0.49 | 0.47 | 2.1 | Excl |
| ORF YPR010C | 1658 P | 796 P | 1568 P | 759 P | 0.48 | 0.48 | 2.1 | Excl |
| ORF YOL061W | 1305 P | 619 P | 1153 P | 570 P | 0.47 | 0.49 | 2.1 | Good |
| SIS2 (YKR072C) | 203 P | 100 A | 233 P | 112 P | 0.49 | 0.48 | 2.1 | Excl |
| ORF YDR361C | 298 P | 143 P | 318 P | 158 P | 0.48 | 0.48 | 2.0 | Excl |
| ORF YHR020W | 1468 P | 709 P | 1966 P | 978 P | 0.48 | 0.50 | 2.0 | Excl |
| GLT1 (YDL171C) | 887 P | 431 P | 729 P | 363 P | 0.49 | 0.50 | 2.0 | Excl |
| ORF YMR100W | 147 P | 72 A | 152 P | 75 P | 0.49 | 0.50 | 2.0 | Good |
| RPL9A (YGL147C) ( | 4547 P | 2234 P | 5268 P | 2632 P | 0.49 | 0.50 | 2.0 | Excl |
| ORF YDR267C | 205 P | 102 P | 230 P | 113 P | 0.50 | 0.49 | 2.0 | Excl |

Figure 4U

Sin4 Up

| Gene | WT#1 | ncWT#1 | MUT#1 | ncMUT#1 | WT#2 | ncWT#2 | MUT#2 | ncMUT#2 | MT1/WT1 | MT2/WT2 | Average Fold Up | Corrected? | Confidence |
|---|---|---|---|---|---|---|---|---|---|---|---|---|---|
| ALD4 (YMR169C) | 35 | P | 94 | P | 36 | P | 88 | P | 2.7 | 2.4 | 2.6 | | Excl |
| AMS1 (YGL156W) | 59 | P | 151 | P | 45 | P | 151 | P | 2.6 | 3.3 | 2.9 | | Excl |
| ARG1 (YOL058W) | 69 | P | 969 | P | 71 | P | 1015 | P | 14.0 | 14.3 | 14.2 | | Excl |
| ARG3 (YJL088W) | 25 | A | 141 | P | 33 | A | 149 | P | 5.6 | 4.6 | 5.1 | | Good |
| CIN1 (YOR349W) | 67 | P | 288 | P | 72 | P | 304 | P | 4.3 | 4.2 | 4.3 | | Excl |
| COT1 (YOR316C) | 452 | P | 921 | P | 442 | P | 923 | P | 2.0 | 2.1 | 2.1 | | Excl |
| COX4 (YGL187C) | 923 | P | 2072 | P | 824 | P | 1859 | P | 2.2 | 2.3 | 2.3 | | Excl |
| CTT1 (YGR088W) | 49 | P | 271 | P | 62 | P | 287 | P | 5.5 | 4.6 | 5.1 | | Excl |
| CWP1 (YKL096W) | 1803 | P | 3931 | P | 1895 | P | 3881 | P | 2.2 | 2.0 | 2.1 | | Excl |
| CYC7 (YEL039C) | 73 | P | 412 | P | 72 | P | 291 | P | 5.6 | 4.0 | 4.8 | | Excl |
| CYT1 (YOR065W) | 107 | P | 426 | P | 118 | P | 515 | P | 4.0 | 4.4 | 4.2 | | Excl |
| FIG1 (YBR040W) | 2 | A | 15 | A | 5 | A | 15 | A | 7.4 | 3.1 | 5.3 | | Good |
| FLO1 (YAR050W) | 29 | P | 782 | P | 36 | P | 843 | P | 27.0 | 23.1 | 25.1 | | Excl |
| FLO9 (YAL064W) | -43 | A | -24 | A | -36 | A | -12 | A | 0.6 | 0.3 | 4.3 | Yes | Med |
| GIN11 (YLL065W) | -42 | A | -22 | A | -38 | A | -14 | A | 0.5 | 0.4 | 4.3 | Yes | Med |
| GPH1 (YPR160W) | 161 | P | 475 | P | 169 | P | 522 | P | 2.9 | 3.1 | 3.0 | | Excl |
| GPM2 (YDL021W) | 37 | P | 80 | P | 34 | P | 72 | P | 2.2 | 2.2 | 2.2 | | Excl |
| GSC2 (YGR032W) | 351 | P | 1357 | P | 376 | P | 1358 | P | 3.9 | 3.6 | 3.7 | | Excl |
| HAP4 (YKL109W) | 180 | P | 505 | P | 203 | P | 472 | P | 2.8 | 2.3 | 2.6 | | Excl |
| HSP12 (YFL014W) | 518 | P | 6075 | P | 476 | P | 5906 | P | 11.7 | 12.4 | 12.1 | | Excl |
| HXT4 (YHR092C) | 352 | P | 1114 | P | 389 | P | 1194 | P | 3.2 | 3.1 | 3.1 | | Excl |
| HXT5 (YHR096C) | 8 | A | 28 | A | 15 | A | 39 | P | 3.5 | 2.6 | 3.0 | | Good |
| HXT7 (YDR342C) | 1554 | P | 4687 | P | 1678 | P | 3927 | P | 3.0 | 2.3 | 2.7 | | Excl |
| INH1 (YDL181W) | 170 | P | 344 | P | 170 | P | 392 | P | 2.0 | 2.3 | 2.2 | | Excl |
| KIN82 (YCR091W) | 12 | P | 38 | P | 23 | P | 48 | P | 3.2 | 2.1 | 2.6 | | Excl |
| KNH1 (YDL049C) | 23 | A | 102 | P | 17 | P | 110 | P | 4.4 | 6.6 | 5.5 | | Good |
| LAP3 (YNL239W) | 629 | P | 1692 | P | 710 | P | 1844 | P | 2.7 | 2.6 | 2.6 | | Excl |
| LAP4 (YKL103C) | 141 | P | 408 | P | 113 | P | 473 | P | 2.9 | 4.2 | 3.5 | | Excl |
| LEE1 (YPL054W) | 0 | A | 46 | P | -8 | A | 36 | A | #DIV/0! | -4.6 | 9.1 | Yes | Med |
| LYS2 (YBR115C) | 666 | P | 1520 | P | 639 | P | 1459 | P | 2.3 | 2.3 | 2.3 | | Excl |

Figure 5A

| | 268 P | 812 P | 277 P | 814 P | | | | | |
|---|---|---|---|---|---|---|---|---|---|
| MET10 (YFR030W) | 559 P | 2527 P | 611 P | 2320 P | 3.0 | 2.9 | 3.0 | | Excl |
| MET14 (YKL001C) | 138 P | 377 P | 109 P | 360 P | 4.5 | 3.8 | 4.2 | | Excl |
| MET16 (YPR167C) | 157 P | 866 P | 167 P | 909 P | 2.7 | 3.3 | 3.0 | | Excl |
| MET2 (YNL277W) | 2596 P | 6509 P | 2542 P | 6588 P | 5.5 | 5.5 | 5.5 | | Excl |
| MET25 (YLR303W) | -6 A | 174 P | -14 A | 162 P | 2.5 | 2.6 | 2.5 | | Excl |
| MET28 (YIR017C) | 132 P | 725 P | 128 P | 697 P | -29.0 | -11.7 | 35.6 | Yes | Med |
| MET3 (YJR010W) | 297 P | 662 P | 312 P | 746 P | 5.5 | 5.4 | 5.5 | | Excl |
| MSN4 (YKL062W) | 122 P | 469 P | 107 P | 430 P | 2.2 | 2.4 | 2.3 | | Excl |
| NCA3 (YJL116C) | 31 P | 80 P | 31 P | 67 P | 3.8 | 4.0 | 3.9 | | Excl |
| ORF YAL028W | 3 A | 22 P | 5 A | 41 P | 2.6 | 2.2 | 2.4 | | Excl |
| ORF YAL066W | -75 A | -22 A | -74 A | -64 A | 7.2 | 8.4 | 7.8 | | Good |
| ORF YAR052C (_i) | -11 A | 8 A | -10 A | 3 A | 0.3 | 0.9 | 6.4 | Yes | Med |
| ORF YAR064W (_f) | 44 P | 493 P | 70 P | 410 P | -0.7 | -0.3 | 3.2 | Yes | Med |
| ORF YBR012C | -42 A | -22 A | -19 A | 38 A | 11.2 | 5.9 | 8.5 | | Excl |
| ORF YBR012W-B exl | -2 A | 23 P | 11 A | 29 P | 0.5 | -2.0 | 7.7 | Yes | Med |
| ORF YCL023C | -7 A | 5 A | -7 A | 7 A | -11.5 | 2.7 | 3.9 | Yes | Med |
| ORF YCL026C (_f) | 1 A | 20 A | 3 A | 45 P | -0.8 | -1.0 | 2.6 | Yes | Med |
| ORF YDL024C | 1 A | 14 A | 4 A | 29 A | 20.3 | 15.1 | 17.7 | | Good |
| ORF YDL085W | -1 A | 22 M | 12 M | 33 P | 13.5 | 7.4 | 10.5 | | Good |
| ORF YDL218W | 5 A | 22 A | 4 A | 40 P | -21.7 | 2.8 | 3.6 | Yes | Med |
| ORF YDL248W (_r) | 814 P | 2225 P | 8431 P | 2265 P | 4.3 | 10.0 | 7.2 | | Good |
| ORF YDR007W | 46 P | 93 P | 17 P | 55 P | 2.7 | 2.7 | 2.7 | | Excl |
| ORF YDR008C | 23 A | 57 P | 13 A | 29 A | 2.0 | 3.3 | 2.7 | | Excl |
| ORF YDR149C | 40 P | 115 P | 46 P | 131 P | 2.5 | 2.3 | 2.4 | | Good |
| ORF YDR253C | 35 P | 95 P | 47 P | 98 P | 2.9 | 2.8 | 2.9 | | Med |
| ORF YDR259C | -10 A | 5 A | -8 M | 9 A | 2.7 | 2.1 | 2.4 | | Excl |
| ORF YDR437W | 27 P | 61 P | 27 P | 63 P | -0.5 | -1.1 | 3.2 | Yes | Med |
| ORF YEL030W | -1 A | 11 A | 7 A | 18 A | 2.3 | 2.4 | 2.3 | | Med |
| ORF YEL073C | 215 P | 462 P | 211 P | 495 P | -11.4 | 2.6 | 2.5 | Yes | Med |
| ORF YER053C | 103 P | 786 P | 113 P | 997 P | 2.2 | 2.3 | 2.2 | | Excl |
| ORF YER150W | -5 A | 32 M | -11 A | 0 A | 7.6 | 8.9 | 8.2 | | Excl |
| ORF YGL090W | -13 A | -1 A | -16 A | 15 A | -6.4 | 0.0 | 4.8 | Yes | Med |
| ORF YGL170C | -8 A | 4 A | -19 A | -6 A | 0.1 | -1.0 | 4.3 | Yes | Med |
| ORF YGL235W | -1 A | 10 A | 0 A | 10 A | -0.5 | 0.3 | 2.4 | Yes | Med |
| ORF YGL249W | | | | | -10.2 | #DIV/0! | 2.1 | Yes | Med |

Figure 5B

| ORF | | | | | | | | | |
|---|---|---|---|---|---|---|---|---|---|
| ORF YGR023W | 27 | A | 81 | P | 16 | A | 80 | P | 3.0 | 5.0 | 4.0 | | Good |
| ORF YGR043C | 43 | P | 119 | P | 15 | P | 156 | P | 2.8 | 10.5 | 6.6 | | Excl |
| ORF YGR052W | 32 | P | 441 | P | 18 | A | 448 | P | 13.8 | 25.2 | 19.5 | | Good |
| ORF YHL040C | 579 | P | 1709 | P | 566 | P | 1616 | P | 3.0 | 2.9 | 2.9 | | Excl |
| ORF YHR087W | 175 | P | 548 | P | 176 | P | 596 | P | 3.1 | 3.4 | 3.3 | | Excl |
| ORF YIL006W | 2 | A | 36 | A | -12 | A | 37 | A | 17.8 | -3.1 | 13.8 | Yes | Med |
| ORF YIL037C | -4 | A | 13 | A | -19 | A | 3 | A | -3.2 | -0.1 | 3.8 | Yes | Med |
| ORF YIL057C | -41 | A | -25 | A | -81 | A | -24 | A | 0.6 | 0.3 | 7.2 | Yes | Med |
| ORF YIL082W-A exd | 112 | P | 259 | P | 135 | P | 325 | P | 2.3 | 2.4 | 2.4 | | Excl |
| ORF YIL120W | 8 | A | 32 | M | -2 | A | 13 | A | 4.0 | -6.5 | 3.5 | Yes | Med |
| ORF YIR018W | 107 | P | 249 | P | 118 | A | 283 | P | 2.3 | 2.4 | 2.4 | | Good |
| ORF YJL077C | -5 | A | 17 | A | -21 | A | 1 | A | -3.3 | -0.1 | 4.4 | Yes | Med |
| ORF YJR023C | -21 | A | 10 | A | -4 | A | 8 | P | -0.5 | -1.9 | 4.4 | Yes | Med |
| ORF YJR025C | 1205 | P | 2857 | P | 1097 | P | 2718 | P | 2.4 | 2.5 | 2.4 | | Excl |
| ORF YJR079W exon | -5 | A | 8 | A | 15 | A | 34 | P | -1.7 | 2.2 | 2.4 | Yes | Med |
| ORF YJR137C | 160 | P | 409 | P | 187 | P | 382 | P | 2.6 | 2.0 | 2.3 | | Excl |
| ORF YJR150C | -32 | A | 162 | A | -35 | A | 139 | A | -5.1 | -3.9 | 36.8 | Yes | Med |
| ORF YKL030W | -7 | A | 22 | A | -13 | A | 31 | A | -3.2 | -2.3 | 7.4 | Yes | Med |
| ORF YKL031W | -51 | A | -35 | A | -84 | A | -17 | A | 0.7 | 0.2 | 8.3 | Yes | Med |
| ORF YKL202W | 10 | A | 52 | P | 7 | A | 58 | P | 5.2 | 8.7 | 6.9 | | Good |
| ORF YKR069W | 222 | P | 482 | P | 219 | P | 483 | P | 2.2 | 2.2 | 2.2 | | Excl |
| ORF YLR012C | -16 | A | 32 | P | -14 | A | 1 | A | -2.0 | -0.1 | 6.4 | Yes | Med |
| ORF YLR035C | -12 | A | 15 | M | -29 | A | -7 | A | -1.3 | 0.2 | 4.9 | Yes | Med |
| ORF YLR080W | 42 | P | 84 | A | 40 | P | 100 | P | 2.0 | 2.5 | 2.3 | | Good |
| ORF YLR092W | 107 | P | 448 | P | 116 | P | 596 | P | 4.2 | 5.1 | 4.7 | | Excl |
| ORF YLR140W | 11 | A | 32 | A | -30 | A | 25 | A | 2.9 | -0.8 | 7.0 | Yes | Med |
| ORF YLR149C | 27 | P | 66 | P | 21 | P | 104 | P | 2.4 | 5.0 | 3.7 | | Excl |
| ORF YLR169W | 13 | A | 28 | A | 9 | A | 31 | A | 2.2 | 3.5 | 2.8 | | Good |
| ORF YLR205C | 138 | P | 346 | P | 154 | P | 598 | P | 2.5 | 3.9 | 3.2 | | Excl |
| ORF YLR235C | -16 | A | -1 | A | -46 | A | 3 | A | 0.1 | -0.1 | 6.4 | Yes | Med |
| ORF YLR254C | 93 | P | 205 | P | 63 | P | 149 | P | 2.2 | 2.4 | 2.3 | | Excl |
| ORF YLR280C (_f) | 12 | A | 44 | A | -8 | A | 45 | P | 3.6 | -5.8 | 7.1 | Yes | Med |
| ORF YLR281C | 10 | A | 70 | A | 34 | A | 77 | P | 7.0 | 2.3 | 4.6 | | Good |
| ORF YLR307W | -3 | A | 22 | M | -11 | A | 1 | A | -7.5 | -0.1 | 3.8 | Yes | Med |
| ORF YLR458W | -36 | A | -14 | A | -41 | A | -7 | A | 0.4 | 0.2 | 5.6 | Yes | Med |

Figure 5C

| | -1 | A | 10 | A | 0 | A | 13 | A | -9.8 | #DIV/0! | 2.3 | Yes | Med |
|---|---|---|---|---|---|---|---|---|---|---|---|---|---|
| ORF YML035C-A | | | | | | | | | | | | | |
| ORF YML087C | 15 | A | 70 | P | -19 | P | 48 | P | 4.7 | -2.5 | 9.0 | Yes | Med |
| ORF YML118W | 25 | P | 51 | P | 15 | P | 46 | P | 2.0 | 3.0 | 2.5 | | Excl |
| ORF YMR040W | 70 | P | 218 | P | 46 | P | 275 | P | 3.1 | 5.9 | 4.5 | | Excl |
| ORF YMR041C | 152 | P | 526 | P | 143 | P | 539 | P | 3.5 | 3.8 | 3.6 | | Med |
| ORF YMR107W | -16 | A | 11 | A | -4 | A | 13 | A | -0.7 | -2.9 | 4.4 | Yes | Excl |
| ORF YMR196W | 44 | P | 167 | P | 76 | P | 166 | P | 3.8 | 2.2 | 3.0 | | Good |
| ORF YMR244W | 28 | A | 81 | P | 17 | A | 83 | P | 2.9 | 4.9 | 3.9 | | Excl |
| ORF YMR250W | 147 | P | 401 | P | 157 | P | 464 | P | 2.7 | 3.0 | 2.8 | | Good |
| ORF YMR251W | 18 | M | 78 | P | 3 | A | 57 | P | 4.3 | 16.9 | 10.6 | | Med |
| ORF YNL018C (_r_) | -88 | A | -70 | A | -82 | A | -25 | A | 0.8 | 0.3 | 7.6 | Yes | Good |
| ORF YNL128W | 3 | M | 19 | A | 15 | A | 31 | P | 6.4 | 2.1 | 4.2 | | Med |
| ORF YNL194C | -7 | A | 20 | M | -29 | A | -5 | A | -2.9 | 0.2 | 5.2 | Yes | Excl |
| ORF YNL200C | 161 | P | 332 | P | 70 | P | 452 | P | 2.1 | 6.5 | 4.3 | | Excl |
| ORF YNL234W | 153 | P | 639 | P | 132 | P | 655 | P | 4.2 | 5.0 | 4.6 | | Good |
| ORF YNL235C | 34 | P | 1119 | P | 27 | A | 1112 | P | 32.9 | 41.1 | 37.0 | | Med |
| ORF YNL319W | -5 | A | 5 | A | -20 | A | -4 | A | -1.1 | 0.2 | 2.7 | Yes | Good |
| ORF YNR060W | 35 | M | 78 | P | 19 | A | 63 | P | 2.2 | 3.3 | 2.8 | | Good |
| ORF YOL047C exon | 12 | A | 37 | A | 10 | A | 31 | A | 3.1 | 3.1 | 3.1 | | Excl |
| ORF YOL053C-A | 559 | P | 1616 | P | 753 | P | 1637 | P | 2.9 | 2.2 | 2.5 | | Med |
| ORF YOR032C | 4 | A | 33 | M | -5 | A | 47 | P | 8.2 | -10.3 | 9.2 | Yes | Excl |
| ORF YOR173W | 36 | P | 134 | P | 52 | P | 142 | P | 3.7 | 2.7 | 3.2 | | Excl |
| ORF YOR347C | 191 | P | 697 | P | 199 | P | 794 | P | 3.7 | 4.0 | 3.8 | | Med |
| ORF YOR376W | -40 | A | -23 | A | -59 | A | 5 | A | 0.6 | -0.1 | 8.1 | Yes | Med |
| ORF YPL130W | -51 | A | -10 | A | -59 | A | -31 | A | 0.2 | 0.5 | 6.9 | Yes | Med |
| ORF YPL136W | -34 | A | -23 | A | -36 | A | -21 | A | 0.7 | 0.6 | 2.6 | Yes | Med |
| ORF YPL186C | -3 | A | 52 | P | 11 | A | 31 | A | -17.3 | 2.8 | 6.9 | Yes | Excl |
| ORF YPL222W | 31 | P | 169 | P | 32 | P | 145 | P | 5.5 | 4.6 | 5.0 | | Excl |
| ORF YPR006C | 91 | P | 194 | P | 82 | P | 220 | P | 2.1 | 2.7 | 2.4 | | Excl |
| ORF YPR077C (_i) | -10 | A | 5 | A | -1 | A | 14 | A | -0.5 | -12.6 | 3.1 | Yes | Med |
| ORF YPR116W | 0 | P | 12 | P | -6 | A | 8 | A | #DIV/0! | -1.4 | 2.6 | Yes | Med |
| ORF YPR150W | -40 | A | -7 | A | -25 | A | -9 | A | 0.2 | 0.4 | 4.9 | Yes | Med |
| ORF YPR151C | 34 | A | 85 | P | 38 | P | 91 | P | 2.5 | 2.4 | 2.4 | | Good |

Figure 5D

| | | | | | | | | |
|---|---|---|---|---|---|---|---|---|
| ORF YPR157W | 10 | A | 105 | P | 16 | M | 74 | A | 10.5 | 4.7 | 7.6 | | Good |
| ORF YPR170C | 1 | A | 30 | P | -5 | A | 13 | A | 30.0 | -2.9 | 16.8 | Yes | Med |
| ORF YPR177C | -23 | A | 30 | P | 6 | A | 25 | P | -1.3 | 4.4 | 7.5 | Yes | Med |
| ORF YPR184W | 66 | P | 157 | P | 42 | P | 153 | P | 2.4 | 3.7 | 3.0 | | Excl |
| ORF YPR192W | -62 | A | 0 | A | -25 | A | -6 | A | 0.0 | 0.3 | 8.0 | Yes | Med |
| ORF YPR194C | 111 | M | 750 | P | 187 | P | 825 | P | 6.8 | 4.4 | 5.6 | | Good |
| PGM2 (YMR105C) | 117 | P | 264 | P | 101 | P | 315 | P | 2.3 | 3.1 | 2.7 | | Excl |
| PIG1 (YLR273C) | 37 | P | 84 | P | 34 | P | 81 | P | 2.3 | 2.4 | 2.3 | | Excl |
| PUT1 (YLR142W) | 65 | P | 170 | P | 59 | P | 185 | P | 2.6 | 3.2 | 2.9 | | Excl |
| PUT4 (YOR348C) | 23 | A | 1706 | P | 20 | A | 2089 | P | 74.2 | 103.0 | 88.6 | | Good |
| QCR10 (YHR001W-A) | 554 | P | 1270 | P | 500 | P | 1241 | P | 2.3 | 2.5 | 2.4 | | Excl |
| SDH2 (YLL041C) | 253 | P | 513 | P | 232 | P | 546 | P | 2.0 | 2.4 | 2.2 | | Excl |
| SOL4 (YGR248W) | 28 | P | 193 | P | 28 | P | 184 | P | 6.9 | 6.6 | 6.8 | | Excl |
| SPS4 (YOR313C) | 80 | P | 250 | P | 84 | P | 256 | P | 3.1 | 3.0 | 3.1 | | Excl |
| STA1 (YIR019C) | 61 | A | 2948 | P | 60 | A | 3154 | P | 48.3 | 52.3 | 50.3 | | Good |
| STF2 (YGR008C) | 917 | P | 2161 | P | 964 | P | 2362 | P | 2.4 | 2.4 | 2.4 | | Excl |
| TFS1 (YLR178C) | 172 | P | 481 | P | 157 | P | 531 | P | 2.8 | 3.4 | 3.1 | | Excl |
| TKL2 (YBR117C) | 29 | P | 58 | P | 13 | P | 38 | P | 2.0 | 3.0 | 2.5 | | Excl |
| XRS2 (YDR369C) | -27 | A | -11 | A | -36 | A | -21 | A | 0.4 | 0.6 | 3.2 | Yes | Med |
| YCRX03c/ (control?) | -14 | A | 16 | A | -7 | A | 5 | A | -1.2 | -0.7 | 4.2 | Yes | Med |
| YPK2 (YMR104C) | 9 | A | 27 | A | -11 | A | 58 | A | 3.0 | -52.1 | 7.4 | Yes | Med |
| YTP1 (YNL237W) | 68 | P | 293 | P | 62 | P | 376 | P | 4.3 | 6.1 | 5.2 | | Excl |

Figure 5E

| Sin4 Up | | | | | | | Avergae | | | |
|---|---|---|---|---|---|---|---|---|---|---|
| Gene | WT#1 nc | WT# MUT#1 nc | MUT#1 | WT#2 | MUT#2 nc | MUT# | MT1/WT1 | MT2/WT2 | Fold Up | Corrected? Confidence |
| PUT4 (YOR348C) | 23 A | 1706 P | 20 A | 2089 P | 74.2 | 103.0 | 88.6 | | | Good |
| STA1 (YIR019C) | 61 A | 2948 P | 60 A | 3154 P | 48.3 | 52.3 | 50.3 | | | Good |
| ORF YNL235C | 34 P | 1119 P | 27 A | 1112 P | 32.9 | 41.1 | 37.0 | | | Good |
| ORF YJR150C | -32 A | 162 A | -35 A | 139 A | -5.1 | -3.9 | 36.8 | Yes | | Med |
| MET28 (YIR017C) | -6 A | 174 P | -14 A | 162 P | -29.0 | -11.7 | 35.6 | Yes | | Excl |
| FLO1 (YAR050W) | 29 P | 782 P | 36 P | 843 P | 27.0 | 23.1 | 25.1 | | | Excl |
| ORF YGR052W | 32 P | 441 P | 18 A | 448 P | 13.8 | 25.2 | 19.5 | | | Good |
| ORF YDL024C | 1 A | 20 A | 3 A | 45 P | 20.3 | 15.1 | 17.7 | | | Med |
| ORF YPR170C | 1 A | 30 P | -5 A | 13 A | 30.0 | -2.9 | 16.8 | Yes | | Med |
| ARG1 (YOL058W) | 69 P | 969 P | 71 P | 1015 P | 14.0 | 14.3 | 14.2 | | | Excl |
| ORF YIL006W | 2 A | 36 A | -12 A | 37 A | 17.8 | -3.1 | 13.8 | Yes | | Med |
| HSP12 (YFL014W) | 518 P | 6075 P | 476 P | 5906 P | 11.7 | 12.4 | 12.1 | | | Excl |
| ORF YMR251W | 18 M | 78 P | 3 A | 57 P | 4.3 | 16.9 | 10.6 | | | Good |
| ORF YDL085W | 1 A | 14 A | 4 A | 29 A | 13.5 | 7.4 | 10.5 | | | Good |
| ORF YOR032C | 4 A | 33 M | -5 A | 47 P | 8.2 | -10.3 | 9.2 | Yes | | Med |
| LEE1 (YPL054W) | 0 A | 46 P | -8 A | 36 A | #DIV/0! | -4.6 | 9.1 | Yes | | Med |
| ORF YML087C | 15 A | 70 P | -19 P | 48 P | 4.7 | -2.5 | 9.0 | Yes | | Med |
| ORF YBR012C | 44 P | 493 P | 70 P | 410 P | 11.2 | 5.9 | 8.5 | | | Excl |
| ORF YKL031W | -51 A | -35 A | -84 A | -17 A | 0.7 | 0.2 | 8.3 | Yes | | Med |
| ORF YER150W | 103 P | 786 P | 113 P | 997 P | 7.6 | 8.9 | 8.2 | | | Excl |
| ORF YOR376W | -40 A | -23 A | -59 A | 5 A | 0.6 | -0.1 | 8.1 | Yes | | Med |
| ORF YPR192W | -62 A | 0 A | -25 A | -6 A | 0.0 | 0.3 | 8.0 | Yes | | Med |
| ORF YAL066W | 3 A | 22 P | 5 A | 41 P | 7.2 | 8.4 | 7.8 | | | Good |
| ORF YBR012W-B ex | -42 A | -22 A | -19 A | 38 A | 0.5 | -2.0 | 7.7 | Yes | | Med |
| ORF YNL018C (_r) | -88 A | -70 A | -82 A | -25 A | 0.8 | 0.3 | 7.6 | Yes | | Med |
| ORF YPR157W | 10 A | 105 P | 16 M | 74 A | 10.5 | 4.7 | 7.6 | | | Good |
| ORF YPR177C | -23 A | 30 P | 6 A | 25 P | -1.3 | 4.4 | 7.5 | Yes | | Med |
| ORF YKL030W | -7 A | 22 A | -13 A | 31 A | -3.2 | -2.3 | 7.4 | Yes | | Med |
| YPK2 (YMR104C) | 9 A | 27 A | -1 A | 58 A | 3.0 | -52.1 | 7.4 | Yes | | Med |
| ORF YIL057C | -41 A | -25 A | -81 A | -24 A | 0.6 | 0.3 | 7.2 | Yes | | Med |
| ORF YDL248W (_r) | 5 A | 22 A | 4 A | 40 P | 4.3 | 10.0 | 7.2 | | | Good |
| ORF YLR280C (_f) | 12 A | 44 A | -8 A | 45 P | 3.6 | -5.8 | 7.1 | Yes | | Med |

Figure 6A

| | | | | | | | | |
|---|---|---|---|---|---|---|---|---|
| | | 11 A | 32 A | -30 A | 25 A | 2.9 | -0.8 | 7.0 Yes | Med |
| ORF YLR140W | | 10 A | 52 P | 7 A | 58 P | 5.2 | 8.7 | 6.9 | Good |
| ORF YKL202W | | -51 A | -10 A | -59 A | -31 A | 0.2 | 0.5 | 6.9 Yes | Med |
| ORF YPL130W | | -3 A | 52 P | 11 A | 31 A | -17.3 | 2.8 | 6.9 Yes | Med |
| ORF YPL186C | | 28 P | 193 P | 28 P | 184 P | 6.9 | 6.6 | 6.8 | Excl |
| SOL4 (YGR248W) | | 43 P | 119 P | 15 P | 156 P | 2.8 | 10.5 | 6.6 | Excl |
| ORF YGR043C | | -16 A | 32 P | -14 A | 1 A | -2.0 | -0.1 | 6.4 Yes | Med |
| ORF YLR012C | | -16 A | -1 A | -46 A | 3 A | 0.1 | -0.1 | 6.4 Yes | Med |
| ORF YLR235C | | -75 A | -22 A | -74 A | -64 A | 0.3 | 0.9 | 6.4 Yes | Med |
| ORF YAR052C (_i) | | 111 M | 750 P | 187 P | 825 P | 6.8 | 4.4 | 5.6 | Good |
| ORF YPR194C | | -36 A | -14 A | -41 A | -7 A | 0.4 | 0.2 | 5.6 Yes | Med |
| ORF YLR458W | | 23 A | 102 P | 17 P | 110 P | 4.4 | 6.6 | 5.5 | Good |
| KNH1 (YDL049C) | | 157 P | 866 P | 167 P | 909 P | 5.5 | 5.5 | 5.5 | Excl |
| MET2 (YNL277W) | | 132 P | 725 P | 128 P | 697 P | 5.5 | 5.4 | 5.5 | Excl |
| MET3 (YJR010W) | | 2 A | 15 A | 5 A | 15 A | 7.4 | 3.1 | 5.3 | Good |
| FIG1 (YBR040W) | | 68 P | 293 P | 62 P | 376 P | 4.3 | 6.1 | 5.2 | Excl |
| YTP1 (YNL237W) | | -7 A | 20 M | -29 A | -5 A | -2.9 | 0.2 | 5.2 Yes | Med |
| ORF YNL194C | | 25 A | 141 P | 33 A | 149 P | 5.6 | 4.6 | 5.1 | Good |
| ARG3 (YJL088W) | | 49 P | 271 P | 62 P | 287 P | 5.5 | 4.6 | 5.1 | Excl |
| CTT1 (YGR088W) | | 31 P | 169 P | 32 P | 145 P | 5.5 | 4.6 | 5.0 | Excl |
| ORF YPL222W | | -12 A | 15 M | -29 A | -7 A | -1.3 | 0.2 | 4.9 Yes | Med |
| ORF YLR035C | | -40 A | -7 A | -25 A | -9 A | 0.2 | 0.4 | 4.9 Yes | Med |
| ORF YPR150W | | 73 P | 412 P | 72 P | 291 P | 5.6 | 4.0 | 4.8 | Excl |
| CYC7 (YEL039C) | | -5 A | 32 M | -11 A | 0 A | -6.4 | 0.0 | 4.8 Yes | Med |
| ORF YGL090W | | 107 P | 448 P | 116 P | 596 P | 4.2 | 5.1 | 4.7 | Excl |
| ORF YLR092W | | 10 A | 70 A | 34 A | 77 P | 7.0 | 2.3 | 4.6 | Good |
| ORF YLR281C | | 153 P | 639 P | 132 P | 655 P | 4.2 | 5.0 | 4.6 | Excl |
| ORF YNL234W | | 70 P | 218 P | 46 P | 275 P | 3.1 | 5.9 | 4.5 | Excl |
| ORF YMR040W | | -16 A | 11 A | -4 A | 13 A | -0.7 | -2.9 | 4.4 Yes | Med |
| ORF YMR107W | | -21 A | 10 A | -4 A | 8 P | -0.5 | -1.9 | 4.4 Yes | Med |
| ORF YJR023C | | -5 A | 17 A | -21 A | 1 A | -3.3 | -0.1 | 4.4 Yes | Med |
| ORF YJL077C | | -43 A | -24 A | -36 A | -12 A | 0.6 | 0.3 | 4.3 Yes | Med |
| FLO9 (YAL064W) | | -42 A | -22 A | -38 A | -14 A | 0.5 | 0.4 | 4.3 Yes | Med |
| GIN11 (YLL065W) | | | | | | | | | |

Figure 6B

| | | | | | | | |
|---|---|---|---|---|---|---|---|
| ORF YGL170C | -13 | A | -1 | A | -16 | A | 15 | A | 0.1 | -1.0 | 4.3 | Yes | Med |
| ORF YNL200C | 161 | P | 332 | P | 70 | P | 452 | P | 2.1 | 6.5 | 4.3 | | Excl |
| CIN1 (YOR349W) | 67 | P | 288 | P | 72 | P | 304 | P | 4.3 | 4.2 | 4.3 | | Excl |
| ORF YNL128W | 3 | M | 19 | A | 15 | A | 31 | P | 6.4 | 2.1 | 4.2 | | Good |
| YCRX03c/ (control?) | -14 | A | 16 | A | -7 | A | 5 | A | -1.2 | -0.7 | 4.2 | Yes | Med |
| CYT1 (YOR065W) | 107 | P | 426 | P | 118 | P | 515 | P | 4.0 | 4.4 | 4.2 | | Excl |
| MET14 (YKL001C) | 559 | P | 2527 | P | 611 | P | 2320 | P | 4.5 | 3.8 | 4.2 | | Excl |
| ORF YGR023W | 27 | A | 81 | P | 16 | A | 80 | P | 3.0 | 5.0 | 4.0 | | Good |
| NCA3 (YJL116C) | 122 | P | 469 | P | 107 | P | 430 | P | 3.8 | 4.0 | 3.9 | | Excl |
| ORF YMR244W | 28 | A | 81 | P | 17 | A | 83 | P | 2.9 | 4.9 | 3.9 | | Good |
| ORF YCL023C | -2 | A | 23 | P | 11 | A | 29 | P | -11.5 | 2.7 | 3.9 | Yes | Med |
| ORF YOR347C | 191 | P | 697 | P | 199 | P | 794 | P | 3.7 | 4.0 | 3.8 | | Excl |
| ORF YIL037C | -4 | A | 13 | A | -19 | A | 3 | A | -3.2 | -0.1 | 3.8 | Yes | Med |
| ORF YLR307W | -3 | A | 22 | M | -11 | A | 1 | A | -7.5 | -0.1 | 3.8 | Yes | Med |
| GSC2 (YGR032W) | 351 | P | 1357 | P | 376 | P | 1358 | P | 3.9 | 3.6 | 3.7 | | Excl |
| ORF YLR149C | 27 | P | 66 | P | 21 | P | 104 | P | 2.4 | 5.0 | 3.7 | | Excl |
| ORF YDL218W | -1 | A | 22 | M | 12 | M | 33 | P | -21.7 | 2.8 | 3.6 | Yes | Med |
| ORF YMR041C | 152 | P | 526 | P | 143 | P | 539 | P | 3.5 | 3.8 | 3.6 | | Excl |
| LAP4 (YKL103C) | 141 | P | 408 | P | 113 | P | 473 | P | 2.9 | 4.2 | 3.5 | | Excl |
| ORF YIL120W | 8 | A | 32 | M | -2 | A | 13 | A | 4.0 | -6.5 | 3.5 | Yes | Med |
| ORF YHR087W | 175 | P | 548 | P | 176 | P | 596 | P | 3.1 | 3.4 | 3.3 | | Excl |
| ORF YAR064W (_f) | -11 | A | 8 | A | -10 | A | 3 | A | -0.7 | -0.3 | 3.2 | Yes | Med |
| ORF YOR173W | 36 | P | 134 | P | 52 | P | 142 | P | 3.7 | 2.7 | 3.2 | | Excl |
| ORF YLR205C | 138 | P | 346 | P | 154 | P | 598 | P | 2.5 | 3.9 | 3.2 | | Excl |
| XRS2 (YDR369C) | -27 | A | -11 | A | -36 | A | -21 | A | 0.4 | 0.6 | 3.2 | Yes | Med |
| ORF YDR437W | -10 | A | 5 | A | -8 | M | 9 | A | -0.5 | -1.1 | 3.2 | Yes | Med |
| HXT4 (YHR092C) | 352 | P | 1114 | P | 389 | P | 1194 | P | 3.2 | 3.1 | 3.2 | | Excl |
| TFS1 (YLR178C) | 172 | P | 481 | P | 157 | P | 531 | P | 2.8 | 3.4 | 3.1 | | Excl |
| ORF YPR077C (_i) | -10 | A | 5 | A | -1 | A | 14 | A | -0.5 | -12.6 | 3.1 | Yes | Med |
| SPS4 (YOR313C) | 80 | P | 250 | P | 84 | P | 256 | P | 3.1 | 3.0 | 3.1 | | Excl |
| ORF YOL047C exon | 12 | A | 37 | A | 10 | A | 31 | A | 3.1 | 3.1 | 3.1 | | Good |
| HXT5 (YHR096C) | 8 | A | 28 | A | 15 | A | 39 | P | 3.5 | 2.6 | 3.0 | | Good |
| ORF YPR184W | 66 | P | 157 | P | 42 | P | 153 | P | 2.4 | 3.7 | 3.0 | | Excl |
| GPH1 (YPR160W) | 161 | P | 475 | P | 169 | P | 522 | P | 2.9 | 3.1 | 3.0 | | Excl |
| MET16 (YPR167C) | 138 | P | 377 | P | 109 | P | 360 | P | 2.7 | 3.3 | 3.0 | | Excl |

Figure 6C

| | | | | | | | | |
|---|---|---|---|---|---|---|---|---|
| ORF YMR196W | 44 | P | 167 | P | 76 | P | 166 | P | 3.8 | 2.2 | 3.0 | | Excl |
| MET10 (YFR030W) | 268 | P | 812 | P | 277 | P | 814 | P | 3.0 | 2.9 | 3.0 | | Excl |
| AMS1 (YGL156W) | 59 | P | 151 | P | 45 | P | 151 | P | 2.6 | 3.3 | 2.9 | | Excl |
| ORF YHL040C | 579 | P | 1709 | P | 566 | P | 1616 | P | 3.0 | 2.9 | 2.9 | | Excl |
| PUT1 (YLR142W) | 65 | P | 170 | P | 59 | P | 185 | P | 2.6 | 3.2 | 2.9 | | Excl |
| ORF YDR253C | 40 | P | 115 | P | 46 | P | 131 | P | 2.9 | 2.8 | 2.9 | | Excl |
| ORF YMR250W | 147 | P | 401 | P | 157 | P | 464 | P | 2.7 | 3.0 | 2.8 | | Excl |
| ORF YLR169W | 13 | A | 28 | A | 9 | A | 31 | A | 2.2 | 3.5 | 2.8 | | Good |
| ORF YNR060W | 35 | M | 78 | P | 19 | A | 63 | P | 2.2 | 3.3 | 2.8 | | Good |
| ORF YDR007W | 814 | P | 2225 | P | 843 | P | 2265 | P | 2.7 | 2.7 | 2.7 | | Excl |
| PGM2 (YMR105C) | 117 | P | 264 | P | 101 | P | 315 | P | 2.3 | 3.1 | 2.7 | | Med |
| ORF YNL319W | -5 | A | 5 | A | -20 | A | -4 | A | -1.1 | 0.2 | 2.7 | Yes | Med |
| HXT7 (YDR342C) (_) | 1554 | P | 4687 | P | 1678 | P | 3927 | P | 3.0 | 2.3 | 2.7 | | Excl |
| ORF YDR008C | 46 | P | 93 | P | 17 | P | 55 | P | 2.0 | 3.3 | 2.7 | | Excl |
| LAP3 (YNL239W) | 629 | P | 1692 | P | 710 | P | 1844 | P | 2.7 | 2.6 | 2.6 | | Excl |
| KIN82 (YCR091W) | 12 | P | 38 | P | 23 | P | 48 | P | 3.2 | 2.1 | 2.6 | | Excl |
| ORF YCL026C (_) | -7 | A | 5 | A | -7 | A | 7 | A | -0.8 | -1.0 | 2.6 | Yes | Med |
| ORF YPL136W | -34 | A | -23 | A | -36 | A | -21 | A | 0.7 | 0.6 | 2.6 | Yes | Med |
| ORF YPR116W | 0 | P | 12 | P | -6 | A | 8 | A | #DIV/0! | -1.4 | 2.6 | Yes | Med |
| HAP4 (YKL109W) | 180 | P | 505 | P | 203 | P | 472 | P | 2.8 | 2.3 | 2.6 | | Excl |
| ALD4 (YMR169C) | 35 | P | 94 | P | 36 | P | 88 | P | 2.7 | 2.4 | 2.6 | | Excl |
| MET25 (YLR303W) | 2596 | P | 6509 | P | 2542 | P | 6588 | P | 2.5 | 2.6 | 2.5 | | Excl |
| ORF YEL073C | -1 | A | 11 | A | 7 | A | 18 | A | -11.4 | 2.6 | 2.5 | Yes | Med |
| ORF YOL053C-A | 559 | P | 1616 | P | 753 | P | 1637 | P | 2.9 | 2.2 | 2.5 | | Excl |
| ORF YML118W | 25 | P | 51 | P | 15 | P | 46 | P | 2.0 | 3.0 | 2.5 | | Excl |
| TKL2 (YBR117C) | 29 | P | 58 | P | 13 | P | 38 | P | 2.0 | 3.0 | 2.5 | | Excl |
| ORF YJR079W exon | -5 | A | 8 | A | 15 | A | 34 | P | -1.7 | 2.2 | 2.4 | Yes | Med |
| ORF YPR151C | 34 | A | 85 | P | 38 | P | 91 | P | 2.5 | 2.4 | 2.4 | | Good |
| ORF YJR025C | 1205 | P | 2857 | P | 1097 | P | 2718 | P | 2.4 | 2.5 | 2.4 | | Excl |
| ORF YGL235W | -8 | A | 4 | A | -19 | A | -6 | A | -0.5 | 0.3 | 2.4 | Yes | Med |
| ORF YPR006C | 91 | P | 194 | P | 82 | P | 220 | P | 2.1 | 2.7 | 2.4 | | Excl |
| STF2 (YGR008C) | 917 | P | 2161 | P | 964 | P | 2362 | P | 2.4 | 2.4 | 2.4 | | Excl |
| ORF YDR259C | 35 | P | 95 | P | 47 | P | 98 | P | 2.7 | 2.1 | 2.4 | | Excl |

Figure 6D

| | | | | | | |
|---|---|---|---|---|---|---|
| QCR10 (YHR001W-A | 554 P | 1270 P | 500 P | 1241 P | 2.3 | 2.5 | 2.4 | Excl |
| ORF YAL028W | 31 P | 80 P | 31 P | 67 P | 2.6 | 2.2 | 2.4 | Excl |
| ORF YDR149C | 23 A | 57 P | 13 A | 29 A | 2.5 | 2.3 | 2.4 | Good |
| ORF YIR018W | 107 P | 249 P | 118 A | 283 P | 2.3 | 2.4 | 2.4 | Good |
| ORF YIL082W-A exc | 112 P | 259 P | 135 P | 325 P | 2.3 | 2.4 | 2.4 | Excl |
| ORF YML035C-A | -1 A | 10 A | 0 A | 13 A | -9.8 | #DIV/0! | 2.3 Yes | Med |
| PIG1 (YLR273C) | 37 P | 84 P | 34 P | 81 P | 2.3 | 2.4 | 2.3 | Excl |
| MSN4 (YKL062W) | 297 P | 662 P | 312 P | 746 P | 2.2 | 2.4 | 2.3 | Excl |
| ORF YEL030W | 27 P | 61 P | 27 P | 63 P | 2.3 | 2.4 | 2.3 | Excl |
| ORF YJR137C | 160 P | 409 P | 187 P | 382 P | 2.6 | 2.0 | 2.3 | Excl |
| ORF YLR254C | 93 P | 205 P | 63 P | 149 P | 2.2 | 2.4 | 2.3 | Excl |
| LYS2 (YBR115C) | 666 P | 1520 P | 639 P | 1459 P | 2.3 | 2.3 | 2.3 | Excl |
| ORF YLR080W | 42 P | 84 A | 40 P | 100 P | 2.0 | 2.5 | 2.3 | Good |
| COX4 (YGL187C) | 923 P | 2072 P | 824 P | 1859 P | 2.2 | 2.3 | 2.3 | Excl |
| ORF YER053C | 215 P | 462 P | 211 P | 495 P | 2.2 | 2.3 | 2.2 | Excl |
| SDH2 (YLL041C) | 253 P | 513 P | 232 P | 546 P | 2.0 | 2.4 | 2.2 | Excl |
| ORF YKR069W | 222 P | 482 P | 219 P | 483 P | 2.2 | 2.2 | 2.2 | Excl |
| INH1 (YDL181W) | 170 P | 344 P | 170 P | 392 P | 2.0 | 2.3 | 2.2 | Excl |
| GPM2 (YDL021W) | 37 P | 80 P | 34 P | 72 P | 2.2 | 2.2 | 2.2 | Excl |
| ORF YGL249W | -1 A | 10 A | 0 A | 10 A | -10.2 | #DIV/0! | 2.1 Yes | Med |
| CWP1 (YKL096W) | 1803 P | 3931 P | 1895 P | 3881 P | 2.2 | 2.0 | 2.1 | Excl |
| COT1 (YOR316C) | 452 P | 921 P | 442 P | 923 P | 2.0 | 2.1 | 2.1 | Excl |

Figure 6E

| Sin4 Down | | | | | | | | | Average | | |
|---|---|---|---|---|---|---|---|---|---|---|---|
| Gene | WT#1 nc | WT#1 | MUT#1 nc | MUT#1 | WT#2 nc | WT#2 | MUT#2 nc | MUT#2 | MT1/WT1 | MT2/WT2 | fold down | Corrected? | Confidence |
| ALPHA1 (YCL066W) | 18 A | | -5 A | | 11 A | | -28 A | | -0.30 | -2.54 | 6.2 | Yes | Med |
| ARG80 (YMR042W) | 131 P | | 51 P | | 131 P | | 28 A | | 0.39 | 0.21 | 3.6 | | Good |
| CHA1 (YCL064C) | 1384 P | | 505 P | | 1282 P | | 459 P | | 0.36 | 0.36 | 2.8 | | Excl |
| CLB1 (YGR108W) | 497 P | | 224 P | | 560 P | | 196 P | | 0.45 | 0.35 | 2.5 | | Excl |
| FET4 (YMR319C) | 464 P | | 224 P | | 581 P | | 218 P | | 0.48 | 0.37 | 2.4 | | Excl |
| GAL4 (YPL248C) | 6 M | | -8 A | | 23 A | | -1 A | | -1.36 | -0.06 | 3.8 | Yes | Med |
| GCV1 (YDR019C) | 850 P | | 411 P | | 826 P | | 392 P | | 0.48 | 0.48 | 2.1 | | Excl |
| GCV3 (YAL044C) | 2054 P | | 881 P | | 1892 P | | 728 P | | 0.43 | 0.38 | 2.5 | | Excl |
| HXT17 (YNR072W) | 165 P | | 10 A | | 24 A | | -9 A | | 0.06 | -0.38 | 11.9 | Yes | Med |
| MSH4 (YFL003C) | 9 A | | -5 A | | 12 A | | -4 A | | -0.56 | -0.33 | 3.0 | Yes | Med |
| ORF YAL058C-A | 40 P | | 14 A | | 46 P | | 12 A | | 0.34 | 0.26 | 3.4 | | Good |
| ORF YAR073W (_r) | 424 P | | 188 P | | 386 P | | 134 P | | 0.44 | 0.35 | 2.6 | | Excl |
| ORF YBR028C | 183 P | | 70 P | | 177 P | | 88 P | | 0.38 | 0.49 | 2.3 | | Excl |
| ORF YBR244W | 618 P | | 282 P | | 646 P | | 251 P | | 0.46 | 0.39 | 2.4 | | Excl |
| ORF YBR296C | 95 P | | 46 P | | 100 P | | 21 A | | 0.48 | 0.21 | 3.4 | | Good |
| ORF YCL068C (_f) | 45 P | | 7 M | | 100 P | | 31 M | | 0.15 | 0.31 | 4.9 | | Good |
| ORF YCR099C | 32 P | | 15 P | | 24 P | | 0 A | | 0.47 | 0.00 | 3.4 | Yes | Med |
| ORF YCR106W | 72 P | | 12 A | | 87 P | | 9 A | | 0.17 | 0.10 | 8.0 | | Good |
| ORF YDL032W | 20 A | | -4 A | | 7 A | | -14 A | | -0.20 | -2.00 | 4.5 | Yes | Med |
| ORF YDL248W (_j) | 20 A | | 0 A | | 15 A | | -19 A | | 0.00 | -1.28 | 5.4 | Yes | Med |
| ORF YDR029W | 17 A | | 0 A | | 13 A | | -2 A | | 0.00 | -0.13 | 3.2 | Yes | Med |
| ORF YDR193W | 49 A | | 7 A | | 291 A | | 7 A | | 0.14 | 0.24 | 5.7 | | Good |
| ORF YDR281C | 444 P | | 176 P | | 354 P | | 103 P | | 0.40 | 0.29 | 3.0 | | Excl |
| ORF YDR290W | 0 A | | -11 A | | 7 A | | -7 A | | #DIV/0! | -1.00 | 2.5 | Yes | Med |
| ORF YEL059W | 17 A | | -9 A | | 0 A | | -26 A | | -0.52 | #DIV/0! | 5.2 | Yes | Med |
| ORF YEL067C | 33 P | | 11 A | | 50 A | | 8 A | | 0.35 | 0.15 | 4.7 | | Good |
| ORF YER066C-A | 41 P | | 17 P | | 44 P | | 8 M | | 0.40 | 0.17 | 4.1 | | Good |
| ORF YER072W | 4724 P | | 2358 P | | 4940 P | | 2362 P | | 0.50 | 0.48 | 2.0 | | Excl |
| ORF YER135C | 15 P | | -4 A | | 23 P | | -15 A | | -0.25 | -0.68 | 5.7 | Yes | Med |
| ORF YFL063W (_j) | 4 A | | -19 A | | 2 A | | -9 A | | -4.76 | -4.56 | 3.4 | Yes | Med |
| ORF YGL183C | 21 P | | -19 A | | 4 A | | -15 A | | -0.91 | -3.91 | 5.9 | Yes | Med |
| ORF YGL262W | 11 A | | -1 A | | 18 A | | -3 A | | -0.12 | -0.14 | 3.3 | Yes | Med |
| ORF YGL263W | 48 P | | 19 A | | 36 P | | 5 A | | 0.40 | 0.14 | 4.7 | | Good |
| ORF YGR050C | 104 P | | -13 A | | 138 P | | 15 A | | -0.12 | 0.11 | 16.2 | Yes | Med |

Figure 7A

| ORF | 19 | P | -4 | A | 27 | P | 3 | A | -0.20 | 0.10 | 7.5 | Yes | Med |
|---|---|---|---|---|---|---|---|---|---|---|---|---|---|
| ORF YGR114C | 19 | P | -4 | A | 27 | P | 3 | A | -0.20 | 0.10 | 7.5 | Yes | Med |
| ORF YHL028W | 40 | M | 14 | M | 69 | P | 6 | A | 0.35 | 0.09 | 6.8 | | Good |
| ORF YHR136C | 650 | P | 55 | A | 722 | P | 58 | P | 0.08 | 0.08 | 12.2 | | Good |
| ORF YHR143W | 1881 | P | 727 | P | 1951 | P | 722 | P | 0.39 | 0.37 | 2.6 | | Excl |
| ORF YHR173C | 24 | P | -11 | A | 63 | P | 27 | A | -0.48 | 0.43 | 4.7 | Yes | Med |
| ORF YJL012C | 2338 | P | 1034 | P | 2078 | P | 1005 | P | 0.44 | 0.48 | 2.2 | | Excl |
| ORF YJL182C | 1 | A | -14 | A | 21 | A | 1 | A | -14.05 | 0.07 | 9.0 | Yes | Med |
| ORF YJR147W | 335 | P | 128 | P | 386 | P | 112 | P | 0.38 | 0.29 | 3.0 | | Excl |
| ORF YJR153W | 75 | P | 31 | A | 80 | P | 24 | M | 0.41 | 0.30 | 2.9 | | Good |
| ORF YKL037W | 131 | A | -11 | A | 67 | A | 32 | A | -0.09 | 0.48 | 15.3 | Yes | Med |
| ORF YKL044W | 241 | P | 79 | P | 252 | P | 108 | P | 0.33 | 0.43 | 2.7 | | Excl |
| ORF YKL177W | 46 | M | 11 | A | 56 | M | 18 | A | 0.24 | 0.32 | 3.6 | | Good |
| ORF YKR040C | 104 | A | 17 | A | 98 | A | 41 | A | 0.16 | 0.41 | 4.3 | | Good |
| ORF YKR075C | 202 | P | 90 | P | 207 | P | 79 | P | 0.45 | 0.38 | 2.4 | | Excl |
| ORF YKR104W | 66 | P | 32 | A | 88 | P | 41 | P | 0.49 | 0.46 | 2.1 | | Good |
| ORF YLL030C | 18 | A | 7 | A | 4 | A | -15 | A | 0.39 | -3.50 | 3.3 | Yes | Med |
| ORF YLL047W | 2 | A | -13 | A | 55 | P | 13 | A | -6.32 | 0.23 | 3.7 | Yes | Med |
| ORF YLR030W | -3 | A | -41 | A | -8 | A | -25 | A | 13.59 | 3.27 | 5.5 | Yes | Med |
| ORF YLR124W | 41 | A | 10 | A | 36 | A | 10 | A | 0.24 | 0.27 | 3.9 | | Good |
| ORF YLR308W | 15 | A | -3 | A | 34 | A | 8 | A | -0.19 | 0.25 | 3.8 | Yes | Med |
| ORF YLR334C | 21 | P | 1 | A | 38 | P | 11 | A | 0.07 | 0.30 | 9.1 | | Good |
| ORF YLR338W | 35 | A | 10 | A | 51 | M | 14 | A | 0.28 | 0.28 | 3.6 | | Good |
| ORF YLR346C | 508 | P | 193 | P | 500 | P | 212 | P | 0.38 | 0.42 | 2.5 | | Excl |
| ORF YMR057C | -2 | A | -49 | A | -2 | A | -48 | A | 24.60 | 21.61 | 9.3 | Yes | Med |
| ORF YMR122C | 12 | A | -32 | A | 43 | P | 14 | A | -2.69 | 0.33 | 6.0 | Yes | Med |
| ORF YMR153C-A | 51 | P | 10 | A | 80 | P | 38 | P | 0.19 | 0.48 | 3.6 | | Good |
| ORF YMR206W | -10 | A | -32 | A | -12 | A | -25 | A | 3.23 | 2.08 | 3.5 | Yes | Med |
| ORF YNL034W (_f) | 0 | A | -15 | A | 11 | M | -6 | A | #DIV/0! | -0.57 | 3.3 | Yes | Med |
| ORF YNL217W | 663 | P | 186 | P | 534 | P | 208 | P | 0.28 | 0.39 | 3.1 | | Excl |
| ORF YNR067C | 1410 | P | 546 | P | 1371 | P | 532 | P | 0.39 | 0.39 | 2.6 | | Excl |
| ORF YOL160W | -10 | A | -20 | A | -7 | A | -25 | A | 2.05 | 3.64 | 2.8 | Yes | Med |

Figure 7B

| ORF | | | | | | | | | |
|---|---|---|---|---|---|---|---|---|---|
| ORF YOL165C (_r) | 136 | P | 27 | P | 143 | P | 22 | M | 0.20 | 0.15 | 5.7 | | Good |
| ORF YOR024W | 11 | A | -1 | A | 12 | A | -10 | A | -0.12 | -0.84 | 3.5 | Yes | Med |
| ORF YOR049C | 92 | P | 27 | A | 82 | P | 38 | P | 0.30 | 0.46 | 2.8 | | Good |
| ORF YOR263C | 50 | A | 7 | A | 56 | A | 14 | A | 0.14 | 0.25 | 5.6 | | Good |
| ORF YPL019C | 4568 | P | 1363 | P | 4160 | P | 1382 | P | 0.30 | 0.33 | 3.2 | | Excl |
| ORF YPL205C | 20 | A | 0 | A | 14 | A | -12 | A | 0.00 | -0.86 | 4.5 | Yes | Med |
| PHO11 (YAR071W) | 2548 | P | 602 | P | 2067 | P | 525 | P | 0.24 | 0.25 | 4.1 | | Excl |
| PHO12 (YHR215W) | 2930 | P | 1006 | P | 2585 | P | 1001 | P | 0.34 | 0.39 | 2.7 | | Excl |
| PHO5 (YBR093C) | 1055 | P | 424 | P | 1233 | P | 363 | P | 0.40 | 0.29 | 2.9 | | Excl |
| PHO81 (YGR233C) | 465 | P | 188 | P | 359 | P | 148 | P | 0.40 | 0.41 | 2.4 | | Excl |
| PHO84 (YML123C) | 8774 | P | 2180 | P | 8833 | P | 1869 | P | 0.25 | 0.21 | 4.4 | | Excl |
| PRY3 (YJL078C) | 223 | P | 79 | P | 198 | P | 72 | P | 0.35 | 0.36 | 2.8 | | Excl |
| PUR5 (YHR216W) | 192 | P | 80 | P | 238 | P | 49 | P | 0.42 | 0.21 | 3.6 | | Excl |
| RPI1 (YIL119C) | 147 | P | 56 | P | 163 | P | 68 | P | 0.38 | 0.42 | 2.5 | | Excl |
| SIM1 (YAL059W) | 1094 | P | 522 | P | 907 | P | 387 | P | 0.48 | 0.43 | 2.2 | | Excl |
| SIN4 (YNL236W) | 363 | P | 85 | M | 349 | P | 89 | P | 0.23 | 0.26 | 4.1 | | Good |
| SRD1 (YCR018C) | 175 | P | 62 | P | 230 | P | 48 | P | 0.36 | 0.21 | 3.8 | | Excl |
| SUL1 (YBR294W) | 11 | A | -3 | A | 16 | P | 3 | A | -0.25 | 0.22 | 3.7 | Yes | Med |
| YHB1 (YGR234W) | 3466 | P | 584 | P | 3258 | P | 561 | P | 0.17 | 0.17 | 5.9 | | Excl |

Figure 7C

| Sin4 Down | | | | | | | | Average | | |
|---|---|---|---|---|---|---|---|---|---|---|
| Gene | WT#1 na | WT#1 MUT#1 | MU WT#2 nc | WT#2 nc MUT#2 | MUT#2 nc | MUT#1 MT1/WT1 | MT2/WT2 | fold down | Corrected? | Confidence |
| ORF YGR050C | 104 | P | -13 | A | 138 | P | 15 | A | -0.12 | 0.11 | 16.2 | Yes | Med |
| ORF YKL037W | 131 | A | -11 | A | 67 | A | 32 | A | -0.09 | 0.48 | 15.3 | Yes | Med |
| ORF YHR136C | 650 | P | 55 | A | 722 | P | 58 | P | 0.08 | 0.08 | 12.2 | | Good |
| HXT17 (YNR072W) | 165 | P | 10 | A | 24 | A | -9 | A | 0.06 | -0.38 | 11.9 | Yes | Med |
| ORF YMR057C | -2 | A | -49 | A | -2 | A | -48 | A | 24.60 | 21.61 | 9.3 | Yes | Med |
| ORF YLR334C | 21 | P | 1 | A | 38 | P | 11 | A | 0.07 | 0.30 | 9.1 | | Good |
| ORF YJL182C | 1 | A | -14 | A | 21 | A | 1 | A | -14.05 | 0.07 | 9.0 | Yes | Med |
| ORF YCR106W | 72 | P | 12 | A | 87 | P | 9 | A | 0.17 | 0.10 | 8.0 | | Good |
| ORF YGR114C | 19 | P | -4 | A | 27 | P | 3 | A | -0.20 | 0.10 | 7.5 | Yes | Med |
| ORF YHL028W | 40 | M | 14 | M | 69 | P | 6 | A | 0.35 | 0.09 | 6.8 | | Good |
| ALPHA1 (YCL066W) | 18 | A | -5 | A | 11 | A | -28 | A | -0.30 | -2.54 | 6.2 | Yes | Med |
| ORF YMR122C | 12 | A | -32 | A | 43 | P | 14 | A | -2.69 | 0.33 | 6.0 | Yes | Med |
| ORF YGL183C | 21 | P | -19 | A | 4 | A | -15 | A | -0.91 | -3.91 | 5.9 | Yes | Med |
| YHB1 (YGR234W) | 3466 | P | 584 | P | 3258 | P | 561 | P | 0.17 | 0.17 | 5.9 | | Excl |
| ORF YOL165C (_r) | 136 | P | 27 | P | 143 | P | 22 | M | 0.20 | 0.15 | 5.7 | | Good |
| ORF YER135C | 15 | P | -4 | A | 23 | P | -15 | A | -0.25 | -0.68 | 5.7 | Yes | Med |
| ORF YDR193W | 49 | A | 7 | A | 29 | A | 7 | A | 0.14 | 0.24 | 5.7 | | Good |
| ORF YOR263C | 50 | A | 7 | A | 56 | A | 14 | A | 0.14 | 0.25 | 5.6 | | Good |
| ORF YLR030W | -3 | A | -41 | A | -8 | A | -25 | A | 13.59 | 3.27 | 5.5 | Yes | Med |
| ORF YDL248W (_i) | 20 | A | 0 | A | 15 | A | -19 | A | 0.00 | -1.28 | 5.4 | Yes | Med |
| ORF YEL059W | 17 | A | -9 | A | 0 | A | -26 | A | -0.52 | #DIV/0! | 5.2 | Yes | Med |
| ORF YCL068C (_f) | 45 | P | 7 | M | 100 | P | 31 | M | 0.15 | 0.31 | 4.9 | | Good |
| ORF YGL263W | 48 | P | 19 | A | 36 | P | 5 | A | 0.40 | 0.14 | 4.7 | | Good |
| ORF YHR173C | 24 | P | -11 | A | 63 | P | 27 | A | -0.48 | 0.43 | 4.7 | Yes | Med |
| ORF YEL067C | 33 | P | 11 | A | 50 | A | 8 | A | 0.35 | 0.15 | 4.7 | | Good |
| ORF YPL205C | 20 | A | 0 | A | 14 | A | -12 | A | 0.00 | -0.86 | 4.5 | Yes | Med |
| ORF YDL032W | 20 | A | -4 | A | 7 | A | -14 | A | -0.20 | -2.00 | 4.5 | Yes | Med |
| PHO84 (YML123C) | 8774 | P | 2180 | P | 8833 | P | 1869 | P | 0.25 | 0.21 | 4.4 | | Excl |
| ORF YKR040C | 104 | A | 17 | A | 98 | A | 41 | A | 0.16 | 0.41 | 4.3 | | Good |
| ORF YER066C-A | 41 | P | 17 | P | 44 | P | 8 | M | 0.40 | 0.17 | 4.1 | | Good |
| SIN4 (YNL236W) | 363 | P | 85 | M | 349 | P | 89 | P | 0.23 | 0.26 | 4.1 | Yes | Med |
| PHO11 (YAR071W) | 2548 | P | 602 | P | 2067 | P | 525 | P | 0.24 | 0.25 | 4.1 | | Excl |
| ORF YLR124W | 41 | A | 10 | A | 36 | A | 10 | A | 0.24 | 0.27 | 3.9 | | Good |
| ORF YLR308W | 15 | A | -3 | A | 34 | A | 8 | A | -0.19 | 0.25 | 3.8 | Yes | Med |

Figure 8A

| Gene | 6 | | -8 | | 23 | | -1 | | | | | |
|---|---|---|---|---|---|---|---|---|---|---|---|---|
| GAL4 (YPL248C) | 6 | M | -8 | A | 23 | A | -1 | A | | | | Med |
| SRD1 (YCR018C) | 175 | P | 62 | P | 230 | P | 48 | P | 0.36 | 0.21 | 3.8 | Excl |
| SUL1 (YBR294W) | 11 | A | -3 | A | 16 | P | 3 | A | -0.25 | 0.22 | 3.7 Yes | Med |
| ORF YLL047W | 2 | A | -13 | A | 55 | P | 13 | A | -6.32 | 0.23 | 3.7 Yes | Med |
| ORF YMR153C-A | 51 | P | 10 | A | 80 | P | 38 | P | 0.19 | 0.48 | 3.6 | Good |
| PUR5 (YHR216W) | 192 | P | 80 | P | 238 | P | 49 | P | 0.42 | 0.21 | 3.6 | Excl |
| ARG80 (YMR042W) | 131 | P | 51 | P | 131 | P | 28 | A | 0.39 | 0.21 | 3.6 | Good |
| ORF YKL177W | 46 | M | 11 | A | 56 | M | 18 | A | 0.24 | 0.32 | 3.6 | Good |
| ORF YLR338W | 35 | A | 10 | A | 51 | M | 14 | A | 0.28 | 0.28 | 3.6 | Good |
| ORF YMR206W | -10 | A | -32 | A | -12 | A | -25 | A | 3.23 | 2.08 | 3.5 Yes | Med |
| ORF YOR024W | 11 | A | -1 | A | 12 | A | -10 | A | -0.12 | -0.84 | 3.5 Yes | Med |
| ORF YBR296C | 95 | P | 46 | P | 100 | P | 21 | A | 0.48 | 0.21 | 3.4 | Good |
| ORF YCR099C | 32 | P | 15 | P | 24 | P | 0 | A | 0.47 | 0.00 | 3.4 Yes | Med |
| ORF YFL063W (_i) | 4 | A | -19 | A | 2 | A | -9 | A | -4.76 | -4.56 | 3.4 Yes | Med |
| ORF YAL058C-A | 40 | P | 14 | A | 46 | P | 12 | A | 0.34 | 0.26 | 3.4 | Good |
| ORF YNL034W (_f) | 0 | A | -15 | A | 11 | M | -6 | A | #DIV/0! | -0.57 | 3.3 Yes | Med |
| ORF YLL030C | 18 | A | 7 | A | 4 | A | -15 | A | 0.39 | -3.50 | 3.3 Yes | Med |
| ORF YGL262W | 11 | A | -1 | A | 18 | A | -3 | A | -0.12 | -0.14 | 3.3 Yes | Med |
| ORF YPL019C | 4568 | P | 1363 | P | 4160 | P | 1382 | P | 0.30 | 0.33 | 3.2 | Excl |
| ORF YDR029W | 17 | A | 0 | A | 13 | A | -2 | A | 0.00 | -0.13 | 3.2 Yes | Med |
| ORF YNL217W | 663 | P | 186 | P | 534 | P | 208 | P | 0.28 | 0.39 | 3.1 | Excl |
| ORF YJR147W | 335 | P | 128 | P | 386 | P | 112 | P | 0.38 | 0.29 | 3.0 | Excl |
| MSH4 (YFL003C) | 9 | A | -5 | A | 12 | A | -4 | A | -0.56 | -0.33 | 3.0 Yes | Med |
| ORF YDR281C | 444 | P | 176 | P | 354 | P | 103 | P | 0.40 | 0.29 | 3.0 | Excl |
| PHO5 (YBR093C) | 1055 | P | 424 | P | 1233 | P | 363 | P | 0.40 | 0.29 | 2.9 | Excl |
| ORF YJR153W | 75 | P | 31 | A | 80 | P | 24 | M | 0.41 | 0.30 | 2.9 | Good |
| ORF YOL160W | -10 | A | -20 | A | -7 | A | -25 | A | 2.05 | 3.64 | 2.8 Yes | Med |
| PRY3 (YJL078C) | 223 | P | 79 | P | 198 | P | 72 | P | 0.35 | 0.36 | 2.8 | Excl |
| ORF YOR049C | 92 | P | 27 | A | 82 | P | 38 | P | 0.30 | 0.46 | 2.8 | Good |
| CHA1 (YCL064C) | 1384 | P | 505 | P | 1282 | P | 459 | P | 0.36 | 0.36 | 2.8 | Excl |
| PHO12 (YHR215W) | 2930 | P | 1006 | P | 2585 | P | 1001 | P | 0.34 | 0.39 | 2.7 | Excl |

Figure 8B

| | | | | | | |
|---|---|---|---|---|---|---|
| ORF YKL044W | 241 P | 79 P | 252 P | 108 P | 0.33 | 0.43 | 2.7 | Excl |
| ORF YHR143W | 1881 P | 727 P | 1951 P | 722 P | 0.39 | 0.37 | 2.6 | Excl |
| ORF YNR067C | 1410 P | 546 P | 1371 P | 532 P | 0.39 | 0.39 | 2.6 | Excl |
| ORF YAR073W (_r) | 424 P | 188 P | 386 P | 134 P | 0.44 | 0.35 | 2.6 | Excl |
| CLB1 (YGR108W) | 497 P | 224 P | 560 P | 196 P | 0.45 | 0.35 | 2.5 | Excl |
| RPI1 (YIL119C) | 147 P | 56 P | 163 P | 68 P | 0.38 | 0.42 | 2.5 | Excl |
| ORF YLR346C | 508 P | 193 P | 500 P | 212 P | 0.38 | 0.42 | 2.5 | Excl |
| GCV3 (YAL044C) | 2054 P | 881 P | 1892 P | 728 P | 0.43 | 0.38 | 2.5 | Excl |
| ORF YDR290W | 0 A | -11 A | 7 A | -7 A | #DIV/0! | -1.00 | 2.5 Yes | Med |
| PHO81 (YGR233C) | 465 P | 188 P | 359 P | 148 P | 0.40 | 0.41 | 2.4 | Excl |
| ORF YKR075C | 202 P | 90 P | 207 P | 79 P | 0.45 | 0.38 | 2.4 | Excl |
| ORF YBR244W | 618 P | 282 P | 646 P | 251 P | 0.46 | 0.39 | 2.4 | Excl |
| FET4 (YMR319C) | 464 P | 224 P | 581 P | 218 P | 0.48 | 0.37 | 2.4 | Excl |
| ORF YBR028C | 183 P | 70 P | 177 P | 88 P | 0.38 | 0.49 | 2.3 | Excl |
| SIM1 (YAL059W) | 1094 P | 522 P | 907 P | 387 P | 0.48 | 0.43 | 2.2 | Excl |
| ORF YJL012C | 2338 P | 1034 P | 2078 P | 1005 P | 0.44 | 0.48 | 2.2 | Excl |
| ORF YKR104W | 66 P | 32 A | 88 P | 41 P | 0.49 | 0.46 | 2.1 | Good |
| GCV1 (YDR019C) | 850 P | 411 P | 826 P | 392 P | 0.48 | 0.48 | 2.1 | Excl |
| ORF YER072W | 4724 P | 2358 P | 4940 P | 2362 P | 0.50 | 0.48 | 2.0 | Excl |

Figure 8C

Gcn5 Up

Gene Expression Results for FH19980406014A

| Gene | WT1val | WT1c | MT1val | MT1c | WT2val | WT2c | MT2val | MT2c | MT1/WT1 | MT2/WT2 | Average Fold Up | Corrected? | Confidence |
|---|---|---|---|---|---|---|---|---|---|---|---|---|---|
| ANB1 (YJR047C) | 7 | P | 58 | P | 11 | A | 63 | P | 8.37 | 5.64 | 7.01 | | Good |
| ARG1 (YOL058W) | 4 | A | 44 | P | 7 | M | 36 | A | 11.43 | 4.93 | 8.18 | | Good |
| ASP3 (YLR158C) | 23 | M | 49 | P | 17 | A | 35 | M | 2.12 | 2.11 | 2.12 | | Good |
| FUN21 (YAL031C) | 15 | A | 44 | A | 15 | A | 37 | A | 2.94 | 2.54 | 2.74 | | Good |
| HIS3 (YOR202W) | 11 | A | 55 | P | 1 | A | 60 | P | 5.09 | 99.06 | 52.07 | | Good |
| IDS2 (YJL146W) | -4 | A | 16 | A | 9 | P | 19 | P | -3.75 | 2.18 | 3.14 | Yes | Med |
| KNH1 (YDL049C) | 3 | A | 16 | P | 0 | A | 16 | A | 5.24 | #DIV/0! | 4.26 | Yes | Med |
| LEU4 (YNL104C) | 206 | P | 439 | P | 275 | P | 614 | P | 2.13 | 2.23 | 2.18 | | Excl |
| NDT80 (YHR124W) | 2 | A | 15 | A | 8 | A | 20 | P | 6.91 | 2.65 | 4.78 | | Good |
| ORF YAR037W (_r) | -12 | A | 3 | A | -27 | A | -11 | A | -0.21 | 0.40 | 3.09 | Yes | Med |
| ORF YBL031W | -6 | A | 18 | A | -5 | A | 7 | A | -3.04 | -1.37 | 3.69 | Yes | Med |
| ORF YBR027C | -9 | A | 2 | A | 12 | P | 27 | P | -0.21 | 2.28 | 2.23 | Yes | Med |
| ORF YBR098W | -11 | A | 0 | A | -15 | A | -1 | A | 0.00 | 0.06 | 2.48 | Yes | Med |
| ORF YBR203W | 12 | A | 28 | P | 7 | P | 23 | P | 2.36 | 3.41 | 2.89 | | Good |
| ORF YBR219C exon | -10 | A | 9 | A | -23 | A | 7 | A | -0.94 | -0.32 | 4.94 | Yes | Med |
| ORF YBR233W | 1 | A | 28 | P | 11 | A | 34 | A | 27.68 | 2.97 | 15.32 | | Good |
| ORF YCL039W | 3 | A | 33 | P | 12 | M | 41 | P | 11.11 | 3.41 | 7.26 | | Good |
| ORF YCL049C | 11 | M | 36 | P | 16 | P | 36 | M | 3.32 | 2.28 | 2.80 | | Good |
| ORF YCR013C | 5 | A | 18 | P | 11 | A | 29 | P | 3.65 | 2.57 | 3.11 | | Good |
| ORF YCR050C | -8 | A | 14 | P | -3 | A | 10 | M | -1.81 | -3.76 | 3.52 | Yes | Med |
| ORF YCR080W | -9 | A | 10 | P | -1 | A | 19 | P | -1.12 | -28.68 | 3.89 | Yes | Med |
| ORF YDL062W | -2 | A | 9 | M | -13 | A | -2 | A | -4.40 | 0.14 | 2.17 | Yes | Med |
| ORF YDL120W | -8 | A | 24 | P | 7 | A | 27 | P | -2.99 | 3.72 | 5.05 | Yes | Med |
| ORF YDL218W | -2 | A | 8 | A | 0 | A | 34 | P | -4.09 | #DIV/0! | 4.39 | Yes | Med |
| ORF YDR042C | -23 | A | -3 | A | 3 | A | 15 | A | 0.14 | 5.80 | 4.89 | Yes | Med |
| ORF YDR053W | 5 | A | 15 | A | 13 | A | 44 | P | 3.02 | 3.28 | 3.15 | | Good |
| ORF YDR109C | 5 | A | 36 | P | -2 | A | 10 | A | 7.17 | -5.01 | 4.79 | Yes | Med |
| ORF YDR124W | -11 | A | 1 | A | 3 | A | 15 | A | -0.06 | 5.46 | 3.89 | Yes | Med |
| ORF YDR305C exon | -8 | A | 4 | P | -4 | A | 11 | P | -0.55 | -2.73 | 2.73 | Yes | Med |
| ORF YDR445C | -2 | A | 11 | M | 2 | A | 17 | P | -5.66 | 8.65 | 5.66 | Yes | Med |
| ORF YDR491C | -2 | A | 13 | A | 10 | P | 27 | A | -6.60 | 2.73 | 2.89 | Yes | Med |
| ORF YDR509W | -7 | A | 3 | A | 7 | A | 26 | M | -0.45 | 3.48 | 2.75 | Yes | Med |
| ORF YDR526C | -12 | A | 4 | A | 3 | A | 15 | A | -0.31 | 5.80 | 4.48 | Yes | Med |
| ORF YER096W | -7 | A | 7 | P | 9 | A | 23 | A | -1.07 | 2.70 | 2.70 | Yes | Med |

Figure 9A

| ORF | | 31 | | 24 | | 50 | | | | | |
|---|---|---|---|---|---|---|---|---|---|---|---|
| ORF YFL034W | 5 | A | 31 | P | 24 | P | 50 | P | 5.63 | 2.12 | 3.87 | Good |
| ORF YFL040W | -26 | A | -4 | A | -6 | A | 5 | A | 0.14 | -0.76 | 3.30 | Yes | Med |
| ORF YFR008W | 2 | A | 12 | P | 8 | A | 22 | P | 5.68 | 2.68 | 4.18 | | Good |
| ORF YFR016C | 20 | P | 51 | P | 26 | P | 56 | P | 2.61 | 2.19 | 2.40 | | Excl |
| ORF YGR025W | -17 | A | 9 | M | 4 | A | 18 | A | -0.52 | 4.40 | 4.85 | Yes | Med |
| ORF YGR203W | 10 | A | 34 | P | 6 | A | 27 | A | 3.46 | 4.87 | 4.16 | | Good |
| ORF YHL048W | 20 | A | 55 | P | 41 | P | 98 | P | 2.80 | 2.40 | 2.60 | | Good |
| ORF YHR209W | 4 | A | 15 | P | -1 | A | 13 | A | 3.33 | -13.00 | 3.08 | Yes | Med |
| ORF YHR210C | -3 | A | 13 | P | -4 | A | 9 | A | -4.12 | -2.62 | 2.95 | Yes | Med |
| ORF YIL006W | -13 | A | -2 | A | -16 | A | 3 | A | 0.12 | -0.19 | 3.07 | Yes | Med |
| ORF YIL097W | -8 | A | 8 | A | -1 | A | 10 | A | -0.99 | -9.94 | 2.62 | Yes | Med |
| ORF YIL169C | 15 | A | 32 | A | 18 | A | 48 | P | 2.08 | 2.71 | 2.40 | | Good |
| ORF YIR020C | -7 | A | 4 | A | -4 | A | 27 | P | -0.66 | -7.65 | 4.13 | Yes | Med |
| ORF YJL037W | -2 | A | 23 | A | -1 | A | 20 | A | -10.37 | -19.89 | 4.58 | Yes | Med |
| ORF YJL043W | -4 | A | 12 | A | -2 | A | 12 | A | -2.72 | -6.12 | 3.05 | Yes | Med |
| ORF YJL058C | -5 | A | 5 | A | 13 | A | 52 | A | -0.89 | 4.10 | 3.08 | Yes | Med |
| ORF YJL161W | -11 | A | 2 | A | -1 | A | 10 | P | -0.21 | -8.17 | 2.44 | Yes | Med |
| ORF YJL162C | 7 | A | 18 | P | 1 | A | 18 | A | 2.55 | 29.96 | 16.25 | | Good |
| ORF YJL201W | -6 | A | 13 | A | 12 | A | 33 | M | -2.22 | 2.81 | 3.35 | Yes | Med |
| ORF YJL202C | -7 | A | 12 | P | -1 | A | 11 | A | -1.74 | -19.07 | 3.08 | Yes | Med |
| ORF YJR038C | -4 | A | 13 | A | 1 | A | 29 | P | -3.11 | 49.03 | 26.28 | Yes | Med |
| ORF YKR033C | -5 | A | 10 | A | -11 | A | 4 | A | -1.97 | -0.33 | 3.03 | Yes | Med |
| ORF YLR187W | 5 | P | 32 | M | 12 | A | 26 | M | 6.16 | 2.18 | 4.17 | | Good |
| ORF YLR235C | -28 | A | -4 | A | -4 | A | 16 | P | 0.13 | -4.54 | 4.36 | Yes | Med |
| ORF YLR265C | 3 | A | 24 | P | 4 | A | 15 | P | 7.10 | 3.50 | 5.30 | | Good |
| ORF YLR279W | -23 | A | 17 | A | -6 | A | 23 | A | -0.71 | -3.81 | 6.84 | Yes | Med |
| ORF YMR063W | -8 | A | 10 | A | -25 | A | 7 | A | -1.31 | -0.28 | 4.98 | Yes | Med |
| ORF YMR069W | -9 | A | 14 | M | 1 | A | 22 | P | -1.61 | 36.32 | 20.41 | Yes | Med |
| ORF YNL014W | 13 | A | 32 | P | 9 | A | 29 | P | 2.45 | 3.19 | 2.82 | | Good |
| ORF YNL095C | -11 | A | 21 | A | 4 | A | 18 | A | -1.90 | 4.23 | 5.26 | Yes | Med |

Figure 9B

| | | | | | | | | |
|---|---|---|---|---|---|---|---|---|
| ORF YNL120C | -9 A | 5 A | -3 A | 9 P | -0.48 | -2.96 | 2.57 Yes | Med |
| ORF YOL157C (_f) | 9 A | 27 P | -1 A | 19 P | 3.21 | -15.94 | 3.65 Yes | Med |
| ORF YOR072W | 0 A | 11 P | 5 A | 34 P | #DIV/0! | 6.33 | 4.29 Yes | Med |
| ORF YOR203W | -9 A | 38 P | -5 A | 40 P | -4.12 | -8.26 | 9.21 Yes | Med |
| ORF YOR318C exon | -9 A | 13 P | 12 A | 33 P | -1.50 | 2.73 | 3.49 Yes | Med |
| ORF YOR389W | 5 A | 21 P | 7 A | 32 P | 3.94 | 4.76 | 4.35 | Good |
| ORF YPL027W | -28 A | -1 A | -6 A | 5 A | 0.03 | -0.80 | 3.80 Yes | Med |
| ORF YPL102C | -2 A | 9 A | 5 A | 23 M | -5.57 | 4.18 | 3.11 Yes | Med |
| ORF YPR202W exor | -2 A | 17 P | -3 A | 12 P | -10.66 | -4.10 | 3.34 Yes | Med |
| RHO4 (YKR055W) | 17 A | 44 P | 12 A | 24 P | 2.57 | 2.04 | 2.31 | Good |
| SPO13 (YHR014W) | -5 A | 18 P | 7 A | 22 A | -3.36 | 3.17 | 3.96 Yes | Med |
| SPS100 (YHR139C) | 1 A | 20 P | 4 A | 30 P | 18.27 | 7.46 | 12.87 | Good |
| SSA4 (YER103W) | 11 A | 35 P | 26 P | 57 P | 3.26 | 2.18 | 2.72 | Good |
| TOP3 (YLR234W) | -9 A | 9 P | -11 A | 7 A | -1.07 | -0.66 | 3.55 Yes | Med |
| UBP11 (YKR098C) | -2 A | 26 P | 12 P | 37 P | -15.28 | 2.94 | 4.27 Yes | Med |
| UTR5 (YEL035C) | -16 A | -3 A | -4 A | 12 A | 0.20 | -3.06 | 2.95 Yes | Med |
| YCLX05c/ (control? | -7 A | 4 A | -18 A | -2 A | -0.63 | 0.10 | 2.76 Yes | Med |
| YCRX19w/ (control: | -2 A | 9 A | -10 A | 26 P | -4.72 | -2.64 | 4.79 Yes | Med |
| ZRT1 (YGL255W) | 46 P | 116 P | 56 P | 123 P | 2.53 | 2.19 | 2.36 | Excl |

Figure 9C

| Gcn5 Up | | | | | | | | | | | Average | | |
|---|---|---|---|---|---|---|---|---|---|---|---|---|---|
| Gene Expression Results for FH1998040601A | | | | | | | | | | | | | |
| Gene | WT1val | WT1c | MT1val | MT1c | WT2val | WT2c | MT2val | MT2c | MT1/WT1 | MT2/WT2 | Fold Up | Corrected? | Confidence |
| HIS3 (YOR202W) | 11 | A | 55 | P | 1 | A | 60 | P | 5.09 | 99.06 | 52.07 | | Good |
| ORF YJR038C | -4 | A | 13 | A | 1 | A | 29 | P | -3.11 | 49.03 | 26.28 | Yes | Med |
| ORF YMR069W | -9 | A | 14 | M | 1 | A | 22 | P | -1.61 | 36.32 | 20.41 | Yes | Med |
| ORF YJL162C | 7 | A | 18 | P | 1 | A | 18 | A | 2.55 | 29.96 | 16.25 | | Good |
| ORF YBR233W | 1 | A | 28 | P | 11 | A | 34 | A | 27.68 | 2.97 | 15.32 | | Good |
| SPS100 (YHR139C) | 1 | A | 20 | P | 4 | A | 30 | P | 18.27 | 7.46 | 12.87 | | Good |
| ORF YOR203W | -9 | A | 38 | P | -5 | A | 40 | P | -4.12 | -8.26 | 9.21 | Yes | Med |
| ARG1 (YOL058W) | 4 | A | 44 | P | 7 | M | 36 | A | 11.43 | 4.93 | 8.18 | | Good |
| ORF YCL039W | 3 | A | 33 | P | 12 | M | 41 | P | 11.11 | 3.41 | 7.26 | | Good |
| ANB1 (YJR047C) | 7 | P | 58 | P | 11 | A | 63 | P | 8.37 | 5.64 | 7.01 | | Good |
| ORF YLR279W | -23 | A | 17 | A | -6 | A | 23 | A | -0.71 | -3.81 | 6.84 | Yes | Med |
| ORF YDR445C | -2 | A | 11 | M | 2 | A | 17 | P | -5.66 | 8.65 | 5.66 | Yes | Med |
| ORF YLR265C | 3 | A | 24 | P | 4 | A | 15 | P | 7.10 | 3.50 | 5.30 | | Good |
| ORF YNL095C | -11 | A | 21 | A | 4 | A | 18 | A | -1.90 | 4.23 | 5.26 | Yes | Med |
| ORF YDL120W | -8 | A | 24 | P | 7 | A | 27 | P | -2.99 | 3.72 | 5.05 | Yes | Med |
| ORF YMR063W | -8 | A | 10 | A | -25 | A | 7 | A | -1.31 | -0.28 | 4.98 | Yes | Med |
| ORF YBR219C exon | -10 | A | 9 | A | -23 | A | 7 | A | -0.94 | -0.32 | 4.94 | Yes | Med |
| ORF YDR042C | -23 | A | -3 | A | 3 | A | 15 | A | 0.14 | 5.80 | 4.89 | Yes | Med |
| ORF YGR025W | -17 | A | 9 | M | 4 | A | 18 | A | -0.52 | 4.40 | 4.85 | Yes | Med |
| YCRX19w/ (control) | -2 | A | 9 | A | -10 | A | 26 | P | -4.72 | -2.64 | 4.79 | Yes | Med |
| ORF YDR109C | 5 | A | 36 | P | -2 | A | 10 | A | 7.17 | -5.01 | 4.79 | Yes | Med |
| NDT80 (YHR124W) | -2 | A | 15 | A | 8 | A | 20 | P | 6.91 | 2.65 | 4.78 | | Good |
| ORF YJL037W | -2 | A | 23 | A | -1 | A | 20 | A | -10.37 | -19.89 | 4.58 | Yes | Med |
| ORF YDR526C | -12 | A | 4 | A | 3 | A | 15 | A | -0.31 | 5.80 | 4.48 | Yes | Med |
| ORF YDL218W | -2 | A | 8 | A | 0 | A | 34 | P | -4.09 | #DIV/0! | 4.39 | Yes | Med |
| ORF YLR235C | -28 | A | -4 | A | -4 | A | 16 | P | 0.13 | -4.54 | 4.36 | Yes | Med |
| ORF YOR389W | 5 | A | 21 | P | 7 | A | 32 | P | 3.94 | 4.76 | 4.35 | | Good |
| ORF YOR072W | 0 | A | 11 | P | 5 | A | 34 | P | #DIV/0! | 6.33 | 4.29 | Yes | Med |
| UBP11 (YKR098C) | -2 | A | 26 | P | 12 | P | 37 | P | -15.28 | 2.94 | 4.27 | Yes | Med |
| KNH1 (YDL049C) | 3 | A | 16 | P | 0 | A | 16 | A | 5.24 | #DIV/0! | 4.26 | Yes | Med |
| ORF YFR008W | 2 | A | 12 | P | 8 | A | 22 | P | 5.68 | 2.68 | 4.18 | | Good |
| ORF YLR187W | 5 | P | 32 | M | 12 | A | 26 | M | 6.16 | 2.18 | 4.17 | | |
| ORF YGR203W | 10 | A | 34 | P | 6 | A | 27 | A | 3.46 | 4.87 | 4.16 | | Good |

Figure 10A

| | | | | | | | |
|---|---|---|---|---|---|---|---|
| ORF YIR020C | -7 A | 4 A | -4 A | 27 P | -0.66 | -7.65 | 4.13 Yes Med |
| SPO13 (YHR014W) | -5 A | 18 P | 7 A | 22 A | -3.36 | 3.17 | 3.96 Yes Med |
| ORF YDR124W | -11 A | 1 A | 3 A | 15 A | -0.06 | 5.46 | 3.89 Yes Med |
| ORF YCR080W | -9 A | 10 P | -1 A | 19 P | -1.12 | -28.68 | 3.89 Yes Med |
| ORF YFL034W | 5 A | 31 P | 24 P | 50 P | 5.63 | 2.12 | 3.87 Good |
| ORF YPL027W | -28 A | -1 A | -6 A | 5 A | 0.03 | -0.80 | 3.80 Yes Med |
| ORF YBL031W | -6 A | 18 A | -5 A | 7 A | -3.04 | -1.37 | 3.69 Yes Med |
| ORF YOL157C (_f) | 9 A | 27 P | -1 A | 19 P | 3.21 | -15.94 | 3.65 Yes Med |
| TOP3 (YLR234W) | -9 A | 9 P | -11 A | 7 A | -1.07 | -0.66 | 3.55 Yes Med |
| ORF YCR050C | -8 A | 14 P | -3 A | 10 M | -1.81 | -3.76 | 3.52 Yes Med |
| ORF YOR318C exon | -9 A | 13 P | 12 A | 33 P | -1.50 | 2.73 | 3.49 Yes Med |
| ORF YJL201W | -6 A | 13 A | 12 A | 33 M | -2.22 | 2.81 | 3.35 Yes Med |
| ORF YPR202W exon | -2 A | 17 P | -3 A | 12 P | -10.66 | -4.10 | 3.34 Yes Med |
| ORF YFL040W | -26 A | -4 A | -6 A | 5 A | 0.14 | -0.76 | 3.30 Yes Med |
| ORF YDR053W | 5 A | 15 A | 13 A | 44 P | 3.02 | 3.28 | 3.15 Good |
| IDS2 (YJL146W) | -4 A | 16 A | 9 P | 19 P | -3.75 | 2.18 | 3.14 Yes Med |
| ORF YCR013C | 5 A | 18 P | 11 A | 29 P | 3.65 | 2.57 | 3.11 Good |
| ORF YPL102C | -2 A | 9 A | 5 A | 23 M | -5.57 | 4.18 | 3.11 Yes Med |
| ORF YAR037W (_r) | -12 A | 3 A | -27 A | -11 A | -0.21 | 0.40 | 3.09 Yes Med |
| ORF YHR209W | 4 A | 15 P | -1 A | 13 A | 3.33 | -13.00 | 3.08 Yes Med |
| ORF YJL202C | -7 A | 12 P | -1 A | 11 A | -1.74 | -19.07 | 3.08 Yes Med |
| ORF YJL058C | -5 A | 5 A | 13 A | 52 A | -0.89 | 4.10 | 3.08 Yes Med |
| ORF YIL006W | -13 A | -2 A | -16 A | 3 A | 0.12 | -0.19 | 3.07 Yes Med |
| ORF YJL043W | -4 A | 12 A | -2 A | 12 A | -2.72 | -6.12 | 3.05 Yes Med |
| ORF YKR033C | -5 A | 10 A | -11 A | 4 A | -1.97 | -0.33 | 3.03 Yes Med |
| ORF YHR210C | -3 A | 13 P | -4 A | 9 A | -4.12 | -2.62 | 3.03 Yes Med |
| UTR5 (YEL035C) | -16 A | -3 A | -4 A | 12 A | 0.20 | -3.06 | 2.95 Yes Med |
| ORF YDR491C | -2 A | 13 A | 10 P | 27 A | -6.60 | 4.10 | 2.95 Yes Med |
| ORF YBR203W | 12 A | 28 P | 7 P | 23 P | 2.36 | 2.73 | 2.89 Yes Good |
| ORF YNL014W | 13 A | 32 P | 9 A | 29 P | 2.45 | 3.41 | 2.89 Good |
| ORF YCL049C | 11 M | 36 P | 16 P | 36 M | 3.32 | 3.19 | 2.82 Good |
| | | | | | | 2.28 | 2.80 Good |

Figure 10B

| | | | | | | | |
|---|---|---|---|---|---|---|---|
| YCLX05c/ (control?) | -7 A | 4 A | -18 A | -2 A | -0.63 | 0.10 | 2.76 Yes | Med |
| ORF YDR509W | -7 A | 3 A | 7 A | 26 M | -0.45 | 3.48 | 2.75 Yes | Med |
| FUN21 (YAL031C) | 15 A | 44 A | 15 A | 37 A | 2.94 | 2.54 | 2.74 | Good |
| ORF YDR305C exon | -8 A | 4 P | -4 A | 11 P | -0.55 | -2.73 | 2.73 Yes | Med |
| SSA4 (YER103W) | 11 A | 35 P | 26 P | 57 P | 3.26 | 2.18 | 2.72 | Good |
| ORF YER096W | -7 A | 7 P | 9 A | 23 A | -1.07 | 2.70 | 2.70 Yes | Med |
| ORF YIL097W | -8 A | 8 A | -1 A | 10 A | -0.99 | -9.94 | 2.62 Yes | Med |
| ORF YHL048W | 20 A | 55 P | 41 P | 98 P | 2.80 | 2.40 | 2.60 | Good |
| ORF YNL120C | -9 A | 5 A | -3 A | 9 P | -0.48 | -2.96 | 2.57 Yes | Med |
| ORF YBR098W | -11 A | 0 A | -15 A | -1 A | 0.00 | 0.06 | 2.48 Yes | Med |
| ORF YJL161W | -11 A | 2 A | -1 A | 10 P | -0.21 | -8.17 | 2.44 Yes | Med |
| ORF YFR016C | 20 P | 51 P | 26 P | 56 P | 2.61 | 2.19 | 2.40 | Excl |
| ORF YIL169C | 15 A | 32 A | 18 A | 48 P | 2.08 | 2.71 | 2.40 | Good |
| ZRT1 (YGL255W) | 46 P | 116 P | 56 P | 123 P | 2.53 | 2.19 | 2.36 | Excl |
| RHO4 (YKR055W) | 17 A | 44 P | 12 A | 24 P | 2.57 | 2.04 | 2.31 | Good |
| ORF YBR027C | -9 A | 2 A | 12 P | 27 P | -0.21 | 2.28 | 2.23 Yes | Med |
| LEU4 (YNL104C) | 206 P | 439 P | 275 P | 614 P | 2.13 | 2.23 | 2.18 | Excl |
| ORF YDL062W | -2 A | 9 M | -13 A | -2 A | -4.40 | 0.14 | 2.17 Yes | Med |
| ASP3 (YLR158C) | 23 M | 49 P | 17 A | 35 M | 2.12 | 2.11 | 2.12 | Good |

Figure 10C

Gcn5 Down

Gene Expression Results for FH1998040601A

| Gene | WT1val | WT1c | MT1val | MT1c | WT2val | WT2c | MT2val | MT2c | MT1/WT1 | MT2/WT2 | Ave | Corrected? | Confidence |
|---|---|---|---|---|---|---|---|---|---|---|---|---|---|
| ADK1 (YDR226W) | 1136 | P | 564 | P | 1217 | P | 517 | P | 0.50 | 0.42 | 2.19 | | Excl |
| ALPHA1 (YCL066W) | 50 | P | 24 | P | 75 | P | 36 | P | 0.48 | 0.47 | 2.11 | | Excl |
| ATF1 (YOR377W) | 46 | P | 18 | P | 22 | M | -3 | A | 0.39 | -0.12 | 3.77 | Yes | Med |
| AXL1 (YPR122W) | 16 | P | 5 | A | 2 | A | -11 | A | 0.30 | -4.55 | 3.01 | Yes | Med |
| BIO2 (YGR286C) | 47 | P | 22 | P | 31 | P | -4 | A | 0.46 | -0.12 | 4.60 | Yes | Med |
| BUD8 (YLR353W) | 40 | P | 18 | M | 28 | P | 8 | P | 0.44 | 0.26 | 3.01 | | Good |
| CDC6 (YJL194W) | 22 | P | 9 | P | 21 | P | 4 | A | 0.43 | 0.21 | 3.58 | | Good |
| CHS2 (YBR038W) | 31 | P | 3 | P | 9 | M | -5 | A | 0.10 | -0.49 | 6.32 | Yes | Med |
| CUP1 (YHR053C) | 4219 | P | 1448 | P | 3668 | P | 1452 | P | 0.34 | 0.40 | 2.72 | | Excl |
| CUP1 (YHR055C) | 3732 | P | 1301 | P | 3474 | P | 1292 | P | 0.35 | 0.37 | 2.78 | | Excl |
| CYP2 (YHR057C) | 151 | P | 56 | P | 142 | P | 63 | P | 0.37 | 0.45 | 2.46 | | Excl |
| DOM34 (YNL001W) | 54 | P | 19 | P | 41 | A | 16 | A | 0.35 | 0.39 | 2.72 | | Good |
| ERG9 (YHR190W) | 189 | P | 68 | P | 217 | P | 82 | P | 0.36 | 0.38 | 2.72 | | Excl |
| FAA3 (YIL009W) | 35 | P | 15 | A | 54 | P | 2 | A | 0.42 | 0.04 | 12.97 | | Good |
| FAR1 (YJL157C) | 109 | P | 44 | P | 138 | P | 39 | P | 0.40 | 0.28 | 3.00 | | Excl |
| FET4 (YMR319C) | 43 | P | 14 | P | 45 | P | 11 | A | 0.31 | 0.24 | 3.66 | | Good |
| FUN53 (YAL033W) | 73 | P | 35 | A | 58 | P | 12 | A | 0.47 | 0.20 | 3.51 | | Good |
| FUR4 (YBR021W) | 28 | A | -1 | A | 48 | P | 4 | A | -0.02 | 0.08 | 9.45 | Yes | Med |
| FZF1 (YGL254W) | 10 | A | -3 | A | 19 | P | -21 | A | -0.33 | -1.09 | 5.30 | Yes | Med |
| GCN5 (YGR252W) | 46 | A | -6 | A | 28 | P | -22 | A | -0.13 | -0.78 | 10.09 | Yes | Med |
| GDH1 (YOR375C) | 567 | P | 249 | P | 562 | P | 173 | P | 0.44 | 0.31 | 2.77 | | Excl |
| HO (YDL227C) | 72 | P | 19 | P | 48 | P | 16 | P | 0.27 | 0.34 | 3.31 | | Excl |
| JEN1 (YKL217W) | 8 | A | -3 | M | 21 | A | -6 | A | -0.36 | -0.31 | 3.77 | Yes | Med |
| KIN28 (YDL108W) e: | 39 | P | 19 | P | 43 | P | 15 | A | 0.48 | 0.34 | 2.50 | | Good |
| KIP1 (YBL063W) | 27 | P | 5 | A | 18 | P | -1 | A | 0.19 | -0.05 | 4.58 | Yes | Med |
| LTE1 (YAL024C) | 4 | A | -38 | A | 0 | A | -22 | A | -9.44 | #DIV/0! | 6.36 | Yes | Med |
| MEC3 (YLR288C) | 21 | P | 10 | A | 15 | P | 2 | A | 0.49 | 0.14 | 4.60 | | Good |
| MF(ALPHA)2 (YGL08 | 828 | P | 127 | P | 722 | P | 99 | P | 0.15 | 0.14 | 6.88 | | Excl |
| MNN1 (YER001W) | 106 | P | 25 | P | 94 | P | 41 | P | 0.23 | 0.43 | 3.29 | | Excl |
| MSF1 (YPR047W) | 23 | P | 9 | P | 25 | P | 1 | A | 0.40 | 0.05 | 10.46 | | Good |
| MSN1 (YOL116W) | 28 | A | 12 | M | 25 | P | -3 | A | 0.43 | -0.14 | 4.03 | Yes | Med |

Figure 11A

| | 22 | | 3 | | 15 | | 4 | | 0.14 | 0.25 | 5.51 | | Good |
|---|---|---|---|---|---|---|---|---|---|---|---|---|---|
| ORF YAR028W | 22 | A | 3 | A | 15 | A | 4 | A | 0.14 | 0.25 | 5.51 | | Good |
| ORF YBL057C | 50 | P | 23 | M | 38 | P | -5 | A | 0.45 | -0.12 | 5.36 | Yes | Med |
| ORF YBL071C | 17 | P | -5 | A | 27 | P | 12 | A | -0.30 | 0.44 | 3.33 | Yes | Med |
| ORF YBR012W-A (_f) | 736 | P | 264 | P | 784 | P | 325 | P | 0.36 | 0.41 | 2.60 | | Excl |
| ORF YBR028C | 26 | P | 11 | A | 25 | P | -2 | A | 0.44 | -0.07 | 3.87 | Yes | Med |
| ORF YBR157C | 12 | A | 1 | A | 29 | P | 10 | A | 0.10 | 0.35 | 6.20 | | Good |
| ORF YBR224W | 3 | A | -16 | A | -16 | A | -35 | A | -5.24 | 2.16 | 3.73 | Yes | Med |
| ORF YCL041C | 14 | A | 4 | A | 7 | A | -5 | A | 0.27 | -0.82 | 3.07 | Yes | Med |
| ORF YCR059C | 57 | P | 23 | P | 61 | P | 13 | A | 0.41 | 0.21 | 3.63 | | Good |
| ORF YCR060W | 87 | P | 25 | P | 33 | P | 9 | A | 0.28 | 0.28 | 3.57 | | Good |
| ORF YCR061W | 16 | A | 3 | A | 5 | A | -11 | A | 0.20 | -2.05 | 4.17 | Yes | Med |
| ORF YCR085W | 18 | P | 3 | A | 7 | A | -4 | A | 0.17 | -0.50 | 3.96 | Yes | Med |
| ORF YCR105W | 20 | A | 8 | A | 27 | P | 0 | M | 0.38 | 0.00 | 4.00 | Yes | Med |
| ORF YCR107W | 29 | P | 1 | A | 21 | P | -9 | A | 0.02 | -0.44 | 26.03 | Yes | Med |
| ORF YDL002C | 82 | P | 35 | P | 86 | P | 37 | P | 0.43 | 0.43 | 2.32 | | Excl |
| ORF YDL038C | 92 | P | 43 | P | 143 | P | 45 | P | 0.46 | 0.31 | 2.67 | | Excl |
| ORF YDL113C | 15 | M | 3 | A | 14 | P | 2 | A | 0.17 | 0.13 | 6.83 | | Good |
| ORF YDL123W | 17 | A | 6 | A | 39 | P | -1 | A | 0.37 | -0.02 | 5.38 | Yes | Med |
| ORF YDL124W | 159 | P | 42 | P | 197 | P | 61 | P | 0.27 | 0.31 | 3.50 | | Excl |
| ORF YDL214C | 15 | A | 3 | A | 21 | A | 7 | A | 0.21 | 0.35 | 3.80 | | Good |
| ORF YDL247W (_j) | 8 | A | -4 | A | 21 | P | 6 | A | -0.47 | 0.30 | 2.85 | Yes | Med |
| ORF YDR080W | 31 | P | 15 | P | 41 | P | 13 | A | 0.49 | 0.31 | 2.62 | | Good |
| ORF YDR121W | 57 | P | 24 | P | 71 | P | 35 | P | 0.42 | 0.48 | 2.22 | | Excl |
| ORF YDR204W | 39 | P | 16 | P | 23 | P | 5 | A | 0.40 | 0.24 | 3.31 | | Good |
| ORF YDR235W | 22 | P | 6 | A | 44 | P | 15 | A | 0.26 | 0.35 | 3.36 | | Good |
| ORF YDR248C | 36 | P | 17 | M | 52 | P | 21 | A | 0.47 | 0.40 | 2.30 | | Good |
| ORF YDR255C | 18 | P | -2 | A | 10 | A | -18 | A | -0.10 | -1.82 | 4.81 | Yes | Med |
| ORF YDR281C | 55 | P | -1 | A | 55 | P | 1 | A | -0.01 | 0.02 | 35.59 | Yes | Med |
| ORF YDR371W | 28 | P | 8 | A | 23 | P | 8 | A | 0.27 | 0.36 | 3.24 | | Good |
| ORF YDR520C | 33 | P | 15 | P | 23 | P | 7 | A | 0.46 | 0.31 | 2.69 | | Good |
| ORF YDR524C | 25 | P | 11 | P | 19 | P | 0 | A | 0.43 | 0.00 | 3.04 | Yes | Med |
| ORF YDR525W | 20 | P | 1 | A | 13 | P | -1 | A | 0.06 | -0.07 | 9.31 | Yes | Med |
| ORF YDR541C | 30 | P | -3 | A | 13 | A | -29 | A | -0.08 | -2.30 | 7.44 | Yes | Med |

Figure 11B

| | | | | | | | | |
|---|---|---|---|---|---|---|---|---|
| ORF YEL008W | 19 | A | 1 | A | 11 | A | -8 | A | 0.06 | -0.73 | 10.43 | Yes | Med |
| ORF YEL066W | 34 | P | 16 | A | 27 | P | -4 | A | 0.48 | -0.14 | 4.10 | Yes | Med |
| ORF YER072W | 715 | P | 187 | P | 742 | P | 152 | P | 0.26 | 0.20 | 4.36 | | Excl |
| ORF YER138C exon | 910 | P | 349 | P | 648 | P | 244 | P | 0.38 | 0.38 | 2.63 | | Excl |
| ORF YER160C exon | 712 | P | 326 | P | 719 | P | 213 | P | 0.46 | 0.30 | 2.78 | | Excl |
| ORF YER182W | 33 | P | 16 | P | 35 | P | 2 | A | 0.49 | 0.07 | 8.64 | | Good |
| ORF YER183C | 35 | P | 15 | P | 29 | P | 5 | M | 0.42 | 0.16 | 4.30 | | Good |
| ORF YER188W | 28 | P | -1 | A | 11 | P | -3 | A | -0.04 | -0.29 | 4.30 | Yes | Med |
| ORF YFL004W | 72 | P | 33 | P | 108 | P | 29 | P | 0.46 | 0.26 | 2.98 | | Excl |
| ORF YFR047C | 99 | P | 44 | P | 72 | P | 28 | P | 0.44 | 0.39 | 2.44 | | Excl |
| ORF YGL052W | 8 | A | -6 | A | 14 | P | -22 | A | -0.85 | -1.59 | 4.93 | Yes | Med |
| ORF YGL053W | 16 | A | 5 | A | 9 | P | -15 | A | 0.30 | -1.80 | 4.09 | Yes | Med |
| ORF YGL081W | 23 | P | 7 | P | 23 | P | 11 | P | 0.31 | 0.48 | 2.69 | | Excl |
| ORF YGL153W | 58 | P | 13 | P | 47 | P | 22 | A | 0.22 | 0.46 | 3.33 | | Good |
| ORF YGL188C | 20 | P | 8 | A | 2 | A | -12 | A | 0.41 | -8.16 | 2.60 | Yes | Med |
| ORF YGL231C | 121 | P | 53 | P | 122 | P | 59 | P | 0.44 | 0.48 | 2.19 | | Excl |
| ORF YGL235W | 4 | A | -6 | A | 5 | A | -7 | A | -1.36 | -1.53 | 2.17 | Yes | Med |
| ORF YGL262W | 24 | P | -7 | A | 8 | A | -8 | A | -0.29 | -0.96 | 4.67 | Yes | Med |
| ORF YGR011W | 28 | P | 6 | A | 28 | P | 8 | A | 0.21 | 0.27 | 4.22 | | Good |
| ORF YGR013W | 20 | M | 9 | A | 13 | A | -4 | A | 0.44 | -0.31 | 2.78 | Yes | Med |
| ORF YGR065C | 28 | P | 13 | A | 25 | P | 12 | A | 0.47 | 0.45 | 2.12 | | Excl |
| ORF YGR206W | 46 | P | 19 | P | 36 | P | 16 | P | 0.41 | 0.47 | 2.34 | | Excl |
| ORF YGR221C | 10 | A | -2 | A | 10 | M | -9 | A | -0.16 | -0.92 | 3.07 | Yes | Med |
| ORF YGR271W | 23 | P | 10 | A | 15 | P | -14 | A | 0.42 | -0.95 | 4.03 | Yes | Med |
| ORF YHL009C | 27 | P | 11 | P | 26 | P | 11 | A | 0.40 | 0.42 | 2.46 | | Good |
| ORF YHR003C | 40 | P | 20 | P | 40 | P | 14 | A | 0.49 | 0.35 | 2.45 | | Good |
| ORF YHR032W | 63 | P | 22 | P | 76 | P | 33 | P | 0.35 | 0.44 | 2.58 | | Excl |
| ORF YHR033W | 24 | A | 6 | A | 2 | A | -8 | A | 0.25 | -4.21 | 3.07 | Yes | Med |
| ORF YHR049W | 121 | P | 46 | P | 148 | P | 47 | P | 0.38 | 0.32 | 2.88 | | Excl |
| ORF YHR078W | 45 | P | 14 | P | 44 | P | 18 | A | 0.31 | 0.40 | 2.85 | | Good |
| ORF YHR136C | 88 | P | 7 | P | 106 | P | 6 | A | 0.08 | 0.06 | 14.89 | | Good |
| ORF YHR159W | 33 | A | 0 | A | 7 | A | -4 | A | 0.00 | -0.55 | 4.36 | Yes | Med |
| ORF YIL026C | 32 | P | 14 | P | 20 | P | 6 | A | 0.44 | 0.31 | 2.76 | | Good |
| ORF YIL071W | 17 | P | 5 | A | 11 | P | -12 | A | 0.31 | -1.17 | 3.91 | Yes | Med |
| ORF YIR013C | 20 | A | -7 | A | 34 | A | -11 | A | -0.36 | -0.32 | 7.11 | Yes | Med |
| ORF YJL011C | 72 | P | 31 | P | 85 | P | 21 | A | 0.43 | 0.25 | 3.19 | | Good |
| ORF YJL012C | 201 | P | 52 | P | 331 | P | 97 | P | 0.26 | 0.29 | 3.66 | | Excl |

Figure 11C

| | | | | | | | |
|---|---|---|---|---|---|---|---|
| ORF YJL047C | 21 | P | 4 | A | 11 | A | -5 | A | 0.21 | -0.51 | 4.00 | Yes | Med |
| ORF YJL050W | 40 | P | 20 | P | 69 | P | 25 | P | 0.49 | 0.37 | 2.37 | | Excl |
| ORF YJL075C | 9 | A | -9 | A | 10 | A | -8 | A | -1.05 | -0.84 | 3.64 | Yes | Med |
| ORF YJL082W | 34 | P | 3 | A | 12 | A | -19 | A | 0.10 | -1.59 | 8.37 | Yes | Med |
| ORF YJL144W | 20 | M | 4 | A | -2 | A | -19 | A | 0.19 | 7.94 | 4.33 | Yes | Med |
| ORF YJR108W | 11 | M | 0 | A | 1 | A | -19 | A | 0.00 | -15.89 | 3.12 | Yes | Med |
| ORF YKL116C | 37 | P | 18 | P | 15 | P | 2 | A | 0.49 | 0.10 | 5.80 | | Good |
| ORF YKL199C | 62 | P | 26 | P | 76 | P | 20 | A | 0.42 | 0.27 | 3.05 | | Good |
| ORF YLR040C | 306 | P | 106 | P | 349 | P | 94 | P | 0.35 | 0.27 | 3.31 | | Excl |
| ORF YLR064W | 53 | P | 15 | P | 52 | P | 12 | P | 0.29 | 0.23 | 3.93 | | Excl |
| ORF YLR073C | 35 | P | 14 | P | 54 | P | 24 | A | 0.39 | 0.43 | 2.43 | | Good |
| ORF YLR121C | 20 | M | 4 | A | 16 | P | 6 | M | 0.19 | 0.37 | 4.03 | | Good |
| ORF YLR145W | 27 | P | 2 | A | 23 | P | 9 | A | 0.07 | 0.40 | 8.49 | | Good |
| ORF YLR152C | 16 | P | 4 | P | 14 | P | 2 | P | 0.25 | 0.12 | 6.19 | | Excl |
| ORF YLR251W | 34 | P | 11 | A | 31 | P | 4 | P | 0.32 | 0.14 | 5.23 | | Good |
| ORF YLR346C | 84 | P | 35 | P | 111 | P | 47 | P | 0.42 | 0.42 | 2.37 | | Excl |
| ORF YLR426W exon | 44 | P | 4 | A | 29 | A | -10 | A | 0.09 | -0.35 | 9.21 | Yes | Med |
| ORF YLR428C | 20 | A | 4 | A | 5 | A | -5 | A | 0.21 | -0.91 | 3.40 | Yes | Med |
| ORF YLR464W exon | 28 | P | 4 | A | 6 | A | -5 | A | 0.15 | -0.91 | 4.55 | Yes | Med |
| ORF YML055W | 72 | P | 36 | P | 56 | P | 24 | P | 0.49 | 0.43 | 2.17 | | Excl |
| ORF YML100W-A | -8 | A | -23 | A | -25 | A | -37 | A | 2.92 | 1.44 | 2.60 | Yes | Med |
| ORF YML107C | 33 | P | 16 | A | 34 | P | -2 | A | 0.48 | -0.06 | 4.69 | Yes | Med |
| ORF YML128C | 20 | P | 5 | M | 15 | P | 3 | A | 0.23 | 0.18 | 4.90 | | Good |
| ORF YMR050C exon | 671 | P | 294 | P | 767 | P | 293 | P | 0.44 | 0.38 | 2.45 | | Excl |
| ORF YMR141C | 14 | A | -1 | A | 14 | P | 1 | A | -0.07 | 0.08 | 8.08 | Yes | Med |
| ORF YMR145C | 304 | P | 145 | P | 266 | P | 120 | P | 0.48 | 0.45 | 2.16 | | Excl |
| ORF YNL040W | 65 | P | 25 | P | 63 | P | 16 | P | 0.38 | 0.25 | 3.32 | | Excl |
| ORF YNL317W | 33 | P | 16 | P | 33 | P | 14 | A | 0.50 | 0.42 | 2.19 | | Good |
| ORF YOL002C | 138 | P | 66 | P | 131 | P | 60 | P | 0.48 | 0.46 | 2.12 | | Excl |
| ORF YOL008W | 27 | P | 13 | P | 25 | P | 12 | P | 0.47 | 0.47 | 2.12 | | Excl |
| ORF YOL013C | 43 | P | 17 | P | 25 | A | 5 | A | 0.39 | 0.19 | 3.86 | | Good |

Figure 11D

| | | | | | | | |
|---|---|---|---|---|---|---|---|
| ORF YOL101C | 29 | P | 8 | P | 17 | P | 3 | A | 0.27 | 0.16 | 4.89 | | Good |
| ORF YOL128C | 43 | P | 18 | P | 41 | A | 9 | A | 0.42 | 0.22 | 3.50 | | Good |
| ORF YOL158C | 107 | P | 42 | P | 143 | P | 34 | P | 0.39 | 0.24 | 3.41 | | Excl |
| ORF YOR013W | 19 | A | -5 | A | 33 | P | 10 | A | -0.24 | 0.32 | 3.89 | Yes | Med |
| ORF YOR066W | 451 | P | 17 | M | 37 | A | 1 | A | 0.38 | 0.02 | 28.12 | | Good |
| ORF YOR110W | 32 | P | 14 | P | 29 | P | 13 | A | 0.43 | 0.45 | 2.28 | | Good |
| ORF YOR225W | 36 | A | 15 | P | 19 | A | -12 | A | 0.41 | -0.62 | 4.25 | Yes | Med |
| ORF YOR238W | 33 | P | 16 | P | 52 | P | 11 | A | 0.50 | 0.21 | 3.40 | | Good |
| ORF YOR306C | 77 | P | 25 | P | 92 | P | 9 | A | 0.33 | 0.10 | 6.66 | | Good |
| ORF YOR339C | 14 | A | 3 | A | 6 | A | -5 | A | 0.24 | -0.80 | 3.15 | Yes | Med |
| ORF YOR381W | 25 | P | 1 | A | 19 | P | -15 | A | 0.05 | -0.81 | 14.39 | Yes | Med |
| ORF YPL019C | 445 | P | 44 | P | 536 | P | 37 | P | 0.10 | 0.07 | 12.35 | | Excl |
| ORF YPL110C | 45 | P | 16 | P | 21 | P | 1 | A | 0.36 | 0.07 | 9.08 | | Good |
| ORF YPL136W | 12 | A | -5 | A | -4 | A | -16 | A | -0.42 | 4.55 | 3.05 | Yes | Med |
| ORF YPL156C | 35 | P | 10 | P | 32 | P | 4 | A | 0.28 | 0.13 | 5.67 | | Good |
| ORF YPL228W | 40 | P | 16 | P | 24 | P | 10 | A | 0.39 | 0.43 | 2.45 | | Good |
| ORF YPR192W | 12 | A | -33 | A | 13 | A | -10 | A | -2.84 | -0.81 | 6.76 | Yes | Med |
| PBN1 (YCL052C) | 51 | P | 23 | P | 55 | P | 27 | P | 0.44 | 0.50 | 2.13 | | Excl |
| PCL2 (YDL127W) | 18 | P | 8 | A | 14 | P | -18 | A | 0.42 | -1.30 | 4.42 | Yes | Med |
| PET54 (YGR222W) | 46 | P | 14 | A | 43 | P | 21 | A | 0.31 | 0.49 | 2.66 | | Good |
| PHO11 (YAR071W) | 281 | P | 8 | A | 270 | P | 37 | P | 0.03 | 0.14 | 20.79 | | Excl |
| PHO12 (YHR215W) | 338 | P | 18 | P | 399 | P | 34 | P | 0.05 | 0.08 | 15.42 | | Excl |
| PHO3 (YBR092C) | 215 | P | 10 | A | 180 | P | 56 | P | 0.05 | 0.31 | 12.30 | | Good |
| PHO5 (YBR093C) | 84 | P | 5 | A | 105 | P | 13 | A | 0.06 | 0.12 | 12.48 | | Good |
| PHO81 (YGR233C) | 35 | P | 9 | A | 52 | P | 3 | A | 0.25 | 0.06 | 10.44 | | Good |
| PHO84 (YML123C) | 1132 | P | 61 | P | 1520 | P | 69 | P | 0.05 | 0.05 | 20.24 | | Excl |
| PHR1 (YOR386W) | 18 | P | 2 | A | 13 | P | -8 | A | 0.08 | -0.65 | 8.02 | Yes | Med |
| PRD1 (YCL057W) | 24 | P | 11 | P | 46 | P | 6 | A | 0.47 | 0.14 | 4.67 | | Good |
| PRP21 (YJL203W) | 22 | P | 3 | A | 18 | P | -3 | A | 0.15 | -0.15 | 5.44 | Yes | Med |
| PUR5 (YHR216W) | 16 | M | 3 | A | 26 | P | -12 | A | 0.20 | -0.44 | 6.31 | Yes | Med |
| RAD59 (YDL059C) | 19 | P | 9 | A | 30 | P | 14 | M | 0.46 | 0.46 | 2.18 | | Good |
| RPL6B (YPL198W) e | 354 | P | 174 | P | 451 | P | 103 | P | 0.49 | 0.23 | 3.21 | | Excl |

Figure 11E

| | 181 | P | 58 | P | 295 | P | 66 | P | | | | | |
|---|---|---|---|---|---|---|---|---|---|---|---|---|---|
| SAG1 (YJR004C) | | | | | | | | | 0.32 | 0.22 | 3.80 | | Excl |
| SAN1 (YDR143C) | 16 | A | 5 | A | 58 | P | 22 | P | 0.31 | 0.38 | 2.92 | | Good |
| SAP155 (YFR040W) | 36 | P | 17 | P | 41 | P | 10 | A | 0.48 | 0.24 | 3.11 | | Good |
| SDC25 (YLL016W) | 20 | P | 7 | P | 2 | A | -8 | A | 0.37 | -3.40 | 2.38 | Yes | Med |
| SNG1 (YGR197C) | 39 | P | 12 | P | 21 | M | -5 | A | 0.32 | -0.22 | 4.11 | Yes | Med |
| SPR6 (YER115C) | 77 | P | 15 | P | 54 | P | 8 | M | 0.19 | 0.14 | 6.19 | | Good |
| SSN3 (YPL042C) | 34 | P | 14 | P | 40 | P | 11 | A | 0.40 | 0.28 | 3.07 | | Excl |
| SST2 (YLR452C) | 53 | P | 14 | P | 54 | P | 24 | P | 0.26 | 0.43 | 3.08 | | Good |
| SSU1 (YPL092W) | 45 | P | 10 | A | 24 | P | 9 | A | 0.22 | 0.37 | 3.65 | | Good |
| STE3 (YKL178C) | 91 | P | 28 | P | 93 | P | 27 | A | 0.30 | 0.29 | 3.38 | | Excl |
| SVS1 (YPL163C) | 225 | P | 110 | P | 253 | P | 51 | P | 0.49 | 0.20 | 3.52 | | Excl |
| TIP1 (YBR067C) | 369 | P | 184 | P | 407 | P | 201 | P | 0.50 | 0.49 | 2.02 | | Med |
| TKL2 (YBR117C) | 9 | A | -3 | A | 5 | A | -9 | A | -0.28 | -1.95 | 2.53 | Yes | Good |
| UBC5 (YDR059C) ex | 39 | P | 9 | A | 39 | P | 17 | A | 0.24 | 0.44 | 3.20 | | Good |
| YAK1 (YJL141C) | 20 | P | 9 | A | 17 | A | 3 | A | 0.44 | 0.19 | 3.79 | | Med |
| YCRX04w/ (control? | 18 | P | -4 | A | -1 | A | -15 | A | -0.21 | 11.61 | 3.59 | Yes | Excl |
| YGP1 (YNL160W) | 180 | P | 38 | P | 213 | P | 50 | P | 0.21 | 0.23 | 4.50 | | Excl |
| YHB1 (YGR234W) | 414 | P | 109 | P | 482 | P | 106 | P | 0.26 | 0.22 | 4.18 | | Med |
| YJU2 (YKL095W) | 23 | P | 11 | P | 20 | M | -6 | A | 0.48 | -0.33 | 3.65 | Yes | Med |
| YNT20 (YLR059C) | 47 | P | 3 | A | 37 | P | -1 | A | 0.07 | -0.03 | 11.04 | Yes | Med |
| YSP3 (YOR003W) | 17 | P | 6 | A | 8 | A | -4 | A | 0.33 | -0.49 | 2.77 | Yes | Med |

Figure 11F

Gcn5 Down

Gene Expression Results for FH1998040601A

| Gene | WT1val | WT1c | MT1val | MT1c | WT2val | WT2c | MT2val | MT2c | MT1/WT1 | MT2/WT2 | Ave | Corrected? | Confidence |
|---|---|---|---|---|---|---|---|---|---|---|---|---|---|
| ORF YDR281C | 55 | P | -1 | A | 55 | P | 1 | A | -0.01 | 0.02 | 35.59 | Yes | Med |
| ORF YOR066W | 45 | P | 17 | M | 37 | A | 1 | A | 0.38 | 0.02 | 28.12 | | Good |
| ORF YCR107W | 29 | P | 1 | A | 21 | P | -9 | A | 0.02 | -0.44 | 26.03 | Yes | Med |
| PHO11 (YAR071W) | 281 | P | 8 | A | 270 | P | 37 | P | 0.03 | 0.14 | 20.79 | | Good |
| PHO84 (YML123C) | 1132 | P | 61 | P | 1520 | P | 69 | P | 0.05 | 0.05 | 20.24 | | Excl |
| PHO12 (YHR215W) | 338 | P | 18 | P | 399 | P | 34 | P | 0.05 | 0.08 | 15.42 | | Excl |
| ORF YHR136C | 88 | P | 7 | P | 106 | P | 6 | A | 0.08 | 0.06 | 14.89 | | Good |
| ORF YOR381W | 25 | P | 1 | A | 19 | P | -15 | A | 0.05 | -0.81 | 14.39 | Yes | Med |
| FAA3 (YIL009W) | 35 | P | 15 | A | 54 | P | 2 | A | 0.42 | 0.04 | 12.97 | | Good |
| PHO5 (YBR093C) | 84 | P | 5 | A | 105 | P | 13 | A | 0.06 | 0.12 | 12.48 | | Good |
| ORF YPL019C | 445 | P | 44 | P | 536 | P | 37 | P | 0.10 | 0.07 | 12.35 | | Excl |
| PHO3 (YBR092C) | 215 | P | 10 | A | 180 | P | 56 | P | 0.05 | 0.31 | 12.30 | | Good |
| YNT20 (YLR059C) | 47 | P | 3 | A | 37 | P | -1 | A | 0.07 | -0.03 | 11.04 | Yes | Med |
| MSF1 (YPR047W) | 23 | P | 9 | P | 25 | P | 1 | A | 0.40 | 0.05 | 10.46 | | Good |
| PHO81 (YGR233C) | 35 | P | 9 | A | 52 | P | 3 | A | 0.25 | 0.06 | 10.44 | | Good |
| ORF YEL008W | 19 | A | 1 | A | 11 | A | -8 | A | 0.06 | -0.73 | 10.43 | Yes | Med |
| GCN5 (YGR252W) | 46 | P | -6 | A | 28 | P | -22 | A | -0.13 | -0.78 | 10.09 | Yes | Med |
| FUR4 (YBR021W) | 28 | A | -1 | A | 48 | P | 4 | A | -0.02 | 0.08 | 9.45 | Yes | Med |
| ORF YDR525W | 20 | P | 1 | A | 13 | P | -1 | A | 0.06 | -0.07 | 9.31 | Yes | Med |
| ORF YLR426W exon | 44 | P | 4 | A | 29 | A | -10 | A | 0.09 | -0.35 | 9.21 | Yes | Med |
| ORF YPL110C | 45 | P | 16 | P | 21 | P | 1 | A | 0.36 | 0.07 | 9.08 | | Good |
| ORF YER182W | 33 | P | 16 | P | 35 | P | 2 | A | 0.49 | 0.07 | 8.64 | | Good |
| ORF YLR145W | 27 | P | 2 | A | 23 | P | 9 | A | 0.07 | 0.40 | 8.49 | | Good |
| ORF YJL082W | 34 | P | 3 | A | 12 | A | -19 | A | 0.10 | -1.59 | 8.37 | Yes | Med |
| ORF YMR141C | 14 | A | -1 | A | 14 | P | 1 | A | -0.07 | 0.08 | 8.08 | Yes | Med |
| PHR1 (YOR386W) | 18 | P | 2 | A | 13 | P | -8 | A | 0.08 | -0.65 | 8.02 | Yes | Med |
| ORF YDR541C | 30 | P | -3 | A | 13 | A | -29 | A | -0.08 | -2.30 | 7.44 | Yes | Med |
| ORF YIR013C | 20 | A | -7 | A | 34 | A | -11 | A | -0.36 | -0.32 | 7.11 | Yes | Med |
| MF(ALPHA)2 (YGL08 | 828 | P | 127 | P | 722 | P | 99 | P | 0.15 | 0.14 | 6.88 | | Excl |
| ORF YDL113C | 15 | M | 3 | A | 14 | P | 2 | A | 0.17 | 0.13 | 6.83 | | Good |
| ORF YPR192W | 12 | A | -33 | A | 13 | A | -10 | A | -2.84 | -0.81 | 6.76 | Yes | Med |
| ORF YOR306C | 77 | P | 25 | P | 92 | P | 9 | A | 0.33 | 0.10 | 6.66 | | Good |
| LTE1 (YAL024C) | 4 | A | -38 | A | 0 | A | -22 | A | -9.44 | #DIV/0! | 6.36 | Yes | Med |
| CHS2 (YBR038W) | 31 | P | 3 | P | 9 | M | -5 | A | 0.10 | -0.49 | 6.32 | Yes | Med |

Figure 12A

| | | | | | | | | |
|---|---|---|---|---|---|---|---|---|
| PUR5 (YHR216W) | 16 | M | 3 | A | 26 | P | -12 | A | 0.20 | -0.44 | 6.31 | Yes | Med |
| ORF YBR157C | 12 | A | 1 | A | 29 | P | 10 | A | 0.10 | 0.35 | 6.20 | | Good |
| SPR6 (YER115C) | 77 | P | 15 | P | 54 | P | 8 | M | 0.19 | 0.14 | 6.19 | | Good |
| ORF YLR152C | 16 | P | 4 | P | 14 | P | 2 | P | 0.25 | 0.12 | 6.19 | | Excl |
| ORF YKL116C | 37 | P | 18 | P | 15 | P | 2 | A | 0.49 | 0.10 | 5.80 | | Good |
| ORF YPL156C | 35 | P | 10 | P | 32 | P | 4 | A | 0.28 | 0.13 | 5.67 | | Good |
| ORF YAR028W | 22 | A | 3 | A | 15 | A | 4 | A | 0.14 | 0.25 | 5.51 | | Good |
| PRP21 (YJL203W) | 22 | P | 3 | A | 18 | P | -3 | A | 0.15 | -0.15 | 5.44 | Yes | Med |
| ORF YDL123W | 17 | A | 6 | A | 39 | P | -1 | A | 0.37 | -0.02 | 5.38 | Yes | Med |
| ORF YBL057C | 50 | P | 23 | M | 38 | P | -5 | A | 0.45 | -0.12 | 5.36 | Yes | Med |
| FZF1 (YGL254W) | 10 | A | -3 | A | 19 | P | -21 | A | -0.33 | -1.09 | 5.30 | Yes | Med |
| ORF YLR251W | 34 | P | 11 | A | 31 | P | 4 | P | 0.32 | 0.14 | 5.23 | | Good |
| ORF YGL052W | 8 | A | -6 | A | 14 | P | -22 | A | -0.85 | -1.59 | 4.93 | Yes | Med |
| ORF YML128C | 20 | P | 5 | M | 15 | P | 3 | A | 0.23 | 0.18 | 4.90 | | Good |
| ORF YOL101C | 29 | P | 8 | P | 17 | P | 3 | A | 0.27 | 0.16 | 4.89 | | Good |
| ORF YDR255C | 18 | P | -2 | A | 10 | A | -18 | A | -0.10 | -1.82 | 4.81 | Yes | Med |
| ORF YML107C | 33 | P | 16 | A | 34 | P | -2 | A | 0.48 | -0.06 | 4.69 | Yes | Med |
| ORF YGL262W | 24 | P | -7 | A | 8 | A | -8 | A | -0.29 | -0.96 | 4.67 | Yes | Med |
| PRD1 (YCL057W) | 24 | P | 11 | P | 46 | P | 6 | A | 0.47 | 0.14 | 4.67 | | Good |
| BIO2 (YGR286C) | 47 | P | 22 | P | 31 | P | -4 | A | 0.46 | -0.12 | 4.60 | Yes | Med |
| MEC3 (YLR288C) | 21 | P | 10 | A | 15 | P | 2 | A | 0.49 | 0.14 | 4.60 | | Good |
| KIP1 (YBL063W) | 27 | P | 5 | A | 18 | P | -11 | A | 0.19 | -0.05 | 4.58 | Yes | Med |
| ORF YLR464W exon | 28 | P | 4 | A | 6 | A | -5 | A | 0.15 | -0.91 | 4.55 | Yes | Med |
| YGP1 (YNL160W) | 180 | P | 38 | P | 213 | P | 50 | P | 0.21 | 0.23 | 4.50 | | Excl |
| PCL2 (YDL127W) | 18 | P | 8 | A | 14 | P | -18 | A | 0.42 | -1.30 | 4.42 | Yes | Med |
| ORF YER072W | 715 | P | 187 | P | 742 | P | 152 | P | 0.26 | 0.20 | 4.36 | | Excl |
| ORF YHR159W | 33 | A | 0 | A | 7 | A | -4 | A | 0.00 | -0.55 | 4.36 | Yes | Med |
| ORF YJL144W | 20 | M | 4 | A | -2 | A | -19 | A | 0.19 | 7.94 | 4.33 | Yes | Med |
| ORF YER183C | 35 | P | 15 | P | 29 | P | 5 | M | 0.42 | 0.16 | 4.30 | | Good |
| ORF YER188W | 28 | P | -1 | A | 11 | P | -3 | A | -0.04 | -0.29 | 4.30 | Yes | Med |

Figure 12B

| | | | | | | | | |
|---|---|---|---|---|---|---|---|---|
| ORF YOR225W | 36 | A | 15 | P | 19 | A | -12 | A | 0.41 | -0.62 | 4.25 | Yes | Med |
| ORF YGR011W | 28 | P | 6 | A | 28 | P | 8 | A | 0.21 | 0.27 | 4.22 | | Good |
| YHB1 (YGR234W) | 414 | P | 109 | P | 482 | P | 106 | P | 0.26 | 0.22 | 4.18 | | Excl |
| ORF YCR061W | 16 | A | 3 | A | 5 | A | -11 | A | 0.20 | -2.05 | 4.17 | Yes | Med |
| SNG1 (YGR197C) | 39 | P | 12 | P | 21 | M | -5 | A | 0.32 | -0.22 | 4.11 | Yes | Med |
| ORF YEL066W | 34 | P | 16 | A | 27 | P | -4 | A | 0.48 | -0.14 | 4.10 | Yes | Med |
| ORF YGL053W | 16 | A | 5 | A | 9 | P | -15 | A | 0.30 | -1.80 | 4.09 | Yes | Med |
| ORF YLR121C | 20 | M | 4 | A | 16 | P | 6 | M | 0.19 | 0.37 | 4.03 | | Good |
| MSN1 (YOL116W) | 28 | A | 12 | M | 25 | P | -3 | A | 0.43 | -0.14 | 4.03 | Yes | Med |
| ORF YGR271W | 23 | P | 10 | A | 15 | P | -14 | A | 0.42 | -0.95 | 4.03 | Yes | Med |
| ORF YJL047C | 21 | P | 4 | A | 11 | A | -5 | A | 0.21 | -0.51 | 4.00 | Yes | Med |
| ORF YCR105W | 20 | A | 8 | A | 27 | P | 0 | M | 0.38 | 0.00 | 4.00 | Yes | Med |
| ORF YCR085W | 18 | P | 3 | A | 7 | A | -4 | A | 0.17 | -0.50 | 3.96 | Yes | Med |
| ORF YLR064W | 53 | P | 15 | P | 52 | P | 12 | P | 0.29 | 0.23 | 3.93 | | Excl |
| ORF YIL071W | 17 | P | 5 | A | 11 | P | -12 | A | 0.31 | -1.17 | 3.91 | Yes | Med |
| ORF YOR013W | 19 | A | -5 | A | 33 | P | 10 | A | -0.24 | 0.32 | 3.89 | Yes | Med |
| ORF YBR028C | 26 | P | 11 | A | 25 | P | -2 | A | 0.44 | -0.07 | 3.87 | Yes | Med |
| ORF YOL013C | 43 | P | 17 | P | 25 | A | 5 | A | 0.39 | 0.19 | 3.86 | | Good |
| ORF YDL214C | 15 | A | 3 | A | 21 | A | 7 | A | 0.21 | 0.35 | 3.80 | | Good |
| SAG1 (YJR004C) | 181 | P | 58 | P | 295 | P | 66 | P | 0.32 | 0.22 | 3.80 | | Excl |
| YAK1 (YJL141C) | 20 | P | 9 | A | 17 | A | 3 | A | 0.44 | 0.19 | 3.79 | | Good |
| ATF1 (YOR377W) | 46 | P | 18 | P | 22 | M | -3 | A | 0.39 | -0.12 | 3.77 | Yes | Med |
| JEN1 (YKL217W) | 8 | A | -3 | M | 21 | A | -6 | A | -0.36 | -0.31 | 3.77 | Yes | Med |
| ORF YBR224W | 3 | A | -16 | A | -16 | A | -35 | A | -5.24 | 2.16 | 3.73 | Yes | Med |
| FET4 (YMR319C) | 43 | P | 14 | P | 45 | P | 11 | A | 0.31 | 0.24 | 3.66 | | Good |
| ORF YJL012C | 201 | P | 52 | P | 331 | P | 97 | P | 0.26 | 0.29 | 3.66 | | Excl |
| SSU1 (YPL092W) | 45 | P | 10 | A | 24 | P | 9 | A | 0.22 | 0.37 | 3.65 | | Good |
| YJU2 (YKL095W) | 23 | P | 11 | P | 20 | M | -6 | A | 0.48 | -0.33 | 3.65 | Yes | Med |
| ORF YJL075C | 9 | A | -9 | A | 10 | A | -8 | A | -1.05 | -0.84 | 3.64 | Yes | Med |
| ORF YCR059C | 57 | P | 23 | P | 61 | P | 13 | A | 0.41 | 0.21 | 3.63 | | Good |
| YCRX04w/ (control?) | 18 | P | -4 | A | -1 | A | -15 | A | -0.21 | 11.61 | 3.59 | Yes | Med |
| CDC6 (YJL194W) | 22 | P | 9 | P | 21 | P | 4 | A | 0.43 | 0.21 | 3.58 | | Good |
| ORF YCR060W | 87 | P | 25 | P | 33 | P | 9 | A | 0.28 | 0.28 | 3.57 | | Good |
| SVS1 (YPL163C) | 225 | P | 110 | P | 253 | P | 51 | P | 0.49 | 0.20 | 3.52 | | Excl |
| FUN53 (YAL033W) | 73 | P | 35 | A | 58 | P | 12 | A | 0.47 | 0.20 | 3.51 | | Good |

Figure 12C

| | 43 | | 18 | | 41 | | 9 | | | | | | |
|---|---|---|---|---|---|---|---|---|---|---|---|---|---|
| ORF YOL128C | 43 | P | 18 | P | 41 | A | 9 | A | 0.42 | 0.22 | 3.50 | | Good |
| ORF YDL124W | 159 | P | 42 | P | 197 | P | 61 | P | 0.27 | 0.31 | 3.50 | | Excl |
| ORF YOL158C | 107 | P | 42 | P | 143 | P | 34 | P | 0.39 | 0.24 | 3.41 | | Excl |
| ORF YLR428C | 20 | A | 4 | A | 5 | A | -5 | A | 0.21 | -0.91 | 3.40 | Yes | Med |
| ORF YOR238W | 33 | P | 16 | P | 52 | P | 11 | A | 0.50 | 0.21 | 3.40 | | Good |
| STE3 (YKL178C) | 91 | P | 28 | P | 93 | P | 27 | A | 0.30 | 0.29 | 3.38 | | Good |
| ORF YDR235W | 22 | P | 6 | A | 44 | P | 15 | A | 0.26 | 0.35 | 3.36 | | Good |
| ORF YGL153W | 58 | P | 13 | P | 47 | P | 22 | A | 0.22 | 0.46 | 3.33 | | Good |
| ORF YBL071C | 17 | P | -5 | A | 27 | P | 12 | A | -0.30 | 0.44 | 3.33 | Yes | Med |
| ORF YNL040W | 65 | P | 25 | P | 63 | P | 16 | P | 0.38 | 0.25 | 3.32 | | Excl |
| ORF YDR204W | 39 | P | 16 | P | 23 | P | 5 | A | 0.40 | 0.24 | 3.31 | | Good |
| ORF YLR040C | 306 | P | 106 | P | 349 | P | 94 | P | 0.35 | 0.27 | 3.31 | | Excl |
| HO (YDL227C) | 72 | P | 19 | P | 48 | P | 16 | P | 0.27 | 0.34 | 3.31 | | Excl |
| MNN1 (YER001W) | 106 | P | 25 | P | 94 | P | 41 | P | 0.23 | 0.43 | 3.29 | | Excl |
| ORF YDR371W | 28 | P | 8 | A | 23 | P | 8 | A | 0.27 | 0.36 | 3.24 | | Good |
| RPL6B (YPL198W) el | 354 | P | 174 | P | 451 | P | 103 | P | 0.49 | 0.23 | 3.21 | | Excl |
| UBC5 (YDR059C) ex | 39 | P | 9 | A | 39 | P | 17 | A | 0.24 | 0.44 | 3.20 | | Good |
| ORF YJL011C | 72 | P | 31 | P | 85 | P | 21 | A | 0.43 | 0.25 | 3.19 | | Good |
| ORF YOR339C | 14 | A | 3 | A | 6 | A | -5 | A | 0.24 | -0.80 | 3.15 | Yes | Med |
| ORF YJR108W | 11 | M | 0 | A | 1 | A | -19 | A | 0.00 | -15.89 | 3.12 | Yes | Med |
| SAP155 (YFR040W) | 36 | P | 17 | P | 41 | P | 10 | A | 0.48 | 0.24 | 3.11 | | Good |
| SST2 (YLR452C) | 53 | P | 14 | P | 54 | P | 24 | P | 0.26 | 0.43 | 3.08 | | Excl |
| ORF YHR033W | 24 | A | 6 | A | 2 | A | -8 | A | 0.25 | -4.21 | 3.07 | Yes | Med |
| ORF YGR221C | 10 | A | -2 | A | 10 | M | -9 | A | -0.16 | -0.92 | 3.07 | Yes | Med |
| SSN3 (YPL042C) | 34 | P | 14 | P | 40 | P | 11 | A | 0.40 | 0.28 | 3.07 | | Good |
| ORF YCL041C | 14 | A | 4 | A | 7 | A | -5 | A | 0.27 | -0.82 | 3.07 | Yes | Med |
| ORF YKL199C | 62 | P | 26 | P | 76 | P | 20 | A | 0.42 | 0.27 | 3.05 | | Good |
| ORF YPL136W | 12 | A | -5 | A | -4 | A | -16 | A | -0.42 | 4.55 | 3.05 | Yes | Med |
| ORF YDR524C | 25 | P | 11 | P | 19 | P | 0 | A | 0.43 | 0.00 | 3.04 | Yes | Good |
| BUD8 (YLR353W) | 40 | P | 18 | M | 28 | P | 8 | P | 0.44 | 0.26 | 3.01 | | Med |
| AXL1 (YPR122W) | 16 | P | 5 | A | 2 | A | -11 | A | 0.30 | -4.55 | 3.01 | Yes | Med |
| FAR1 (YJL157C) | 109 | P | 44 | P | 138 | P | 39 | P | 0.40 | 0.28 | 3.00 | | Excl |
| ORF YFL004W | 72 | P | 33 | P | 108 | P | 29 | P | 0.46 | 0.26 | 2.98 | | Excl |

Figure 12D

| | | | | | | | | |
|---|---|---|---|---|---|---|---|---|
| SAN1 (YDR143C) | 16 | A | 5 | A | 58 | P | 22 | P | | | | Good |
| ORF YHR049W | 121 | P | 46 | P | 148 | P | 47 | P | | 2.88 | | Excl |
| ORF YDL247W (_i) | 8 | A | -4 | A | 21 | P | 6 | A | 0.31 | 2.85 | Yes | Med |
| ORF YHR078W | 45 | P | 14 | P | 44 | P | 18 | A | 0.38 | 2.85 | | Good |
| ORF YGR013W | 20 | M | 9 | A | 13 | A | -4 | A | -0.47 | 2.78 | Yes | Med |
| ORF YER160C exon | 712 | P | 326 | P | 719 | P | 213 | P | 0.31 | 2.78 | | Excl |
| CUP1 (YHR055C) (_ | 3732 | P | 1301 | P | 3474 | P | 1292 | P | 0.44 | 2.78 | | Excl |
| YSP3 (YOR003W) | 17 | P | 6 | A | 8 | A | -4 | A | 0.46 | 2.77 | Yes | Med |
| GDH1 (YOR375C) | 567 | P | 249 | P | 562 | P | 173 | P | 0.35 | 2.77 | | Excl |
| ORF YIL026C | 32 | P | 14 | P | 20 | P | 6 | A | 0.33 | 2.76 | | Good |
| CUP1 (YHR053C) (_ | 4219 | P | 1448 | P | 3668 | P | 1452 | P | 0.44 | 2.72 | | Excl |
| ERG9 (YHR190W) | 189 | P | 68 | P | 217 | P | 82 | P | 0.34 | 2.72 | | Excl |
| DOM34 (YNL001W) | 54 | P | 19 | P | 41 | A | 16 | A | 0.36 | 2.72 | | Good |
| ORF YDR520C | 33 | P | 15 | P | 23 | P | 7 | A | 0.35 | 2.69 | | Good |
| ORF YGL081W | 23 | P | 7 | P | 23 | P | 11 | P | 0.46 | 2.69 | | Excl |
| ORF YDL038C | 92 | P | 43 | P | 143 | P | 45 | P | 0.31 | 2.67 | | Excl |
| PET54 (YGR222W) | 46 | P | 14 | A | 43 | P | 21 | A | 0.46 | 2.66 | | Good |
| ORF YER138C exon | 910 | P | 349 | P | 648 | P | 244 | P | 0.31 | 2.63 | | Excl |
| ORF YDR080W | 31 | P | 15 | P | 41 | P | 13 | A | 0.38 | 2.62 | | Good |
| ORF YBR012W-A (_fi | 736 | P | 264 | P | 784 | P | 325 | P | 0.49 | 2.60 | | Excl |
| ORF YGL188C | 20 | P | 8 | A | 2 | A | -12 | A | 0.36 | 2.60 | Yes | Med |
| ORF YML100W-A | -8 | A | -23 | A | -25 | A | -37 | A | 0.41 | 2.60 | Yes | Med |
| ORF YHR032W | 63 | P | 22 | P | 76 | P | 33 | P | 2.92 | 2.58 | | Excl |
| TKL2 (YBR117C) | 9 | A | -3 | A | 5 | A | -9 | A | 0.35 | 2.53 | Yes | Med |
| KIN28 (YDL108W) et | 39 | P | 19 | P | 43 | P | 15 | A | -0.28 | 2.50 | | Good |
| CYP2 (YHR057C) | 151 | P | 56 | P | 142 | P | 63 | P | 0.48 | 2.46 | | Excl |
| ORF YHL009C | 27 | P | 11 | P | 26 | P | 11 | A | 0.37 | 2.46 | | Good |
| ORF YMR050C exon | 671 | P | 294 | P | 767 | P | 293 | P | 0.40 | 2.45 | | Excl |
| ORF YPL228W | 40 | P | 16 | P | 24 | P | 10 | A | 0.44 | 2.45 | | Good |
| ORF YHR003C | 40 | P | 20 | P | 40 | P | 14 | A | 0.39 | 2.45 | | Good |
| ORF YFR047C | 99 | P | 44 | P | 72 | P | 28 | P | 0.49 | 2.44 | | Excl |
| ORF YLR073C | 35 | P | 14 | P | 54 | P | 24 | A | 0.44 | 2.43 | | Excl |
| SDC25 (YLL016W) | 20 | P | 7 | P | 2 | A | -8 | A | 0.39 | 2.38 | Yes | Med |
| ORF YLR346C | 84 | P | 35 | P | 111 | P | 47 | P | 0.37 | 2.37 | | Excl |
| ORF YJL050W | 40 | P | 20 | P | 69 | P | 25 | P | 0.42 | 2.37 | | Excl |
| ORF YGR206W | 46 | P | 19 | P | 36 | P | 16 | P | 0.49 | 2.34 | | Excl |
| ORF YDL002C | 82 | P | 35 | P | 86 | P | 37 | P | 0.41 | 2.32 | | Excl |
| ORF YDR248C | 36 | P | 17 | M | 52 | P | 21 | A | 0.43 | 2.30 | | Good |

Figure 12E

| | | | | | | | |
|---|---|---|---|---|---|---|---|
| ORF YOR110W | 32 P | 14 P | 29 P | 13 A | 0.43 | 0.45 | 2.28 | | Good |
| ORF YDR121W | 57 P | 24 P | 71 P | 35 P | 0.42 | 0.48 | 2.22 | | Excl |
| ORF YNL317W | 33 P | 16 P | 33 P | 14 A | 0.50 | 0.42 | 2.19 | | Good |
| ORF YGL231C | 121 P | 53 P | 122 P | 59 P | 0.44 | 0.48 | 2.19 | | Excl |
| ADK1 (YDR226W) | 1136 P | 564 P | 1217 P | 517 P | 0.50 | 0.42 | 2.19 | | Excl |
| RAD59 (YDL059C) | 19 P | 9 A | 30 P | 14 M | 0.46 | 0.46 | 2.18 | | Good |
| ORF YGL235W | 4 A | -6 A | 5 A | -7 A | -1.36 | -1.53 | 2.17 | Yes | Med |
| ORF YML055W | 72 P | 36 P | 56 P | 24 P | 0.49 | 0.43 | 2.17 | | Excl |
| ORF YMR145C | 304 P | 145 P | 266 P | 120 P | 0.48 | 0.45 | 2.16 | | Excl |
| PBN1 (YCL052C) | 51 P | 23 P | 55 P | 27 P | 0.44 | 0.50 | 2.13 | | Excl |
| ORF YOL008W | 27 P | 13 P | 25 P | 12 P | 0.47 | 0.47 | 2.12 | | Excl |
| ORF YOL002C | 138 P | 66 P | 131 P | 60 P | 0.48 | 0.46 | 2.12 | | Excl |
| ORF YGR065C | 28 P | 13 A | 25 P | 12 A | 0.47 | 0.47 | 2.12 | | Good |
| ALPHA1 (YCL066W) | 50 P | 24 P | 75 P | 36 P | 0.48 | 0.47 | 2.11 | | Excl |
| TIP1 (YBR067C) | 369 P | 184 P | 407 P | 201 P | 0.50 | 0.49 | 2.02 | | Excl |

Figure 12F

Srb2 Up

Gene Expression Results for FH1998040601A

| Gene | SRB WT#1 | WT#1 SRB2#1 | SR | SRB WT#2 | WT SRB2#2 | SR | SR#MT1/WT1 | MT2/WT2 | Ave | Corrected? | Confidence |
|---|---|---|---|---|---|---|---|---|---|---|---|
| CYC2 (YOR037W) | 26 | A | 64 | A | 15 | A | 31 | P | 2.44 | 2.03 | 2.2 | | Good |
| FBP1 (YLR377C) | -3 | A | 57 | A | 19 | A | 44 | P | -21.78 | 2.38 | 7.2 | Yes | Med |
| HAP5 (YOR358W) | -174 | A | -6 | A | 22 | A | 46 | P | 0.03 | 2.13 | 17.9 | Yes | Med |
| HXT10 (YFL011W) | -66 | A | -51 | A | -11 | A | 5 | A | 0.78 | -0.43 | 3.0 | Yes | Med |
| HXT15 (YDL245C) | -40 | A | -19 | A | 5 | A | 15 | P | 0.48 | 3.01 | 3.6 | Yes | Med |
| HXT9 (YJL219W) | 37 | A | 80 | P | 6 | A | 21 | P | 2.18 | 3.38 | 2.8 | | Good |
| MUP3 (YHL036W) | 79 | P | 223 | P | 75 | P | 193 | P | 2.81 | 2.56 | 2.7 | | Excl |
| ORF YAL045C | -30 | A | 65 | A | 5 | A | 25 | A | -2.15 | 4.93 | 12.0 | Yes | Med |
| ORF YBR008C | 287 | A | 984 | P | 280 | P | 926 | P | 3.42 | 3.31 | 3.4 | | Good |
| ORF YBR033W | -6 | A | 27 | A | 11 | A | 26 | A | -4.26 | 2.37 | 4.5 | Yes | Med |
| ORF YBR051W | -8 | A | 3 | A | 8 | A | 18 | A | -0.34 | 2.31 | 2.2 | Yes | Med |
| ORF YBR182C | -89 | A | 36 | A | 3 | A | 14 | A | -0.41 | 4.79 | 14.9 | Yes | Med |
| ORF YCR010C | -33 | A | 16 | A | 5 | A | 40 | P | -0.49 | 7.95 | 8.9 | Yes | Med |
| ORF YCR056W | -41 | A | 3 | A | 7 | A | 36 | A | -0.07 | 5.09 | 6.9 | Yes | Med |
| ORF YDL118W | -3 | A | 19 | A | -4 | A | 45 | A | -5.96 | -11.30 | 7.1 | Yes | Med |
| ORF YDL152W | -32 | A | 57 | P | 28 | P | 64 | P | -1.79 | 2.30 | 10.0 | Yes | Med |
| ORF YDL196W | -8 | A | 35 | A | 6 | A | 21 | A | -4.43 | 3.42 | 6.0 | Yes | Med |
| ORF YDR029W | -103 | A | -14 | A | 7 | A | 21 | A | 0.13 | 2.94 | 10.4 | Yes | Med |
| ORF YDR187C | -2 | A | 12 | A | -13 | A | 13 | A | -7.66 | -1.00 | 4.0 | Yes | Med |
| ORF YDR220C | 38 | A | 85 | A | 42 | P | 91 | P | 2.23 | 2.17 | 2.2 | | Good |
| ORF YDR271C | -37 | A | 77 | P | 3 | A | 19 | M | -2.11 | 6.39 | 14.5 | Yes | Med |
| ORF YDR446W | -46 | A | -30 | A | -2 | A | 10 | A | 0.65 | -5.14 | 2.9 | Yes | Med |
| ORF YEL028W | 2 | A | 150 | A | 34 | P | 72 | P | 79.50 | 2.09 | 40.8 | | Good |
| ORF YEL070W (_f) | -40 | A | 47 | A | 14 | A | 35 | P | -1.19 | 2.56 | 10.0 | Yes | Med |
| ORF YEL071W | 362 | P | 990 | P | 273 | P | 597 | P | 2.73 | 2.19 | 2.5 | | Excl |
| ORF YER039C | -64 | A | -3 | A | -12 | A | 24 | M | 0.04 | -1.97 | 9.8 | Yes | Med |
| ORF YER081W | 62 | A | 443 | P | 110 | P | 447 | P | 7.11 | 4.08 | 5.6 | | Med |
| ORF YER096W | -2 | A | 9 | A | 7 | A | 19 | P | -4.54 | 2.76 | 2.4 | Yes | Med |
| ORF YER116C | 13 | A | 60 | A | 14 | P | 43 | P | 4.54 | 3.11 | 3.8 | | Med |
| ORF YER184C | 13 | A | 41 | A | 8 | A | 19 | P | 3.14 | 2.30 | 2.7 | | Good |
| ORF YFL013W-A | 21 | A | 44 | A | -14 | A | 0 | A | 2.13 | 0.00 | 2.4 | Yes | Med |
| ORF YFL056C | 19 | A | 50 | P | 29 | P | 62 | P | 2.65 | 2.16 | 2.4 | | Med |
| ORF YFR008W | -2 | A | 31 | A | 22 | A | 45 | P | -16.66 | 2.07 | 4.4 | Yes | Good |
| ORF YFR046C | 2 | A | 33 | A | 8 | A | 25 | M | 17.41 | 3.04 | 10.2 | | Good |

Figure 13A

| | | | | | | | |
|---|---|---|---|---|---|---|---|
| ORF YGL090W | -30 | A | 9 | A | -29 | A | 3 | A | -0.28 | -0.09 | 7.0 | Yes | Med |
| ORF YGL165C | -6 | A | 9 | A | -25 | A | 31 | A | -1.51 | -0.14 | 4.2 | Yes | Med |
| ORF YGL194C | -34 | A | 43 | A | 12 | P | 28 | P | -1.26 | 2.30 | 8.8 | Yes | Med |
| ORF YGL214W | 4 | A | 24 | A | 7 | A | 18 | P | 6.44 | 2.66 | 4.5 | | Good |
| ORF YGR018C | -43 | A | 47 | A | 12 | A | 26 | P | -1.09 | 2.14 | 10.1 | Yes | Med |
| ORF YGR051C | -57 | A | -24 | A | -23 | A | -5 | A | 0.43 | 0.20 | 5.1 | Yes | Med |
| ORF YGR052W | -19 | A | 4 | A | 11 | A | 23 | P | -0.23 | 2.10 | 3.4 | Yes | Med |
| ORF YGR291C (_f) | -34 | A | -20 | A | -16 | A | 12 | A | 0.59 | -0.74 | 4.3 | Yes | Med |
| ORF YHR048W | 28 | A | 157 | P | 41 | P | 83 | P | 5.55 | 2.02 | 3.8 | | Good |
| ORF YIL025C | -21 | A | -4 | A | -26 | A | -2 | A | 0.21 | 0.08 | 4.0 | Yes | Med |
| ORF YIR013C | -15 | A | 46 | A | 5 | A | 127 | A | -3.03 | 23.18 | 17.7 | Yes | Med |
| ORF YIR042C | 2 | A | 29 | A | 3 | A | 18 | P | 15.14 | 6.66 | 10.9 | | Good |
| ORF YJL032W | 13 | A | 31 | A | 16 | M | 38 | P | 2.38 | 2.30 | 2.3 | | Good |
| ORF YJL064W | -19 | A | 9 | A | -4 | A | 24 | P | -0.45 | -5.75 | 5.5 | Yes | Med |
| ORF YJL114W (_f) | -76 | A | 27 | A | 7 | A | 22 | A | -0.35 | 3.12 | 11.9 | Yes | Med |
| ORF YJR037W | -18 | A | 20 | A | 7 | A | 18 | A | -1.06 | 2.47 | 5.0 | Yes | Med |
| ORF YJR162C (_f) | 34 | A | 73 | A | 1 | A | 21 | A | 2.14 | 20.30 | 11.2 | Yes | Good |
| ORF YJR162C (_r_i) | 18 | A | 43 | A | -7 | A | 19 | A | 2.32 | -2.69 | 3.8 | Yes | Med |
| ORF YKL131W | -47 | A | 41 | A | 12 | A | 27 | A | -0.88 | 2.19 | 10.0 | Yes | Med |
| ORF YKL225W | 16 | A | 345 | P | 21 | P | 64 | P | 21.86 | 3.12 | 12.5 | | Good |
| ORF YKR105C | 47 | A | 154 | P | 10 | A | 59 | A | 3.24 | 5.71 | 4.5 | | Good |
| ORF YLL062C | -21 | A | 68 | A | 33 | P | 69 | P | -3.24 | 2.09 | 10.0 | Yes | Med |
| ORF YLR162W | -8 | A | 7 | A | -19 | A | -5 | A | -0.93 | 0.25 | 2.9 | Yes | Med |
| ORF YLR279W | 5 | A | 67 | A | 5 | A | 58 | A | 12.74 | 11.28 | 12.0 | | Good |
| ORF YLR318W | 11 | A | 63 | P | 14 | P | 32 | P | 6.02 | 2.20 | 4.1 | | Good |
| ORF YLR338W | 0 | A | 46 | P | 9 | A | 20 | P | #DIV/0! | 2.17 | 5.7 | Yes | Med |
| ORF YML032C-A | -29 | A | 33 | A | 12 | A | 35 | P | -1.14 | 2.82 | 7.6 | Yes | Med |
| ORF YML058C-A | -58 | A | 7 | A | 2 | A | 14 | A | -0.13 | 6.77 | 9.9 | Yes | Med |
| ORF YMR193C-A | -58 | A | 1 | A | 19 | A | 38 | P | -0.02 | 2.05 | 6.9 | Yes | Med |
| ORF YMR206W | -32 | A | -18 | A | -12 | A | 25 | P | 0.58 | -2.01 | 5.0 | Yes | Med |

Figure 13B

| | | | | | | | | |
|---|---|---|---|---|---|---|---|---|
| ORF YMR244W | -121 | A | 69 | A | 13 | M | 33 | A | -0.57 | 2.53 | 20.2 | Yes | Med |
| ORF YNL120C | -37 | A | 30 | M | 7 | A | 19 | A | -0.81 | 2.85 | 8.1 | Yes | Med |
| ORF YNL150W | -16 | A | 190 | P | 77 | P | 171 | P | -12.03 | 2.22 | 21.7 | Yes | Med |
| ORF YNR069C | -121 | A | 69 | P | 11 | A | 36 | P | -0.57 | 3.32 | 20.6 | Yes | Med |
| ORF YNR077C (_f) | -26 | A | 4 | A | 21 | P | 79 | P | -0.16 | 3.84 | 5.0 | Yes | Med |
| ORF YOL118C | -47 | A | 49 | A | -2 | A | 8 | A | -1.03 | -3.79 | 10.6 | Yes | Med |
| ORF YOR055W | -32 | A | 30 | A | 2 | A | 16 | P | -0.95 | 7.59 | 10.0 | Yes | Med |
| ORF YOR146W | -95 | A | 53 | P | 14 | A | 41 | A | -0.56 | 2.92 | 16.2 | Yes | Med |
| ORF YOR218C | -16 | A | 49 | A | 25 | P | 67 | P | -3.08 | 2.68 | 7.8 | Yes | Med |
| ORF YOR225W | -195 | A | -31 | A | 41 | A | 111 | P | 0.16 | 2.70 | 17.7 | Yes | Med |
| ORF YPL033C | -74 | A | -44 | A | -4 | A | 7 | A | 0.60 | -1.66 | 4.1 | Yes | Med |
| ORF YPL197C | 37 | A | 83 | P | 221 | P | 51 | P | 2.25 | 2.32 | 2.3 | | Good |
| ORF YPL261C | -74 | A | -17 | A | 9 | A | 34 | A | 0.23 | 3.91 | 7.6 | Yes | Med |
| ORF YPL275W (_f) | -63 | A | 70 | M | 7 | A | 31 | A | -1.11 | 4.74 | 15.7 | Yes | Med |
| ORF YPL279C (_f) | -16 | M | 69 | P | 100 | P | 357 | P | -4.34 | 3.57 | 10.2 | Yes | Med |
| ORF YPL280W (_f) | -21 | A | 40 | A | 23 | A | 146 | P | -1.90 | 6.41 | 9.3 | Yes | Med |
| ORF YPL281C (_f) | -21 | A | 41 | A | 2 | A | 58 | P | -1.97 | 26.56 | 19.5 | Yes | Med |
| ORF YPR014C | -158 | A | 23 | A | -9 | A | 21 | A | -0.14 | -2.37 | 21.0 | Yes | Med |
| ORF YPR078C | -58 | A | 16 | A | 11 | P | 30 | P | -0.27 | 2.75 | 8.7 | Yes | Med |
| ORF YPR151C | -189 | A | 0 | A | 5 | A | 58 | P | 0.00 | 10.62 | 24.3 | Yes | Med |
| ORF YPR152C | -68 | A | 0 | A | 23 | P | 95 | P | 0.00 | 4.16 | 8.9 | Yes | Med |
| ORF YPR170C | -116 | A | -29 | A | 1 | A | 21 | M | 0.25 | 18.97 | 18.2 | Yes | Med |
| ORF YPR194C | 42 | A | 141 | A | 43 | P | 89 | P | 3.36 | 2.04 | 2.7 | | Good |
| PET56 (YOR199W) | -68 | A | -10 | A | 0 | A | 19 | A | 0.15 | #DIV/0! | 7.7 | Yes | Med |
| PUT1 (YLR142W) | 29 | A | 91 | M | 44 | P | 89 | P | 3.16 | 2.01 | 2.6 | | Good |
| REC104 (YHR157W) | 8 | A | 70 | P | 18 | A | 36 | P | 9.28 | 2.01 | 5.6 | | Good |
| VMA4 (YOR331C) | -137 | A | 34 | A | 23 | P | 69 | P | -0.25 | 3.03 | 18.6 | Yes | Med |
| YCLX09w/ (control? | -22 | A | -1 | A | 4 | A | 17 | A | 0.06 | 4.28 | 4.2 | Yes | Med |
| YCRX03c/ (control? | -5 | A | 12 | A | 5 | M | 27 | P | -2.55 | 5.48 | 4.4 | Yes | Med |
| YCRX20c/ (control? | -10 | A | 26 | A | 7 | A | 18 | A | -2.70 | 2.64 | 4.8 | Yes | Med |

Figure 13C

| Srb2 Up | | | | | | | | | |
|---|---|---|---|---|---|---|---|---|---|
| Gene Expression Results for FH19980406601A | | | | | | | | | |
| Gene | SRB WT#1 | WT SRB2#1 | SRI SRB WT#2 | WT SRB2#2 | SR MT1/WT1 | MT2/WT2 | Ave | Corrected? | Confidence |
| ORF YEL028W | 2 A | 150 A | 34 P | 72 P | 79.50 | 2.09 | 40.8 | | Good |
| ORF YPR151C | -189 A | 0 A | 5 A | 58 P | 0.00 | 10.62 | 24.3 | Yes | Med |
| ORF YNL150W | -16 A | 190 P | 77 P | 171 P | -12.03 | 2.22 | 21.7 | Yes | Med |
| ORF YPR014C | -158 A | 23 A | -9 A | 21 A | -0.14 | -2.37 | 21.0 | Yes | Med |
| ORF YNR069C | -121 A | 69 P | 11 A | 36 P | -0.57 | 3.32 | 20.6 | Yes | Med |
| ORF YMR244W | -121 A | 69 A | 13 M | 33 A | -0.57 | 2.53 | 20.2 | Yes | Med |
| ORF YPL281C (_f) | -21 A | 41 A | 2 A | 58 P | -1.97 | 26.56 | 19.5 | Yes | Med |
| VMA4 (YOR331C) | -137 A | 34 A | 23 P | 69 P | -0.25 | 3.03 | 18.6 | Yes | Med |
| ORF YPR170C | -116 A | -29 A | 1 A | 21 M | 0.25 | 18.97 | 18.2 | Yes | Med |
| HAP5 (YOR358W) | -174 A | -6 A | 22 A | 46 P | 0.03 | 2.13 | 17.9 | Yes | Med |
| ORF YOR225W | -195 A | -31 A | 41 A | 111 P | 0.16 | 2.70 | 17.7 | Yes | Med |
| ORF YIR013C | -15 A | 46 A | 5 A | 127 A | -3.03 | 23.18 | 17.7 | Yes | Med |
| ORF YOR146W | -95 A | 53 P | 14 A | 41 A | -0.56 | 2.92 | 16.2 | Yes | Med |
| ORF YPL275W (_f) | -63 A | 70 M | 7 A | 31 A | -1.11 | 4.74 | 15.7 | Yes | Med |
| ORF YBR182C | -89 A | 36 A | 3 A | 14 A | -0.41 | 4.79 | 14.9 | Yes | Med |
| ORF YDR271C | -37 A | 77 P | 3 A | 19 M | -2.11 | 6.39 | 14.5 | Yes | Med |
| ORF YKL225W | 16 A | 345 P | 21 P | 64 P | 21.86 | 3.12 | 12.5 | | Good |
| ORF YLR279W | 5 A | 67 A | 5 A | 58 A | 12.74 | 11.28 | 12.0 | | Good |
| ORF YAL045C | -30 A | 65 A | 5 A | 25 A | -2.15 | 4.93 | 12.0 | Yes | Med |
| ORF YJL114W (_f) | -76 A | 27 A | 7 A | 22 A | -0.35 | 3.12 | 11.9 | Yes | Med |
| ORF YJR162C (_f) | 34 A | 73 A | 1 A | 21 A | 2.14 | 20.30 | 11.2 | | Good |
| ORF YIR042C | 2 A | 29 A | 3 A | 18 P | 15.14 | 6.66 | 10.9 | | Good |
| ORF YOL118C | -47 A | 49 A | -2 A | 8 A | -1.03 | -3.79 | 10.6 | Yes | Med |
| ORF YDR029W | -103 A | -14 A | 7 A | 21 A | 0.13 | 2.94 | 10.4 | Yes | Med |
| ORF YFR046C | 2 A | 33 A | 8 A | 25 M | 17.41 | 3.04 | 10.2 | | Good |
| ORF YPL279C (_f) | -16 M | 69 P | 100 P | 357 P | -4.34 | 3.57 | 10.2 | Yes | Med |
| ORF YGR018C | -43 A | 47 A | 12 A | 26 P | -1.09 | 2.14 | 10.1 | Yes | Med |
| ORF YDL152W | -32 A | 57 P | 28 P | 64 P | -1.79 | 2.30 | 10.0 | Yes | Med |
| ORF YLL062C | -21 A | 68 A | 33 P | 69 P | -3.24 | 2.09 | 10.0 | Yes | Med |
| ORF YKL131W | -47 A | 41 A | 12 A | 27 A | -0.88 | 2.19 | 10.0 | Yes | Med |
| ORF YEL070W (_f) | -40 A | 47 A | 14 A | 35 P | -1.19 | 2.56 | 10.0 | Yes | Med |
| ORF YOR055W | -32 A | 30 A | 2 A | 16 P | -0.95 | 7.59 | 10.0 | Yes | Med |

Figure 14A

| | | | | | | | | |
|---|---|---|---|---|---|---|---|---|
| ORF YML058C-A | -58 | A | 7 | A | 2 | A | 14 | A | -0.13 | 6.77 | 9.9 | Yes | Med |
| ORF YER039C | -64 | A | -3 | A | -12 | A | 24 | M | 0.04 | -1.97 | 9.8 | Yes | Med |
| ORF YPL280W (_f) | -21 | A | 40 | A | 23 | A | 146 | P | -1.90 | 6.41 | 9.3 | Yes | Med |
| ORF YCR010C | -33 | A | 16 | A | 5 | A | 40 | P | -0.49 | 7.95 | 8.9 | Yes | Med |
| ORF YPR152C | -68 | A | 0 | A | 23 | P | 95 | P | 0.00 | 4.16 | 8.9 | Yes | Med |
| ORF YGL194C | -34 | A | 43 | A | 12 | P | 28 | P | -1.26 | 2.30 | 8.8 | Yes | Med |
| ORF YPR078C | -58 | A | 16 | A | 11 | P | 30 | P | -0.27 | 2.75 | 8.7 | Yes | Med |
| ORF YNL120C | -37 | A | 30 | M | 7 | A | 19 | A | -0.81 | 2.85 | 8.1 | Yes | Med |
| ORF YOR218C | -16 | A | 49 | A | 25 | P | 67 | P | -3.08 | 2.68 | 7.8 | Yes | Med |
| PET56 (YOR199W) | -68 | A | -10 | A | 0 | A | 19 | A | 0.15 | #DIV/0! | 7.7 | Yes | Med |
| ORF YPL261C | -74 | A | -17 | A | 9 | A | 34 | A | 0.23 | 3.91 | 7.6 | Yes | Med |
| ORF YML032C-A | -29 | A | 33 | A | 12 | A | 35 | P | -1.14 | 2.82 | 7.6 | Yes | Med |
| FBP1 (YLR377C) | -3 | A | 57 | A | 19 | A | 44 | P | -21.78 | 2.38 | 7.2 | Yes | Med |
| ORF YDL118W | -3 | A | 19 | A | -4 | A | 45 | A | -5.96 | -11.30 | 7.1 | Yes | Med |
| ORF YGL090W | -30 | A | 9 | A | -29 | A | 3 | A | -0.28 | -0.09 | 7.0 | Yes | Med |
| ORF YCR056W | -41 | A | 3 | A | 7 | A | 36 | A | -0.07 | 5.09 | 6.9 | Yes | Med |
| ORF YMR193C-A | -58 | A | 1 | A | 19 | A | 38 | P | -0.02 | 2.05 | 6.9 | Yes | Med |
| ORF YDL196W | -8 | A | 35 | A | 6 | A | 21 | A | -4.43 | 3.42 | 6.0 | Yes | Med |
| ORF YLR338W | 0 | A | 46 | P | 9 | A | 20 | P | #DIV/0! | 2.17 | 5.7 | Yes | Med |
| REC104 (YHR157W) | 8 | A | 70 | P | 18 | A | 36 | P | 9.28 | 2.01 | 5.6 | | Good |
| ORF YER081W | 62 | A | 443 | P | 110 | P | 447 | P | 7.11 | 4.08 | 5.6 | | Good |
| ORF YJL064W | -19 | A | 9 | A | -4 | A | 24 | P | -0.45 | -5.75 | 5.5 | Yes | Med |
| ORF YGR051C | -57 | A | -24 | A | -23 | A | -5 | A | 0.43 | 0.20 | 5.1 | Yes | Med |
| ORF YMR206W | -32 | A | -18 | A | -12 | A | 25 | P | 0.58 | -2.01 | 5.0 | Yes | Med |
| ORF YJR037W | -18 | A | 20 | A | 7 | A | 18 | A | -1.06 | 2.47 | 5.0 | Yes | Med |
| ORF YNR077C (_f) | -26 | A | 4 | A | 21 | P | 79 | P | -0.16 | 3.84 | 5.0 | Yes | Med |
| YCRX20c/ (control?) | -10 | A | 26 | A | 7 | A | 18 | A | -2.70 | 2.64 | 4.8 | Yes | Med |
| ORF YGL214W | 4 | A | 24 | A | 7 | A | 18 | P | 6.44 | 2.66 | 4.5 | | Good |
| ORF YBR033W | -6 | A | 27 | A | 11 | A | 26 | A | -4.26 | 2.37 | 4.5 | Yes | Med |
| ORF YKR105C | 47 | A | 154 | P | 10 | A | 59 | A | 3.24 | 5.71 | 4.5 | | Good |
| YCRX03c/ (control?) | -5 | A | 12 | A | 5 | M | 27 | P | -2.55 | 5.48 | 4.4 | Yes | Med |
| ORF YFR008W | -2 | A | 31 | A | 22 | A | 45 | P | -16.66 | 2.07 | 4.4 | Yes | Med |

Figure 14B

| | | | | | | | |
|---|---|---|---|---|---|---|---|
| ORF YGR291C (_f) | -34 A | -20 A | -16 A | 12 A | 0.59 | -0.74 | 4.3 Yes | Med |
| YCLX09w/ (control? | -22 A | -1 A | 4 A | 17 A | 0.06 | 4.28 | 4.2 Yes | Med |
| ORF YGL165C | -6 A | 9 A | -25 A | 3 A | -1.51 | -0.14 | 4.2 Yes | Med |
| ORF YLR318W | 11 A | 63 P | 14 P | 32 P | 6.02 | 2.20 | 4.1 | Good |
| ORF YPL033C | -74 A | -44 A | -4 A | 7 A | 0.60 | -1.66 | 4.1 Yes | Med |
| ORF YIL025C | -21 A | -4 A | -26 A | -2 A | 0.21 | 0.08 | 4.0 Yes | Med |
| ORF YDR187C | -2 A | 12 A | -13 A | 13 A | -7.66 | -1.00 | 4.0 Yes | Med |
| ORF YER116C | 13 A | 60 A | 14 P | 43 P | 4.54 | 3.11 | 3.8 | Good |
| ORF YJR162C (_r_i) | 18 A | 43 A | -7 A | 19 A | 2.32 | -2.69 | 3.8 Yes | Med |
| ORF YHR048W | 28 A | 157 P | 41 P | 83 P | 5.55 | 2.02 | 3.8 | Good |
| HXT15 (YDL245C) | -40 A | -19 A | 5 A | 15 P | 0.48 | 3.01 | 3.6 Yes | Med |
| ORF YBR008C | 287 A | 984 P | 280 P | 926 P | 3.42 | 3.31 | 3.4 | Good |
| ORF YGR052W | -19 A | 4 A | 11 A | 23 P | -0.23 | 2.10 | 3.4 Yes | Med |
| HXT10 (YFL011W) | -66 A | -51 A | -11 A | 5 A | 0.78 | -0.43 | 3.0 Yes | Med |
| ORF YLR162W | -8 A | 7 A | -19 A | -5 A | -0.93 | 0.25 | 2.9 Yes | Med |
| ORF YDR446W | -46 A | -30 A | -2 A | 10 A | 0.65 | -5.14 | 2.9 Yes | Med |
| HXT9 (YJL219W) | 37 A | 80 P | 6 A | 21 P | 2.18 | 3.38 | 2.8 | Good |
| ORF YER184C | 13 A | 41 A | 8 A | 19 P | 3.14 | 2.30 | 2.7 | Good |
| ORF YPR194C | 42 A | 141 A | 43 P | 89 P | 3.36 | 2.04 | 2.7 | Good |
| MUP3 (YHL036W) | 79 P | 223 P | 75 P | 193 P | 2.81 | 2.56 | 2.7 | Excl |
| PUT1 (YLR142W) | 29 A | 91 M | 44 P | 89 P | 3.16 | 2.01 | 2.6 | Good |
| ORF YEL071W | 362 P | 990 P | 273 P | 597 P | 2.73 | 2.19 | 2.5 | Excl |
| ORF YFL013W-A | 21 A | 44 A | -14 A | 0 A | 2.13 | 0.00 | 2.4 Yes | Med |
| ORF YER096W | -2 A | 9 A | 7 A | 19 P | -4.54 | 2.76 | 2.4 Yes | Med |
| ORF YFL056C | 19 A | 50 P | 29 P | 62 P | 2.65 | 2.16 | 2.4 | Good |
| ORF YJL032W | 13 A | 31 A | 16 M | 38 P | 2.38 | 2.30 | 2.3 | Good |
| ORF YPL197C | 37 A | 83 P | 22 P | 51 P | 2.25 | 2.32 | 2.3 | Good |
| CYC2 (YOR037W) | 26 A | 64 A | 15 A | 31 P | 2.44 | 2.03 | 2.2 | Good |
| ORF YBR051W | -8 A | 3 A | 8 A | 18 A | -0.34 | 2.31 | 2.2 Yes | Med |
| ORF YDR220C | 38 A | 85 A | 42 P | 91 P | 2.23 | 2.17 | 2.2 | Good |

Figure 14C

Srb2 Down

Gene Expression Results for FH1998040601A

| Gene | SRB WT# | WT | SRB2#1 | SRI | SRB WT# | WT | SRB2#2 | SRI | MT1/WT1 | MT2/WT2 | Ave | Corrected? | Confidence |
|---|---|---|---|---|---|---|---|---|---|---|---|---|---|
| AGA1 (YNR044W) | 863 | P | 239 | P | 609 | P | 158 | P | 0.28 | 0.26 | 3.74 | | Excl |
| ALPHA1 (YCR040W) | 8 | A | -35 | A | -8 | A | -25 | A | -4.43 | 3.08 | 5.97 | Yes | Med |
| ATP10 (YLR393W) | -50 | A | -78 | A | 12 | A | -32 | A | 1.56 | -2.57 | 7.22 | Yes | Med |
| CHA1 (YCL064C) | 763 | P | 91 | P | 910 | P | 66 | P | 0.12 | 0.07 | 11.14 | | Excl |
| CTP1 (YBR291C) | 179 | A | 81 | A | 192 | P | 40 | P | 0.45 | 0.21 | 3.48 | | Good |
| CYT1 (YOR065W) | 311 | A | -54 | A | 102 | P | 10 | P | -0.17 | 0.10 | 41.44 | Yes | Med |
| DCG1 (YIR030C) | 15 | A | -43 | A | 30 | P | 9 | A | -2.84 | 0.31 | 7.39 | Yes | Med |
| DIT1 (YDR403W) | 21 | A | 4 | A | 25 | P | 5 | A | 0.20 | 0.22 | 4.83 | | Good |
| FAB1 (YFR019W) | 21 | A | -6 | A | 84 | P | 23 | P | -0.28 | 0.27 | 4.47 | Yes | Med |
| FAR1 (YJL157C) | 679 | P | 180 | P | 541 | P | 214 | P | 0.27 | 0.40 | 3.15 | | Excl |
| FLO9 (YAL064W) | -24 | A | -103 | A | -4 | A | -22 | A | 4.31 | 5.48 | 9.68 | Yes | Med |
| FSP2 (YJL221C) (f) | 74 | A | -15 | A | 44 | P | -5 | A | -0.20 | -0.10 | 13.73 | Yes | Med |
| FUS1 (YCL027W) | 146 | P | 54 | A | 97 | P | 45 | A | 0.37 | 0.47 | 2.42 | | Good |
| GPM2 (YDL021W) | -6 | A | -39 | A | 22 | P | 1 | A | 6.17 | 0.03 | 19.34 | Yes | Med |
| GSY1 (YFR015W) | 45 | A | 16 | A | 19 | P | -3 | A | 0.35 | -0.18 | 3.70 | Yes | Med |
| HES1 (YOR237W) | 37 | A | 4 | A | 13 | A | -211 | A | 0.12 | -16.20 | 26.74 | Yes | Med |
| HMS1 (YMR070W) | 50 | P | 10 | M | 123 | P | 58 | P | 0.20 | 0.47 | 3.62 | | Good |
| HSP12 (YFL014W) | 279 | P | 77 | A | 204 | P | 22 | P | 0.28 | 0.11 | 6.39 | | Good |
| INH1 (YDL181W) | 52 | A | 15 | A | 117 | P | 6 | A | 0.28 | 0.05 | 11.25 | | Good |
| KIP2 (YPL155C) | 74 | A | 24 | A | 68 | P | 33 | P | 0.33 | 0.48 | 2.55 | | Good |
| KNH1 (YDL049C) | 3 | A | -51 | A | 19 | A | -5 | A | -16.18 | -0.29 | 7.90 | Yes | Med |
| LEE1 (YPL054W) | 5 | A | -44 | A | 9 | A | -11 | A | -8.41 | -1.30 | 6.96 | Yes | Med |
| MAL32 (YBR299W) | 37 | P | -100 | A | 36 | A | 14 | A | -2.74 | 0.38 | 14.96 | Yes | Med |
| MET28 (YIR017C) | -62 | A | -99 | A | 5 | A | -42 | A | 1.58 | -7.65 | 8.37 | Yes | Med |
| MFA1 (YDR461W) | 2290 | P | 407 | P | 1719 | P | 604 | P | 0.18 | 0.35 | 4.24 | | Excl |
| MFA2 (YNL145W) | 10468 | P | 3607 | P | 5137 | P | 2263 | P | 0.34 | 0.44 | 2.59 | | Excl |
| MRK1 (YDL079C) ext | 33 | A | 7 | A | -10 | A | -31 | A | 0.20 | 3.08 | 4.55 | Yes | Med |
| MSH4 (YFL003C) | 36 | A | -31 | A | 11 | A | 0 | A | -0.88 | 0.00 | 7.82 | Yes | Med |
| ORF YAR037W (_r) | -19 | A | -68 | A | -27 | A | -53 | A | 3.55 | 1.98 | 7.49 | Yes | Med |
| ORF YAR040C | 13 | A | -36 | A | -5 | A | -16 | A | -2.87 | 3.29 | 6.06 | Yes | Med |
| ORF YAR068W (_f) | -29 | A | -69 | A | 82 | P | 27 | A | 2.41 | 0.33 | 5.57 | Yes | Med |
| ORF YBL013W | -46 | A | -131 | A | -11 | A | -22 | A | 2.85 | 1.99 | 9.60 | Yes | Med |
| ORF YBR057C | 75 | M | 16 | A | 47 | P | 20 | M | 0.22 | 0.42 | 3.48 | | Good |

Figure 15A

| | | | | | | | |
|---|---|---|---|---|---|---|---|
| ORF YBR076W | -2 | A | -18 | A | 4 | A | -7 | A | 11.07 | -1.71 | 2.68 | Yes | Med |
| ORF YBR168W | 57 | P | 9 | A | 64 | P | 31 | A | 0.17 | 0.48 | 4.06 | | Good |
| ORF YBR219C exon | -25 | A | -36 | A | -5 | A | -34 | A | 1.44 | 6.85 | 4.03 | Yes | Med |
| ORF YBR219C exon | 5 | A | -46 | A | -2 | A | -12 | A | -9.65 | 6.16 | 6.10 | Yes | Med |
| ORF YBR232C | -5 | A | -20 | A | 19 | P | 6 | A | 4.26 | 0.32 | 3.09 | Yes | Med |
| ORF YBR250W | 19 | A | -16 | A | 21 | P | 8 | A | -0.85 | 0.39 | 4.80 | Yes | Med |
| ORF YBR259W | 63 | P | 18 | A | 48 | P | 20 | P | 0.28 | 0.41 | 3.02 | | Good |
| ORF YCL065W | 22 | A | -28 | A | 2 | A | -25 | A | -1.28 | -12.33 | 7.73 | Yes | Med |
| ORF YCR006C | 2 | A | -30 | A | 19 | P | 5 | A | -18.73 | 0.25 | 5.11 | Yes | Med |
| ORF YCR007C | 62 | A | -24 | A | 17 | P | 5 | A | -0.39 | 0.32 | 10.17 | Yes | Med |
| ORF YCR032W | 122 | A | 59 | P | 70 | P | 32 | P | 0.49 | 0.45 | 2.14 | | Excl |
| ORF YCR074C | -59 | A | -103 | A | -36 | A | -56 | A | 1.75 | 1.56 | 6.41 | Yes | Med |
| ORF YCR100C | 32 | A | -61 | A | 27 | P | -9 | A | -1.92 | -0.33 | 12.85 | Yes | Med |
| ORF YDL022W | 1084 | P | 491 | P | 1669 | P | 492 | P | 0.45 | 0.30 | 2.80 | | Excl |
| ORF YDL026W | 14 | A | -27 | A | 2 | A | -10 | A | -1.89 | -5.14 | 5.36 | Yes | Med |
| ORF YDL038C | 232 | P | 105 | M | 423 | P | 97 | P | 0.45 | 0.23 | 3.29 | | Good |
| ORF YDL057W | -6 | A | -38 | A | 35 | P | -11 | A | 5.96 | -0.31 | 7.74 | Yes | Med |
| ORF YDL113C | 63 | A | 27 | A | 73 | P | 35 | P | 0.43 | 0.48 | 2.22 | | Good |
| ORF YDL129W | 143 | P | 42 | A | 81 | P | 26 | A | 0.29 | 0.32 | 3.26 | | Good |
| ORF YDL146W | 46 | A | 22 | A | 37 | P | 6 | A | 0.47 | 0.17 | 4.07 | | Good |
| ORF YDL179W | 87 | A | 43 | A | 151 | P | 58 | A | 0.50 | 0.38 | 2.32 | | Good |
| ORF YDL186W | 8 | A | -11 | A | -1 | A | -17 | A | -1.36 | 17.12 | 3.49 | Yes | Med |
| ORF YDL221W | -8 | A | -42 | A | -22 | A | -40 | A | 5.28 | 1.81 | 5.17 | Yes | Med |
| ORF YDL248W (_j) | 40 | A | -19 | A | 37 | P | -16 | A | -0.48 | -0.43 | 11.14 | Yes | Med |
| ORF YDL248W (_r) | 37 | M | 5 | A | 32 | P | 14 | P | 0.15 | 0.43 | 4.54 | | Good |
| ORF YDR033W | 5497 | P | 2118 | P | 4162 | P | 1714 | P | 0.39 | 0.41 | 2.51 | | Excl |
| ORF YDR102C | 24 | A | -5 | A | -1 | A | -14 | A | -0.23 | 14.38 | 4.26 | Yes | Med |
| ORF YDR203W | 22 | A | -9 | A | 4 | A | -14 | A | -0.43 | -3.42 | 4.94 | Yes | Med |
| ORF YDR259C | 41 | A | 9 | A | 53 | P | 25 | P | 0.23 | 0.48 | 3.23 | | Good |
| ORF YDR359C | 130 | A | 35 | A | 43 | P | 0 | A | 0.27 | 0.00 | 6.15 | Yes | Med |
| ORF YDR374C | 10 | A | -16 | A | 7 | A | -31 | A | -1.70 | -4.40 | 6.36 | Yes | Med |

Figure 15B

| ORF | | | | | | | | | |
|---|---|---|---|---|---|---|---|---|---|
| ORF YDR491C | 92 | A | -4 | A | 32 | P | 14 | A | -0.04 | 0.43 | 10.78 | Yes | Med |
| ORF YDR539W | 13 | A | -35 | A | 189 | P | 66 | P | -2.77 | 0.35 | 6.22 | Yes | Med |
| ORF YDR540C | -125 | A | -139 | A | 13 | A | -12 | A | 1.11 | -0.90 | 3.84 | Yes | Med |
| ORF YDR541C | -19 | A | -47 | A | 55 | P | 11 | A | 2.48 | 0.20 | 5.33 | Yes | Med |
| ORF YEL057C | 77 | A | 27 | A | 32 | P | 10 | A | 0.35 | 0.32 | 2.98 | | Good |
| ORF YEL076C-A exo | 60 | A | -43 | A | 42 | M | 16 | A | -0.71 | 0.38 | 11.63 | Yes | Med |
| ORF YER037W | 13 | A | -33 | A | 47 | P | 7 | A | -2.49 | 0.15 | 8.05 | Yes | Med |
| ORF YER075C | 72 | M | 10 | A | 70 | P | 30 | P | 0.14 | 0.43 | 4.76 | | Good |
| ORF YER187W | 30 | A | -20 | A | 12 | M | -11 | A | -0.66 | -0.93 | 7.40 | Yes | Med |
| ORF YER188W | 100 | P | -9 | A | 21 | P | -5 | A | -0.09 | -0.26 | 13.45 | Yes | Med |
| ORF YFR032C | 89 | P | -4 | A | 25 | A | 1 | A | -0.05 | 0.05 | 18.42 | Yes | Med |
| ORF YGL033W exon | 25 | A | 7 | A | 121 | A | -8 | A | 0.29 | -0.66 | 3.76 | Yes | Med |
| ORF YGL034C | -42 | A | -90 | A | 23 | P | -1 | A | 2.17 | -0.03 | 7.25 | Yes | Med |
| ORF YGL045W | 134 | P | 1 | A | 38 | P | 181 | A | 0.01 | 0.48 | 47.94 | | Good |
| ORF YGL051W | -2 | A | -14 | A | 30 | P | 10 | A | 7.57 | 0.34 | 2.73 | Yes | Med |
| ORF YGL069C | 30 | A | -43 | A | -3 | A | -61 | A | -1.42 | 22.20 | 13.11 | Yes | Med |
| ORF YGL072C | 15 | A | -26 | A | 49 | P | 16 | P | -1.70 | 0.33 | 5.60 | Yes | Med |
| ORF YGL170C | -32 | A | -61 | A | 33 | A | -9 | A | 1.92 | -0.29 | 7.17 | Yes | Med |
| ORF YGL184C | 25 | A | 1 | A | 53 | P | 9 | A | 0.06 | 0.18 | 11.41 | | Good |
| ORF YGL263W | 2 | A | -9 | A | 14 | A | -5 | A | -4.54 | -0.35 | 2.89 | Yes | Med |
| ORF YGR023W | 15 | A | -20 | A | 26 | A | -5 | P | -1.33 | -0.21 | 6.65 | Yes | Med |
| ORF YGR068C | -60 | A | -101 | A | 37 | M | 1 | A | 1.68 | 0.02 | 31.47 | Yes | Med |
| ORF YGR131W | 58 | A | 24 | A | 36 | A | 16 | A | 0.42 | 0.46 | 2.30 | | Good |
| ORF YGR225W | 21 | A | -1 | A | 181 | A | -9 | A | -0.07 | -0.49 | 4.88 | Yes | Med |
| ORF YGR230W | 75 | P | 31 | A | 60 | P | 26 | A | 0.42 | 0.44 | 2.34 | | Good |
| ORF YGR238C | 53 | A | 23 | A | 25 | A | 7 | A | 0.43 | 0.30 | 2.81 | | Good |
| ORF YHL028W | 62 | A | -60 | A | 33 | M | -1 | A | -0.96 | -0.02 | 15.58 | Yes | Med |
| ORF YHL035C | 77 | M | 30 | A | 164 | P | 76 | P | 0.39 | 0.46 | 2.38 | | Good |
| ORF YHR087W | 40 | A | 17 | A | 221 | P | 64 | P | 0.43 | 0.29 | 2.87 | | Good |
| ORF YHR177W | 49 | A | -39 | A | 1 | A | -11 | A | -0.79 | -7.89 | 9.98 | Yes | Med |
| ORF YIL057C | -17 | A | -54 | A | -37 | A | -72 | A | 3.20 | 1.95 | 7.26 | Yes | Med |
| ORF YIL080W (_f) | 236 | P | 103 | P | 210 | P | 74 | P | 0.44 | 0.35 | 2.56 | | Excl |
| ORF YIL092W | 49 | A | 19 | A | 38 | P | 111 | A | 0.38 | 0.30 | 2.99 | | Good |
| ORF YIL120W | 32 | P | 1 | A | 15 | P | -7 | A | 0.04 | -0.45 | 13.41 | Yes | Med |
| ORF YIR018W | 53 | A | 3 | A | 49 | A | 11 | A | 0.05 | 0.22 | 11.53 | | Good |
| ORF YJL108C | 139 | A | 67 | A | 79 | P | 24 | A | 0.48 | 0.30 | 2.69 | | Good |

Figure 15C

| | | | | | | | | | |
|---|---|---|---|---|---|---|---|---|---|
| ORF YJL161W | 24 | A | -39 | A | 8 | A | -14 | A | -1.65 | -1.69 | 8.49 | Yes | Med |
| ORF YJL225C exon 1 | 71 | A | 17 | A | 32 | P | 12 | A | 0.24 | 0.39 | 3.37 | | Good |
| ORF YJR108W | 45 | A | 18 | A | 14 | P | -3 | A | 0.41 | -0.21 | 2.98 | Yes | Med |
| ORF YJR128W | -18 | A | -41 | A | 12 | A | -6 | A | 2.25 | -0.50 | 4.16 | Yes | Med |
| ORF YJR137C | 84 | A | -17 | A | 47 | P | 22 | P | -0.20 | 0.46 | 11.22 | Yes | Med |
| ORF YKL031W | -82 | A | -191 | A | -31 | A | -111 | A | 2.35 | 3.58 | 18.98 | Yes | Med |
| ORF YKL047W | 66 | P | 18 | A | 73 | P | 20 | A | 0.28 | 0.28 | 3.61 | | Good |
| ORF YKL171W | 5 | A | -13 | A | 28 | P | -7 | A | -2.55 | -0.25 | 5.35 | Yes | Med |
| ORF YKL198C | 132 | P | 46 | A | 46 | P | 19 | P | 0.35 | 0.42 | 2.62 | | Good |
| ORF YKR005C | 11 | A | -7 | A | 14 | P | -10 | A | -0.70 | -0.70 | 4.24 | Yes | Med |
| ORF YKR017C | 55 | A | 13 | A | 52 | P | 26 | P | 0.24 | 0.50 | 3.07 | | Good |
| ORF YKR045C | 50 | A | 23 | A | 97 | A | 16 | A | 0.46 | 0.16 | 4.20 | | Good |
| ORF YLL005C | 61 | M | -23 | A | 14 | A | -15 | A | -0.38 | -1.02 | 11.29 | Yes | Med |
| ORF YLL066C exon | 8 | A | -5 | A | 69 | P | 29 | P | -0.62 | 0.42 | 2.48 | Yes | Med |
| ORF YLR004C | 68 | P | -11 | A | 21 | A | 5 | A | -0.16 | 0.23 | 10.16 | Yes | Med |
| ORF YLR030W | 21 | A | -46 | A | 3 | A | -10 | A | -2.20 | -3.26 | 8.06 | Yes | Med |
| ORF YLR035C | 32 | A | -21 | A | 10 | P | -12 | A | -0.66 | -1.13 | 7.42 | Yes | Med |
| ORF YLR040C | 71 | A | 7 | A | 90 | P | 21 | P | 0.10 | 0.23 | 7.00 | | Good |
| ORF YLR042C | 21 | A | -35 | A | 34 | P | 0 | A | -1.68 | 0.00 | 9.04 | Yes | Med |
| ORF YLR236C | 45 | A | -70 | A | -2 | A | -19 | A | -1.55 | 9.40 | 13.16 | Yes | Med |
| ORF YLR269C | 13 | A | -4 | A | 18 | P | 6 | P | -0.28 | 0.35 | 3.09 | Yes | Med |
| ORF YLR307W | 39 | A | -1 | A | 4 | A | -9 | A | -0.03 | -2.26 | 5.41 | Yes | Med |
| ORF YLR312C | 37 | A | 0 | A | 12 | A | -9 | A | 0.00 | -0.75 | 5.85 | Yes | Med |
| ORF YLR315W | -8 | A | -20 | A | 11 | A | 1 | A | 2.47 | 0.07 | 8.48 | Yes | Med |
| ORF YLR341W | 0 | A | -30 | A | 6 | A | -4 | A | #DIV/0! | -0.63 | 4.05 | Yes | Med |
| ORF YMR018W | 5 | A | -20 | A | 19 | P | 5 | A | -3.71 | 0.29 | 4.19 | Yes | Med |
| ORF YMR026C | 124 | A | 51 | A | 87 | P | 33 | M | 0.41 | 0.38 | 2.51 | | Good |
| ORF YMR068W | 55 | A | -27 | A | 31 | P | -28 | A | -0.49 | -0.90 | 14.09 | Yes | Med |
| ORF YMR069W | 84 | A | -26 | A | 27 | P | -3 | A | -0.30 | -0.12 | 13.97 | Yes | Med |
| ORF YMR095C | 18 | A | -13 | A | -2 | A | -45 | A | -0.73 | 21.81 | 7.47 | Yes | Med |
| ORF YMR101C | 63 | P | -48 | A | -2 | A | -17 | A | -0.75 | 8.27 | 12.57 | Yes | Med |
| ORF YMR102C | 103 | A | 39 | A | 252 | P | 116 | P | 0.38 | 0.46 | 2.40 | | Good |

Figure 15D

| | | | | | | | |
|---|---|---|---|---|---|---|---|
| ORF YMR103C | 84 A | 15 A | 82 P | 14 A | 0.17 | 0.17 | 5.83 | Good |
| ORF YMR106C | 63 M | 4 A | 15 A | 0 A | 0.06 | 0.00 | 10.18 Yes | Med |
| ORF YMR151W | 53 A | -18 A | 0 A | -13 A | -0.35 | #DIV/0! | 8.41 Yes | Med |
| ORF YMR320W | 163 A | 23 A | 29 A | 14 A | 0.14 | 0.49 | 4.59 | Good |
| ORF YMR322C (_f) | 74 A | 16 A | 23 A | 6 A | 0.21 | 0.27 | 4.19 | Good |
| ORF YMR326C | 84 A | -11 A | -10 A | -22 A | -0.14 | 2.21 | 10.75 Yes | Med |
| ORF YNL014W | 132 A | 26 A | 17 P | -3 A | 0.20 | -0.18 | 4.61 Yes | Med |
| ORF YNL017C (_f) | 126 M | 14 A | 7 A | -4 A | 0.11 | -0.63 | 5.49 Yes | Med |
| ORF YNL018C (_r_) | 84 P | -39 A | -7 A | -47 A | -0.46 | 7.27 | 16.37 Yes | Med |
| ORF YNL143C | 58 M | 9 A | 30 P | 13 P | 0.15 | 0.44 | 4.51 | Good |
| ORF YNL194C | 11 A | -93 A | 13 A | -1 A | -8.82 | -0.08 | 11.75 Yes | Med |
| ORF YNR005C | 79 A | 4 A | 4 A | -11 A | 0.05 | -2.61 | 10.78 Yes | Med |
| ORF YNR062C | 163 A | -9 A | 11 A | -12 A | -0.05 | -1.14 | 19.50 Yes | Med |
| ORF YOL024W | 153 P | -7 A | 10 A | -5 A | -0.05 | -0.53 | 17.47 Yes | Med |
| ORF YOL025W | 116 A | 44 A | 30 P | 7 A | 0.38 | 0.24 | 3.42 | Good |
| ORF YOL035C | 26 A | -10 A | 0 A | -34 A | -0.38 | #DIV/0! | 7.03 Yes | Med |
| ORF YOL084W | 68 A | 11 A | 18 A | -5 A | 0.17 | -0.28 | 5.36 Yes | Med |
| ORF YOL105C | 121 A | -27 A | 88 P | 24 P | -0.22 | 0.27 | 16.68 Yes | Med |
| ORF YOL128C | 111 A | 46 A | 87 P | 43 P | 0.41 | 0.50 | 2.21 | Good |
| ORF YOL160W | 42 A | -20 A | 3 A | -12 A | -0.48 | -3.79 | 7.77 Yes | Med |
| ORF YOL162W | 126 A | -19 A | 30 P | 9 A | -0.15 | 0.30 | 16.13 Yes | Med |
| ORF YOR040W | 153 A | 63 A | 54 P | 23 A | 0.41 | 0.42 | 2.41 | Good |
| ORF YOR105W (_f) | 242 P | 59 P | 86 P | 32 A | 0.24 | 0.37 | 3.41 | Good |
| ORF YOR192C | 11 A | -11 A | 11 A | -4 A | -1.09 | -0.38 | 3.69 Yes | Med |
| ORF YOR282W | 68 A | -14 A | 12 A | -1 A | -0.21 | -0.09 | 9.57 Yes | Med |
| ORF YOR314W | 121 A | 53 A | 7 A | -7 A | 0.44 | -1.11 | 2.52 Yes | Med |
| ORF YOR334W | 79 A | -6 A | 34 P | -7 A | -0.07 | -0.21 | 12.56 Yes | Med |
| ORF YOR364W | 468 A | -27 A | 14 P | 1 A | -0.06 | 0.07 | 56.41 Yes | Med |
| ORF YOR389W | 453 A | 139 P | 50 P | 24 M | 0.31 | 0.47 | 2.69 | Good |
| ORF YPL044C | 47 A | -11 A | 3 A | -11 A | -0.24 | -3.48 | 7.34 Yes | Med |
| ORF YPL068C | 274 A | 37 A | 80 P | 27 A | 0.14 | 0.33 | 5.18 | Good |
| ORF YPL073C | 47 A | -16 A | -1 A | -11 A | -0.33 | 10.43 | 7.33 Yes | Med |
| ORF YPL141C | 205 A | 94 P | 125 P | 53 P | 0.46 | 0.42 | 2.28 | Med |
| ORF YPL186C | 116 A | 16 A | 18 M | 2 A | 0.14 | 0.11 | 8.17 | Good |
| ORF YPL205C | 100 A | -36 A | -2 A | -21 A | -0.36 | 9.48 | 15.42 Yes | Med |

Figure 15E

| | | | | | | | |
|---|---|---|---|---|---|---|---|
| ORF YPL216W | 53 A | -11 A | 17 M | 6 A | -0.22 | 0.36 | 7.81 Yes | Med |
| ORF YPR030W | 116 P | 56 M | 20 P | 6 A | 0.48 | 0.32 | 2.62 | Good |
| ORF YPR039W | 53 A | -17 A | 12 A | -7 A | -0.33 | -0.60 | 8.89 Yes | Med |
| ORF YPR077C (_i) | 195 A | 16 A | 22 P | 5 A | 0.08 | 0.24 | 8.30 | Good |
| ORF YPR200C | -21 A | -46 A | 10 A | -20 A | 2.17 | -2.00 | 5.40 Yes | Med |
| PAC1 (YOR269W) | 163 A | 70 A | 116 P | 58 P | 0.43 | 0.50 | 2.17 | Good |
| PAC11 (YDR488C) | 60 A | -1 A | 48 P | 9 A | -0.02 | 0.19 | 8.86 Yes | Med |
| PES4 (YFR023W) | 30 A | -7 A | 23 A | -3 A | -0.24 | -0.12 | 6.33 Yes | Med |
| RCK1 (YGL158W) | 26 A | -9 A | 41 P | 15 P | -0.32 | 0.36 | 4.88 Yes | Med |
| RGM1 (YMR182C) | 45 A | -7 A | 28 P | 6 A | -0.16 | 0.22 | 7.45 Yes | Med |
| SIP4 (YJL089W) | 66 A | 7 A | 6 A | -12 A | 0.11 | -1.88 | 6.28 Yes | Med |
| SPO1 (YNL012W) | 74 A | 21 A | 17 A | -4 A | 0.29 | -0.24 | 3.87 Yes | Med |
| SPS4 (YOR313C) | 137 A | 9 A | 22 M | 6 A | 0.06 | 0.28 | 9.74 | Good |
| SRB2 (YHR041C) exd | 240 P | -37 A | 171 P | 7 A | -0.16 | 0.04 | 40.35 Yes | Med |
| STE2 (YFL026W) | 872 P | 323 P | 1273 P | 574 P | 0.37 | 0.45 | 2.46 | Excl |
| STE6 (YKL209C) | 574 P | 277 P | 690 P | 312 P | 0.48 | 0.45 | 2.14 | Excl |
| STP4 (YDL048C) | 240 P | 15 A | 319 P | 45 P | 0.06 | 0.14 | 11.64 | Good |
| SWI1 (YPL016W) | 121 A | 39 A | 107 P | 41 P | 0.32 | 0.39 | 2.86 | Good |
| TPS2 (YDR074W) | 179 P | 51 A | 130 P | 62 P | 0.29 | 0.47 | 2.80 | Good |
| TSL1 (YML100W) | 200 P | -5 A | 322 P | 61 P | -0.02 | 0.19 | 23.11 Yes | Med |
| UGX2 (YDL169C) | 11 A | -50 A | 13 A | -10 A | -4.50 | -0.79 | 8.44 Yes | Med |
| YCRX15w/_f (control | 68 A | -27 A | 39 P | 9 M | -0.40 | 0.23 | 11.72 Yes | Med |
| YHR079BC/SAE3_i ( | 30 A | -36 A | 1 A | -14 A | -1.18 | -10.36 | 8.15 Yes | Med |
| ZDS1 (YMR273C) | 226 A | -3 A | 82 P | 4 A | -0.01 | 0.05 | 32.80 Yes | Med |

Figure 15F

Srb2 Down

Gene Expression Results for FH1998040601A

| Gene | SRB WT#WT;SRB2#1 | SR | SRB WT#WT SRB2#2 | SR | SR | MT1/WT1 | MT2/WT2 | Ave | Corrected? | Confidence |
|---|---|---|---|---|---|---|---|---|---|---|
| ORF YMR151W | 53 | A | -18 | A | 0 | A | -13 | A | -0.35 | #DIV/0! | 8.41 | Yes | Med |
| ORF YOL035C | 26 | A | -10 | A | 0 | A | -34 | A | -0.38 | #DIV/0! | 7.03 | Yes | Med |
| ORF YGL069C | 30 | A | -43 | A | -3 | A | -61 | A | -1.42 | 22.20 | 13.11 | Yes | Med |
| ORF YMR095C | 18 | A | -13 | A | -2 | A | -45 | A | -0.73 | 21.81 | 7.47 | Yes | Med |
| ORF YDL186W | 8 | A | -11 | A | -1 | A | -17 | A | -1.36 | 17.12 | 3.49 | Yes | Med |
| ORF YDR102C | 24 | A | -5 | A | -1 | A | -14 | A | -0.23 | 14.38 | 4.26 | Yes | Med |
| ORF YPL073C | 47 | A | -16 | A | -1 | A | -11 | A | -0.33 | 10.43 | 7.33 | Yes | Med |
| ORF YPL205C | 100 | A | -36 | A | -2 | A | -21 | A | -0.36 | 9.48 | 15.42 | Yes | Med |
| ORF YLR236C | 45 | A | -70 | A | -2 | A | -19 | A | -1.55 | 9.40 | 13.16 | Yes | Med |
| ORF YMR101C | 63 | P | -48 | A | -2 | A | -17 | A | -0.75 | 8.27 | 12.57 | Yes | Med |
| ORF YNL018C (_r_i) | 84 | P | -39 | A | -7 | A | -47 | A | -0.46 | 7.27 | 16.37 | Yes | Med |
| ORF YBR219C exon | -25 | A | -36 | A | -5 | A | -34 | A | 1.44 | 6.85 | 4.03 | Yes | Med |
| ORF YBR219C exon | 5 | A | -46 | A | -2 | A | -12 | A | -9.65 | 6.16 | 6.10 | Yes | Med |
| FLO9 (YAL064W) (_ | -24 | A | -103 | A | -4 | A | -22 | A | 4.31 | 5.48 | 9.68 | Yes | Med |
| ORF YKL031W | -82 | A | -191 | A | -31 | A | -111 | A | 2.35 | 3.58 | 18.98 | Yes | Med |
| ORF YAR040C | 13 | A | -36 | A | -5 | A | -16 | A | -2.87 | 3.29 | 6.06 | Yes | Med |
| MRK1 (YDL079C) exi | 33 | A | 7 | A | -10 | A | -31 | A | 0.20 | 3.08 | 4.55 | Yes | Med |
| ALPHA1 (YCR040W) | 8 | A | -35 | A | -8 | A | -25 | A | -4.43 | 3.08 | 5.97 | Yes | Med |
| ORF YMR326C | 84 | A | -11 | A | -10 | A | -22 | A | -0.14 | 2.21 | 10.75 | Yes | Med |
| ORF YBL013W | -46 | A | -131 | A | -11 | A | -22 | A | 2.85 | 1.99 | 9.60 | Yes | Med |
| ORF YAR037W (_r) | -19 | A | -68 | A | -27 | A | -53 | A | 3.55 | 1.98 | 7.49 | Yes | Med |
| ORF YIL057C | -17 | A | -54 | A | -37 | A | -72 | A | 3.20 | 1.95 | 7.26 | Yes | Med |
| ORF YDL221W | -8 | A | -42 | A | -22 | A | -40 | A | 5.28 | 1.81 | 5.17 | Yes | Med |
| ORF YCR074C | -59 | A | -103 | A | -36 | A | -56 | A | 1.75 | 1.56 | 6.41 | Yes | Med |
| ORF YOL128C | 111 | A | 46 | A | 87 | P | 43 | P | 0.41 | 0.50 | 2.21 | | Good |
| PAC1 (YOR269W) | 163 | A | 70 | A | 116 | P | 58 | P | 0.43 | 0.50 | 2.17 | | Good |
| ORF YKR017C | 55 | A | 13 | A | 52 | P | 26 | P | 0.24 | 0.50 | 3.07 | | Good |
| ORF YMR320W | 163 | A | 23 | A | 29 | A | 14 | A | 0.14 | 0.49 | 4.59 | | Good |
| KIP2 (YPL155C) | 74 | A | 24 | A | 68 | P | 33 | P | 0.33 | 0.48 | 2.55 | | Good |
| ORF YBR168W | 57 | P | 9 | A | 64 | P | 31 | A | 0.17 | 0.48 | 4.06 | | Good |
| ORF YDL113C | 63 | A | 27 | A | 73 | P | 35 | A | 0.43 | 0.48 | 2.22 | | Good |
| ORF YDR259C | 41 | A | 9 | A | 53 | P | 25 | P | 0.23 | 0.48 | 3.23 | | Good |

Figure 16A

| | | | | | | | | |
|---|---|---|---|---|---|---|---|---|
| ORF YGL045W | 134 P | 1 A | 38 P | 18 A | 0.01 | 0.48 | 47.94 | | Good |
| ORF YOR389W | 453 A | 139 P | 50 P | 24 M | 0.31 | 0.47 | 2.69 | | Good |
| TPS2 (YDR074W) | 179 P | 51 A | 130 P | 62 P | 0.29 | 0.47 | 2.80 | | Good |
| HMS1 (YMR070W) | 50 P | 10 M | 123 P | 58 P | 0.20 | 0.47 | 3.62 | | Good |
| FUS1 (YCL027W) | 146 P | 54 A | 97 P | 45 A | 0.37 | 0.47 | 2.42 | | Good |
| ORF YMR102C | 103 A | 39 A | 252 P | 116 P | 0.38 | 0.46 | 2.40 | | Good |
| ORF YHL035C | 77 M | 30 A | 164 P | 76 P | 0.39 | 0.46 | 2.38 | | Good |
| ORF YJR137C | 84 A | -17 A | 47 P | 22 P | -0.20 | 0.46 | 11.22 | Yes | Med |
| ORF YGR131W | 58 A | 24 A | 36 A | 16 A | 0.42 | 0.46 | 2.30 | | Good |
| STE6 (YKL209C) | 574 A | 277 P | 690 P | 312 P | 0.48 | 0.45 | 2.14 | | Excl |
| STE2 (YFL026W) | 872 P | 323 P | 1273 P | 574 P | 0.37 | 0.45 | 2.46 | | Excl |
| ORF YCR032W | 122 P | 59 P | 70 P | 32 P | 0.49 | 0.45 | 2.14 | | Excl |
| MFA2 (YNL145W) | 10468 P | 3607 P | 5137 P | 2263 P | 0.34 | 0.44 | 2.59 | | Excl |
| ORF YNL143C | 58 M | 9 A | 30 P | 13 P | 0.15 | 0.44 | 4.51 | | Good |
| ORF YGR230W | 75 P | 31 A | 60 P | 26 A | 0.42 | 0.44 | 2.34 | | Good |
| ORF YDR491C | 92 A | -4 A | 32 P | 14 A | -0.04 | 0.43 | 10.78 | Yes | Med |
| ORF YDL248W (_r) | 37 M | 5 A | 32 P | 14 P | 0.15 | 0.43 | 4.54 | | Good |
| ORF YER075C | 72 M | 10 A | 70 P | 30 P | 0.14 | 0.43 | 4.76 | | Good |
| ORF YBR057C | 75 M | 16 A | 47 P | 20 M | 0.22 | 0.42 | 3.48 | | Good |
| ORF YPL141C | 205 A | 94 P | 125 P | 53 P | 0.46 | 0.42 | 2.28 | | Good |
| ORF YKL198C | 132 P | 46 A | 46 P | 19 P | 0.35 | 0.42 | 2.62 | | Good |
| ORF YOR040W | 153 A | 63 A | 54 P | 23 A | 0.41 | 0.42 | 2.41 | | Good |
| ORF YLL066C exon | 8 A | -5 A | 69 P | 29 P | -0.62 | 0.42 | 2.48 | Yes | Med |
| ORF YBR259W | 63 P | 18 A | 48 P | 20 P | 0.28 | 0.41 | 3.02 | | Good |
| ORF YDR033W | 5497 P | 2118 P | 4162 P | 1714 P | 0.39 | 0.41 | 2.51 | | Excl |
| FAR1 (YJL157C) | 679 P | 180 P | 541 P | 214 P | 0.27 | 0.40 | 3.15 | | Excl |
| ORF YBR250W | 19 A | -16 A | 21 P | 8 A | -0.85 | 0.39 | 4.80 | Yes | Med |
| ORF YJL225C exon | 71 A | 17 A | 32 P | 12 A | 0.24 | 0.39 | 3.37 | | Good |
| SWI1 (YPL016W) | 121 A | 39 A | 107 P | 41 P | 0.32 | 0.39 | 2.86 | | Good |
| ORF YMR026C | 124 A | 51 A | 87 P | 33 M | 0.41 | 0.38 | 2.51 | | Good |
| ORF YEL076C-A exo | 60 A | -43 A | 42 M | 16 A | -0.71 | 0.38 | 11.63 | Yes | Med |
| ORF YDL179W | 87 A | 43 A | 151 P | 58 A | 0.50 | 0.38 | 2.32 | | Good |

Figure 16B

| | | | | | | | | |
|---|---|---|---|---|---|---|---|---|
| MAL32 (YBR299W) | 37 P | -100 A | 36 A | 14 A | -2.74 | 0.38 | 14.96 | Yes | Med |
| ORF YOR105W (_f) | 242 P | 59 P | 86 P | 32 A | 0.24 | 0.37 | 3.41 | | Good |
| RCK1 (YGL158W) | 26 A | -9 A | 41 P | 15 P | -0.32 | 0.36 | 4.88 | Yes | Med |
| ORF YPL216W | 53 A | -11 A | 17 M | 6 A | -0.22 | 0.36 | 7.81 | Yes | Med |
| ORF YIL080W (_f) | 236 P | 103 P | 210 P | 74 P | 0.44 | 0.35 | 2.56 | | Excl |
| ORF YLR269C | 13 A | -4 A | 18 P | 6 P | -0.28 | 0.35 | 3.09 | Yes | Med |
| MFA1 (YDR461W) | 2290 P | 407 P | 1719 P | 604 P | 0.18 | 0.35 | 4.24 | | Excl |
| ORF YDR539W | 131 A | -35 A | 189 P | 66 P | -2.77 | 0.35 | 6.22 | Yes | Med |
| ORF YGL051W | -2 A | -14 A | 30 P | 10 A | 7.57 | 0.34 | 2.73 | Yes | Med |
| ORF YPL068C | 274 A | 37 A | 80 P | 27 A | 0.14 | 0.33 | 5.18 | | Good |
| ORF YGL072C | 15 A | -26 A | 49 P | 16 P | -1.70 | 0.33 | 5.60 | Yes | Med |
| ORF YAR068W (_f) | -29 A | -69 A | 82 P | 27 A | 2.41 | 0.33 | 5.57 | Yes | Med |
| ORF YBR232C | -5 A | -20 A | 19 P | 6 A | 4.26 | 0.32 | 3.09 | Yes | Med |
| ORF YCR007C | 62 A | -24 A | 17 P | 5 A | -0.39 | 0.32 | 10.17 | Yes | Med |
| ORF YEL057C | 77 A | 27 A | 32 P | 10 A | 0.35 | 0.32 | 2.98 | | Good |
| ORF YDL129W | 143 P | 42 A | 81 P | 26 A | 0.29 | 0.32 | 3.26 | | Good |
| ORF YPR030W | 116 P | 56 M | 20 P | 6 A | 0.48 | 0.32 | 2.62 | | Good |
| DCG1 (YIR030C) | 15 A | -43 A | 30 P | 9 A | -2.84 | 0.31 | 7.39 | Yes | Excl |
| ORF YOL162W | 126 A | -19 A | 30 P | 9 A | -0.15 | 0.30 | 16.13 | Yes | Med |
| ORF YJL108C | 139 A | 67 A | 79 P | 24 A | 0.48 | 0.30 | 2.69 | | Good |
| ORF YGR239C | 53 A | 23 A | 25 A | 7 A | 0.43 | 0.30 | 2.81 | | Good |
| ORF YIL092W | 49 A | 19 A | 38 P | 11 A | 0.38 | 0.30 | 2.99 | | Good |
| ORF YDL022W | 1084 P | 491 P | 1669 P | 492 P | 0.45 | 0.30 | 2.80 | | Excl |
| ORF YMR018W | 5 A | -20 A | 19 P | 5 A | -3.71 | 0.29 | 4.19 | Yes | Med |
| ORF YHR087W | 40 A | 17 A | 221 P | 64 P | 0.43 | 0.29 | 2.87 | | Good |
| SPS4 (YOR313C) | 137 A | 9 A | 22 M | 6 A | 0.06 | 0.28 | 9.74 | | Good |
| ORF YKL047W | 66 P | 18 A | 73 P | 20 A | 0.28 | 0.28 | 3.61 | | Good |
| FAB1 (YFR019W) | 21 A | -6 A | 84 P | 23 P | -0.28 | 0.27 | 4.47 | Yes | Med |
| ORF YMR322C (_f) | 74 A | 16 A | 23 A | 6 A | 0.21 | 0.27 | 4.19 | | Good |
| ORF YOL105C | 121 A | -27 A | 88 P | 24 P | -0.22 | 0.27 | 16.68 | Yes | Med |
| AGA1 (YNR044W) | 863 P | 239 P | 609 P | 158 P | 0.28 | 0.26 | 3.74 | | Excl |
| ORF YCR006C | 2 A | -30 A | 19 P | 5 A | -18.73 | 0.25 | 5.11 | Yes | Med |
| ORF YPR077C (_j) | 195 A | 16 A | 22 P | 5 A | 0.08 | 0.24 | 8.30 | | Good |
| ORF YOL025W | 116 A | 44 A | 30 P | 7 A | 0.38 | 0.24 | 3.42 | | Good |
| ORF YLR040C | 71 A | 7 A | 90 P | 21 P | 0.10 | 0.23 | 7.00 | | Good |

Figure 16C

| YCRX15w/_f (control) | 68 | A | -27 | A | 39 | P | 9 | M | -0.40 | 0.23 | 11.72 | Yes | Med |
|---|---|---|---|---|---|---|---|---|---|---|---|---|---|
| ORF YDL038C | 232 | P | 105 | M | 423 | P | 97 | P | 0.45 | 0.23 | 3.29 | | Good |
| ORF YLR004C | 68 | P | -11 | A | 21 | A | 5 | A | -0.16 | 0.23 | 10.16 | Yes | Med |
| RGM1 (YMR182C) | 45 | A | -7 | A | 28 | P | 6 | A | -0.16 | 0.22 | 7.45 | Yes | Med |
| ORF YIR018W | 53 | A | 3 | A | 49 | A | 11 | A | 0.05 | 0.22 | 11.53 | | Good |
| DIT1 (YDR403W) | 21 | A | 4 | A | 25 | P | 5 | A | 0.20 | 0.22 | 4.83 | | Good |
| CTP1 (YBR291C) | 179 | A | 81 | A | 192 | P | 40 | P | 0.45 | 0.21 | 3.48 | | Good |
| ORF YDR541C | -19 | A | -47 | A | 55 | P | 11 | A | 2.48 | 0.20 | 5.33 | Yes | Med |
| TSL1 (YML100W) | 200 | P | -5 | A | 322 | P | 61 | P | -0.02 | 0.19 | 23.11 | Yes | Med |
| PAC11 (YDR488C) | 60 | A | -1 | A | 48 | P | 9 | A | -0.02 | 0.19 | 8.86 | Yes | Good |
| ORF YGL184C | 25 | A | 1 | A | 53 | P | 9 | A | 0.06 | 0.18 | 11.41 | | Good |
| ORF YMR103C | 84 | A | 15 | A | 82 | P | 14 | A | 0.17 | 0.17 | 5.83 | | Good |
| ORF YDL146W | 46 | A | 22 | A | 37 | P | 6 | A | 0.47 | 0.17 | 4.07 | | Good |
| ORF YKR045C | 50 | A | 23 | A | 97 | P | 16 | A | 0.46 | 0.16 | 4.20 | | Med |
| ORF YER037W | 13 | A | -33 | A | 47 | P | 7 | A | -2.49 | 0.15 | 8.05 | Yes | Good |
| STP4 (YDL048C) | 240 | P | 15 | A | 319 | P | 45 | P | 0.06 | 0.14 | 11.64 | | Med |
| ORF YPL186C | 116 | A | 16 | A | 18 | M | 2 | A | 0.14 | 0.11 | 8.17 | | Med |
| HSP12 (YFL014W) | 279 | P | 77 | A | 204 | P | 22 | P | 0.28 | 0.11 | 6.39 | | Good |
| CYT1 (YOR065W) | 311 | A | -54 | A | 102 | P | 10 | P | -0.17 | 0.10 | 41.44 | Yes | Med |
| ORF YOR364W | 468 | A | -27 | A | 14 | P | 1 | A | -0.06 | 0.07 | 56.41 | Yes | Med |
| CHA1 (YCL064C) | 763 | P | 91 | P | 910 | P | 66 | P | 0.12 | 0.07 | 11.14 | | Excl |
| ORF YLR315W | -8 | A | -20 | A | 111 | A | 1 | A | 2.47 | 0.07 | 8.48 | Yes | Med |
| ORF YFR032C | 89 | P | -4 | A | 25 | A | 1 | A | -0.05 | 0.05 | 18.42 | Yes | Med |
| INH1 (YDL181W) | 52 | A | 15 | A | 117 | P | 6 | A | 0.28 | 0.05 | 11.25 | | Good |
| ZDS1 (YMR273C) | 226 | A | -3 | A | 82 | P | 4 | A | -0.01 | 0.05 | 32.80 | Yes | Med |
| SRB2 (YHR041C) exd | 240 | P | -37 | A | 171 | P | 7 | A | -0.16 | 0.04 | 40.35 | Yes | Med |
| GPM2 (YDL021W) | -6 | A | -39 | A | 22 | P | 1 | A | 6.17 | 0.03 | 19.34 | Yes | Med |
| ORF YGR068C | -60 | A | -101 | A | 37 | M | 1 | A | 1.68 | 0.02 | 31.47 | Yes | Med |
| ORF YDR359C | 130 | A | 35 | A | 43 | P | 0 | A | 0.27 | 0.00 | 6.15 | Yes | Med |
| MSH4 (YFL003C) | 36 | A | -31 | A | 11 | A | 0 | A | -0.88 | 0.00 | 7.82 | Yes | Med |
| ORF YLR042C | 21 | A | -35 | A | 34 | P | 0 | A | -1.68 | 0.00 | 9.04 | Yes | Med |
| ORF YMR106C | 63 | M | 4 | A | 15 | A | 0 | A | 0.06 | 0.00 | 10.18 | Yes | Med |
| ORF YHL028W | 62 | A | -60 | A | 33 | M | -1 | A | -0.96 | -0.02 | 15.58 | Yes | Med |

Figure 16D

| | | | | | | | |
|---|---|---|---|---|---|---|---|
| ORF YGL034C | -42 | A | -90 | A | 23 | P | -1 | A | 2.17 | -0.03 | 7.25 | Yes | Med |
| ORF YNL194C | 11 | A | -93 | A | 13 | A | -1 | A | -8.82 | -0.08 | 11.75 | Yes | Med |
| ORF YOR282W | 68 | A | -14 | A | 12 | A | -1 | A | -0.21 | -0.09 | 9.57 | Yes | Med |
| FSP2 (YJL221C) (_f) | 74 | A | -15 | A | 44 | P | -5 | A | -0.20 | -0.10 | 13.73 | Yes | Med |
| ORF YMR069W | 84 | A | -26 | A | 27 | P | -3 | A | -0.30 | -0.12 | 13.97 | Yes | Med |
| PES4 (YFR023W) | 30 | A | -7 | A | 23 | A | -3 | A | -0.24 | -0.12 | 6.33 | Yes | Med |
| GSY1 (YFR015C) | 45 | A | 16 | A | 19 | P | -3 | A | 0.35 | -0.18 | 3.70 | Yes | Med |
| ORF YNL014W | 132 | A | 26 | A | 17 | P | -3 | A | 0.20 | -0.18 | 4.61 | Yes | Med |
| ORF YGR023W | 15 | A | -20 | A | 26 | A | -5 | P | -1.33 | -0.21 | 6.65 | Yes | Med |
| ORF YOR334W | 79 | A | -6 | A | 34 | P | -7 | A | -0.07 | -0.21 | 12.56 | Yes | Med |
| ORF YJR108W | 45 | A | 18 | A | 14 | P | -3 | A | 0.41 | -0.21 | 2.98 | Yes | Med |
| SPO1 (YNL012W) | 74 | A | 21 | A | 17 | A | -4 | A | 0.29 | -0.24 | 3.87 | Yes | Med |
| ORF YKL171W | 5 | A | -13 | A | 28 | P | -7 | A | -2.55 | -0.25 | 5.35 | Yes | Med |
| ORF YER188W | 100 | P | -9 | A | 21 | P | -5 | A | -0.09 | -0.26 | 13.45 | Yes | Med |
| ORF YOL084W | 68 | A | 11 | A | 18 | A | -5 | A | 0.17 | -0.28 | 5.36 | Yes | Med |
| ORF YGL170C | -32 | A | -61 | A | 33 | A | -9 | A | 1.92 | -0.29 | 7.17 | Yes | Med |
| KNH1 (YDL049C) | 3 | A | -51 | A | 19 | A | -5 | A | -16.18 | -0.29 | 7.90 | Yes | Med |
| ORF YDL057W | -6 | A | -38 | A | 35 | P | -11 | A | 5.96 | -0.31 | 7.74 | Yes | Med |
| ORF YCR100C | 32 | A | -61 | A | 27 | P | -9 | A | -1.92 | -0.33 | 12.85 | Yes | Med |
| ORF YGL263W | 2 | A | -9 | A | 14 | A | -5 | A | -4.54 | -0.35 | 2.89 | Yes | Med |
| ORF YOR192C | 11 | A | -11 | A | 11 | A | -4 | A | -1.09 | -0.38 | 3.69 | Yes | Med |
| ORF YDL248W (_j) | 40 | A | -19 | A | 37 | P | -16 | A | -0.48 | -0.43 | 11.14 | Yes | Med |
| ORF YIL120W | 32 | P | 1 | A | 15 | P | -7 | A | 0.04 | -0.45 | 13.41 | Yes | Med |
| ORF YGR225W | 21 | A | -1 | A | 18 | A | -9 | A | -0.07 | -0.49 | 4.88 | Yes | Med |
| ORF YJR128W | -18 | A | -41 | A | 12 | A | -6 | A | 2.25 | -0.50 | 4.16 | Yes | Med |
| ORF YOL024W | 153 | P | -7 | A | 10 | A | -5 | A | -0.05 | -0.53 | 17.47 | Yes | Med |
| ORF YPR039W | 53 | A | -17 | A | 12 | A | -7 | A | -0.33 | -0.60 | 8.89 | Yes | Med |
| ORF YLR341W | 0 | A | -30 | A | 6 | A | -4 | A | #DIV/0! | -0.63 | 4.05 | Yes | Med |
| ORF YNL017C (_f) | 126 | M | 14 | A | 7 | A | -4 | A | 0.11 | -0.63 | 5.49 | Yes | Med |
| ORF YGL033W exon | 25 | A | 7 | A | 12 | A | -8 | A | 0.29 | -0.66 | 3.76 | Yes | Med |
| ORF YKR005C | 11 | A | -7 | A | 14 | P | -10 | A | -0.70 | -0.70 | 4.24 | Yes | Med |
| ORF YLR312C | 37 | A | 0 | A | 12 | A | -9 | A | 0.00 | -0.75 | 5.85 | Yes | Med |
| UGX2 (YDL169C) | 11 | A | -50 | A | 13 | A | -10 | A | -4.50 | -0.79 | 8.44 | Yes | Med |
| ORF YDR540C | -125 | A | -139 | A | 13 | A | -12 | A | 1.11 | -0.90 | 3.84 | Yes | Med |
| ORF YMR068W | 55 | A | -27 | A | 31 | P | -28 | A | -0.49 | -0.90 | 14.09 | Yes | Med |

Figure 16E

| ORF YER187W | 30 | A | -20 | A | 12 | M | -11 | A | -0.66 | -0.93 | 7.40 | Yes | Med |
|---|---|---|---|---|---|---|---|---|---|---|---|---|---|
| ORF YLL005C | 61 | M | -23 | A | 14 | A | -15 | A | -0.38 | -1.02 | 11.29 | Yes | Med |
| ORF YOR314W | 121 | A | 53 | A | 7 | A | -7 | A | 0.44 | -1.11 | 2.52 | Yes | Med |
| ORF YLR035C | 32 | A | -21 | A | 10 | P | -12 | A | -0.66 | -1.13 | 7.42 | Yes | Med |
| ORF YNR062C | 163 | A | -9 | A | 11 | A | -12 | A | -0.05 | -1.14 | 19.50 | Yes | Med |
| LEE1 (YPL054W) | 5 | A | -44 | A | 9 | A | -11 | A | -8.41 | -1.30 | 6.96 | Yes | Med |
| ORF YJL161W | 24 | A | -39 | A | 8 | A | -14 | A | -1.65 | -1.69 | 8.49 | Yes | Med |
| ORF YBR076W | -2 | A | -18 | A | 4 | A | -7 | A | 11.07 | -1.71 | 2.68 | Yes | Med |
| SIP4 (YJL089W) | 66 | A | 7 | A | 6 | A | -12 | A | 0.11 | -1.88 | 6.28 | Yes | Med |
| ORF YPR200C | -21 | A | -46 | A | 10 | A | -20 | A | 2.17 | -2.00 | 5.40 | Yes | Med |
| ORF YLR307W | 39 | A | -1 | A | 4 | A | -9 | A | -0.03 | -2.26 | 5.41 | Yes | Med |
| ATP10 (YLR393W) | -50 | A | -78 | A | 12 | A | -32 | A | 1.56 | -2.57 | 7.22 | Yes | Med |
| ORF YNR005C | 79 | A | 4 | A | 4 | A | -11 | A | 0.05 | -2.61 | 10.78 | Yes | Med |
| ORF YLR030W | 21 | A | -46 | A | 3 | A | -10 | A | -2.20 | -3.26 | 8.06 | Yes | Med |
| ORF YDR203W | 22 | A | -9 | A | 4 | A | -14 | A | -0.43 | -3.42 | 4.94 | Yes | Med |
| ORF YPL044C | 47 | A | -11 | A | 3 | A | -11 | A | -0.24 | -3.48 | 7.34 | Yes | Med |
| ORF YOL160W | 42 | A | -20 | A | 3 | A | -12 | A | -0.48 | -3.79 | 7.77 | Yes | Med |
| ORF YDR374C | 10 | A | -16 | A | 7 | A | -31 | A | -1.70 | -4.40 | 6.36 | Yes | Med |
| ORF YDL026W | 14 | A | -27 | A | 2 | A | -10 | A | -1.89 | -5.14 | 5.36 | Yes | Med |
| MET28 (YIR017C) | -62 | A | -99 | A | 5 | A | -42 | A | 1.58 | -7.65 | 8.37 | Yes | Med |
| ORF YHR177W | 49 | A | -39 | A | 1 | A | -11 | A | -0.79 | -7.89 | 9.98 | Yes | Med |
| YHR079BC/SAE3_i | 30 | A | -36 | A | 1 | A | -14 | A | -1.18 | -10.36 | 8.15 | Yes | Med |
| ORF YCL065W | 22 | A | -28 | A | 2 | A | -25 | A | -1.28 | -12.33 | 7.73 | Yes | Med |
| HES1 (YOR237W) | 37 | A | 4 | A | 13 | A | -211 | A | 0.12 | -16.20 | 26.74 | Yes | Med |

Figure 16F

Swi2 Up

Gene Expression Results for FH1998040601A

| | WT1val | WT1 | MT1val | MT1 | WT2val | WT2 | MT2val | MT2 | MT1/WT1 | MT2/WT2 | Ave | Corrected? | Confidence |
|---|---|---|---|---|---|---|---|---|---|---|---|---|---|
| AAC1 (YMR056C) | 96 | P | 375 | P | 70 | P | 437 | P | 3.9 | 6.3 | 5.1 | | Excl |
| ACH1 (YBL015W) | 151 | P | 313 | P | 119 | P | 285 | P | 2.1 | 2.4 | 2.2 | | Excl |
| AHT1 (YHR093W) | -40 | A | -24 | A | -27 | A | -7 | A | 0.6 | 0.3 | 3.6 | Yes | Med |
| AMS1 (YGL156W) | 43 | P | 263 | P | 39 | P | 195 | P | 6.1 | 5.0 | 5.6 | | Excl |
| ARE2 (YNR019W) | 242 | P | 652 | P | 157 | P | 542 | P | 2.7 | 3.5 | 3.1 | | Excl |
| ARG4 (YHR018C) | 771 | P | 1834 | P | 765 | P | 1906 | P | 2.4 | 2.5 | 2.4 | | Excl |
| ARG5,6" (YER069W) | 404 | P | 1226 | P | 327 | P | 1224 | P | 3.0 | 3.7 | 3.4 | | Excl |
| ATF1 (YOR377W) | 67 | P | 168 | P | 57 | P | 160 | P | 2.5 | 2.8 | 2.6 | | Excl |
| BAR1 (YIL015W) | 12 | A | 31 | P | 3 | A | 26 | P | 2.6 | 9.0 | 5.8 | | Good |
| CAR1 (YPL111W) | 687 | P | 1500 | P | 550 | P | 1263 | P | 2.2 | 2.3 | 2.2 | | Excl |
| CAT8 (YMR280C) | 17 | A | 75 | P | 9 | A | 34 | P | 4.4 | 3.8 | 4.1 | | Good |
| CYC3 (YAL039C) | 344 | P | 721 | P | 336 | P | 683 | P | 2.1 | 2.0 | 2.1 | | Excl |
| FBP26 (YJL155C) | 77 | P | 168 | P | 78 | P | 185 | P | 2.2 | 2.4 | 2.3 | | Excl |
| FUN34 (YNR002C) | 36 | P | 85 | P | 21 | A | 57 | P | 2.4 | 2.7 | 2.5 | | Excl |
| FUS1 (YCL027W) | 67 | P | 228 | P | 92 | P | 209 | P | 3.4 | 2.3 | 2.8 | | Excl |
| GAL3 (YDR009W) | 12 | A | 24 | A | 1 | A | 13 | P | 2.0 | 17.4 | 9.7 | | Good |
| GDH3 (YAL062W) | 22 | P | 89 | P | 23 | P | 73 | P | 4.0 | 3.2 | 3.6 | | Excl |
| GLC3 (YEL011W) | 88 | P | 183 | P | 77 | P | 188 | P | 2.1 | 2.4 | 2.3 | | Excl |
| GLK1 (YCL040W) | 1172 | P | 2615 | P | 802 | P | 2523 | P | 2.2 | 3.1 | 2.7 | | Excl |
| GPM2 (YDL021W) | 15 | A | 51 | A | 6 | A | 44 | P | 3.4 | 7.4 | 5.4 | | Good |
| GUT2 (YIL155C) | 97 | P | 256 | P | 60 | P | 322 | P | 2.6 | 5.4 | 4.0 | | Excl |
| HSP26 (YBR072W) | 33 | P | 169 | P | 38 | P | 109 | P | 5.1 | 2.9 | 4.0 | | Excl |
| HSP42 (YDR171W) | 241 | P | 808 | P | 164 | P | 660 | P | 3.4 | 4.0 | 3.7 | | Excl |
| HSP78 (YDR258C) | 167 | P | 354 | P | 119 | P | 370 | P | 2.1 | 3.1 | 2.6 | | Excl |
| HXT5 (YHR096C) | 21 | M | 138 | P | 16 | A | 89 | P | 6.7 | 5.5 | 6.1 | | Good |
| LAP4 (YKL103C) | 99 | P | 321 | P | 70 | P | 438 | P | 3.2 | 6.3 | 4.8 | | Excl |
| MAL1 (YGR292W) | 0 | A | 30 | P | 7 | A | 32 | P | #DIV/0! | 4.8 | 5.4 | Yes | Med |
| MET2 (YNL277W) | 154 | P | 340 | P | 82 | P | 333 | P | 2.2 | 4.0 | 3.1 | | Excl |
| MET25 (YLR303W) | 3029 | P | 6554 | P | 2321 | P | 5602 | P | 2.2 | 2.4 | 2.3 | | Excl |
| MET28 (YIR017C) | -12 | A | 81 | P | 6 | A | 118 | P | -6.8 | 20.8 | 19.6 | Yes | Med |
| MET6 (YER091C) | 1548 | P | 3578 | P | 1596 | P | 3627 | P | 2.3 | 2.3 | 2.3 | | Excl |
| MET8 (YBR213W) | 39 | P | 96 | P | 15 | A | 93 | P | 2.5 | 6.2 | 4.3 | | Good |

Figure 17A

| | 108 | | 250 | | 105 | | 289 | | 2.3 | 2.8 | 2.5 | |
|---|---|---|---|---|---|---|---|---|---|---|---|---|
| MRS4 (YKR052C) | 108 | P | 250 | P | 105 | P | 289 | P | 2.3 | 2.8 | 2.5 | Excl |
| MSH4 (YFL003C) | -2 | A | 23 | P | -4 | A | 9 | A | -9.7 | -2.3 | 3.8 Yes | Med |
| MSP1 (YGR028W) | 122 | P | 304 | P | 133 | P | 276 | P | 2.5 | 2.1 | 2.3 | Excl |
| ORF YAL037W | 22 | P | 95 | P | 28 | P | 65 | P | 4.3 | 2.4 | 3.3 | Excl |
| ORF YAL053W | 275 | P | 708 | P | 283 | P | 572 | P | 2.6 | 2.0 | 2.3 | Excl |
| ORF YAR043C | -7 | A | 14 | A | -7 | A | 16 | A | -1.9 | -2.1 | 4.4 Yes | Med |
| ORF YAR052C (_i) | -78 | A | -51 | A | -81 | A | -68 | A | 0.7 | 0.8 | 4.0 Yes | Med |
| ORF YAR068W (_f) | 36 | P | 198 | P | 48 | P | 183 | P | 5.5 | 3.8 | 4.7 | Excl |
| ORF YBL012C | 4 | A | 27 | A | -4 | A | 8 | A | 6.8 | -2.1 | 4.6 Yes | Med |
| ORF YBL044W | -2 | A | 19 | A | -6 | A | 6 | A | -9.7 | -1.0 | 3.3 Yes | Med |
| ORF YBL078C | 91 | P | 468 | P | 83 | P | 357 | P | 5.1 | 4.3 | 4.7 | Excl |
| ORF YBR005W | 56 | P | 223 | P | 63 | P | 135 | P | 4.0 | 2.1 | 3.1 | Excl |
| ORF YBR066C | 69 | P | 230 | P | 81 | P | 168 | P | 3.3 | 2.1 | 2.7 | Excl |
| ORF YBR070C | 119 | P | 474 | P | 124 | P | 427 | P | 4.0 | 3.4 | 3.7 | Excl |
| ORF YBR077C | 140 | P | 395 | P | 134 | P | 343 | P | 2.8 | 2.5 | 2.7 | Excl |
| ORF YBR101C | 252 | P | 656 | P | 246 | P | 511 | P | 2.6 | 2.1 | 2.3 | Excl |
| ORF YBR178W | -1 | A | 20 | A | 0 | A | 13 | A | -20.3 | #DIV/0! | 3.4 Yes | Med |
| ORF YBR224W | -45 | A | -34 | A | -25 | A | -3 | A | 0.8 | 0.1 | 3.3 Yes | Med |
| ORF YBR230C exon | 250 | P | 531 | P | 196 | P | 462 | P | 2.1 | 2.4 | 2.2 | Excl |
| ORF YBR269C | 160 | P | 406 | P | 102 | P | 364 | P | 2.5 | 3.6 | 3.0 | Excl |
| ORF YBR302C (_f) | 417 | P | 1220 | P | 441 | P | 933 | P | 2.9 | 2.1 | 2.5 | Excl |
| ORF YCL035C | 571 | P | 1273 | P | 513 | P | 1032 | P | 2.2 | 2.0 | 2.1 | Excl |
| ORF YCL041C | 12 | A | 45 | A | 17 | P | 51 | P | 3.7 | 3.0 | 3.3 | Good |
| ORF YDL057W | 32 | P | 76 | P | 13 | A | 85 | P | 2.4 | 6.7 | 4.5 | Good |
| ORF YDL110C | 171 | P | 381 | P | 125 | P | 373 | P | 2.2 | 3.0 | 2.6 | Excl |
| ORF YDL173W | 402 | P | 852 | P | 325 | P | 725 | P | 2.1 | 2.2 | 2.2 | Excl |
| ORF YDL199C | 4 | A | 15 | A | 9 | A | 33 | P | 3.6 | 3.7 | 3.7 | Good |
| ORF YDL214C | 25 | A | 91 | A | 16 | A | 73 | P | 3.6 | 4.7 | 4.2 | Good |
| ORF YDR010C | -25 | A | 21 | A | -4 | A | 11 | A | -0.9 | -2.5 | 6.2 Yes | Med |
| ORF YDR070C | 17 | A | 46 | A | 8 | A | 33 | P | 2.7 | 4.0 | 3.4 | Good |
| ORF YDR111C | 84 | P | 227 | P | 56 | P | 214 | P | 2.7 | 3.8 | 3.3 | Excl |
| ORF YDR223W | -5 | A | 9 | A | -14 | A | 8 | A | -1.7 | -0.6 | 3.6 Yes | Med |

Figure 17B

| ORF | | | | | | | | |
|---|---|---|---|---|---|---|---|---|
| ORF YDR260C | 105 | P | 222 | P | 92 | P | 207 | P | 2.1 | 2.3 | 2.2 | | Excl |
| ORF YDR476C | 189 | P | 419 | P | 158 | P | 334 | P | 2.2 | 2.1 | 2.2 | | Excl |
| ORF YEL020C | 79 | P | 171 | P | 66 | P | 134 | P | 2.2 | 2.0 | 2.1 | | Excl |
| ORF YEL044W | 415 | P | 1111 | P | 292 | P | 1022 | P | 2.7 | 3.5 | 3.1 | | Excl |
| ORF YEL066W | 153 | P | 318 | P | 124 | P | 352 | P | 2.1 | 2.8 | 2.5 | | Excl |
| ORF YEL073C | -2 | A | 15 | A | -13 | A | 19 | A | -6.4 | -1.5 | 5.0 | Yes | Med |
| ORF YEL074W (_f) | -28 | A | 2 | A | -15 | A | 14 | A | -0.1 | -1.0 | 5.9 | Yes | Med |
| ORF YER039C | 17 | A | 49 | A | 4 | A | 35 | P | 3.0 | 9.3 | 6.1 | | Good |
| ORF YER042W | 512 | P | 1624 | P | 377 | P | 1317 | P | 3.2 | 3.5 | 3.3 | | Excl |
| ORF YER081W | 101 | P | 3357 | P | 116 | P | 3254 | P | 33.4 | 28.1 | 30.7 | | Excl |
| ORF YER092W | 167 | P | 349 | P | 162 | P | 374 | P | 2.1 | 2.3 | 2.2 | | Excl |
| ORF YFL015C | -22 | A | 18 | A | -24 | A | 2 | A | -0.8 | -0.1 | 6.5 | Yes | Med |
| ORF YFL030W | 25 | A | 83 | P | 28 | A | 113 | P | 3.4 | 4.0 | 3.7 | | Good |
| ORF YFL043C | 114 | P | 245 | P | 97 | P | 254 | P | 2.2 | 2.6 | 2.4 | | Excl |
| ORF YFL052W | -2 | A | 11 | A | -26 | A | 15 | P | -4.7 | -0.6 | 5.4 | Yes | Med |
| ORF YFL068W (_f) | -45 | A | 3 | A | -7 | A | 21 | A | -0.1 | -3.1 | 7.6 | Yes | Med |
| ORF YGL007W | -42 | A | -4 | A | -17 | A | 14 | P | 0.1 | -0.8 | 6.9 | Yes | Med |
| ORF YGL039W | 226 | P | 461 | P | 259 | P | 567 | P | 2.0 | 2.2 | 2.1 | | Excl |
| ORF YGL053W | 42 | P | 89 | P | 41 | A | 105 | P | 2.1 | 2.6 | 2.3 | | Good |
| ORF YGL117W | 103 | P | 244 | P | 92 | P | 188 | P | 2.4 | 2.0 | 2.2 | | Excl |
| ORF YGL125W | 66 | P | 297 | P | 90 | P | 302 | P | 4.5 | 3.4 | 3.9 | | Excl |
| ORF YGL170C | 0 | A | 10 | A | -22 | A | -8 | A | #DIV/0! | 0.4 | 2.4 | Yes | Med |
| ORF YGL184C | 20 | P | 99 | P | 11 | A | 114 | P | 5.0 | 10.0 | 7.5 | | Good |
| ORF YGL185C | 74 | P | 174 | P | 62 | P | 140 | P | 2.3 | 2.3 | 2.3 | | Excl |
| ORF YGR043C | 32 | A | 109 | P | 39 | P | 81 | P | 3.5 | 2.1 | 2.8 | | Good |
| ORF YGR050C | 56 | P | 164 | P | 12 | A | 168 | P | 2.9 | 13.6 | 8.3 | | Good |
| ORF YGR052W | 18 | A | 73 | P | 15 | P | 57 | P | 4.0 | 3.8 | 3.9 | | Good |
| ORF YGR107W | -6 | A | 16 | A | 2 | A | 16 | P | -2.9 | 8.5 | 6.4 | Yes | Med |
| ORF YGR110W | 60 | P | 218 | P | 41 | P | 182 | P | 3.6 | 4.5 | 4.0 | | Excl |
| ORF YGR136W | 328 | P | 677 | P | 310 | P | 619 | P | 2.1 | 2.0 | 2.0 | | Excl |
| ORF YGR142W | 58 | P | 339 | P | 43 | P | 249 | P | 5.9 | 5.8 | 5.8 | | Excl |
| ORF YGR146C | 156 | P | 394 | P | 165 | P | 384 | P | 2.5 | 2.3 | 2.4 | | Excl |
| ORF YGR161C | 59 | P | 698 | P | 55 | P | 545 | P | 11.9 | 9.9 | 10.9 | | Excl |
| ORF YGR221C | -24 | A | 2 | A | -9 | A | 18 | A | -0.1 | -2.1 | 5.2 | Yes | Med |
| ORF YGR243W | 15 | A | 274 | P | 50 | A | 204 | P | 18.2 | 4.0 | 11.1 | | Good |
| ORF YHL024W | 28 | P | 70 | P | 4 | P | 91 | P | 2.5 | 23.9 | 13.2 | | Excl |

Figure 17C

| | | | | | | | | |
|---|---|---|---|---|---|---|---|---|
| ORF YHR112C | 154 | P | 403 | P | 167 | P | 602 | P | 2.6 | 3.6 | 3.1 | | Excl |
| ORF YHR138C | 192 | P | 726 | P | 178 | P | 585 | P | 3.8 | 3.3 | 3.5 | | Excl |
| ORF YHR214W-A | 82 | P | 279 | P | 90 | P | 301 | P | 3.4 | 3.3 | 3.4 | | Excl |
| ORF YIL015C-A | 75 | P | 162 | P | 62 | P | 211 | P | 2.2 | 3.4 | 2.8 | | Excl |
| ORF YIL050W | 128 | P | 330 | P | 123 | P | 323 | P | 2.6 | 2.6 | 2.6 | | Excl |
| ORF YIL055C | 28 | P | 61 | P | 22 | M | 76 | P | 2.2 | 3.5 | 2.8 | | Good |
| ORF YIL073C | 17 | P | 55 | P | 10 | A | 43 | P | 3.2 | 4.2 | 3.7 | | Good |
| ORF YIL117C | 214 | P | 552 | P | 205 | P | 629 | P | 2.6 | 3.1 | 2.8 | | Excl |
| ORF YIL153W | -7 | A | 38 | P | 5 | M | 66 | P | -5.4 | 13.9 | 11.5 | Yes | Med |
| ORF YIR033W | 106 | P | 216 | P | 111 | P | 251 | P | 2.0 | 2.3 | 2.1 | | Excl |
| ORF YIR039C | 40 | P | 89 | P | 32 | P | 83 | P | 2.2 | 2.6 | 2.4 | | Excl |
| ORF YIR042C | 5 | A | 35 | A | -6 | A | 19 | P | 7.4 | -3.2 | 6.1 | Yes | Med |
| ORF YJL066C | 14 | M | 47 | A | 34 | P | 78 | P | 3.3 | 2.3 | 2.8 | | Good |
| ORF YJL107C | 16 | A | 98 | P | 20 | P | 91 | P | 6.1 | 4.5 | 5.3 | | Good |
| ORF YJL108C | 87 | P | 279 | P | 95 | P | 244 | P | 3.2 | 2.6 | 2.9 | | Excl |
| ORF YJL113W exon | 5 | A | 16 | A | -8 | A | 10 | A | 3.3 | -1.4 | 3.4 | Yes | Med |
| ORF YJL144W | -3 | A | 186 | P | 7 | A | 116 | P | -66.5 | 17.3 | 27.6 | Yes | Med |
| ORF YJL163C | 34 | P | 72 | A | 15 | M | 58 | P | 2.1 | 3.8 | 3.0 | | Good |
| ORF YJR023C | -6 | A | 7 | A | -18 | A | -4 | A | -1.1 | 0.2 | 2.8 | Yes | Med |
| ORF YJR078W | 45 | P | 142 | P | 25 | P | 106 | P | 3.2 | 4.2 | 3.7 | | Excl |
| ORF YJR079W exon | 43 | P | 302 | P | 30 | P | 244 | P | 7.1 | 8.1 | 7.6 | | Excl |
| ORF YJR106W | 21 | P | 43 | P | 6 | A | 38 | P | 2.1 | 6.5 | 4.3 | | Good |
| ORF YKL031W | -62 | A | -41 | A | -43 | A | -28 | A | 0.7 | 0.7 | 3.6 | Yes | Med |
| ORF YKL107W | 11 | P | 32 | P | 9 | A | 23 | P | 3.0 | 2.5 | 2.7 | | Good |
| ORF YKL151C | 290 | P | 984 | P | 177 | P | 755 | P | 3.4 | 4.3 | 3.8 | | Excl |
| ORF YKL208W | 36 | P | 92 | P | 40 | P | 97 | P | 2.6 | 2.4 | 2.5 | | Excl |
| ORF YKL218C | 88 | P | 181 | P | 68 | P | 140 | P | 2.1 | 2.4 | 2.1 | | Excl |
| ORF YKR046C | 740 | P | 2030 | P | 479 | P | 1956 | P | 2.7 | 4.1 | 3.4 | | Excl |
| ORF YLL061W | 166 | P | 346 | P | 122 | P | 367 | P | 2.1 | 3.0 | 2.6 | | Excl |
| ORF YLR031W | 2 | A | 17 | A | -5 | A | 12 | A | 8.1 | -2.4 | 5.8 | Yes | Med |
| ORF YLR154C | 168 | P | 396 | P | 147 | P | 384 | P | 2.4 | 2.6 | 2.5 | | Excl |
| ORF YLR187W | 0 | A | 24 | A | 11 | A | 36 | P | #DIV/0! | 3.3 | 4.1 | Yes | Med |

Figure 17D

| ORF | | | | | | | | | |
|---|---|---|---|---|---|---|---|---|---|
| ORF YLR231C | 268 | P | 593 | P | 185 | P | 538 | P | 2.2 | 2.9 | 2.6 | Excl |
| ORF YLR260W | 117 | P | 237 | P | 102 | P | 214 | P | 2.0 | 2.1 | 2.1 | Excl |
| ORF YLR311C | 1 | A | 14 | A | 1 | A | 29 | P | 20.6 | 34.6 | 27.6 | Good |
| ORF YLR312C | 5 | A | 57 | A | 13 | A | 77 | P | 11.6 | 6.1 | 8.8 | Good |
| ORF YLR327C | 68 | P | 196 | P | 27 | P | 221 | P | 2.9 | 8.2 | 5.6 | Excl |
| ORF YLR331C | 4 | A | 17 | A | 0 | A | 14 | P | 4.9 | #DIV/0! | 3.8 | Yes | Med |
| ORF YLR348C | 115 | P | 258 | P | 110 | P | 270 | P | 2.2 | 2.5 | 2.3 | Excl |
| ORF YLR350W | 482 | P | 1273 | P | 466 | P | 1047 | P | 2.6 | 2.2 | 2.4 | Excl |
| ORF YLR414C | 293 | P | 942 | P | 256 | P | 789 | P | 3.2 | 3.1 | 3.1 | Excl |
| ORF YLR415C | 8 | A | 44 | A | 5 | A | 21 | A | 5.7 | 4.2 | 5.0 | Good |
| ORF YLR417W | 94 | P | 256 | P | 81 | P | 218 | P | 2.7 | 2.7 | 2.7 | Excl |
| ORF YMR017W | 7 | A | 38 | P | 1 | A | 26 | P | 5.4 | 30.6 | 18.0 | Good |
| ORF YMR034C | 44 | P | 108 | P | 22 | P | 94 | P | 2.4 | 4.3 | 3.4 | Excl |
| ORF YMR040W | 36 | P | 111 | P | 18 | P | 108 | P | 3.1 | 5.8 | 4.5 | Excl |
| ORF YMR062C | 165 | P | 417 | P | 140 | P | 331 | P | 2.5 | 2.4 | 2.4 | Excl |
| ORF YMR110C | 137 | P | 319 | P | 141 | P | 336 | P | 2.3 | 2.4 | 2.4 | Excl |
| ORF YMR184W | 261 | P | 664 | P | 248 | P | 596 | P | 2.5 | 2.4 | 2.5 | Excl |
| ORF YMR191W | 137 | P | 336 | P | 96 | P | 295 | P | 2.4 | 3.1 | 2.8 | Excl |
| ORF YMR244C-A | 157 | P | 435 | P | 115 | P | 466 | P | 2.8 | 4.0 | 3.4 | Excl |
| ORF YMR245W | 7 | M | 41 | A | 0 | A | 36 | P | 5.8 | #DIV/0! | 6.5 | Yes | Med |
| ORF YMR316W | 91 | P | 258 | P | 58 | P | 189 | P | 2.8 | 3.2 | 3.0 | Excl |
| ORF YNL092W | 8 | P | 45 | P | 16 | A | 35 | P | 5.8 | 2.2 | 4.0 | Good |
| ORF YNL193W | 77 | P | 171 | P | 58 | P | 124 | P | 2.2 | 2.1 | 2.2 | Excl |
| ORF YNL194C | -21 | A | 0 | A | -16 | A | 16 | A | 0.0 | -1.0 | 5.2 | Yes | Med |
| ORF YNL332W (_f) | 64 | P | 219 | P | 42 | P | 129 | P | 3.4 | 3.1 | 3.3 | Excl |
| ORF YNL336W (_r) | 24 | P | 132 | P | 37 | P | 93 | P | 5.5 | 2.5 | 4.0 | Excl |
| ORF YNR066C | -17 | A | 15 | A | -16 | A | 19 | A | -0.9 | -1.2 | 6.6 | Yes | Med |
| ORF YOL032W | 128 | P | 268 | P | 72 | P | 193 | P | 2.1 | 2.7 | 2.4 | Excl |
| ORF YOL048C | 144 | P | 306 | P | 98 | P | 235 | P | 2.1 | 2.4 | 2.3 | Excl |
| ORF YOL101C | 135 | P | 357 | P | 103 | P | 269 | P | 2.6 | 2.6 | 2.6 | Excl |
| ORF YOL113W | 90 | P | 194 | P | 74 | P | 193 | P | 2.2 | 2.6 | 2.4 | Excl |
| ORF YOR220W | 148 | P | 455 | P | 90 | P | 351 | P | 3.1 | 3.9 | 3.5 | Excl |
| ORF YOR222W | 410 | P | 888 | P | 243 | P | 853 | P | 2.2 | 3.5 | 2.8 | Excl |
| ORF YOR227W | 117 | P | 276 | P | 58 | P | 260 | P | 2.4 | 4.5 | 3.4 | Excl |
| ORF YOR289W | 122 | P | 400 | P | 78 | P | 240 | P | 3.3 | 3.1 | 3.2 | Excl |
| ORF YOR318C exon | 12 | P | 58 | P | 18 | A | 66 | P | 5.0 | 3.6 | 4.3 | Good |
| ORF YOR325W | -16 | A | 35 | A | -15 | A | -3 | A | -2.1 | 0.2 | 6.3 | Yes | Med |

Figure 17E

| | -2 | | 40 | | 0 | | 42 | | -17.0 | #DIV/0! | 8.4 | Yes | |
|---|---|---|---|---|---|---|---|---|---|---|---|---|---|
| ORF YPL025C | | A | | A | | A | | P | | 3.3 | 8.4 | Yes | Med |
| ORF YPL222W | 29 | P | 115 | P | 39 | P | 129 | P | 4.0 | 3.3 | 3.7 | | Excl |
| ORF YPL250C | 224 | P | 607 | P | 172 | P | 612 | P | 2.7 | 3.5 | 3.1 | | Excl |
| ORF YPR013C | 26 | P | 75 | P | 33 | A | 97 | P | 2.8 | 2.9 | 2.9 | | Good |
| ORF YPR077C (_j) | 2 | A | 41 | M | 10 | A | 26 | P | 17.4 | 2.7 | 10.1 | | Good |
| ORF YPR092W | 13 | M | 28 | P | -10 | A | 9 | P | 2.1 | -1.0 | 3.0 | Yes | Med |
| ORF YPR130C | 16 | P | 37 | A | 2 | A | 16 | P | 2.4 | 8.1 | 5.2 | | Good |
| ORF YPR151C | 63 | P | 126 | P | 16 | A | 136 | P | 2.0 | 8.8 | 5.4 | | Good |
| PDI1 (YCL043C) | 1624 | P | 3397 | P | 1178 | P | 2357 | P | 2.1 | 2.0 | 2.0 | | Excl |
| PES4 (YFR023W) | 8 | A | 19 | A | -3 | A | 11 | A | 2.4 | -4.0 | 2.6 | Yes | Med |
| POS5 (YPL188W) | 118 | P | 258 | P | 90 | P | 253 | P | 2.2 | 2.8 | 2.5 | | Excl |
| PRB1 (YEL060C) | 338 | P | 779 | P | 234 | P | 682 | P | 2.3 | 2.9 | 2.6 | | Excl |
| RIB1 (YBL033C) | 291 | P | 738 | P | 302 | P | 634 | P | 2.5 | 2.1 | 2.3 | | Excl |
| RTA1 (YGR213C) | -1 | A | 157 | P | -19 | A | 83 | P | -198.7 | -4.4 | 26.0 | Yes | Med |
| SEO1 (YAL067C) | 12 | P | 47 | P | 7 | M | 27 | P | 4.0 | 3.6 | 3.8 | | Good |
| SHR5 (YOL110W) | 92 | P | 258 | P | 92 | P | 262 | P | 2.8 | 2.8 | 2.8 | | Excl |
| SIP2 (YGL208W) | 42 | P | 92 | P | 28 | P | 104 | P | 2.2 | 3.6 | 2.9 | | Excl |
| SNC1 (YAL030W) et | 116 | P | 339 | P | 128 | P | 264 | P | 2.9 | 2.1 | 2.5 | | Excl |
| SNF2 (YOR290C) | 251 | P | 642 | P | 198 | P | 643 | P | 2.6 | 3.3 | 2.9 | | Excl |
| SOL4 (YGR248W) | 62 | P | 125 | P | 25 | P | 135 | P | 2.0 | 5.5 | 3.8 | | Good |
| SON1 (YDL020C) | 243 | P | 519 | P | 202 | P | 458 | P | 2.1 | 2.3 | 2.2 | | Excl |
| SPO1 (YNL012W) | 12 | P | 29 | A | 11 | A | 22 | P | 2.3 | 2.1 | 2.2 | | Good |
| SPO11 (YHL022C) | 6 | A | 26 | P | 1 | A | 11 | A | 4.8 | 11.9 | 8.3 | | Good |
| SSE2 (YBR169C) | 103 | P | 256 | P | 70 | P | 192 | P | 2.5 | 2.7 | 2.6 | | Excl |
| STF2 (YGR008C) | 734 | P | 1933 | P | 648 | P | 1475 | P | 2.6 | 2.3 | 2.5 | | Excl |
| THI11 (YJR156C) ( | 95 | P | 247 | P | 60 | P | 160 | P | 2.6 | 2.6 | 2.6 | | Excl |
| THI5 (YFL058W) ( | 43 | P | 206 | P | 62 | P | 154 | P | 4.8 | 2.5 | 3.7 | | Excl |
| TSL1 (YML100W) | 329 | P | 763 | P | 252 | P | 819 | P | 2.3 | 3.3 | 2.8 | | Excl |
| UBC5 (YDR059C) ex | 86 | P | 194 | P | 31 | P | 185 | P | 2.3 | 6.1 | 4.2 | | Excl |
| UBC5 (YDR059C) ex | 140 | P | 353 | P | 108 | P | 319 | P | 2.5 | 3.0 | 2.7 | | Excl |
| UBI4 (YLL039C) | 737 | P | 1760 | P | 619 | P | 1753 | P | 2.4 | 2.8 | 2.6 | | Excl |
| UFD1 (YGR048W) | 110 | P | 224 | P | 91 | P | 184 | P | 2.0 | 2.0 | 2.0 | | Excl |
| URA3 (YEL021W) | 1051 | P | 7170 | P | 678 | P | 6216 | P | 6.8 | 9.2 | 8.0 | | Excl |
| YAP3 (YLR120C) | 267 | P | 783 | P | 250 | P | 586 | P | 2.9 | 2.3 | 2.6 | | Excl |

Figure 17F

| Swi2 Up | | | | | | | | | | |
|---|---|---|---|---|---|---|---|---|---|---|
| Gene Expression Results for FH1998040601A | | | | | | | | | | |
| | WT1val | WT1 | MT1val | MT1 | WT2val | WT2 | MT2val | MT2c | MT1/WT1 | MT2/WT2 | Ave | Corrected? | Confidence |
| ORF YER081W | 101 | P | 3357 | P | 116 | P | 3254 | P | 33.4 | 28.1 | 30.7 | | Excl |
| ORF YLR311C | 1 | A | 14 | A | 1 | A | 29 | P | 20.6 | 34.6 | 27.6 | | Good |
| ORF YJL144W | -3 | A | 186 | P | 7 | A | 116 | P | -66.5 | 17.3 | 27.6 | Yes | Med |
| RTA1 (YGR213C) | -1 | A | 157 | P | -19 | A | 83 | P | -198.7 | -4.4 | 26.0 | Yes | Med |
| MET28 (YIR017C) | -12 | A | 81 | P | 6 | A | 118 | P | -6.8 | 20.8 | 19.6 | Yes | Med |
| ORF YMR017W | 7 | A | 38 | P | 1 | A | 26 | P | 5.4 | 30.6 | 18.0 | | Good |
| ORF YHL024W | 28 | P | 70 | P | 4 | P | 91 | P | 2.5 | 23.9 | 13.2 | | Excl |
| ORF YIL153W | -7 | A | 38 | P | 5 | M | 66 | P | -5.4 | 13.9 | 11.5 | Yes | Med |
| ORF YGR243W | 15 | A | 274 | P | 50 | A | 204 | P | 18.2 | 4.0 | 11.1 | | Good |
| ORF YGR161C | 59 | P | 698 | P | 55 | P | 545 | P | 11.9 | 9.9 | 10.9 | | Excl |
| ORF YPR077C (_i) | 2 | A | 41 | M | 10 | A | 26 | P | 17.4 | 2.7 | 10.1 | | Good |
| GAL3 (YDR009W) | 12 | A | 24 | A | 1 | A | 13 | P | 2.0 | 17.4 | 9.7 | | Good |
| ORF YLR312C | 5 | A | 57 | A | 13 | A | 77 | P | 11.6 | 6.1 | 8.8 | | Good |
| ORF YPL025C | -2 | A | 40 | A | 0 | A | 42 | P | -17.0 | #DIV/0! | 8.4 | Yes | Med |
| SPO11 (YHL022C) | 6 | A | 26 | P | 1 | A | 11 | A | 4.8 | 11.9 | 8.3 | | Good |
| ORF YGR050C | 56 | P | 164 | P | 12 | A | 168 | P | 2.9 | 13.6 | 8.3 | | Good |
| URA3 (YEL021W) | 1051 | P | 7170 | P | 678 | P | 6216 | P | 6.8 | 9.2 | 8.0 | | Excl |
| ORF YFL068W (_f) | -45 | A | 3 | A | -7 | A | 21 | A | -0.1 | -3.1 | 7.6 | Yes | Med |
| ORF YJR079W exon | 43 | P | 302 | P | 30 | P | 244 | P | 7.1 | 8.1 | 7.6 | | Excl |
| ORF YGL184C | 20 | P | 99 | P | 11 | A | 114 | P | 5.0 | 10.0 | 7.5 | | Good |
| ORF YGL007W | -42 | A | -4 | A | -17 | A | 14 | P | 0.1 | -0.8 | 6.9 | Yes | Med |
| ORF YNR066C | -17 | A | 15 | A | -16 | A | 19 | A | -0.9 | -1.2 | 6.6 | Yes | Med |
| ORF YFL015C | -22 | A | 18 | A | -24 | A | 2 | A | -0.8 | -0.1 | 6.5 | Yes | Med |
| ORF YMR245W | 7 | M | 41 | A | 0 | A | 36 | P | 5.8 | #DIV/0! | 6.5 | Yes | Med |
| ORF YGR107W | -6 | A | 16 | A | 2 | A | 16 | P | -2.9 | 8.5 | 6.4 | Yes | Med |
| ORF YOR325W | -16 | A | 35 | A | -15 | A | -3 | A | -2.1 | 0.2 | 6.3 | Yes | Med |
| ORF YDR010C | -25 | A | 21 | A | -4 | A | 11 | A | -0.9 | -2.5 | 6.2 | Yes | Med |
| ORF YER039C | 17 | A | 49 | A | 4 | A | 35 | P | 3.0 | 9.3 | 6.1 | | Med |
| HXT5 (YHR096C) | 21 | M | 138 | P | 16 | A | 89 | P | 6.7 | 5.5 | 6.1 | | Good |
| ORF YIR042C | 5 | A | 35 | A | -6 | A | 19 | P | 7.4 | -3.2 | 6.1 | Yes | Med |
| ORF YEL074W (_f) | -28 | A | 2 | A | -15 | A | -14 | A | -0.1 | -1.0 | 5.9 | Yes | Med |
| ORF YGR142W | 58 | P | 339 | P | 43 | P | 249 | P | 5.9 | 5.8 | 5.8 | | Excl |

Figure 18A

| | 12 | | 31 | | 3 | | 26 | | 2.6 | 9.0 | 5.8 | | Good |
|---|---|---|---|---|---|---|---|---|---|---|---|---|---|
| BAR1 (YIL015W) | 12 | A | 31 | P | 3 | A | 26 | P | 2.6 | 9.0 | 5.8 | | Good |
| ORF YLR031W | 2 | A | 17 | A | -5 | A | 12 | A | 8.1 | -2.4 | 5.8 | Yes | Med |
| AMS1 (YGL156W) | 43 | P | 263 | P | 39 | P | 195 | P | 6.1 | 5.0 | 5.6 | | Excl |
| ORF YLR327C | 68 | P | 196 | P | 27 | P | 221 | P | 2.9 | 8.2 | 5.6 | | Excl |
| ORF YFL052W | -2 | A | 11 | A | -26 | A | 15 | P | -4.7 | -0.6 | 5.4 | Yes | Med |
| ORF YPR151C | 63 | P | 126 | P | 16 | A | 136 | P | 2.0 | 8.8 | 5.4 | | Good |
| GPM2 (YDL021W) | 15 | A | 51 | A | 6 | A | 44 | P | 3.4 | 7.4 | 5.4 | | Good |
| MAL1 (YGR292W) | 0 | A | 30 | P | 7 | A | 32 | P | #DIV/0! | 4.8 | 5.4 | Yes | Med |
| ORF YJL107C | 16 | A | 98 | P | 20 | P | 91 | P | 6.1 | 4.5 | 5.3 | | Good |
| ORF YPR130C | 16 | P | 37 | A | 2 | A | 16 | A | 2.4 | 8.1 | 5.2 | | Good |
| ORF YNL194C | -21 | A | 0 | A | -16 | A | 16 | A | 0.0 | -1.0 | 5.2 | Yes | Med |
| ORF YGR221C | -24 | A | 2 | A | -9 | A | 18 | A | -0.1 | -2.1 | 5.2 | Yes | Med |
| AAC1 (YMR056C) | 96 | P | 375 | P | 70 | P | 437 | P | 3.9 | 6.3 | 5.1 | | Excl |
| ORF YEL073C | -2 | A | 15 | A | -13 | A | 19 | A | -6.4 | -1.5 | 5.0 | Yes | Med |
| ORF YLR415C | 8 | A | 44 | A | 5 | A | 21 | A | 5.7 | 4.2 | 5.0 | | Good |
| LAP4 (YKL103C) | 99 | P | 321 | P | 70 | P | 438 | P | 3.2 | 6.3 | 4.8 | | Excl |
| ORF YBL078C | 91 | P | 468 | P | 83 | P | 357 | P | 5.1 | 4.3 | 4.7 | | Excl |
| ORF YAR068W (_f) | 36 | P | 198 | P | 48 | P | 183 | P | 5.5 | 3.8 | 4.7 | | Excl |
| ORF YBL012C | 4 | A | 27 | A | -4 | A | 8 | A | 6.8 | -2.1 | 4.6 | Yes | Med |
| ORF YDL057W | 32 | P | 76 | P | 13 | A | 85 | P | 2.4 | 6.7 | 4.5 | | Good |
| ORF YMR040W | 36 | P | 111 | P | 18 | P | 108 | P | 3.1 | 5.8 | 4.5 | | Excl |
| ORF YAR043C | -7 | A | 14 | A | -7 | A | 16 | A | -1.9 | -2.1 | 4.4 | Yes | Med |
| MET8 (YBR213W) | 39 | P | 96 | P | 15 | A | 93 | P | 2.5 | 6.2 | 4.3 | | Good |
| ORF YJR106W | 21 | P | 43 | P | 6 | A | 38 | P | 2.1 | 6.5 | 4.3 | | Good |
| ORF YOR318C exon | 12 | P | 58 | P | 18 | A | 66 | P | 5.0 | 3.6 | 4.3 | | Good |
| UBC5 (YDR059C) ex | 86 | P | 194 | P | 31 | P | 185 | P | 2.3 | 6.1 | 4.2 | | Excl |
| ORF YDL214C | 25 | A | 91 | A | 16 | A | 73 | P | 3.6 | 4.7 | 4.2 | | Good |
| CAT8 (YMR280C) | 17 | A | 75 | P | 9 | A | 34 | P | 4.4 | 3.8 | 4.1 | | Good |
| ORF YLR187W | 0 | A | 24 | A | 11 | A | 36 | P | #DIV/0! | 3.3 | 4.1 | Yes | Med |
| ORF YGR110W | 60 | P | 218 | P | 41 | P | 182 | P | 3.6 | 4.5 | 4.0 | | Excl |
| ORF YNL092W | 8 | P | 45 | P | 16 | A | 35 | P | 5.8 | 2.2 | 4.0 | | Good |
| GUT2 (YIL155C) | 97 | P | 256 | P | 60 | P | 322 | P | 2.6 | 5.4 | 4.0 | | Excl |

Figure 18B

| ORF | | | | | | | |
|---|---|---|---|---|---|---|---|
| ORF YNL336W (_r_) | 24 P | 132 P | 37 P | 93 P | 5.5 | 2.5 | 4.0 | Excl |
| HSP26 (YBR072W) | 33 P | 169 P | 38 P | 109 P | 5.1 | 2.9 | 4.0 | Excl |
| ORF YAR052C (_i_) | -78 A | -51 A | -81 A | -68 A | 0.7 | 0.8 | 4.0 Yes | Med |
| ORF YGL125W | 66 P | 297 P | 90 P | 302 P | 4.5 | 3.4 | 3.9 | Excl |
| ORF YGR052W | 18 A | 73 P | 15 P | 57 P | 4.0 | 3.8 | 3.9 | Good |
| ORF YKL151C | 290 P | 984 P | 177 P | 755 P | 3.4 | 4.3 | 3.8 | Excl |
| MSH4 (YFL003C) | -2 A | 23 P | -4 A | 9 A | -9.7 | -2.3 | 3.8 Yes | Med |
| ORF YLR331C | 4 A | 17 A | 0 A | 14 P | 4.9 | #DIV/0! | 3.8 Yes | Med |
| SEO1 (YAL067C) | 12 P | 47 P | 7 M | 27 P | 4.0 | 3.6 | 3.8 | Good |
| SOL4 (YGR248W) | 62 P | 125 P | 25 P | 135 P | 2.0 | 5.5 | 3.8 | Excl |
| ORF YBR070C | 119 P | 474 P | 124 P | 427 P | 4.0 | 3.4 | 3.7 | Excl |
| ORF YJR078W | 45 P | 142 P | 25 P | 106 P | 3.2 | 4.2 | 3.7 | Excl |
| HSP42 (YDR171W) | 241 P | 808 P | 164 P | 660 P | 3.4 | 4.0 | 3.7 | Excl |
| ORF YPL222W | 29 P | 115 P | 39 P | 129 P | 4.0 | 3.3 | 3.7 | Excl |
| ORF YFL030W | 25 A | 83 P | 28 A | 113 P | 3.4 | 4.0 | 3.7 | Good |
| ORF YIL073C | 17 P | 55 P | 10 A | 43 P | 3.2 | 4.2 | 3.7 | Good |
| THI5 (YFL058W) (_) | 43 P | 206 P | 62 P | 154 P | 4.8 | 2.5 | 3.7 | Excl |
| ORF YDL199C | 4 A | 15 A | 9 A | 33 P | 3.6 | 3.7 | 3.7 | Good |
| ORF YKL031W | -62 A | -41 A | -43 A | -28 A | 0.7 | 0.7 | 3.6 Yes | Med |
| GDH3 (YAL062W) | 22 P | 89 P | 23 P | 73 P | 4.0 | 3.2 | 3.6 | Excl |
| ORF YDR223W | -5 A | 9 A | -14 A | 8 A | -1.7 | -0.6 | 3.6 Yes | Med |
| AHT1 (YHR093W) | -40 A | -24 A | -27 A | -7 A | 0.6 | 0.3 | 3.6 Yes | Med |
| ORF YHR138C | 192 P | 726 P | 178 P | 585 P | 3.8 | 3.3 | 3.5 | Excl |
| ORF YOR220W | 148 P | 455 P | 90 P | 351 P | 3.1 | 3.9 | 3.5 | Excl |
| ORF YBR178W | -1 A | 20 A | 0 A | 13 A | -20.3 | #DIV/0! | 3.4 Yes | Med |
| ORF YJL113W exon | 5 A | 16 A | -8 A | 10 A | 3.3 | -1.4 | 3.4 Yes | Med |
| ORF YOR227W | 117 P | 276 P | 58 P | 260 P | 2.4 | 4.5 | 3.4 | Excl |
| ORF YKR046C | 740 P | 2030 P | 479 P | 1956 P | 2.7 | 4.1 | 3.4 | Excl |
| ORF YMR244C-A | 157 P | 435 P | 115 P | 466 P | 2.8 | 4.0 | 3.4 | Excl |
| ARG5,6" (YER069W) | 404 P | 1226 P | 327 P | 1224 P | 3.0 | 3.7 | 3.4 | Excl |
| ORF YMR034C | 44 P | 108 P | 22 P | 94 P | 2.4 | 4.3 | 3.4 | Excl |
| ORF YHR214W-A (_) | 82 P | 279 P | 90 P | 301 P | 3.4 | 3.3 | 3.4 | Excl |
| ORF YDR070C | 17 A | 46 A | 81 A | 33 P | 2.7 | 4.0 | 3.4 | Good |
| ORF YCL041C | 12 A | 45 A | 17 P | 51 P | 3.7 | 3.0 | 3.3 | Good |
| ORF YBL044W | -2 A | 19 A | -6 A | 6 A | -9.7 | -1.0 | 3.3 Yes | Med |

Figure 18C

| | 22 | | 95 | | 28 | | 65 | | 4.3 | 2.4 | 3.3 | | |
|---|---|---|---|---|---|---|---|---|---|---|---|---|---|
| ORF YAL037W | 22 | P | 95 | P | 28 | P | 65 | P | 4.3 | 2.4 | 3.3 | | Excl |
| ORF YER042W | 512 | P | 1624 | P | 377 | P | 1317 | P | 3.2 | 3.5 | 3.3 | | Excl |
| ORF YBR224W | -45 | A | -34 | A | -25 | A | -3 | A | 0.8 | 0.1 | 3.3 | Yes | Med |
| ORF YNL332W (_f) | 64 | P | 219 | P | 42 | P | 129 | P | 3.4 | 3.1 | 3.3 | | Excl |
| ORF YDR111C | 84 | P | 227 | P | 56 | P | 214 | P | 2.7 | 3.8 | 3.3 | | Excl |
| ORF YOR289W | 122 | P | 400 | P | 78 | P | 240 | P | 3.3 | 3.1 | 3.2 | | Excl |
| ORF YLR414C | 293 | P | 942 | P | 256 | P | 789 | P | 3.2 | 3.1 | 3.1 | | Excl |
| ORF YPL250C | 224 | P | 607 | P | 172 | P | 612 | P | 2.7 | 3.5 | 3.1 | | Excl |
| MET2 (YNL277W) | 154 | P | 340 | P | 82 | P | 333 | P | 2.2 | 4.0 | 3.1 | | Excl |
| ORF YHR112C | 154 | P | 403 | P | 167 | P | 602 | P | 2.6 | 3.6 | 3.1 | | Excl |
| ORF YEL044W | 415 | P | 1111 | P | 292 | P | 1022 | P | 2.7 | 3.5 | 3.1 | | Excl |
| ARE2 (YNR019W) | 242 | P | 652 | P | 157 | P | 542 | P | 2.7 | 3.5 | 3.1 | | Excl |
| ORF YBR005W | 56 | P | 223 | P | 63 | P | 135 | P | 4.0 | 2.1 | 3.1 | | Excl |
| ORF YBR269C | 160 | P | 406 | P | 102 | P | 364 | P | 2.5 | 3.6 | 3.0 | | Excl |
| ORF YMR316W | 91 | P | 258 | P | 58 | P | 189 | P | 2.8 | 3.2 | 3.0 | | Excl |
| ORF YJL163C | 34 | P | 72 | A | 15 | M | 58 | P | 2.1 | 3.8 | 3.0 | | Good |
| ORF YPR092W | 13 | M | 28 | P | -10 | A | 9 | P | 2.1 | -1.0 | 3.0 | Yes | Med |
| SIP2 (YGL208W) | 42 | P | 92 | P | 28 | P | 104 | P | 2.2 | 3.6 | 2.9 | | Excl |
| SNF2 (YOR290C) | 251 | P | 642 | P | 198 | P | 643 | P | 2.6 | 3.3 | 2.9 | | Excl |
| ORF YJL108C | 87 | P | 279 | P | 95 | P | 244 | P | 3.2 | 2.6 | 2.9 | | Excl |
| ORF YPR013C | 26 | P | 75 | P | 33 | A | 97 | P | 2.8 | 2.9 | 2.9 | | Good |
| ORF YIL055C | 28 | P | 61 | P | 22 | M | 76 | P | 2.2 | 3.5 | 2.8 | | Good |
| FUS1 (YCL027W) | 67 | P | 228 | P | 92 | P | 209 | P | 3.4 | 2.3 | 2.8 | | Excl |
| ORF YOR222W | 410 | P | 888 | P | 243 | P | 853 | P | 2.2 | 3.5 | 2.8 | | Excl |
| ORF YIL117C | 214 | P | 552 | P | 205 | P | 629 | P | 2.6 | 3.1 | 2.8 | | Excl |
| SHR5 (YOL110W) | 92 | P | 258 | P | 92 | P | 262 | P | 2.8 | 2.8 | 2.8 | | Excl |
| ORF YJL066C | 14 | M | 47 | A | 34 | P | 78 | P | 3.3 | 2.3 | 2.8 | | Good |
| ORF YIL015C-A | 75 | P | 162 | P | 62 | P | 211 | P | 2.2 | 3.4 | 2.8 | | Excl |
| TSL1 (YML100W) | 329 | P | 763 | P | 252 | P | 819 | P | 2.3 | 3.3 | 2.8 | | Excl |
| ORF YGR043C | 32 | A | 109 | P | 39 | P | 81 | P | 3.5 | 2.1 | 2.8 | | Good |
| ORF YJR023C | -6 | A | 7 | A | -18 | A | -4 | A | -1.1 | 0.2 | 2.8 | Yes | Med |
| ORF YMR191W | 137 | P | 336 | P | 96 | P | 295 | P | 2.4 | 3.1 | 2.8 | | Excl |
| ORF YKL107W | 11 | P | 32 | P | 9 | A | 23 | P | 3.0 | 2.5 | 2.7 | | Good |

Figure 18D

| | | | | | | | | |
|---|---|---|---|---|---|---|---|---|
| UBC5 (YDR059C) ex | 140 P | 353 P | 108 P | 319 P | 2.5 | 3.0 | 2.7 | Excl |
| ORF YLR417W | 94 P | 256 P | 81 P | 218 P | 2.7 | 2.7 | 2.7 | Excl |
| ORF YBR066C | 69 P | 230 P | 81 P | 168 P | 3.3 | 2.1 | 2.7 | Excl |
| GLK1 (YCL040W) | 1172 P | 2615 P | 802 P | 2523 P | 2.2 | 3.1 | 2.7 | Excl |
| ORF YBR077C | 140 P | 395 P | 134 P | 343 P | 2.8 | 2.5 | 2.7 | Excl |
| ATF1 (YOR377W) | 67 P | 168 P | 57 P | 160 P | 2.5 | 2.8 | 2.6 | Excl |
| YAP3 (YLR120C) | 267 P | 783 P | 250 P | 586 P | 2.9 | 2.3 | 2.6 | Excl |
| ORF YOL101C | 135 P | 357 P | 103 P | 269 P | 2.6 | 2.6 | 2.6 | Excl |
| PES4 (YFR023W) | 8 A | 19 A | -3 A | 11 A | 2.4 | -4.0 | 2.6 Yes | Med |
| THI11 (YJR156C) | 95 P | 247 P | 60 P | 160 P | 2.6 | 2.6 | 2.6 | Excl |
| HSP78 (YDR258C) | 167 P | 354 P | 119 P | 370 P | 2.1 | 3.1 | 2.6 | Excl |
| PRB1 (YEL060C) | 338 P | 779 P | 234 P | 682 P | 2.3 | 2.9 | 2.6 | Excl |
| SSE2 (YBR169C) | 103 P | 256 P | 70 P | 192 P | 2.5 | 2.7 | 2.6 | Excl |
| UBI4 (YLL039C) | 737 P | 1760 P | 619 P | 1753 P | 2.4 | 2.8 | 2.6 | Excl |
| ORF YDL110C | 171 P | 381 P | 125 P | 373 P | 2.2 | 3.0 | 2.6 | Excl |
| ORF YIL050W | 128 P | 330 P | 123 P | 323 P | 2.6 | 2.6 | 2.6 | Excl |
| ORF YLR231C | 268 P | 593 P | 185 P | 538 P | 2.2 | 2.9 | 2.6 | Excl |
| ORF YLL061W | 166 P | 346 P | 122 P | 367 P | 2.1 | 3.0 | 2.5 | Excl |
| MRS4 (YKR052C) | 108 P | 250 P | 105 P | 289 P | 2.3 | 2.8 | 2.5 | Excl |
| ORF YBR302C (_f) | 417 P | 1220 P | 441 P | 933 P | 2.9 | 2.1 | 2.5 | Excl |
| FUN34 (YNR002C) | 36 P | 85 P | 21 A | 57 P | 2.4 | 2.7 | 2.5 | Good |
| POS5 (YPL188W) | 118 P | 258 P | 90 P | 253 P | 2.2 | 2.8 | 2.5 | Excl |
| SNC1 (YAL030W) e| | 116 P | 339 P | 128 P | 264 P | 2.9 | 2.1 | 2.5 | Excl |
| ORF YLR154C | 168 P | 396 P | 147 P | 384 P | 2.4 | 2.6 | 2.5 | Excl |
| ORF YKL208W | 36 P | 92 P | 40 P | 97 P | 2.6 | 2.4 | 2.5 | Excl |
| ORF YMR184W | 261 P | 664 P | 248 P | 596 P | 2.5 | 2.4 | 2.5 | Excl |
| ORF YEL066W | 153 P | 318 P | 124 P | 352 P | 2.1 | 2.8 | 2.5 | Excl |
| STF2 (YGR008C) | 734 P | 1933 P | 648 P | 1475 P | 2.6 | 2.3 | 2.5 | Excl |
| ORF YMR062C | 165 P | 417 P | 140 P | 331 P | 2.5 | 2.4 | 2.5 | Excl |
| ORF YLR350W | 482 P | 1273 P | 466 P | 1047 P | 2.6 | 2.2 | 2.4 | Excl |
| ARG4 (YHR018C) | 771 P | 1834 P | 765 P | 1906 P | 2.4 | 2.5 | 2.4 | Excl |
| ORF YGR146C | 156 P | 394 P | 165 P | 384 P | 2.5 | 2.3 | 2.4 | Excl |
| ORF YGL170C | 0 A | 10 A | -22 A | -8 A | #DIV/0! | 0.4 | 2.4 Yes | Med |
| ORF YIR039C | 40 P | 89 P | 32 P | 83 P | 2.2 | 2.6 | 2.4 | Excl |
| ORF YOL032W | 128 P | 268 P | 72 P | 193 P | 2.1 | 2.7 | 2.4 | Excl |
| ORF YOL113W | 90 P | 194 P | 74 P | 193 P | 2.2 | 2.6 | 2.4 | Excl |
| ORF YFL043C | 114 P | 245 P | 97 P | 254 P | 2.2 | 2.6 | 2.4 | Excl |
| ORF YMR110C | 137 P | 319 P | 141 P | 336 P | 2.3 | 2.4 | 2.4 | Excl |

Figure 18E

| | | | | | | | | |
|---|---|---|---|---|---|---|---|---|
| ORF YLR348C | 115 | P | 258 | P | 110 | P | 270 | P | 2.2 | 2.5 | 2.3 | Excl |
| ORF YGL053W | 42 | P | 89 | P | 41 | A | 105 | P | 2.1 | 2.6 | 2.3 | Good |
| ORF YBR101C | 252 | P | 656 | P | 246 | P | 511 | P | 2.6 | 2.1 | 2.3 | Excl |
| RIB1 (YBL033C) | 291 | P | 738 | P | 302 | P | 634 | P | 2.5 | 2.1 | 2.3 | Excl |
| ORF YGL185C | 74 | P | 174 | P | 62 | P | 140 | P | 2.3 | 2.3 | 2.3 | Excl |
| ORF YAL053W | 275 | P | 708 | P | 283 | P | 572 | P | 2.6 | 2.0 | 2.3 | Excl |
| MET6 (YER091C) | 1548 | P | 3578 | P | 1596 | P | 3627 | P | 2.3 | 2.3 | 2.3 | Excl |
| MET25 (YLR303W) | 3029 | P | 6554 | P | 2321 | P | 5602 | P | 2.2 | 2.4 | 2.3 | Excl |
| MSP1 (YGR028W) | 122 | P | 304 | P | 133 | P | 276 | P | 2.5 | 2.1 | 2.3 | Excl |
| FBP26 (YJL155C) | 77 | P | 168 | P | 78 | P | 185 | P | 2.2 | 2.4 | 2.3 | Excl |
| ORF YOL048C | 144 | P | 306 | P | 98 | P | 235 | P | 2.1 | 2.4 | 2.3 | Excl |
| GLC3 (YEL011W) | 88 | P | 183 | P | 77 | P | 188 | P | 2.1 | 2.4 | 2.3 | Excl |
| ORF YBR230C exon | 250 | P | 531 | P | 196 | P | 462 | P | 2.1 | 2.4 | 2.2 | Excl |
| CAR1 (YPL111W) | 687 | P | 1500 | P | 550 | P | 1263 | P | 2.2 | 2.3 | 2.2 | Excl |
| ACH1 (YBL015W) | 151 | P | 313 | P | 119 | P | 285 | P | 2.1 | 2.4 | 2.2 | Excl |
| ORF YGL117W | 103 | P | 244 | P | 92 | P | 188 | P | 2.4 | 2.0 | 2.2 | Good |
| SON1 (YDL020C) | 243 | P | 519 | P | 202 | P | 458 | P | 2.1 | 2.3 | 2.2 | Excl |
| ORF YER092W | 167 | P | 349 | P | 162 | P | 374 | P | 2.1 | 2.3 | 2.2 | Excl |
| ORF YDR260C | 105 | P | 222 | P | 92 | P | 207 | P | 2.1 | 2.3 | 2.2 | Excl |
| SPO1 (YNL012W) | 12 | P | 29 | A | 11 | A | 22 | P | 2.3 | 2.1 | 2.2 | Excl |
| ORF YNL193W | 77 | P | 171 | P | 58 | P | 124 | P | 2.2 | 2.1 | 2.2 | Excl |
| ORF YDL173W | 402 | P | 852 | P | 325 | P | 725 | P | 2.1 | 2.2 | 2.2 | Excl |
| ORF YDR476C | 189 | P | 419 | P | 158 | P | 334 | P | 2.2 | 2.1 | 2.1 | Excl |
| ORF YIR033W | 106 | P | 216 | P | 111 | P | 251 | P | 2.0 | 2.3 | 2.1 | Excl |
| ORF YCL035C | 571 | P | 1273 | P | 513 | P | 1032 | P | 2.2 | 2.0 | 2.1 | Excl |
| ORF YGL039W | 226 | P | 461 | P | 259 | P | 567 | P | 2.0 | 2.2 | 2.1 | Excl |
| ORF YEL020C | 79 | P | 171 | P | 66 | P | 134 | P | 2.2 | 2.0 | 2.1 | Excl |
| CYC3 (YAL039C) | 344 | P | 721 | P | 336 | P | 683 | P | 2.1 | 2.0 | 2.1 | Excl |
| ORF YLR260W | 117 | P | 237 | P | 102 | P | 214 | P | 2.0 | 2.1 | 2.1 | Excl |
| ORF YKL218C | 88 | P | 181 | P | 68 | P | 140 | P | 2.1 | 2.0 | 2.1 | Excl |
| PDI1 (YCL043C) | 1624 | P | 3397 | P | 1178 | P | 2357 | P | 2.1 | 2.0 | 2.0 | Excl |
| ORF YGR136W | 328 | P | 677 | P | 310 | P | 619 | P | 2.1 | 2.0 | 2.0 | Excl |
| UFD1 (YGR048W) | 110 | P | 224 | P | 91 | P | 184 | P | 2.0 | 2.0 | 2.0 | Excl |

Figure 18F

Swi2 Down

Gene Expression Results for FH1998040601A

| | WT1val | WT1c | MT1val | MT1c | WT2val | WT2iMT2val | MT2i | MT1/WT1 | MT2/WT2 | Ave | Corrected? | Confidence |
|---|---|---|---|---|---|---|---|---|---|---|---|---|
| ADH3 (YMR083W) | 1696 | P | 747 | P | 1667 | P | 725 | P | 0.44 | 0.43 | 2.29 | | Excl |
| ADH5 (YBR145W) | 114 | P | 52 | M | 121 | P | 36 | P | 0.46 | 0.30 | 2.77 | | Good |
| ASH1 (YKL185W) | 328 | P | 147 | P | 289 | P | 113 | P | 0.45 | 0.39 | 2.40 | | Excl |
| ASN1 (YPR145W) | 2440 | P | 867 | P | 2086 | P | 692 | P | 0.36 | 0.33 | 2.91 | | Excl |
| ATF2 (YGR177C) | 105 | P | 4 | A | 92 | P | 16 | A | 0.04 | 0.17 | 16.05 | | Good |
| CAR2 (YLR438W) | 286 | P | 95 | A | 362 | P | 56 | P | 0.33 | 0.16 | 4.71 | | Good |
| CLB1 (YGR108W) | 322 | P | 121 | P | 329 | P | 121 | P | 0.38 | 0.37 | 2.69 | | Excl |
| COX5B (YIL111W) ex | 155 | P | 73 | P | 150 | P | 51 | P | 0.47 | 0.34 | 2.55 | | Excl |
| CTP1 (YBR291C) | 198 | P | 78 | P | 246 | P | 80 | P | 0.40 | 0.33 | 2.80 | | Excl |
| CWP1 (YKL096W) | 1472 | P | 511 | P | 1381 | P | 443 | P | 0.35 | 0.32 | 3.00 | | Excl |
| DIP5 (YPL265W) | 303 | P | 127 | P | 253 | P | 62 | P | 0.42 | 0.24 | 3.24 | | Excl |
| FAA3 (YIL009W) | 196 | P | 66 | P | 211 | P | 39 | P | 0.34 | 0.18 | 4.21 | | Excl |
| GIN11 (YLL065W) ( | -20 | A | -32 | A | 3 | A | -13 | A | 1.61 | -3.82 | 2.81 | Yes | Med |
| GPH1 (YPR160W) | 137 | P | 49 | P | 88 | P | 36 | P | 0.36 | 0.40 | 2.64 | | Good |
| HEM13 (YDR044W) | 118 | P | 56 | A | 154 | P | 75 | P | 0.48 | 0.49 | 2.07 | | Good |
| HXT1 (YHR094C) | 2077 | P | 862 | P | 2056 | P | 918 | P | 0.42 | 0.45 | 2.32 | | Excl |
| HXT4 (YHR092W) | 801 | P | 162 | P | 679 | P | 227 | P | 0.20 | 0.33 | 3.97 | | Excl |
| MF(ALPHA)2 (YGL08 | 1791 | P | 776 | P | 2676 | P | 926 | P | 0.43 | 0.35 | 2.60 | | Excl |
| MNN1 (YER001W) | 499 | P | 148 | P | 419 | P | 142 | P | 0.30 | 0.34 | 3.15 | | Excl |
| MRS2 (YOR333C) | 33 | A | 7 | A | 20 | P | 8 | M | 0.23 | 0.41 | 3.42 | | Good |
| NCE2 (YPR149W) | 2724 | P | 854 | P | 1967 | P | 871 | P | 0.31 | 0.44 | 2.72 | | Excl |
| ORF YAL028W | 30 | A | 12 | A | 35 | P | 1 | A | 0.39 | 0.03 | 18.81 | | Excl |
| ORF YAR010C (_f) | 3879 | P | 686 | P | 3585 | P | 594 | P | 0.18 | 0.17 | 5.85 | | Excl |
| ORF YBL005W-A (_f) | 200 | P | 40 | P | 223 | P | 38 | P | 0.20 | 0.17 | 5.45 | | Excl |
| ORF YBL005W-B exc | 241 | P | 21 | P | 222 | P | 21 | P | 0.09 | 0.09 | 10.93 | | Excl |
| ORF YBL042C | 325 | P | 160 | P | 343 | P | 156 | P | 0.49 | 0.45 | 2.12 | | Excl |
| ORF YBR012W-A (_f) | 4648 | P | 657 | P | 3799 | P | 567 | P | 0.14 | 0.15 | 6.89 | | Excl |
| ORF YBR012W-B exc | 4536 | P | 623 | P | 3715 | P | 566 | P | 0.14 | 0.15 | 6.93 | | Excl |
| ORF YBR012W-B exoi | -24 | M | -44 | A | -27 | A | -37 | A | 1.82 | 1.38 | 2.97 | Yes | Med |
| ORF YBR158W | 1015 | P | 430 | P | 1059 | P | 347 | P | 0.42 | 0.33 | 2.71 | | Excl |
| ORF YBR238C | 132 | P | 43 | A | 167 | P | 50 | P | 0.32 | 0.30 | 3.21 | | Good |
| ORF YBR244W | 377 | P | 33 | A | 351 | P | 70 | P | 0.09 | 0.20 | 8.23 | | Good |

Figure 19A

| ORF | 23 | | -12 | | 9 | | -21 | | | | | | |
|---|---|---|---|---|---|---|---|---|---|---|---|---|---|
| | | | | | | | | | | | | | |
| ORF YDL032W | 186 | P | 42 | A | 258 | P | 58 | A | -0.51 | -0.22 | 4.56 | Yes | Med |
| ORF YDL037C | 520 | P | 104 | P | 616 | P | 102 | P | 0.22 | 0.23 | 4.45 | | Good |
| ORF YDL038C | 920 | P | 198 | P | 1025 | P | 236 | P | 0.20 | 0.17 | 5.52 | | Excl |
| ORF YDL039C | 187 | P | 20 | A | 121 | P | 47 | P | 0.22 | 0.23 | 4.48 | | Excl |
| ORF YDL179W | 4437 | P | 678 | P | 3476 | P | 962 | P | 0.11 | 0.39 | 5.88 | | Good |
| ORF YDR033W | 969 | P | 281 | P | 721 | P | 337 | P | 0.15 | 0.28 | 5.08 | | Excl |
| ORF YDR055W | -16 | A | -30 | A | -12 | A | -22 | A | 0.29 | 0.47 | 2.80 | | Excl |
| ORF YDR187C | 193 | P | 70 | P | 122 | P | 47 | P | 1.88 | 1.84 | 2.41 | Yes | Med |
| ORF YDR380W | 367 | P | 97 | P | 341 | P | 85 | P | 0.36 | 0.39 | 2.68 | | Excl |
| ORF YDR384C | -13 | A | -23 | A | -6 | A | -19 | A | 0.26 | 0.25 | 3.89 | | Excl |
| ORF YDR535C exon 1 | 325 | P | 81 | P | 234 | P | 80 | P | 1.79 | 3.19 | 2.33 | Yes | Med |
| ORF YEL065W | 432 | P | 78 | P | 317 | P | 80 | P | 0.25 | 0.34 | 3.46 | | Excl |
| ORF YER124C | 4480 | P | 690 | P | 4350 | P | 719 | P | 0.18 | 0.25 | 4.73 | | Excl |
| ORF YER138C exon 1 | 4765 | P | 791 | P | 4095 | P | 653 | P | 0.15 | 0.17 | 6.27 | | Excl |
| ORF YER160C exon 1 | 4605 | P | 2187 | P | 3817 | P | 1687 | P | 0.17 | 0.16 | 6.15 | | Excl |
| ORF YER160C exon 2 | 230 | P | 62 | P | 195 | P | 37 | P | 0.47 | 0.44 | 2.18 | | Excl |
| ORF YFR055W | 914 | P | 157 | P | 953 | P | 178 | P | 0.27 | 0.19 | 4.47 | | Excl |
| ORF YGL028C | 149 | P | 57 | P | 145 | P | 31 | P | 0.17 | 0.19 | 5.59 | | Excl |
| ORF YGR035C | 140 | P | 51 | P | 146 | P | 68 | P | 0.38 | 0.21 | 3.69 | | Excl |
| ORF YGR041W | 32 | P | 6 | A | 18 | P | 6 | P | 0.36 | 0.47 | 2.44 | | Excl |
| ORF YHR022C | 47 | P | 11 | A | 37 | P | 18 | P | 0.20 | 0.31 | 4.14 | | Good |
| ORF YHR048W | 82 | P | 29 | A | 161 | P | 25 | P | 0.24 | 0.48 | 3.14 | | Good |
| ORF YHR136C | 148 | P | 58 | P | 125 | P | 31 | P | 0.35 | 0.15 | 4.65 | | Good |
| ORF YHR137W | 1128 | P | 309 | P | 1114 | P | 338 | P | 0.39 | 0.24 | 3.32 | | Excl |
| ORF YHR143W | 22 | A | 2 | A | 14 | P | -2 | A | 0.27 | 0.30 | 3.47 | | Excl |
| ORF YHR185C | 4996 | P | 853 | P | 5015 | P | 924 | P | 0.07 | -0.11 | 8.53 | Yes | Med |
| ORF YHR214C-B exo | 4542 | P | 1996 | P | 4526 | P | 1807 | P | 0.17 | 0.18 | 5.64 | | Excl |
| ORF YHR214C-B exo | 37 | A | -13 | A | 17 | A | -14 | A | 0.44 | 0.40 | 2.39 | | Excl |
| ORF YIL017W | 22 | A | 5 | A | 47 | A | 19 | A | -0.34 | -0.85 | 8.15 | Yes | Med |
| ORF YIR013C | 5 | A | -14 | A | 9 | A | -2 | A | 0.22 | 0.41 | 3.54 | | Good |
| ORF YIR040C (f) | | | | | | | | | -2.86 | -0.19 | 2.85 | Yes | Med |
| ORF YJL200C | 414 | P | 160 | P | 459 | P | 144 | P | 0.39 | 0.31 | 2.89 | | Excl |

Figure 19B

| | | | | | | | | |
|---|---|---|---|---|---|---|---|---|
| ORF YJL217W | 515 | P | 225 | P | 437 | P | 143 | P | 0.44 | 0.33 | 2.68 | | Excl |
| ORF YJR026W (_f) | 3896 | P | 573 | P | 3363 | P | 521 | P | 0.15 | 0.15 | 6.63 | | Excl |
| ORF YJR027W exon | 4162 | P | 625 | P | 3810 | P | 583 | P | 0.15 | 0.15 | 6.60 | | Excl |
| ORF YJR027W exon | 3543 | P | 1562 | P | 2309 | P | 1003 | P | 0.44 | 0.43 | 2.28 | | Excl |
| ORF YJR028W (_f) | 4663 | P | 740 | P | 3852 | P | 653 | P | 0.16 | 0.17 | 6.10 | | Excl |
| ORF YJR029W exon | 4744 | P | 715 | P | 3670 | P | 659 | P | 0.15 | 0.18 | 6.10 | | Excl |
| ORF YJR029W exon | 3471 | P | 1097 | P | 2464 | P | 789 | P | 0.32 | 0.32 | 3.14 | | Excl |
| ORF YJR147W | 119 | P | -14 | A | 133 | P | 24 | P | -0.12 | 0.18 | 16.12 | Yes | Med |
| ORF YKL044W | 103 | P | 32 | M | 136 | P | 38 | P | 0.31 | 0.28 | 3.40 | | Good |
| ORF YKL225W | 309 | P | 32 | A | 96 | P | 17 | P | 0.10 | 0.18 | 7.70 | | Good |
| ORF YLL013C | 46 | P | 15 | P | 23 | P | 7 | M | 0.34 | 0.30 | 3.14 | | Good |
| ORF YLL052C | 164 | P | 44 | P | 103 | P | 44 | P | 0.27 | 0.42 | 3.04 | | Excl |
| ORF YLL053C | 364 | P | 90 | P | 242 | P | 79 | P | 0.25 | 0.33 | 3.56 | | Excl |
| ORF YLR161W (_f) | 4 | A | -14 | A | 5 | A | -6 | A | -3.43 | -1.19 | 2.96 | Yes | Med |
| ORF YLR279W | 57 | A | -2 | A | 21 | A | -6 | A | -0.03 | -0.29 | 8.55 | Yes | Med |
| ORF YLR413W | 1103 | P | 167 | P | 1114 | P | 139 | P | 0.15 | 0.13 | 7.31 | | Excl |
| ORF YML013C-A | 3 | A | -18 | A | 10 | A | -4 | A | -6.43 | -0.42 | 3.52 | Yes | Med |
| ORF YML039W exon | 4584 | P | 586 | P | 4023 | P | 646 | P | 0.13 | 0.16 | 7.02 | | Excl |
| ORF YML039W exon | 3716 | P | 1710 | P | 2496 | P | 1159 | P | 0.46 | 0.46 | 2.16 | | Excl |
| ORF YML040W (_f) | 3856 | P | 622 | P | 3513 | P | 590 | P | 0.16 | 0.17 | 6.08 | | Excl |
| ORF YML045W exon | 4716 | P | 777 | P | 4383 | P | 712 | P | 0.16 | 0.16 | 6.11 | | Excl |
| ORF YML045W exon | 4997 | P | 2032 | P | 4362 | P | 1926 | P | 0.41 | 0.44 | 2.36 | | Excl |
| ORF YMR006C | 244 | P | 86 | P | 226 | P | 63 | P | 0.35 | 0.28 | 3.20 | | Excl |
| ORF YMR045C exon | 330 | P | 12 | A | 273 | P | 39 | P | 0.04 | 0.14 | 17.57 | | Good |
| ORF YMR045C exon | 3051 | P | 1167 | P | 2529 | P | 1134 | P | 0.38 | 0.45 | 2.42 | | Excl |
| ORF YMR046C (_f) | 319 | P | 24 | P | 269 | P | 38 | P | 0.08 | 0.14 | 10.06 | | Excl |
| ORF YMR050C exon | 4177 | P | 566 | P | 3618 | P | 627 | P | 0.14 | 0.17 | 6.57 | | Excl |
| ORF YMR050C exon | 3539 | P | 1417 | P | 2762 | P | 1344 | P | 0.40 | 0.49 | 2.28 | | Excl |
| ORF YMR051C (_f) | 4090 | P | 598 | P | 3278 | P | 561 | P | 0.15 | 0.17 | 6.34 | | Excl |
| ORF YMR173W | 323 | P | 60 | P | 163 | P | 78 | P | 0.19 | 0.48 | 3.72 | | Excl |
| ORF YMR173W-A | 4707 | P | 1581 | P | 3899 | P | 1711 | P | 0.34 | 0.44 | 2.63 | | Excl |
| ORF YMR254C | 29 | A | 12 | A | 12 | A | 1 | A | 0.42 | 0.09 | 6.74 | | Good |
| ORF YNL327W | 2041 | P | 607 | P | 1570 | P | 641 | P | 0.30 | 0.41 | 2.91 | | Excl |
| ORF YNR067C | 730 | P | 116 | P | 455 | P | 101 | P | 0.16 | 0.22 | 5.41 | | Excl |
| ORF YOL152W | 47 | P | 23 | A | 23 | P | 6 | A | 0.49 | 0.27 | 2.86 | | Good |

Figure 19C

| | 31 | | 6 | | 36 | | 15 | | | | | |
|---|---|---|---|---|---|---|---|---|---|---|---|---|
| ORF YOR013W | 24 | A | 6 | A | 25 | A | 0 | A | 0.21 | 0.41 | 3.63 | | Good |
| ORF YOR032C | 136 | P | 161 | A | 150 | P | 37 | P | 0.23 | 0.00 | 4.70 | Yes | Med |
| ORF YOR315W | 22 | P | 2 | A | 18 | P | 8 | A | 0.12 | 0.24 | 6.38 | | Good |
| ORF YOR366W | 1141 | P | 298 | P | 1154 | P | 273 | P | 0.08 | 0.46 | 7.21 | | Good |
| ORF YPL019C | 172 | P | 79 | P | 129 | P | 49 | P | 0.26 | 0.24 | 4.03 | | Excl |
| ORF YPL158C | 25 | A | -3 | A | 13 | A | -2 | A | 0.46 | 0.38 | 2.39 | | Excl |
| ORF YPR027C | 109 | P | 49 | P | 113 | P | 42 | P | -0.11 | -0.17 | 4.23 | Yes | Med |
| ORF YPR106W | 202 | P | 88 | P | 247 | P | 62 | P | 0.45 | 0.37 | 2.47 | | Excl |
| PHD1 (YKL043W) | 231 | P | 105 | P | 408 | P | 58 | P | 0.44 | 0.25 | 3.15 | | Excl |
| PHO11 (YAR071W) | 381 | P | 90 | P | 550 | P | 75 | P | 0.45 | 0.14 | 4.62 | | Excl |
| PHO12 (YHR215W) | 743 | P | 104 | P | 682 | P | 108 | P | 0.24 | 0.14 | 5.78 | | Excl |
| PHO3 (YBR092C) | 4124 | P | 153 | A | 3904 | P | 105 | P | 0.14 | 0.16 | 6.74 | | Excl |
| PHO84 (YML123C) | 161 | P | -26 | A | 127 | P | 55 | P | 0.04 | 0.03 | 32.04 | | Good |
| PRY3 (YJL078C) | 474 | P | 79 | P | 451 | P | 45 | P | -0.16 | 0.43 | 19.86 | Yes | Med |
| PTR2 (YKR093W) | 35 | A | 17 | A | 26 | P | 13 | A | 0.17 | 0.10 | 7.98 | | Excl |
| REV1 (YOR345C) | 348 | P | 121 | P | 344 | P | 116 | P | 0.47 | 0.48 | 2.09 | | Good |
| RME1 (YGR044C) | 66 | P | 22 | A | 54 | P | 21 | P | 0.35 | 0.34 | 2.93 | | Excl |
| RPI1 (YIL119C) | 430 | P | 209 | P | 846 | P | 191 | P | 0.34 | 0.39 | 2.76 | | Good |
| SAG1 (YJR004C) | 107 | P | 29 | A | 87 | P | 32 | P | 0.49 | 0.23 | 3.24 | | Excl |
| SRD1 (YCR018C) | 235 | P | 111 | P | 261 | P | 115 | P | 0.27 | 0.37 | 3.20 | | Good |
| STP4 (YDL048C) | 788 | P | 317 | P | 1216 | P | 322 | P | 0.47 | 0.44 | 2.19 | | Excl |
| TIP1 (YBR067C) | 1207 | P | 323 | P | 1716 | P | 314 | P | 0.40 | 0.26 | 3.14 | | Excl |
| TWT2 (YJR148W) | 824 | P | 290 | P | 1038 | P | 223 | P | 0.27 | 0.18 | 4.60 | | Excl |
| VAP1 (YBR069C) | 23359 | P | 365 | P | 1237 | P | 243 | P | 0.35 | 0.22 | 3.75 | | Excl |
| YGP1 (YNL160W) | 4663 | P | 975 | P | 3793 | P | 1292 | P | 0.15 | 0.20 | 5.78 | | Excl |
| YHB1 (YGR234W) | 396 | P | 88 | P | 313 | P | 62 | P | 0.21 | 0.34 | 3.86 | | Excl |
| YRO2 (YBR054W) | | | | | | | | | 0.22 | 0.20 | 4.77 | | Excl |

Figure 19D

Swi2 Down

Gene Expression Results for FH1998040601A

| | WT1val | WT1c | MT1val | WT1c | MT1c | WT2val | WT2c | MT2val | MT2c | MT1/WT1 | MT2/WT2 | Ave | Corrected? | Confidence |
|---|---|---|---|---|---|---|---|---|---|---|---|---|---|---|
| PHO84 (YML123C) | 4124 | P | 153 | A | 3904 | P | 105 | P | 0.04 | 0.03 | 32.04 | | Good |
| PRY3 (YJL078C) | 161 | P | -26 | A | 127 | P | 55 | P | -0.16 | 0.43 | 19.86 | Yes | Med |
| ORF YAL028W | 30 | A | 12 | A | 35 | P | 1 | A | 0.39 | 0.03 | 18.81 | | Good |
| ORF YMR045C exon | 330 | P | 12 | A | 273 | P | 39 | P | 0.04 | 0.14 | 17.57 | | Good |
| ORF YJR147W | 119 | P | -14 | A | 133 | P | 24 | P | -0.12 | 0.18 | 16.12 | Yes | Med |
| ATF2 (YGR177C) | 105 | P | 4 | A | 92 | P | 16 | A | 0.04 | 0.17 | 16.05 | | Good |
| ORF YBL005W-B exo | 241 | P | 21 | P | 222 | P | 21 | P | 0.09 | 0.09 | 10.93 | | Excl |
| ORF YMR046C (_f) | 319 | P | 24 | P | 269 | P | 38 | P | 0.08 | 0.14 | 10.06 | | Excl |
| ORF YLR279W | 57 | A | -2 | A | 21 | A | -6 | A | -0.03 | -0.29 | 8.55 | Yes | Med |
| ORF YHR185C | 22 | A | 2 | A | 14 | P | -2 | A | 0.07 | -0.11 | 8.53 | Yes | Med |
| ORF YBR244W | 377 | P | 33 | A | 351 | P | 70 | P | 0.09 | 0.20 | 8.23 | | Good |
| ORF YIL017W | 37 | A | -13 | A | 17 | A | -14 | A | -0.34 | -0.85 | 8.15 | Yes | Med |
| PTR2 (YKR093W) | 474 | P | 79 | P | 451 | P | 45 | P | 0.17 | 0.10 | 7.98 | | Excl |
| ORF YKL225W | 309 | P | 32 | A | 96 | P | 17 | P | 0.10 | 0.18 | 7.70 | | Good |
| ORF YLR413W | 1103 | P | 167 | P | 1114 | P | 139 | P | 0.15 | 0.13 | 7.31 | | Excl |
| ORF YOR366W | 22 | P | 2 | A | 18 | P | 8 | A | 0.08 | 0.46 | 7.21 | | Good |
| ORF YML039W exon | 4584 | P | 586 | P | 4023 | P | 646 | P | 0.13 | 0.16 | 7.02 | | Excl |
| ORF YBR012W-B exc | 4536 | P | 623 | P | 3715 | P | 566 | P | 0.14 | 0.15 | 6.93 | | Excl |
| ORF YBR012W-A (_f) | 4648 | P | 657 | P | 3799 | P | 567 | P | 0.14 | 0.15 | 6.89 | | Excl |
| ORF YMR254C | 29 | A | 12 | A | 12 | A | 1 | A | 0.42 | 0.09 | 6.74 | | Good |
| PHO3 (YBR092C) | 743 | P | 104 | P | 682 | P | 108 | P | 0.14 | 0.16 | 6.74 | | Excl |
| ORF YJR026W (_f) | 3896 | P | 573 | P | 3363 | P | 521 | P | 0.15 | 0.15 | 6.63 | | Excl |
| ORF YJR027W exon | 4162 | P | 625 | P | 3810 | P | 583 | P | 0.15 | 0.15 | 6.60 | | Excl |
| ORF YMR050C exon | 4177 | P | 566 | P | 3618 | P | 627 | P | 0.14 | 0.17 | 6.57 | | Excl |
| ORF YOR315W | 136 | P | 16 | A | 150 | P | 37 | P | 0.12 | 0.24 | 6.38 | | Good |
| ORF YMR051C (_f) | 4090 | P | 598 | P | 3278 | P | 561 | P | 0.15 | 0.17 | 6.34 | | Excl |
| ORF YER138C exon | 4480 | P | 690 | P | 4350 | P | 719 | P | 0.15 | 0.17 | 6.27 | | Excl |
| ORF YER160C exon | 4765 | P | 791 | P | 4095 | P | 653 | P | 0.17 | 0.16 | 6.15 | | Excl |
| ORF YML045W exon | 4716 | P | 777 | P | 4383 | P | 712 | P | 0.16 | 0.16 | 6.11 | | Excl |
| ORF YJR029W exon | 4744 | P | 715 | P | 3670 | P | 659 | P | 0.15 | 0.18 | 6.10 | | Excl |
| ORF YJR028W (_f) | 4663 | P | 740 | P | 3852 | P | 653 | P | 0.16 | 0.17 | 6.10 | | Excl |

Figure 20A

| | | | | | | | |
|---|---|---|---|---|---|---|---|
| ORF YML040W (_f) | 3856 P | 622 P | 3513 P | 590 P | 0.16 | 0.17 | 6.08 | Excl |
| ORF YDL179W | 187 P | 20 A | 121 P | 47 P | 0.11 | 0.39 | 5.88 | Good |
| ORF YAR010C (_f) | 3879 P | 686 P | 3585 P | 594 P | 0.18 | 0.17 | 5.85 | Excl |
| PHO12 (YHR215W) | 381 P | 90 P | 550 P | 75 P | 0.24 | 0.14 | 5.78 | Excl |
| YGP1 (YNL160W) | 2359 P | 365 P | 1237 P | 243 P | 0.15 | 0.20 | 5.78 | Excl |
| ORF YHR214C-B exo | 4996 P | 853 P | 5015 P | 924 P | 0.17 | 0.18 | 5.64 | Excl |
| ORF YGL028C | 914 P | 157 P | 953 P | 178 P | 0.17 | 0.19 | 5.59 | Excl |
| ORF YDL038C | 520 P | 104 P | 616 P | 102 P | 0.20 | 0.17 | 5.52 | Excl |
| ORF YBL005W-A (_f) | 200 P | 40 P | 223 P | 38 P | 0.20 | 0.17 | 5.45 | Excl |
| ORF YNR067C | 730 P | 116 P | 455 P | 101 P | 0.16 | 0.22 | 5.41 | Excl |
| ORF YDR033W | 4437 P | 678 P | 3476 P | 962 P | 0.15 | 0.28 | 5.08 | Good |
| YRO2 (YBR054W) | 396 P | 88 P | 313 P | 62 P | 0.22 | 0.20 | 4.77 | Excl |
| ORF YER124C | 432 P | 78 P | 317 P | 80 P | 0.18 | 0.25 | 4.73 | Excl |
| CAR2 (YLR438W) | 286 P | 95 A | 362 P | 56 P | 0.33 | 0.16 | 4.71 | Excl |
| ORF YOR032C | 24 P | 6 A | 25 A | 0 A | 0.23 | 0.00 | 4.70 Yes | Med |
| ORF YHR136C | 82 P | 29 A | 161 P | 25 P | 0.35 | 0.15 | 4.65 | Good |
| PHO11 (YAR071W) ( | 231 P | 105 P | 408 P | 58 P | 0.45 | 0.14 | 4.62 | Excl |
| TWT2 (YJR148W) | 1207 P | 323 P | 1716 P | 314 P | 0.27 | 0.18 | 4.60 | Excl |
| ORF YDL032W | 23 A | -12 A | 9 A | -2 M | -0.51 | -0.22 | 4.56 Yes | Med |
| ORF YDL039C | 920 P | 198 P | 1025 P | 236 P | 0.22 | 0.23 | 4.48 | Excl |
| ORF YFR055W | 230 P | 62 P | 195 P | 37 P | 0.27 | 0.19 | 4.47 | Excl |
| ORF YDL037C | 186 P | 42 A | 258 P | 58 A | 0.22 | 0.23 | 4.45 | Good |
| ORF YPR027C | 25 A | -3 A | 13 A | -2 A | -0.11 | -0.17 | 4.23 Yes | Med |
| FAA3 (YIL009W) | 196 P | 66 P | 211 P | 39 P | 0.34 | 0.18 | 4.21 | Excl |
| ORF YHR022C | 32 P | 6 A | 18 P | 6 P | 0.20 | 0.31 | 4.14 | Good |
| ORF YPL019C | 1141 P | 298 P | 1154 P | 273 P | 0.26 | 0.24 | 4.03 | Excl |
| HXT4 (YHR092C) | 801 P | 162 P | 679 P | 227 P | 0.20 | 0.33 | 3.97 | Excl |
| ORF YDR384C | 367 P | 97 P | 341 P | 85 P | 0.26 | 0.25 | 3.89 | Excl |
| YHB1 (YGR234W) | 4663 P | 975 P | 3793 P | 1292 P | 0.21 | 0.34 | 3.86 | Excl |
| VAP1 (YBR069C) | 824 P | 290 P | 1038 P | 223 P | 0.35 | 0.22 | 3.75 | Excl |
| ORF YMR173W | 323 P | 60 P | 163 P | 78 P | 0.19 | 0.48 | 3.72 | Excl |
| ORF YGR035C | 149 P | 57 P | 145 P | 31 P | 0.38 | 0.21 | 3.69 | Excl |
| ORF YOR013W | 31 A | 6 A | 36 A | 15 A | 0.21 | 0.41 | 3.63 | Good |

Figure 20B

| ORF | | | | | | | | | |
|---|---|---|---|---|---|---|---|---|---|
| ORF YLL053C | 364 | P | 90 | P | 242 | P | 79 | P | 0.25 | 0.33 | 3.56 | | Excl |

| ORF | C1 | | C2 | | C3 | | C4 | | V1 | V2 | V3 | Flag | Qual |
|---|---|---|---|---|---|---|---|---|---|---|---|---|---|
| ORF YLL053C | 364 | P | 90 | P | 242 | P | 79 | P | 0.25 | 0.33 | 3.56 |  | Excl |
| ORF YIR013C | 22 | A | 5 | A | 47 | A | 19 | A | 0.22 | 0.41 | 3.54 |  | Good |
| ORF YML013C-A | 3 | A | -18 | A | 10 | A | -4 | A | -6.43 | -0.42 | 3.52 | Yes | Med |
| ORF YHR143W | 1128 | P | 309 | P | 1114 | P | 338 | P | 0.27 | 0.30 | 3.47 |  | Excl |
| ORF YEL065W | 325 | P | 81 | P | 234 | P | 80 | P | 0.25 | 0.34 | 3.46 |  | Excl |
| MRS2 (YOR333C) | 33 | A | 7 | A | 20 | P | 8 | M | 0.23 | 0.41 | 3.42 |  | Good |
| ORF YKL044W | 103 | P | 32 | M | 136 | P | 38 | P | 0.31 | 0.28 | 3.40 |  | Good |
| ORF YHR137W | 148 | P | 58 | P | 125 | P | 31 | P | 0.39 | 0.24 | 3.32 |  | Excl |
| SAG1 (YJR004C) | 430 | P | 209 | P | 846 | P | 191 | P | 0.49 | 0.23 | 3.24 |  | Excl |
| DIP5 (YPL265W) | 303 | P | 127 | P | 253 | P | 62 | P | 0.42 | 0.24 | 3.24 |  | Excl |
| ORF YBR238C | 132 | A | 43 | A | 167 | P | 50 | P | 0.32 | 0.30 | 3.21 |  | Good |
| SRD1 (YCR018C) | 107 | A | 29 | A | 87 | P | 32 | P | 0.27 | 0.37 | 3.20 |  | Good |
| ORF YMR006C | 244 | P | 86 | P | 226 | P | 63 | P | 0.35 | 0.28 | 3.20 |  | Excl |
| MNN1 (YER001W) | 499 | P | 148 | P | 419 | P | 142 | P | 0.30 | 0.34 | 3.15 |  | Excl |
| PHD1 (YKL043W) | 202 | P | 88 | P | 247 | P | 62 | P | 0.44 | 0.25 | 3.15 |  | Excl |
| ORF YLL013C | 46 | P | 15 | P | 23 | P | 7 | M | 0.34 | 0.30 | 3.14 |  | Good |
| ORF YJR029W exon | 3471 | P | 1097 | P | 2464 | P | 789 | P | 0.32 | 0.32 | 3.14 |  | Excl |
| TIP1 (YBR067C) | 788 | P | 317 | P | 1216 | P | 322 | P | 0.40 | 0.26 | 3.14 |  | Excl |
| ORF YHR048W | 47 | P | 11 | A | 37 | P | 18 | P | 0.24 | 0.48 | 3.14 |  | Good |
| ORF YLL052C | 164 | P | 44 | P | 103 | P | 44 | P | 0.27 | 0.42 | 3.04 |  | Excl |
| CWP1 (YKL096W) | 1472 | P | 511 | P | 1381 | P | 443 | P | 0.35 | 0.32 | 3.00 |  | Excl |
| ORF YBR012W-B exon | -24 | M | -44 | A | -27 | A | -37 | A | 1.82 | 1.38 | 2.97 | Yes | Med |
| ORF YLR161W (_f) | 4 | A | -14 | A | 5 | A | -6 | A | -3.43 | -1.19 | 2.96 | Yes | Med |
| RME1 (YGR044C) | 348 | P | 121 | P | 344 | P | 116 | P | 0.35 | 0.34 | 2.93 |  | Excl |
| ASN1 (YPR145W) | 2440 | P | 867 | P | 2086 | P | 692 | P | 0.36 | 0.33 | 2.91 |  | Excl |
| ORF YNL327W | 2041 | P | 607 | P | 1570 | P | 641 | P | 0.30 | 0.41 | 2.91 |  | Excl |
| ORF YJL200C | 414 | P | 160 | P | 459 | P | 144 | P | 0.39 | 0.31 | 2.89 |  | Excl |
| ORF YOL152W | 47 | P | 23 | A | 23 | P | 6 | A | 0.49 | 0.27 | 2.86 |  | Good |
| ORF YIR040C (_f) | 5 | A | -14 | A | 9 | A | -2 | A | -2.86 | -0.19 | 2.85 | Yes | Med |
| GIN11 (YLL065W) (_f) | -20 | A | -32 | A | 3 | A | -13 | A | 1.61 | -3.82 | 2.81 | Yes | Med |
| CTP1 (YBR291C) | 198 | P | 78 | P | 246 | P | 80 | P | 0.40 | 0.33 | 2.80 |  | Excl |
| ORF YDR055W | 969 | P | 281 | P | 721 | P | 337 | P | 0.29 | 0.47 | 2.80 |  | Excl |
| ADH5 (YBR145W) | 114 | P | 52 | M | 121 | P | 36 | P | 0.46 | 0.30 | 2.77 |  | Good |
| RPI1 (YIL119C) | 66 | P | 22 | A | 54 | P | 21 | P | 0.34 | 0.39 | 2.76 |  | Good |

Figure 20C

| | | | | | | | | |
|---|---|---|---|---|---|---|---|---|
| NCE2 (YPR149W) | 2724 | P | 854 | P | 1967 | P | 871 | P | 0.31 | 0.44 | 2.72 | Excl |
| ORF YBR158W | 1015 | P | 430 | P | 1059 | P | 347 | P | 0.42 | 0.33 | 2.71 | Excl |
| CLB1 (YGR108W) | 322 | P | 121 | P | 329 | P | 121 | P | 0.38 | 0.37 | 2.69 | Excl |
| ORF YDR380W | 193 | P | 70 | P | 122 | P | 47 | P | 0.36 | 0.39 | 2.68 | Excl |
| ORF YJL217W | 515 | P | 225 | P | 437 | P | 143 | P | 0.44 | 0.33 | 2.68 | Excl |
| GPH1 (YPR160W) | 137 | P | 49 | A | 88 | P | 36 | P | 0.36 | 0.40 | 2.64 | Good |
| ORF YMR173W-A | 4707 | P | 1581 | P | 3899 | P | 1711 | P | 0.34 | 0.44 | 2.63 | Excl |
| MF(ALPHA)2 (YGL08 | 1791 | P | 776 | P | 2676 | P | 926 | P | 0.43 | 0.35 | 2.60 | Excl |
| COX5B (YIL111W) ex | 155 | P | 73 | P | 150 | P | 51 | P | 0.47 | 0.34 | 2.55 | Excl |
| ORF YPR106W | 109 | P | 49 | P | 113 | P | 42 | P | 0.45 | 0.37 | 2.47 | Excl |
| ORF YGR041W | 140 | P | 51 | P | 146 | P | 68 | P | 0.36 | 0.47 | 2.44 | Excl |
| ORF YMR045C exon | 3051 | P | 1167 | P | 2529 | P | 1134 | P | 0.38 | 0.45 | 2.42 | Excl |
| ORF YDR187C | -16 | A | -30 | A | -12 | A | -22 | A | 1.88 | 1.84 | 2.41 | Yes | Med |
| ASH1 (YKL185W) | 328 | P | 147 | P | 289 | P | 113 | P | 0.45 | 0.39 | 2.40 | Excl |
| ORF YPL158C | 172 | P | 79 | P | 129 | P | 49 | P | 0.46 | 0.38 | 2.39 | Excl |
| ORF YHR214C-B exo | 4542 | P | 1996 | P | 4526 | P | 1807 | P | 0.44 | 0.40 | 2.39 | Excl |
| ORF YML045W exon | 4997 | P | 2032 | P | 4362 | P | 1926 | P | 0.41 | 0.44 | 2.36 | Excl |
| ORF YDR535C exon | -13 | A | -23 | A | -6 | A | -19 | A | 1.79 | 3.19 | 2.33 | Yes | Med |
| HXT1 (YHR094C) | 2077 | P | 862 | P | 2056 | P | 918 | P | 0.42 | 0.45 | 2.32 | Excl |
| ADH3 (YMR083W) | 1696 | P | 747 | P | 1667 | P | 725 | P | 0.44 | 0.43 | 2.29 | Excl |
| ORF YJR027W exon | 3543 | P | 1562 | P | 2309 | P | 1003 | P | 0.44 | 0.43 | 2.28 | Excl |
| ORF YMR050C exon | 3539 | P | 1417 | P | 2762 | P | 1344 | P | 0.40 | 0.49 | 2.28 | Excl |
| STP4 (YDL048C) | 235 | P | 111 | P | 261 | P | 115 | P | 0.47 | 0.44 | 2.19 | Excl |
| ORF YER160C exon | 4605 | P | 2187 | P | 3817 | P | 1687 | P | 0.47 | 0.44 | 2.18 | Excl |
| ORF YML039W exon | 3716 | P | 1710 | P | 2496 | P | 1159 | P | 0.46 | 0.46 | 2.16 | Excl |
| ORF YBL042C | 325 | P | 160 | P | 343 | P | 156 | P | 0.49 | 0.45 | 2.12 | Excl |
| REV1 (YOR345C) | 35 | A | 17 | A | 26 | P | 13 | A | 0.47 | 0.48 | 2.09 | Good |
| HEM13 (YDR044W) | 118 | P | 56 | A | 154 | P | 75 | P | 0.48 | 0.49 | 2.07 | Good |

Figure 20D

| TAF145 45 min 37 deg - UP | | | | | | | | | Average | | | |
|---|---|---|---|---|---|---|---|---|---|---|---|---|
| Gene | WT1val | WT1ca | MT1val | MT1ca | WT2val | WT2ca | MT2ca | MT1/WT1 | MT2/WT2 | Fold Up | Corrected? | Confidence |
| ALD4 (YMR169C) | -5 | A | 56 | P | 23 | P | 77 | P | -10.53 | 3.33 | 7.8 | Yes | Med |
| ARG3 (YJL088W) | 64 | P | 144 | P | 66 | P | 172 | P | 2.23 | 2.58 | 2.4 | | Exc |
| ASP3 (YLR157C) (f) | -16 | A | 10 | A | -6 | A | 4 | A | -0.65 | -0.61 | 3.7 | Yes | Med |
| HSP30 (YCR021C) | 332 | P | 714 | P | 340 | P | 711 | P | 2.15 | 2.09 | 2.1 | | Exc |
| HXT17 (YNR072W) | -4 | A | 13 | A | 11 | A | 23 | A | -3.66 | 2.14 | 2.7 | Yes | Med |
| MLS1 (YNL117W) | 0 | A | 28 | A | -7 | A | 7 | A | #DIV/0! | -0.88 | 4.2 | Yes | Med |
| NUF2 (YOL069W) | -19 | A | 4 | A | -10 | A | 51 | A | -0.20 | -5.38 | 8.4 | Yes | Med |
| ORF YBR113W | 29 | P | 64 | P | 18 | A | 43 | P | 2.20 | 2.44 | 2.3 | | Good |
| ORF YBR178W | -9 | A | 6 | A | -23 | A | 1 | A | -0.70 | -0.04 | 3.9 | Yes | Med |
| ORF YBR296C | 1 | A | 12 | P | -2 | A | 16 | A | 11.92 | -7.82 | 7.8 | Yes | Med |
| ORF YCL021W | 16 | P | 33 | P | 6 | A | 16 | M | 2.06 | 2.61 | 2.3 | | Good |
| ORF YCL041C | 0 | A | 27 | P | -3 | A | 17 | P | #DIV/0! | -5.48 | 4.8 | Yes | Med |
| ORF YCL075W | 6 | A | 22 | P | -4 | A | 10 | A | 3.62 | -2.35 | 3.2 | Yes | Med |
| ORF YDL070W | 70 | P | 173 | P | 42 | P | 87 | P | 2.46 | 2.09 | 2.3 | | Exc |
| ORF YDL096C | 15 | P | 30 | P | -4 | A | 7 | M | 2.01 | -1.76 | 2.2 | Yes | Med |
| ORF YDL162C | 1 | A | 20 | P | -19 | A | -4 | A | 19.64 | 0.22 | 11.3 | Yes | Med |
| ORF YDL222C | 92 | P | 255 | P | 118 | P | 315 | P | 2.77 | 2.66 | 2.7 | | Exc |
| ORF YDL247W (r,i) | -7 | A | 17 | A | -2 | A | 13 | M | -2.40 | -6.26 | 3.9 | Yes | Med |
| ORF YDR149C | 3 | A | 25 | A | 7 | A | 22 | M | 8.42 | 3.02 | 5.7 | | Good |
| ORF YDR193W | -5 | A | 30 | A | 5 | A | 15 | A | -6.03 | 2.97 | 5.0 | Yes | Med |
| ORF YDR220C | 8 | A | 32 | P | 9 | A | 20 | A | 3.94 | 2.17 | 3.1 | | Good |
| ORF YDR250C | 5 | A | 20 | A | 0 | A | 11 | P | 4.07 | #DIV/0! | 3.1 | Yes | Med |
| ORF YDR355C | -18 | A | 6 | A | -7 | A | 6 | A | -0.31 | -0.78 | 3.7 | Yes | Med |
| ORF YDR360W | -8 | A | 2 | A | -18 | A | -3 | A | -0.26 | 0.18 | 2.4 | Yes | Med |
| ORF YDR535C exon 1 | -72 | A | -46 | A | -36 | A | -24 | A | 0.64 | 0.67 | 3.8 | Yes | Med |
| ORF YDR535C exon 2 | -58 | A | -9 | A | -48 | A | -18 | A | 0.16 | 0.37 | 7.9 | Yes | Med |
| ORF YDR537C | -34 | A | -18 | A | -37 | A | 1 | A | 0.54 | -0.02 | 5.4 | Yes | Med |
| ORF YER081W | 52 | P | 157 | P | 41 | P | 146 | P | 3.03 | 3.57 | 3.3 | | Exc |
| ORF YHR136C | 73 | P | 232 | P | 51 | P | 145 | P | 3.16 | 2.82 | 3.0 | | Exc |
| ORF YJL077C | -2 | A | 8 | A | -12 | A | 3 | A | -3.85 | -0.22 | 2.4 | Yes | Med |
| ORF YKL171W | 0 | A | 23 | P | -2 | A | 12 | P | #DIV/0! | -5.82 | 3.6 | Yes | Med |
| ORF YKL225W | 6 | A | 133 | P | 41 | P | 100 | P | 21.48 | 2.42 | 12.0 | | Good |

Figure 21A

| | | | | | | | | |
|---|---|---|---|---|---|---|---|---|
| ORF YLR053C | -1 | A | 27 | P | 6 | A | 26 | P | -31.01 | 4.70 | 5.2 | Yes | Med |
| ORF YLR302C | -19 | A | -1 | A | -10 | A | 1 | A | 0.03 | -0.09 | 2.9 | Yes | Med |
| ORF YML083C | 3 | A | 19 | A | 2 | A | 16 | P | 7.22 | 6.47 | 6.8 | | Good |
| ORF YMR107W | 63 | P | 226 | P | 69 | P | 233 | P | 3.59 | 3.36 | 3.5 | | Exc |
| ORF YMR245W | -17 | A | 21 | A | -2 | A | 18 | P | -1.24 | -8.31 | 5.7 | Yes | Med |
| ORF YNL194C | 6 | A | 45 | P | 10 | A | 34 | P | 7.62 | 3.59 | 5.6 | | Good |
| ORF YNL260C | -13 | A | 6 | P | -1 | A | 15 | P | -0.47 | -14.24 | 3.5 | Yes | Med |
| ORF YNR025C | -10 | A | 19 | M | -19 | A | 15 | M | -2.02 | -0.76 | 6.3 | Yes | Med |
| ORF YOR055W | -7 | A | 5 | A | -30 | A | -2 | A | -0.75 | 0.07 | 4.0 | Yes | Med |
| ORF YOR137C | -1 | A | 13 | P | 0 | A | 18 | P | -10.97 | #DIV/0! | 3.2 | Yes | Med |
| ORF YOR225W | -1 | A | 28 | A | 1 | A | 18 | A | -23.88 | 17.09 | 11.5 | Yes | Med |
| ORF YOR282W | 12 | A | 55 | A | -13 | A | 4 | A | 4.65 | -0.32 | 4.0 | Yes | Med |
| ORF YPL200W | -33 | A | -7 | A | -23 | A | 10 | A | 0.21 | -0.43 | 6.0 | Yes | Med |
| ORF YPL250C | 52 | P | 139 | P | 67 | P | 137 | P | 2.64 | 2.05 | 2.3 | | Exc |
| ORF YPR015C | -26 | A | -5 | A | -11 | A | 1 | A | 0.18 | -0.09 | 3.3 | Yes | Med |
| ORF YPR096C | -6 | A | 17 | A | -1 | A | 21 | P | -2.84 | -19.46 | 4.5 | Yes | Med |
| ORF YPR153W | -8 | A | 5 | A | 2 | A | 17 | P | -0.65 | 7.83 | 5.3 | Yes | Med |
| ORF YPR179C | -7 | A | 10 | A | -11 | A | 4 | A | -1.40 | -0.33 | 3.1 | Yes | Med |
| ORF YPR192W | -21 | A | -5 | A | -30 | A | 26 | A | 0.25 | -0.86 | 7.1 | Yes | Med |
| ORF YPR197C | 0 | A | 12 | A | -12 | A | 4 | A | #DIV/0! | -0.35 | 2.7 | Yes | Med |
| PUT4 (YOR348C) | -11 | A | 6 | A | -11 | A | 11 | P | -0.57 | -1.00 | 3.8 | Yes | Med |
| RPI1 (YIL119C) | 8 | M | 19 | P | 0 | A | 12 | P | 2.51 | #DIV/0! | 2.5 | Yes | Med |
| STL1 (YDR536W) | -35 | A | -21 | A | -11 | A | 1 | A | 0.60 | -0.07 | 2.6 | Yes | Med |
| YCRX18c/ (control?) | -7 | A | 8 | A | -10 | A | 6 | A | -1.20 | -0.63 | 3.2 | Yes | Med |
| YCRX19w/ (control?) | -2 | A | 12 | A | 2 | A | 17 | P | -5.96 | 8.22 | 5.5 | Yes | Med |

Figure 21B

| TAF145 45 min 37 deg, Down | | | | | | | Average | | |
|---|---|---|---|---|---|---|---|---|---|
| | WT1val | WT1cMT1val | MT1cWT2val | WT2cMT2val | MT2c | MT1/WT1 | MT2/WT2 | Fold Down | Fit | Confidence |
| ORF YNR051C | 52 P | 0 A | 49 P | 1 A | 0.00 | 0.01 | 193.81 | <5 min | Good |
| ORF YIL122W | 19 P | 4 A | 22 P | -4 A | 0.22 | -0.20 | 85.56 | <5 min | Good |
| KSS1 (YGR040W) | 29 P | 6 A | 27 P | -5 A | 0.22 | -0.19 | 79.75 | <5 min | Good |
| ORF YIL056W | 54 P | 5 A | 49 P | -3 A | 0.10 | -0.07 | 72.76 | <5 min | Good |
| BRR2 (YER172C) | 79 P | 1 A | 29 P | 1 A | 0.01 | 0.03 | 54.80 | <5 min | Good |
| ORF YDR279W | 17 P | -1 A | 19 P | 2 A | -0.04 | 0.09 | 43.78 | <5 min | Good |
| ORF YPL125W | 27 P | -4 A | 64 P | 12 A | -0.14 | 0.19 | 40.35 | <5 min | Good |
| ORF YNL256W | 51 P | -8 A | 54 P | 11 A | -0.15 | 0.20 | 36.58 | <5 min | Good |
| ORF YBR220C | 51 P | -13 A | 39 P | 12 A | -0.25 | 0.31 | 32.60 | <5 min | Good |
| PAC1 (YOR269W) | 70 P | -12 A | 40 P | 11 P | -0.18 | 0.27 | 20.04 | <5 min | Good |
| ORF YEL023C | 20 P | 4 A | 111 P | -9 A | 0.19 | -0.08 | 18.72 | <5 min | Good |
| ORF YNL227C | 42 P | 2 A | 39 P | 4 A | 0.06 | 0.09 | 13.78 | <5 min | Good |
| ORF YOL165C (_r) | 49 P | 11 P | 21 P | -2 A | 0.22 | -0.07 | 13.41 | <5 min | Good |
| ORF YPL141C | 49 P | -1 A | 36 P | 6 M | -0.02 | 0.17 | 13.18 | <5 min | Good |
| ORF YJL033W | 42 P | 4 A | 34 P | 2 A | 0.10 | 0.05 | 13.02 | <5 min | Good |
| MCM3 (YEL032W) | 89 P | 3 A | 70 P | 9 A | 0.04 | 0.12 | 12.52 | <5 min | Good |
| ORF YPR117W | 16 P | -1 A | 25 P | 6 P | -0.05 | 0.24 | 10.66 | <5 min | Good |
| ORF YDR222W | 30 P | 4 A | 33 P | 2 A | 0.12 | 0.07 | 10.51 | <5 min | Good |
| ORF YHR182W | 58 P | 11 A | 55 P | 0 A | 0.19 | 0.00 | 10.43 | <5 min | Good |
| ORF YGR021W | 61 P | 17 A | 61 P | -5 A | 0.28 | -0.09 | 10.36 | <5 min | Good |
| ORF YML111W | 36 P | 3 A | 27 P | 3 A | 0.07 | 0.13 | 10.09 | <5 min | Good |
| ORF YGR198W | 36 P | 3 A | 44 P | 5 A | 0.09 | 0.12 | 9.71 | <5 min | Good |
| SNM1 (YMR137C) | 19 P | 7 P | 12 P | -2 A | 0.36 | -0.15 | 9.37 | <5 min | Good |
| ORF YBL094C | 25 P | 3 A | 59 P | 6 M | 0.11 | 0.11 | 9.01 | <5 min | Good |
| ORF YHR036W | 44 P | 11 A | 27 P | -1 A | 0.26 | -0.03 | 8.95 | <5 min | Good |
| ORF YNL023C | 178 P | 21 P | 114 P | 13 A | 0.12 | 0.11 | 8.78 | <5 min | Good |
| ORF YMR247C | 76 P | 6 A | 68 P | 10 A | 0.08 | 0.15 | 8.73 | <5 min | Good |
| ORF YMR253C | 29 P | 9 P | 39 P | -4 A | 0.32 | -0.09 | 8.59 | <5 min | Good |
| ORF YLR137W | 45 P | -2 A | 28 P | 8 A | -0.05 | 0.28 | 8.50 | <5 min | Good |
| ORF YMR014W | 83 P | 17 P | 33 P | 2 A | 0.20 | 0.05 | 7.96 | <5 min | Good |
| RAD3 (YER171W) | 39 P | 5 A | 45 P | 6 A | 0.12 | 0.13 | 7.79 | <5 min | Good |

Figure 22A

| | | | | | | | |
|---|---|---|---|---|---|---|---|
| ORF YNL273W | 31 | P | 5 | A | 36 | P | 4 | A | 0.15 | 0.11 | 7.67 | <5 min | Good |
| ORF YPL077C | 30 | P | 4 | A | 19 | P | 3 | P | 0.13 | 0.13 | 7.66 | <5 min | Good |
| ORF YDR094W | 58 | P | 4 | A | 52 | P | 11 | P | 0.06 | 0.20 | 7.58 | <5 min | Good |
| MKC7 (YDR144C) | 95 | P | 13 | P | 78 | P | 10 | A | 0.14 | 0.13 | 7.53 | <5 min | Good |
| BIM1 (YER016W) | 41 | P | 3 | A | 50 | P | 10 | A | 0.08 | 0.19 | 7.45 | <5 min | Good |
| ORF YOR390W (_f) | 29 | P | 15 | P | 32 | P | -9 | A | 0.54 | -0.27 | 7.44 | <5 min | Good |
| MDM1 (YML104C) | 38 | P | 4 | M | 16 | P | 3 | A | 0.11 | 0.16 | 7.39 | <5 min | Good |
| ORF YLR419W | 36 | P | 3 | A | 44 | P | 8 | P | 0.09 | 0.19 | 7.31 | <5 min | Good |
| PPT1 (YGR123C) | 54 | P | 11 | A | 54 | P | 4 | A | 0.20 | 0.08 | 7.20 | <10 min | Good |
| ORF YGL180W | 17 | P | 4 | A | 26 | P | 1 | A | 0.26 | 0.03 | 6.91 | <5 min | Good |
| ORF YOR381W | 21 | P | -3 | A | 25 | P | 11 | P | -0.14 | 0.44 | 6.86 | <5 min | Good |
| ORF YBL077W | 39 | P | 3 | A | 22 | P | 5 | A | 0.07 | 0.22 | 6.77 | <5 min | Good |
| CBF2 (YGR140W) | 40 | P | 14 | P | 26 | P | -2 | A | 0.36 | -0.07 | 6.76 | <10 min | Good |
| ORF YGR260W | 234 | P | 37 | P | 231 | P | 32 | P | 0.16 | 0.14 | 6.75 | <10 min | Excl |
| ORF YKR004C | 27 | P | 2 | A | 18 | P | 4 | A | 0.06 | 0.24 | 6.71 | <5 min | Good |
| ORF YHR062C | 64 | P | 11 | M | 51 | P | 7 | A | 0.16 | 0.14 | 6.66 | <5 min | Good |
| ORF YDR141C | 64 | P | 11 | M | 48 | P | 6 | A | 0.16 | 0.14 | 6.66 | <5 min | Good |
| ORF YPR010C | 526 | P | 89 | P | 604 | P | 79 | P | 0.17 | 0.13 | 6.65 | <10 min | Excl |
| ORF YEL055C | 53 | P | 14 | P | 71 | P | 3 | A | 0.27 | 0.04 | 6.54 | <10 min | Good |
| ORF YPL012W | 190 | P | 34 | P | 273 | P | 36 | P | 0.18 | 0.13 | 6.42 | <10 min | Excl |
| PET54 (YGR222W) | 82 | P | 16 | P | 51 | P | 6 | A | 0.19 | 0.12 | 6.41 | <5 min | Good |
| ORF YMR166C | 74 | P | 6 | M | 54 | P | 13 | P | 0.08 | 0.23 | 6.38 | <5 min | Good |
| ORF YHR175W | 66 | P | 19 | P | 28 | P | 1 | A | 0.28 | 0.03 | 6.38 | <5 min | Good |
| ORF YGR245C | 111 | P | 13 | P | 100 | P | 20 | P | 0.12 | 0.20 | 6.37 | <10 min | Excl |
| ORF YER071C | 74 | P | 18 | P | 86 | P | 6 | A | 0.24 | 0.07 | 6.37 | <5 min | Good |
| ORF YNR008W | 62 | P | 3 | A | 32 | P | 9 | P | 0.05 | 0.27 | 6.28 | <5 min | Good |
| ORF YER077C | 67 | P | 12 | P | 66 | P | 10 | A | 0.18 | 0.14 | 6.26 | <5 min | Good |
| ORF YBR176W | 44 | P | -8 | A | 33 | P | 17 | P | -0.19 | 0.51 | 6.21 | <5 min | Good |
| ORF YER146W | 222 | P | 39 | P | 252 | P | 37 | P | 0.18 | 0.15 | 6.15 | <5 min | Excl |
| TRK1 (YJL129C) | 75 | P | 16 | M | 65 | P | 8 | A | 0.21 | 0.12 | 6.14 | <5 min | Good |
| MIP1 (YOR330C) | 45 | P | 6 | A | 45 | P | 9 | A | 0.14 | 0.19 | 6.10 | <5 min | Good |
| BIO2 (YGR286C) | 60 | P | 5 | A | 52 | P | 13 | A | 0.08 | 0.25 | 6.09 | <10 min | Good |
| SPE2 (YOL052C) | 123 | P | 16 | P | 105 | P | 21 | P | 0.13 | 0.20 | 6.01 | <5 min | Excl |
| SCP160 (YJL080C) | 180 | P | 39 | P | 248 | P | 29 | P | 0.22 | 0.12 | 5.99 | <10 min | Excl |

Figure 22B

| | | | | | | | |
|---|---|---|---|---|---|---|---|
| ENA5 (YDR038C) | 159 | P | 23 | P | 120 | P | 23 | P | 0.15 | 0.19 | 5.98 | <5 min | Excl |
| ORF YDL219W exon | 259 | P | 39 | P | 222 | P | 41 | P | 0.15 | 0.19 | 5.96 | <10 min | Excl |
| ORF YGR156W | 24 | P | 12 | P | 36 | P | -5 | A | 0.48 | -0.14 | 5.91 | <5 min | Good |
| ORF YIL091C | 71 | P | 22 | P | 66 | P | 2 | A | 0.31 | 0.03 | 5.90 | <5 min | Good |
| CAM1 (YPL048W) | 292 | P | 48 | P | 251 | P | 44 | P | 0.16 | 0.18 | 5.88 | <5 min | Excl |
| ORF YLR426W exon | 40 | P | 8 | A | 77 | P | 11 | A | 0.20 | 0.15 | 5.85 | <5 min | Good |
| ORF YNL126W | 31 | P | 0 | A | 19 | P | 7 | A | 0.00 | 0.34 | 5.83 | <5 min | Good |
| ORF YIL014W | 131 | P | 30 | P | 99 | P | 11 | A | 0.23 | 0.11 | 5.79 | <10 min | Good |
| ORF YPL049C | 131 | P | 30 | A | 119 | P | 14 | P | 0.23 | 0.12 | 5.76 | <10 min | Good |
| ORF YGL257C | 40 | P | 15 | A | 43 | P | -2 | A | 0.39 | -0.04 | 5.71 | <10 min | Excl |
| ORF YER110C | 149 | P | 28 | P | 155 | P | 26 | P | 0.19 | 0.17 | 5.66 | <10 min | Good |
| ORF YKR012C | 65 | P | 7 | M | 27 | P | 7 | P | 0.10 | 0.25 | 5.61 | <5 min | Good |
| ORF YBL004W | 104 | P | 17 | P | 42 | P | 8 | A | 0.16 | 0.20 | 5.60 | <5 min | Good |
| SWI4 (YER111C) | 24 | P | 11 | P | 54 | P | -4 | A | 0.44 | -0.08 | 5.59 | <10 min | Good |
| ATF2 (YGR177C) | 23 | P | 9 | A | 24 | P | -1 | A | 0.40 | -0.04 | 5.56 | <5 min | Good |
| RAD5 (YLR032W) | 60 | P | 5 | A | 25 | P | 7 | A | 0.09 | 0.27 | 5.56 | <5 min | Good |
| ORF YBR272C | 44 | P | 13 | A | 42 | P | 2 | A | 0.30 | 0.06 | 5.53 | <5 min | Good |
| ORF YLR106C | 78 | P | 14 | P | 89 | P | 16 | P | 0.18 | 0.18 | 5.49 | <5 min | Excl |
| ORF YMR171C | 46 | P | 5 | A | 24 | P | 6 | A | 0.11 | 0.25 | 5.49 | <5 min | Good |
| ORF YIL173W (_f) | 26 | P | 3 | A | 23 | P | 6 | A | 0.10 | 0.26 | 5.49 | <10 min | Good |
| RPA190 (YOR341W) | 93 | P | 23 | P | 139 | P | 16 | P | 0.25 | 0.12 | 5.49 | <10 min | Excl |
| ORF YER190W (_f) | 610 | P | 141 | P | 662 | P | 88 | P | 0.23 | 0.13 | 5.48 | <10 min | Excl |
| ORF YMR128W | 128 | P | 25 | P | 101 | P | 17 | P | 0.19 | 0.17 | 5.48 | <10 min | Good |
| ORF YHR054C (_r) | 60 | P | 23 | P | 66 | P | -1 | A | 0.38 | -0.01 | 5.46 | <5 min | Excl |
| PHO3 (YBR092C) | 288 | P | 50 | P | 217 | P | 41 | P | 0.18 | 0.19 | 5.46 | <10 min | Excl |
| ORF YLR087C | 28 | P | 3 | A | 19 | P | 5 | M | 0.09 | 0.28 | 5.45 | <5 min | Good |
| ORF YPL270W | 48 | P | 5 | A | 59 | P | 15 | P | 0.11 | 0.25 | 5.45 | <5 min | Good |
| YTX1 (YHR119W) | 49 | P | 15 | P | 64 | P | 3 | A | 0.31 | 0.05 | 5.44 | <5 min | Good |
| ORF YLR453C | 53 | P | 3 | M | 15 | P | 5 | P | 0.05 | 0.32 | 5.42 | <5 min | Good |
| ORF YBR075W | 110 | P | 22 | M | 74 | P | 12 | A | 0.20 | 0.17 | 5.42 | <10 min | Good |
| ORF YJR110W | 30 | P | 5 | A | 32 | P | 7 | P | 0.15 | 0.22 | 5.40 | <5 min | Good |
| ORF YGR272C | 1390 | P | 241 | P | 1298 | P | 257 | P | 0.17 | 0.20 | 5.39 | <10 min | Excl |
| TRX1 (YLR043C) | 617 | P | 123 | P | 594 | P | 105 | P | 0.20 | 0.18 | 5.34 | <5 min | Excl |
| SJH1 (YIL002C) | 31 | P | 9 | A | 40 | P | 3 | A | 0.29 | 0.09 | 5.30 | <5 min | Good |
| ORF YCR060W | 177 | P | 34 | P | 150 | P | 28 | P | 0.19 | 0.18 | 5.30 | <5 min | Excl |
| ORF YPR204W (_f) | 609 | P | 122 | P | 747 | P | 134 | P | 0.20 | 0.18 | 5.28 | <10 min | Excl |

Figure 22C

| | | | | | | | | |
|---|---|---|---|---|---|---|---|---|
| PEA2 (YER149C) | 42 | P | 10 | A | 70 | P | 10 | A | 0.23 | 0.15 | 5.28 | <10 min | Good |
| MIS1 (YBR084W) | 182 | P | 38 | P | 133 | P | 23 | P | 0.21 | 0.17 | 5.27 | <10 min | Excl |
| ORF YNL282W | 31 | P | -2 | A | 51 | P | 22 | A | -0.05 | 0.44 | 5.19 | <5 min | Good |
| ORF YPR003C | 26 | P | 2 | A | 28 | P | 9 | A | 0.06 | 0.33 | 5.16 | <5 min | Good |
| BAS1 (YKR099W) | 108 | P | 26 | P | 96 | P | 14 | P | 0.24 | 0.15 | 5.15 | <10 min | Excl |
| ORF YJL109C | 165 | P | 41 | P | 134 | P | 19 | P | 0.25 | 0.14 | 5.14 | <10 min | Excl |
| ORF YDR027C | 54 | P | 21 | P | 79 | P | 0 | A | 0.39 | 0.00 | 5.13 | <5 min | Good |
| ORF YPL273W | 253 | P | 68 | P | 300 | P | 37 | P | 0.27 | 0.12 | 5.10 | <10 min | Excl |
| APS1 (YLR170C) | 198 | P | 36 | P | 193 | P | 41 | P | 0.18 | 0.21 | 5.09 | <5 min | Excl |
| ORF YNL186W | 399 | P | 72 | P | 288 | P | 62 | P | 0.18 | 0.22 | 5.07 | <10 min | Excl |
| ORF YMR215W | 129 | P | 27 | P | 146 | P | 27 | P | 0.21 | 0.19 | 5.06 | <5 min | Good |
| ORF YGR151C (_r) | 222 | P | 40 | P | 185 | P | 40 | M | 0.18 | 0.22 | 5.06 | <10 min | Good |
| ORF YDL031W | 153 | P | 25 | M | 73 | P | 17 | P | 0.16 | 0.23 | 5.06 | <5 min | Excl |
| ORF YLR384C | 108 | P | 25 | P | 115 | P | 19 | P | 0.24 | 0.16 | 5.05 | <5 min | Good |
| ORF YMR321C (_l) | 446 | P | 118 | P | 572 | P | 76 | P | 0.26 | 0.13 | 5.05 | <10 min | Excl |
| ORF YMR160W | 25 | P | 5 | A | 23 | P | 5 | P | 0.19 | 0.21 | 5.05 | <5 min | Good |
| CDC46 (YLR274W) | 111 | P | 101 | A | 57 | P | 17 | P | 0.09 | 0.30 | 5.03 | <5 min | Good |
| ARD1 (YHR013C) | 102 | P | 28 | P | 93 | P | 11 | P | 0.28 | 0.12 | 5.03 | <10 min | Excl |
| ORF YHL050C exon_r | 778 | P | 168 | P | 814 | P | 150 | P | 0.22 | 0.18 | 5.01 | <10 min | Excl |
| ORF YOR193W | 26 | P | 2 | A | 27 | P | 9 | A | 0.06 | 0.34 | 4.99 | <5 min | Good |
| RAD50 (YNL250W) | 92 | P | 14 | A | 20 | P | 5 | A | 0.15 | 0.25 | 4.99 | <5 min | Good |
| ORF YDR097C | 62 | P | 26 | P | 58 | P | -1 | A | 0.42 | -0.01 | 4.94 | <10 min | Good |
| ORF YFR008W | 28 | P | 3 | A | 42 | P | 13 | A | 0.10 | 0.31 | 4.93 | <5 min | Good |
| ORF YEL044W | 156 | P | 32 | P | 141 | P | 29 | P | 0.20 | 0.20 | 4.91 | <10 min | Excl |
| ORF YOL054W | 55 | P | 13 | A | 59 | P | 10 | P | 0.24 | 0.17 | 4.90 | <10 min | Good |
| ORF YDL019C | 66 | P | 7 | A | 59 | P | 18 | P | 0.11 | 0.30 | 4.90 | <10 min | Good |
| ORF YPL183C | 76 | P | 13 | P | 57 | P | 14 | P | 0.17 | 0.24 | 4.89 | <10 min | Excl |
| ORF YDR407C | 31 | P | 17 | A | 36 | P | -5 | A | 0.54 | -0.13 | 4.89 | <5 min | Good |
| PSD2 (YGR170W) | 33 | P | 9 | A | 40 | P | 6 | A | 0.26 | 0.15 | 4.89 | <5 min | Good |
| DHS1 (YOR033C) | 89 | P | 121 | A | 57 | P | 16 | P | 0.13 | 0.28 | 4.87 | <5 min | Good |
| GCN1 (YGL195W) | 189 | P | 51 | P | 175 | P | 25 | P | 0.27 | 0.14 | 4.87 | <5 min | Excl |
| ORF YOR342C | 150 | P | 29 | P | 178 | P | 39 | P | 0.19 | 0.22 | 4.85 | <10 min | Excl |

Figure 22D

| | | | | | | | |
|---|---|---|---|---|---|---|---|
| RFC1 (YOR217W) | 58 P | 12 A | 72 P | 16 P | 0.20 | 0.22 | 4.83 <10 min | Good |
| ORF YNL283C | 85 P | 23 P | 106 P | 15 P | 0.27 | 0.14 | 4.82 <10 min | Excl |
| KIP2 (YPL155C) | 16 P | 4 A | 36 P | 6 A | 0.25 | 0.17 | 4.81 <5 min | Good |
| ORF YJL162C | 36 P | 8 P | 18 P | 3 A | 0.23 | 0.19 | 4.81 <10 min | Good |
| ASN2 (YGR124W) | 368 P | 88 P | 354 P | 63 P | 0.24 | 0.18 | 4.78 <10 min | Good |
| ORF YJR079W exon 1 | 167 P | 25 M | 73 P | 20 P | 0.15 | 0.27 | 4.77 <5 min | Excl |
| DPM1 (YPR183W) | 131 P | 23 A | 155 P | 38 P | 0.18 | 0.24 | 4.76 <10 min | Good |
| ORF YFL066C (_f) | 108 P | 35 P | 91 P | 9 A | 0.32 | 0.10 | 4.76 <10 min | Good |
| ORF YPR011C | 78 P | 14 P | 48 P | 12 P | 0.18 | 0.24 | 4.75 <10 min | Excl |
| ORF YGR089W | 41 P | 8 P | 27 P | 6 A | 0.20 | 0.23 | 4.74 <5 min | Good |
| ORF YDR213W | 45 P | 11 A | 34 P | 6 A | 0.23 | 0.19 | 4.72 <5 min | Good |
| ORF YOR109W | 97 P | 22 M | 103 P | 21 A | 0.22 | 0.20 | 4.72 <10 min | Good |
| IMP1 (YMR150C) | 117 P | 24 M | 131 P | 29 P | 0.21 | 0.22 | 4.70 <5 min | Good |
| ORF YHR032W | 127 P | 37 P | 94 P | 13 A | 0.29 | 0.14 | 4.68 <10 min | Good |
| ORF YFR016C | 81 P | 24 A | 84 P | 11 A | 0.30 | 0.13 | 4.66 <10 min | Good |
| ORF YGR296W exon | 699 P | 150 P | 780 P | 168 P | 0.21 | 0.22 | 4.65 <10 min | Excl |
| ORF YER089C | 113 P | 19 A | 176 P | 47 P | 0.16 | 0.27 | 4.64 <10 min | Good |
| ORF YDR512C | 84 P | 25 M | 75 P | 10 A | 0.30 | 0.13 | 4.64 <10 min | Good |
| ORF YGL164C | 54 P | 11 A | 45 P | 10 A | 0.21 | 0.23 | 4.59 <5 min | Good |
| ORF YGR283C | 96 P | 35 P | 85 P | 6 A | 0.36 | 0.07 | 4.59 <5 min | Good |
| SLN1 (YIL147C) | 72 P | 16 P | 62 P | 13 A | 0.23 | 0.21 | 4.55 <10 min | Good |
| ORF YNL132W | 105 P | 36 P | 138 P | 13 M | 0.34 | 0.09 | 4.55 <10 min | Good |
| ORF YML102W | 58 P | 11 A | 48 P | 12 P | 0.20 | 0.24 | 4.55 <5 min | Good |
| TFC4 (YGR047C) | 47 P | 9 A | 50 P | 13 A | 0.18 | 0.26 | 4.54 <5 min | Good |
| ORF YOL012C | 73 P | 18 P | 70 P | 13 M | 0.25 | 0.19 | 4.54 <10 min | Good |
| ORF YJR001W | 52 P | 10 P | 61 P | 15 P | 0.20 | 0.24 | 4.53 <10 min | Excl |
| ORF YDR545W (_f) | 452 P | 101 P | 450 P | 98 P | 0.22 | 0.22 | 4.53 <10 min | Excl |
| ORF YLR390W | 105 P | 25 P | 103 P | 21 A | 0.24 | 0.21 | 4.53 <10 min | Good |
| GDA1 (YEL042W) | 82 P | 9 A | 51 P | 17 A | 0.10 | 0.34 | 4.52 <10 min | Good |
| ORF YHR020W | 415 P | 110 P | 429 P | 76 P | 0.27 | 0.18 | 4.51 <10 min | Excl |
| ORF YMR016C | 69 P | 11 P | 50 P | 14 P | 0.17 | 0.28 | 4.51 <10 min | Excl |
| FMI1 (YMR229C) | 172 P | 37 P | 144 P | 33 P | 0.21 | 0.23 | 4.50 <10 min | Excl |
| ORF YNL339C exon | 698 P | 209 P | 1046 P | 152 P | 0.30 | 0.15 | 4.49 <10 min | Excl |
| ORF YPL283C exon | 565 P | 161 P | 756 P | 122 P | 0.28 | 0.16 | 4.49 <10 min | Excl |
| ORF YHR029C | 55 P | 17 P | 77 P | 10 A | 0.31 | 0.14 | 4.48 <5 min | Excl |
| ORF YGR090W | 179 P | 37 P | 171 P | 41 P | 0.21 | 0.24 | 4.48 <10 min | Excl |
| ORF YBR216C | 25 P | 15 P | 24 P | -4 A | 0.62 | -0.17 | 4.47 <5 min | Good |

Figure 22E

| | | | | | | | | |
|---|---|---|---|---|---|---|---|---|
| SRP40 (YKR092C) | 150 P | 42 P | 97 P | 16 P | 0.28 | 0.17 | 4.47 | <10 min | Excl |
| TEF4 (YKL081W) exc | 264 P | 61 P | 213 P | 47 P | 0.23 | 0.22 | 4.47 | <10 min | Excl |
| HST2 (YPL015C) | 44 P | 12 A | 48 P | 8 M | 0.28 | 0.17 | 4.47 | <10 min | Good |
| ORF YGL120C | 206 P | 53 P | 178 P | 34 P | 0.26 | 0.19 | 4.46 | <10 min | Excl |
| ORF YBL111C exon | 113 P | 19 P | 81 P | 23 P | 0.17 | 0.28 | 4.46 | <10 min | Excl |
| NUP145 (YGL092W) | 89 P | 21 P | 105 P | 23 P | 0.23 | 0.21 | 4.46 | <10 min | Excl |
| ORF YHR219W (_f) | 601 P | 128 P | 633 P | 150 P | 0.21 | 0.24 | 4.45 | <10 min | Excl |
| CDC39 (YCR093W) | 56 P | 14 P | 45 P | 9 A | 0.25 | 0.20 | 4.44 | <5 min | Good |
| VAS1 (YGR094W) | 428 P | 108 P | 352 P | 70 P | 0.25 | 0.20 | 4.42 | <10 min | Excl |
| ORF YER166W | 45 P | 14 P | 45 P | 6 A | 0.32 | 0.13 | 4.42 | <10 min | Good |
| ORF YNL193W | 23 P | 3 A | 29 P | 9 P | 0.14 | 0.32 | 4.42 | <5 min | Good |
| ORF YOR229W | 93 P | 29 P | 84 P | 12 A | 0.31 | 0.14 | 4.42 | <10 min | Good |
| ORF YPR112C | 180 P | 32 P | 119 P | 33 P | 0.18 | 0.28 | 4.40 | <10 min | Excl |
| ORF YBR210W | 114 P | 34 P | 63 P | 10 A | 0.30 | 0.15 | 4.39 | <5 min | Good |
| ORF YBL112C (_f) | 220 P | 41 P | 125 P | 33 P | 0.19 | 0.27 | 4.39 | <10 min | Excl |
| ORF YNL029C | 61 P | 16 A | 74 P | 14 A | 0.27 | 0.19 | 4.39 | <5 min | Good |
| ORF YDR119W | 64 P | 20 P | 65 P | 10 P | 0.31 | 0.15 | 4.39 | <10 min | Excl |
| ORF YHR207C | 69 P | 18 P | 66 P | 13 A | 0.26 | 0.20 | 4.38 | <10 min | Good |
| ESR1 (YBR136W) | 49 P | 15 A | 36 P | 6 A | 0.30 | 0.16 | 4.38 | <5 min | Good |
| ORF YJL066C | 60 P | 23 P | 61 P | 4 A | 0.39 | 0.07 | 4.34 | <5 min | Good |
| ORF YPL142C | 48 P | 12 P | 37 P | 8 A | 0.26 | 0.20 | 4.33 | <5 min | Good |
| ORF YNL021W | 74 P | 7 A | 52 P | 19 P | 0.09 | 0.37 | 4.33 | <10 min | Good |
| ORF YDR179W-A | 23 P | 15 P | 23 P | -4 A | 0.64 | -0.18 | 4.32 | <5 min | Good |
| BUD4 (YJR092W) | 50 P | 2 A | 36 P | 15 P | 0.04 | 0.42 | 4.30 | <5 min | Good |
| ORF YGL064C | 34 P | 3 A | 23 P | 9 A | 0.09 | 0.37 | 4.29 | <10 min | Good |
| ORF YMR029C | 45 P | 3 M | 26 P | 10 P | 0.07 | 0.40 | 4.28 | <5 min | Good |
| ORF YML093W | 126 P | 34 P | 71 P | 14 P | 0.27 | 0.20 | 4.28 | <10 min | Excl |
| HFA1 (YMR207C) | 31 P | 1 A | 37 P | 16 P | 0.03 | 0.43 | 4.28 | <5 min | Good |
| RAM1 (YDL090C) | 53 P | 9 A | 38 P | 11 P | 0.17 | 0.30 | 4.27 | <10 min | Good |
| ORF YMR102C | 82 P | 18 P | 71 P | 18 P | 0.21 | 0.25 | 4.27 | <10 min | Excl |
| ORF YFL024C | 42 P | 14 P | 49 P | 6 A | 0.35 | 0.12 | 4.26 | <10 min | Good |

Figure 22F

| | | | | | | | |
|---|---|---|---|---|---|---|---|
| ORF YDR326C | 57 P | 12 P | 53 P | 14 P | 0.21 | 0.26 | 4.26 <5 min | Excl |
| ORF YLR467W (_f) | 710 P | 170 P | 614 P | 142 P | 0.24 | 0.23 | 4.25 <10 min | Excl |
| ORF YLR456W | 36 P | 3 A | 27 P | 11 P | 0.07 | 0.40 | 4.22 <10 min | Good |
| ARG11 (YOR130C) | 30 P | 12 A | 52 P | 5 A | 0.39 | 0.09 | 4.22 <10 min | Good |
| ORF YEL077C (_f) | 396 P | 95 P | 489 P | 115 P | 0.24 | 0.24 | 4.20 <10 min | Excl |
| MYO1 (YHR023W) | 62 P | 11 P | 65 P | 20 P | 0.17 | 0.31 | 4.20 <5 min | Excl |
| ORF YDR334W | 48 P | 14 P | 35 P | 6 A | 0.29 | 0.18 | 4.20 <5 min | Good |
| ORF YOR034C | 72 P | 24 P | 93 P | 14 A | 0.33 | 0.15 | 4.17 <5 min | Good |
| KIN4 (YOR233W) | 81 P | 25 P | 85 P | 14 P | 0.31 | 0.17 | 4.17 <10 min | Excl |
| AAC1 (YMR056C) | 74 P | 13 P | 56 P | 17 P | 0.17 | 0.31 | 4.17 <10 min | Excl |
| SEN1 (YLR430W) | 70 P | 17 P | 44 P | 10 M | 0.24 | 0.24 | 4.15 <5 min | Good |
| ORF YLL066C exon 2 | 880 P | 193 P | 717 P | 188 P | 0.22 | 0.26 | 4.15 <10 min | Excl |
| ORF YGR199W | 85 P | 30 P | 91 P | 111 A | 0.36 | 0.12 | 4.15 <10 min | Good |
| CBP2 (YHL038C) | 45 P | 22 P | 35 P | 0 A | 0.48 | 0.00 | 4.13 <5 min | Good |
| ORF YNL087W | 63 P | 16 P | 88 P | 20 P | 0.26 | 0.23 | 4.13 <10 min | Excl |
| ORF YMR218C | 50 P | 12 A | 40 P | 10 P | 0.25 | 0.24 | 4.12 <10 min | Good |
| ARG81 (YML099C) | 27 P | 14 P | 40 P | -1 A | 0.51 | -0.02 | 4.10 <10 min | Good |
| NUP188 (YML103C) | 95 P | 23 P | 64 P | 16 P | 0.25 | 0.24 | 4.09 <5 min | Excl |
| ORF YML133C exon | 665 P | 163 P | 599 P | 146 P | 0.25 | 0.24 | 4.09 <10 min | Excl |
| ORF YBR125C | 75 P | 29 P | 76 P | 7 A | 0.39 | 0.10 | 4.09 <10 min | Excl |
| ORF YDL112W | 135 P | 27 P | 110 P | 32 P | 0.20 | 0.29 | 4.08 <10 min | Excl |
| BCK1 (YJL095W) | 43 P | 14 P | 26 P | 4 A | 0.32 | 0.17 | 4.07 <10 min | Excl |
| ORF YJR030C | 42 P | 7 M | 34 P | 11 P | 0.16 | 0.33 | 4.07 <5 min | Good |
| ORF YKL033W | 42 P | 9 P | 38 P | 10 A | 0.22 | 0.27 | 4.07 <5 min | Good |
| ORF YBR017C | 23 P | 12 M | 33 P | -1 A | 0.52 | -0.02 | 4.05 <5 min | Good |
| ORF YIL151C | 49 P | 13 P | 52 P | 12 A | 0.26 | 0.23 | 4.04 <5 min | Good |
| ORF YPL093W | 357 P | 103 P | 320 P | 67 P | 0.29 | 0.21 | 4.02 <10 min | Excl |
| ORF YDL231C | 34 P | 11 P | 29 P | 5 A | 0.33 | 0.17 | 4.02 <5 min | Good |
| SIN3 (YOL004W) | 125 P | 42 P | 160 P | 26 P | 0.34 | 0.16 | 4.01 <10 min | Excl |
| ORF YLR242C | 39 P | 8 P | 22 P | 6 P | 0.20 | 0.30 | 4.01 <5 min | Good |
| ORF YDR299W | 91 P | 33 P | 77 P | 111 A | 0.36 | 0.14 | 4.00 <10 min | Excl |
| BUD6 (YLR319C) | 34 P | 9 A | 35 P | 9 P | 0.26 | 0.25 | 4.00 <10 min | Good |
| SSB2 (YNL209W) | 986 P | 339 P | 1236 P | 196 P | 0.34 | 0.16 | 3.98 <10 min | Excl |
| TAF145 (YGR274C) | 269 P | 62 P | 246 P | 67 P | 0.23 | 0.27 | 3.98 <5 min | Excl |
| SPO12 (YHR152W) | 136 P | 42 P | 123 P | 24 A | 0.31 | 0.20 | 3.95 <10 min | Good |
| ORF YLL067C exon 2 | 703 P | 171 P | 624 P | 164 P | 0.24 | 0.26 | 3.95 <10 min | Excl |
| ORF YCR046C | 210 P | 50 P | 149 P | 40 P | 0.24 | 0.27 | 3.95 <10 min | Excl |

Figure 22G

| | | | | | | | | |
|---|---|---|---|---|---|---|---|---|
| MRS3 (YJL133W) | 126 | P | 29 | P | 101 | P | 28 | P | 0.23 | 0.28 | 3.94 | <10 min | Excl |
| ORF YPR037C | 135 | P | 44 | P | 171 | P | 31 | A | 0.33 | 0.18 | 3.93 | <10 min | Good |
| ORC3 (YLL004W) | 75 | P | 21 | P | 65 | P | 15 | P | 0.28 | 0.23 | 3.93 | <10 min | Excl |
| YAR1 (YPL239W) | 287 | P | 72 | P | 322 | P | 83 | P | 0.25 | 0.26 | 3.93 | <5 min | Excl |
| ORF YFL044C | 61 | P | 22 | P | 73 | P | 11 | M | 0.36 | 0.15 | 3.91 | <5 min | Good |
| ORF YKR079C | 65 | P | 16 | P | 71 | P | 19 | P | 0.25 | 0.26 | 3.91 | <10 min | Excl |
| ORF YBL113C (_f) | 438 | P | 118 | P | 333 | P | 81 | P | 0.27 | 0.24 | 3.90 | <10 min | Excl |
| MSI4 (YOR370C) | 218 | P | 62 | P | 266 | P | 61 | P | 0.29 | 0.23 | 3.89 | <5 min | Excl |
| PRP22 (YER013W) | 21 | P | 2 | A | 31 | P | 14 | P | 0.07 | 0.44 | 3.88 | <5 min | Good |
| PWP2 (YCR055C) | 114 | P | 32 | P | 75 | P | 18 | P | 0.28 | 0.24 | 3.88 | <5 min | Excl |
| ORF YDR341C | 595 | P | 185 | P | 535 | P | 110 | P | 0.31 | 0.21 | 3.87 | <10 min | Excl |
| ORF YPL112C | 63 | P | 23 | P | 74 | P | 12 | A | 0.37 | 0.16 | 3.84 | <5 min | Good |
| MYO3 (YKL129C) | 57 | P | 2 | A | 49 | P | 24 | P | 0.04 | 0.49 | 3.83 | <5 min | Good |
| ORF YMR212C | 45 | P | 13 | A | 62 | P | 14 | P | 0.30 | 0.22 | 3.83 | <10 min | Good |
| CDC55 (YGL190C) | 52 | P | 21 | P | 61 | P | 7 | A | 0.41 | 0.11 | 3.82 | <5 min | Good |
| ORF YML029W | 41 | P | 9 | A | 45 | P | 14 | A | 0.22 | 0.31 | 3.81 | <5 min | Good |
| BEM2 (YER155C) | 136 | P | 41 | P | 143 | P | 32 | P | 0.30 | 0.22 | 3.81 | <10 min | Excl |
| NHP6A (YPR052C) | 203 | P | 50 | P | 197 | P | 55 | P | 0.25 | 0.28 | 3.79 | <10 min | Good |
| ORF YNR015W | 119 | P | 33 | P | 117 | P | 29 | P | 0.28 | 0.25 | 3.79 | <10 min | Excl |
| ORF YGR210C | 194 | P | 65 | P | 202 | P | 39 | P | 0.33 | 0.19 | 3.79 | <10 min | Excl |
| ORF YML124C exon t | 251 | P | 49 | P | 191 | P | 64 | P | 0.19 | 0.33 | 3.79 | <5 min | Excl |
| POM152 (YMR129W) | 34 | P | 4 | A | 36 | P | 15 | P | 0.11 | 0.42 | 3.78 | <10 min | Good |
| STH1 (YIL126W) | 61 | P | 16 | P | 54 | P | 14 | A | 0.27 | 0.26 | 3.78 | <10 min | Good |
| FZF1 (YGL254W) | 22 | P | 11 | M | 17 | P | 1 | A | 0.48 | 0.05 | 3.78 | <5 min | Good |
| ORF YIL055C | 30 | P | 13 | M | 36 | P | 3 | A | 0.44 | 0.10 | 3.76 | <5 min | Good |
| ORF YOR066W | 60 | P | 26 | P | 53 | P | 5 | A | 0.44 | 0.09 | 3.75 | <5 min | Good |
| CDC4 (YFL009W) | 80 | P | 28 | P | 91 | P | 17 | P | 0.34 | 0.19 | 3.74 | <10 min | Excl |
| ORF YML010W-B (_i) | 74 | P | 24 | P | 124 | P | 27 | P | 0.32 | 0.22 | 3.73 | <10 min | Excl |
| ORF YOL029C | 64 | P | 22 | P | 76 | P | 15 | P | 0.35 | 0.19 | 3.72 | <5 min | Excl |
| ORF YHR108W | 71 | P | 21 | P | 47 | P | 11 | P | 0.30 | 0.24 | 3.71 | <5 min | Excl |
| ORF YPR128C | 44 | P | 16 | A | 66 | P | 12 | P | 0.37 | 0.18 | 3.69 | <10 min | Good |

Figure 22H

| Name | | | | | | | | |
|---|---|---|---|---|---|---|---|---|
| KSP1 (YHR082C) | 139 | P | 52 | P | 129 | P | 22 | P | 0.38 | 0.17 | 3.68 | <10 min | Excl |
| ORF YPR144C | 95 | P | 32 | P | 92 | P | 20 | A | 0.33 | 0.21 | 3.68 | <10 min | Good |
| PPX1 (YHR201C) | 111 | P | 36 | P | 83 | P | 18 | P | 0.33 | 0.22 | 3.66 | <10 min | Excl |
| UBP11 (YKR098C) | 53 | P | 12 | P | 38 | P | 13 | P | 0.22 | 0.33 | 3.64 | <5 min | Excl |
| MRPL39 (YML009C) | 312 | P | 76 | P | 329 | P | 101 | P | 0.24 | 0.31 | 3.63 | <5 min | Excl |
| SUR4 (YLR372W) | 441 | P | 149 | P | 559 | P | 119 | P | 0.34 | 0.21 | 3.63 | <10 min | Excl |
| KEM1 (YGL173C) | 252 | P | 77 | P | 210 | P | 52 | P | 0.30 | 0.25 | 3.63 | <10 min | Excl |
| CDC20 (YGL116W) | 42 | P | 21 | P | 42 | P | 3 | A | 0.49 | 0.06 | 3.62 | <10 min | Good |
| ORF YJR041C | 34 | P | 0 | M | 16 | P | 9 | P | 0.00 | 0.55 | 3.62 | <5 min | Good |
| SPA2 (YLL021W) | 73 | P | 16 | P | 63 | P | 21 | P | 0.22 | 0.33 | 3.62 | <10 min | Excl |
| SPR6 (YER115C) | 80 | P | 23 | P | 73 | P | 19 | P | 0.29 | 0.26 | 3.61 | <10 min | Excl |
| ORF YBR025C | 939 | P | 262 | P | 710 | P | 196 | P | 0.28 | 0.28 | 3.61 | <10 min | Excl |
| ORF YDR206W | 59 | P | 15 | A | 43 | P | 13 | A | 0.25 | 0.31 | 3.60 | <5 min | Good |
| YOR001W | 167 | P | 33 | P | 116 | P | 41 | P | 0.20 | 0.36 | 3.60 | <10 min | Excl |
| ORF YIR033W | 30 | P | 1 | A | 35 | P | 18 | P | 0.04 | 0.52 | 3.59 | <10 min | Good |
| SCJ1 (YMR214W) | 94 | P | 17 | A | 77 | P | 29 | P | 0.18 | 0.38 | 3.58 | <10 min | Good |
| DPB3 (YBR278W) | 54 | P | 13 | A | 47 | P | 15 | P | 0.25 | 0.31 | 3.57 | <10 min | Excl |
| ORF YAR014C | 64 | P | 21 | P | 46 | P | 11 | P | 0.33 | 0.23 | 3.57 | <10 min | Excl |
| MSI1 (YBR195C) | 45 | P | 19 | P | 52 | P | 7 | A | 0.42 | 0.14 | 3.56 | <10 min | Good |
| ORF YPL134C | 89 | P | 22 | P | 75 | P | 24 | P | 0.24 | 0.32 | 3.56 | <10 min | Excl |
| ORF YLR276C | 192 | P | 47 | P | 134 | P | 43 | P | 0.24 | 0.32 | 3.56 | <10 min | Excl |
| ORF YPR008W | 156 | P | 42 | P | 178 | P | 53 | P | 0.27 | 0.30 | 3.55 | <10 min | Excl |
| ORF YER004W | 204 | P | 63 | P | 241 | P | 62 | P | 0.31 | 0.26 | 3.55 | <5 min | Excl |
| ORF YOR040W | 66 | P | 19 | P | 103 | P | 28 | P | 0.29 | 0.27 | 3.52 | <10 min | Excl |
| SEC7 (YDR170C) | 152 | P | 27 | P | 128 | P | 50 | P | 0.18 | 0.39 | 3.52 | <10 min | Good |
| ORF YOL026C | 112 | P | 44 | P | 125 | P | 22 | A | 0.39 | 0.18 | 3.52 | <5 min | Good |
| ORF YNL140C (_r) | 62 | P | 10 | P | 69 | P | 28 | P | 0.16 | 0.41 | 3.51 | <5 min | Good |
| ORF YIL172C (_l) | 23 | P | 9 | A | 30 | P | 6 | A | 0.37 | 0.20 | 3.49 | <10 min | Good |
| ORF YFR039C | 97 | P | 36 | P | 61 | P | 12 | M | 0.37 | 0.20 | 3.49 | <10 min | Good |
| ORF YLR036C | 37 | P | 14 | P | 40 | P | 7 | P | 0.39 | 0.18 | 3.49 | <10 min | Excl |
| ORF YIL137C | 38 | P | 12 | M | 29 | P | 8 | M | 0.31 | 0.27 | 3.48 | <10 min | Good |
| ORF YHR116W | 70 | P | 20 | P | 36 | P | 10 | A | 0.29 | 0.29 | 3.47 | <10 min | Excl |
| ORF YKL075C | 64 | P | 13 | P | 39 | P | 15 | P | 0.20 | 0.37 | 3.46 | <10 min | Excl |
| ORF YHR056C | 67 | P | 27 | P | 78 | P | 14 | A | 0.40 | 0.18 | 3.46 | <5 min | Good |
| ORF YGL197W | 36 | P | 16 | P | 38 | P | 5 | A | 0.44 | 0.14 | 3.46 | <10 min | Good |
| ORF YHR114W | 58 | P | 20 | P | 54 | P | 13 | P | 0.34 | 0.24 | 3.44 | <10 min | Excl |

Figure 22I

| | | | | | | | | |
|---|---|---|---|---|---|---|---|---|
| ORF YBR194W | 41 P | 7 A | 37 P | 15 P | 0.17 | 0.41 | 3.42 <10 min | Good |
| ORF YFL033C | 65 P | 23 P | 89 P | 20 P | 0.36 | 0.23 | 3.42 <5 min | Excl |
| MAK3 (YPR051W) | 92 P | 27 A | 113 P | 33 P | 0.29 | 0.29 | 3.42 <10 min | Good |
| SEC16 (YPL085W) | 120 P | 42 P | 151 P | 36 P | 0.35 | 0.24 | 3.41 <10 min | Excl |
| GIN10 (YKL173W) | 60 P | 19 P | 42 P | 11 P | 0.32 | 0.27 | 3.40 <10 min | Excl |
| ORF YML010W-A (_r) | 240 P | 63 P | 225 P | 73 P | 0.26 | 0.32 | 3.40 <10 min | Excl |
| ORF YGL160W | 26 P | 2 A | 29 P | 15 A | 0.08 | 0.51 | 3.40 <10 min | Good |
| RPL10E (YLR340W) | 1232 P | 400 P | 1220 P | 327 P | 0.32 | 0.27 | 3.37 <10 min | Excl |
| ORF YER132C | 75 P | 23 P | 72 P | 21 A | 0.31 | 0.29 | 3.37 <5 min | Good |
| SAC1 (YKL212W) | 180 P | 48 P | 128 P | 42 P | 0.27 | 0.33 | 3.36 <5 min | Excl |
| ORF YGR035C | 44 P | 25 P | 37 P | 1 A | 0.57 | 0.02 | 3.36 <5 min | Good |
| ORF YDR045C | 252 P | 76 P | 219 P | 64 P | 0.30 | 0.29 | 3.35 <10 min | Excl |
| ORF YGL211W | 36 P | 14 P | 44 P | 10 A | 0.38 | 0.22 | 3.34 <10 min | Good |
| ORF YFL047W | 69 P | 25 M | 57 P | 14 A | 0.36 | 0.24 | 3.31 <5 min | Good |
| ORF YLR277C | 68 P | 2 A | 30 P | 17 P | 0.03 | 0.57 | 3.30 <5 min | Good |
| SAP190 (YKR028W) | 99 P | 26 P | 90 P | 31 P | 0.26 | 0.34 | 3.30 <5 min | Excl |
| VPH1 (YOR270C) | 925 P | 326 P | 1030 P | 263 P | 0.35 | 0.26 | 3.29 <10 min | Excl |
| ORF YOL070C | 80 P | 22 P | 70 P | 24 P | 0.27 | 0.34 | 3.29 <10 min | Good |
| ORF YNR013C | 106 P | 40 P | 120 P | 28 P | 0.38 | 0.23 | 3.29 <10 min | Excl |
| ORF YCR017C | 133 P | 43 P | 105 P | 30 P | 0.32 | 0.29 | 3.29 <5 min | Excl |
| ORF YDL073W | 33 P | 9 A | 42 P | 14 P | 0.28 | 0.33 | 3.29 <5 min | Good |
| PSE1 (YMR308C) | 410 P | 171 P | 524 P | 102 P | 0.42 | 0.19 | 3.28 <10 min | Excl |
| CMK1 (YFR014C) | 26 P | 7 P | 20 P | 7 A | 0.26 | 0.35 | 3.26 <5 min | Good |
| STV1 (YMR054W) | 156 P | 53 P | 158 P | 44 P | 0.34 | 0.28 | 3.25 <10 min | Excl |
| ORF YNL136W | 87 P | 18 P | 51 P | 21 P | 0.20 | 0.42 | 3.23 <5 min | Excl |
| SSK2 (YNR031C) | 80 P | 31 P | 111 P | 26 P | 0.39 | 0.24 | 3.22 <5 min | Excl |
| NMT1 (YLR195C) | 103 P | 27 P | 69 P | 25 P | 0.26 | 0.36 | 3.22 <10 min | Excl |
| GAL11 (YOL051W) | 123 P | 38 P | 183 P | 57 P | 0.31 | 0.31 | 3.22 <10 min | Excl |
| MYO2 (YOR326W) | 118 P | 45 P | 208 P | 49 P | 0.38 | 0.24 | 3.22 <10 min | Excl |
| ORF YGR196C | 28 P | 8 P | 45 P | 16 P | 0.28 | 0.34 | 3.20 <10 min | Excl |
| ORF YMR040W | 41 P | 6 A | 50 P | 24 P | 0.14 | 0.49 | 3.19 <5 min | Good |
| ORF YIR002C | 57 P | 26 P | 62 P | 10 A | 0.46 | 0.17 | 3.19 <10 min | Good |

Figure 22J

| | | | | | | | | |
|---|---|---|---|---|---|---|---|---|
| FRE2 (YKL220C) | 17 | P | 8 | P | 13 | P | 2 | A | 0.49 | 0.13 | 3.19 | <10 min | Good |
| ORF YLR253W | 27 | P | 9 | A | 28 | P | 8 | P | 0.34 | 0.29 | 3.18 | <10 min | Good |
| CCA1 (YER168C) | 49 | P | 18 | P | 61 | P | 16 | A | 0.37 | 0.26 | 3.17 | <5 min | Good |
| UBP2 (YOR124C) | 172 | P | 62 | P | 210 | P | 56 | P | 0.36 | 0.27 | 3.17 | <10 min | Excl |
| SEC31 (YDL195W) | 375 | P | 107 | P | 240 | P | 83 | P | 0.29 | 0.35 | 3.17 | <5 min | Excl |
| ORF YLR425W | 54 | P | 14 | P | 32 | P | 12 | M | 0.26 | 0.37 | 3.17 | <5 min | Good |
| ORF YIL048W | 70 | P | 23 | P | 85 | P | 26 | P | 0.33 | 0.31 | 3.16 | <10 min | Excl |
| PEP5 (YMR231W) | 37 | P | 12 | A | 32 | P | 10 | A | 0.33 | 0.30 | 3.16 | <10 min | Good |
| YCRX08w/ f (contro | 108 | P | 32 | P | 111 | P | 37 | P | 0.30 | 0.34 | 3.15 | <5 min | Excl |
| ORF YDR091C | 121 | P | 36 | P | 78 | P | 26 | P | 0.30 | 0.33 | 3.15 | <10 min | Excl |
| ORF YER082C | 98 | P | 28 | P | 98 | P | 35 | P | 0.28 | 0.35 | 3.15 | <10 min | Excl |
| SEC61 (YLR378C) | 256 | P | 91 | P | 319 | P | 91 | P | 0.35 | 0.28 | 3.13 | <10 min | Excl |
| POS5 (YPL188W) | 61 | P | 15 | P | 46 | P | 18 | P | 0.25 | 0.39 | 3.13 | <5 min | Excl |
| ORF YGR111W | 46 | P | 28 | P | 49 | P | 2 | A | 0.61 | 0.04 | 3.11 | <10 min | Good |
| VPS15 (YBR097W) | 24 | P | 15 | P | 34 | P | 0 | A | 0.64 | 0.00 | 3.11 | <5 min | Excl |
| HMG2 (YLR450W) | 34 | P | 16 | A | 471 | P | 9 | A | 0.45 | 0.19 | 3.11 | <10 min | Excl |
| CSE1 (YGL238W) | 132 | P | 46 | P | 142 | P | 42 | P | 0.35 | 0.30 | 3.10 | <5 min | Excl |
| RNA1 (YMR235C) | 274 | P | 85 | P | 190 | P | 63 | P | 0.31 | 0.33 | 3.10 | <10 min | Excl |
| ORF YPR125W | 113 | P | 41 | P | 102 | P | 29 | P | 0.36 | 0.29 | 3.09 | <10 min | Excl |
| SNF8 (YPL002C) | 104 | P | 35 | P | 99 | P | 30 | P | 0.34 | 0.31 | 3.09 | <10 min | Good |
| ORF YNL074C | 39 | P | 20 | P | 62 | P | 9 | A | 0.51 | 0.14 | 3.09 | <5 min | Good |
| NDC1 (YML031W) | 69 | P | 17 | P | 63 | P | 25 | P | 0.24 | 0.41 | 3.09 | <10 min | Excl |
| RMS1 (YDR257C) | 36 | P | 8 | A | 53 | P | 22 | P | 0.23 | 0.41 | 3.09 | <5 min | Excl |
| ORF YOL078W | 19 | P | 9 | P | 36 | P | 6 | A | 0.48 | 0.17 | 3.07 | <5 min | Good |
| ORF YML076C | 27 | P | 5 | A | 38 | P | 18 | P | 0.18 | 0.48 | 3.07 | <10 min | Good |
| ORF YGL140C | 58 | P | 19 | P | 59 | P | 19 | A | 0.33 | 0.32 | 3.06 | <10 min | Good |
| PHO87 (YCR037C) | 140 | P | 43 | P | 137 | P | 48 | P | 0.31 | 0.35 | 3.05 | <10 min | Excl |
| AAP1' (YHR047C) | 120 | P | 37 | P | 128 | P | 45 | P | 0.31 | 0.35 | 3.04 | <5 min | Excl |
| KTI12 (YKL110C) | 171 | P | 43 | P | 132 | P | 54 | P | 0.25 | 0.41 | 3.04 | <10 min | Excl |
| ACE2 (YLR131C) | 20 | P | 5 | A | 13 | P | 5 | P | 0.25 | 0.40 | 3.04 | <10 min | Good |
| ORF YDR080W | 36 | P | 16 | P | 73 | P | 15 | A | 0.45 | 0.21 | 3.03 | <5 min | Good |
| DYN1 (YKR054C) | 56 | P | 21 | A | 26 | P | 16 | P | 0.04 | 0.62 | 3.03 | <5 min | Good |
| ORF YHL047C | 69 | P | 29 | P | 66 | P | 16 | A | 0.43 | 0.23 | 3.02 | <10 min | Good |
| SMX3 (YPR182W) | 66 | P | 5 | A | 63 | P | 36 | P | 0.08 | 0.58 | 3.02 | <10 min | Good |
| ORF YER093C-A exor | 39 | P | 7 | A | 35 | P | 16 | A | 0.19 | 0.47 | 3.02 | <5 min | Good |

Figure 22K

| | | | | | | | |
|---|---|---|---|---|---|---|---|
| ORF YHR192W | 97 P | 36 P | 98 P | 29 P | 0.37 | 0.29 | 3.01 | <10 min | Excl |
| ORF YLR209C | 69 P | 18 P | 59 P | 24 P | 0.26 | 0.40 | 3.00 | <10 min | Excl |
| ORF YLR138W | 105 P | 34 P | 77 P | 27 P | 0.32 | 0.35 | 3.00 | <10 min | Excl |
| YSC84 (YHR016C) ex | 23 P | 7 A | 28 P | 10 A | 0.33 | 0.34 | 3.00 | <5 min | Good |
| ARE1 (YCR048W) | 136 P | 39 P | 100 P | 38 P | 0.28 | 0.38 | 3.00 | <5 min | Excl |
| SPT16 (YGL207W) | 109 P | 47 P | 112 P | 26 A | 0.43 | 0.23 | 3.00 | <5 min | Good |
| ORC5 (YNL261W) | 69 P | 34 P | 88 P | 16 P | 0.49 | 0.18 | 2.97 | <5 min | Excl |
| ORF YIL161W | 62 P | 38 P | 57 P | 3 A | 0.61 | 0.06 | 2.97 | <10 min | Good |
| ORF YER119C | 82 P | 29 P | 76 P | 241 A | 0.36 | 0.32 | 2.95 | <10 min | Good |
| FPR1 (YNL135C) | 1464 P | 596 P | 1738 P | 472 P | 0.41 | 0.27 | 2.95 | <5 min | Excl |
| ORF YMR304W | 47 P | 25 A | 65 P | 9 A | 0.55 | 0.13 | 2.95 | <10 min | Good |
| ORF YIL149C | 64 P | 36 P | 44 P | 5 A | 0.56 | 0.12 | 2.95 | <5 min | Good |
| ORF YGR211W | 183 P | 60 P | 162 P | 57 P | 0.33 | 0.35 | 2.95 | <10 min | Excl |
| SRP72 (YPL210C) | 58 P | 12 P | 77 P | 36 P | 0.21 | 0.47 | 2.95 | <10 min | Excl |
| ORF YNL185C | 74 P | 31 P | 69 P | 18 P | 0.42 | 0.26 | 2.94 | <10 min | Excl |
| CSE2 (YNR010W) | 224 P | 34 P | 47 P | 25 P | 0.15 | 0.53 | 2.94 | <5 min | Excl |
| ORF YLR454W | 114 P | 44 P | 147 P | 43 P | 0.39 | 0.29 | 2.94 | <5 min | Excl |
| ORF YOR005C | 52 P | 12 P | 37 P | 17 P | 0.22 | 0.46 | 2.94 | <5 min | Excl |
| GEF1 (YJR040W) | 57 P | 4 A | 30 P | 19 P | 0.07 | 0.61 | 2.93 | <10 min | Good |
| PDR1 (YGL013C) | 90 P | 31 P | 116 P | 39 P | 0.35 | 0.33 | 2.93 | <10 min | Excl |
| TYS1 (YGR185C) | 266 P | 105 P | 248 P | 72 P | 0.39 | 0.29 | 2.93 | <5 min | Excl |
| ORF YFR037C | 130 P | 45 P | 99 P | 34 P | 0.34 | 0.34 | 2.92 | <10 min | Excl |
| ORF YGL245W | 621 P | 224 P | 672 P | 218 P | 0.36 | 0.33 | 2.92 | <10 min | Excl |
| UFD1 (YGR048W) | 32 P | 9 A | 43 P | 17 A | 0.28 | 0.40 | 2.92 | <5 min | Good |
| ORF YBR235W | 64 P | 11 P | 40 P | 21 P | 0.16 | 0.52 | 2.92 | <10 min | Excl |
| SPT6 (YGR116W) | 32 P | 15 P | 47 P | 10 A | 0.48 | 0.20 | 2.91 | <10 min | Good |
| ORF YHR101C exon 1 | 13 P | 7 A | 21 P | 3 A | 0.52 | 0.17 | 2.90 | <5 min | Good |
| SSM4 (YIL030C) | 114 P | 33 P | 86 P | 35 P | 0.29 | 0.40 | 2.90 | <10 min | Excl |
| ORF YFL010C | 434 P | 167 P | 479 P | 147 P | 0.38 | 0.31 | 2.89 | <10 min | Excl |
| ORF YGL014W | 43 P | 13 P | 36 P | 14 P | 0.31 | 0.38 | 2.88 | <10 min | Excl |
| ORF YIR009W | 27 P | 15 A | 36 P | 5 A | 0.55 | 0.14 | 2.88 | <10 min | Good |
| ORF YER176W | 79 P | 30 P | 73 P | 23 A | 0.38 | 0.32 | 2.87 | <5 min | Good |
| RTA1 (YGR213C) | 46 P | 14 P | 43 P | 16 P | 0.31 | 0.38 | 2.87 | <5 min | Excl |

Figure 22L

| | | | | | | | |
|---|---|---|---|---|---|---|---|
| NMD2 (YHR077C) | 73 P | 26 P | 79 P | 28 P | 0.35 | 0.35 | 2.85 <10 min Excl |
| SIN4 (YNL236W) | 33 P | 15 P | 66 P | 16 P | 0.46 | 0.24 | 2.83 <10 min Excl |
| ORF YMR178W | 57 P | 18 P | 50 P | 20 P | 0.31 | 0.40 | 2.83 <10 min Excl |
| ORF YDL117W | 76 P | 34 P | 89 P | 23 P | 0.45 | 0.25 | 2.83 <5 min Excl |
| ORF YGR276C | 130 P | 55 P | 120 P | 34 P | 0.43 | 0.28 | 2.82 <5 min Excl |
| ALR2 (YFL050C) | 24 P | 11 A | 26 P | 7 P | 0.44 | 0.27 | 2.82 <5 min Good |
| PUS1 (YPL212C) | 111 P | 54 P | 141 P | 32 P | 0.49 | 0.22 | 2.81 <10 min Excl |
| CYP2 (YHR057C) | 282 P | 106 P | 283 P | 94 P | 0.38 | 0.33 | 2.81 <10 min Excl |
| VPS17 (YOR132W) | 120 P | 51 P | 117 P | 34 P | 0.42 | 0.29 | 2.81 <5 min Excl |
| TOR1 (YJR066W) | 34 P | 8 P | 34 P | 16 P | 0.23 | 0.48 | 2.81 <5 min Excl |
| ORF YER107C | 98 P | 41 P | 86 P | 25 P | 0.42 | 0.29 | 2.80 <10 min Excl |
| ORF YOL075C | 57 P | 18 P | 46 P | 19 P | 0.31 | 0.41 | 2.79 <10 min Excl |
| ORF YER002W | 259 P | 94 P | 236 P | 85 P | 0.36 | 0.36 | 2.78 <10 min Excl |
| ORF YNL313C | 153 P | 65 P | 171 P | 50 P | 0.43 | 0.29 | 2.76 <10 min Excl |
| RPS24B (YLR367W) | 776 P | 284 P | 801 P | 288 P | 0.37 | 0.36 | 2.76 <5 min Excl |
| ORF YLL048C | 254 P | 75 P | 208 P | 89 P | 0.30 | 0.43 | 2.75 <10 min Excl |
| ORF YBR077C | 99 P | 30 P | 69 P | 29 P | 0.30 | 0.43 | 2.73 <10 min Excl |
| ORF YFL028C | 152 P | 53 P | 137 P | 53 P | 0.35 | 0.38 | 2.73 <10 min Excl |
| HOG1 (YLR113W) | 277 P | 99 P | 235 P | 89 P | 0.36 | 0.38 | 2.71 <10 min Excl |
| ORF YML081W | 64 P | 26 P | 95 P | 32 P | 0.41 | 0.33 | 2.71 <10 min Excl |
| ORF YGR271W | 142 P | 36 P | 108 P | 53 P | 0.25 | 0.49 | 2.71 <5 min Excl |
| ORF YKL206C | 71 P | 20 P | 53 P | 24 P | 0.29 | 0.45 | 2.71 <5 min Excl |
| ORF YFL025C | 40 P | 16 P | 33 P | 11 P | 0.40 | 0.35 | 2.69 <10 min Excl |
| ORF YOR256C | 72 P | 27 P | 93 P | 34 P | 0.38 | 0.37 | 2.69 <5 min Excl |
| ORF YHR186C | 38 P | 7 A | 37 P | 21 A | 0.20 | 0.56 | 2.65 <10 min Good |
| CPT1 (YNL130C) excl | 193 P | 99 P | 340 P | 83 P | 0.51 | 0.24 | 2.64 <10 min Excl |
| ORF YDL100C | 340 P | 130 P | 310 P | 116 P | 0.38 | 0.37 | 2.64 <10 min Excl |
| IPP1 (YBR011C) | 596 P | 261 P | 464 P | 149 P | 0.44 | 0.32 | 2.64 <5 min Excl |
| ORF YML030W | 102 P | 34 P | 117 P | 50 P | 0.33 | 0.43 | 2.63 <10 min Excl |
| ORF YBR293W | 58 P | 17 A | 55 P | 26 P | 0.29 | 0.47 | 2.62 <10 min Good |
| RPO41 (YFL036W) | 96 P | 43 P | 80 P | 25 P | 0.45 | 0.31 | 2.62 <5 min Excl |
| QRI5 (YLR204W) | 148 P | 48 P | 113 P | 50 P | 0.32 | 0.44 | 2.62 <5 min Excl |
| KIN3 (YAR018C) | 43 P | 17 P | 22 P | 8 A | 0.39 | 0.37 | 2.62 <10 min Good |
| ORF YHR122W | 89 P | 32 P | 70 P | 29 P | 0.36 | 0.41 | 2.61 <10 min Excl |
| ORF YIL024C | 44 P | 20 P | 38 P | 12 A | 0.45 | 0.32 | 2.61 <5 min Good |
| ORF YIL129C | 210 P | 88 P | 176 P | 62 P | 0.42 | 0.35 | 2.61 <5 min Excl |
| ORF YOR152C | 52 P | 25 P | 58 P | 17 M | 0.48 | 0.28 | 2.60 <10 min Good |

Figure 22M

| | | | | | | | | |
|---|---|---|---|---|---|---|---|---|
| ORF YIL158W | 107 | P | 40 | P | 79 | P | 31 | P | 0.38 | 0.39 | 2.60 | <10 min | Excl |
| ORF YDR196C | 135 | P | 55 | P | 141 | P | 51 | P | 0.41 | 0.36 | 2.59 | <10 min | Excl |
| GRR1 (YJR090C) | 40 | P | 16 | P | 27 | P | 10 | A | 0.40 | 0.37 | 2.59 | <5 min | Good |
| CYR1 (YJL005W) | 34 | P | 10 | P | 28 | P | 14 | A | 0.28 | 0.50 | 2.57 | <5 min | Good |
| BNI1 (YNL271C) | 88 | P | 45 | P | 135 | P | 36 | P | 0.51 | 0.27 | 2.56 | <10 min | Excl |
| PDR12 (YPL058C) | 126 | P | 55 | P | 148 | P | 51 | P | 0.44 | 0.34 | 2.55 | <10 min | Excl |
| UBC1 (YDR177W) | 385 | P | 182 | P | 400 | P | 124 | P | 0.47 | 0.31 | 2.55 | <5 min | Excl |
| PPQ1 (YPL179W) | 61 | P | 37 | P | 131 | P | 23 | A | 0.61 | 0.18 | 2.55 | <10 min | Good |
| ORF YDL010W | 89 | P | 43 | P | 90 | P | 28 | P | 0.48 | 0.31 | 2.54 | <10 min | Excl |
| ORF YNL059C | 38 | P | 16 | P | 50 | P | 18 | P | 0.42 | 0.36 | 2.54 | <10 min | Excl |
| ORF YGR232W | 178 | P | 76 | P | 202 | P | 74 | P | 0.43 | 0.37 | 2.52 | <10 min | Excl |
| ORF YDR379W | 40 | P | 15 | P | 48 | P | 19 | P | 0.39 | 0.41 | 2.52 | <10 min | Excl |
| UTR1 (YJR049C) | 403 | P | 99 | P | 153 | P | 84 | P | 0.25 | 0.55 | 2.51 | <10 min | Excl |
| IFH1 (YLR223C) | 216 | P | 60 | P | 122 | P | 63 | P | 0.28 | 0.52 | 2.50 | <5 min | Excl |
| HLJ1 (YMR161W) | 42 | P | 19 | P | 49 | P | 17 | A | 0.46 | 0.34 | 2.49 | <5 min | Good |
| NUM1 (YDR150W) | 81 | P | 36 | P | 76 | P | 27 | P | 0.45 | 0.35 | 2.49 | <5 min | Excl |
| IMH1 (YLR309C) | 133 | P | 44 | P | 98 | P | 47 | P | 0.33 | 0.48 | 2.47 | <10 min | Excl |
| ORF YDR349C | 218 | P | 75 | P | 181 | P | 84 | P | 0.34 | 0.47 | 2.46 | <10 min | Excl |
| ORF YHL030W | 76 | P | 31 | P | 61 | P | 24 | P | 0.42 | 0.40 | 2.45 | <5 min | Excl |
| CDC37 (YDR168W) | 110 | P | 36 | P | 89 | P | 44 | P | 0.33 | 0.49 | 2.45 | <10 min | Excl |
| MGM1 (YOR211C) | 58 | P | 26 | P | 48 | P | 18 | P | 0.45 | 0.37 | 2.45 | <10 min | Excl |
| SBE2 (YDR351W) | 46 | P | 13 | P | 42 | P | 22 | P | 0.29 | 0.53 | 2.45 | <5 min | Excl |
| ORF YDL132W | 112 | P | 48 | P | 115 | P | 45 | P | 0.43 | 0.39 | 2.44 | <5 min | Excl |
| ORF YLR455W | 28 | P | 7 | P | 20 | P | 12 | M | 0.24 | 0.58 | 2.44 | <5 min | Good |
| ORF YFL049W | 42 | P | 21 | P | 56 | P | 17 | P | 0.51 | 0.31 | 2.43 | <5 min | Excl |
| PDR11 (YIL013C) | 54 | P | 23 | M | 65 | P | 26 | P | 0.42 | 0.40 | 2.43 | <5 min | Good |
| ORF YMR192W | 36 | P | 12 | P | 24 | P | 12 | P | 0.33 | 0.49 | 2.43 | <5 min | Excl |
| ORF YDR338C | 45 | P | 18 | P | 38 | P | 16 | P | 0.41 | 0.42 | 2.42 | <10 min | Excl |
| ORF YGR178C | 181 | P | 73 | P | 190 | P | 81 | A | 0.40 | 0.43 | 2.40 | <10 min | Good |
| SNF2 (YOR290C) | 64 | P | 26 | P | 74 | P | 32 | P | 0.41 | 0.43 | 2.40 | <10 min | Excl |
| ORF YJR046W | 39 | P | 18 | P | 52 | P | 20 | P | 0.45 | 0.38 | 2.39 | <5 min | Excl |

Figure 22N

| | | | | | | | |
|---|---|---|---|---|---|---|---|
| ORF YDL173W | 276 P | 114 P | 214 P | 92 P | 0.41 | 0.43 | 2.37 <10 min | Excl |
| ORF YHR065C | 152 P | 78 P | 109 P | 36 P | 0.51 | 0.33 | 2.37 <10 min | Excl |
| ORF YGL036W | 116 P | 60 P | 130 P | 43 P | 0.51 | 0.33 | 2.36 <5 min | Excl |
| UBR1 (YGR184C) | 60 P | 28 P | 54 P | 21 A | 0.47 | 0.39 | 2.34 <5 min | Good |
| ORF YDR152W | 156 P | 67 P | 116 P | 50 P | 0.43 | 0.43 | 2.33 <5 min | Excl |
| CRM1 (YGR218W) | 107 P | 52 P | 90 P | 34 P | 0.48 | 0.38 | 2.33 <5 min | Excl |
| STE5 (YDR103W) | 37 P | 17 P | 35 P | 15 M | 0.45 | 0.41 | 2.30 <5 min | Good |
| RPS24B (YLR367W) | 599 P | 227 P | 484 P | 240 P | 0.38 | 0.50 | 2.29 <5 min | Excl |
| ORF YGR223C | 71 P | 28 P | 79 P | 38 P | 0.39 | 0.48 | 2.28 <10 min | Excl |
| ORF YJR056C | 65 P | 27 P | 59 P | 27 P | 0.42 | 0.46 | 2.28 <5 min | Excl |
| ORF YER185W | 19 P | 13 M | 26 P | 4 A | 0.71 | 0.17 | 2.27 <5 min | Good |
| RRN3 (YKL125W) | 111 P | 50 P | 75 P | 32 P | 0.45 | 0.43 | 2.27 <10 min | Excl |
| SED4 (YCR067C) | 85 P | 40 P | 73 P | 31 P | 0.47 | 0.42 | 2.23 <5 min | Excl |
| ORF YPL238C | 45 P | 13 A | 30 P | 18 P | 0.29 | 0.61 | 2.22 <5 min | Good |
| SPT23 (YKL020C) | 34 P | 14 P | 46 P | 22 P | 0.43 | 0.48 | 2.20 <10 min | Excl |
| ORF YOR227W | 64 P | 37 P | 84 P | 28 P | 0.57 | 0.34 | 2.20 <5 min | Excl |
| ORF YHR171W | 20 P | 14 A | 35 P | 8 A | 0.69 | 0.22 | 2.20 <10 min | Good |
| UBC8 (YEL012W) | 103 P | 63 P | 128 P | 39 A | 0.61 | 0.30 | 2.19 <10 min | Good |
| ORF YGL244W | 101 P | 48 P | 101 P | 44 P | 0.48 | 0.44 | 2.19 <10 min | Excl |
| SEC3 (YER008C) | 61 P | 25 P | 65 P | 33 A | 0.41 | 0.50 | 2.19 <10 min | Good |
| ORF YMR298W | 216 P | 115 P | 222 P | 86 P | 0.53 | 0.39 | 2.18 <5 min | Excl |
| ORF YDL012C exon 1 | 277 P | 101 P | 214 P | 120 P | 0.36 | 0.56 | 2.16 <10 min | Excl |
| CLG1 (YGL215W) | 128 P | 66 P | 154 P | 62 P | 0.52 | 0.41 | 2.16 <5 min | Excl |
| STB2 (YMR053C) | 19 P | 13 A | 34 P | 9 A | 0.66 | 0.27 | 2.14 <5 min | Good |
| MDJ1 (YFL016C) | 137 P | 69 P | 156 P | 68 P | 0.50 | 0.44 | 2.12 <5 min | Excl |
| ORF YKL123W | 57 P | 26 P | 55 P | 27 P | 0.46 | 0.49 | 2.11 <5 min | Excl |
| APT2 (YDR441C) | 169 P | 89 P | 158 P | 67 P | 0.53 | 0.42 | 2.11 <10 min | Excl |
| ORF YJL168C | 27 P | 13 P | 15 P | 7 P | 0.49 | 0.47 | 2.10 <10 min | Excl |
| ORF YJR117W | 125 P | 61 P | 154 P | 73 P | 0.49 | 0.48 | 2.08 <10 min | Excl |
| ORF YOR007C | 1109 P | 583 P | 1709 P | 751 P | 0.53 | 0.44 | 2.07 <10 min | Excl |

Figure 22O

| | | | | | | | |
|---|---|---|---|---|---|---|---|
| ORF YDR309C | 72 P | 25 P | 69 P | 42 P | 0.35 | 0.62 | 2.07 <5 min | Excl |
| ORF YLR422W | 57 P | 29 P | 41 P | 19 P | 0.50 | 0.47 | 2.05 <10 min | Excl |
| ORF YGL087C exon 1 | 197 P | 99 P | 177 P | 85 P | 0.50 | 0.48 | 2.04 <5 min | Excl |
| ORF YIL097W | 19 P | 19 P | 26 P | 0 A | 0.99 | 0.00 | 2.03 <5 min | Good |
| ORF YDR457W | 74 P | 45 P | 89 P | 34 P | 0.61 | 0.38 | 2.02 <5 min | Excl |
| ORF YMR191W | 95 P | 44 P | 111 P | 60 P | 0.47 | 0.54 | 1.98 <5 min | Excl |
| ORF YLR254C | 60 P | 19 P | 38 P | 26 P | 0.31 | 0.70 | 1.98 <5 min | Excl |
| PCA1 (YBR295W) | 61 P | 32 P | 27 P | 14 P | 0.52 | 0.51 | 1.94 <10 min | Good |
| SAP155 (YFR040W) | 46 P | 13 M | 29 P | 22 A | 0.29 | 0.74 | 1.94 <10 min | Good |
| RAD24 (YER173W) | 19 P | 12 M | 36 P | 14 A | 0.65 | 0.38 | 1.93 <5 min | Excl |
| ORF YPL110C | 79 P | 34 P | 75 P | 47 P | 0.43 | 0.62 | 1.90 <10 min | Excl |
| TSM1 (YCR042C) | 84 P | 41 P | 52 P | 29 P | 0.49 | 0.56 | 1.89 <10 min | Excl |
| ORF YCR026C | 228 P | 112 P | 157 P | 93 P | 0.49 | 0.59 | 1.85 <10 min | Excl |
| ORF YBR150C | 24 P | 10 A | 32 P | 22 P | 0.41 | 0.68 | 1.83 <5 min | Good |
| PPZ1 (YML016C) | 78 P | 46 P | 65 P | 33 P | 0.59 | 0.51 | 1.82 <5 min | Excl |
| ORF YJL015C | 18 P | 14 P | 21 P | 7 A | 0.77 | 0.33 | 1.82 <5 min | Good |
| ORF YLL051C | 157 P | 75 P | 105 P | 68 P | 0.48 | 0.65 | 1.78 <10 min | Excl |

Figure 22P

| Srb10 UP | | | | | | | | Average | | |
|---|---|---|---|---|---|---|---|---|---|---|
| Gene | WT#1 no | WT#10-3#1 | 10-3WT#2 | no WT#10-3#2 | 10-3MT1/WT1 | MT2/WT2 | Fold Up | Corrected? | Confidence |
| ADR1 (YDR216W) | 14 P | 33 P | 45 P | 130 P | 2.4 | 2.9 | 2.6 | | Excl |
| ALD4 (YMR169C) | 5 A | 180 P | 16 A | 323 P | 36.0 | 20.2 | 28.1 | | Good |
| ALP1 (YNL270C) | -6 A | 34 P | 10 A | 30 P | -5.7 | 3.2 | 5.6 | Yes | Med |
| ARG1 (YOL058W) | 29 P | 202 P | 140 P | 392 P | 7.0 | 2.8 | 4.9 | | Excl |
| CIT2 (YCR005C) | 100 P | 228 P | 223 P | 475 P | 2.3 | 2.1 | 2.2 | | Excl |
| CIT3 (YPR001W) | 11 A | 23 P | 6 A | 26 P | 2.1 | 4.1 | 3.1 | | Good |
| CTT1 (YGR088W) | 31 P | 269 P | 36 A | 421 P | 8.7 | 11.5 | 10.1 | | Excl |
| CYC7 (YEL039C) | 142 P | 863 P | 45 P | 467 P | 6.1 | 10.5 | 8.3 | | Excl |
| ENO1 (YGR254W) | 1660 P | 4724 P | 3024 P | 6843 P | 2.8 | 2.3 | 2.6 | | Excl |
| FLO1 (YAR050W) | 14 P | 1749 P | 51 P | 4052 P | 124.9 | 79.4 | 102.2 | | Excl |
| FOX2 (YKR009C) | -2 A | 23 A | 10 A | 20 P | -11.5 | 2.0 | 3.5 | Yes | Med |
| GCY1 (YOR120W) | 45 P | 181 P | 50 P | 162 P | 4.0 | 3.2 | 3.6 | | Excl |
| GIP2 (YER054C) | -1 A | 27 P | 3 A | 16 A | -27.0 | 5.9 | 5.7 | Yes | Med |
| GLC3 (YEL011W) | 28 P | 139 P | 28 P | 130 P | 5.0 | 4.6 | 4.8 | | Excl |
| GLK1 (YCL040W) | 422 P | 1230 P | 551 P | 1448 P | 2.9 | 2.6 | 2.8 | | Excl |
| GPH1 (YPR160W) | 56 P | 377 P | 86 P | 733 P | 6.7 | 8.5 | 7.6 | | Excl |
| GPM2 (YDL021W) | 10 P | 43 P | 22 P | 52 P | 4.3 | 2.4 | 3.3 | | Excl |
| GSC2 (YGR032W) | 60 P | 236 P | 211 P | 568 P | 3.9 | 2.7 | 3.3 | | Excl |
| GSP2 (YOR185C) | 117 P | 235 P | 229 P | 478 P | 2.0 | 2.1 | 2.0 | | Excl |
| GSY1 (YFR015C) | 20 P | 61 P | 19 P | 63 P | 3.1 | 3.4 | 3.2 | | Excl |
| GSY2 (YLR258W) | 101 P | 258 P | 237 P | 479 P | 2.6 | 2.0 | 2.3 | | Excl |
| HOR2 (YER062C) | 224 P | 695 P | 332 P | 928 P | 3.1 | 2.8 | 2.9 | | Excl |
| HSP12 (YFL014W) | 544 P | 4872 P | 201 P | 5449 P | 9.0 | 27.1 | 18.0 | | Excl |
| HSP26 (YBR072W) | 43 P | 1282 P | 51 P | 1134 P | 29.8 | 22.2 | 26.0 | | Excl |
| HXK1 (YFR053C) | 422 P | 1916 P | 531 P | 2252 P | 4.5 | 4.2 | 4.4 | | Excl |
| HXT5 (YHR096C) | 4 A | 21 P | 0 A | 27 A | 5.3 | #DIV/0! | 5.3 | Yes | Med |
| HXT7 (YDR342C) (_f) | 1221 P | 2606 P | 1268 P | 3852 P | 2.1 | 3.0 | 2.6 | | Excl |
| IDP2 (YLR174W) | -3 A | 20 P | 14 A | 47 P | -6.7 | 3.3 | 4.0 | Yes | Med |
| ISF1 (YMR081C) | 11 P | 54 P | 13 M | 34 P | 4.9 | 2.6 | 3.8 | | Good |
| LAP4 (YKL103C) | 23 P | 112 P | 56 P | 121 P | 4.9 | 2.2 | 3.5 | | Excl |
| MBR1 (YKL093W) | 0 A | 35 P | 14 A | 44 P | #DIV/0! | 3.1 | 5.1 | Yes | Med |
| MCR1 (YKL150W) | 204 P | 628 P | 279 P | 650 P | 3.1 | 2.3 | 2.7 | | Excl |
| MET2 (YNL277W) | 25 P | 65 P | 30 P | 66 P | 2.6 | 2.2 | 2.4 | | Excl |

Figure 23A

| | 7 | | 19 | | 5 | | 23 | | 2.7 | 4.3 | 3.5 | | |
|---|---|---|---|---|---|---|---|---|---|---|---|---|---|
| MET28 (YIR017C) | 7 | A | 19 | P | 5 | A | 23 | P | 2.7 | 4.3 | 3.5 | | Good |
| MF(ALPHA)2 (YGL089 | 10 | A | 24 | P | -14 | A | 25 | A | 2.4 | -1.9 | 5.1 | Yes | Med |
| MGA1 (YGR249W) | -2 | A | 12 | A | 5 | A | 54 | P | -6.0 | 10.0 | 6.4 | Yes | Med |
| MLS1 (YNL117W) | 0 | A | 21 | A | 4 | A | 20 | P | #DIV/0! | 4.6 | 4.4 | Yes | Med |
| MRK1 (YDL079C) exo| | -5 | A | 7 | P | -10 | A | 5 | A | -1.4 | -0.5 | 2.7 | Yes | Med |
| NCA3 (YJL116C) | 37 | P | 303 | P | 66 | P | 516 | P | 8.2 | 7.8 | 8.0 | | Excl |
| OM45 (YIL136W) | 51 | P | 383 | P | 51 | M | 171 | P | 7.5 | 3.3 | 5.4 | | Good |
| ORF YAL061W | 18 | A | 100 | P | 18 | P | 138 | P | 5.6 | 7.7 | 6.6 | | Good |
| ORF YAR047C | 2 | A | 26 | A | 8 | A | 120 | P | 13.0 | 15.0 | 14.0 | | Good |
| ORF YBL043W | 34 | P | 86 | P | 60 | P | 168 | P | 2.5 | 2.8 | 2.7 | | Excl |
| ORF YBL048W | 21 | P | 60 | P | 26 | P | 55 | P | 2.9 | 2.1 | 2.5 | | Excl |
| ORF YBL101W-B exo| | 50 | P | 122 | P | 308 | P | 691 | P | 2.4 | 2.2 | 2.3 | | Excl |
| ORF YBR012C | 42 | P | 336 | P | 54 | P | 341 | P | 8.0 | 6.3 | 7.2 | | Excl |
| ORF YBR116C | 8 | A | 48 | P | 1 | A | 116 | P | 6.0 | 116.2 | 61.1 | | Good |
| ORF YBR128C | 6 | A | 17 | A | 0 | A | 12 | M | 2.8 | #DIV/0! | 2.6 | Yes | Med |
| ORF YBR147W | 6 | A | 56 | P | 3 | A | 33 | P | 9.3 | 11.0 | 10.2 | | Good |
| ORF YBR157C | 51 | P | 111 | P | 59 | P | 136 | P | 2.2 | 2.3 | 2.2 | | Excl |
| ORF YBR300C (_i) | 16 | A | 33 | P | 18 | P | 47 | P | 2.1 | 2.6 | 2.3 | | Good |
| ORF YCL021W | 12 | P | 30 | P | 23 | P | 49 | P | 2.5 | 2.1 | 2.3 | | Excl |
| ORF YCL042W | 60 | P | 133 | P | 67 | P | 155 | P | 2.2 | 2.3 | 2.3 | | Excl |
| ORF YCR010C | -1 | A | 14 | A | 5 | A | 25 | M | -14.0 | 5.1 | 4.0 | Yes | Med |
| ORF YDL032W | -7 | A | 10 | A | -2 | A | 26 | P | -1.4 | -13.1 | 4.5 | Yes | Med |
| ORF YDL118W | 1 | A | 25 | A | -4 | A | 15 | M | 25.0 | -3.7 | 14.4 | Yes | Med |
| ORF YDL183C | 12 | A | 26 | P | 28 | P | 56 | P | 2.2 | 2.0 | 2.1 | | Good |
| ORF YDL204W | 14 | P | 192 | P | 30 | P | 189 | P | 13.7 | 6.3 | 10.0 | | Excl |
| ORF YDL222C | -7 | A | 142 | P | 15 | A | 205 | P | -20.3 | 13.7 | 21.7 | Yes | Med |
| ORF YDL223C | 19 | P | 117 | P | 72 | P | 424 | P | 6.2 | 5.9 | 6.0 | | Excl |
| ORF YDR070C | 10 | A | 201 | P | 17 | P | 112 | P | 20.1 | 6.6 | 13.3 | | Good |
| ORF YDR453C | 24 | P | 195 | P | 52 | P | 129 | P | 8.1 | 2.5 | 5.3 | | Excl |
| ORF YEL059W | -15 | A | 4 | A | -18 | A | 2 | A | -0.3 | -0.1 | 3.9 | Yes | Med |
| ORF YER037W | 39 | P | 111 | P | 46 | P | 156 | P | 2.8 | 3.4 | 3.1 | | Excl |
| ORF YER067W | 56 | P | 171 | P | 14 | P | 100 | P | 3.1 | 7.4 | 5.2 | | Excl |

Figure 23B

| ORF | | | | | | | | |
|---|---|---|---|---|---|---|---|---|
| ORF YER081W | 60 | P | 125 | P | 108 | P | 270 | P | 2.1 | 2.5 | 2.3 | | Excl |
| ORF YER150W | 34 | P | 1157 | P | 55 | A | 780 | P | 34.0 | 14.1 | 24.1 | | Good |
| ORF YER158C | 27 | P | 59 | P | 43 | P | 90 | P | 2.2 | 2.1 | 2.1 | | Excl |
| ORF YER187W | 13 | P | 33 | P | 12 | M | 25 | P | 2.5 | 2.1 | 2.3 | | Good |
| ORF YFL012W | 0 | A | 12 | A | -3 | A | 19 | P | #DIV/0! | -7.0 | 3.4 | Yes | Med |
| ORF YFL013W-A | -7 | A | 4 | A | -14 | A | 5 | A | -0.6 | -0.4 | 2.9 | Yes | Med |
| ORF YFL030W | 29 | P | 123 | P | 9 | M | 60 | P | 4.2 | 6.4 | 5.3 | | Good |
| ORF YFR017C | 22 | P | 99 | P | 36 | P | 79 | P | 4.5 | 2.2 | 3.3 | | Excl |
| ORF YFR046C | 4 | A | 16 | P | 8 | A | 25 | P | 4.0 | 3.1 | 3.6 | | Good |
| ORF YGL075C | 9 | A | 21 | A | 12 | A | 40 | P | 2.3 | 3.3 | 2.8 | | Good |
| ORF YGL121C | 56 | P | 359 | P | 43 | P | 91 | P | 6.4 | 2.1 | 4.3 | | Excl |
| ORF YGL165C | -16 | A | 3 | A | -24 | A | 6 | A | -0.2 | -0.2 | 4.9 | Yes | Med |
| ORF YGR023W | 9 | A | 20 | A | 26 | A | 60 | P | 2.2 | 2.3 | 2.3 | | Good |
| ORF YGR043C | 22 | P | 183 | P | 19 | A | 169 | P | 8.3 | 8.9 | 8.6 | | Good |
| ORF YGR052W | 0 | A | 65 | P | 11 | A | 65 | P | #DIV/0! | 6.0 | 9.5 | Yes | Med |
| ORF YGR066C | -2 | A | 11 | A | -14 | A | -2 | A | -5.5 | 0.2 | 2.4 | Yes | Med |
| ORF YGR146C | 103 | P | 387 | P | 272 | P | 575 | P | 3.8 | 2.1 | 2.9 | | Excl |
| ORF YGR212W | -3 | A | 8 | A | -8 | A | 4 | A | -2.7 | -0.5 | 2.3 | Yes | Med |
| ORF YGR243W | 47 | P | 125 | P | 301 | A | 62 | P | 2.7 | 2.1 | 2.4 | | Good |
| ORF YGR290W | -6 | A | 7 | A | -14 | A | 6 | A | -1.2 | -0.5 | 3.3 | Yes | Med |
| ORF YHR087W | 99 | P | 764 | P | 218 | P | 753 | P | 7.7 | 3.5 | 5.6 | | Excl |
| ORF YHR140W | 0 | A | 16 | A | -11 | A | 3 | A | #DIV/0! | -0.3 | 3.0 | Yes | Med |
| ORF YIL025C | -12 | A | -1 | A | -26 | A | -3 | A | 0.1 | 0.1 | 3.4 | Yes | Med |
| ORF YIL055C | 4 | A | 25 | P | 15 | A | 53 | P | 6.3 | 3.6 | 4.9 | | Good |
| ORF YIL087C | 28 | P | 84 | P | 36 | P | 109 | P | 3.0 | 3.0 | 3.0 | | Good |
| ORF YIL113W | 9 | A | 41 | P | 4 | P | 32 | A | 4.6 | 7.8 | 6.2 | | Good |
| ORF YIR038C | 173 | P | 467 | P | 266 | P | 562 | P | 2.7 | 2.1 | 2.4 | | Excl |
| ORF YIR043C (i) | -11 | A | 9 | A | -31 | A | -10 | A | -0.8 | 0.3 | 4.2 | Yes | Med |
| ORF YJL066C | 6 | A | 43 | P | 12 | A | 37 | P | 7.2 | 3.0 | 5.1 | | Good |
| ORF YJL144W | 9 | A | 53 | P | 8 | A | 28 | P | 5.9 | 3.5 | 4.7 | | Good |
| ORF YJL218W | 67 | P | 214 | P | 52 | P | 163 | P | 3.2 | 3.1 | 3.2 | | Excl |
| ORF YJR028W (f) | 172 | P | 403 | P | 1546 | P | 3195 | P | 2.3 | 2.1 | 2.2 | | Excl |
| ORF YKL151C | 103 | P | 553 | P | 172 | P | 584 | P | 5.4 | 3.4 | 4.4 | | Good |
| ORF YKL187C | 4 | A | 47 | P | 18 | P | 80 | P | 11.8 | 4.4 | 8.1 | | Good |
| ORF YKL201C | 33 | P | 93 | P | 78 | P | 194 | P | 2.8 | 2.5 | 2.7 | | Excl |

Figure 23C

| | | | | | | | | |
|---|---|---|---|---|---|---|---|---|
| ORF YKL221W | 3 | A | 19 | P | 4 | A | 17 | P | 6.3 | 4.3 | 5.3 | Good |
| ORF YKR102W | 3 | A | 15 | P | 19 | P | 79 | P | 5.0 | 4.1 | 4.6 | Good |
| ORF YLR149C | 6 | A | 42 | P | 37 | P | 78 | P | 7.0 | 2.1 | 4.5 | Good |
| ORF YLR161W (_f) | 9 | A | 30 | P | 31 | P | 101 | P | 3.3 | 3.3 | 3.3 | Good |
| ORF YLR237W | 78 | P | 276 | P | 150 | P | 330 | P | 3.5 | 2.2 | 2.9 | Excl |
| ORF YLR251W | 89 | P | 214 | P | 105 | P | 231 | P | 2.4 | 2.2 | 2.3 | Excl |
| ORF YLR267W | -11 | A | 1 | A | -1 | A | 14 | A | -0.1 | -13.8 | 2.7 | Yes | Med |
| ORF YLR297W | 231 | P | 497 | P | 302 | P | 728 | P | 2.2 | 2.4 | 2.3 | Excl |
| ORF YLR311C | 6 | A | 35 | P | 10 | A | 41 | P | 5.8 | 4.1 | 5.0 | Good |
| ORF YLR312C | 14 | P | 35 | P | 12 | A | 46 | P | 2.5 | 3.8 | 3.2 | Good |
| ORF YLR343W | 4 | A | 16 | P | 20 | P | 41 | P | 4.0 | 2.1 | 3.0 | Good |
| ORF YML039W exon | 161 | P | 357 | P | 1556 | P | 3205 | P | 2.2 | 2.1 | 2.1 | Excl |
| ORF YML087C | 5 | A | 28 | P | 6 | A | 35 | P | 5.6 | 5.9 | 5.7 | Good |
| ORF YML128C | 50 | P | 343 | P | 87 | P | 731 | P | 6.9 | 8.4 | 7.6 | Excl |
| ORF YMR040W | 44 | P | 134 | P | 46 | P | 98 | P | 3.0 | 2.1 | 2.6 | Excl |
| ORF YMR050C exon 1 | 150 | P | 424 | P | 1492 | P | 3168 | P | 2.8 | 2.1 | 2.5 | Excl |
| ORF YMR090W | 114 | P | 330 | P | 179 | P | 505 | P | 2.9 | 2.8 | 2.9 | Excl |
| ORF YMR107W | 1 | A | 53 | P | -4 | A | 45 | P | 53.0 | -11.2 | 31.4 | Yes | Med |
| ORF YMR196W | 10 | A | 42 | P | 36 | P | 77 | P | 4.2 | 2.1 | 3.2 | Good |
| ORF YMR250W | 52 | P | 224 | P | 56 | P | 345 | P | 4.3 | 6.1 | 5.2 | Excl |
| ORF YMR265C | 7 | A | 19 | A | 29 | P | 61 | P | 2.7 | 2.1 | 2.4 | Good |
| ORF YMR290W-A | 11 | A | 23 | P | 6 | A | 46 | P | 2.1 | 7.2 | 4.6 | Good |
| ORF YMR317W | -8 | A | 8 | A | -1 | A | 46 | P | -1.0 | -43.2 | 6.3 | Yes | Med |
| ORF YMR320W | 10 | P | 24 | A | 29 | A | 59 | P | 2.4 | 2.1 | 2.2 | Good |
| ORF YNL092W | 1 | A | 23 | A | 9 | A | 24 | P | 23.0 | 2.8 | 12.9 | Good |
| ORF YNL171C | 6 | A | 27 | A | 10 | A | 23 | P | 4.5 | 2.4 | 3.5 | Good |
| ORF YNL194C | -15 | A | 55 | P | 13 | A | 26 | P | -3.7 | 2.0 | 8.0 | Yes | Med |
| ORF YNL195C | 10 | A | 52 | P | 11 | A | 54 | P | 5.2 | 5.1 | 5.1 | Good |
| ORF YNL196C | -8 | A | 15 | A | -12 | A | 5 | A | -1.9 | -0.4 | 3.9 | Yes | Med |
| ORF YNL234W | 25 | P | 69 | P | 84 | P | 190 | P | 2.8 | 2.3 | 2.5 | Excl |
| ORF YNL274C | 100 | P | 231 | P | 112 | P | 241 | P | 2.3 | 2.2 | 2.2 | Excl |
| ORF YNL285W | 1 | A | 18 | P | -2 | A | 17 | P | 18.0 | -7.8 | 10.9 | Yes | Med |
| ORF YNL319W | -4 | A | 8 | A | -10 | A | 11 | A | -2.0 | -1.2 | 3.3 | Yes | Med |

Figure 23D

| | | | | | | | | |
|---|---|---|---|---|---|---|---|---|
| ORF YOL053C-A | 255 | P | 2674 | P | 253 | P | 2170 | P | 10.5 | 8.6 | 9.5 | | Excl |
| ORF YOR173W | 5 | A | 61 | P | 24 | P | 90 | P | 12.2 | 3.7 | 7.9 | | Good |
| ORF YOR193W | 7 | A | 21 | A | 20 | P | 63 | P | 3.0 | 3.1 | 3.1 | | Excl |
| ORF YOR289W | 36 | P | 87 | P | 65 | P | 162 | P | 2.4 | 2.5 | 2.5 | | Excl |
| ORF YOR364W | 5 | A | 19 | A | 14 | P | 38 | P | 3.8 | 2.7 | 3.3 | | Good |
| ORF YOR376W | -1 | A | 18 | A | -15 | A | 4 | A | -18.0 | -0.3 | 3.8 | Yes | Med |
| ORF YOR382W | 117 | P | 560 | P | 482 | P | 1737 | P | 4.8 | 3.6 | 4.2 | | Excl |
| ORF YPL123C | 5 | A | 39 | P | 20 | P | 56 | P | 7.8 | 2.8 | 5.3 | | Good |
| ORF YPL186C | 18 | P | 60 | P | 18 | M | 48 | P | 3.3 | 2.7 | 3.0 | | Good |
| ORF YPL222W | -12 | A | 0 | A | 17 | P | 57 | P | 0.0 | 3.3 | 2.9 | Yes | Med |
| ORF YPL223C | 5 | A | 200 | P | 18 | A | 182 | P | 40.0 | 10.1 | 25.0 | | Good |
| ORF YPL230W | 10 | A | 47 | P | 11 | A | 63 | P | 4.7 | 5.9 | 5.3 | | Good |
| ORF YPL281C (_i) | -2 | A | 10 | A | 2 | A | 30 | P | -5.0 | 14.0 | 8.2 | Yes | Med |
| ORF YPR064W | 0 | A | 16 | A | -7 | A | 6 | A | #DIV/0! | -0.8 | 2.9 | Yes | Med |
| ORF YPR123C | -10 | A | 5 | A | 10 | A | 27 | P | -0.5 | 2.8 | 2.9 | Yes | Med |
| ORF YPR184W | -1 | A | 26 | P | 37 | P | 110 | P | -26.0 | 2.9 | 4.2 | Yes | Med |
| ORF YPR192W | -10 | A | 85 | P | -15 | A | 102 | P | -8.5 | -6.8 | 21.2 | Yes | Med |
| ORF YPR194C | 40 | P | 81 | P | 43 | P | 87 | P | 2.0 | 2.0 | 2.0 | | Excl |
| PAI3 (YMR174C) | 27 | P | 195 | P | 65 | P | 249 | P | 7.2 | 3.8 | 5.5 | | Excl |
| PBI2 (YNL015W) | 362 | P | 1097 | P | 515 | P | 1124 | P | 3.0 | 2.2 | 2.6 | | Excl |
| PCK1 (YKR097W) | 14 | M | 54 | P | 23 | P | 51 | P | 3.9 | 2.2 | 3.0 | | Excl |
| PGM2 (YMR105C) | 40 | P | 216 | P | 56 | P | 357 | P | 5.4 | 6.4 | 5.9 | | Excl |
| POT1 (YIL160C) | 2 | A | 25 | P | 15 | A | 34 | P | 12.5 | 2.3 | 7.4 | | Good |
| PUT4 (YOR348C) | 7 | A | 56 | P | 14 | A | 116 | P | 8.0 | 8.4 | 8.2 | | Good |
| RCK1 (YGL158W) | 2 | A | 67 | P | 41 | P | 83 | P | 33.5 | 2.1 | 17.8 | | Good |
| RTA1 (YGR213C) | 6 | A | 53 | P | 31 | A | 58 | P | 8.8 | 21.4 | 15.1 | | Good |
| SIP18 (YMR175W) | -1 | A | 492 | P | 6 | A | 289 | P | -492.0 | 48.2 | 73.4 | Yes | Med |
| SOL4 (YGR248W) | 27 | P | 261 | P | 26 | P | 178 | P | 9.7 | 6.9 | 8.3 | | Excl |
| SPS100 (YHR139C) | 24 | P | 65 | P | 41 | M | 84 | P | 2.7 | 2.1 | 2.4 | | Good |
| STA1 (YIR019C) | 19 | A | 219 | P | 136 | P | 2615 | P | 11.5 | 19.2 | 15.3 | | Good |
| STF2 (YGR008C) | 799 | P | 1964 | P | 626 | P | 1582 | P | 2.5 | 2.5 | 2.5 | | Excl |
| STP4 (YDL048C) | 75 | P | 198 | P | 319 | P | 655 | P | 2.6 | 2.1 | 2.3 | | Excl |
| TDH1 (YJL052W) | 322 | P | 2256 | P | 691 | P | 2674 | P | 7.0 | 3.9 | 5.4 | | Excl |
| TFS1 (YLR178C) | 69 | P | 323 | P | 130 | P | 373 | P | 4.7 | 2.9 | 3.8 | | Good |
| TKL2 (YBR117C) | 4 | A | 41 | P | 14 | P | 132 | P | 10.3 | 9.5 | 9.9 | | Good |
| TPS2 (YDR074W) | 53 | P | 215 | P | 130 | P | 386 | P | 4.1 | 3.0 | 3.5 | | Excl |
| TSL1 (YML100W) | 95 | P | 619 | P | 312 | P | 1594 | P | 6.5 | 5.1 | 5.8 | | Excl |
| YFL-TyB/_f_ (control?) | 49 | P | 153 | P | 219 | P | 606 | P | 3.1 | 2.8 | 2.9 | | Excl |
| YGP1 (YNL160W) | 1574 | P | 3840 | P | 2212 | P | 4733 | P | 2.4 | 2.1 | 2.3 | | Excl |
| YRO2 (YBR054W) | 391 | P | 960 | P | 642 | P | 1508 | P | 2.5 | 2.3 | 2.4 | | Excl |

Figure 23E

Srb10 UP

| Gene | WT#1 no | WT#1 | 10-3 #1 | 10-3 #1 | 10-3 WT#2 no | WT#2 | 10-3 #2 | 10-3 #2 | MT1/WT1 | MT2/WT2 | Average Fold Up | Corrected? | Confidence |
|---|---|---|---|---|---|---|---|---|---|---|---|---|---|
| FLO1 (YAR050W) | 14 | P | 1749 | P | 51 | P | 4052 | P | 124.9 | 79.4 | 102.2 | | Excl |
| SIP18 (YMR175W) | -1 | A | 492 | P | 6 | A | 289 | P | -492.0 | 48.2 | 73.4 | Yes | Med |
| ORF YBR116C | 8 | A | 48 | P | 1 | A | 116 | P | 6.0 | 116.2 | 61.1 | | Good |
| ORF YMR107W | 1 | A | 53 | P | -4 | A | 45 | P | 53.0 | -11.2 | 31.4 | Yes | Med |
| ALD4 (YMR169C) | 5 | A | 180 | P | 16 | A | 323 | P | 36.0 | 20.2 | 28.1 | | Good |
| HSP26 (YBR072W) | 43 | P | 1282 | P | 51 | P | 1134 | P | 29.8 | 22.2 | 26.0 | | Excl |
| ORF YPL223C | 5 | A | 200 | P | 18 | A | 182 | P | 40.0 | 10.1 | 25.0 | | Good |
| ORF YER150W | 34 | P | 1157 | P | 55 | A | 780 | P | 34.0 | 14.1 | 24.1 | | Good |
| ORF YDL222C | -7 | A | 142 | P | 15 | A | 205 | P | -20.3 | 13.7 | 21.7 | Yes | Med |
| ORF YPR192W | -10 | A | 85 | P | -15 | A | 102 | P | -8.5 | -6.8 | 21.2 | Yes | Med |
| HSP12 (YFL014W) | 544 | P | 4872 | P | 201 | P | 5449 | P | 9.0 | 27.1 | 18.0 | | Excl |
| RCK1 (YGL158W) | 2 | A | 67 | P | 41 | P | 83 | P | 33.5 | 2.1 | 17.8 | | Good |
| STA1 (YIR019C) | 19 | A | 219 | P | 136 | P | 2615 | P | 11.5 | 19.2 | 15.3 | | Good |
| RTA1 (YGR213C) | 6 | A | 53 | P | 3 | A | 58 | P | 8.8 | 21.4 | 15.1 | | Good |
| ORF YDL118W | 1 | A | 25 | A | -4 | A | 15 | M | 25.0 | -3.7 | 14.4 | Yes | Med |
| ORF YAR047C | 2 | A | 26 | A | 8 | A | 120 | P | 13.0 | 15.0 | 14.0 | | Good |
| ORF YDR070C | 10 | A | 201 | P | 17 | P | 112 | P | 20.1 | 6.6 | 13.3 | | Good |
| ORF YNL092W | 1 | A | 23 | A | 9 | A | 24 | P | 23.0 | 2.8 | 12.9 | | Good |
| ORF YNL285W | 1 | A | 18 | A | -2 | A | 17 | P | 18.0 | -7.8 | 10.9 | Yes | Med |
| ORF YBR147W | 6 | A | 56 | P | 3 | A | 33 | P | 9.3 | 11.0 | 10.2 | | Good |
| CTT1 (YGR088W) | 31 | P | 269 | P | 36 | A | 421 | P | 8.7 | 11.5 | 10.1 | | Good |
| ORF YDL204W | 14 | P | 192 | P | 30 | P | 189 | P | 13.7 | 6.3 | 10.0 | | Excl |
| TKL2 (YBR117C) | 4 | A | 41 | P | 14 | P | 132 | P | 10.3 | 9.5 | 9.9 | | Good |
| ORF YOL053C-A | 255 | P | 2674 | P | 253 | P | 2170 | P | 10.5 | 8.6 | 9.5 | | Excl |
| ORF YGR052W | 0 | A | 65 | P | 11 | A | 65 | P | #DIV/0! | 6.0 | 9.5 | Yes | Med |
| ORF YGR043C | 22 | P | 183 | P | 19 | A | 169 | P | 8.3 | 8.9 | 8.6 | | Good |
| SOL4 (YGR248W) | 27 | P | 261 | P | 26 | P | 178 | P | 9.7 | 6.9 | 8.3 | | Excl |
| CYC7 (YEL039C) | 142 | P | 863 | P | 45 | P | 467 | P | 6.1 | 10.5 | 8.3 | | Excl |
| ORF YPL281C | -2 | A | 10 | A | 2 | A | 30 | P | -5.0 | 14.0 | 8.2 | Yes | Med |
| PUT4 (YOR348C) | 7 | A | 56 | P | 14 | A | 116 | P | 8.0 | 8.4 | 8.2 | | Good |
| ORF YKL187C | 4 | A | 47 | P | 18 | P | 80 | P | 11.8 | 4.4 | 8.1 | | Good |
| ORF YNL194C | -15 | A | 55 | P | 13 | A | 26 | P | -3.7 | 2.0 | 8.0 | Yes | Med |
| NCA3 (YJL116C) | 37 | P | 303 | P | 66 | P | 516 | P | 8.2 | 7.8 | 8.0 | | Excl |

Figure 24A

| ORF | 5 A | 61 P | 24 P | 90 P | 12.2 | 3.7 | 7.9 | | |
|---|---|---|---|---|---|---|---|---|---|
| ORF YOR173W | 5 A | | | | | | 7.9 | | Good |
| ORF YML128C | 50 P | 343 P | 87 P | 731 P | 6.9 | 8.4 | 7.6 | | Excl |
| GPH1 (YPR160W) | 56 P | 377 P | 86 P | 733 P | 6.7 | 8.5 | 7.6 | | Excl |
| POT1 (YIL160C) | 2 A | 25 P | 15 A | 34 P | 12.5 | 2.3 | 7.4 | | Good |
| ORF YBR012C | 42 P | 336 P | 54 P | 341 P | 8.0 | 6.3 | 7.2 | | Excl |
| ORF YAL061W | 18 A | 100 P | 18 P | 138 P | 5.6 | 7.7 | 6.6 | | Good |
| MGA1 (YGR249W) | -2 A | 12 A | 5 A | 54 P | -6.0 | 10.0 | 6.4 | Yes | Med |
| ORF YMR317W | -8 A | 8 A | -1 A | 46 P | -1.0 | -43.2 | 6.3 | Yes | Med |
| ORF YIL113W | 9 A | 41 P | 4 A | 32 A | 4.6 | 7.8 | 6.2 | | Good |
| ORF YDL223C | 19 P | 117 P | 72 P | 424 P | 6.2 | 5.9 | 6.0 | | Excl |
| PGM2 (YMR105C) | 40 P | 216 P | 56 P | 357 P | 5.4 | 6.4 | 5.9 | | Excl |
| TSL1 (YML100W) | 95 P | 619 P | 312 P | 1594 P | 6.5 | 5.1 | 5.8 | | Excl |
| GIP2 (YER054C) | -1 A | 27 P | 3 A | 16 A | -27.0 | 5.9 | 5.7 | Yes | Med |
| ORF YML087C | 5 A | 28 P | 6 A | 35 P | 5.6 | 5.9 | 5.7 | | Good |
| ALP1 (YNL270C) | -6 A | 34 P | 10 A | 30 P | -5.7 | 3.2 | 5.6 | Yes | Med |
| ORF YHR087W | 99 P | 764 P | 218 P | 753 P | 7.7 | 3.5 | 5.6 | | Excl |
| PAI3 (YMR174C) | 27 P | 195 P | 65 P | 249 P | 7.2 | 3.8 | 5.5 | | Excl |
| TDH1 (YJL052W) | 322 P | 2256 P | 691 P | 2674 P | 7.0 | 3.9 | 5.4 | | Excl |
| OM45 (YIL136W) | 51 P | 383 P | 51 M | 171 P | 7.5 | 3.3 | 5.4 | | Good |
| HXT5 (YHR096C) | 4 A | 21 P | 0 A | 27 A | 5.3 | #DIV/0! | 5.3 | Yes | Med |
| ORF YFL030W | 29 P | 123 P | 9 M | 60 P | 4.2 | 6.4 | 5.3 | | Good |
| ORF YDR453C | 24 P | 195 P | 52 P | 129 P | 8.1 | 2.5 | 5.3 | | Excl |
| ORF YKL221W | 3 A | 19 P | 4 A | 17 P | 6.3 | 4.3 | 5.3 | | Good |
| ORF YPL230W | 10 A | 47 P | 11 A | 63 P | 4.7 | 5.9 | 5.3 | | Good |
| ORF YPL123C | 5 A | 39 P | 20 P | 56 P | 7.8 | 2.8 | 5.3 | | Good |
| ORF YER067W | 56 P | 171 P | 14 P | 100 P | 3.1 | 7.4 | 5.2 | | Excl |
| ORF YMR250W | 52 P | 224 P | 56 P | 345 P | 4.3 | 6.1 | 5.2 | | Excl |
| ORF YNL195C | 10 A | 52 P | 11 A | 54 P | 5.2 | 5.1 | 5.1 | | Good |
| MF(ALPHA)2 (YG | 10 A | 24 P | -14 A | 25 A | 2.4 | -1.9 | 5.1 | Yes | Med |
| ORF YJL066C | 6 A | 43 P | 12 A | 37 P | 7.2 | 3.0 | 5.1 | | Good |
| MBR1 (YKL093W) | 0 A | 35 P | 14 A | 44 P | #DIV/0! | 3.1 | 5.1 | Yes | Med |
| ORF YLR311C | 6 A | 35 P | 10 A | 41 P | 5.8 | 4.1 | 5.0 | | Good |

Figure 24B

| | | | | | | | | |
|---|---|---|---|---|---|---|---|---|
| ORF YIL055C | 4 A | 25 P | 15 A | 53 P | 6.3 | 3.6 | 4.9 | Good |
| ORF YGL165C | -16 A | 3 A | -24 A | 6 A | -0.2 | -0.2 | 4.9 Yes | Med |
| ARG1 (YOL058W) | 29 P | 202 P | 140 P | 392 P | 7.0 | 2.8 | 4.9 | Excl |
| GLC3 (YEL011W) | 28 P | 139 P | 28 P | 130 P | 5.0 | 4.6 | 4.8 | Excl |
| ORF YJL144W | 9 A | 53 P | 8 A | 28 P | 5.9 | 3.5 | 4.7 | Good |
| ORF YMR290W-A | 11 A | 23 P | 6 A | 46 P | 2.1 | 7.2 | 4.6 | Good |
| ORF YKR102W | 3 A | 15 P | 19 P | 79 P | 5.0 | 4.1 | 4.6 | Good |
| ORF YLR149C | 6 A | 42 P | 37 P | 78 P | 7.0 | 2.1 | 4.5 | Good |
| ORF YDL032W | -7 A | 10 A | -2 A | 26 P | -1.4 | -13.1 | 4.5 Yes | Med |
| MLS1 (YNL117W) | 0 A | 21 A | 4 A | 20 P | #DIV/0! | 4.6 | 4.4 Yes | Med |
| HXK1 (YFR053C) | 422 P | 1916 P | 531 P | 2252 P | 4.5 | 4.2 | 4.4 | Excl |
| ORF YKL151C | 103 P | 553 P | 172 P | 584 P | 5.4 | 3.4 | 4.4 | Excl |
| ORF YGL121C | 56 P | 359 P | 43 P | 91 P | 6.4 | 2.1 | 4.3 | Excl |
| ORF YOR382W | 117 P | 560 P | 482 P | 1737 P | 4.8 | 3.6 | 4.2 | Excl |
| ORF YPR184W | -1 A | 26 P | 37 P | 110 P | -26.0 | 2.9 | 4.2 Yes | Med |
| ORF YIR043C (_) | -11 A | 9 A | -31 A | -10 A | -0.8 | 0.3 | 4.2 Yes | Med |
| ORF YCR010C | -1 A | 14 A | 5 A | 25 M | -14.0 | 5.1 | 4.0 Yes | Med |
| IDP2 (YLR174W) | -3 A | 20 P | 14 A | 47 P | -6.7 | 3.3 | 4.0 Yes | Med |
| ORF YNL196C | -8 A | 15 A | -12 A | 5 A | -1.9 | -0.4 | 3.9 Yes | Med |
| ORF YEL059W | -15 A | 4 A | -18 A | 2 A | -0.3 | -0.1 | 3.9 Yes | Med |
| ORF YOR376W | -1 A | 18 A | -15 A | 4 A | -18.0 | -0.3 | 3.8 Yes | Med |
| TFS1 (YLR178C) | 69 P | 323 P | 130 P | 373 P | 4.7 | 2.9 | 3.8 | Excl |
| ISF1 (YMR081C) | 11 P | 54 P | 13 M | 34 P | 4.9 | 2.6 | 3.8 | Good |
| GCY1 (YOR120W) | 45 P | 181 P | 50 P | 162 P | 4.0 | 3.2 | 3.6 | Excl |
| ORF YFR046C | 4 A | 16 P | 8 A | 25 P | 4.0 | 3.1 | 3.6 | Good |
| LAP4 (YKL103C) | 23 P | 112 P | 56 P | 121 P | 4.9 | 2.2 | 3.5 | Excl |
| TPS2 (YDR074W) | 53 P | 215 P | 130 P | 386 P | 4.1 | 3.0 | 3.5 | Excl |
| FOX2 (YKR009C) | -2 A | 23 A | 10 A | 20 P | -11.5 | 2.0 | 3.5 Yes | Med |
| MET28 (YIR017C) | 7 A | 19 P | 5 A | 23 P | 2.7 | 4.3 | 3.5 | Good |
| ORF YNL171C | 6 A | 27 A | 10 A | 23 P | 4.5 | 2.4 | 3.5 | Good |
| ORF YFL012W | 0 A | 12 A | -3 A | 19 P | #DIV/0! | -7.0 | 3.4 Yes | Med |
| ORF YIL025C | -12 A | -1 A | -26 A | -3 A | 0.1 | 0.1 | 3.4 Yes | Med |
| GPM2 (YDL021W) | 10 P | 43 P | 22 P | 52 P | 4.3 | 2.4 | 3.3 | Excl |
| ORF YFR017C | 22 P | 99 P | 36 P | 79 P | 4.5 | 2.2 | 3.3 | Excl |

Figure 24C

| | 60 | P | 236 | P | 211 | P | 568 | P | 3.9 | 2.7 | 3.3 | |
|---|---|---|---|---|---|---|---|---|---|---|---|---|
| GSC2 (YGR032W) | | | | | | | | | | | 3.3 | Excl |
| ORF YNL319W | -4 | A | 8 | A | -10 | A | 11 | A | -2.0 | -1.2 | 3.3 | Yes Med |
| ORF YLR161W | 9 | A | 30 | P | 31 | P | 101 | P | 3.3 | 3.3 | 3.3 | Good |
| ORF YGR290W | -6 | A | 7 | A | -14 | A | 6 | A | -1.2 | -0.5 | 3.3 | Yes Med |
| ORF YOR364W | 5 | A | 19 | A | 14 | P | 38 | P | 3.8 | 2.7 | 3.3 | Good |
| GSY1 (YFR015C) | 20 | P | 61 | P | 19 | P | 63 | P | 3.1 | 3.4 | 3.2 | Excl |
| ORF YMR196W | 10 | A | 42 | P | 36 | P | 77 | P | 4.2 | 2.1 | 3.2 | Good |
| ORF YJL218W | 67 | P | 214 | P | 52 | P | 163 | P | 3.2 | 3.1 | 3.2 | Excl |
| ORF YLR312C | 14 | P | 35 | P | 12 | A | 46 | P | 2.5 | 3.8 | 3.2 | Good |
| ORF YER037W | 39 | P | 111 | P | 46 | P | 156 | P | 2.8 | 3.4 | 3.1 | Excl |
| CIT3 (YPR001W) | 11 | A | 23 | P | 6 | A | 26 | P | 2.1 | 4.1 | 3.1 | Good |
| ORF YOR193W | 7 | A | 21 | A | 20 | P | 63 | P | 3.0 | 3.1 | 3.1 | Good |
| PCK1 (YKR097W) | 14 | M | 54 | P | 23 | P | 51 | P | 3.9 | 2.2 | 3.0 | Good |
| ORF YLR343W | 4 | A | 16 | P | 20 | P | 41 | P | 4.0 | 2.1 | 3.0 | Good |
| ORF YPL186C | 18 | P | 60 | P | 18 | M | 48 | P | 3.3 | 2.7 | 3.0 | Good |
| ORF YHR140W | 0 | A | 16 | A | -11 | A | 3 | A | #DIV/0! | -0.3 | 3.0 | Yes Med |
| ORF YIL087C | 28 | P | 84 | P | 36 | A | 109 | P | 3.0 | 3.0 | 3.0 | Good |
| HOR2 (YER062C) | 224 | P | 695 | P | 332 | P | 928 | P | 3.1 | 2.8 | 2.9 | Excl |
| YFL-TyB/_f (con) | 49 | P | 153 | P | 219 | P | 606 | P | 3.1 | 2.8 | 2.9 | Excl |
| ORF YGR146C | 103 | P | 387 | P | 272 | P | 575 | P | 3.8 | 2.1 | 2.9 | Excl |
| ORF YFL013W-A | -7 | A | 4 | A | -14 | A | 5 | A | -0.6 | -0.4 | 2.9 | Yes Med |
| ORF YPR064W | 0 | A | 16 | A | -7 | A | 6 | A | #DIV/0! | -0.8 | 2.9 | Yes Med |
| ORF YPR123C | -10 | A | 5 | A | 10 | A | 27 | P | -0.5 | 2.8 | 2.9 | Yes Med |
| ORF YPL222W | -12 | A | 0 | A | 17 | P | 57 | P | 0.0 | 3.3 | 2.9 | Yes Med |
| ORF YLR237W | 78 | P | 276 | P | 150 | P | 330 | P | 3.5 | 2.2 | 2.9 | Excl |
| ORF YMR090W | 114 | P | 330 | P | 179 | P | 505 | P | 2.9 | 2.8 | 2.9 | Excl |
| ORF YGL075C | 9 | A | 21 | A | 12 | A | 40 | P | 2.3 | 3.3 | 2.8 | Good |
| GLK1 (YCL040W) | 422 | P | 1230 | P | 551 | P | 1448 | P | 2.9 | 2.6 | 2.8 | Excl |
| MCR1 (YKL150W) | 204 | P | 628 | P | 279 | P | 650 | P | 3.1 | 2.3 | 2.7 | Excl |
| ORF YLR267W | -11 | A | 1 | A | -1 | A | 14 | A | -0.1 | -13.8 | 2.7 | Yes Med |
| ORF YBL043W | 34 | P | 86 | P | 60 | P | 168 | P | 2.5 | 2.8 | 2.7 | Excl |
| MRK1 (YDL079C) | -5 | A | 7 | P | -10 | A | 5 | A | -1.4 | -0.5 | 2.7 | Yes Med |
| ORF YKL201C | 33 | P | 93 | P | 78 | P | 194 | P | 2.8 | 2.5 | 2.7 | Excl |
| ADR1 (YDR216W) | 14 | P | 33 | P | 45 | P | 130 | P | 2.4 | 2.9 | 2.6 | Excl |

Figure 24D

| | | | | | | | | |
|---|---|---|---|---|---|---|---|---|
| PBI2 (YNL015W) | 362 | P | 1097 | P | 515 | P | 1124 | P | 3.0 | 2.2 | 2.6 | | Excl |
| ORF YMR040W | 44 | P | 134 | P | 46 | P | 98 | P | 3.0 | 2.1 | 2.6 | | Excl |
| HXT7 (YDR342C) | 1221 | P | 2606 | P | 1268 | P | 3852 | P | 2.1 | 3.0 | 2.6 | | Excl |
| ORF YBR128C | 6 | A | 17 | A | 0 | A | 12 | M | 2.8 | #DIV/0! | 2.6 | Yes | Med |
| ENO1 (YGR254W) | 1660 | P | 4724 | P | 3024 | P | 6843 | P | 2.8 | 2.3 | 2.6 | | Excl |
| ORF YNL234W | 25 | P | 69 | P | 84 | P | 190 | P | 2.8 | 2.3 | 2.5 | | Excl |
| STF2 (YGR008C) | 799 | P | 1964 | P | 626 | P | 1582 | P | 2.5 | 2.5 | 2.5 | | Excl |
| ORF YBL048W | 21 | P | 60 | P | 26 | P | 55 | P | 2.9 | 2.1 | 2.5 | | Excl |
| ORF YMR050C e | 150 | P | 424 | P | 1492 | P | 3168 | P | 2.8 | 2.1 | 2.5 | | Excl |
| ORF YOR289W | 36 | P | 87 | P | 65 | P | 162 | P | 2.4 | 2.5 | 2.5 | | Excl |
| ORF YMR265C | 7 | A | 19 | A | 29 | P | 61 | P | 2.7 | 2.1 | 2.4 | | Good |
| ORF YGR066C | -2 | A | 11 | A | -14 | A | -2 | A | -5.5 | 0.2 | 2.4 | Yes | Med |
| ORF YIR038C | 173 | P | 467 | P | 266 | P | 562 | P | 2.7 | 2.1 | 2.4 | | Excl |
| YRO2 (YBR054W) | 391 | P | 960 | P | 642 | P | 1508 | P | 2.5 | 2.3 | 2.4 | | Excl |
| MET2 (YNL277W) | 25 | P | 65 | P | 30 | P | 66 | P | 2.6 | 2.2 | 2.4 | | Excl |
| SPS100 (YHR139) | 24 | P | 65 | P | 41 | M | 84 | P | 2.7 | 2.1 | 2.4 | | Excl |
| ORF YGR243W | 47 | P | 125 | P | 30 | A | 62 | P | 2.7 | 2.1 | 2.4 | | Good |
| STP4 (YDL048C) | 75 | P | 198 | P | 319 | P | 655 | P | 2.6 | 2.1 | 2.3 | | Good |
| ORF YBL101W-B | 50 | P | 122 | P | 308 | P | 691 | P | 2.4 | 2.2 | 2.3 | | Excl |
| ORF YBR300C | 16 | A | 33 | P | 18 | P | 47 | P | 2.1 | 2.6 | 2.3 | | Good |
| ORF YCL021W | 12 | P | 30 | P | 23 | P | 49 | P | 2.5 | 2.1 | 2.3 | | Excl |
| ORF YER187W | 13 | P | 33 | P | 12 | M | 25 | P | 2.5 | 2.1 | 2.3 | | Good |
| ORF YGR212W | -3 | A | 8 | A | -8 | A | 4 | A | -2.7 | -0.5 | 2.3 | Yes | Med |
| ORF YLR251W | 89 | P | 214 | P | 105 | P | 231 | P | 2.4 | 2.2 | 2.3 | | Excl |
| YGP1 (YNL160W) | 1574 | P | 3840 | P | 2212 | P | 4733 | P | 2.4 | 2.1 | 2.3 | | Excl |
| ORF YER081W | 60 | P | 125 | P | 108 | P | 270 | P | 2.1 | 2.5 | 2.3 | | Excl |
| GSY2 (YLR258W) | 101 | P | 258 | P | 237 | P | 479 | P | 2.6 | 2.0 | 2.3 | | Excl |
| ORF YLR297W | 231 | P | 497 | P | 302 | P | 728 | P | 2.2 | 2.4 | 2.3 | | Excl |
| ORF YGR023W | 9 | A | 20 | A | 26 | A | 60 | P | 2.2 | 2.3 | 2.3 | | Good |
| ORF YCL042W | 60 | P | 133 | P | 67 | P | 155 | P | 2.2 | 2.3 | 2.3 | | Excl |
| ORF YBR157C | 51 | P | 111 | P | 59 | P | 136 | P | 2.2 | 2.3 | 2.2 | | Excl |
| ORF YNL274C | 100 | P | 231 | P | 112 | P | 241 | P | 2.3 | 2.2 | 2.2 | | Good |
| ORF YMR320W | 10 | P | 24 | A | 29 | A | 59 | P | 2.4 | 2.1 | 2.2 | | Excl |
| ORF YJR028W | 172 | P | 403 | P | 1546 | P | 3195 | P | 2.3 | 2.1 | 2.2 | | Excl |
| CIT2 (YCR005C) | 100 | P | 228 | P | 223 | P | 475 | P | 2.3 | 2.1 | 2.2 | | Excl |
| ORF YML039W e | 161 | P | 357 | P | 1556 | P | 3205 | P | 2.2 | 2.1 | 2.1 | | Good |
| ORF YER158C | 27 | P | 59 | P | 43 | P | 90 | P | 2.2 | 2.1 | 2.1 | | Excl |
| ORF YDL183C | 12 | A | 26 | P | 28 | P | 56 | P | 2.2 | 2.0 | 2.1 | | Good |
| GSP2 (YOR185C) | 117 | P | 235 | P | 229 | P | 478 | P | 2.0 | 2.1 | 2.0 | | Excl |
| ORF YPR194C | 40 | P | 81 | P | 43 | P | 87 | P | 2.0 | 2.0 | 2.0 | | Excl |

Figure 24E

| Gal11 Down | | | | | | | | |
|---|---|---|---|---|---|---|---|---|
| Gene Expression Results for FH1998040601A | | | | | | | Average | |
| Gene | WT#1 rav | WT#1 GAL11#1 | GALWT#2 r | WT#1 GAL11#2 | GAL1:MT1/WT1 | MT2/WT2 | Fold Down | Corrected? Confidence |
| AFR1 (YDR085C) | 64 P | 15 P | 61 P | -148 A | 0.24 | -2.43 | 23.01 Yes | Med |
| ALPHA1 (YCL066W) | 18 A | -5 A | 11 A | -30 A | -0.28 | -2.69 | 6.37 Yes | Med |
| CHA1 (YCL064C) | 1384 P | 405 P | 1301 P | 484 P | 0.29 | 0.37 | 3.05 | Excl |
| CTA1 (YDR256C) | 12 A | -19 A | 20 A | -1 A | -1.55 | -0.06 | 5.19 Yes | Med |
| HO (YDL227C) | 556 P | 261 P | 454 P | 188 P | 0.47 | 0.41 | 2.27 | Excl |
| HXT15 (YDL245C) | 2 A | -32 A | 22 P | 2 A | -16.10 | 0.11 | 7.88 Yes | Med |
| ORF YAL043C-A | -3 P | -15 A | 5 A | -6 A | 5.08 | -1.23 | 2.34 Yes | Med |
| ORF YAR037W (_r) | -9 A | -46 A | -34 A | -68 A | 5.08 | 2.00 | 7.07 Yes | Med |
| ORF YBR089W | 20 P | 7 A | 16 P | 5 A | 0.34 | 0.31 | 3.10 | Good |
| ORF YBR134W | 16 A | -3 A | 11 P | -9 A | -0.21 | -0.79 | 3.90 Yes | Med |
| ORF YBR158W | 2102 P | 739 P | 2168 P | 620 P | 0.35 | 0.29 | 3.17 | Excl |
| ORF YBR186W | 5 A | -31 A | 27 P | 10 A | -6.10 | 0.37 | 4.92 Yes | Med |
| ORF YBR209W | -1 A | -42 A | -6 A | -22 A | 42.37 | 3.70 | 5.76 Yes | Med |
| ORF YCL046W | 12 A | -29 A | 28 P | 9 A | -2.40 | 0.31 | 5.70 Yes | Med |
| ORF YCR074C | -22 A | -73 A | -5 A | -101 A | 3.31 | 20.25 | 14.71 Yes | Excl |
| ORF YDL022W | 2501 P | 905 P | 2362 P | 816 P | 0.36 | 0.35 | 2.83 | Excl |
| ORF YDL037C | 114 P | 20 A | 165 M | 42 A | 0.18 | 0.25 | 4.77 | Good |
| ORF YDL204W | 59 P | 19 P | 433 P | 32 P | 0.32 | 0.07 | 8.33 | Excl |
| ORF YDL221W | -11 A | -51 A | -10 A | -32 A | 4.62 | 3.21 | 6.19 Yes | Med |
| ORF YDR007W | 814 P | 261 P | 856 P | 209 P | 0.32 | 0.24 | 3.61 | Excl |
| ORF YDR008C | 46 P | 12 A | 17 P | -23 A | 0.26 | -1.38 | 5.98 Yes | Med |
| ORF YDR070C | 51 P | 25 M | 39 P | 4 A | 0.50 | 0.09 | 6.27 | Good |
| ORF YDR095C | 8 A | -3 A | 30 A | 1 A | -0.42 | 0.04 | 13.29 Yes | Med |
| ORF YDR193W | 49 A | -14 A | 29 A | -1 A | -0.28 | -0.04 | 9.28 Yes | Med |
| ORF YDR344C | -1 A | -73 A | 15 A | -27 A | 72.88 | -1.81 | 11.40 Yes | Med |
| ORF YDR359C | 52 P | 24 P | 46 P | 16 P | 0.46 | 0.35 | 2.53 | Excl |
| ORF YDR380W | 291 P | 137 P | 447 P | 186 P | 0.47 | 0.42 | 2.26 | Excl |
| ORF YDR442W | -26 A | -39 A | -6 A | -25 A | 1.50 | 4.12 | 3.17 Yes | Med |
| ORF YDR446W | -7 A | -27 A | 7 A | -22 A | 3.87 | -3.17 | 4.93 Yes | Med |
| ORF YEL059W | 17 A | 0 A | 0 A | -26 A | 0.00 | #DIV/0! | 4.30 Yes | Med |

Figure 25A

| | | | | | | | | |
|---|---|---|---|---|---|---|---|---|
| ORF YGL183C | 21 | P | 5 | A | 4 | A | -22 | A | 0.22 | -5.50 | 4.91 | Yes | Med |
| ORF YGL217C | 27 | P | 13 | A | 11 | A | -8 | A | 0.46 | -0.73 | 2.98 | Yes | Med |
| ORF YGL259W | -8 | A | -22 | A | -19 | A | -36 | A | 2.70 | 1.89 | 3.06 | Yes | Med |
| ORF YIL037C | -4 | A | -22 | A | -19 | A | -38 | A | 5.40 | 2.00 | 3.66 | Yes | Med |
| ORF YJL113W exon 1 | 19 | A | 7 | A | 7 | A | -6 | A | 0.38 | -0.87 | 2.62 | Yes | Med |
| ORF YKL037W | 131 | A | 63 | A | 61 | A | 23 | A | 0.48 | 0.37 | 2.38 | | Good |
| ORF YMR069W | 34 | A | 15 | A | 15 | A | -6 | A | 0.45 | -0.40 | 3.21 | Yes | Med |
| ORF YMR317W | 20 | A | 4 | A | 4 | A | -49 | A | 0.20 | -12.24 | 7.80 | Yes | Med |
| ORF YNL194C | -7 | A | -26 | A | -26 | A | -71 | A | 3.71 | 2.75 | 6.44 | Yes | Med |
| ORF YNL195C | 42 | P | 20 | P | 20 | P | -8 | A | 0.48 | -0.41 | 3.87 | Yes | Med |
| ORF YNR066C | 11 | A | -7 | A | -7 | A | -27 | A | -0.64 | 3.79 | 3.75 | Yes | Med |
| ORF YOL050C | 37 | P | 18 | A | 18 | A | 4 | A | 0.49 | 0.23 | 3.23 | | Good |
| ORF YOR055W | 7 | A | -8 | A | -8 | A | -22 | A | -1.14 | 2.81 | 2.94 | Yes | Med |
| ORF YOR314W | 19 | A | 6 | A | 6 | A | -57 | A | 0.32 | -9.52 | 7.90 | Yes | Med |
| ORF YOR378W | 16 | A | 2 | A | 2 | A | -20 | A | 0.13 | -10.20 | 6.24 | Yes | Med |
| ORF YPR077C (_f) | 9 | A | -13 | A | -13 | A | -33 | A | -1.44 | 2.51 | 4.17 | Yes | Med |
| PDR15 (YDR406W) | 153 | P | 68 | P | 156 | P | 75 | P | 0.44 | 0.48 | 2.16 | | Excl |
| STP4 (YDL048C) | 111 | P | 47 | P | 147 | P | 26 | A | 0.43 | 0.18 | 4.00 | | Good |
| YCRX12w (control?) | 17 | P | -22 | A | 14 | A | 0 | A | -1.30 | 0.00 | 5.30 | Yes | Med |
| YRO2 (YBR054W) | 413 | P | 108 | P | 422 | P | 144 | P | 0.26 | 0.34 | 3.36 | | Excl |

Figure 25B

Gal11 Down

Gene Expression Results for FH19980040601A

| Gene | WT#1 raw | WT# GAL11#1 | GAL WT#2 r | WT#: GAL11#2r | GAL1:MT1/WT1 | MT2/WT2 | Average Fold Down | Corrected? | Confidence |
|---|---|---|---|---|---|---|---|---|---|
| AFR1 (YDR085C) | 64 P | 15 P | 61 P | -148 A | 0.24 | -2.43 | 23.01 | Yes | Med |
| ORF YCR074C | -22 A | -73 A | -5 A | -101 A | 3.31 | 20.25 | 14.71 | Yes | Med |
| ORF YDR095C | 8 A | -3 A | 30 A | 1 A | -0.42 | 0.04 | 13.29 | Yes | Med |
| ORF YDR344C | -1 A | -73 A | 15 A | -27 A | 72.88 | -1.81 | 11.40 | Yes | Med |
| ORF YDR193W | 49 A | -14 A | 29 A | -1 A | -0.28 | -0.04 | 9.28 | Yes | Med |
| ORF YDL204W | 59 P | 19 P | 433 P | 32 P | 0.32 | 0.07 | 8.33 | | Excl |
| ORF YOR314W | 19 A | 6 A | 6 A | -57 A | 0.32 | -9.52 | 7.90 | Yes | Med |
| HXT15 (YDL245C) (_) | 2 A | -32 A | 22 P | 2 A | -16.10 | 0.11 | 7.88 | Yes | Med |
| ORF YMR317W | 20 A | 4 A | 4 A | -49 A | 0.20 | -12.24 | 7.80 | Yes | Med |
| ORF YAR037W (_r) | -9 A | -46 A | -34 A | -68 A | 5.08 | 2.00 | 7.07 | Yes | Med |
| ORF YNL194C | -7 A | -26 A | -26 A | -71 A | 3.71 | 2.75 | 6.44 | Yes | Med |
| ALPHA1 (YCL066W) | 18 A | -5 A | 11 A | -30 A | -0.28 | -2.69 | 6.37 | Yes | Med |
| ORF YDR070C | 51 P | 25 M | 39 P | 4 A | 0.50 | 0.09 | 6.27 | | Good |
| ORF YOR378W | 16 A | 2 A | 2 A | -20 A | 0.13 | -10.20 | 6.24 | Yes | Med |
| ORF YDL221W | -11 A | -51 A | -10 A | -32 A | 4.62 | 3.21 | 6.19 | Yes | Med |
| ORF YDR008C | 46 P | 12 A | 17 P | -23 A | 0.26 | -1.38 | 5.98 | Yes | Med |
| ORF YBR209W | -1 A | -42 A | -6 A | -22 A | 42.37 | 3.70 | 5.76 | Yes | Med |
| ORF YCL046W | 12 A | -29 A | 28 P | 9 A | -2.40 | 0.31 | 5.70 | Yes | Med |
| YCRX12w/ (control?) | 17 P | -22 A | 14 A | 0 A | -1.30 | 0.00 | 5.30 | Yes | Med |
| CTA1 (YDR256C) | 12 A | -19 A | 20 A | -1 A | -1.55 | -0.06 | 5.19 | Yes | Med |
| ORF YDR446W | -7 A | -27 A | 7 A | -22 A | 3.87 | -3.17 | 4.93 | Yes | Med |
| ORF YBR186W | 5 A | -31 A | 27 P | 10 A | -6.10 | 0.37 | 4.92 | Yes | Med |
| ORF YGL183C | 21 P | 5 A | 4 A | -22 A | 0.22 | -5.50 | 4.91 | Yes | Med |
| ORF YDL037C | 114 P | 20 A | 165 M | 42 A | 0.18 | 0.25 | 4.77 | | Good |
| ORF YEL059W | 17 A | 0 A | 0 A | -26 A | 0.00 | #DIV/0! | 4.30 | Yes | Med |
| ORF YPR077C (_f) | 9 A | -13 A | -13 A | -33 A | -1.44 | 2.51 | 4.17 | Yes | Med |
| STP4 (YDL048C) | 111 P | 47 P | 147 P | 26 A | 0.43 | 0.18 | 4.00 | | Good |
| ORF YBR134W | 16 A | -3 A | 11 P | -9 A | -0.21 | -0.79 | 3.90 | Yes | Med |
| ORF YNL195C | 42 P | 20 P | 20 P | -8 A | 0.48 | -0.41 | 3.87 | Yes | Med |

Figure 26A

| | 11 | A | -7 | A | -7 | A | -27 | A | -0.64 | 3.79 | 3.75 | Yes | Med |
|---|---|---|---|---|---|---|---|---|---|---|---|---|---|
| ORF YNR066C | | | | | | | | | | | | | |
| ORF YIL037C | -4 | A | -22 | A | -19 | A | -38 | A | 5.40 | 2.00 | 3.66 | Yes | Med |
| ORF YDR007W | 814 | P | 261 | P | 856 | P | 209 | P | 0.32 | 0.24 | 3.61 | | Excl |
| YRO2 (YBR054W) | 413 | P | 108 | P | 422 | P | 144 | P | 0.26 | 0.34 | 3.36 | | Excl |
| ORF YOL050C | 37 | P | 18 | A | 18 | A | 4 | A | 0.49 | 0.23 | 3.23 | | Good |
| ORF YMR069W | 34 | A | 15 | A | 15 | A | -6 | A | 0.45 | -0.40 | 3.21 | Yes | Med |
| ORF YBR158W | 2102 | P | 739 | P | 2168 | P | 620 | P | 0.35 | 0.29 | 3.17 | | Excl |
| ORF YDR442W | -26 | A | -39 | A | -6 | A | -25 | A | 1.50 | 4.12 | 3.17 | Yes | Med |
| ORF YBR089W | 20 | P | 7 | A | 16 | P | 5 | A | 0.34 | 0.31 | 3.10 | | Good |
| ORF YGL259W | -8 | A | -22 | A | -19 | A | -36 | A | 2.70 | 1.89 | 3.06 | Yes | Med |
| CHA1 (YCL064C) | 1384 | P | 405 | P | 1301 | P | 484 | P | 0.29 | 0.37 | 3.05 | | Excl |
| ORF YGL217C | 27 | P | 13 | A | 11 | A | -8 | A | 0.46 | -0.73 | 2.98 | Yes | Med |
| ORF YOR055W | 7 | A | -8 | A | -8 | A | -22 | A | -1.14 | 2.81 | 2.94 | Yes | Med |
| ORF YDL022W | 2501 | P | 905 | P | 2362 | P | 816 | P | 0.36 | 0.35 | 2.83 | | Excl |
| ORF YJL113W exon 1 | 19 | A | 7 | A | 7 | A | -6 | A | 0.38 | -0.87 | 2.62 | Yes | Med |
| ORF YDR359C | 52 | P | 24 | P | 46 | P | 16 | P | 0.46 | 0.35 | 2.53 | | Excl |
| ORF YKL037W | 131 | A | 63 | A | 61 | A | 23 | A | 0.48 | 0.37 | 2.38 | | Good |
| ORF YAL043C-A | -3 | A | -15 | A | 5 | A | -6 | A | 5.08 | -1.23 | 2.34 | Yes | Med |
| HO (YDL227C) | 556 | P | 261 | P | 454 | P | 188 | P | 0.47 | 0.41 | 2.27 | | Excl |
| ORF YDR380W | 291 | P | 137 | P | 447 | P | 186 | P | 0.47 | 0.42 | 2.26 | | Excl |
| PDR15 (YDR406W) | 153 | P | 68 | P | 156 | P | 75 | P | 0.44 | 0.48 | 2.16 | | Excl |

Figure 26B

Up Gal11

Gene Expression Results for FH19980040601A

| Gene | WT#1 rWT# | GAL11#1:GAL | WT#2 rWT#2 | GAL11#2 | GAL11:MT1/WT1 | MT2/WT2 | Average Fold Up | Corrected? | Confidence |
|---|---|---|---|---|---|---|---|---|---|
| ADH5 (YBR145W) | 147 P | 451 P | 138 P | 400 P | 3.1 | 2.9 | 3.0 | | Excl |
| ADR1 (YDR216W) | 103 P | 219 P | 116 P | 328 P | 2.1 | 2.8 | 2.5 | | Excl |
| AMD2 (YDR242W) | 33 P | 86 P | 32 P | 70 P | 2.6 | 2.2 | 2.4 | | Excl |
| APE3 (YBR286W) | 2268 P | 4990 P | 2205 P | 4702 P | 2.2 | 2.1 | 2.2 | | Excl |
| CAT2 (YML042W) | 12 M | 62 P | 60 P | 129 P | 5.2 | 2.1 | 3.7 | | Good |
| CIT2 (YCR005C) | 504 P | 1537 P | 560 P | 1147 P | 3.1 | 2.0 | 2.5 | | Excl |
| ENA1 (YDR040C) | 8 A | 58 P | -4 A | 152 P | 7.2 | -38.0 | 19.2 | Yes | Med |
| EXM2 (YDL087C) | 40 A | 100 P | 27 P | 81 P | 2.5 | 3.0 | 2.8 | | Good |
| FIG1 (YBR040W) | 2 A | 44 P | 5 A | 21 A | 22.0 | 4.2 | 13.1 | | Good |
| FLO9 (YAL064W) | -43 A | -31 A | -37 A | -20 A | 0.7 | 0.5 | 3.0 | Yes | Med |
| GAL7 (YBR018C) | -5 A | 24 A | -27 A | 6 A | -4.7 | -0.2 | 6.2 | Yes | Med |
| GDH2 (YDL215C) | 447 P | 1093 P | 393 P | 994 P | 2.4 | 2.5 | 2.5 | | Excl |
| GDH3 (YAL062W) | 61 P | 215 P | 69 P | 194 P | 3.5 | 2.8 | 3.2 | | Excl |
| GPM2 (YDL021W) | 37 P | 132 P | 34 P | 122 P | 3.6 | 3.6 | 3.6 | | Excl |
| KIN82 (YCR091W) | 12 P | 78 P | 23 P | 77 P | 6.5 | 3.3 | 4.9 | | Excl |
| LYS2 (YBR115C) | 666 P | 1893 P | 649 P | 1777 P | 2.8 | 2.7 | 2.8 | | Excl |
| ORF YAR030C | 12 A | 68 A | 14 P | 60 P | 5.6 | 4.3 | 5.0 | | Good |
| ORF YAR031W | 36 P | 78 A | 22 P | 48 P | 2.2 | 2.2 | 2.2 | | Good |
| ORF YAR052C (_f) | 13 A | 56 P | 33 A | 67 P | 4.3 | 2.0 | 3.2 | | Good |
| ORF YAR052C (_i) | -75 A | -37 A | -75 A | -40 A | 0.5 | 0.5 | 7.3 | Yes | Med |
| ORF YAR064W (_f) | -11 A | 5 A | -10 A | 9 A | -0.5 | -0.9 | 3.5 | Yes | Med |
| ORF YAR066W (_f) | 129 P | 308 P | 148 P | 374 P | 2.4 | 2.5 | 2.5 | | Excl |
| ORF YAR068W (_f) | 203 P | 649 P | 221 P | 654 P | 3.2 | 3.0 | 3.1 | | Excl |
| ORF YAR074C | -2 A | 39 A | 9 A | 22 A | -19.5 | 2.5 | 5.3 | Yes | Med |
| ORF YBL078C | 115 P | 358 P | 139 P | 295 P | 3.1 | 2.1 | 2.6 | | Excl |
| ORF YBR005W | 79 P | 171 P | 84 P | 253 P | 2.2 | 3.0 | 2.6 | | Excl |
| ORF YBR012C | 44 P | 264 P | 71 P | 256 P | 6.0 | 3.6 | 4.8 | | Med |
| ORF YBR051W | 11 A | 46 P | -7 A | 26 P | 4.2 | -3.7 | 5.4 | Yes | Med |
| ORF YBR113W | 74 P | 164 M | 104 P | 227 P | 2.2 | 2.2 | 2.2 | | Good |
| ORF YBR147W | 15 A | 83 A | 51 A | 96 P | 5.5 | 19.3 | 12.4 | | Good |
| ORF YBR178W | -40 A | -17 A | -40 A | -22 A | 0.4 | 0.6 | 4.1 | Yes | Med |
| ORF YBR224W | -27 A | 15 A | -60 A | -11 A | -0.6 | 0.2 | 9.1 | Yes | Med |
| ORF YBR240C | 3 A | 39 A | 16 A | 32 A | 13.0 | 2.0 | 7.5 | | Good |

Figure 27A

| | 95 | P | 856 | P | 101 | P | 747 | P | 9.0 | 7.4 | 8.2 | | |
|---|---|---|---|---|---|---|---|---|---|---|---|---|---|
| ORF YBR296C | 95 | P | 856 | P | 101 | P | 747 | P | | | | | Excl |
| ORF YBR300C (_f) | 13 | A | 37 | A | 4 | A | 22 | M | 2.9 | 5.6 | 4.2 | | Good |
| ORF YBR300C (_i) | 24 | P | 147 | P | 30 | P | 136 | P | 6.1 | 4.5 | 5.3 | | Excl |
| ORF YBR300C (_r) | 22 | P | 127 | P | 23 | P | 107 | P | 5.8 | 4.7 | 5.2 | | Excl |
| ORF YCL023C | -2 | A | 15 | A | 11 | A | 32 | P | -7.6 | 2.9 | 3.2 | Yes | Med |
| ORF YCL049C | 70 | A | 219 | P | 93 | P | 549 | P | 3.1 | 5.9 | 4.5 | | Good |
| ORF YCL053C | 33 | P | 76 | A | 35 | P | 77 | P | 2.3 | 2.2 | 2.2 | | Good |
| ORF YCL075W | 13 | A | 73 | P | 7 | A | 30 | M | 5.6 | 4.2 | 4.9 | | Good |
| ORF YCR049C | -4 | A | 7 | A | 4 | A | 15 | A | -1.7 | 3.7 | 2.9 | Yes | Med |
| ORF YDL016C | -6 | A | 7 | A | 3 | A | 19 | A | -1.1 | 6.2 | 4.4 | Yes | Med |
| ORF YDL172C | 44 | A | 136 | P | 36 | A | 111 | A | 3.1 | 3.1 | 3.1 | | Good |
| ORF YDL239C | 24 | P | 54 | P | 16 | M | 32 | P | 2.3 | 2.0 | 2.1 | | Good |
| ORF YDL247W (_r) | -19 | A | 41 | A | -40 | A | -11 | A | -2.1 | 0.3 | 8.9 | Yes | Med |
| ORF YDL248W (_r) | 5 | A | 47 | M | 4 | A | 65 | P | 9.5 | 16.4 | 12.9 | | Good |
| ORF YDR010C | -29 | A | -2 | A | -17 | A | 17 | A | 0.1 | -1.0 | 6.2 | Yes | Med |
| ORF YDR132C | 38 | P | 92 | P | 33 | P | 68 | P | 2.4 | 2.1 | 2.2 | | Excl |
| ORF YDR220C | 13 | A | 80 | P | 20 | A | 112 | P | 6.1 | 5.6 | 5.9 | | Good |
| ORF YDR317W | 73 | P | 149 | P | 63 | P | 157 | P | 2.0 | 2.5 | 2.3 | | Excl |
| ORF YDR437W | -10 | A | 2 | A | -8 | M | 44 | A | -0.2 | -5.6 | 6.4 | Yes | Med |
| ORF YDR525W | 7 | A | 19 | A | -2 | A | 27 | P | 2.7 | -13.6 | 4.2 | Yes | Med |
| ORF YDR534C | 103 | P | 263 | P | 54 | P | 274 | P | 2.6 | 5.1 | 3.8 | | Excl |
| ORF YDR541C | 63 | P | 195 | P | 65 | P | 184 | P | 3.1 | 2.8 | 3.0 | | Excl |
| ORF YEL008W | 0 | A | 18 | A | 16 | A | 46 | A | #DIV/0! | 2.9 | 3.3 | Yes | Med |
| ORF YFL019C | 10 | P | 20 | M | 18 | M | 48 | A | 2.0 | 2.7 | 2.4 | | Good |
| ORF YHR160C | 2 | A | 14 | A | 12 | A | 48 | A | 6.8 | 4.0 | 5.4 | | Good |
| ORF YHR210C | 15 | A | 43 | A | 38 | A | 128 | P | 2.9 | 3.4 | 3.1 | | Good |
| ORF YJL037W | 11 | A | 25 | M | 22 | M | 106 | A | 2.3 | 4.8 | 3.5 | | Good |
| ORF YLR162W | -33 | A | -14 | A | -14 | A | 3 | A | 0.4 | -0.2 | 3.6 | Yes | Med |
| ORF YLR232W | -22 | A | 16 | A | 16 | A | 35 | M | -0.7 | 2.2 | 4.9 | Yes | Med |
| ORF YLR281C | 10 | A | 32 | A | 31 | A | 74 | P | 3.2 | 2.4 | 2.8 | | Good |
| ORF YMR095C | -24 | A | -3 | A | -3 | A | 42 | P | 0.1 | -14.1 | 6.6 | Yes | Med |

Figure 27B

| | | | | | | | |
|---|---|---|---|---|---|---|---|
| ORF YMR107W | -16 | A | -4 | A | -4 | A | 23 | A | 0.3 | -5.7 | 3.9 | Yes | Med |
| ORF YNL324W | 8 | A | 19 | P | 19 | P | 49 | P | 2.4 | 2.6 | 2.5 | | Good |
| ORF YOL163W | -11 | A | 17 | A | 17 | A | 61 | M | -1.5 | 3.6 | 4.6 | Yes | Med |
| ORF YOR050C | -57 | A | -35 | A | -35 | A | 16 | A | 0.6 | -0.5 | 7.3 | Yes | Med |
| ORF YOR388C (_i) | -64 | A | -46 | A | -46 | A | -24 | A | 0.7 | 0.5 | 4.0 | Yes | Med |
| ORF YPL186C | -3 | A | 10 | A | 10 | A | 29 | A | -3.3 | 2.9 | 2.7 | Yes | Med |
| ORF YPL276W (_f) | -23 | A | -8 | A | -8 | A | 6 | A | 0.3 | -0.8 | 2.9 | Yes | Med |
| ORF YPR150W | -40 | A | -22 | A | -22 | A | -4 | A | 0.6 | 0.2 | 3.6 | Yes | Med |
| PHO5 (YBR093C) | 1055 | P | 2871 | P | 1251 | P | 2760 | P | 2.7 | 2.2 | 2.5 | | Excl |
| PXA1 (YPL147W) | 1 | A | 12 | A | 12 | A | 37 | P | 12.0 | 3.1 | 7.5 | | Good |
| RGM1 (YMR182C) | -6 | A | 10 | A | 10 | A | 21 | M | -1.7 | 2.1 | 2.7 | Yes | Med |
| SEO1 (YAL067C) | -1 | A | 47 | A | 18 | P | 58 | P | -47.5 | 3.2 | 6.5 | Yes | Med |
| UBC5 (YDR059C) e | 49 | P | 205 | P | 79 | P | 198 | P | 4.2 | 2.5 | 3.3 | | Excl |
| UBC5 (YDR059C) e | 135 | P | 369 | P | 160 | P | 463 | P | 2.7 | 2.9 | 2.8 | | Excl |
| XRS2 (YDR369C) | -27 | A | -12 | A | -37 | A | 16 | A | 0.4 | -0.4 | 6.8 | Yes | Med |
| YCLX04w/ (control | 5 | A | 19 | A | 8 | A | 23 | M | 3.7 | 2.9 | 3.3 | | Good |
| YCLX08c/ (control | 38 | P | 80 | P | 22 | P | 73 | P | 2.1 | 3.3 | 2.7 | | Excl |
| YCLX11w/ (control | -9 | A | 24 | A | -18 | A | 4 | A | -2.6 | -0.2 | 5.4 | Yes | Med |
| YCRX04w/ (control | -5 | A | 15 | M | 12 | P | 30 | P | -3.1 | 2.5 | 3.3 | Yes | Med |
| YCRX18c/ (control | 0 | A | 44 | P | 7 | A | 25 | P | #DIV/0! | 3.5 | 6.2 | Yes | Med |
| YCRX19w/ (control | 8 | A | 24 | A | 15 | A | 47 | P | 3.0 | 3.1 | 3.0 | | Good |

Figure 27C

Up Gal11

Gene Expression Results for FH1998040601A

| Gene | WT#1 r | WT#1 r | GAL11#1 | GAL11#1 | GAL11#2 | GAL11#2 | rWT#2 | rWT#2 | GAL11 MT1/WT1 | GAL11 MT2/WT2 | Average Fold Up | Corrected? | Confidence |
|---|---|---|---|---|---|---|---|---|---|---|---|---|---|
| ENA1 (YDR040C) | 8 | A | 58 | P | 152 | P | -4 | A | 7.2 | -38.0 | 19.2 | Yes | Med |
| FIG1 (YBR040W) | 2 | A | 44 | P | 21 | A | 5 | A | 22.0 | 4.2 | 13.1 | | Good |
| ORF YDL248W (_r) | 5 | A | 47 | M | 65 | P | 4 | A | 9.5 | 16.4 | 12.9 | | Good |
| ORF YBR147W | 15 | A | 83 | A | 96 | P | 5 | A | 5.5 | 19.3 | 12.4 | | Good |
| ORF YBR224W | -27 | A | 15 | A | -11 | A | -60 | A | -0.6 | 0.2 | 9.1 | Yes | Med |
| ORF YDL247W (_r) | -19 | A | 41 | A | -11 | A | -40 | A | -2.1 | 0.3 | 8.9 | Yes | Med |
| ORF YBR296C | 95 | P | 856 | P | 747 | P | 101 | P | 9.0 | 7.4 | 8.2 | | Excl |
| PXA1 (YPL147W) | 1 | A | 12 | A | 37 | P | 12 | A | 12.0 | 3.1 | 7.5 | | Good |
| ORF YBR240C | 3 | A | 39 | A | 32 | A | 16 | A | 13.0 | 2.0 | 7.5 | | Good |
| ORF YOR050C | -57 | A | -35 | A | 16 | A | -35 | A | 0.6 | -0.5 | 7.3 | Yes | Med |
| ORF YAR052C (_i) | -75 | A | -37 | A | -40 | A | -75 | A | 0.5 | 0.5 | 7.3 | Yes | Med |
| XRS2 (YDR369C) | -27 | A | -12 | A | 16 | A | -37 | A | 0.4 | -0.4 | 6.8 | Yes | Med |
| ORF YMR095C | -24 | A | -3 | A | 42 | P | -3 | A | 0.1 | -14.1 | 6.6 | Yes | Med |
| SEO1 (YAL067C) | -1 | A | 47 | A | 58 | P | 18 | P | -47.5 | 3.2 | 6.5 | Yes | Med |
| ORF YDR437W | -10 | A | 2 | A | 44 | A | -8 | M | -0.2 | -5.6 | 6.4 | Yes | Med |
| GAL7 (YBR018C) | -5 | A | 24 | A | 6 | A | -27 | A | -4.7 | -0.2 | 6.2 | Yes | Med |
| YCRX18c/ control | 0 | A | 44 | P | 25 | P | 7 | A | #DIV/0! | 3.5 | 6.2 | Yes | Med |
| ORF YDR010C | -29 | A | -2 | A | 17 | A | -17 | A | 0.1 | -1.0 | 6.2 | Yes | Med |
| ORF YDR220C | 13 | A | 80 | P | 112 | P | 20 | A | 6.1 | 5.6 | 5.9 | | Good |
| YCLX11w/ control | -9 | A | 24 | A | 4 | A | -18 | A | -2.6 | -0.2 | 5.4 | Yes | Med |
| ORF YHR160C | 2 | A | 14 | A | 48 | A | 12 | A | 6.8 | 4.0 | 5.4 | | Good |
| ORF YBR051W | 11 | A | 46 | P | 26 | P | -7 | A | 4.2 | -3.7 | 5.4 | Yes | Med |
| ORF YBR300C (_i) | 24 | P | 147 | P | 136 | P | 30 | P | 6.1 | 4.5 | 5.3 | | Excl |
| ORF YAR074C | -2 | A | 39 | A | 22 | A | 9 | A | -19.5 | 2.5 | 5.3 | Yes | Med |
| ORF YBR300C (_r) | 22 | P | 127 | P | 107 | P | 23 | P | 5.8 | 4.7 | 5.2 | | Excl |
| ORF YAR030C | 12 | A | 68 | A | 60 | P | 14 | P | 5.6 | 4.3 | 5.0 | | Good |
| ORF YLR232W | -22 | A | 16 | A | 35 | M | 16 | A | -0.7 | 2.2 | 4.9 | Yes | Med |
| ORF YCL075W | 13 | A | 73 | P | 30 | M | 7 | A | 5.6 | 4.2 | 4.9 | | Good |
| KIN82 (YCR091W) | 12 | P | 78 | P | 77 | P | 23 | P | 6.5 | 3.3 | 4.9 | | Excl |
| ORF YBR012C | 44 | P | 264 | P | 256 | P | 71 | P | 6.0 | 3.6 | 4.8 | | Excl |
| ORF YOL163W | -11 | A | 17 | A | 61 | M | 17 | A | -1.5 | 3.6 | 4.6 | Yes | Med |
| ORF YCL049C | 70 | A | 219 | P | 549 | P | 93 | P | 3.1 | 5.9 | 4.5 | | Good |
| ORF YDL016C | -6 | A | 7 | A | 19 | A | 3 | A | -1.1 | 6.2 | 4.4 | Yes | Med |

Figure 28A

| | 7 | | 19 | | -2 | | 27 | | 2.7 | -13.6 | 4.2 | Yes | Med |
|---|---|---|---|---|---|---|---|---|---|---|---|---|---|
| ORF YDR525W | 7 | A | 19 | A | -2 | A | 27 | P | 2.7 | -13.6 | 4.2 | Yes | Med |
| ORF YBR300C (_f) | 13 | A | 37 | A | 4 | A | 22 | M | 2.9 | 5.6 | 4.2 | | Good |
| ORF YBR178W | -40 | A | -17 | A | -40 | A | -22 | A | 0.4 | 0.6 | 4.1 | Yes | Med |
| ORF YOR388C (_i) | -64 | A | -46 | A | -46 | A | -24 | A | 0.7 | 0.5 | 4.0 | Yes | Med |
| ORF YMR107W | -16 | A | -4 | A | -4 | A | 23 | A | 0.3 | -5.7 | 3.9 | Yes | Med |
| ORF YDR534C | 103 | P | 263 | P | 54 | P | 274 | P | 2.6 | 5.1 | 3.8 | | Excl |
| CAT2 (YML042W) | 12 | M | 62 | P | 60 | P | 129 | P | 5.2 | 2.1 | 3.7 | | Good |
| ORF YPR150W | -40 | A | -22 | A | -22 | A | -4 | A | 0.6 | 0.2 | 3.6 | Yes | Med |
| GPM2 (YDL021W) | 37 | P | 132 | P | 34 | P | 122 | P | 3.6 | 3.6 | 3.6 | | Excl |
| ORF YLR162W | -33 | A | -14 | A | -14 | A | 3 | A | 0.4 | -0.2 | 3.6 | Yes | Med |
| ORF YJL037W | 11 | A | 25 | M | 22 | M | 106 | A | 2.3 | 4.8 | 3.5 | | Good |
| ORF YAR064W (_f) | -11 | A | 5 | A | -10 | A | 91 | A | -0.5 | -0.9 | 3.5 | Yes | Med |
| UBC5 (YDR059C) e | 49 | P | 205 | P | 79 | P | 198 | P | 4.2 | 2.5 | 3.3 | | Excl |
| YCLX04w/ (control | 5 | A | 19 | A | 8 | A | 23 | M | 3.7 | 2.9 | 3.3 | | Good |
| YCRX04w/ (control | -5 | A | 15 | M | 12 | P | 30 | P | -3.1 | 2.5 | 3.3 | | Med |
| ORF YEL008W | 0 | A | 18 | A | 16 | A | 46 | A | #DIV/0! | 2.9 | 3.3 | Yes | Med |
| ORF YCL023C | -2 | A | 15 | A | 11 | A | 32 | P | -7.6 | 2.9 | 3.2 | Yes | Med |
| GDH3 (YAL062W) | 61 | P | 215 | P | 69 | P | 194 | P | 3.5 | 2.8 | 3.2 | | Excl |
| ORF YAR052C (_f) | 13 | A | 56 | P | 33 | A | 67 | P | 4.3 | 2.0 | 3.2 | | Good |
| ORF YHR210C | 15 | A | 43 | A | 38 | A | 128 | P | 2.9 | 3.4 | 3.1 | | Good |
| ORF YDL172C | 44 | A | 136 | P | 36 | A | 111 | A | 3.1 | 3.1 | 3.1 | | Excl |
| ORF YAR068W (_f) | 203 | P | 649 | P | 221 | P | 654 | P | 3.2 | 3.0 | 3.1 | | Excl |
| YCRX19w/ (control | 8 | A | 24 | A | 15 | A | 47 | P | 3.0 | 3.1 | 3.0 | | Excl |
| ADH5 (YBR145W) | 147 | P | 451 | P | 138 | P | 400 | P | 3.1 | 2.9 | 3.0 | | Excl |
| FLO9 (YAL064W) | -43 | A | -31 | A | -37 | A | -20 | A | 0.7 | 0.5 | 3.0 | Yes | Med |
| ORF YDR541C | 63 | P | 195 | P | 65 | P | 184 | P | 3.1 | 2.8 | 3.0 | | Med |
| ORF YCR049C | -4 | A | 7 | A | 4 | A | 15 | A | -1.7 | 3.7 | 2.9 | Yes | Med |
| ORF YPL276W (_f) | -23 | A | -8 | A | -8 | A | 6 | A | 0.3 | -0.8 | 2.9 | Yes | Med |
| UBC5 (YDR059C) e | 135 | P | 369 | P | 160 | P | 463 | P | 2.7 | 2.9 | 2.8 | | Excl |
| ORF YLR281C | 10 | A | 32 | A | 31 | A | 74 | P | 3.2 | 2.4 | 2.8 | | Good |
| LYS2 (YBR115C) | 666 | P | 1893 | P | 649 | P | 1777 | P | 2.8 | 2.7 | 2.8 | | Excl |

Figure 28B

| | | | | | | | | | |
|---|---|---|---|---|---|---|---|---|---|
| EXM2 (YDL087C) | 40 | A | 100 | P | 27 | P | 81 | P | 2.5 | 3.0 | 2.8 | Good |
| ORF YPL186C | -3 | A | 10 | A | 10 | A | 29 | A | -3.3 | 2.9 | 2.7 Yes | Med |
| YCLX08c/ (control) | 38 | P | 80 | P | 22 | P | 73 | P | 2.1 | 3.3 | 2.7 | Excl |
| RGM1 (YMR182C) | -6 | A | 10 | A | 10 | A | 21 | M | -1.7 | 2.1 | 2.7 Yes | Med |
| ORF YBL078C | 115 | P | 358 | P | 139 | P | 295 | P | 3.1 | 2.1 | 2.6 | Excl |
| ORF YBR005W | 79 | P | 171 | P | 84 | P | 253 | P | 2.2 | 3.0 | 2.6 | Excl |
| CIT2 (YCR005C) | 504 | P | 1537 | P | 560 | P | 1147 | P | 3.1 | 2.0 | 2.5 | Excl |
| GDH2 (YDL215C) | 447 | P | 1093 | P | 393 | P | 994 | P | 2.4 | 2.5 | 2.5 | Excl |
| ADR1 (YDR216W) | 103 | P | 219 | P | 116 | P | 328 | P | 2.1 | 2.8 | 2.5 | Excl |
| ORF YNL324W | 8 | A | 19 | P | 19 | P | 49 | P | 2.4 | 2.6 | 2.5 | Good |
| PHO5 (YBR093C) | 1055 | P | 2871 | P | 1251 | P | 2760 | P | 2.7 | 2.2 | 2.5 | Excl |
| ORF YAR066W (_f) | 129 | P | 308 | P | 148 | P | 374 | P | 2.4 | 2.5 | 2.5 | Excl |
| AMD2 (YDR242W) | 33 | P | 86 | P | 32 | P | 70 | P | 2.6 | 2.2 | 2.4 | Excl |
| ORF YFL019C | 10 | P | 20 | M | 18 | M | 48 | A | 2.0 | 2.7 | 2.4 | Good |
| ORF YDR317W | 73 | P | 149 | P | 63 | P | 157 | P | 2.0 | 2.5 | 2.3 | Excl |
| ORF YCL053C | 33 | P | 76 | A | 35 | P | 77 | P | 2.3 | 2.2 | 2.2 | Good |
| ORF YDR132C | 38 | P | 92 | P | 33 | P | 68 | P | 2.4 | 2.1 | 2.2 | Excl |
| ORF YBR113W | 74 | P | 164 | M | 104 | P | 227 | P | 2.2 | 2.2 | 2.2 | Good |
| ORF YAR031W | 36 | P | 78 | A | 22 | P | 48 | P | 2.2 | 2.2 | 2.2 | Good |
| APE3 (YBR286W) | 2268 | P | 4990 | P | 2205 | P | 4702 | P | 2.2 | 2.1 | 2.2 | Excl |
| ORF YDL239C | 24 | P | 54 | P | 16 | M | 32 | P | 2.3 | 2.0 | 2.1 | Good |

Figure 28C

Med6 Up

Gene Expression Results for FH1998040601A

| Gene | WT#1 n | WT#1 | TS#1 n | TS#1 | WT#2 n | WT#2 | TS#2 n | TS#2 | MT1/WT1 | MT2/WT2 |
|---|---|---|---|---|---|---|---|---|---|---|
| SSA3 (YBL075C) | 24 | P | 211 | P | 67 | P | 434 | P | 8.79 | 6.53 |
| HSP30 (YCR021C) | 93 | P | 318 | P | 138 | P | 436 | P | 3.42 | 3.16 |
| SSA4 (YER103W) | 288 | P | 924 | P | 369 | P | 1555 | P | 3.20 | 4.21 |
| ORF YGR142W | 15 | P | 95 | P | 43 | P | 348 | P | 6.25 | 8.15 |
| ORF YHL048W | 4 | A | 47 | A | 6 | A | 38 | P | 11.05 | 6.50 |
| ORF YIL057C | -21 | A | -11 | A | -14 | A | -3 | A | 0.50 | 0.20 |
| ORF YIL006W | -4 | A | 12 | P | 2 | A | 14 | P | -2.73 | 8.68 |
| ORF YEL074W (_f) | -18 | A | 3 | A | -11 | A | 0 | A | -0.18 | -0.05 |
| ORF YKL031W | -8 | A | 5 | A | -36 | A | -11 | A | -0.65 | 0.29 |
| ORF YJR157W (_f) | -15 | A | -3 | A | -15 | A | -3 | A | 0.17 | 0.17 |
| ORF YOL032W | 39 | P | 90 | P | 85 | P | 215 | P | 2.33 | 2.52 |
| HIS3 (YOR202W) | -8 | A | 996 | P | -9 | A | 1133 | P | -119.51 | -131.76 |
| ORF YOR203W | 1 | A | 388 | P | -7 | A | 632 | P | 418.85 | -86.44 |
| ORF YPR158W | -3 | A | 40 | P | 45 | P | 97 | P | -14.50 | 2.13 |
| ORF YPR192W | -15 | A | 3 | A | -18 | A | -5 | A | -0.23 | 0.26 |

Figure 29

Med6 Down

Gene Expression Results for FH1998040601A

| Gene | WT#1 n | WT#1TS#1 n | TS#WT#2 n | WT#2TS#2 n | TS#2MT1/WT1 | MT2/WT2 | Ave | Fit | | Confidence |
|---|---|---|---|---|---|---|---|---|---|---|
| ASE1 (YOR058C) | 18 P | 5 P | 17 P | 5 P | 0.30 | 0.28 | 0.29 | <5min | Excl |
| CAR1 (YPL111W) | 182 P | 58 P | 263 P | 31 P | 0.32 | 0.12 | 0.22 | <10min | Excl |
| CAR2 (YLR438W) | 92 P | 23 P | 77 P | 10 P | 0.25 | 0.13 | 0.19 | <5min | Excl |
| CDC39 (YCR093W) | 48 P | 26 P | 75 P | 31 P | 0.55 | 0.41 | 0.48 | <5min | Excl |
| CHA1 (YCL064C) | 124 P | 37 P | 250 P | 36 P | 0.29 | 0.15 | 0.22 | <10min | Excl |
| CHS2 (YBR038W) | 30 P | 6 P | 40 P | 10 P | 0.21 | 0.26 | 0.24 | <5min | Excl |
| DAL4 (YIR028W) | 27 P | 3 A | 16 P | 10 P | 0.13 | 0.61 | 0.37 | <10min | Good |
| DBP2 (YNL112W) exa | 392 P | 104 P | 434 P | 87 P | 0.27 | 0.20 | 0.23 | <10min | Excl |
| DBP2 (YNL112W) exa | 443 P | 105 P | 866 P | 178 P | 0.24 | 0.20 | 0.22 | <5min | Excl |
| DUR1,2" (YBR208C)" | 49 P | 11 P | 88 P | 28 P | 0.23 | 0.32 | 0.28 | <10min | Excl |
| EUG1 (YDR518W) | 35 P | 12 P | 70 P | 12 P | 0.35 | 0.17 | 0.26 | <10min | Excl |
| FCY21 (YER060W) (_ | 16 P | 2 A | 34 P | 4 A | 0.10 | 0.12 | 0.11 | <5min | Good |
| FET4 (YMR319C) | 25 P | 8 M | 39 P | 6 P | 0.34 | 0.16 | 0.25 | <10min | Good |
| FLO1 (YAR050W) | 36 P | 11 P | 23 P | 11 P | 0.32 | 0.49 | 0.40 | <5min | Excl |
| FRE2 (YKL220C) | 16 P | 3 A | 19 P | 8 P | 0.20 | 0.42 | 0.31 | <10min | Good |
| GLK1 (YCL040W) | 436 P | 197 P | 510 P | 220 P | 0.45 | 0.43 | 0.44 | <10min | Excl |
| GLT1 (YDL171C) | 171 P | 71 P | 312 P | 85 P | 0.41 | 0.27 | 0.34 | <5min | Excl |
| GSC2 (YGR032W) | 248 P | 55 P | 287 P | 48 P | 0.22 | 0.17 | 0.19 | <5min | Excl |
| HAP1 (YLR256W) | 18 P | 3 A | 36 P | 10 P | 0.16 | 0.27 | 0.22 | <5min | Good |
| HHO1 (YPL127C) | 69 P | 14 P | 89 P | 18 P | 0.20 | 0.20 | 0.20 | <10min | Excl |
| HXK1 (YFR053C) | 250 P | 92 P | 269 P | 72 P | 0.37 | 0.27 | 0.32 | <10min | Excl |
| HXT12 (YIL171W) (_i | 66 P | 16 P | 44 P | 18 P | 0.25 | 0.41 | 0.33 | <10min | Good |
| KIP1 (YBL063W) | 16 P | 3 A | 28 P | 9 P | 0.17 | 0.34 | 0.25 | <10min | Good |
| KTR2 (YKR061W) | 85 P | 17 P | 107 P | 30 P | 0.20 | 0.28 | 0.24 | <5min | Excl |
| MAK31 (YCR020C-A) | 45 P | 21 P | 78 P | 29 P | 0.47 | 0.37 | 0.42 | <10min | Excl |
| MEP1 (YGR121C) | 30 P | 7 P | 41 P | 10 P | 0.23 | 0.24 | 0.24 | <10min | Excl |
| MUD1 (YBR119W) exc | 22 P | 6 P | 42 P | 14 P | 0.27 | 0.33 | 0.30 | <10min | Excl |
| NCA3 (YJL116C) | 63 P | 20 P | 69 P | 20 P | 0.32 | 0.29 | 0.31 | <10min | Excl |
| NCE1 (YJL206C-A) ex | 51 P | 18 P | 105 P | 18 P | 0.35 | 0.17 | 0.26 | <10min | Excl |
| NMD5 (YJR132W) | 23 P | 5 A | 51 P | 12 P | 0.21 | 0.24 | 0.22 | <10min | Good |

Figure 30A

| ORF | 104 | | 44 | | 132 | | 60 | | 0.42 | 0.46 | 0.44 | <10min | Excl |
|---|---|---|---|---|---|---|---|---|---|---|---|---|---|
| ORF YAL068C (_f) | 104 | P | 44 | P | 132 | P | 60 | P | 0.42 | 0.46 | 0.44 | <10min | Excl |
| ORF YAR053W (_f) | 16 | P | 2 | A | 20 | P | 3 | A | 0.14 | 0.13 | 0.14 | <5min | Good |
| ORF YBL018C exon 2 | 42 | P | 12 | P | 110 | P | 21 | P | 0.28 | 0.20 | 0.24 | <10min | Excl |
| ORF YBL019W | 21 | P | 1 | A | 19 | P | 5 | P | 0.04 | 0.27 | 0.15 | <5min | Good |
| ORF YBL029W | 22 | P | 9 | A | 28 | P | 7 | P | 0.39 | 0.25 | 0.32 | <10min | Good |
| ORF YBL053W | 22 | P | 9 | A | 23 | P | 8 | P | 0.42 | 0.33 | 0.37 | <5min | Good |
| ORF YBL094C | 17 | P | 5 | A | 29 | P | 8 | P | 0.30 | 0.28 | 0.29 | <5min | Good |
| ORF YBL101W-A (_f) | 108 | P | 27 | P | 148 | P | 57 | P | 0.25 | 0.39 | 0.32 | <5min | Excl |
| ORF YBL101W-B exon | 111 | P | 28 | P | 142 | P | 57 | P | 0.26 | 0.40 | 0.33 | <10min | Excl |
| ORF YBR004C | 81 | P | 26 | P | 127 | P | 42 | P | 0.32 | 0.33 | 0.33 | <5min | Excl |
| ORF YBR005W | 148 | P | 60 | P | 129 | P | 42 | P | 0.40 | 0.32 | 0.36 | <5min | Excl |
| ORF YBR027C | 12 | P | 2 | A | 10 | P | 7 | P | 0.19 | 0.73 | 0.46 | <5min | Good |
| ORF YBR050C | 46 | P | 16 | P | 43 | P | 20 | P | 0.36 | 0.47 | 0.41 | <10min | Excl |
| ORF YBR059C | 66 | P | 28 | P | 80 | P | 30 | P | 0.42 | 0.38 | 0.40 | <5min | Excl |
| ORF YBR066C | 32 | P | 9 | P | 39 | P | 15 | P | 0.29 | 0.39 | 0.34 | <10min | Excl |
| ORF YBR108W | 44 | P | -4 | A | 40 | P | 18 | P | -0.09 | 0.47 | 0.19 | <5min | Good |
| ORF YBR203W | 27 | P | 11 | P | 29 | P | 16 | P | 0.39 | 0.55 | 0.47 | <5min | Excl |
| ORF YBR230C exon 1 | 96 | P | 29 | P | 124 | P | 48 | P | 0.30 | 0.39 | 0.34 | <10min | Excl |
| ORF YBR244W | 34 | P | 7 | P | 53 | P | 12 | P | 0.21 | 0.23 | 0.22 | <5min | Excl |
| ORF YBR302C (_f) | 92 | P | 19 | P | 193 | P | 38 | P | 0.21 | 0.20 | 0.20 | <5min | Excl |
| ORF YCL006C | 12 | P | 4 | A | 9 | P | 4 | P | 0.30 | 0.43 | 0.37 | <10min | Good |
| ORF YCL019W | 590 | P | 255 | P | 733 | P | 364 | P | 0.43 | 0.50 | 0.46 | <10min | Excl |
| ORF YCL020W (_f) | 93 | P | 29 | P | 158 | P | 51 | P | 0.31 | 0.32 | 0.32 | <10min | Excl |
| ORF YCL047C | 45 | P | 16 | P | 101 | P | 28 | P | 0.36 | 0.28 | 0.32 | <10min | Excl |
| ORF YCL061C | 11 | P | 4 | A | 24 | P | 6 | P | 0.37 | 0.25 | 0.31 | <5min | Good |
| ORF YCR060W | 91 | P | 29 | P | 152 | P | 29 | P | 0.32 | 0.19 | 0.26 | <10min | Excl |
| ORF YCR071C | 36 | P | 16 | P | 45 | P | 19 | P | 0.44 | 0.43 | 0.44 | <10min | Excl |
| ORF YCR105W | 13 | P | 4 | P | 19 | P | 11 | P | 0.32 | 0.62 | 0.47 | <5min | Excl |
| ORF YDL018C | 34 | P | 13 | P | 72 | P | 16 | P | 0.38 | 0.22 | 0.30 | <10min | Excl |
| ORF YDL019C | 45 | P | 10 | P | 68 | P | 14 | P | 0.22 | 0.21 | 0.22 | <10min | Excl |
| ORF YDL098C | 26 | P | 4 | P | 61 | P | 18 | P | 0.16 | 0.29 | 0.22 | <10min | Excl |
| ORF YDL109C | 27 | P | 7 | A | 29 | P | 10 | P | 0.27 | 0.34 | 0.31 | <10min | Good |
| ORF YDL244W (_f) | 35 | P | 14 | P | 41 | P | 15 | P | 0.40 | 0.36 | 0.38 | <10min | Excl |
| ORF YDR380W | 50 | P | 4 | P | 52 | P | 16 | P | 0.07 | 0.30 | 0.19 | <10min | Excl |

Figure 30B

| ORF | | | | | | | | | | |
|---|---|---|---|---|---|---|---|---|---|---|
| ORF YDR428C | 25 | P | 4 | A | 37 | P | 5 | P | 0.15 | 0.13 | 0.14 | <5min | Good |
| ORF YDR438W | 9 | P | 2 | A | 13 | P | 7 | P | 0.20 | 0.55 | 0.38 | <10min | Good |
| ORF YDR453C | 16 | P | 4 | A | 28 | P | 4 | P | 0.26 | 0.15 | 0.21 | <10min | Good |
| ORF YDR516C | 52 | P | 19 | P | 63 | P | 22 | P | 0.36 | 0.34 | 0.35 | <10min | Excl |
| ORF YDR542W (_f) | 100 | P | 45 | P | 72 | P | 38 | P | 0.45 | 0.52 | 0.49 | <10min | Excl |
| ORF YEL015W | 36 | P | 0 | P | 49 | P | 33 | P | 0.00 | 0.68 | 0.34 | <10min | Good |
| ORF YEL022W | 55 | P | 4 | A | 96 | P | 52 | P | 0.07 | 0.54 | 0.30 | <10min | Good |
| ORF YEL031W | 224 | P | -134 | A | 344 | P | 248 | P | -0.60 | 0.72 | 0.06 | <5min | Good |
| ORF YEL047C | 92 | P | 4 | P | 155 | P | 52 | P | 0.04 | 0.33 | 0.19 | <5min | Good |
| ORF YEL064C | 13 | P | 2 | A | 28 | P | 8 | P | 0.12 | 0.30 | 0.21 | <5min | Excl |
| ORF YEL066W | 111 | P | 28 | P | 138 | P | 28 | P | 0.25 | 0.21 | 0.23 | <10min | Good |
| ORF YER005W | 70 | P | -17 | P | 102 | P | 41 | P | -0.24 | 0.40 | 0.08 | <5min | Excl |
| ORF YER089C | 171 | P | 27 | P | 102 | P | 37 | P | 0.16 | 0.36 | 0.26 | <10min | Excl |
| ORF YER152C | 101 | P | 26 | P | 149 | P | 24 | P | 0.26 | 0.16 | 0.21 | <10min | Excl |
| ORF YER160C exon 1 | 1235 | P | 784 | P | 1187 | P | -117 | A | 0.63 | -0.10 | 0.27 | <10min | Good |
| ORF YER185W | 13 | P | 9 | P | 18 | P | 8 | P | 0.70 | 0.45 | 0.58 | <5min | Excl |
| ORF YFL017C | 78 | P | 15 | P | 80 | P | 15 | P | 0.19 | 0.19 | 0.19 | <10min | Good |
| ORF YFL055W | 20 | P | 9 | P | 21 | P | 4 | M | 0.45 | 0.19 | 0.32 | <10min | Good |
| ORF YFR022W | 24 | P | 8 | P | 21 | P | 3 | A | 0.36 | 0.14 | 0.25 | <10min | Good |
| ORF YGL088W | 13 | P | 4 | P | 23 | P | 9 | P | 0.33 | 0.39 | 0.36 | <5min | Good |
| ORF YGL196W | 48 | P | 12 | P | 82 | P | 26 | P | 0.25 | 0.32 | 0.28 | <10min | Excl |
| ORF YGR041W | 33 | P | 7 | P | 31 | P | 5 | P | 0.21 | 0.16 | 0.19 | <10min | Excl |
| ORF YGR131W | 15 | P | 5 | A | 15 | P | 3 | P | 0.34 | 0.18 | 0.26 | <10min | Good |
| ORF YGR260W | 119 | P | 12 | P | 151 | P | 20 | P | 0.10 | 0.13 | 0.12 | <5min | Excl |
| ORF YHL044W | 12 | P | 1 | A | 25 | P | 4 | P | 0.05 | 0.15 | 0.10 | <5min | Excl |
| ORF YHR054C (_r) | 51 | P | 13 | P | 140 | P | 50 | P | 0.25 | 0.36 | 0.30 | <5min | Good |
| ORF YHR101C exon 1 | 17 | P | 1 | A | 9 | P | 5 | A | 0.06 | 0.52 | 0.29 | <5min | Good |
| ORF YHR198C | 24 | P | 5 | P | 25 | P | 10 | P | 0.22 | 0.39 | 0.31 | <10min | Good |
| ORF YIL011W | 119 | P | 28 | P | 80 | P | 27 | P | 0.23 | 0.33 | 0.28 | <10min | Excl |
| ORF YIL067C | 38 | P | 18 | P | 60 | P | 5 | A | 0.47 | 0.08 | 0.28 | <10min | Good |
| ORF YIL101C | 53 | P | 18 | M | 19 | P | 9 | P | 0.33 | 0.48 | 0.41 | <5min | Good |
| ORF YIL159W | 15 | P | 5 | P | 35 | P | 7 | P | 0.35 | 0.19 | 0.27 | <5min | Excl |
| ORF YIL169C | 28 | P | 8 | M | 30 | P | 10 | P | 0.28 | 0.34 | 0.31 | <5min | Good |
| ORF YIL173W (_f) | 12 | P | 2 | A | 30 | P | 6 | P | 0.13 | 0.21 | 0.17 | <5min | Good |
| ORF YIR033W | 27 | P | 7 | P | 25 | P | 8 | P | 0.25 | 0.30 | 0.27 | <10min | Excl |
| ORF YIR041W (_f) | 48 | P | 16 | P | 44 | P | 13 | P | 0.32 | 0.29 | 0.31 | <5min | Excl |

Figure 30C

| ORF | | | | | | | | | |
|---|---|---|---|---|---|---|---|---|---|
| ORF YJL009W | 18 P | 6 P | 12 P | -3 A | 0.34 | -0.22 | 0.06 | <5min | Good |
| ORF YJL103C | 13 P | 4 M | 17 P | 4 P | 0.27 | 0.23 | 0.25 | <5min | Good |
| ORF YJL222W (_f) | 22 P | 4 P | 31 P | 8 P | 0.18 | 0.28 | 0.23 | <10min | Excl |
| ORF YJR079W exon 1 | 64 P | 4 A | 119 P | 17 P | 0.07 | 0.14 | 0.11 | <5min | Good |
| ORF YJR151C | 39 P | 11 P | 40 P | 7 P | 0.28 | 0.17 | 0.22 | <5min | Excl |
| ORF YJR155W | 24 P | 8 P | 24 P | 12 P | 0.34 | 0.50 | 0.42 | <10min | Excl |
| ORF YKL066W | 42 P | 12 M | 55 P | 14 P | 0.28 | 0.25 | 0.27 | <5min | Good |
| ORF YKL084W | 59 P | 14 P | 141 P | 23 P | 0.24 | 0.16 | 0.20 | <10min | Excl |
| ORF YKL086W | 19 P | 5 A | 27 P | 4 A | 0.25 | 0.16 | 0.21 | <5min | Good |
| ORF YKL111C | 15 P | 1 A | 18 P | 6 P | 0.08 | 0.36 | 0.22 | <5min | Good |
| ORF YKL136W | 10 P | 0 A | 16 P | 14 P | 0.00 | 0.86 | 0.43 | <10min | Good |
| ORF YLR087C | 22 P | 7 P | 26 P | 8 P | 0.31 | 0.30 | 0.30 | <10min | Excl |
| ORF YLR112W | 34 P | 15 P | 39 P | 15 P | 0.44 | 0.39 | 0.41 | <5min | Excl |
| ORF YLR126C | 34 P | 8 P | 67 P | 12 P | 0.24 | 0.18 | 0.21 | <10min | Excl |
| ORF YLR154C | 94 P | 20 P | 145 P | 19 P | 0.21 | 0.13 | 0.17 | <10min | Excl |
| ORF YLR171W | 15 P | 5 P | 26 P | 8 P | 0.34 | 0.30 | 0.32 | <10min | Excl |
| ORF YLR213C | 11 P | -1 A | 12 P | 3 P | -0.13 | 0.27 | 0.07 | <5min | Good |
| ORF YLR217W | 7 P | 2 A | 16 P | 13 P | 0.29 | 0.84 | 0.56 | <10min | Good |
| ORF YLR231C | 45 P | 6 P | 100 P | 9 P | 0.14 | 0.10 | 0.12 | <10min | Excl |
| ORF YLR364W | 36 P | 9 P | 46 P | 13 P | 0.26 | 0.29 | 0.28 | <10min | Excl |
| ORF YLR413W | 253 P | 71 P | 277 P | 40 P | 0.28 | 0.14 | 0.21 | <10min | Excl |
| ORF YLR424W | 10 P | 1 A | 14 P | 8 P | 0.06 | 0.54 | 0.30 | <10min | Good |
| ORF YLR456W | 14 P | 3 A | 24 P | 6 P | 0.21 | 0.26 | 0.24 | <10min | Excl |
| ORF YML101C | 53 P | 9 P | 87 P | 15 P | 0.17 | 0.17 | 0.17 | <5min | Excl |
| ORF YML132W (_f) | 83 P | 21 P | 170 P | 45 P | 0.26 | 0.27 | 0.26 | <10min | Excl |
| ORF YMR025W | 11 P | 3 A | 12 P | 5 P | 0.24 | 0.43 | 0.33 | <10min | Good |
| ORF YMR041C | 26 P | 15 P | 25 P | 13 P | 0.58 | 0.53 | 0.55 | <10min | Excl |
| ORF YMR155W | 9 P | 1 A | 14 P | 5 P | 0.10 | 0.34 | 0.22 | <5min | Good |
| ORF YMR163C | 14 P | 2 A | 15 P | 6 P | 0.12 | 0.42 | 0.27 | <10min | Good |
| ORF YNL126W | 16 P | 4 A | 26 P | 12 P | 0.28 | 0.45 | 0.36 | <10min | Good |
| ORF YNL336W (_f) | 100 P | 30 P | 238 P | 47 P | 0.30 | 0.20 | 0.25 | <10min | Excl |
| ORF YOL047C exon 1 | 15 P | 2 A | 14 P | 3 A | 0.16 | 0.19 | 0.17 | <5min | Good |
| ORF YOL078W | 24 P | 13 P | 36 P | 14 P | 0.55 | 0.39 | 0.47 | <10min | Excl |
| ORF YOL151W | 118 P | 46 P | 155 P | 91 P | 0.39 | 0.59 | 0.49 | <10min | Excl |
| ORF YOR013W | 33 P | 7 A | 39 P | 12 P | 0.20 | 0.30 | 0.25 | <10min | Good |
| ORF YOR040W | 31 P | 4 P | 63 P | 18 P | 0.14 | 0.28 | 0.21 | <5min | Excl |
| ORF YOR306C | 119 P | 28 P | 206 P | 43 P | 0.24 | 0.21 | 0.22 | <5min | Excl |
| ORF YOR382W | 74 P | 42 P | 106 P | 37 P | 0.57 | 0.35 | 0.46 | <10min | Excl |

Figure 30D

| | | | | | | | |
|---|---|---|---|---|---|---|---|
| ORFYPL134C | 47 P | 14 P | 61 P | 16 P | 0.30 | 0.27 | 0.29 <10min | Excl |
| ORFYPL164C | 26 P | 7 P | 24 P | 9 P | 0.26 | 0.39 | 0.33 <10min | Excl |
| ORFYPR006C | 37 P | 3 A | 65 P | 4 P | 0.07 | 0.06 | 0.07 <5min | Good |
| ORFYPR011C | 31 P | 8 P | 41 P | 11 P | 0.26 | 0.26 | 0.26 <10min | Excl |
| ORFYPR172W | 35 P | 10 P | 38 P | 6 P | 0.28 | 0.17 | 0.22 <10min | Excl |
| PAI3 (YMR174C) | 52 P | 14 P | 88 P | 18 P | 0.28 | 0.20 | 0.24 <10min | Excl |
| PAU3 (YCR104W) (_f) | 327 P | 95 P | 225 P | 112 P | 0.29 | 0.50 | 0.39 <10min | Excl |
| PCA1 (YBR295W) | 27 P | 13 P | 38 P | 20 P | 0.47 | 0.53 | 0.50 <10min | Excl |
| PDR11 (YIL013C) | 38 P | 15 P | 39 P | 21 P | 0.39 | 0.52 | 0.46 <5min | Excl |
| PHO5 (YBR093C) | 130 P | 32 P | 215 P | 34 P | 0.25 | 0.16 | 0.20 <10min | Excl |
| PMT5 (YDL093W) | 39 P | 14 P | 87 P | 22 P | 0.35 | 0.25 | 0.30 <10min | Excl |
| RAD23 (YEL037C) | 145 P | 85 P | 173 P | -34 A | 0.59 | -0.20 | 0.20 <5min | Good |
| RDI1 (YDL135C) | 82 P | 30 P | 233 P | 54 P | 0.36 | 0.23 | 0.30 <10min | Excl |
| RNR2 (YJL026W) | 320 P | 74 P | 291 P | 61 P | 0.23 | 0.21 | 0.22 <10min | Excl |
| RNR3 (YIL066C) | 62 P | 16 P | 55 P | 8 M | 0.26 | 0.14 | 0.20 <5min | Good |
| RPS24B (YLR367W) e | 443 P | 241 P | 644 P | 329 P | 0.54 | 0.51 | 0.53 <10min | Excl |
| RTA1 (YGR213C) | 16 P | 6 A | 19 P | -1 A | 0.38 | -0.04 | 0.17 <5min | Good |
| SAG1 (YJR004C) | 49 P | 14 P | 40 P | 16 P | 0.29 | 0.39 | 0.34 <10min | Excl |
| SCS3 (YGL126W) | 179 P | 40 P | 283 P | 47 P | 0.22 | 0.17 | 0.19 <10min | Excl |
| SEC6 (YIL068C) | 35 P | 25 P | 66 P | -18 A | 0.71 | -0.28 | 0.22 <10min | Good |
| SHR5 (YOL110W) | 31 P | 8 A | 34 P | 10 P | 0.27 | 0.31 | 0.29 <10min | Good |
| SPS19 (YNL202W) | 25 P | 8 M | 78 P | 15 P | 0.31 | 0.19 | 0.25 <10min | Good |
| SRB2 (YHR041C) exon | 52 P | 14 P | 72 P | 10 M | 0.28 | 0.14 | 0.21 <10min | Good |
| SRD1 (YCR018C) | 56 P | 15 P | 69 P | 28 P | 0.26 | 0.40 | 0.33 <5min | Excl |
| SWE1 (YJL187C) | 23 P | 7 P | 39 P | 8 P | 0.29 | 0.20 | 0.24 <10min | Excl |
| TEL1 (YBL088C) | 31 P | 11 P | 30 P | 15 P | 0.35 | 0.49 | 0.42 <10min | Excl |
| THI11 (YJR156C) (_f) | 44 P | 15 P | 50 P | 17 P | 0.34 | 0.35 | 0.34 <10min | Excl |
| THI4 (YGR144W) | 38 P | 6 P | 32 P | 9 P | 0.15 | 0.30 | 0.22 <5min | Excl |
| THI5 (YFL058W) (_f) | 25 P | 10 P | 36 P | 11 P | 0.39 | 0.32 | 0.36 <10min | Excl |
| TIR1 (YER011W) | 251 P | 70 P | 381 P | 106 P | 0.28 | 0.28 | 0.28 <10min | Excl |
| TOR1 (YJR066W) | 18 P | 8 P | 33 P | 14 P | 0.47 | 0.44 | 0.46 <5min | Excl |
| TPS2 (YDR074W) | 51 P | 21 P | 56 P | 16 P | 0.42 | 0.29 | 0.36 <10min | Excl |
| URA3 (YEL021W) | 708 P | 5 A | 1232 P | 11 P | 0.01 | 0.01 | 0.01 <5min | Good |
| URA8 (YJR103W) | 111 P | 34 P | 110 P | 41 P | 0.30 | 0.37 | 0.34 <10min | Excl |
| YAT1 (YAR035W) | 31 P | 7 A | 26 P | 9 P | 0.22 | 0.35 | 0.29 <5min | Good |
| YCRX02c/_r (control)? | 24 P | 13 P | 17 P | 7 P | 0.53 | 0.41 | 0.47 <5min | Excl |
| YST1 (YGR214W) exc | 605 P | 184 P | 842 P | 55 P | 0.30 | 0.07 | 0.18 <10min | Excl |
| YSY6 (YBR162W-A) | 128 P | 34 P | 252 P | 48 P | 0.27 | 0.19 | 0.23 <10min | Excl |
| ZIP1 (YDR285W) | 18 P | 7 P | 25 P | 10 P | 0.38 | 0.42 | 0.40 <5min | Excl |

Figure 30E

Med6 Down

Gene Expression Results for FH1998040601A

| Gene | WT#1 n | WT#1 | TS#1 n | TS#1 | WT#2 n | WT#2 | TS#2 n | TS#2 | TS#2MT1/WT1 | MT2/WT2 | Ave | Fit | Confidence |
|---|---|---|---|---|---|---|---|---|---|---|---|---|---|
| URA3 (YEL021W) | 708 | P | 5 | A | 1232 | P | 11 | P | 0.01 | 0.01 | 126.91 | <5min | Good |
| ORF YJL009W | 18 | P | 6 | P | 12 | P | -3 | A | 0.34 | -0.22 | 16.58 | <5min | Good |
| ORF YEL031W | 224 | P | -134 | A | 344 | P | 248 | P | -0.60 | 0.72 | 16.44 | <5min | Good |
| ORF YPR006C | 37 | P | 3 | A | 65 | P | 4 | P | 0.07 | 0.06 | 14.82 | <5min | Good |
| ORF YLR213C | 11 | P | -1 | A | 12 | P | 3 | P | -0.13 | 0.27 | 13.89 | <5min | Good |
| ORF YER005W | 70 | P | -17 | P | 102 | P | 41 | P | -0.24 | 0.40 | 13.00 | <5min | Excl |
| ORF YHL044W | 12 | P | 1 | A | 25 | P | 4 | P | 0.05 | 0.15 | 10.02 | <5min | Good |
| ORF YJR079W exon 1 | 64 | P | 4 | A | 119 | P | 17 | P | 0.07 | 0.14 | 9.51 | <5min | Good |
| FCY21 (YER060W) | 16 | P | 2 | A | 34 | P | 4 | A | 0.10 | 0.12 | 9.10 | <5min | Good |
| ORF YGR260W | 119 | P | 12 | P | 151 | P | 20 | P | 0.10 | 0.13 | 8.58 | <5min | Excl |
| ORF YLR231C | 45 | P | 6 | P | 100 | P | 9 | P | 0.14 | 0.10 | 8.54 | <10min | Excl |
| ORF YAR053W (_f) | 16 | P | 2 | A | 20 | P | 3 | A | 0.14 | 0.13 | 7.25 | <5min | Good |
| ORF YDR428C | 25 | P | 4 | A | 37 | P | 5 | P | 0.15 | 0.13 | 7.19 | <5min | Good |
| ORF YBL019W | 21 | P | 1 | A | 19 | P | 5 | P | 0.04 | 0.27 | 6.45 | <5min | Good |
| ORF YLR154C | 94 | P | 20 | P | 145 | P | 19 | P | 0.21 | 0.13 | 5.86 | <10min | Excl |
| ORF YIL173W (_f) | 12 | P | 2 | A | 30 | P | 6 | P | 0.13 | 0.21 | 5.85 | <5min | Excl |
| ORF YML101C | 53 | P | 9 | P | 87 | P | 15 | P | 0.17 | 0.17 | 5.81 | <5min | Excl |
| ORF YOL047C exon 1 | 15 | P | 2 | A | 14 | P | 3 | A | 0.16 | 0.19 | 5.78 | <5min | Good |
| RTA1 (YGR213C) | 16 | P | 6 | A | 19 | P | -1 | A | 0.38 | -0.04 | 5.77 | <5min | Excl |
| YST1 (YGR214W) exc | 605 | P | 184 | P | 842 | P | 55 | P | 0.30 | 0.07 | 5.41 | <10min | Excl |
| ORF YDR380W | 50 | P | 4 | P | 52 | P | 16 | P | 0.07 | 0.30 | 5.40 | <10min | Excl |
| ORF YBR108W | 44 | P | -4 | A | 40 | P | 18 | P | -0.09 | 0.47 | 5.38 | <5min | Good |
| ORF YGR041W | 33 | P | 7 | P | 31 | P | 5 | P | 0.21 | 0.16 | 5.33 | <10min | Excl |
| CAR2 (YLR438W) | 92 | P | 23 | P | 77 | P | 10 | P | 0.25 | 0.13 | 5.31 | <5min | Excl |
| ORF YEL047C | 92 | P | 4 | P | 155 | P | 52 | P | 0.04 | 0.33 | 5.29 | <5min | Excl |
| ORF YFL017C | 78 | P | 15 | P | 80 | P | 15 | P | 0.19 | 0.19 | 5.22 | <10min | Excl |
| SCS3 (YGL126W) | 179 | P | 40 | P | 283 | P | 47 | P | 0.22 | 0.17 | 5.16 | <10min | Excl |
| GSC2 (YGR032W) | 248 | P | 55 | P | 287 | P | 48 | P | 0.22 | 0.17 | 5.14 | <5min | Excl |
| RAD23 (YEL037C) | 145 | P | 85 | P | 173 | P | -34 | A | 0.59 | -0.20 | 5.09 | <5min | Good |
| RNR3 (YIL066C) | 62 | P | 16 | P | 55 | P | 8 | M | 0.26 | 0.14 | 5.01 | <5min | Good |

Figure 31A

| | | | | | | | | |
|---|---|---|---|---|---|---|---|---|
| HHO1 (YPL127C) | 69 | P | 14 | P | 89 | P | 18 | P | 0.20 | 0.20 | 4.99 | <10min | Excl |
| ORF YKL084W | 59 | P | 14 | P | 141 | P | 23 | P | 0.24 | 0.16 | 4.97 | <10min | Excl |
| ORF YBR302C (_f) | 92 | P | 19 | P | 193 | P | 38 | P | 0.21 | 0.20 | 4.93 | <5min | Excl |
| PHO5 (YBR093C) | 130 | P | 32 | P | 215 | P | 34 | P | 0.25 | 0.16 | 4.91 | <10min | Excl |
| ORF YDR453C | 16 | P | 4 | A | 28 | P | 4 | P | 0.26 | 0.15 | 4.87 | <10min | Good |
| ORF YKL086W | 19 | P | 5 | A | 27 | P | 4 | A | 0.25 | 0.16 | 4.86 | <5min | Good |
| ORF YLR126C | 34 | P | 8 | P | 67 | P | 12 | P | 0.24 | 0.18 | 4.83 | <10min | Excl |
| SRB2 (YHR041C) exor | 52 | P | 14 | P | 72 | P | 10 | M | 0.28 | 0.14 | 4.80 | <10min | Good |
| ORF YER152C | 101 | P | 26 | P | 149 | P | 24 | P | 0.26 | 0.16 | 4.80 | <10min | Excl |
| ORF YEL064C | 13 | P | 2 | A | 28 | P | 8 | P | 0.12 | 0.30 | 4.78 | <5min | Good |
| ORF YOR040W | 31 | P | 4 | P | 63 | P | 18 | P | 0.14 | 0.28 | 4.73 | <5min | Excl |
| ORF YLR413W | 253 | P | 71 | P | 277 | P | 40 | P | 0.28 | 0.14 | 4.70 | <10min | Excl |
| ORF YDL019C | 45 | P | 10 | P | 68 | P | 14 | P | 0.22 | 0.21 | 4.64 | <10min | Excl |
| ORF YKL111C | 15 | P | 1 | A | 18 | P | 6 | P | 0.08 | 0.36 | 4.63 | <5min | Good |
| HAP1 (YLR256W) | 18 | P | 3 | A | 36 | P | 10 | P | 0.16 | 0.27 | 4.63 | <5min | Good |
| ORF YMR155W | 9 | P | 1 | A | 14 | P | 5 | P | 0.10 | 0.34 | 4.59 | <5min | Good |
| CAR1 (YPL111W) | 182 | P | 58 | P | 263 | P | 31 | P | 0.32 | 0.12 | 4.58 | <10min | Good |
| SEC6 (YIL068C) | 35 | P | 25 | P | 66 | P | -18 | A | 0.71 | -0.28 | 4.58 | <10min | Excl |
| CHA1 (YCL064C) | 124 | P | 37 | P | 250 | P | 36 | P | 0.29 | 0.15 | 4.55 | <10min | Excl |
| RNR2 (YJL026W) | 320 | P | 74 | P | 291 | P | 61 | P | 0.23 | 0.21 | 4.54 | <10min | Excl |
| ORF YBR244W | 34 | P | 7 | P | 53 | P | 12 | P | 0.21 | 0.23 | 4.53 | <10min | Excl |
| DBP2 (YNL112W) exo | 443 | P | 105 | P | 866 | P | 178 | P | 0.24 | 0.20 | 4.52 | <10min | Excl |
| ORF YPR172W | 35 | P | 10 | P | 38 | P | 6 | P | 0.28 | 0.17 | 4.49 | <10min | Excl |
| ORF YJR151C | 39 | P | 11 | P | 40 | P | 7 | P | 0.28 | 0.17 | 4.48 | <5min | Excl |
| ORF YOR306C | 119 | P | 28 | P | 206 | P | 43 | P | 0.24 | 0.21 | 4.48 | <5min | Excl |
| THI4 (YGR144W) | 38 | P | 6 | P | 32 | P | 9 | P | 0.15 | 0.30 | 4.47 | <5min | Excl |
| ORF YDL098C | 26 | P | 4 | P | 61 | P | 18 | P | 0.16 | 0.29 | 4.45 | <10min | Excl |
| NMD5 (YJR132W) | 23 | P | 5 | A | 51 | P | 12 | P | 0.21 | 0.24 | 4.45 | <10min | Good |
| ORF YJL222W (_f) | 22 | P | 4 | P | 31 | P | 8 | P | 0.18 | 0.28 | 4.40 | <10min | Excl |
| ORF YEL066W | 111 | P | 28 | P | 138 | P | 28 | P | 0.25 | 0.21 | 4.36 | <10min | Excl |
| YSY6 (YBR162W-A) | 128 | P | 34 | P | 252 | P | 48 | P | 0.27 | 0.19 | 4.35 | <10min | Excl |
| DBP2 (YNL112W) exo | 392 | P | 104 | P | 434 | P | 87 | P | 0.27 | 0.20 | 4.29 | <10min | Excl |
| CHS2 (YBR038W) | 30 | P | 6 | P | 40 | P | 10 | P | 0.21 | 0.26 | 4.24 | <5min | Excl |
| ORF YLR456W | 14 | P | 3 | A | 24 | P | 6 | P | 0.21 | 0.26 | 4.22 | <10min | Good |

Figure 31B

| | | | | | | | | |
|---|---|---|---|---|---|---|---|---|
| MEP1 (YGR121C) | 30 | P | 7 | P | 41 | P | 10 | P | 0.23 | 0.24 | 4.21 | <10min | Excl |
| ORF YBL018C exon 2 | 42 | P | 12 | P | 110 | P | 21 | P | 0.28 | 0.20 | 4.19 | <10min | Excl |
| PAI3 (YMR174C) | 52 | P | 14 | P | 88 | P | 18 | P | 0.28 | 0.20 | 4.17 | <10min | Excl |
| KTR2 (YKR061W) | 85 | P | 17 | P | 107 | P | 30 | P | 0.20 | 0.28 | 4.11 | <5min | Excl |
| SWE1 (YJL187C) | 23 | P | 7 | P | 39 | P | 8 | P | 0.29 | 0.20 | 4.10 | <10min | Good |
| ORF YJL103C | 13 | P | 4 | M | 17 | P | 4 | P | 0.27 | 0.23 | 4.07 | <5min | Good |
| FET4 (YMR319C) | 25 | P | 8 | M | 39 | P | 6 | P | 0.34 | 0.16 | 4.07 | <10min | Good |
| ORF YOR013W | 33 | P | 7 | A | 39 | P | 12 | P | 0.20 | 0.30 | 4.02 | <10min | Good |
| ORF YFR022W | 24 | P | 8 | P | 21 | P | 3 | A | 0.36 | 0.14 | 3.99 | <10min | Good |
| ORF YNL336W (_f) | 100 | P | 30 | P | 238 | P | 47 | P | 0.30 | 0.20 | 3.97 | <10min | Excl |
| SPS19 (YNL202W) | 25 | P | 8 | M | 78 | P | 15 | P | 0.31 | 0.19 | 3.95 | <10min | Good |
| KIP1 (YBL063W) | 16 | P | 3 | A | 28 | P | 9 | P | 0.17 | 0.34 | 3.94 | <10min | Good |
| ORF YCR060W | 91 | P | 29 | P | 152 | P | 29 | P | 0.32 | 0.19 | 3.92 | <10min | Excl |
| ORF YPR011C | 31 | P | 8 | P | 41 | P | 11 | P | 0.26 | 0.26 | 3.88 | <10min | Excl |
| ORF YER089C | 171 | P | 27 | P | 102 | P | 37 | P | 0.16 | 0.36 | 3.87 | <10min | Excl |
| NCE1 (YJL206C-A) ex | 51 | P | 18 | P | 105 | P | -117 | A | 0.35 | 0.17 | 3.85 | <10min | Excl |
| ORF YML132W (_f) | 83 | P | 21 | P | 170 | P | 6 | P | 0.26 | 0.27 | 3.82 | <10min | Excl |
| EUG1 (YDR518W) | 35 | P | 12 | P | 70 | P | 7 | P | 0.35 | 0.17 | 3.80 | <10min | Excl |
| ORF YGR131W | 15 | P | 5 | A | 15 | P | 8 | P | 0.34 | 0.18 | 3.79 | <10min | Good |
| ORF YKL066W | 42 | P | 12 | M | 55 | P | 3 | P | 0.28 | 0.25 | 3.77 | <5min | Good |
| ORF YER160C exon 1 | 1235 | P | 784 | P | 1187 | P | 14 | P | 0.63 | -0.10 | 3.73 | <10min | Good |
| ORF YMR163C | 14 | P | 2 | A | 15 | P | 6 | P | 0.12 | 0.42 | 3.70 | <10min | Good |
| ORF YIL159W | 15 | P | 5 | P | 35 | P | 7 | P | 0.35 | 0.19 | 3.68 | <5min | Excl |
| ORF YIR033W | 27 | P | 7 | P | 25 | P | 8 | P | 0.25 | 0.30 | 3.66 | <10min | Excl |
| ORF YIL067C | 38 | P | 18 | P | 60 | P | 5 | A | 0.47 | 0.08 | 3.63 | <10min | Good |
| ORF YLR364W | 36 | P | 9 | P | 46 | P | 13 | P | 0.26 | 0.29 | 3.61 | <10min | Excl |
| TIR1 (YER011W) | 251 | P | 70 | P | 381 | P | 106 | P | 0.28 | 0.28 | 3.60 | <10min | Excl |
| DUR1,2" (YBR208C)" | 49 | P | 11 | P | 88 | P | 28 | P | 0.23 | 0.32 | 3.59 | <10min | Excl |
| ORF YIL011W | 119 | P | 28 | P | 80 | P | 27 | P | 0.23 | 0.33 | 3.55 | <10min | Excl |
| ORF YGL196W | 48 | P | 12 | P | 82 | P | 26 | P | 0.25 | 0.32 | 3.52 | <10min | Excl |
| ORF YPL134C | 47 | P | 14 | P | 61 | P | 16 | P | 0.30 | 0.27 | 3.50 | <10min | Good |
| YAT1 (YAR035W) | 31 | P | 7 | A | 26 | P | 9 | P | 0.22 | 0.35 | 3.50 | <5min | Good |
| ORF YBL094C | 17 | P | 5 | A | 29 | P | 8 | P | 0.30 | 0.28 | 3.50 | <5min | Good |
| ORF YHR101C exon 1 | 17 | P | 1 | A | 9 | P | 5 | A | 0.06 | 0.52 | 3.48 | <5min | Good |
| ASE1 (YOR058C) | 18 | P | 5 | P | 17 | P | 5 | P | 0.30 | 0.28 | 3.48 | <5min | Excl |

Figure 31C

| | | | | | | | | |
|---|---|---|---|---|---|---|---|---|
| SHR5 (YOL110W) | 31 P | 8 A | 34 P | 10 P | 0.27 | 0.31 | 3.47 | <10min | Good |
| RDI1 (YDL135C) | 82 P | 30 P | 233 P | 54 P | 0.36 | 0.23 | 3.37 | <10min | Excl |
| ORF YDL018C | 34 P | 13 P | 72 P | 16 P | 0.38 | 0.22 | 3.36 | <10min | Excl |
| MUD1 (YBR119W) exg | 22 P | 6 P | 42 P | 14 P | 0.27 | 0.33 | 3.35 | <10min | Good |
| ORF YLR424W | 10 P | 1 A | 14 P | 8 P | 0.06 | 0.54 | 3.35 | <10min | Excl |
| PMT5 (YDL093W) | 39 P | 14 P | 87 P | 22 P | 0.35 | 0.25 | 3.30 | <10min | Excl |
| ORF YLR087C | 22 P | 7 P | 26 P | 8 P | 0.31 | 0.30 | 3.30 | <10min | Good |
| ORF YEL022W | 55 P | 4 A | 96 P | 52 P | 0.07 | 0.54 | 3.30 | <10min | Excl |
| ORF YHR054C (_r) | 51 P | 13 P | 140 P | 50 P | 0.25 | 0.36 | 3.29 | <5min | Good |
| ORF YIR041W (_f) | 48 P | 16 P | 44 P | 13 P | 0.32 | 0.29 | 3.27 | <5min | Excl |
| FRE2 (YKL220C) | 16 P | 3 A | 19 P | 8 P | 0.20 | 0.42 | 3.26 | <10min | Good |
| ORF YHR198C | 24 P | 5 P | 25 P | 10 P | 0.22 | 0.39 | 3.25 | <10min | Excl |
| ORF YDL109C | 27 P | 7 A | 29 P | 10 P | 0.27 | 0.34 | 3.25 | <10min | Good |
| NCA3 (YJL116C) | 63 P | 20 P | 69 P | 20 P | 0.32 | 0.29 | 3.24 | <10min | Excl |
| ORF YIL169C | 28 P | 8 M | 30 P | 10 P | 0.28 | 0.34 | 3.23 | <5min | Good |
| ORF YCL061C | 11 P | 4 A | 24 P | 6 P | 0.37 | 0.25 | 3.19 | <5min | Good |
| HXK1 (YFR053C) | 250 P | 92 P | 269 P | 72 P | 0.37 | 0.27 | 3.16 | <10min | Excl |
| ORF YCL047C | 45 P | 16 P | 101 P | 28 P | 0.36 | 0.28 | 3.16 | <10min | Excl |
| ORF YCL020W (_f) | 93 P | 29 P | 158 P | 51 P | 0.31 | 0.32 | 3.14 | <10min | Excl |
| ORF YLR171W | 15 P | 5 P | 26 P | 8 P | 0.34 | 0.30 | 3.14 | <10min | Excl |
| ORF YFL055W | 20 P | 9 P | 21 P | 4 M | 0.45 | 0.19 | 3.13 | <10min | Good |
| ORF YBL101W-A (_f) | 108 P | 27 P | 148 P | 57 P | 0.25 | 0.39 | 3.12 | <5min | Excl |
| ORF YBL029W | 22 P | 9 A | 28 P | 7 P | 0.39 | 0.25 | 3.09 | <10min | Good |
| ORF YPL164C | 26 P | 7 P | 24 P | 9 P | 0.26 | 0.39 | 3.08 | <10min | Excl |
| HXT12 (YIL171W) (_i) | 66 P | 16 P | 44 P | 18 P | 0.25 | 0.41 | 3.07 | <10min | Excl |
| ORF YBL101W-B exor | 111 P | 28 P | 142 P | 57 P | 0.26 | 0.40 | 3.05 | <10min | Excl |
| ORF YBR004C | 81 P | 26 P | 127 P | 42 P | 0.32 | 0.33 | 3.05 | <5min | Excl |
| SRD1 (YCR018C) | 56 P | 15 P | 69 P | 28 P | 0.26 | 0.40 | 3.04 | <5min | Good |
| ORF YMR025W | 11 P | 3 A | 12 P | 5 P | 0.24 | 0.43 | 2.99 | <10min | Good |
| ORF YBR066C | 32 P | 9 P | 39 P | 15 P | 0.29 | 0.39 | 2.98 | <10min | Excl |
| URA8 (YJR103W) | 111 P | 34 P | 110 P | 41 P | 0.30 | 0.37 | 2.95 | <10min | Excl |
| ORF YEL015W | 36 P | 0 P | 49 P | 33 P | 0.00 | 0.68 | 2.93 | <10min | Excl |
| THI11 (YJR156C) (_f) | 44 P | 15 P | 50 P | 17 P | 0.34 | 0.35 | 2.92 | <10min | Excl |

Figure 31D

| | | | | | | | |
|---|---|---|---|---|---|---|---|
| GLT1 (YDL171C) | 171 P | 71 P | 312 P | 85 P | 0.41 | 0.27 | 2.92 <5min | Excl |
| SAG1 (YJR004C) | 49 P | 14 P | 40 P | 16 P | 0.29 | 0.39 | 2.92 <10min | Excl |
| ORF YBR230C exon 1 | 96 P | 29 P | 124 P | 48 P | 0.30 | 0.39 | 2.90 <10min | Excl |
| ORF YDR516C | 52 P | 19 P | 63 P | 22 P | 0.36 | 0.34 | 2.84 <10min | Excl |
| THI5 (YFL058W) (_f) | 25 P | 10 P | 36 P | 11 P | 0.39 | 0.32 | 2.81 <10min | Excl |
| TPS2 (YDR074W) | 51 P | 21 P | 56 P | 16 P | 0.42 | 0.29 | 2.81 <5min | Excl |
| ORF YGL088W | 13 P | 4 P | 23 P | 9 P | 0.33 | 0.39 | 2.79 <5min | Excl |
| ORF YNL126W | 16 P | 4 A | 26 P | 12 P | 0.28 | 0.45 | 2.76 <10min | Good |
| ORF YBR005W | 148 P | 60 P | 129 P | 42 P | 0.40 | 0.32 | 2.75 <5min | Excl |
| DAL4 (YIR028W) | 27 P | 3 A | 16 P | 10 P | 0.13 | 0.61 | 2.72 <10min | Good |
| ORF YCL006C | 12 P | 4 A | 9 P | 4 P | 0.30 | 0.43 | 2.71 <10min | Good |
| ORF YBL053W | 22 P | 9 A | 23 P | 8 P | 0.42 | 0.33 | 2.67 <5min | Good |
| ORF YDR438W | 9 P | 2 A | 13 P | 7 P | 0.20 | 0.55 | 2.65 <10min | Good |
| ORF YDL244W (_f) | 35 P | 14 P | 41 P | 15 P | 0.40 | 0.36 | 2.62 <10min | Good |
| PAU3 (YCR104W) (_f) | 327 P | 95 P | 225 P | 112 P | 0.29 | 0.50 | 2.54 <10min | Excl |
| ZIP1 (YDR285W) | 18 P | 7 P | 25 P | 10 P | 0.38 | 0.42 | 2.51 <5min | Excl |
| ORF YBR059C | 66 P | 28 P | 80 P | 30 P | 0.42 | 0.38 | 2.51 <5min | Excl |
| FLO1 (YAR050W) | 36 P | 11 P | 23 P | 11 P | 0.32 | 0.49 | 2.49 <5min | Excl |
| ORF YIL101C | 53 P | 18 M | 19 P | 9 P | 0.33 | 0.48 | 2.46 <5min | Good |
| ORF YBR050C | 46 P | 16 P | 43 P | 20 P | 0.36 | 0.47 | 2.42 <10min | Excl |
| ORF YLR112W | 34 P | 15 P | 39 P | 15 P | 0.44 | 0.39 | 2.42 <5min | Excl |
| MAK31 (YCR020C-A) | 45 P | 21 P | 78 P | 29 P | 0.47 | 0.37 | 2.39 <10min | Excl |
| ORF YJR155W | 24 P | 8 P | 24 P | 12 P | 0.34 | 0.50 | 2.38 <10min | Excl |
| TEL1 (YBL088C) | 31 P | 11 P | 30 P | 15 P | 0.35 | 0.49 | 2.38 <10min | Excl |
| ORF YKL136W | 10 P | 0 A | 16 P | 14 P | 0.00 | 0.86 | 2.34 <10min | Good |
| ORF YCR071C | 36 P | 16 P | 45 P | 19 P | 0.44 | 0.43 | 2.28 <10min | Excl |
| ORF YAL068C (_f) | 104 P | 44 P | 132 P | 60 P | 0.42 | 0.46 | 2.28 <10min | Excl |
| GLK1 (YCL040W) | 436 P | 197 P | 510 P | 220 P | 0.45 | 0.43 | 2.26 <10min | Excl |
| PDR11 (YIL013C) | 38 P | 15 P | 39 P | 21 P | 0.39 | 0.52 | 2.19 <5min | Excl |
| TOR1 (YJR066W) | 18 P | 8 P | 33 P | 14 P | 0.47 | 0.44 | 2.18 <5min | Excl |
| RPS24B (YLR367W) e | 74 P | 42 P | 106 P | 37 P | 0.57 | 0.35 | 2.17 <10min | Excl |
| ORF YBR027C | 12 P | 2 A | 10 P | 7 P | 0.19 | 0.73 | 2.17 <5min | Good |
| ORF YCL019W | 590 P | 255 P | 733 P | 364 P | 0.43 | 0.50 | 2.15 <10min | Excl |
| ORF YCR105W | 13 P | 4 P | 19 P | 11 P | 0.32 | 0.62 | 2.14 <5min | Excl |
| ORF YBR203W | 27 P | 11 P | 29 P | 16 P | 0.39 | 0.55 | 2.14 <5min | Excl |
| YCRX02c/_r (control? | 24 P | 13 P | 17 P | 7 P | 0.53 | 0.41 | 2.12 <5min | Excl |
| ORF YOL078W | 24 P | 13 P | 36 P | 14 P | 0.55 | 0.39 | 2.11 <10min | Excl |
| CDC39 (YCR093W) | 48 P | 26 P | 75 P | 31 P | 0.55 | 0.41 | 2.07 <5min | Excl |
| ORF YOL151W | 118 P | 46 P | 155 P | 91 P | 0.39 | 0.59 | 2.05 <10min | Excl |
| ORF YDR542W (_f) | 100 P | 45 P | 72 P | 38 P | 0.45 | 0.52 | 2.05 <10min | Excl |
| PCA1 (YBR295W) | 27 P | 13 P | 38 P | 20 P | 0.47 | 0.53 | 2.00 <10min | Excl |
| RPS24B (YLR367W) e | 443 P | 241 P | 644 P | 329 P | 0.54 | 0.51 | 1.90 <5min | Excl |
| ORF YMR041C | 26 P | 15 P | 25 P | 13 P | 0.58 | 0.53 | 1.81 <10min | Excl |
| ORF YLR217W | 7 P | 2 A | 16 P | 13 P | 0.29 | 0.84 | 1.78 <10min | Good |
| ORF YER185W | 13 P | 9 P | 18 P | 8 P | 0.70 | 0.45 | 1.74 <5min | Excl |

Figure 31E

Med6 Down

Gene Expression Results for FH1998040601A

| Gene | WT#1 n | WT#1 | TS#1 n | TS#1 | WT#2 n | WT#2 | TS#2 n | TS#2 | MT1/WT1 | MT2/WT2 | Average | Fit | Confidence |
|---|---|---|---|---|---|---|---|---|---|---|---|---|---|
| ASE1 (YOR058C) | 18 | P | 5 | P | 17 | P | 5 | P | 0.30 | 0.28 | 3.5 | <5min | Excl |
| CAR1 (YPL111W) | 182 | P | 58 | P | 263 | P | 31 | P | 0.32 | 0.12 | 4.6 | <10min | Excl |
| CAR2 (YLR438W) | 92 | P | 23 | P | 77 | P | 10 | P | 0.25 | 0.13 | 5.3 | <5min | Excl |
| CDC39 (YCR093W) | 48 | P | 26 | P | 75 | P | 31 | P | 0.55 | 0.41 | 2.1 | <5min | Excl |
| CHA1 (YCL064C) | 124 | P | 37 | P | 250 | P | 36 | P | 0.29 | 0.15 | 4.5 | <10min | Excl |
| CHS2 (YBR038W) | 30 | P | 6 | P | 40 | P | 10 | P | 0.21 | 0.26 | 4.2 | <5min | Excl |
| DAL4 (YIR028W) | 27 | P | 3 | A | 16 | P | 10 | P | 0.13 | 0.61 | 2.7 | <10min | Good |
| DBP2 (YNL112W) exo | 392 | P | 104 | P | 434 | P | 87 | P | 0.27 | 0.20 | 4.3 | <10min | Excl |
| DBP2 (YNL112W) exo | 443 | P | 105 | P | 866 | P | 178 | P | 0.24 | 0.20 | 4.5 | <10min | Excl |
| DUR1,2" (YBR208C)" | 49 | P | 11 | P | 88 | P | 28 | P | 0.23 | 0.32 | 3.6 | <10min | Excl |
| EUG1 (YDR518W) | 35 | P | 12 | P | 70 | P | 12 | P | 0.35 | 0.17 | 3.8 | <10min | Excl |
| FCY21 (YER060W) (_ | 16 | P | 2 | A | 34 | P | 4 | A | 0.10 | 0.12 | 9.1 | <5min | Good |
| FET4 (YMR319C) | 25 | P | 8 | M | 39 | P | 6 | P | 0.34 | 0.16 | 4.1 | <10min | Good |
| FLO1 (YAR050W) | 36 | P | 11 | P | 23 | P | 11 | P | 0.32 | 0.49 | 2.5 | <5min | Excl |
| FRE2 (YKL220C) | 16 | P | 3 | A | 19 | P | 8 | P | 0.20 | 0.42 | 3.3 | <10min | Good |
| GLK1 (YCL040W) | 436 | P | 197 | P | 510 | P | 220 | P | 0.45 | 0.43 | 2.3 | <10min | Excl |
| GLT1 (YDL171C) | 171 | P | 71 | P | 312 | P | 85 | P | 0.41 | 0.27 | 2.9 | <5min | Excl |
| GSC2 (YGR032W) | 248 | P | 55 | P | 287 | P | 48 | P | 0.22 | 0.17 | 5.1 | <5min | Excl |
| HAP1 (YLR256W) | 18 | P | 3 | A | 36 | P | 10 | P | 0.16 | 0.27 | 4.6 | <5min | Excl |
| HHO1 (YPL127C) | 69 | P | 14 | P | 89 | P | 18 | P | 0.20 | 0.20 | 5.0 | <10min | Excl |
| HXK1 (YFR053C) | 250 | P | 92 | P | 269 | P | 72 | P | 0.37 | 0.27 | 3.2 | <10min | Excl |
| HXT12 (YIL171W) (_ | 66 | P | 16 | P | 44 | P | 18 | P | 0.25 | 0.41 | 3.1 | <10min | Excl |
| KIP1 (YBL063W) | 16 | P | 3 | A | 28 | P | 9 | P | 0.17 | 0.34 | 3.9 | <10min | Good |
| KTR2 (YKR061W) | 85 | P | 17 | P | 107 | P | 30 | P | 0.20 | 0.28 | 4.1 | <5min | Excl |
| MAK31 (YCR020C-A) | 45 | P | 21 | P | 78 | P | 29 | P | 0.47 | 0.37 | 2.4 | <10min | Excl |
| MEP1 (YGR121C) | 30 | P | 7 | P | 41 | P | 10 | P | 0.23 | 0.24 | 4.2 | <10min | Excl |
| MUD1 (YBR119W) exd | 22 | P | 6 | P | 42 | P | 14 | P | 0.27 | 0.33 | 3.4 | <10min | Excl |
| NCA3 (YJL116C) | 63 | P | 20 | P | 69 | P | 20 | P | 0.32 | 0.29 | 3.2 | <10min | Excl |
| NCE1 (YJL206C-A) ex | 51 | P | 18 | P | 105 | P | 18 | P | 0.35 | 0.17 | 3.9 | <10min | Excl |
| NMD5 (YJR132W) | 23 | P | 5 | A | 51 | P | 12 | P | 0.21 | 0.24 | 4.5 | <10min | Good |
| ORF YAL068C (_f) | 104 | P | 44 | P | 132 | P | 60 | P | 0.42 | 0.46 | 2.3 | <10min | Excl |
| ORF YAR053W (_f) | 16 | P | 2 | A | 20 | P | 3 | A | 0.14 | 0.13 | 7.2 | <5min | Good |

Figure 32A

| | | | | | | | | |
|---|---|---|---|---|---|---|---|---|
| ORF YBL018C exon 2 | 42 P | 12 P | 110 P | 21 P | 0.28 | 0.20 | 4.2 | <10min | Excl |
| ORF YBL019W | 21 P | 1 A | 19 P | 5 P | 0.04 | 0.27 | 6.5 | <5min | Good |
| ORF YBL029W | 22 P | 9 A | 28 P | 7 P | 0.39 | 0.25 | 3.1 | <10min | Good |
| ORF YBL053W | 22 P | 9 A | 23 P | 8 P | 0.42 | 0.33 | 2.7 | <5min | Good |
| ORF YBL094C | 17 P | 5 A | 29 P | 8 P | 0.30 | 0.28 | 3.5 | <5min | Good |
| ORF YBL101W-A (_f) | 108 P | 27 P | 148 P | 57 P | 0.25 | 0.39 | 3.1 | <5min | Excl |
| ORF YBL101W-B exon | 111 P | 28 P | 142 P | 57 P | 0.26 | 0.40 | 3.1 | <10min | Excl |
| ORF YBR004C | 81 P | 26 P | 127 P | 42 P | 0.32 | 0.33 | 3.0 | <5min | Excl |
| ORF YBR005W | 148 P | 60 P | 129 P | 42 P | 0.40 | 0.32 | 2.7 | <5min | Excl |
| ORF YBR027C | 12 P | 2 A | 10 P | 7 P | 0.19 | 0.73 | 2.2 | <5min | Good |
| ORF YBR050C | 46 P | 16 P | 43 P | 20 P | 0.36 | 0.47 | 2.4 | <10min | Excl |
| ORF YBR059C | 66 P | 28 P | 80 P | 30 P | 0.42 | 0.38 | 2.5 | <5min | Excl |
| ORF YBR066C | 32 P | 9 P | 39 P | 15 P | 0.29 | 0.39 | 3.0 | <10min | Excl |
| ORF YBR108W | 44 P | -4 A | 40 P | 18 P | -0.09 | 0.47 | 5.4 | <5min | Good |
| ORF YBR203W | 27 P | 11 P | 29 P | 16 P | 0.39 | 0.55 | 2.1 | <5min | Excl |
| ORF YBR230C exon 1 | 96 P | 29 P | 124 P | 48 P | 0.30 | 0.39 | 2.9 | <10min | Excl |
| ORF YBR244W | 34 P | 7 P | 53 P | 12 P | 0.21 | 0.23 | 4.5 | <10min | Excl |
| ORF YBR302C (_f) | 92 P | 19 P | 193 P | 38 P | 0.21 | 0.20 | 4.9 | <5min | Excl |
| ORF YCL006C | 12 P | 4 A | 9 P | 4 P | 0.30 | 0.43 | 2.7 | <10min | Good |
| ORF YCL019W | 590 P | 255 P | 733 P | 364 P | 0.43 | 0.50 | 2.2 | <10min | Excl |
| ORF YCL020W (_f) | 93 P | 29 P | 158 P | 51 P | 0.31 | 0.32 | 3.1 | <10min | Excl |
| ORF YCL047C | 45 P | 16 P | 101 P | 28 P | 0.36 | 0.28 | 3.2 | <10min | Excl |
| ORF YCL061C | 11 P | 4 A | 24 P | 6 P | 0.37 | 0.25 | 3.2 | <5min | Good |
| ORF YCR060W | 91 P | 29 P | 152 P | 29 P | 0.32 | 0.19 | 3.9 | <10min | Excl |
| ORF YCR071C | 36 P | 16 P | 45 P | 19 P | 0.44 | 0.43 | 2.3 | <10min | Excl |
| ORF YCR105W | 13 P | 4 P | 19 P | 11 P | 0.32 | 0.62 | 2.1 | <5min | Good |
| ORF YDL018C | 34 P | 13 P | 72 P | 16 P | 0.38 | 0.22 | 3.4 | <10min | Excl |
| ORF YDL019C | 45 P | 10 P | 68 P | 14 P | 0.22 | 0.21 | 4.6 | <10min | Excl |
| ORF YDL098C | 26 P | 4 P | 61 P | 18 P | 0.16 | 0.29 | 4.5 | <10min | Excl |
| ORF YDL109C | 27 P | 7 A | 29 P | 10 P | 0.27 | 0.34 | 3.3 | <10min | Good |
| ORF YDL244W (_f) | 35 P | 14 P | 41 P | 15 P | 0.40 | 0.36 | 2.6 | <10min | Excl |
| ORF YDR380W | 50 P | 4 P | 52 P | 16 P | 0.07 | 0.30 | 5.4 | <10min | Excl |

Figure 32B

| ORF | | | | | | | | | |
|---|---|---|---|---|---|---|---|---|---|
| ORF YDR428C | 25 | P | 4 | A | 37 | P | 5 | P | 0.15 | 0.13 | 7.2 | <5min | Good |
| ORF YDR438W | 9 | P | 2 | A | 13 | P | 7 | P | 0.20 | 0.55 | 2.6 | <10min | Good |
| ORF YDR453C | 16 | P | 4 | A | 28 | P | 4 | P | 0.26 | 0.15 | 4.9 | <10min | Good |
| ORF YDR516C | 52 | P | 19 | P | 63 | P | 22 | P | 0.36 | 0.34 | 2.8 | <10min | Excl |
| ORF YDR542W (_r) | 100 | P | 45 | P | 72 | P | 38 | P | 0.45 | 0.52 | 2.1 | <10min | Excl |
| ORF YEL015W | 36 | P | 0 | P | 49 | P | 33 | P | 0.00 | 0.68 | 2.9 | <10min | Excl |
| ORF YEL022W | 55 | P | 4 | A | 96 | P | 52 | P | 0.07 | 0.54 | 3.3 | <10min | Good |
| ORF YEL031W | 224 | P | -134 | A | 344 | P | 248 | P | -0.60 | 0.72 | 16.4 | <5min | Good |
| ORF YEL047C | 92 | P | 4 | P | 155 | P | 52 | P | 0.04 | 0.33 | 5.3 | <5min | Excl |
| ORF YEL064C | 13 | P | 2 | A | 28 | P | 8 | P | 0.12 | 0.30 | 4.8 | <5min | Good |
| ORF YEL066W | 111 | P | 28 | P | 138 | P | 28 | P | 0.25 | 0.21 | 4.4 | <10min | Excl |
| ORF YER005W | 70 | P | -17 | P | 102 | P | 41 | P | -0.24 | 0.40 | 13.0 | <10min | Excl |
| ORF YER089C | 171 | P | 27 | P | 102 | P | 37 | P | 0.16 | 0.36 | 3.9 | <10min | Excl |
| ORF YER152C | 101 | P | 26 | P | 149 | P | 24 | P | 0.26 | 0.16 | 4.8 | <10min | Excl |
| ORF YER160C exon 1 | 1235 | P | 784 | P | 1187 | P | -117 | A | 0.63 | -0.10 | 3.7 | <10min | Good |
| ORF YER185W | 13 | P | 9 | P | 18 | P | 8 | P | 0.70 | 0.45 | 1.7 | <5min | Excl |
| ORF YFL017C | 78 | P | 15 | P | 80 | P | 15 | P | 0.19 | 0.19 | 5.2 | <10min | Excl |
| ORF YFL055W | 20 | P | 9 | P | 21 | P | 4 | M | 0.45 | 0.19 | 3.1 | <10min | Good |
| ORF YFR022W | 24 | P | 8 | P | 21 | P | 3 | A | 0.36 | 0.14 | 4.0 | <10min | Good |
| ORF YGL088W | 13 | P | 4 | P | 23 | P | 9 | P | 0.33 | 0.39 | 2.8 | <5min | Good |
| ORF YGL196W | 48 | P | 12 | P | 82 | P | 26 | P | 0.25 | 0.32 | 3.5 | <10min | Excl |
| ORF YGR041W | 33 | P | 7 | P | 31 | P | 5 | P | 0.21 | 0.16 | 5.3 | <10min | Good |
| ORF YGR131W | 15 | P | 5 | A | 15 | P | 3 | P | 0.34 | 0.18 | 3.8 | <10min | Good |
| ORF YGR260W | 119 | P | 12 | P | 151 | P | 20 | P | 0.10 | 0.13 | 8.6 | <5min | Excl |
| ORF YHL044W | 12 | P | 1 | A | 25 | P | 4 | P | 0.05 | 0.15 | 10.0 | <5min | Good |
| ORF YHR054C (_r) | 51 | P | 13 | P | 140 | P | 50 | P | 0.25 | 0.36 | 3.3 | <5min | Excl |
| ORF YHR101C exon 1 | 17 | P | 1 | A | 9 | P | 5 | A | 0.06 | 0.52 | 3.5 | <5min | Good |
| ORF YHR198C | 24 | P | 5 | P | 25 | P | 10 | P | 0.22 | 0.39 | 3.3 | <10min | Excl |
| ORF YIL011W | 119 | P | 28 | P | 80 | P | 27 | P | 0.23 | 0.33 | 3.5 | <10min | Excl |
| ORF YIL067C | 38 | P | 18 | P | 60 | P | 5 | A | 0.47 | 0.08 | 3.6 | <10min | Good |
| ORF YIL101C | 53 | P | 18 | M | 19 | P | 9 | P | 0.33 | 0.48 | 2.5 | <5min | Good |
| ORF YIL159W | 15 | P | 5 | P | 35 | P | 7 | P | 0.35 | 0.19 | 3.7 | <5min | Excl |
| ORF YIL169C | 28 | P | 8 | M | 30 | P | 10 | P | 0.28 | 0.34 | 3.2 | <5min | Good |
| ORF YIL173W (_f) | 12 | P | 2 | A | 30 | P | 6 | P | 0.13 | 0.21 | 5.9 | <5min | Good |
| ORF YIR033W | 27 | P | 7 | P | 25 | P | 8 | P | 0.25 | 0.30 | 3.7 | <10min | Excl |
| ORF YIR041W (_f) | 48 | P | 16 | P | 44 | P | 13 | P | 0.32 | 0.29 | 3.3 | <5min | Excl |
| ORF YJL009W | 18 | P | 6 | P | 12 | P | -3 | A | 0.34 | -0.22 | 16.6 | <5min | Good |
| ORF YJL103C | 13 | P | 4 | M | 17 | P | 4 | P | 0.27 | 0.23 | 4.1 | <5min | Good |

Figure 32C

| ORF | | | | | | | | | |
|---|---|---|---|---|---|---|---|---|---|
| ORF YJL222W (_f) | 22 | P | 4 | P | 31 | P | 8 | P | 0.18 | 0.28 | 4.4 | <10min | Excl |
| ORF YJR079W exon 1 | 64 | P | 4 | A | 119 | P | 17 | P | 0.07 | 0.14 | 9.5 | <5min | Good |
| ORF YJR151C | 39 | P | 11 | P | 40 | P | 7 | P | 0.28 | 0.17 | 4.5 | <5min | Excl |
| ORF YJR155W | 24 | P | 8 | P | 24 | P | 12 | P | 0.34 | 0.50 | 2.4 | <10min | Excl |
| ORF YKL066W | 42 | P | 12 | M | 55 | P | 14 | P | 0.28 | 0.25 | 3.8 | <5min | Good |
| ORF YKL084W | 59 | P | 14 | P | 141 | P | 23 | P | 0.24 | 0.16 | 5.0 | <10min | Excl |
| ORF YKL086W | 19 | P | 5 | A | 27 | P | 4 | A | 0.25 | 0.16 | 4.9 | <5min | Excl |
| ORF YKL111C | 15 | P | 1 | A | 18 | P | 6 | P | 0.08 | 0.36 | 4.6 | <5min | Good |
| ORF YKL136W | 10 | P | 0 | A | 16 | P | 14 | P | 0.00 | 0.86 | 2.3 | <10min | Good |
| ORF YLR087C | 22 | P | 7 | P | 26 | P | 8 | P | 0.31 | 0.30 | 3.3 | <10min | Excl |
| ORF YLR112W | 34 | P | 15 | P | 39 | P | 15 | P | 0.44 | 0.39 | 2.4 | <5min | Excl |
| ORF YLR126C | 34 | P | 8 | P | 67 | P | 12 | P | 0.24 | 0.18 | 4.8 | <10min | Excl |
| ORF YLR154C | 94 | P | 20 | P | 145 | P | 19 | P | 0.21 | 0.13 | 5.9 | <10min | Excl |
| ORF YLR171W | 15 | P | 5 | P | 26 | P | 8 | P | 0.34 | 0.30 | 3.1 | <10min | Excl |
| ORF YLR213C | 11 | P | -1 | A | 12 | P | 3 | P | -0.13 | 0.27 | 13.9 | <5min | Good |
| ORF YLR217W | 7 | P | 2 | A | 16 | P | 13 | P | 0.29 | 0.84 | 1.8 | <10min | Good |
| ORF YLR231C | 45 | P | 6 | P | 100 | P | 9 | P | 0.14 | 0.10 | 8.5 | <10min | Excl |
| ORF YLR364W | 36 | P | 9 | P | 46 | P | 13 | P | 0.26 | 0.29 | 3.6 | <10min | Excl |
| ORF YLR413W | 253 | P | 71 | P | 277 | P | 40 | P | 0.28 | 0.14 | 4.7 | <10min | Excl |
| ORF YLR424W | 10 | P | 1 | A | 14 | P | 8 | P | 0.06 | 0.54 | 3.3 | <10min | Good |
| ORF YLR456W | 14 | P | 3 | A | 24 | P | 6 | P | 0.21 | 0.26 | 4.2 | <10min | Excl |
| ORF YML101C | 53 | P | 9 | P | 87 | P | 15 | P | 0.17 | 0.17 | 5.8 | <5min | Excl |
| ORF YML132W (_f) | 83 | P | 21 | P | 170 | P | 45 | P | 0.26 | 0.27 | 3.8 | <10min | Excl |
| ORF YMR025W | 11 | P | 3 | A | 12 | P | 5 | P | 0.24 | 0.43 | 3.0 | <10min | Good |
| ORF YMR041C | 26 | P | 15 | P | 25 | P | 13 | P | 0.58 | 0.53 | 1.8 | <10min | Excl |
| ORF YMR155W | 9 | P | 1 | A | 14 | P | 5 | P | 0.10 | 0.34 | 4.6 | <5min | Good |
| ORF YMR163C | 14 | P | 2 | A | 15 | P | 6 | P | 0.12 | 0.42 | 3.7 | <10min | Good |
| ORF YNL126W | 16 | P | 4 | A | 26 | P | 12 | P | 0.28 | 0.45 | 2.8 | <10min | Good |
| ORF YNL336W (_f) | 100 | P | 30 | P | 238 | P | 47 | P | 0.30 | 0.20 | 4.0 | <10min | Good |
| ORF YOL047C exon 1 | 15 | P | 2 | A | 14 | P | 3 | A | 0.16 | 0.19 | 5.8 | <5min | Good |
| ORF YOL078W | 24 | P | 13 | P | 36 | P | 14 | P | 0.55 | 0.39 | 2.1 | <10min | Excl |
| ORF YOL151W | 118 | P | 46 | P | 155 | P | 91 | P | 0.39 | 0.59 | 2.1 | <10min | Excl |
| ORF YOR013W | 33 | P | 7 | A | 39 | P | 12 | P | 0.20 | 0.30 | 4.0 | <10min | Good |
| ORF YOR040W | 31 | P | 4 | P | 63 | P | 18 | P | 0.14 | 0.28 | 4.7 | <5min | Excl |
| ORF YOR306C | 119 | P | 28 | P | 206 | P | 43 | P | 0.24 | 0.21 | 4.5 | <5min | Excl |
| ORF YOR382W | 74 | P | 42 | P | 106 | P | 37 | P | 0.57 | 0.35 | 2.2 | <10min | Excl |
| ORF YPL134C | 47 | P | 14 | P | 61 | P | 16 | P | 0.30 | 0.27 | 3.5 | <10min | Excl |
| ORF YPL164C | 26 | P | 7 | P | 24 | P | 9 | P | 0.26 | 0.39 | 3.1 | <10min | Excl |
| ORF YPR006C | 37 | P | 3 | A | 65 | P | 4 | P | 0.07 | 0.06 | 14.8 | <5min | Good |

Figure 32D

| ORF YPR011C | 31 | P | | P | 41 | P | 11 | P | 0.26 | 0.26 | 3.9 | <10min | Excl |
|---|---|---|---|---|---|---|---|---|---|---|---|---|---|
| ORF YPR172W | 35 | P | 10 | P | 38 | P | 6 | P | 0.28 | 0.17 | 4.5 | <10min | Excl |
| PAI3 (YMR174C) | 52 | P | 14 | P | 88 | P | 18 | P | 0.28 | 0.20 | 4.2 | <10min | Excl |
| PAU3 (YCR104W) (_f) | 327 | P | 95 | P | 225 | P | 112 | P | 0.29 | 0.50 | 2.5 | <10min | Excl |
| PCA1 (YBR295W) | 27 | P | 13 | P | 38 | P | 20 | P | 0.47 | 0.53 | 2.0 | <10min | Excl |
| PDR11 (YIL013C) | 38 | P | 15 | P | 39 | P | 21 | P | 0.39 | 0.52 | 2.2 | <5min | Excl |
| PHO5 (YBR093C) | 130 | P | 32 | P | 215 | P | 34 | P | 0.25 | 0.16 | 4.9 | <10min | Excl |
| PMT5 (YDL093W) | 39 | P | 14 | P | 87 | P | 22 | P | 0.35 | 0.25 | 3.3 | <10min | Excl |
| RAD23 (YEL037C) | 145 | P | 85 | P | 173 | P | -34 | A | 0.59 | -0.20 | 5.1 | <5min | Good |
| RDI1 (YDL135C) | 82 | P | 30 | P | 233 | P | 54 | P | 0.36 | 0.23 | 3.4 | <10min | Excl |
| RNR2 (YJL026W) | 320 | P | 74 | P | 291 | P | 61 | P | 0.23 | 0.21 | 4.5 | <10min | Excl |
| RNR3 (YIL066C) | 62 | P | 16 | P | 55 | P | 8 | M | 0.26 | 0.14 | 5.0 | <5min | Good |
| RPS24B (YLR367W) e | 443 | P | 241 | P | 644 | P | 329 | P | 0.54 | 0.51 | 1.9 | <10min | Excl |
| RTA1 (YGR213C) | 16 | P | 6 | A | 19 | P | -1 | A | 0.38 | -0.04 | 5.8 | <5min | Good |
| SAG1 (YJR004C) | 49 | P | 14 | P | 40 | P | 16 | P | 0.29 | 0.39 | 2.9 | <10min | Excl |
| SCS3 (YGL126W) | 179 | P | 40 | P | 283 | P | 47 | P | 0.22 | 0.17 | 5.2 | <10min | Excl |
| SEC6 (YIL068C) | 35 | P | 25 | P | 66 | P | -18 | A | 0.71 | -0.28 | 4.6 | <10min | Good |
| SHR5 (YOL110W) | 31 | P | 8 | A | 34 | P | 10 | P | 0.27 | 0.31 | 3.5 | <10min | Good |
| SPS19 (YNL202W) | 25 | P | 8 | M | 78 | P | 15 | P | 0.31 | 0.19 | 4.0 | <10min | Good |
| SRB2 (YHR041C) exo | 52 | P | 14 | P | 72 | P | 10 | M | 0.28 | 0.14 | 4.8 | <10min | Good |
| SRD1 (YCR018C) | 56 | P | 15 | P | 69 | P | 28 | P | 0.26 | 0.40 | 3.0 | <5min | Excl |
| SWE1 (YJL187C) | 23 | P | 7 | P | 39 | P | 8 | P | 0.29 | 0.20 | 4.1 | <10min | Excl |
| TEL1 (YBL088C) | 31 | P | 11 | P | 30 | P | 15 | P | 0.35 | 0.49 | 2.4 | <10min | Excl |
| THI11 (YJR156C) (_f) | 44 | P | 15 | P | 50 | P | 17 | P | 0.34 | 0.35 | 2.9 | <10min | Excl |
| THI4 (YGR144W) | 38 | P | 6 | P | 32 | P | 9 | P | 0.15 | 0.30 | 4.5 | <5min | Excl |
| THI5 (YFL058W) (_f) | 25 | P | 10 | P | 36 | P | 11 | P | 0.39 | 0.32 | 2.8 | <10min | Excl |
| TIR1 (YER011W) | 251 | P | 70 | P | 381 | P | 106 | P | 0.28 | 0.28 | 3.6 | <10min | Excl |
| TOR1 (YJR066W) | 18 | P | 8 | P | 33 | P | 14 | P | 0.47 | 0.44 | 2.2 | <5min | Excl |
| TPS2 (YDR074W) | 51 | P | 21 | P | 56 | P | 16 | P | 0.42 | 0.29 | 2.8 | <10min | Excl |
| URA3 (YEL021W) | 708 | P | 5 | A | 1232 | P | 11 | P | 0.01 | 0.01 | 126.9 | <5min | Good |
| URA8 (YJR103W) | 111 | P | 34 | P | 110 | P | 41 | P | 0.30 | 0.37 | 2.9 | <10min | Excl |
| YAT1 (YAR035W) | 31 | P | 7 | A | 26 | P | 9 | P | 0.22 | 0.35 | 3.5 | <5min | Good |
| YCRX02c/_r (control? | 24 | P | 13 | P | 17 | P | 7 | P | 0.53 | 0.41 | 2.1 | <5min | Excl |
| YST1 (YGR214W) exo | 605 | P | 184 | P | 842 | P | 55 | P | 0.30 | 0.07 | 5.4 | <10min | Excl |
| YSY6 (YBR162W-A) | 128 | P | 34 | P | 252 | P | 48 | P | 0.27 | 0.19 | 4.4 | <10min | Excl |
| ZIP1 (YDR285W) | 18 | P | 7 | P | 25 | P | 10 | P | 0.38 | 0.42 | 2.5 | <5min | Excl |

Figure 32E

| SRB10 LIST UP 2X BOTH OR > 10 BOTH IF AROUND 0 | | | | | | | | | | Fold Up | | |
|---|---|---|---|---|---|---|---|---|---|---|---|---|
| Gene | WT #1 | No Wt | WT #2 | No Wt | 10-3 #1 | No 10-3 #1 | 10-3 #2 | No 10-3 #2 | MUT #1/ WT #1 | MUT #2/ WT #2 | Average | Ave Diff | PPPP |
| FLO1 (YAR050W) | 14 | P | 51 | P | 1749 | P | 4052 | P | 124.93 | 79.44 | 102.19 | 2868 | PPPP |
| ORF YBR116C | 8 | A | 1 | A | 48 | P | 115 | P | 6.00 | 116.15 | 61.08 | 78 | |
| ALD4 (YMR169C) | 5 | A | 5181 | A | 180 | P | 323 | P | 36.00 | 20.21 | 28.11 | 241 | |
| HSP26 (YBR072W) | 43 | P | 51 | P | 1282 | P | 1134 | P | 29.81 | 22.23 | 26.02 | 1161 | PPPP |
| ORF YPL223C | 5 | A | 18 | A | 200 | P | 182 | P | 40.00 | 10.07 | 25.04 | 180 | |
| ORF YER150W | 34 | P | 55 | P | 1157 | P | 780 | P | 34.03 | 14.08 | 24.06 | 924 | |
| ORF YMR107W | 1 | A | -4 | A | 53 | P | 45 | P | 53.00 | -11.17 | 20.91 | 50 | |
| HSP12 (YFL014W) | 544 | P | 201 | P | 4872 | P | 5449 | P | 8.96 | 27.06 | 18.01 | 4788 | PPPP |
| RCK1 (YGL158W) | 2 | A | 41 | P | 67 | P | 83 | P | 33.50 | 2.06 | 17.78 | 54 | |
| ORF YPL017C | 1 | A | 2 | A | 27 | P | 10 | P | 27.00 | 4.86 | 15.93 | 17 | |
| STA1 (YIR019C) | 19 | A | 136 | A | 219 | P | 2615 | P | 11.53 | 19.16 | 15.34 | 1339 | |
| RTA1 (YGR213C) | 6 | A | 3 | A | 53 | P | 58 | P | 8.83 | 21.44 | 15.13 | 51 | |
| ORF YAR047C | 2 | A | 8 | A | 26 | P | 120 | P | 13.00 | 15.00 | 14.00 | 68 | |
| ORF YDR070C | 10 | A | 17 | P | 201 | P | 112 | P | 20.10 | 6.56 | 13.33 | 143 | |
| ORF YNL092W | 1 | A | 9 | A | 23 | A | 24 | P | 23.00 | 2.84 | 12.92 | 19 | |
| ORF YOL183W | 2 | A | 1 | A | 11 | A | 17 | P | 5.50 | 16.21 | 10.85 | 13 | |
| ORF TDL118W | 1 | A | -4 | A | 25 | A | 15 | M | 25.00 | -3.65 | 10.67 | 21 | |
| ORF YBR147W | 6 | A | 3 | A | 56 | P | 33 | P | 9.33 | 11.03 | 10.18 | 40 | |
| CTT1 (YGR088W) | 31 | P | 36 | P | 289 | P | 421 | P | 8.66 | 11.53 | 10.10 | 311 | |
| ORF YDL204W | 14 | P | 30 | P | 192 | P | 189 | P | 13.71 | 6.31 | 10.01 | 169 | |
| TKL2 (YBR117C) | 4 | A | 14 | P | 41 | P | 132 | P | 10.25 | 9.45 | 9.85 | 78 | |
| ORF TOL053C-A | 255 | P | 253 | P | 2874 | P | 2170 | P | 10.49 | 8.57 | 9.53 | 2188 | PPPP |
| ORF YGR043C | 22 | P | 19 | A | 183 | P | 169 | P | 8.32 | 8.94 | 8.63 | 156 | |

Figure 33A

| Gene | WT #1 | No Wt | WT #2 | No Wt | 10-3 #1 | No 10-3 #1 | 10-3 #2 | No 10-3 #2 | MUT #1/ WT #1 | MUT #2/ WT #2 | Average | Ave Diff | PPPP |
|---|---|---|---|---|---|---|---|---|---|---|---|---|---|
| ORF YFR027W | 17 | A | 1 | A | 32 | P | 21 | P | 1.88 | 15.27 | 8.58 | 17 | |
| SOL4 (YGR248W) | 27 | P | 26 | P | 281 | P | 178 | P | 8.67 | 6.92 | 8.30 | 193 | PPPP |
| CYC7 (YEL039C) | 142 | P | 45 | P | 863 | P | 467 | P | 8.08 | 10.46 | 8.27 | 572 | PPPP |
| PUT4 (YOR348C) | 7 | A | 14 | A | 56 | P | 118 | P | 8.00 | 8.35 | 8.18 | 75 | |
| ORF YKL187C | 4 | A | 18 | P | 47 | P | 80 | P | 11.75 | 4.43 | 8.09 | 52 | |
| NCA3 (YJL116C) | 37 | P | 66 | P | 303 | P | 516 | P | 8.19 | 7.82 | 8.00 | 358 | PPPP |
| ORF YOR173W | 5 | A | 24 | P | 61 | P | 90 | P | 12.20 | 3.69 | 7.94 | 61 | |
| ORF YML128C | 50 | P | 87 | P | 343 | P | 731 | P | 6.86 | 8.40 | 7.83 | 468 | PPPP |
| GPH1 (YPR160W) | 56 | P | 86 | P | 377 | P | 733 | P | 6.73 | 8.50 | 7.82 | 484 | PPPP |
| POT1 (YIL160C) | 2 | A | 15 | A | 25 | P | 34 | P | 12.50 | 2.30 | 7.40 | 21 | |
| ORF YBR012C | 42 | P | 54 | P | 336 | P | 341 | P | 8.00 | 6.31 | 7.16 | 290 | PPPP |
| ORF YAL061W | 18 | A | 18 | A | 100 | P | 138 | P | 5.56 | 7.69 | 6.62 | 101 | |
| ORF YIL113W | 9 | A | 4 | A | 41 | P | 32 | A | 4.56 | 7.83 | 6.19 | 30 | |
| ORF YDL223C | 19 | P | 72 | P | 117 | P | 424 | P | 6.16 | 5.89 | 6.02 | 225 | PPPP |
| PGM2 (YMR105C) | 40 | P | 56 | P | 216 | P | 357 | P | 5.40 | 6.38 | 5.89 | 239 | PPPP |
| YSL1 (YML100W) | 95 | P | 312 | P | 619 | P | 1594 | P | 6.52 | 5.11 | 5.81 | 903 | PPPP |
| ORF YML087C | 5 | A | 5 | A | 28 | P | 35 | P | 5.60 | 5.85 | 5.73 | 26 | |
| ORF YHR087W | 99 | P | 218 | P | 764 | P | 753 | P | 7.72 | 3.46 | 5.59 | 600 | PPPP |
| PAI3 (YMR174C) | 27 | P | 65 | P | 195 | P | 249 | P | 7.22 | 3.83 | 5.53 | 176 | PPPP |
| TDH1 (YJL052W) | 322 | P | 691 | P | 2258 | P | 2674 | P | 7.01 | 3.87 | 5.44 | 1959 | PPPP |
| OM45 (YIL038W) | 51 | P | 51 | M | 383 | P | 171 | P | 7.51 | 3.32 | 5.42 | 226 | |
| ORF YFL030W | 29 | P | 9 | M | 123 | P | 60 | P | 4.24 | 6.38 | 5.31 | 72 | |
| ORF YDR453C | 24 | P | 52 | P | 195 | P | 129 | P | 8.13 | 2.49 | 5.31 | 124 | PPPP |
| ORF YKL221W | 3 | A | 4 | A | 19 | P | 17 | P | 8.33 | 4.26 | 5.29 | 15 | |

Figure 33B

| Gene | WT #1 | No Wt | WT #2 | No Wt | 10-3 #1 | No 10-3 #1 | 10-3 #2 | No 10-3 #2 | MUT #1/ WT #1 | MUT #2/ WT #2 | Average | Ave Diff | PPPP |
|---|---|---|---|---|---|---|---|---|---|---|---|---|---|
| ORF YPL230W | 10 | A | 11 | A | 47 | P | 63 | P | 4.70 | 5.89 | 5.29 | 45 | |
| ORF YPL123C | 5 | A | 20 | A | 39 | P | 56 | P | 7.80 | 2.79 | 5.29 | 35 | |
| ORF YER067W | 56 | P | 14 | P | 171 | P | 100 | P | 3.05 | 7.40 | 5.23 | 101 | PPPP |
| ORF YMR250W | 52 | P | 56 | P | 224 | P | 345 | P | 4.31 | 6.13 | 5.22 | 231 | PPPP |
| ORF YNL195C | 10 | A | 11 | A | 52 | P | 54 | P | 5.20 | 5.08 | 5.14 | 43 | |
| ORF YJL066C | 6 | A | 12 | A | 43 | P | 37 | P | 7.17 | 3.00 | 5.08 | 31 | |
| ORF YNL285W | 1 | A | -2 | A | 18 | A | 17 | P | 18.00 | -7.83 | 5.08 | 18 | |
| ORF YLR416C | 2 | A | 4 | A | 16 | A | 9 | A | 8.00 | 2.13 | 5.08 | 9 | |
| ORF YLR311C | 6 | A | 10 | A | 35 | P | 41 | P | 5.83 | 4.15 | 4.99 | 30 | |
| ORF YIL055C | 4 | A | 15 | A | 25 | P | 53 | P | 6.25 | 3.58 | 4.91 | 30 | |
| ARG1 (YOL058W) | 29 | P | 140 | P | 202 | P | 392 | P | 6.97 | 2.79 | 4.88 | 212 | PPPP |
| ORF YJL150W | 2 | A | 3 | A | 8 | A | 17 | P | 4.00 | 5.67 | 4.84 | 10 | |
| GLC3 (YEL011W) | 28 | P | 28 | P | 139 | P | 130 | P | 4.96 | 4.59 | 4.78 | 106 | PPPP |
| ORF YJL144W | 9 | A | 8 | A | 53 | P | 28 | P | 5.89 | 3.46 | 4.67 | 32 | |
| ORF YMR290W-A | 11 | A | 8 | A | 23 | P | 46 | P | 2.09 | 7.20 | 4.65 | 26 | |
| ORF YKR102W | 3 | A | 19 | P | 15 | P | 79 | P | 5.00 | 4.14 | 4.57 | 36 | |
| SAE2 (YGL175C) | 1 | A | 5 | A | 5 | A | 22 | P | 5.00 | 4.11 | 4.56 | 10 | |
| ORF YLR149C | 6 | A | 37 | P | 42 | P | 78 | P | 7.00 | 2.10 | 4.55 | 38 | |
| ORF YPL281C (_f) | -2 | A | 2 | A | 10 | A | 30 | P | -5.00 | 14.05 | 4.52 | 20 | |
| ORF YLR338W | 2 | A | 9 | A | 12 | A | 27 | P | 6.00 | 2.96 | 4.48 | 14 | |
| HXK1 (YFR053C) | 422 | P | 531 | P | 1916 | P | 2252 | P | 4.54 | 4.24 | 4.39 | 1607 | PPPP |
| ORF YKL151C | 103 | P | 172 | P | 553 | P | 584 | P | 5.37 | 3.40 | 4.38 | 431 | PPPP |
| ORF YGL121C | 56 | P | 43 | P | 359 | P | 91 | P | 6.41 | 2.11 | 4.26 | 176 | PPPP |
| YCRX11w/ (control?) | 1 | A | 5 | A | 6 | A | 12 | P | 6.00 | 2.46 | 4.23 | 6 | |

Figure 33C

| Gene | WT #1 | No Wt | WT #2 | No Wt | 10-3 #1 | No 10-3 #1 | 10-3 #2 | No 10-3 #2 | MUT #1/ WT #1 | MUT #2/ WT #2 | Average | Ave Diff | PPPP |
|---|---|---|---|---|---|---|---|---|---|---|---|---|---|
| ORF YOR378W | 4 | A | 6 | A | 24 | M | 16 | P | 6.00 | 2.43 | 4.22 | 15 | |
| ORF YJL135W | 2 | A | 5 | A | 7 | A | 24 | A | 3.50 | 4.89 | 4.20 | 12 | |
| ORF YOR382W | 117 | P | 482 | P | 560 | P | 1737 | P | 4.79 | 3.60 | 4.20 | 849 | PPPP |
| TFS1 (YLR178C) | 69 | P | 130 | P | 323 | P | 373 | P | 4.88 | 2.87 | 3.78 | 249 | PPPP |
| ISF1 (YMR081C) | 12 | P | 13 | M | 54 | P | 34 | P | 4.91 | 2.62 | 3.76 | 32 | |
| ORF YKL086W | 12 | P | 30 | P | 65 | P | 59 | P | 5.42 | 1.95 | 3.68 | 41 | PPPP |
| GCY1 (YOR120W) | 45 | P | 50 | P | 181 | P | 162 | P | 4.02 | 3.24 | 3.63 | 124 | PPPP |
| ZRT1 (YGL255W) | 189 | P | 386 | P | 1003 | P | 744 | P | 5.31 | 1.93 | 3.62 | 586 | PPPP |
| ORF YFR046C | 4 | A | 8 | A | 16 | A | 25 | P | 4.00 | 3.13 | 3.57 | 15 | |
| ORF YAL045C | 6 | A | 5 | A | 14 | A | 24 | A | 2.33 | 4.77 | 3.55 | 13 | |
| LAP4 (YKL103C) | 23 | P | 56 | P | 112 | P | 121 | P | 4.87 | 2.17 | 3.52 | 77 | PPPP |
| TPS2 (YDR074W) | 53 | P | 130 | P | 215 | P | 386 | P | 4.06 | 2.97 | 3.51 | 209 | PPPP |
| MET28 (YIR017C) | 7 | A | 5 | A | 19 | P | 23 | P | 2.71 | 4.26 | 3.49 | 15 | |
| ORF YNL171C | 8 | A | 13 | A | 27 | A | 23 | P | 4.50 | 2.40 | 3.45 | 17 | |
| BUB1 (YGR188C) | 4 | A | 3 | A | 11 | A | 11 | A | 2.75 | 4.11 | 3.43 | 8 | |
| GPM2 (YDL021W) | 10 | P | 22 | P | 43 | P | 52 | P | 4.30 | 2.38 | 3.34 | 32 | PPPP |
| ORF YFR017C | 22 | P | 36 | P | 99 | P | 79 | P | 4.50 | 2.18 | 3.34 | 60 | PPPP |
| GSC2 (YGR032W) | 60 | P | 211 | P | 236 | P | 568 | P | 3.93 | 2.70 | 3.31 | 267 | PPPP |
| ORF YLR161W (_f) | 9 | A | 31 | P | 30 | P | 101 | P | 3.33 | 3.26 | 3.30 | 46 | |
| ORF YOR384W | 5 | A | 14 | P | 19 | A | 38 | P | 3.80 | 2.74 | 3.27 | 19 | |
| ORF YPR151C | 4 | A | 5 | A | 10 | A | 32 | A | 2.50 | 4.00 | 3.25 | 11 | |
| GSY1 (YFR015C) | 20 | P | 19 | P | 61 | P | 63 | P | 3.05 | 3.36 | 3.20 | 43 | PPPP |
| ORF YMR196W | 10 | A | 36 | P | 42 | P | 77 | P | 4.20 | 2.13 | 3.16 | 36 | |
| ORF YJL218W | 67 | P | 52 | P | 214 | P | 163 | P | 3.19 | 3.13 | 3.16 | 129 | PPPP |

Figure 33D

| Gene | WT #1 | No Wt | WT #2 | No Wt | 10-3 #1 | No 10-3 #1 | 10-3 #2 | No 10-3 #2 | MUT #1/ WT #1 | MUT #2/ WT #2 | Average | Ave Diff | PPPP |
|---|---|---|---|---|---|---|---|---|---|---|---|---|---|
| ORF YLR312C | 14 | P | 12 | A | 35 | P | 46 | P | 2.50 | 3.81 | 3.16 | 27 | |
| ORF YER037W | 39 | P | 46 | P | 111 | P | 156 | P | 2.85 | 3.40 | 3.12 | 91 | PPPP |
| CIT3 (YPR001W) | 11 | A | 6 | A | 23 | P | 26 | P | 2.09 | 4.05 | 3.07 | 16 | |
| ORF YOR193W | 7 | A | 20 | P | 21 | A | 63 | P | 3.00 | 3.13 | 3.06 | 29 | |
| PCK1 (YKR097W) | 14 | M | 23 | P | 54 | P | 51 | P | 3.86 | 2.22 | 3.04 | 34 | |
| ORF YLR343W | 4 | A | 20 | P | 16 | P | 41 | P | 4.00 | 2.07 | 3.04 | 17 | |
| ORF YPL186C | 18 | P | 18 | M | 60 | P | 18 | P | 3.33 | 2.87 | 3.00 | 36 | |
| ORF YIL087C | 28 | P | 36 | A | 84 | P | 109 | P | 3.00 | 2.98 | 2.99 | 64 | |
| ORF YDL196W | 2 | A | 8 | A | 5 | A | 21 | A | 2.50 | 3.46 | 2.98 | 9 | |
| HOR2 (YER062C) | 224 | P | 332 | P | 695 | P | 928 | P | 3.10 | 2.79 | 2.95 | 533 | PPPP |
| YFL-TyB/_f (control?) | 49 | P | 219 | P | 153 | P | 606 | P | 3.12 | 2.77 | 2.95 | 246 | PPPP |
| ORF YGR146C | 103 | P | 272 | P | 387 | P | 575 | P | 3.76 | 2.12 | 2.94 | 293 | PPPP |
| ORF YLR237W | 78 | P | 150 | P | 276 | P | 330 | P | 3.54 | 2.20 | 2.87 | 189 | PPPP |
| ORF YMR090W | 114 | P | 179 | P | 330 | P | 505 | P | 2.89 | 2.82 | 2.86 | 271 | PPPP |
| ORF YGL240W | 8 | A | 3 | A | 13 | A | 10 | M | 2.17 | 3.52 | 2.85 | 7 | |
| ORF YGL075C | 9 | A | 12 | A | 21 | P | 40 | P | 2.33 | 3.33 | 2.83 | 20 | |
| GLK1 (YCL040W) | 422 | P | 551 | P | 1230 | P | 1448 | P | 2.91 | 2.63 | 2.77 | 852 | PPPP |
| MCR1 (YKL150W) | 204 | P | 279 | P | 628 | P | 650 | P | 3.08 | 2.33 | 2.70 | 398 | PPPP |
| ORF YBL043W | 34 | P | 60 | P | 86 | P | 168 | P | 2.53 | 2.79 | 2.66 | 80 | PPPP |
| ORF YKL210C | 33 | P | 78 | P | 93 | P | 194 | P | 2.82 | 2.48 | 2.65 | 88 | PPPP |
| ADR1 (YDR216W) | 14 | P | 45 | P | 33 | P | 130 | P | 2.36 | 2.89 | 2.62 | 52 | PPPP |
| ORF YLR041W | 3 | P | 10 | A | 9 | A | 22 | P | 3.00 | 2.23 | 2.62 | 9 | |
| PB12 (YNL015W) | 362 | P | 515 | P | 1097 | P | 1124 | P | 3.03 | 2.18 | 2.61 | 672 | PPPP |
| ORF YMR040W | 44 | P | 48 | P | 134 | P | 98 | P | 3.05 | 2.13 | 2.59 | 71 | PPPP |

Figure 33E

| Gene | WT #1 | No Wt | WT #2 | No Wt | 10-3 #1 | No 10-3 #1 | 10-3 #2 | No 10-3 #2 | MUT #1/ WT #1 | MUT #2/ WT #2 | Average | Ave Diff | PPPP |
|---|---|---|---|---|---|---|---|---|---|---|---|---|---|
| HXT/ (YDR342C) (_f) | 1221 | P | 1268 | P | 2606 | P | 3852 | P | 2.13 | 3.04 | 2.59 | 1985 | PPPP |
| YCLX09w/ (control?) | 3 | A | 4 | A | 9 | A | 8 | M | 3.00 | 2.12 | 2.56 | 5 | PPPP |
| AST2 (YER101C) | 6 | A | 12 | A | 15 | A | 32 | P | 2.50 | 2.61 | 2.56 | 14 | |
| ENO1 (YGR254W) | 1660 | P | 3024 | P | 4724 | P | 8843 | P | 2.85 | 2.26 | 2.55 | 3441 | PPPP |
| ORF YJR079W exon | 2 | A | 5 | A | 5 | A | 13 | P | 2.50 | 2.55 | 2.53 | 5 | |
| ORF YNL234W | 25 | P | 84 | P | 89 | P | 190 | P | 2.76 | 2.26 | 2.51 | 75 | PPPP |
| STF2 (YGR008C) | 799 | P | 828 | P | 1964 | P | 1582 | P | 2.46 | 2.53 | 2.49 | 1061 | PPPP |
| ORF YBL048W | 21 | P | 28 | P | 80 | P | 55 | P | 2.86 | 2.10 | 2.48 | 34 | PPPP |
| ORF YMR050C exon | 150 | P | 1492 | P | 424 | P | 3168 | P | 2.83 | 2.12 | 2.48 | 975 | PPPP |
| ORF YOR289W | 36 | P | 85 | P | 87 | P | 162 | P | 2.42 | 2.50 | 2.48 | 74 | PPPP |
| ORF YJL160C | 4 | A | 8 | A | 11 | A | 17 | A | 2.75 | 2.13 | 2.44 | 8 | |
| ORF YMR265C | 7 | A | 29 | P | 19 | A | 61 | P | 2.71 | 2.14 | 2.43 | 22 | |
| ORF YIR038C | 173 | P | 286 | P | 467 | P | 562 | P | 2.70 | 2.11 | 2.41 | 295 | PPPP |
| YRO2 (YBR054W) | 391 | P | 642 | P | 960 | P | 1508 | P | 2.48 | 2.35 | 2.40 | 717 | PPPP |

Figure 33F

| SW12 2X Up both or more than 10 if around 0 | | | | | | | | | | | Fold up | | | |
|---|---|---|---|---|---|---|---|---|---|---|---|---|---|---|
| Gene | w1 | w1c | w2 | w2c | m1 | m1c | m2 | m2c | MUT#1/WT | MUT#2/WT | Average | UP both | Ave diff | PPPP |
| ORF YER081W | 101 | P | 116 | P | 3357 | P | 3254 | P | 33.39 | 28.09 | 30.74 | LP | 31.97 | PPPP |
| ORF YLR311C | 1 | A | 1 | A | 14 | A | 29 | P | 30.57 | 34.63 | 27.60 | LP | 21 | PPPP |
| ORF YMR017W | 7 | A | 1 | A | 38 | P | 26 | P | 5.40 | 30.55 | 17.98 | LP | 28 | |
| ORF YHL024W | 28 | P | 4 | P | 70 | P | 91 | P | 2.54 | 23.93 | 13.23 | LP | 65 | PPPP |
| ORF YGR243W | 15 | A | 50 | A | 274 | P | 204 | P | 18.21 | 4.04 | 11.13 | LP | 206 | |
| ORF YGR161C | 59 | P | 55 | P | 698 | P | 545 | P | 11.93 | 9.90 | 10.91 | LP | 565 | PPPP |
| ORF YPP077C (_l) | 2 | A | 10 | A | 41 | M | 26 | P | 17.41 | 2.71 | 10.06 | LP | 27 | |
| GAL3 (YDR009W) | 12 | A | 1 | A | 24 | A | 13 | P | 2.02 | 17.44 | 9.73 | LP | 12 | |
| ORF YLR312C | 5 | A | 13 | A | 57 | A | 77 | P | 11.57 | 6.11 | 8.84 | LP | 58 | |
| SPC11 (YHL022C) | 6 | A | 1 | A | 26 | P | 11 | A | 4.75 | 11.86 | 8.31 | LP | 16 | |
| ORF YGR050C | 58 | P | 12 | A | 164 | P | 168 | P | 2.93 | 13.62 | 8.27 | LP | 132 | |
| URA3 (YEL021W) | 1051 | P | 678 | P | 7170 | P | 6216 | P | 8.82 | 9.17 | 8.00 | LP | 5829 | PPPP |
| ORF YJR079W exon | 43 | P | 30 | P | 302 | P | 244 | P | 7.06 | 8.06 | 7.56 | LP | 236 | PPPP |
| ORF YGL184C | 20 | P | 11 | P | 99 | P | 114 | P | 5.00 | 10.03 | 7.51 | LP | 91 | |
| ORF YER039C | 17 | A | 4 | A | 49 | A | 35 | P | 2.98 | 9.32 | 6.15 | LP | 32 | |
| HXT3 (YHRC96C) | 21 | M | 16 | A | 138 | P | 89 | P | 6.71 | 5.53 | 6.12 | LP | 95 | |
| MEI4 (YER044C-A 8 | 8 | A | 1 | A | 21 | A | 9 | P | 2.82 | 9.32 | 5.97 | LP | 10 | PPPP |
| ORF YGR142W | 58 | P | 43 | P | 339 | P | 249 | P | 5.87 | 5.82 | 5.84 | LP | 244 | |
| BAR1 (YIL015W) | 12 | A | 3 | A | 31 | P | 26 | P | 2.62 | 9.04 | 5.83 | LP | 21 | PPPP |
| AMS1 (YGL156W) | 43 | P | 39 | P | 263 | P | 195 | P | 6.14 | 5.02 | 5.58 | LP | 188 | PPPP |
| ORF YLR327C | 68 | P | 27 | P | 196 | P | 221 | P | 2.89 | 8.24 | 5.57 | LP | 161 | PPPP |
| ORF YPR151C | 63 | P | 18 | A | 126 | P | 136 | P | 2.01 | 8.79 | 5.40 | LP | 92 | |

Figure 34A

| Gene | w1 | w1c | w2 | w2c | m1 | m1c | m2 | m2c | MUT#1/WT | MUT#2/WT | Average | UP both | Ave diff | PPPP |
|---|---|---|---|---|---|---|---|---|---|---|---|---|---|---|
| GPM2 (YDL021W) | 15 | A | 6 | A | 51 | A | 44 | P | 3.42 | 7.38 | 5.40 | LP | 37 | |
| ORF YJL107C | 16 | A | 20 | P | 98 | P | 91 | P | 6.09 | 4.50 | 5.30 | LP | 76 | |
| ORF YPR130C | 18 | P | 2 | A | 37 | A | 16 | P | 2.37 | 8.12 | 5.25 | LP | 18 | |
| AAC1 (YMR056C) | 96 | A | 70 | P | 375 | P | 437 | P | 3.91 | 6.27 | 5.09 | LP | 323 | PPPP |
| ORF YLR415C | 8 | A | 5 | A | 44 | A | 21 | A | 5.73 | 4.24 | 4.99 | LP | 26 | |
| LAP4 (YKL103C) | 99 | P | 70 | P | 321 | P | 438 | P | 3.23 | 6.29 | 4.76 | LP | 295 | PPPP |
| ORF YBL078C | 91 | P | 83 | P | 468 | P | 357 | P | 5.14 | 4.30 | 4.72 | LP | 325 | PPPP |
| ORF YAR068W (_f) | 36 | P | 48 | P | 198 | P | 183 | P | 5.51 | 3.84 | 4.67 | LP | 149 | PPPP |
| SIP4 (YJL089W) | 13 | A | 1 | A | 50 | A | 4 | A | 4.00 | 5.09 | 4.55 | LP | 21 | |
| ORF YDL057W | 32 | P | 13 | P | 76 | P | 85 | P | 2.36 | 6.71 | 4.53 | LP | 58 | |
| ORF YMR040W | 36 | P | 18 | P | 111 | P | 108 | P | 3.10 | 5.83 | 4.47 | LP | 82 | PPPP |
| MET8 (YBR213W) | 39 | P | 15 | A | 96 | P | 93 | P | 2.46 | 8.24 | 4.35 | LP | 68 | |
| ORF TJR106W | 21 | P | 6 | A | 43 | P | 38 | P | 2.06 | 6.55 | 4.30 | LP | 27 | |
| ORF YOR318C exon | 12 | P | 18 | P | 58 | P | 66 | P | 4.98 | 3.59 | 4.29 | LP | 47 | |
| UBC5 (YDR059C) exon | 86 | P | 31 | P | 194 | P | 185 | P | 2.25 | 6.05 | 4.15 | LP | 131 | PPPP |
| ORF TDL214C | 25 | A | 16 | A | 91 | A | 73 | P | 3.64 | 4.66 | 4.15 | LP | 62 | |
| CAT8 (YMR280C) | 17 | A | 9 | A | 75 | P | 34 | P | 4.37 | 3.85 | 4.11 | LP | 41 | |
| ORF YGR110W | 60 | P | 41 | P | 218 | P | 182 | P | 3.62 | 4.45 | 4.04 | LP | 149 | PPPP |
| ORF YNL092W | 8 | A | 16 | A | 45 | P | 35 | P | 5.81 | 2.23 | 4.02 | LP | 28 | |
| ORF YER096W | 4 | A | 4 | A | 18 | A | 13 | P | 4.64 | 3.39 | 4.01 | LP | 12 | |
| GUT2 (YIL155C) | 97 | P | 60 | P | 256 | P | 322 | P | 2.63 | 5.38 | 4.01 | LP | 210 | PPPP |
| ORF YNL336W (_f) | 24 | P | 37 | P | 132 | P | 93 | P | 5.47 | 2.54 | 4.00 | LP | 82 | PPPP |
| HSP26 (YBR072W) | 33 | P | 38 | P | 169 | P | 109 | P | 5.13 | 2.87 | 4.00 | LP | 104 | PPPP |
| ORF YGL125W | 66 | P | 90 | P | 297 | P | 302 | P | 4.52 | 3.35 | 3.94 | LP | 222 | PPPP |

Figure 34B

| Gene | w1 | w1c | w2 | w2c | m1 | m1c | m2 | m2c | MUT#1/WT | MUT#2/WT | Average | UP both | Ave diff | PPPP |
|---|---|---|---|---|---|---|---|---|---|---|---|---|---|---|
| ORF YGR052W | 18 | A | 15 | P | 73 | P | 57 | P | 3.99 | 3.78 | 3.88 | LP | 48 | PPPP |
| ORF YKL151C | 290 | P | 177 | P | 984 | P | 755 | P | 3.39 | 4.27 | 3.83 | LP | 636 | PPPP |
| SEO1 (YAL067C) | 12 | P | 7 | M | 47 | P | 27 | P | 3.95 | 3.62 | 3.79 | LP | 28 | |
| SOL4 (YGR248W) | 62 | P | 25 | P | 125 | P | 135 | P | 2.03 | 5.47 | 3.75 | LP | 87 | PPPP |
| ORF YBR070C | 119 | P | 124 | P | 474 | P | 427 | P | 3.99 | 3.44 | 3.71 | LP | 329 | PPPP |
| ORF YJR078W | 45 | P | 25 | P | 142 | P | 106 | P | 3.17 | 4.21 | 3.69 | LP | 89 | PPPP |
| HSP42 (YDR171W) | 241 | P | 164 | P | 808 | P | 660 | P | 3.36 | 4.02 | 3.68 | LP | 531 | PPPP |
| ORF YPL222W | 29 | P | 39 | P | 115 | P | 129 | P | 4.01 | 3.33 | 3.87 | LP | 88 | PPPP |
| ORF YFL030W | 25 | A | 28 | A | 83 | P | 113 | P | 3.38 | 3.95 | 3.67 | LP | 71 | |
| ORF YIL073C | 17 | P | 10 | A | 55 | P | 43 | P | 3.16 | 4.18 | 3.66 | LP | 35 | |
| THI5 (YFL058W) (_f) | 43 | P | 62 | P | 206 | P | 154 | P | 4.82 | 2.50 | 3.66 | LP | 128 | PPPP |
| ORF YDL199C | 4 | A | 9 | A | 15 | A | 33 | P | 3.36 | 3.69 | 3.66 | LP | 17 | |
| ORF YBR089W | 3 | A | 3 | A | 10 | A | 12 | P | 3.23 | 4.02 | 3.63 | LP | 8 | |
| GDH3 (YAL062W) | 22 | P | 23 | P | 89 | P | 73 | P | 4.05 | 3.16 | 3.60 | LP | 59 | PPPP |
| ORF YML068C | 1 | A | 2 | A | 7 | A | 3 | A | 5.14 | 2.04 | 3.59 | LP | 4 | |
| ORFYHR138C | 192 | P | 178 | P | 726 | P | 585 | P | 3.78 | 3.29 | 3.54 | LP | 471 | PPPP |
| ORF YOR220W | 148 | P | 90 | P | 455 | P | 351 | P | 3.07 | 3.90 | 3.48 | LP | 284 | PPPP |
| ORF YOL050C | 7 | P | 5 | A | 29 | A | 14 | P | 4.09 | 2.81 | 3.45 | LP | 15 | |
| ORF YOR227W | 117 | P | 58 | P | 276 | P | 260 | P | 2.36 | 4.47 | 3.42 | LP | 181 | PPPP |
| ORF YKR048C | 740 | P | 479 | P | 2030 | P | 1958 | P | 2.74 | 4.08 | 3.41 | LP | 1383 | PPPP |
| ORF YMR244C-A | 157 | P | 115 | P | 435 | P | 466 | P | 2.77 | 4.04 | 3.41 | LP | 3.14 | PPPP |
| ARG5,6 (YER069W) | 404 | P | 327 | P | 1226 | P | 1224 | P | 3.03 | 3.75 | 3.39 | LP | 860 | PPPP |
| ORF YMP034C | 44 | P | 22 | P | 108 | P | 94 | P | 2.45 | 4.31 | 3.38 | LP | 68 | PPPP |
| ORF YHR214W-A (_f) | 82 | P | 90 | P | 279 | P | 301 | P | 3.39 | 3.34 | 3.36 | LP | 204 | PPPP |

Figure 34C

| Gene | w1 | w1c | w2 | w2c | m1 | m1c | m2 | m2c | MUT#1/WT | MUT#2/WT | Average | UP both | Ave diff | PPPP |
|---|---|---|---|---|---|---|---|---|---|---|---|---|---|---|
| ORF YDR070C | 17 | A | 8 | A | 46 | A | 33 | P | 2.68 | 4.02 | 3.35 | UP | 27 | |
| ORF YCL041C | 12 | A | 17 | P | 45 | A | 51 | P | 3.71 | 2.97 | 3.34 | UP | 33 | |
| ORF YOR177C | 9 | A | 6 | A | 39 | A | 15 | P | 4.15 | 2.53 | 3.34 | UP | 19 | |
| ORF YAL037W | 22 | P | 28 | P | 95 | P | 65 | P | 4.31 | 2.36 | 3.33 | UP | 55 | PPPP |
| ORF YER042W | 512 | P | 377 | P | 1624 | P | 1317 | P | 3.17 | 3.49 | 3.33 | UP | 1026 | PPPP |
| ORF YNL332W (_f) | 64 | P | 42 | P | 219 | P | 129 | P | 3.44 | 3.10 | 3.27 | UP | 121 | PPPP |
| ORF YDR111C | 84 | P | 56 | P | 227 | P | 214 | P | 2.70 | 2.83 | 3.26 | UP | 150 | PPPP |
| ORF YOR289W | 122 | P | 78 | P | 400 | P | 240 | P | 3.28 | 3.06 | 3.17 | UP | 220 | PPPP |
| ORF YLR414C | 293 | P | 256 | P | 942 | P | 789 | P | 3.22 | 3.08 | 3.15 | UP | 591 | PPPP |
| ORF YPL250C | 224 | P | 172 | P | 607 | P | 612 | P | 2.71 | 3.55 | 3.13 | UP | 411 | PPPP |
| MET2 (YNL277W) | 154 | P | 82 | P | 340 | P | 333 | P | 2.20 | 4.04 | 3.12 | UP | 218 | PPPP |
| ORF YHR112C | 154 | P | 167 | P | 403 | P | 802 | P | 2.63 | 3.60 | 3.11 | UP | 342 | PPPP |
| ORF YEL044W | 415 | P | 292 | P | 1111 | P | 1022 | P | 2.68 | 3.49 | 3.09 | UP | 713 | PPPP |
| ARE2 (YNR019W) | 242 | P | 157 | P | 852 | P | 542 | P | 2.69 | 3.45 | 3.07 | UP | 398 | PPPP |
| ORF YBR005W | 56 | P | 63 | P | 223 | P | 135 | P | 3.98 | 2.13 | 3.05 | UP | 119 | PPPP |
| ORF YBR269C | 160 | P | 102 | P | 406 | P | 364 | P | 2.54 | 3.55 | 3.04 | UP | 253 | PPPP |
| ORF YMR316W | 91 | P | 58 | P | 258 | P | 189 | P | 2.84 | 3.25 | 3.04 | UP | 149 | PPPP |
| ORF YJL163C | 34 | P | 15 | M | 72 | A | 58 | P | 2.10 | 3.85 | 2.87 | UP | 40 | |
| REC102 (YLR329W) | 15 | M | 7 | A | 53 | P | 16 | P | 3.45 | 2.42 | 2.93 | UP | 24 | |
| SIP2 (YGL208W) | 42 | P | 28 | P | 92 | P | 104 | P | 2.19 | 3.64 | 2.92 | UP | 63 | PPPP |
| ORF YHR173C | 6 | A | 5 | A | 21 | A | 12 | A | 3.28 | 2.54 | 2.91 | UP | 11 | |
| SNF2 (YOR290C) | 251 | P | 198 | P | 642 | P | 643 | P | 2.55 | 3.25 | 2.90 | UP | 418 | PPPP |
| ORF YJL108C | 87 | P | 95 | P | 279 | P | 244 | P | 3.21 | 2.58 | 2.90 | UP | 171 | PPPP |
| ORF YPR013C | 26 | P | 33 | A | 75 | P | 97 | P | 2.83 | 2.93 | 2.88 | UP | 56 | |
| ORF YIL055C | 28 | P | 22 | M | 61 | P | 76 | P | 2.22 | 3.46 | 2.84 | UP | 44 | |

Figure 34D

| Gene | w1 | w1c | w2 | w2c | m1 | m1c | m2 | m2c | MUT#1/WT | MUT#2/WT | Average | UP both | Ave diff | PPPP |
|---|---|---|---|---|---|---|---|---|---|---|---|---|---|---|
| FUS1 (YCL027W) | 67 | P | 92 | P | 228 | P | 209 | P | 3.40 | 2.28 | 2.84 | LP | 139 | PPPP |
| ORF YOR222W | 410 | P | 243 | P | 888 | P | 853 | P | 2.17 | 3.51 | 2.84 | LP | 544 | PPPP |
| ORF YIL117C | 214 | P | 205 | P | 552 | P | 629 | P | 2.58 | 3.07 | 2.82 | LP | 381 | PPPP |
| SHR5 (YOL110W) | 92 | P | 92 | P | 258 | P | 262 | P | 2.79 | 2.85 | 2.82 | LP | 168 | PPPP |
| ORF YJL066C | 14 | M | 34 | P | 47 | A | 78 | P | 3.31 | 2.28 | 2.79 | LP | 38 | |
| ORF YIL015C-A | 75 | P | 82 | P | 162 | P | 211 | P | 2.16 | 3.41 | 2.79 | LP | 118 | PPPP |
| TSL1 (YML100W) | 329 | P | 252 | P | 763 | P | 819 | P | 2.32 | 3.25 | 2.78 | LP | 500 | PPPP |
| ORF YGR043C | 32 | A | 39 | P | 109 | P | 81 | P | 3.45 | 2.09 | 2.77 | LP | 60 | |
| ORF YMR191W | 137 | P | 96 | P | 336 | P | 295 | P | 2.45 | 3.06 | 2.75 | LP | 198 | PPPP |
| ORF YKL107W | 11 | P | 9 | A | 32 | P | 23 | P | 3.00 | 2.50 | 2.75 | LP | 17 | |
| UBC5 (YDR059C) exon | 140 | P | 108 | P | 353 | P | 319 | P | 2.52 | 2.96 | 2.74 | LP | 212 | PPPP |
| ORF YLR417W | 94 | P | 81 | P | 258 | P | 218 | P | 2.72 | 2.71 | 2.72 | LP | 150 | PPPP |
| ORF YBR066C | 69 | P | 81 | P | 230 | P | 168 | P | 3.34 | 2.09 | 2.71 | LP | 125 | PPPP |
| GLK1 (YCL040W) | 1172 | P | 802 | P | 2615 | P | 2523 | P | 2.23 | 3.15 | 2.69 | LP | 1582 | PPPP |
| ORF YBR077C | 140 | P | 134 | P | 395 | P | 343 | P | 2.82 | 2.55 | 2.69 | LP | 232 | PPPP |
| ORF YCL075W | 12 | A | 5 | A | 32 | A | 14 | A | 2.66 | 2.68 | 2.67 | LP | 14 | |
| ATF1 (YOR377W) | 67 | P | 57 | P | 168 | P | 160 | P | 2.48 | 2.81 | 2.64 | LP | 102 | PPPP |
| YAP3 (YLR120C) | 267 | P | 250 | P | 783 | P | 586 | P | 2.94 | 2.34 | 2.64 | LP | 426 | PPPP |
| ORF YOL101C | 135 | P | 103 | P | 357 | P | 269 | P | 2.65 | 2.51 | 2.63 | LP | 194 | PPPP |
| THI11 (YJR158C) (_f) | 95 | P | 60 | P | 247 | P | 160 | P | 2.59 | 2.65 | 2.62 | LP | 125 | PPPP |
| HSP78 (YDR258C) | 167 | P | 119 | P | 354 | P | 370 | P | 2.12 | 3.11 | 2.62 | LP | 219 | PPPP |
| PRB1 (YEL060C) | 338 | P | 234 | P | 779 | P | 682 | P | 2.31 | 2.92 | 2.61 | LP | 445 | PPPP |
| SSE2 (YBR169C) | 103 | P | 70 | P | 256 | P | 192 | P | 2.48 | 2.74 | 2.51 | LP | 137 | PPPP |
| UB14 (YLL039C) | 737 | P | 619 | P | 1760 | P | 1753 | P | 2.39 | 2.83 | 2.61 | LP | 1079 | PPPP |
| ORF YDL110C | 171 | P | 125 | P | 381 | P | 373 | P | 2.23 | 2.97 | 2.60 | LP | 228 | PPPP |

Figure 34E

| Gene | w1 | w1c | w2 | w2c | m1 | m1c | m2 | m2c | MUT#1/WT | MUT#2/WT | Average | UP both | Ave diff | PPPP |
|---|---|---|---|---|---|---|---|---|---|---|---|---|---|---|
| ORF YIL050W | 128 | P | 123 | P | 330 | P | 323 | P | 2.58 | 2.61 | 2.60 | LP | 201 | PPPP |
| ORF YLR231C | 268 | P | 185 | P | 593 | P | 538 | P | 2.21 | 2.90 | 2.56 | LP | 339 | PPPP |
| ORF YLL061W | 166 | P | 122 | P | 346 | P | 367 | P | 2.08 | 3.02 | 2.55 | LP | 213 | PPPP |
| MRS4 (YKR052C) | 108 | P | 105 | P | 250 | P | 289 | P | 2.32 | 2.75 | 2.54 | LP | 163 | PPPP |
| ORF YBR302C (_f) | 417 | P | 441 | P | 1220 | P | 933 | P | 2.93 | 2.12 | 2.52 | LP | 648 | PPPP |
| FUN34 (YNR002C) | 36 | P | 21 | A | 85 | P | 57 | P | 2.37 | 2.66 | 2.52 | LP | 42 | |
| POS5 (YPL188W) | 118 | P | 90 | P | 258 | P | 253 | P | 2.19 | 2.81 | 2.50 | LP | 151 | PPPP |
| SNC1 (YAL030W) exon | 116 | P | 128 | P | 339 | P | 264 | P | 2.92 | 2.06 | 2.49 | LP | 179 | PPPP |
| ORF YLR154C | 168 | P | 147 | P | 396 | P | 384 | P | 2.36 | 2.62 | 2.49 | LP | 233 | PPPP |
| ORF YKL208W | 36 | P | 40 | P | 92 | P | 97 | P | 2.57 | 2.40 | 2.48 | LP | 56 | PPPP |
| ORF YMR184W | 261 | P | 248 | P | 664 | P | 596 | P | 2.55 | 2.40 | 2.47 | LP | 376 | PPPP |
| ORF YEL066W | 153 | P | 124 | P | 318 | P | 352 | P | 2.08 | 2.83 | 2.46 | LP | 196 | PPPP |
| STF2 (YGR008C) | 734 | P | 648 | P | 1933 | P | 1475 | P | 2.63 | 2.28 | 2.46 | LP | 1013 | PPPP |

SW12 LIST 2x DOWN BOTH OR BY 10 IN BOTH IF AROUND DOWN 0

| Gene | w1 | w1c | w2 | w2c | m1 | m1c | m2 | m2c | MUT #1/WT | MUT #2/WT | Average | Fold down | Ave diff | PPPP |
|---|---|---|---|---|---|---|---|---|---|---|---|---|---|---|
| PHO84 (YML123C) | 4124 | P | 3904 | P | 153 | A | 105 | P | 0.04 | 0.03 | 0.03 | 31.23 | -3885 | |
| ORF YMR045C exon | 330 | P | 273 | P | 12 | A | 39 | P | 0.04 | 0.14 | 0.09 | 11.6 | -276 | |
| ORF YBL005W-B exon | 241 | P | 222 | P | 21 | P | 21 | P | 0.09 | 0.09 | 0.09 | 10.92 | -210 | PPPP |
| AIF2 (YGR177C) | 105 | P | 92 | P | 4 | A | 16 | A | 0.04 | 0.17 | 0.11 | 9041 | -89 | |
| ORF YMR046C (_f) | 319 | P | 269 | P | 24 | P | 38 | P | 0.08 | 0.14 | 0.11 | 9.13 | -263 | PPPP |
| ORF YOR032C | 24 | P | 25 | P | 6 | A | 0 | A | 0.23 | 0.00 | 0.11 | 8.71 | -22 | |
| PTR2 (YKR093W) | 474 | P | 451 | P | 79 | P | 45 | P | 0.17 | 0.10 | 0.13 | 7.48 | -400 | PPPP |
| ORF YLR413W | 1103 | P | 1114 | P | 167 | P | 139 | P | 0.15 | 0.13 | 0.14 | 7.25 | -9.6 | PPPP |
| ORF YKL225W | 309 | P | 96 | P | 32 | A | 17 | P | 0.10 | 0.18 | 0.14 | 7.12 | -178 | |
| ORF YBR244W | 377 | P | 351 | P | 33 | A | 70 | P | 0.09 | 0.20 | 0.14 | 5.97 | -312 | |
| ORF YMR029W exon | 4584 | P | 4023 | P | 586 | P | 646 | P | 0.13 | 0.16 | 0.14 | 6.93 | -3687 | PPPP |
| ORF YBR012W-B exon | 4536 | P | 3715 | P | 623 | P | 568 | P | 0.14 | 0.15 | 0.14 | 6.91 | -3531 | PPPP |
| ORF YBR012W-A (_f) | 4648 | P | 3799 | P | 657 | P | 567 | P | 0.14 | 0.15 | 0.15 | 6.88 | -3611 | PPPP |
| PHO3 (YBR092C) | 743 | P | 682 | P | 104 | P | 108 | P | 0.14 | 0.16 | 0.15 | 6.71 | -606 | PPPP |
| ORF YJR026W (_f) | 3896 | P | 3363 | P | 573 | P | 521 | P | 0.15 | 0.15 | 0.15 | 6.62 | -3083 | PPPP |
| ORF YJR027W exon | 4162 | P | 3810 | P | 625 | P | 583 | P | 0.15 | 0.15 | 0.15 | 6.60 | -3383 | PPPP |
| ORF YMR050C exon | 4177 | P | 3818 | P | 566 | P | 627 | P | 0.14 | 0.17 | 0.15 | 6.47 | -3301 | PPPP |
| ORF YMR051C (_f) | 4090 | P | 3278 | P | 598 | P | 561 | P | 0.15 | 0.17 | 0.16 | 6.30 | -3104 | PPPP |
| ORF YER138C exon | 4480 | P | 4350 | P | 690 | P | 719 | P | 0.15 | 0.17 | 0.18 | 6.28 | -3711 | PPPP |
| ORF YER160C exon | 4765 | P | 4095 | P | 791 | P | 653 | P | 0.17 | 0.16 | 0.16 | 6.14 | -3708 | PPPP |
| ORF YML045W exon | 4716 | P | 4383 | P | 777 | P | 712 | P | 0.16 | 0.16 | 0.16 | 6.11 | -3805 | PPPP |
| ORF YJR028W (_f) | 4663 | P | 3852 | P | 740 | P | 853 | P | 0.18 | 0.17 | 0.16 | 6.09 | -3561 | PPPP |

| Gene | w1 | w1c | w2 | w2c | m1 | m1c | m2 | m2c | MUT #1/WT | MUT #2/WT | Average | Fold down | Ave diff | PPPP |
|---|---|---|---|---|---|---|---|---|---|---|---|---|---|---|
| ORF YML040W (_f) | 3856 | P | 3513 | P | 622 | P | 590 | P | 0.16 | 0.17 | 0.16 | 6.08 | -3079 | PPPP |
| ORF YJR029W exon | 4744 | P | 3670 | P | 715 | P | 659 | P | 0.15 | 0.18 | 0.17 | 6.08 | -3520 | PPPP |
| ORF YAR010C (_f) | 3879 | P | 3585 | P | 686 | P | 594 | P | 0.18 | 0.17 | 0.17 | 5.84 | -3092 | PPPP |
| YGP1 (YNL180W) | 2359 | P | 1237 | P | 365 | P | 243 | P | 0.15 | 0.20 | 0.18 | 5.69 | -1494 | PPPP |
| ORF YHR214C-B exon | 4996 | P | 5015 | P | 853 | P | 924 | P | 0.17 | 0.18 | 0.18 | 5.84 | -4117 | PPPP |
| ORF YGL028C | 914 | P | 953 | P | 157 | P | 178 | P | 0.17 | 0.19 | 0.18 | 5.58 | -766 | PPPP |
| ORF YOR315W | 136 | P | 150 | P | 16 | A | 37 | P | 0.12 | 0.24 | 0.18 | 5.56 | -117 | |
| ORF YDL038C | 520 | P | 616 | P | 104 | P | 102 | P | 0.20 | 0.17 | 0.18 | 5.48 | -465 | PPPP |
| ORF YBL005W-A (_f) | 200 | P | 223 | P | 40 | P | 38 | P | 0.20 | 0.17 | 0.18 | 5.42 | -173 | PPPP |
| PHO12 (YHR215W) | 381 | P | 550 | P | 90 | P | 75 | P | 0.24 | 0.14 | 0.19 | 5.36 | -383 | PPPP |
| ORF YNR067C | 730 | P | 455 | P | 116 | P | 101 | P | 0.18 | 0.22 | 0.19 | 5.26 | -484 | PPPP |
| ORF YAL028W | 30 | A | 35 | P | 12 | A | 1 | A | 0.39 | 0.03 | 0.21 | 4.81 | -26 | |
| YRO2 (YBR054W) | 396 | P | 313 | P | 88 | P | 62 | P | 0.22 | 0.20 | 0.21 | 4.75 | -279 | PPPP |
| ORF YDR033W | 4437 | P | 3476 | P | 678 | P | 962 | P | 0.15 | 0.28 | 0.21 | 4.66 | -3137 | PPPP |
| ORF YER124C | 432 | P | 317 | P | 78 | P | 80 | P | 0.18 | 0.25 | 0.22 | 4.60 | -295 | PPPP |
| ORF YDL039C | 920 | P | 1025 | P | 198 | P | 236 | P | 0.22 | 0.23 | 0.22 | 4.48 | -755 | PPPP |
| ORF YDL037C | 186 | P | 258 | P | 42 | P | 58 | P | 0.22 | 0.23 | 0.22 | 4.45 | -172 | |
| TWT2 (YJR148W) | 1207 | P | 1716 | P | 323 | P | 314 | P | 0.27 | 0.18 | 0.23 | 4.43 | -1143 | PPPP |
| ORF YFR055W | 230 | P | 195 | P | 62 | P | 37 | P | 0.27 | 0.19 | 0.23 | 4.33 | -162 | PPPP |
| ORF YGL262W | 17 | P | 12 | A | 5 | A | 2 | A | 0.28 | 0.20 | 0.24 | 4.25 | -11 | |
| CAR2 (YLR438W) | 286 | P | 362 | P | 95 | P | 56 | P | 0.33 | 0.16 | -0.24 | 4.08 | -248 | PPPP |
| ORF YPL019C | 1141 | P | 1154 | P | 298 | P | 273 | P | 0.25 | 0.24 | 0.25 | 4.02 | -862 | |
| ORF YDL179W | 187 | P | 121 | P | 20 | A | 47 | P | 0.11 | 0.39 | 0.25 | 4.02 | -120 | |

Figure 34H

| Gene | w1 | w1c | w2 | w2c | m1 | m1c | m2 | m2c | MUT #1/WT | MUT #2/WT | Average | Fold down | Ave diff | PPPP |
|---|---|---|---|---|---|---|---|---|---|---|---|---|---|---|
| ORF YHR136C | 82 | P | 161 | P | 29 | A | 25 | P | 0.35 | 0.15 | 0.25 | 3.94 | -95 | |
| ORF YMR254C | 29 | A | 12 | A | 12 | A | 1 | A | 0.42 | 0.09 | 0.25 | 3.94 | -14 | |
| ORF YHR022C | 32 | P | 18 | P | 8 | A | 6 | P | 0.20 | 0.31 | 0.25 | 3.93 | -19 | |
| ORF YDR384C | 367 | P | 341 | P | 97 | P | 85 | P | 0.26 | 0.25 | 0.26 | 3.89 | -263 | PPPP |
| FAA3 (YIL009W) | 196 | P | 211 | P | 86 | P | 39 | P | 0.34 | 0.18 | 0.26 | 3.84 | -151 | PPPP |
| HXT4 (YHR092C) | 801 | P | 679 | P | 162 | P | 227 | P | 0.20 | 0.33 | 0.27 | 3.73 | -545 | PPPP |
| ORF YOR366W | 22 | P | 18 | P | 2 | A | 8 | A | 0.08 | 0.46 | 0.27 | 3.72 | -15 | |
| YH81 (YGR234W) | 4663 | P | 3793 | P | 975 | P | 1292 | P | 0.21 | 0.34 | 0.27 | 3.64 | -3095 | PPPP |
| VAP1 (YBR069C) | 824 | P | 1038 | P | 290 | P | 223 | P | 0.35 | 0.22 | 0.28 | 3.53 | -675 | PPPP |
| ORF YLL053C | 364 | P | 242 | P | 90 | P | 79 | P | 0.25 | 0.33 | 0.29 | 3.49 | -219 | PPPP |
| ORF YHR143W | 1126 | P | 1114 | P | 309 | P | 338 | P | 0.27 | 0.30 | 0.29 | 3.46 | -797 | PPPP |
| ORF YEL065W | 325 | P | 234 | P | 81 | P | 80 | P | 0.25 | 0.34 | 0.30 | 3.38 | -199 | PPPP |
| ORF YGR035C | 149 | P | 145 | P | 57 | P | 31 | P | 0.38 | 0.21 | 0.30 | 3.38 | -103 | PPPP |
| ORF YKL044W | 103 | P | 136 | P | 32 | M | 38 | P | 0.31 | 0.28 | 0.30 | 3.38 | -84 | |
| PHO11 (YAR071W) | 231 | P | 408 | P | 105 | P | 58 | P | 0.45 | 0.14 | 0.30 | 3.36 | -238 | PPPP |
| ORF YOR013W | 31 | A | 36 | A | 6 | A | 15 | A | 0.21 | 0.41 | 0.31 | 3.24 | -23 | |
| ORF YIR013C | 22 | A | 47 | P | 5 | A | 19 | A | 0.22 | 0.41 | 0.31 | 3.21 | -23 | |
| ORF YBR238C | 132 | P | 167 | P | 43 | P | 50 | P | 0.32 | 0.30 | 0.31 | 3.21 | -103 | |
| ORF YMR006C | 244 | P | 226 | P | 86 | P | 63 | P | 0.35 | 0.28 | 0.32 | 3.18 | -160 | PPPP |
| ORF YJR029W exon | 3471 | P | 2464 | P | 1097 | P | 789 | P | 0.32 | 0.32 | 0.32 | 3.14 | -2024 | PPPP |
| ORF YHR137W | 148 | P | 125 | P | 58 | P | 31 | P | 0.39 | 0.24 | 0.32 | 3.14 | -92 | PPPP |
| MNN1 (YER001W) | 499 | P | 419 | P | 148 | P | 142 | P | 0.30 | 0.34 | 0.32 | 3.14 | -313 | PPPP |
| ORF YLL013C | 46 | P | 23 | P | 15 | P | 7 | M | 0.34 | 0.30 | 0.32 | 3.13 | -23 | |
| SRO1 (YCR013C) | 107 | P | 87 | P | 29 | A | 32 | P | 0.27 | 0.37 | 0.32 | 3.13 | -67 | |

Figure 34I

| Gene | w1 | w1c | w2 | w2c | m1 | m1c | m2 | m2c | MUT #1/WT | MUT #2/WT | Average | Fold down | Ave diff | PPPP |
|---|---|---|---|---|---|---|---|---|---|---|---|---|---|---|
| MRS2 (YOR333C) | 33 | A | 20 | P | 7 | A | 8 | M | 0.23 | 0.41 | 0.32 | 3.13 | -19 | |
| DIP5 (YPL265W) | 303 | P | 253 | P | 127 | P | 62 | P | 0.42 | 0.24 | 0.33 | 3.01 | -184 | PPPP |
| ORF YMR173W | 323 | P | 163 | P | 60 | P | 78 | P | 0.19 | 0.48 | 0.33 | 3.01 | -174 | PPPP |
| TIP1 (YBR067C) | 788 | P | 1216 | P | 317 | P | 322 | P | 0.40 | 0.25 | 0.33 | 3.00 | -883 | PPPP |
| CWP1 (YKL096W) | 1472 | P | 1381 | P | 511 | P | 443 | P | 0.35 | 0.32 | 0.33 | 3.00 | -950 | PPPP |
| RME1 (YGR044C) | 348 | P | 344 | P | 121 | P | 116 | P | 0.44 | 0.34 | 0.34 | 2.93 | -228 | PPPP |
| PHD1 (YKL043W) | 202 | P | 247 | P | 88 | P | 62 | P | 0.36 | 0.25 | 0.34 | 2.91 | -149 | PPPP |
| ASN1 (YPR145W) | 2440 | P | 2086 | P | 867 | P | 692 | P | 0.27 | 0.23 | 0.34 | 2.91 | -1483 | PPPP |
| ORF YLL062C | 164 | P | 103 | P | 44 | P | 44 | P | 0.39 | 0.42 | 0.35 | 2.99 | -90 | PPPP |
| ORF YJL200C | 414 | P | 459 | P | 160 | P | 144 | P | 0.30 | 0.31 | 0.35 | 2.86 | -285 | PPPP |
| ORF YNL327W | 2041 | P | 1570 | P | 607 | P | 641 | P | 0.49 | 0.41 | 0.35 | 2.83 | -1182 | PPPP |
| SAG1 (YJR004C) | 430 | P | 845 | P | 209 | P | 191 | P | 0.23 | 0.23 | 0.36 | 2.81 | -438 | PPPP |
| ORF YLR213C | 39 | P | 18 | P | 9 | A | 9 | P | 0.24 | 0.48 | 0.36 | 2.8 | -20 | |
| ORF THR048W | 47 | P | 37 | P | 11 | A | 18 | P | 0.40 | 0.48 | 0.36 | 2.79 | -27 | |
| CTP1 (YBR291C) | 198 | P | 246 | P | 78 | P | 80 | P | 0.34 | 0.33 | 0.36 | 2.77 | -143 | PPPP |
| RPI1 (YIL119C) | 68 | P | 54 | P | 22 | P | 21 | P | 0.45 | 0.39 | 0.36 | 2.75 | -38 | |
| ORF YDL218W | 13 | A | 21 | P | 5 | A | 8 | A | 0.38 | 0.29 | 0.37 | 2.72 | -11 | |
| CLB1 (YGR108W) | 322 | P | 329 | P | 121 | P | 121 | P | 0.36 | 0.37 | 0.37 | 2.69 | -204 | PPPP |
| ORF YDR380W | 193 | P | 122 | P | 70 | P | 47 | P | 0.42 | 0.39 | 0.37 | 2.67 | -99 | PPPP |
| ORF YBR158W | 1015 | P | 1059 | P | 430 | P | 347 | P | 0.31 | 0.33 | 0.38 | 2.66 | -649 | PPPP |
| NCE2 (YPR149W) | 2724 | P | 1967 | P | 854 | P | 871 | P | 0.29 | 0.44 | 0.38 | 2.64 | -1483 | PPPP |
| ORF YDR055W | 969 | P | 721 | P | 281 | P | 337 | P | 0.46 | 0.47 | 0.38 | 2.64 | -537 | PPPP |
| ADH5 (YBR145W) | 114 | P | 121 | P | 52 | M | 38 | P | 0.36 | 0.30 | 0.38 | 2.64 | -73 | |
| GPH1 (YPR160W) | 137 | P | 88 | P | 49 | A | 36 | P | 0.44 | 0.40 | 0.38 | 2.63 | -71 | |

Figure 34J

| Gene | w1 | w1c | w2 | w2c | m1 | m1c | m2 | m2c | MUT #1/WT | MUT #2/WT | Average | Fold down | Ave diff | PPPP |
|---|---|---|---|---|---|---|---|---|---|---|---|---|---|---|
| ORF YJL217W | 515 | P | 437 | P | 225 | P | 143 | P | 0.49 | 0.33 | 0.38 | 2.62 | -292 | PPPP |
| ORF YOL152W | 47 | P | 23 | P | 23 | P | 6 | A | 0.34 | 0.27 | 0.38 | 2.61 | -20 | |
| ORF YMR173W-A | 4707 | P | 3899 | P | 1581 | P | 1711 | P | 0.43 | 0.44 | 0.39 | 2.58 | -2657 | PPPP |
| MF(ALPHA)2 (YGL08) | 1791 | P | 2676 | P | 778 | P | 928 | P | 0.47 | 0.35 | 0.39 | 2.57 | -1383 | PPPP |
| COX5B (YIL111W) exon | 155 | P | 150 | P | 73 | P | 51 | P | 0.45 | 0.34 | 0.40 | 2.48 | -91 | PPPP |
| ORF YPR106W | 109 | P | 113 | P | 49 | P | 42 | P | 0.38 | 0.37 | 0.41 | 2.45 | -66 | PPPP |
| ORF YMR045C exon | 3051 | P | 2529 | P | 1167 | P | 1134 | P | 0.36 | 0.45 | 0.42 | 2.41 | -1639 | PPPP |
| ORF YGR041W | 140 | P | 145 | P | 51 | P | 58 | P | 0.45 | 0.47 | 0.42 | 2.40 | -83 | PPPP |
| ASH1 (YKL185W) | 328 | P | 289 | P | 147 | P | 113 | P | 0.44 | 0.39 | 0.42 | 2.39 | -179 | PPPP |
| ORF YHR214C-B exon | 4542 | P | 4526 | P | 1996 | P | 1807 | P | 0.46 | 0.40 | 0.42 | 2.28 | -2632 | PPPP |
| ORF YPL158C | 172 | P | 129 | P | 79 | P | 49 | P | 0.41 | 0.38 | 0.42 | 2.37 | -86 | PPPP |
| ORF YML045W exon | 4997 | P | 4362 | P | 2022 | P | 1925 | P | 0.42 | 0.44 | 0.42 | 2.36 | -2700 | PPPP |
| HXT1 (YHR094C) | 2077 | P | 2056 | P | 862 | P | 918 | P | 0.44 | 0.45 | 0.43 | 2.32 | -1176 | PPPP |
| ADH3 (YMR083W) | 1896 | P | 1667 | P | 747 | P | 725 | P | 0.44 | 0.43 | 0.44 | 2.29 | -946 | PPPP |
| ORF YJR027W exon | 3543 | P | 2309 | P | 1582 | P | 1003 | P | 0.40 | 0.43 | 0.44 | 2.29 | -1643 | PPPP |
| ORF YMR050C exon | 3539 | P | 2762 | P | 1417 | P | 1344 | P | 0.39 | 0.49 | 0.44 | 2.25 | -1770 | PPPP |
| FRE1 (YLR214W) | 777 | P | 441 | P | 303 | P | 223 | P | 0.37 | 0.51 | 0.45 | 2.23 | -345 | PPPP |
| ORF YJL012C | 982 | P | 656 | P | 359 | P | 345 | P | 0.40 | 0.53 | 0.45 | 2.22 | -457 | PPPP |
| RAS1 (YOR101W) | 278 | P | 208 | P | 112 | P | 105 | P | 0.47 | 0.50 | 0.45 | 2.20 | -134 | PPPP |
| STP4 (YDL048C) | 235 | P | 261 | P | 111 | P | 115 | P | 0.47 | 0.44 | 0.46 | 2.18 | -135 | PPPP |
| ORF YER180C exon | 4805 | P | 3817 | P | 2187 | P | 1587 | P | 0.46 | 0.44 | 0.46 | 2.18 | -2274 | PPPP |
| ORF YML039W exon | 3718 | P | 2496 | P | 1710 | P | 1159 | P | 0.49 | 0.46 | 0.46 | 2.16 | -1672 | PPPP |
| ORF YBL042C | 325 | P | 343 | P | 160 | P | 156 | P | 0.47 | 0.45 | 0.47 | 2.11 | -176 | PPPP |

Figure 34K

| Gene | w1 | w1c | w2 | w2c | m1 | m1c | m2 | m2c | MUT #1/ WT | MUT #2/ WT | Average | Fold down | Ave diff | PPPP |
|---|---|---|---|---|---|---|---|---|---|---|---|---|---|---|
| ORF YJL212C | 420 | P | 370 | P | 186 | P | 188 | P | 0.44 | 0.50 | 0.47 | 2.11 | -208 | PPPP |
| REV1 (YOR345C) | 35 | P | 26 | P | 17 | A | 13 | A | 0.47 | 0.48 | 0.48 | 2.09 | -16 | |
| HEM13 (YDR044W) | 118 | P | 154 | P | 56 | A | 75 | P | 0.48 | 0.49 | 0.48 | 2.07 | -70 | |

Figure 34L

| TAF145 | % WT Expression |
|---|---|
| Gene | TS/WT |
| ORF YGR245C | 1 |
| ORF YLR057W | 1 |
| ORF YKL221W | 3 |
| ORF YOR277C | 3 |
| ORF YDR179W-A | 3 |
| ORF YDR132C | 3 |
| ORF YLR465C (_f) | 3 |
| KAR3 (YPR141C) | 3 |
| ORF YDR419W | 3 |
| ORF YMR153C-A | 3 |
| ORF YKL014C | 3 |
| ORF YJR053W | 3 |
| PET309 (YLR087C) | 4 |
| TOP3 (YLR234W) | 4 |
| ORF YPL269W | 4 |
| ORF YKL222C | 5 |
| ORF YGR272C | 5 |
| ORF YOR242C | 5 |
| ORF YHR101C exon 2 | 5 |
| ORF YER089C | 5 |
| ORF YJR020W | 5 |
| ORF YHR036W | 5 |
| FIG2 (YCR089W) | 6 |
| ERR1 (YOR393W (_f) | 6 |
| STU2 (YLR045C) | 6 |
| ORF YMR141C | 6 |
| ORF YJR041C | 6 |
| ENA1 (YDR040C) | 6 |
| ORF YJL073W | 6 |
| ORF YPL164C | 7 |
| ORF YPL257W | 7 |
| ORF YJL035C | 7 |
| PDR3 (YBL005W) | 7 |
| ORF YAR060C (_f) | 7 |
| TAF145 (YGR274C) | 7 |
| MF(ALPHA)1 (YPL187W) | 7 |
| REC104 (YHR157W) | 7 |
| ORF YKR102W | 7 |
| ORF YDL026W | 8 |
| ORF YDR467C | 8 |
| ORF YIR020C | 8 |
| CLI (YER065C) | 8 |
| ORF YGR198W | 8 |
| ORF YMR163C | 8 |
| MBR1 (YKL093W) | 8 |
| ORF YLR122C | 8 |
| ORF YJR137C | 8 |
| ORF YPR015C | 8 |
| ORF YNL337W (_f) | 8 |
| ORF YPR083W | 8 |
| ORF YOR339C | 8 |
| TRF4 (YOL115W) | 8 |
| ORF YDR426C | 8 |
| ORF YCR041W | 8 |
| ORF YCR032W | 8 |
| AGT1 (YGR289C) | 9 |
| MAL63 (YPR196W) | 9 |
| MAD3 (YJL013C) | 9 |
| ASP3 (YLR155C) (_f) | 9 |
| ORF YDR114C | 9 |
| ORF YDL149W | 9 |
| ORF YBR090C exon 1 | 9 |
| ORF YDR015C | 9 |

Figure 35A

| TAF145 | % WT Expression |
|---|---|
| ASP3 (YLR153C) (_f) | 9 |
| ALR2 (YF050C) | 9 |
| ORF YLR318W | 10 |
| TRX1 (YLR043C) | 10 |
| ORF YHR054C (_f) | 10 |
| ORF YKR005C | 10 |
| ORF YPR152C | 10 |
| ORF TOR376W | 10 |
| ORF YIR015W | 10 |
| ORF YAR062W (_f) | 10 |
| ORF YDR029W | 10 |
| ORF YDR334W | 10 |
| ORF YDR273W | 10 |
| ORF YML066C | 10 |
| ATP10 (YLR393W) | 10 |
| ORF YJR153W | 10 |
| ORF YMR075C-A | 10 |
| ORF YPL125W | 10 |
| ORF YPL141C | 10 |
| ORF YOR381W | 10 |
| ORF YJL051W | 11 |
| ORF YJL085W | 11 |
| PKC1 (YBL105C) | 11 |
| ORF YGR271W | 11 |
| RNA14 (YMR061W) | 11 |
| ORF YLR313C | 11 |
| ORF YJR180C (_f) | 11 |
| POL4 (YCR014C) | 11 |
| ORF YER039C | 11 |
| ORF YIL166C | 11 |
| ORF YGR107W | 11 |
| ORF YBL065W | 12 |
| ORF YOL045W | 12 |
| ORF YMR025W | 12 |
| ASE1 (YOR058C) | 12 |
| PDC2 (YDR081C) | 12 |
| BRR2 (YER172C) | 12 |
| ORF YLR381W | 12 |
| ORF YCR007C | 13 |
| ORF YCR045C | 13 |
| ORF YDR357C | 13 |
| ORF YGR071C | 13 |
| ORF YLR373C | 13 |
| HXT12 (YIL171W) (_f) | 13 |
| ORF YDR141C | 13 |
| ORF YOR364W | 13 |
| ORF YNL311C | 13 |
| ORF YPR197C | 13 |
| ORF YPR038W | 13 |
| ORF YHR101C axon 1 | 13 |
| ORF YLR415C | 13 |
| MAL33 (YBR297W) | 13 |
| PEL1 (YCL004W) | 13 |
| ORF YBR210W | 14 |
| ORF YHR095W | 14 |
| ORF YHR075C | 14 |
| ORF YGR293C (_f) | 14 |
| ORF YJL007C | 14 |
| SDL1 (YIL168W) | 14 |
| ORF YKL083W | 14 |
| ORF YKL177W | 14 |
| ORF YOL163W | 14 |
| ORF YPL222W | 14 |
| ORF YNL295W | 14 |

Figure 35B

| TAF145 | % WT Expression |
|---|---|
| ORF YMR252C | 14 |
| ORF YKL187C | 14 |
| RIB5 (YBR258C) | 14 |
| SEC22 (YLR268W) | 14 |
| ORF YGR275W | 15 |
| YPT53 (YNL093W) | 15 |
| ORF YJL160C | 15 |
| ORF YKR105C | 15 |
| PAK1 (YER129W) | 15 |
| ORF YBL012C | 15 |
| ORF YBR264W | 15 |
| ORF YDR252W | 15 |
| BUD3 (YCL014W) | 15 |
| DHS1 (YOR033C) | 15 |
| ORF YHR213W (_f) | 15 |
| PUR5 (YHR218W) | 15 |
| SIP4 (YJL089W) | 15 |
| ORF YJR071W | 15 |
| ORF YML035C-A | 15 |
| ORF YLR269C | 15 |
| ORF YDL243C (_f) | 15 |
| CDC45 (YLR274W) | 16 |
| ORF YLR317W | 16 |
| SAS3 (YBL060W) | 16 |
| ORF YBR102C | 16 |
| ORF YBR033W | 16 |
| ORF YIL169C | 16 |
| HMG2 (YLR450W) | 16 |
| ORF YMR018W | 17 |
| ORF YJL207C | 17 |
| ORF YDR185C | 17 |
| ORF YML124C exon 1 | 17 |
| ORF YIL158W | 17 |
| ORF YCR076C | 17 |
| ORF YDL073W | 17 |
| RPS24B (YLR367W) axon | 17 |
| ORF YIL144W | 17 |
| ORF YIL024C | 17 |
| YSC84 (YHR016C) exon 1 | 17 |
| HXT12 (YIL171W (_f) | 17 |
| ORF YGR025W | 17 |
| ORF YHL047C | 17 |
| ORF YGL133W | 17 |
| KIN82 (YCR091W) | 17 |
| ORF YPL166W | 17 |
| PXA1 (YPL147W) | 17 |
| ORF YJR108W | 18 |
| ORF YLR108C | 18 |
| ORF YBR218C | 18 |
| ORF YDR520C | 18 |
| ERS1 (YCR075C) | 18 |
| CDC39 (YCR093W) | 18 |
| BIO3 (YNR058W) | 18 |
| HFA1 (YMR207C) | 18 |
| ORF YJR110W | 18 |
| ORF YJL120W | 18 |
| ORF YLR247C | 18 |
| ORF YOR054C | 18 |
| ORF YDR259C | 18 |
| ORF YJR046W | 18 |
| ORF YLR035C | 18 |
| ORF YLR444C | 18 |
| ORF YLR230W | 18 |
| ORF YML089C | 18 |

Figure 35C

| TAF145 | % WT Expression |
|---|---|
| ALPHA1 (YCL066W) (_f) | 19 |
| ORF YAL065C-A | 19 |
| CTA1 (YDR256C) | 19 |
| OIT1 (YDR403W) | 19 |
| ORF YDR278C | 19 |
| ORF YKL123W | 19 |
| ADP1 (YCR011C) | 19 |
| ORF YMR178W | 19 |
| HXT16 (YJR158W) (_f) | 19 |
| ORF YLR453C | 19 |
| ORF YMR317W | 20 |
| DAL4 (YIR028W) | 20 |
| SRB8 (YCR081w) | 20 |
| ORF YCL012W | 20 |
| PET130 (YJL023C) | 20 |
| ARE1 (YCR048W) | 20 |
| ORF YCL023C | 21 |
| ORF YJL150W | 21 |
| ESR1 (YBR136W) | 21 |
| NPL4 (YBR170C) | 21 |
| ORF YPL238C | 21 |
| DSK2 (YOR035C) | 21 |
| ORF YBL048W | 21 |
| ORF YAL035C-A | 21 |
| APA2 (YDR530C) | 21 |
| THI5 (YFL058W) (_f) | 22 |
| ORF YLR352W | 22 |
| SAP155 (YFR040W) | 22 |
| RPS24B (YLR367W) exon | 22 |
| EMP47 (YFL048C) | 22 |
| ORF YCR023C | 22 |
| ORF YDR082W | 22 |
| ORF YIL129C | 22 |
| ARG82 (YDR173C) | 22 |
| ORG YOR147W | 22 |
| SSH4 (YKL124W) | 22 |
| DYN1 (YKR054C) | 23 |
| FPR1 (YNL135C) | 23 |
| ORF YJR012C | 23 |
| CDC15 (YAR019C) | 23 |
| ORF YKR033C | 23 |
| ORF YJR039W | 23 |
| ORF YBR150C | 23 |
| ORF YJL049W | 24 |
| ORF YCL053C | 24 |
| ORF YLR443W | 24 |
| ORF YCR054C | 24 |
| ORF YIL148C | 24 |
| MNR2 (YKL064W) | 24 |
| QRI5 (YLR204W) | 24 |
| APA1 (YCL050C) | 24 |
| SBE2 (YDR351W) | 25 |
| APT2 (YDR441C) | 25 |
| SSL2 (YIL143C) | 25 |
| ORF YLR312C | 25 |
| ORF YLR345W | 25 |
| ORF YOL162W | 25 |
| ORF YL047W | 25 |
| ORF YKL200C | 25 |
| ORF YHR180W | 25 |
| ORF YCL063W | 25 |
| ORF YBR266C | 25 |
| ORF YDR078C | 25 |
| ORF YCR073C | 25 |

Figure 35D

| TAF145 | % WT Expression |
|---|---|
| ORF YDL218W | 25 |
| ORF YPR042C | 25 |
| ORF YCR004C | 25 |
| ORF YBL057C | 26 |
| GSY1 (YFR015C) | 26 |
| ORF YER097W | 26 |
| ORF YGR284C | 26 |
| PET18 (YCR020C) | 26 |
| ORF YNL008C | 26 |
| ORF YMR191W | 26 |
| ORF YCR033W | 26 |
| ORF YJL132W | 27 |
| ORF YIL028W | 27 |
| ORF YDR534C | 27 |
| A2 (YCR096C) (_f) | 27 |
| RPO41 (YFL038W) | 27 |
| ORF YBR138C | 27 |
| ORF YGR164W | 28 |
| ORF YGL177W | 28 |
| ORF YIL071W | 28 |
| ORF YKL066W | 28 |
| ALPHA2 (YCL067C) (_f) | 28 |
| ALPHA2 (YCR039C (_f) | 28 |
| YCRX10w/ (control?) | 28 |
| ORF YCR024C | 28 |
| RSC5 (YCR052W) | 28 |
| HSL1 (YKL101W) | 29 |
| CYR1 (YJL005W) | 29 |
| ORF YDL010W | 29 |
| ORF YCR026C | 29 |
| ORF YIL054W | 29 |
| ORF YCL049C | 29 |
| ORF YMR040W | 29 |
| PRD1 (YCL057W) | 29 |
| ORF YCL039W | 29 |

Figure 35E

| Gene | Description | Fold-reduction |
|------|-------------|----------------|
| MFA1 | Mating pheromone a-factor | 28 |
| STE2 | Alpha factor receptor | 12 |
| MFA2 | Mating pheromone a-factor | 11 |
| BAR1 | Protease that degrades alpha factor | 10 |
| SST2 | Involved in desensitization to alpha factor | 9 |
| FAR1 | Inhibitor of CDKs involved in cell-cycle arrest for mating | 8 |
| FUS2 | Protein required for cell fusion during mating | 6 |
| STE6 | Membrane transporter; exports a-factor | 6 |
| AGA2 | a-agglutinin binding subunit | 6 |
| AGA1 | a-agglutinin anchor subunit | 5 |
| STE12 | Transcription factor binds to pheromone response element | 4 |
| GPA1 | GTP-binding subunit of pheromone response pathway | 4 |
| STE13 | Involved in maturation of alpha factor | 4 |
| KAR4 | Required for pheromone induction of karyogamy genes | 4 |

FIG. 39A

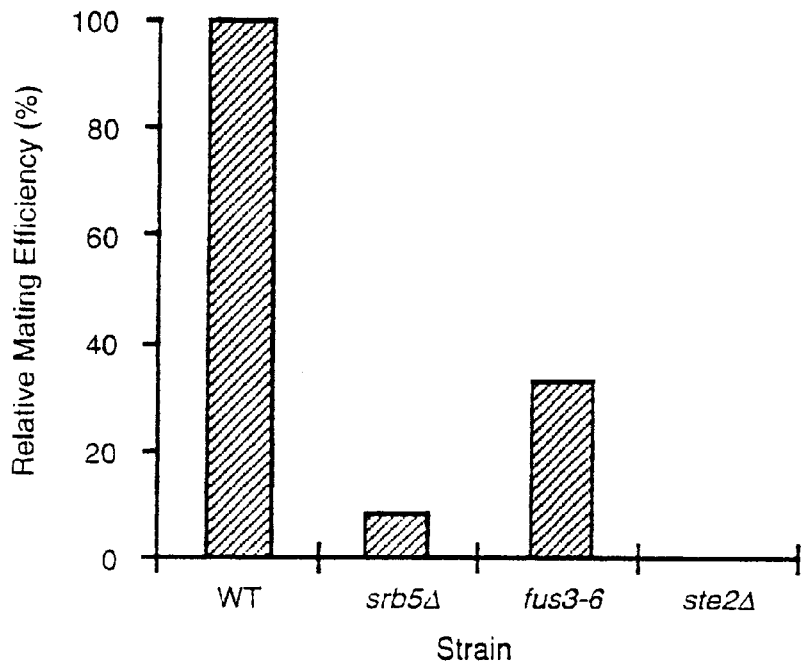

| Gene | Description | Fold Up |
|---|---|---|
| FLO1 | Flocculence cell wall protein | 102 |
| SIP18 | Induced by osmotic stress | 74 |
| YBR116C | Induced by diauxic shift | 61 |
| YMR107W | Induced by diauxic shift | 32 |
| ALD3 | Induced by diauxic shift | 28 |
| HSP26 | Induced by osmotic stress, diauxic shift | 26 |
| GRE1 | Induced by osmotic stress, diauxic shift | 25 |
| YER150W | Induced by diauxic shift | 24 |
| HSP12 | Induced by numerous stresses | 18 |
| RCK1 | Serine/threonine protein kinase | 18 |
| FLO11 | Flocculence | 15 |
| RTA1 | Involved in 7-aminocholesterol resistance | 15 |
| YDR070C | Induced by diauxic shift | 13 |
| YBR147W | Induced by diauxic shift | 10 |
| CTT1 | Induced by osmotic stress, diauxic shift | 10 |
| YDL204W | Induced by diauxic shift | 10 |
| TKL2 | Induced by diauxic shift | 10 |
| YGR043C | Induced by diauxic shift | 9 |
| YNL194C | Induced by diauxic shift | 9 |
| SOL4 | Induced by diauxic shift | 8 |
| CYC7 | Induced by numerous stresses, diauxic shift | 8 |
| PUT4 | Proline permease, nitrogen induced | 8 |
| YKL187C | Induced by diauxic shift | 8 |
| NCA3 | Life-span determination | 8 |
| YML128C | Induced by diauxic shift | 8 |
| GPH1 | Induced by diauxic shift | 8 |
| POT1 | Induced by diauxic shift | 7 |

FIG. 40B

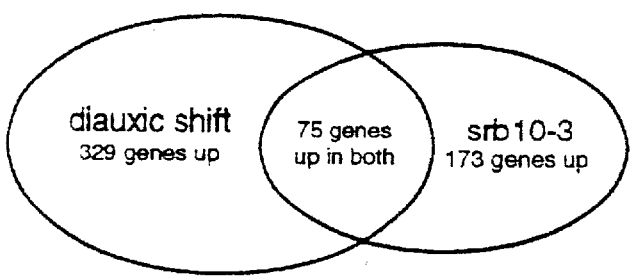

FIG. 40C

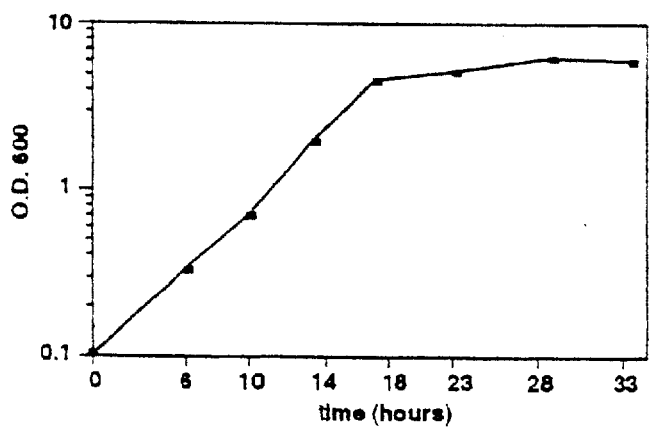

DISSECTING THE REGULATORY CIRCUITRY OF A EUKARYOTIC GENOMEI

RELATED APPLICATIONS

This application claims the benefit of the following applications:

U.S. patent application No. 60/087,909 filed Jun. 4, 1998, entitled Genome Control Map by Frank Holstege and Richard A. Young;

U.S. patent application No. 60/097,498 filed Aug. 21, 1998, entitled Dissecting the Regulatory Circuitry of a Eukaryotic Genome by Frank Holstege and Richard A. Young;

U.S. patent application No. 60/109,534, filed Nov. 23, 1998, entitled Dissecting the Regulatory Circuitry of a Eukaryotic Genome by Frank Holstege and Richard A. Young; and U.S. patent application No. 60/110,051 filed Nov. 25, 1998 entitled Dissecting the Regulatory Circuitry of a Eukaryotic Genome by Richard A. Young.

This application is also related to U.S. patent application No. 60/075,291 filed Feb. 20, 1998, entitled Temperature Sensitive ts SRB4 Mutation by Rick Young.

The entire teachings of the referenced applications are incorporated herein by reference.

BACKGROUND OF THE INVENTION

Much of biological regulation occurs at the level of transcription initiation. Genes contain promoter sequences which are bound by transcriptional activators and repressors (Struhl, K. (1995) *Annu Rev Genet* 29, 651–74; Ptashne, M. and Gann, A. (1997) *Nature* 386, 569–77). Activators recruit the transcriptional initiation machinery, which for protein-coding genes consists of RNA polymerase II and at least 50 additional components (Orphanides et al. (1996) *Genes Dev* 10, 2657–83; Roeder, R. G., (1996) *Trends Biochem Sci* 21, 327–35; Greenblatt, J. (1997) *Curr Opin Cell Biol* 9, 310–9; Hampsey, M. (1998) *Microbiology and Molecular Biology Reviews* 62, 465–503; Myer, V. and Young, R. A. (1998) *J. Biol. Chem.* 273, 27757–27760). The transcriptional initiation machinery includes factors which bind to DNA, cyclin-dependent kinases which regulate polymerase activity, and acetylases and other enzymes which modify chromatin (Burley, S. K., and Roeder, R. G. (1996) *Annu Rev Biochem* 65, 769–99; Kingston, R. E. et al., *Genes and Development* 10, 905–20; Roth, S. Y. and Allis, C. D. (1996) *Cell* 87, 5–8; Sgeger, D. J. and Wovleman, J. L. (1996) *Bioessays* 18, 875–84, Tsukiyama, T. and Wu, C. (1997) *Curr. Opin. Genet. Dev.* 7, 182–91; Hengartner C. J. et al., (1998) *Genes and Development* 9, 897–910).

The understanding of eukaryotic gene expression remains limited in several ways. The complete set of transcriptional regulators has yet to be identified. How these regulators interact with and regulate components of the transcriptional machinery is not yet clear. The functions of just a fraction of the components of the transcriptional machinery are understood, and then only with respect to a small set of genes. Cells must adjust genome expression to accommodate changes in their environment and in their programs of growth control and development, but precisely how to coordinate remodeling of genome expression is accomplished for signal transduction pathways or for the cell cycle clock has yet to be learned.

SUMMARY OF THE INVENTION

Described herein are results of genome-wide expression analysis, which was carried out to identify the key components of the transcription initiation machinery in a eukaryote, in order to dissect the regulatory circuitry of the genome. Key components of the transcription initiation machinery (key components of the RNA polymerase II transcriptional machinery) were identified in yeast, as described herein. Assessment of the requirement for key components was carried out using high density oligonucleotide arrays (HDAs) (Wodicka, L. et al (1997) *Nat. Biotech.*, 15, 1359–67) to determine the genome-wide effects of mutations in components of the transcriptional machinery. At any given promoter, the transcriptional machinery might include any or all of the following, among others: the RNA polymerase II core enzyme, the general transcription factors (GTFs), the core Srb/mediator complex, the Srb10 CDK complex, the Swi/Snf complex and the SAGA complex. The components of the transcription apparatus which were the focus of this study were selected because they are among the key subunits of the major multiprotein complexes which have roles in transcription of protein-coding genes. One or more subunits of each of these components has been investigated for its role in genome-wide gene expression through the use of mutations which affect either the function or the physical presence of the subunit.

Results showed that components of the RNA polymerase II holoenzyme, the general transcription factor TFIID and the SAGA chromatin modification complex have roles in expression of distinct sets of genes. They further showed that the Rpb1 subunit of core RNA polymerase II, the Srb4 subunit of the Srb/mediator complex and the Kin28 subunit of TFIIH are generally required for transcription of protein-coding genes. Two were found to be required for more than half, but not all, genes (Tfa1, Taf17). Most components investigated thus far were necessary for transcription of less than a fifth of the genome (Srb5, Med6, Srb10, Swi2, Taf145, Gcn5). In this latter group, the evidence indicates that Srb5, Med6, and Taf 145 have predominantly positive roles, Srb10 has an almost exclusively negative role, and Swi2 and Gcn5 can have either a positive or a negative role in gene expression.

Work described herein shows that distinct sets of genes require the function of distinct components of the transcription machinery. Thus, coordinate regulation of large sets of genes can be accomplished by affecting the function of specific components of the transcription machinery. It follows that functional relationships exist among some genes within the sets of genes whose regulation is accomplished in this manner. Results described herein also revealed an unanticipated level of regulation that is available to the cell in addition to that provided by gene-specific regulators; the expression of specific sets of genes can be regulated by affecting the availability or function of a specific component of the general machinery. Results also showed a novel mechanism for co-ordinate regulation of specific sets of genes when cells encounter nutrient deprivation or limitation and evidence that the ultimate targets of signal transduction pathways can be identified within the initiation apparatus.

In one embodiment, the present invention is a method of determining regulatory interrelationships among genes in a cell. The method comprises the steps of:

(a) hybridizing a transcription indicator of a test cell to a set of nucleic acid probes;

(b) hybridizing a transcription indicator of a control cell to the set of nucleic acid probes, wherein the transcription indicators are selected from the group consisting of mRNA, cDNA and cRNA, wherein the test cell contains a mutant component of the general transcription machinery and the control cell is the wild-type isogenic counterpart of the test cell;

(c) detecting amounts of the transcription indicators which hybridize to each of said set of nucleic acid probes; and (d) identifying a gene as a member of the regulatory pathway of the general transcription factor if hybridization of the transcription indicator of the test cell to a probe comprising a portion of the gene is higher or lower than hybridization using a transcription indicator from the control cell.

In various embodiments of the method, the difference in hybridization between the control and the test cell varies. There can be, for example, at least a 2-fold difference in hybridization between the control and the test cell, at least a 3-fold difference, at least a 5-fold difference or at least a 10-fold difference in hybridization between the control and the test cell. In various embodiments of the method, the mutant component of the general transcription machinery is a mutual general transcription factor, such as a temperature sensitive mutant, a point mutant or a deletion mutant. The mutant component of the general transcription machinery can be, for example, a component of RNA polymerase II holoenzyme. The mutant component of the general transcription machinery can be a component necessary to reconstitute promoter-dependent transcription in vitro with core RNA polymerase II. Also the subject of this invention is a pair of isogenic eukaryotic cells which comprises a test cell which contains a mutant component of the general transcription machinery and a control cell which is the wild-type isogenic counterpart of the test cell. Such pairs can include a test cell in which the mutant component of the general transcription machinery is a mutant general transcription factor. They also can include a test cell in which the mutant component of the general transcription machinery is a temperature sensitive mutant, a point mutant or a deletion mutant. In such pairs, the mutant component of the general transcription machinery can be a component of RNA polymerase II holenzyme; the mutant component of the general transcription machinery can be one which is necessary to reconstitute promoter-dependent transcription id vitro with core RNA polymerase II.

The invention further relates to a method of studying the effects of drugs on cells. The method comprises:

(a) contacting a cell with a drug; and (b) determining the effect of the drug on the cell by assessing expression of one or more of the genes which are determined to be members of the regulatory pathway of the general transcription factor according to methods described herein.

A further embodiment of the invention is a method of identifying a cellular regulatory circuit which employs a component of a subcomplex of regulatory proteins within the RNA polymerase II holoenzyme, referred to as the transcription initiation apparatus.

The method comprises:

(a) comparing genome expression signature during cellular responses to environmental or other stimuli with the genome expression signature produced by a defect in the transcription initiation apparatus; and (b) determining differences between the two genome expression signatures and relating the differences to the defect in the transcription initiation apparatus, thereby identifying a component of the transcription initiation apparatus which is responsible for regulation of genes in the cells.

In various embodiments the cellular regulatory circuit is a yeast cell regulatory circuit, a primate (e.g., human) or other vertebrate cell regulatory circuit or a non-vertebrate cell regulatory circuit.

Thus, genome-wide expression analysis provides insights into the transcriptional regulatory circuitry of eukaryotic cells, as well as the foundation and context for interpreting mechanistic studies in control of gene expression.

BRIEF DESCRIPTION OF THE DRAWINGS

The file of this patent contains at least one drawing executed in color. Copies of the patent with color drawing(s) will be provided by the Patent and Trademark Office upon request and payment of the necessary fee.

FIGS. 1A–1B show genes which go up in Srb5 mutants.

FIGS. 2A–2B show genes which go up in Srb5 mutants.

FIGS. 3A–3U show genes which go down in Srb5 mutants.

FIGS. 4A–4U show genes which go down in Srb5 mutants.

FIGS. 5A–5E show genes which go up in Sin4 mutants.

FIGS. 6A–6E show genes which go up in Sin4 mutants.

FIGS. 7A–7C show genes which go down in Sin4 mutants.

FIGS. 8A–8C show genes which go down in Sin4 mutants.

FIGS. 9A–9C show genes which go up in Gcn5 mutants.

FIGS. 10A–10C show genes which go up in Gcn5 mutants.

FIGS. 11A–11F show genes which go down in Gcn5 mutants.

FIGS. 12A–12F show genes which go down in Gcn5 mutants.

FIGS. 13A–13C show genes which go up in Srb2 mutants.

FIGS. 14A–14C show genes which go up in Srb2 mutants.

FIGS. 15A–15F show genes which go down in Srb2 mutants.

FIGS. 16A–16F show genes which go down in Srb2 mutants.

FIGS. 17A–17F show genes which go up in Swi2 mutants.

FIGS. 18A–18F show genes which go up in Swi2 mutants.

FIGS. 19A–19D show genes which go down in Swi2 mutants.

FIGS. 20A–20D show genes which go down in Swi2 mutants.

FIGS. 21A–21B show genes which go up in TAF145 (45 min 37 deg) mutants.

FIGS. 22A–22P show genes which go down in TAF 145 (45 min 37 deg) mutants.

FIGS. 23A–23E show genes which go up in Srb10 mutants.

FIGS. 24A–24E show genes which go up in Srb10 mutants.

FIGS. 25A–25B show genes which go down in Gal11 mutants.

FIGS. 26A–26B show genes which go down in Gal11 mutants.

FIGS. 27A–27C show genes which go up in Gal11 mutants.

FIGS. 28A–28C show genes which go up in Gal 11 mutants.

FIG. 29 shows genes which go up in Med6 mutants.

FIGS. 30A–30E show genes which go down in Med6 mutants.

FIGS. 31A–31E show genes which go down in Med6 mutants.

FIGS. 32A–32E show genes which go down in Med6 mutants.

FIGS. 33A–33F show genes which are affected in Srb10 mutants; all of these genes go up and the list is in rank order of degree affected. See especially column headed Gene and column headed Fold up.

FIGS. 34A–34L show genes which are affected in SWI2 mutants; those in FIGS. 34A–34F go up and those in FIGS. 34G–34L go down. See especially column headed Fold up and column headed Fold down.

FIGS. 35A–35E show genes which go down in TAF$_{145}$ mutants. See especially columns headed Gene and % of WT expression.

FIG. 37A shows results for Rpb1; 37B shows results for Med6; 37C shows results for Srb10; and 37D shows results for Swi2.

FIG. 38A illustrates that RNA polymerase II holoenzyme components show distinct patterns of genome control. It is a Venn diagram depicting Srb5-, Swi2-, Srb10- and Med6-dependent genes (small circles) in relation to the whole transcriptome (Rpb1-, Srb4- and Kin28 dependent, large circle). The numbers under each subunit name are the sum of genes whose expression depends on that subunit. FIG. 38B illustrates genome control patterns of components of TFIID and SAGA.

FIGS. 39A and 39B present results showing that Srb5 is required for expression of pheromone response genes. FIG. 39A shows the pheromone response genes whose expression is reduced in the absence of Srb5. FIG. 39B is a graph showing that cells lacking Srb5are defective in mating. The mating efficiencies for mutant strains are expressed as a percentage of the mating efficiency of an isogenic wildtype strain. For comparison, strains with mutations in two components of the mating signal transduction pathway (FUS3 and STE2) are included.

FIGS. 40A–40C present results showing that Srb10 CDK represses genes elevated during response to nutrient starvation. FIG. 40A is a subset of 173 genes whose expression is depressed in cells lacking Srb10 kinase activity. FIG. 40B is a Venn diagram showing the number of genes which are depressed during the nutrient deprivation which occurs during the diauxic shift and the fraction of these which are depressed in cells lacking Srb10 kinase activity. FIG. 40C is a graph which shows that Srb10 protein is depleted from cells as they enter the diauxic shift. The graph shows the growth curve of a yeast strain allowed to grow to stationary phase (33 hours).

DETAILED DESCRIPTION OF THE INVENTION

Figure 36:
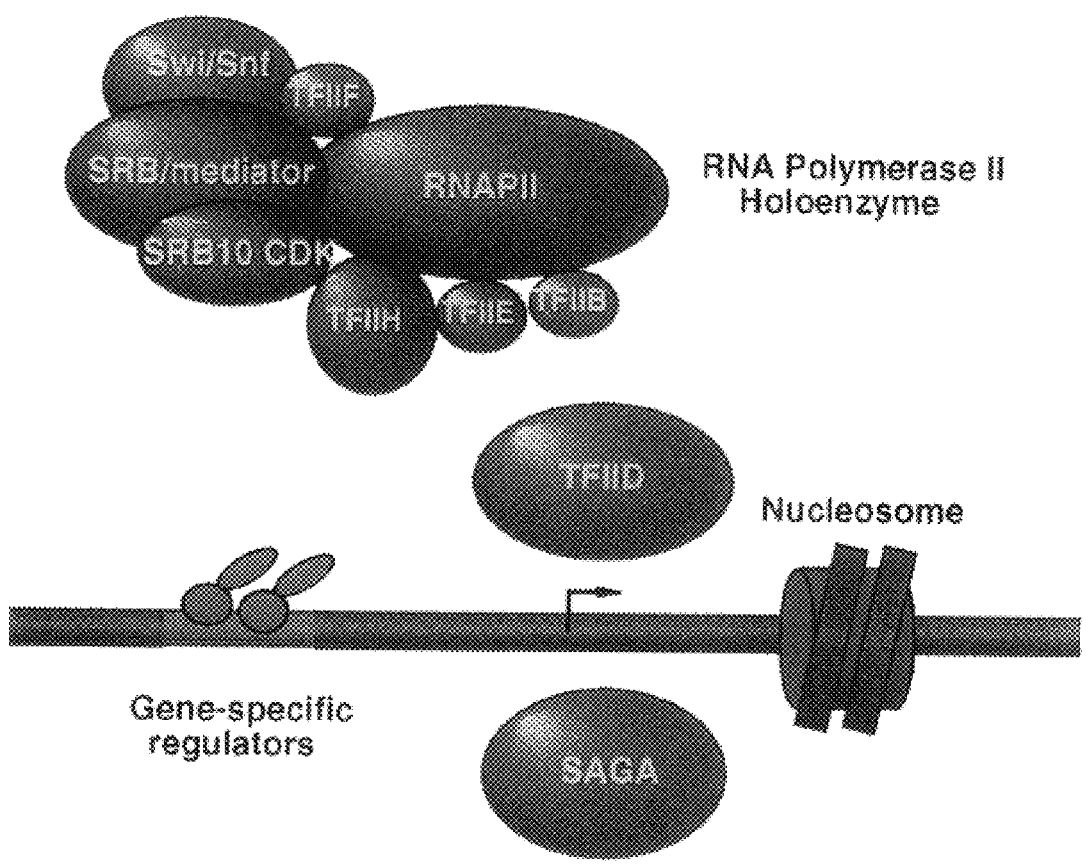
FIG. 36 is a schematic representation of a model of RNA polymerase II transcription initiation machinery which, as depicted here, encompasses more than 85 polypeptides in 10 (sub) complexes: core RNA polymerase II (RNAPII) consists of 12 subunits; TFIIH, 9 subunits; TFIIE, 2 subunits; TFDIIF, 3 subunits; TFIID, 14 subunits; core SRB/mediator, more than 16 subunits; Swi/Snf complex, 11 subunits; Srb10 kinase complex, 4 subunits and SAGA, 13 subunits (see http://www.wi.mit.edu/young/expression.html. site for more details). As detailed in Table 1, representative subunits of these complexes were chosen for analysis of genome-wide transcription dependence.

Detailed information and databases supporting all aspects of the work described herein, including experimental procedures, genetic reagents, HDA technology and data analysis can be found on the Internet at http://www.wi.mit.edu/young/expression.html. The entire contents of this Web site are incorporated herein by reference.

As described herein, HDAs were used to determine the effects of mutations on key components of the RNA polymerase II transcriptional machinery genome-wide in eukaryotic cells and, as a result, to assess the requirements for these components. As described in the examples which follow, the levels of all detectable mRNA species in yeast were determined using HDAs. Results showed that transcripts from 80% of expressed yeast genes exist at steady state levels of 0.1 to 2 molecules/cell.

Dependence of genome expression on key components of the transcriptional machinery was assessed, using mutations which affect either the function or the physical presence of one or more subunits of machinery components (RNA polymerase II core enzyme, the general transcriptional factors (GTFs), the core Srb/mediator complex, the Srb10 CDK complex, the Swi/Snf complex and the SAGA complex). Specifically described in the examples is work which resulted in determination of the levels of all detectable mRNA species in yeast, which is useful in evaluating the degree to which these levels depend on any one component of the transcription apparatus. Also described in the examples is assessment of the roles of components of the transcriptional machinery in genome-wide gene expression, using yeast as a eukaryotic model. As described, one or more subunits of the RNA polymerase II core enzyme, the general transcription factors (GTFs), the core Srb/mediator complex, the Srb10 CDK complex, the Swi/Snf complex and the SAGA complex have been investigated for their roles in genome-wide expression. This was carried out through the use of mutations which affect either the function or the physical presence of the subunit being assessed (see Table 1). The work described herein was carried out using yeast, but a similar approach (in which mutations which affect either the function or physical presence of one or more subunits of the transcription initiation machinery are used to assess dependence of genome expression on machinery components) can be used in other eukaryotic cells, including cells from vertebrates (e.g., cells of human and other primate origin, murine, canine, feline and bovine origin) and cells from non-vertebrates (e.g., cells from worms and flies).

Results showed that the Rpb1 subunit of core RNA polymerase II, the Srb4 subunit of the Srb/mediator complex and the Kin28 subunit of the general transcription factor TFIIH are generally required for transcription of protein-coding genes. Results also showed that only a subset of genes is dependent on Med6, Srb5, Srb10, Swi2, TAF$_{II}$145, TAF$_{II}$17 and Gcn5. The sets of genes whose expression requires various RNA polymerase II holoenzyme components are compared in the Venn diagram of FIG. 38A. The sets of genes whose expression requires various TFIID and SAGA components are shown in the Venn diagram of FIG. 38B. Together, these diagrams show how distinct sets of genes require the function of distinct components of the transcription machinery.

Figure 38A:
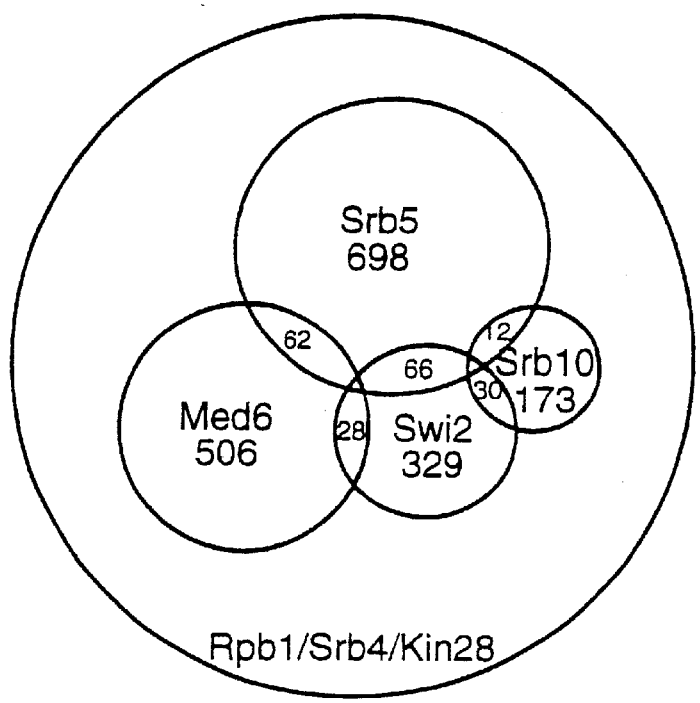
FIG. 38A and 38B are Venn diagrams illustrating the genome-wide dependence on key components of the transcription machinery.
Figure 38B:
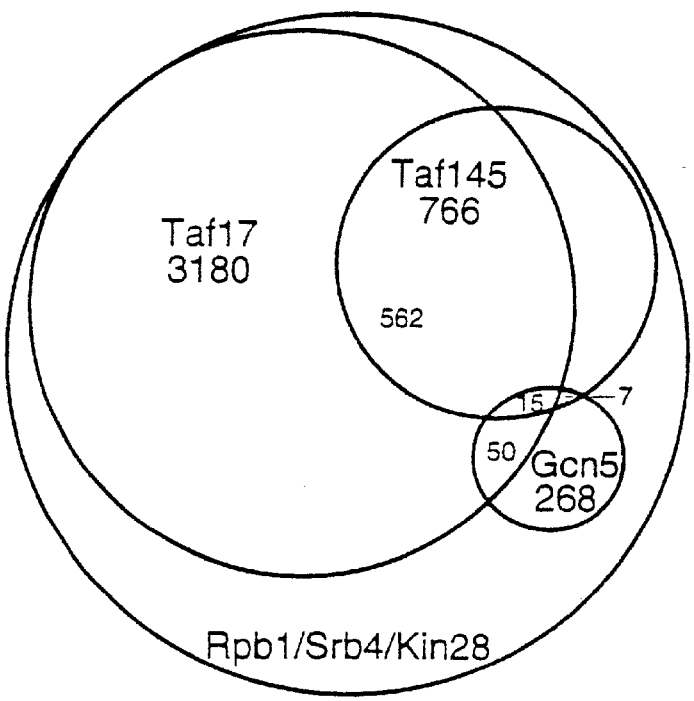

Thus, coordinate regulation of large sets of genes can be accomplished by affecting the function of specific components of the transcriptional machinery. For example, FIG. 38A shows, in addition to the three key RNAPII holoenzyme components which are generally required for transcription of protein-coding genes, at least four other components which regulate expression of subsets of genes. Specifically, Srb5 regulates expression of 698 genes; Med6 regulates expression of 506 genes; Swi2 regulates expression of 329 genes and Srb10 regulates expression of 173 genes. Coordinate regulation of genes in each of these sets of genes can be effected by altering (enhancing or reducing/repressing) function or activity of the respective regulating components (e.g., Srb5, Med6, Swi2, Srb10). Even broader coordination can be accomplished by altering (enhancing or reducing/repressing) function of one or more of the three RNAPII holoenzyme components (Rpb1, Srb4, Kin28) shown to be generally required for transcription of protein-coding genes. It is interesting to note the "overlap" of genes regulated; that is, the fact that expression of some genes is regulated by two components(e.g., 62 genes are regulated by Srb5 and Med6; 86 by Srb5 and Swi2; 12 by Srb5 and Srb10; 30 by Srb10 and Swi2 and 28 by Swi2 and Med6). FIG. 38B presents comparable information for TFIID and SAGA components. In addition to Rpb1, Srb4 and Kin28, other components regulate a large number of genes: TAF$_{II}$ 17, 3180 genes; TAF$_{II}$145, 766 genes; and Gcn5, 268 genes. Here, too, overlap is evident: TAF$_{II}$17 and TAF$_{II}$145 regulate 562 genes in common; TAF$_{II}$17 and Gcn5 regulate 50 genes in common; TAF$_{II}$145 and Gcn5 regulate 7 genes in common and the three regulate 15 genes in common.

The following is a summary of results described in greater detail herein.
General Factors Rpb1 and Srb4 proteins are generally required for expression of protein-coding genes, and they are both associated tightly and exclusively with RNA polymerase II and the mediator complex, respectively (Koleske, A. J. and Young, R. A. (1994) *Nature* 368, 29970–7; Kim, Y. J. et al., (1994) *Cell* 77, 599–608; Myers, L. C. et al., *Genes Dev* 12, 45–54). Therefore, it is reasonable to infer that RNA polymerase II and the core mediator complex are generally required for transcription. Assuming that the function of Kin28 is restricted to TFIIH, the data obtained with the Kin28 mutant demonstrates that TFIIH is a general factor. The expression of 54% of yeast genes is as dependent on Tfa1 as it is on Rpb1, supporting the idea that TFIIE is directly involved in expression of at least 54% of protein-coding genes. Without knowing the contribution of Tfa2, the other subunit of TFIIE, one cannot eliminate the possibility that TFIIE has roles at additional genes.
SRB/Mediator Complex The SRB/mediator core complex is essential for general transcription, as evidenced by the requirement for Srb4, but components such as Srb5 and Med6 have roles at specific subsets of genes. These results are consistent with the proposal that the Srb/mediator complex is recruited to promoters of most genes together with RNA polymerase II, where it acts in a manner analogous to a signal processor with the capacity to integrate the combinatorial effects of multiple inputs from gene-specific transcriptional activators and repressors. (Koleske, A. J. and Young, R. A. (1994) *Nature* 368, 466–9; Kim, Y. J. et al., (1994) *Cell* 77, 599–608; Koh, S. S. et al., (1998) *Cell* 1, 895–904; Myers, L. C. et al., *Genes Dev* 12, 45–54; Sun, X. et al., (1998) *Molecular Cell* 2,1–11)
Srb10 CDK Complex The function of the Srb10 CDK complex can be defined by the kinase itself, since loss-of-function mutations in any of the four components of this complex produce identical phenotypes (Hengartner, C. J. et al (1995) *Genes and Development* 9, 897–910). The Srb10 kinase is a negative regulator of a substantial fraction of genes which are repressed when cells grow vegetatively in rich media and are induced as cells experience nutrient deprivation. The genes regulated by Srb10 include those which are critical for the morphological change which permits foraging for nutrients and stress responses. Srb10 is physically depleted from cells as they enter the diauxic shift, providing a mechanism for derepression of this set of genes. Srb10 in wild type cells is, thus, responsible for repressing this set of genes when cells are in exponential growth on glucose, but no longer performs this function as cells enter the diauxic shift.
Swi/Snf Complex If the function of the Swi/Snf complex is ATP-dependent remodeling of chromatin, (Laurent, B. C. et al., (1993) *Genes Development* 7, 583–91; Cote, J. et al., (1994) *Science* 265, 53–60), then the effects observed herein due to the Swi2 ATPase mutation should represent the dependence of genome-wide expression on the entire Swi/Snf complex. The results indicate that a greater number of genes is negatively regulated by Swi/Snf than is positively regulated. This is surprising in view of the model that Swi/Snf-catalyzed remodeling of chromatin facilitates activator binding. It is possible that chromatin remodeling may facilitate binding of negative factors as well as positive factors. An alternative possibility is suggested by recent data indicating that the Swi/Snf complex can remodel chromatin in both directions: it can convert a repressive nucleosome structure towards a more accessible state and vice versa (Schnitzler, G. et al (1998) *Cell* 94, 17–27). It is thus possible that Swi/Snf helps produce a nucleosome structure conducive to transcription at some promoters, and a structure which is repressive at others.
TFIID and SAGA The general transcription factor TFIID and the SAGA complex share two features: they both contain a subunit capable of histone acetylation (TAF$_{II}$145 in the case of TFIID and Gcn5 in the case of SAGA) and they share multiple subunits, among which is the histone H3-like TAF, TAF$_{II}$17 (Grant, P. A. et al (1998) *Cell* 94, 45–53). As summarized in FIGS. 39A–39B, the results indicate that Gcn5, TAF$_{II}$145 and TAF$_{II}$17 are necessary for expression of 5%, 16% and 67% of yeast genes, respectively. Two models can account for this data: one posits that TAF$_{II}$17 functions exclusively within the TFIID and SAGA complexes, and the other that TAF$_{II}$17 is a component of one or more additional complexes. If TAF$_{II}$17 functions exclusively within the TFIID and SAGA, then TAF$_{II}$45 and Gcn5 do not fully represent the functions of the two complexes, since the sum of genes which require TAF$_{II}$145 and Gcn5 function is much smaller than the number of genes which require TAF$_{II}$17. In this model, one or both complexes contain subunits which make different contributions to gene expression, as might be expected if different subunits are targets of different transcriptional activators and repressors. The results can also be accommodated in a second model, in which $TAF_{II}17$ is a component of one or more complexes in addition to TFIID and SAGA. The results described here lay a useful foundation for the additional experiments necessary to gain a fuller understanding of the roles of TFIID and SAGA subunits in gene expression.

The data presented herein, in conjunction with that of previous studies, reveal several striking similarities between $TAF_{II}145$ and prokaryotic sigma factors. First, both sigma factors and $TAF_{II}145$ are components of the general transcription machinery. Second, many sigma factors are required for the expression of a related subset of genes; similarly, it has been shown that $TAF_{II}145$ appears to be required for expression of a set of genes involved in chromosomal synthesis and G1/S progression. Finally, both sigma factors and $TAF_{II}145$ act through core promoter elements by direct DNA contacts.

An unexpected finding of the work described herein is the role Srb5 has in pheromone response. It was striking that many of the genes whose mRNA levels are most dramatically affected by the loss of Srb5 fall into the pheromone response pathway. The 15 genes involved in the pheromone response which are expressed at substantially lower levels in the absence of Srb5 are shown in FIG. 39A. Dramatic effects are seen in genes involved in mating factor production and export; the expression of MFA 1 and MFA2, the two genes encoding mating pheromone a-factor, are down 28-fold and 11-fold, respectively. Additional genes involved in maturation (STE13) and export (STE6) of mating factor are expressed at substantially lower levels than in the cognate wild type. Furthermore, several components of the signal transduction pathway that responds to mating pheromone are expressed at reduced levels in the Srb5 mutant. These genes include the receptor for pheromone (STE2), subunits of the signaling G-protein (GPA1), and the transcription factor which is itself the target of the signaling response and directly regulates subsequent gene expression (STE12).

The genome-wide expression profile for the Srb5 mutant suggests that these cells should exhibit a defect in mating efficiency, a phenotype which was not previously suspected or investigated. Indeed, quantitative mating assays show that Srb5 mutant does have a significant defect in mating (FIG. 39B). The mating defect was more pronounced than that due to mutations in Fus3, a MAP kinase required for cell cycle arrest and cell fusion during mating, but less pronounced than that due to mutations in STE12. The defect in mating deficiency exhibited by the Srb5 mutant may reflect coordinate regulation of the set of pheromone response genes identified through genome-wide expression analysis.

The present invention is illustrated by the following examples, which are not intended to be limiting in any way. Detailed information and databases supporting all aspects of this study can be found on the Internet at http://www.wi.mit.edu/young/expression.html. The entire content of this web site, including the content of all linked sites (e.g., hypertext) is expressly incorporated herein by reference in its entirety.

EXAMPLE 2
Determination of the Levels of All Detectable MRNA Species in Yeast

Knowledge of the levels of all detectable mRNA species in yeast is useful for evaluating the degree to which these levels depend on any one component of the transcription apparatus. To obtain this information and to assess the reproducibility of the HAD technology, RNA was harvested from two independent wild type cultures and compared using two sets of HDAs on two separate days (see Example 1, above. The HDAs used here can score mRNA levels for up to 6181 genes. This is a more accurate representation of the transcriptome than that previously determined because it is better able to score mRNA species which are expressed at very low levels (5460 genes were scored using HDAs, whereas 4465 genes were scored with SAGA). It is particularly valuable to have information on transcripts from genes expressed at low levels because many of the regulatory components of the cell are expressed at low levels.

Of the 5460 genes whose mRNA levels were accurately determined and compared in both experiments, 99% of the mRNAs differed no more than 1.7 fold, and only 35 transcripts (0.65) showed more than a two-fold change. In order to prevent these minimal variations from influencing the results, all experiments were performed in duplicate. The levels determined for the 5460 transcripts in wild type yeast cells and additional information derived from this experiment are described above. The SAGA method has previously been used to determine values for 4465 transcripts, the results of which has been termed the yeast transcriptome. (Velculescu, V. E. et al (1997) *Cell,* 88, 243–51). The sensitivity of the HDA technology permitted a determination of the levels of many additional gene products, and revealed that transcripts from 80% of expressed yeast genes exist at steady state levels of 0.1 to 2 molecules/cell.

EXAMPLE 2
Assessment of the Role of Components of Transcriptional Machinery in Genome-Wide Gene Expression At any one promoter, the transcriptional machinery might include the RNA polymerase II core enzyme, the general transcription factors (GTFs), the core Srb/mediator complex, the Srb10 CDK complex, the Swi/Snf complex, and the SAGA complex, among others (FIG. 36). One or more subunits of each of these components has been investigated for its role in genome-wide gene expression through the use of mutations which affect either the function or the physical presence of the subunit (Table 1). Loss-of-function mutations in various components of the transcription apparatus were constructed or obtained from various investigators Example 1, above. Two types of mutations have proven to be useful in this study. For essential components of the apparatus, temperature-sensitive (ts) mutations are valuable because they allow the investigator to examine effects on gene expression at any point after inactivating the factor. Point mutations which knock out the catalytic function of known enzymatic activities or complete deletion mutations were used to study non-essential components. In each experiment, a mutant cell and its isogenic wild-type counterpart are grown to mid-log phase, the two populations are harvested, RNA is prepared, and hybridization to HDAs is carried out, all in duplicate.

Dependence on Core RNA Polymerase II
To determine the genome-wide dependence of gene expression on core RNA polymerase II, RNA was isolated from an rpb1-1 temperature sensitive ts cell and its wild type counterpart 45 minutes after a shift to the nonpermissive temperature and was hybridized to HDAs. Because rpb1-1 cells shut down transcription of protein-coding genes immediately after a temperature shift, these cells have been used as described here and by other investigators to determine the half-life of various yeast mRNAs (Nonet M. et al. (1987) *Mol Cell Biol* 7, 1602–11; Herrick D. et al (1990) *Mol Cell Biol* 10, 2269–84). The 45 minute time point was used for the analysis of all ts mutants in this study because it is sufficiently long to detect a significant (i.e. a two-fold or more) loss of mRNA levels for 94% of detectable gene products without any loss of rRNA (Nonet M. et al., (1987) *Mol Cell Biol* 7, 1602–11). In addition, the 45 minutes time point is short enough to minimize the potentially complicating effects of cell cycle arrest and cell death.

Figure 37A:
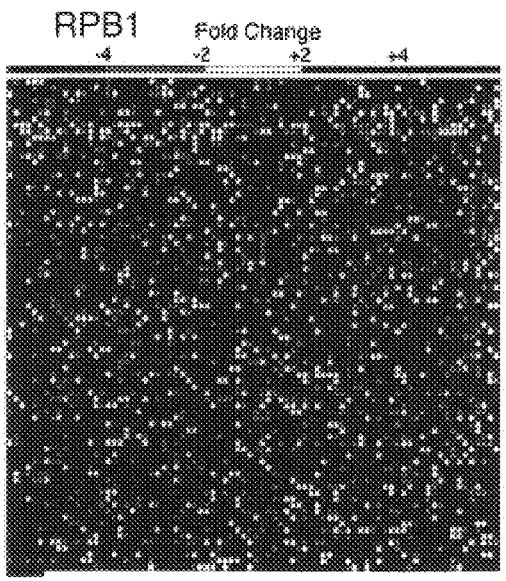
FIGS. 37A–37D show genome-wide expression data for selected components of the RNA polymerase II holoenzyme; data reflecting the change in mRNA levels when a mutant is compared to its isogenic wild type counterpart is presented in a grid format. In the grid, the upper left grid square represents the left-most gene on chromosome I, and the squares to its right represent adjacent genes, proceeding in a linear fashion through chromosome I, then II, the III, etc., until the last gene on the right arm of chromosome XVI is reached at the bottom of the grid.

The results of genome wide expression analysis of the rpb1-1 mutant as compared to an isogenic wild type strain are shown in a grid format in FIG. 37A. The grid shows the change in mRNA level for each gene, beginning with the left most gene on chromosome I and proceeding in a linear fashion, left to right, through chromosome I and II, then III, etc., until the last gene on the right arm of chromosome IVI is reached at the lower right hand corner. 5735 genes were scored in this analysis. The vast majority of mRNAs are reduced more than two-fold in the mutant cells relative to wild type cells, and this reduction provides an apparent half-life for each of the mRNA species Example 1, above. The value determined with this approach is an approximation, but is useful for comparative purposes. Comparison of this data with that obtained for another ts factor identifies the set of genes whose expression is equivalently dependent on RNA polymerase II and the factor of interest.

There is a set of genes whose mRNAs are not significantly reduced in the mutant cells. These consist of genes that have stable messages as well as genes whose mRNA levels are slightly elevated in the mutant cells relative to wild-type. In this latter group are many known heat shock or stress response genes (e.g. SSA4, SSA3, HSP26, HSP30, HSP42 and SSL2), plus additional ORFs of unknown but perhaps related function. Similar results were obtained using ts mutants in other general transcription factors.

Dependence on Srb/Mediator Core Subunits

The Srb/mediator complex is tightly associated with RNA polymerase II in a complex which has been termed the holoenzyme (Koleske A. J., and Young, R. A. (1994) *Nature* 368, 466–9; Kim, Y. J. et al., (1994) *Cell* 77, 599–608). Srb4 is an essential component of the Srb/mediator complex (Thompson, C. M. et al., (1993) *Cell* 73, 1361–75; Kim, Y. J. et al., (1994) *Cell* 77, 599–608); Hengartner, et al., (1995) *Genes and Development* 9, 897–910). A ts mutant in Srb4 (srb4-138) was previously used to obtain evidence that several protein-coding genes require the function of Srb4, and are thus likely to have the holoenzyme form of RNA polymerase II recruited to their promoters (Thompson, C. M., and Young, R. A. (1995) *Proc Natl Acad Sci USA* 92, 4587–90). Genome-wide expression analysis provides a more rigorous test of the model that expression of all protein-coding genes is dependent on Srb4. The experiment was carried out with the same protocol used with the Rpb1 ts mutant. Of the 5361 genes whose mRNA expression levels could be compared (i.e., those that had a greater than two-fold decrease in the experiment with Rpb1 ts and were scored in the Srb4 ts experiment), 93% showed a decrease that closely fit the decreased observed in the Rpb1 ts experiment. Of the mRNAs that did not closely fit the Rpb1 ts decay, only 2 could be found that reproducibly showed large differences in their decay in the two experiments performed. Furthermore, the set of genes whose mRNAs are not significantly reduced in the Rpb1 ts mutant exhibit the same behavior in the Srb4 ts experiment. The results indicate that genome-wide expression is a dependent on Srb4 as it is on core RNA polymerase II (see Genome-Wide Expression Data on the Web site for details). Srb4 is associated tightly and exclusively with the RNA polymerase II holoenzyme (Koleske, A. J., and Young, R. A. (1994) *Nature* 368, 466–9; Kim, Y. J. et al., (1994) *Cell* 77, 599–608; and Myers, L. C. et al., (1998) *Genes Development* 12, 45–54). Thus, it is reasonable to infer Srb4-containing RNA polymerase II holoenzyme is generally required for transcription.

Figure 37B:
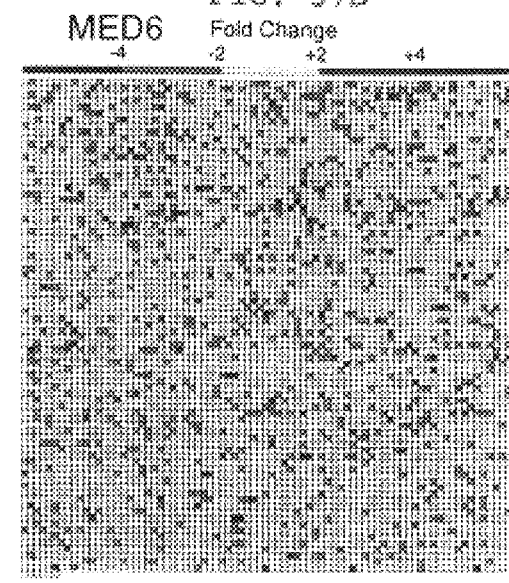

Med6 is another essential component of the Srb/Mediator complex and appears to be physically associated with Srb4 (Li, Y. et al., (1995) *Proc Natl Acad Sci USA* 92, 1064–68; Myers, L. C. et al., (1998) *Genes Development* 12, 45–54; Lee, T. I. et al., (1998). A Med6 ts mutant has been generated and used to demonstrate that Med6 is necessary for full induction of GAL, SUC2, MFA1 and PKY1 genes, but is not required for expression of several others. (Lee, Y. C. et al., (1997) *Mol Cell Biol* 17,4622–32). The genome-wide dependence of gene expression on Med6 was determined with this Med6 ts strain as described above for Rpb1. The results indicate that the expression of 10% of yeast genes is as dependent on Med6 as it is on Rpb1 (FIG. 37B; see the Web site for detailed information).

The reduction in mRNA levels observed in ts mutants soon after a temperature shift (i.e., 45 minutes) is likely a consequence of primary effects due to factor inactivation because the time required to produce most secondary effects involves a substantial reduction in both a transcript and its translation product. Nonetheless, the results obtained in this type of experiment must be regarded as the sum of primary and secondary effects. To identify the set of genes whose change in expression is most likely a direct consequence of the loss of function of the ts factor, data from ts inactivation of RNA polymerase II was compared with that obtained by ts inactivation of any other factor. Comparison of the two data sets reveals the transcripts with equivalent decay kinetics in rpb1-1 and the other ts mutant Example 1, above. For those genes affected by ts disruption of Med6 where such a comparison could be made, the mRNAs of 506 genes decreased with similar kinetics in the Med6 and Rpb1 experiments. Thus, the expression of 10% of yeast genes is as dependent on Med6 as it is on Rpb1. These 506 genes are most likely to have a direct requirement for Med6 function. The genes whose transcript levels do not fit the Rpb1 kinetics could have a direct, but partial, requirement for Med6 function, or the effects observed at these genes are a secondary consequence of some other gene's altered mRNA levels. The 506 genes identified which require Med6 function to the same extent as Rpb1 function are those at which promoter-associated transcriptional regulators are most likely to function through interactions with Med6.

Srb5 is a component of the Srb/Mediator complex whose function is also not known (Thompson, C. M. et al., (1993) *Cell* 73, 1361–75; Kim, Y. J. et al., (1994) *Cell* 77, 599–608); Koleske, A. J., and Young, R. A., (1994) *Nature* 368, 466–9; Hengartner, C. J. et al., (1995) *Genes and Development* 9, 897–910; Myers, L. C. et al., (1998) *Genes and Development* 12, 45–54). To determine the genome-wide dependence of gene expression on Srb5, a strain lacking an SRB5 gene and its wild type counterpart were compared (Example 1 above). The results indicate that 16% of all genes require Srb5 function for their expression. With the SRB5 deletion strain and other constitutive mutants analyzed here, it is not possible to distinguish between results which are a direct consequence of the loss of Srb5 function and those which are due to a secondary effect such as the loss of another transcriptional regulator. Nonetheless, these results provide important information in that they reveal the complete set of genes which are directly or indirectly affected by loss of Srb5 function. It was striking that expression of many genes central to the pheromone response pathway are dramatically affected by the loss of Srb5, as discussed herein.

Dependence on SRb10 CDK Complex

Figure 37C:
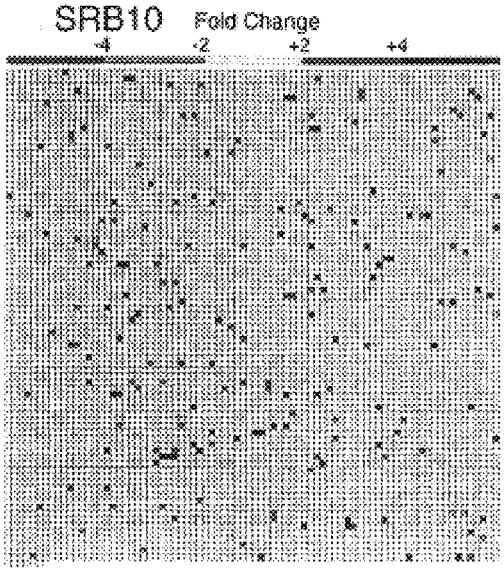

Srb10 is cyclin dependent kinase which is part of a holoenzyme subcomplex containing Srb8, 9, 10 and 11 proteins (Liao, S. M. et al., (1995) *Nature* 374, 193–6; Hengartner, C. J. et al., (1995) *Genes and Development* 9, 897–910). Srb10 and its associated proteins have been proposed to form a negative regulatory complex which functions through phosphorylation of the RNA polymerase II complex CTD (Hengartner, C. J. et al., (1998) *Molecular Cell* 2, 45–53). To determine how gene expression depends on Srb10, RNA was isolated from an Srb10 point mutant which lacks catalytic activity and the expression profile was compared to that of its wild type counterpart. The results are shown in a grid format in FIG. 37C. Of the 5626 genes which were scored, 173 gene products showed 2-fold or greater increases in mRNA levels in the mutant relative to the wild type. This indicates that Srb10 is normally a negative regulator of these 173 genes (approximately 3% of the genome).

It is notable that nearly half of these genes are derepressed during the nutrient deprivation which occurs during the diauxic shift. (DeRisi, J. et al., (1997) *Science* 278, 680–86). (FIGS. 40A–40C) Yeast cells undergo a diauxic shift as nutrients are depleted in culture, and a variety of genes which enable the cell to survive nutrient-limiting conditions are derepressed (Johnston, M., and Carlson, M. (1992) *Gene Expression p.* 193; Yin, Z. et al., (1996) *Molecular Microbiology* 20, 751–64). These include genes involved in dimorphic morphology (nutrient starved cells alter their morphology to permit foraging for nutrients) and stress responses (starved cells are apparently better able to survive nutrient deprivation when stress proteins are elevated). Srb10 in wild type cells is most likely responsible for repressing this set of genes when cells are in exponential growth on glucose, but no longer performs this function as cells enter the diauxic shift. Coordinate regulation of this set of genes could be accomplished by eliminating the function of Srb10 as cells enter the diauxic shift.

To determine whether Srb10 is physically lost from cells as they enter the diauxic shift, cells containing an epitope-tagged Srb10 protein were grown in YPD media and sampled at various times during the growth curve. (FIG. 40C). Cell lysates were prepared from each sample and the levels of Srb10 were assayed by Western blot. Results showed that Srb10 is physically depleted as cells enter the diauxic phase of growth. This result is consistent with evidence that the levels of Srbl 1, the cyclin partner of Srb10, are reduced when cells are exposed to the limiting nutrient environment in sporulation media. (Cooper, K. F. et al., (1997) *EMBO J* 16, 4665–75.) It may also explain why a form of yeast holoenzyme purified from commercially available yeast cells lacks the Srb10/Srb11 kinase/cyclin pair (Li, Y. et al., (1995) *Proc Natl Acad Sci USA* 92, 10864–8; Myers, L. C. et al., (1998) *Genes Development* 12, 45–54), as these cells are typically grown past mid-log phase. The results thus indicate that the nutrient starvation response is mediated, in part, through the physical loss of the Srb10 CDK from the holoenzyme. This novel mechanism provides one example of how coordinate regulation of gene expression can be accomplished through regulation of components of the general initiation machinery.

FLO11, which encodes a cell wall protein which is highly expressed in pseudohyphal cells, is expressed at 15-fold higher levels when Srb10 function is lost (FIG. 40A). The dramatic increase in the expression of FLO11 and other genes whose products are involved in the dimorphic shift led Applicants to determine whether the absence of Srb10 function produces a pseudohyphal phenotype. Both copies of the SRB10 gene were deleted from a diploid strain which is generally used to assay this phenotype, and colony morphology was examined under the microscope. Results demonstrated that the loss of Srb10 causes cells to grow preferentially in a pseudohyphal form. This again shows that expression analysis is useful for predicting unexpected phenotypes. More importantly, specific signal transduction pathways control the dimorphic shift (Madhani, H. D., and Fink, G. R., (1998) *Trends Cell Biology* 8, 348–53), and these results suggest that one of the ultimate targets of these pathways is the Srb10 kinase.

Dependence on Swi/Snf

Figure 37D:
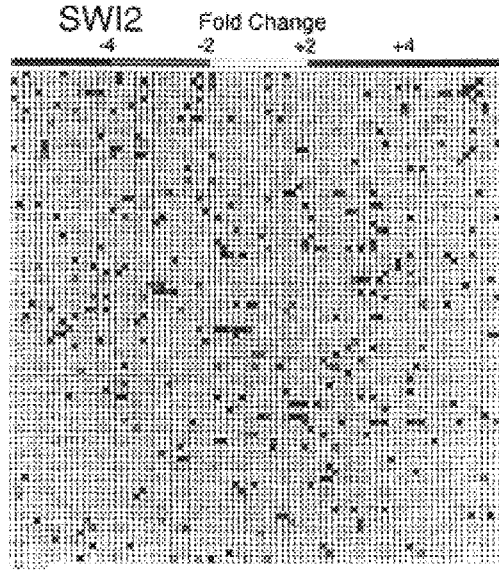

Swi2 ATPase activity plays an essential role in the ability of the Swi/Snf complex to remodel chromatin (Laurent, B. C. et al., (1993) *Genes Development* 7, 583–91; Cote, J. et al., (1994) *Science* 265, 53–60; Khavari, P. A. et al., (1993) *Nature* 366, 170–4). This activity is thought to facilitate activator and transcription apparatus binding to promoter regions for a small number of genes, thereby overcoming repression by nucleosomes at those promoters (Cote, J. et al., (1994) *Science* 265, 53–60; Imbalzano, A. N. et al., (1994) *Nature* 370, 481–5; Kwon, H. et al., (1994) *Nature* 370, 477–81; Burns, L. G. and Peterson, C. L., (1997) *Mol Cell Biol* 17, 4811–9). Consequently, it was expected that a small number of genes would be reduced in expression levels in the Swi2/Snf2 mutant. To determine the genome-wide dependence of gene expression on the Swi/Snf complex, RNA was isolated from a Swi2/Snf2 point mutant which lacks ATPase activity and its wild type counterpart and the two RNA preparations were hybridized to HDAs. The surprising result was that a greater number of genes appear to be negatively regulated by Swi/Snf than are positively regulated (FIG. 37D; Example 1, above). The data show that 203 gene products were elevated 2-fold or more in the mutant relative to the wild type, while just 126 transcripts decreased 2-fold or more (See Genome-Wide Expression Data on the Web site). As described herein, this result may be explained by recent data indicating that the Swi/Snf complex can catalyze chromatin remodeling in either direction (Schnitzler, G. et al., (1998) *Cell* 94, 17–27).

Dependence on General Transcription Factors

The general transcription factors are necessary to reconstitute promoter-dependent transcription in vitro with core RNA polymerase II. These factors include TFIID, TFIIB, TFIIF, TFIIE and TFIIH. Among these factors, TFIIE and TFIIH are of particular interest because numerous reports have suggested that they are in fact not generally required for gene expression (Parvin, J. D. et al., (1992) *Cell* 68, 1135–44; Serizawa, H. et al., (1993) *Nature* 363, 371–4; Timmers, H. (1994) *EMBO J* 13, 391–9; Holstege, F. C. et al., (1995) *EMBO J* 14, 810–9; Sakurai, H. et al., (1997) *J Biol Chem* 272, 15936–42; Kuldell, N. H., and Buratowski, S., (1997) *Mol Cell Biol* 17, 5288–98; Tijerina, P., and Sayre, M. H., (1998) *J Biol Chem* 273, 1107–13). Genome-wide expression analysis was carried out on a Kin28 ts cell and its isogenic wild type counterpart using the same experimental protocol used for the Rpb1 ts mutant. Kin28, a CDK subunit of TFIIH, is an RNA polymerase II CTD kinase which is involved in the transition from initiation to elongation (Dahmus, M. (1996) *J Biol Chem.* 271, 19009–19012). The results reveal that Kin28 is generally required for expression of protein-coding genes (Example 1, above). TFIIE is thought to facilitate certain functions of TFIIH. In contrast to the results obtained with Kin28, analysis of genome-wide expression with a Tfa1 ts mutant shows that only 54% of yeast genes require the largest subunit of TFIIE to the same extent as core RNA polymerase II (see Example 1, above).

The TBP-associated factors (TAF$_{II}$S) of TFIID are especially interesting because they have been postulated to play important roles in promoter selectivity and gene activation (Burley, S. K., and Roeder, R. G., (1996) *Annu Rev Biochem* 65, 769–99; Veirijzer, C. P., and Tijan, R., (1996) *Trends Biochem Sci* 21, 338–42; Lee, T. I., and Young, R. A., (1998) *Genes and Development* 12, 1398–1408). A ts mutation in the TFIID subunit $TAF_{II}145$ (Walker, S. S. et al., (1997) *Cell* 90, 607–14) was used to determine the genome-wide dependence of gene expression on this TAF. Of the 5441 genes which were scored, 1618 genes products were reduced by 2-fold or greater on average in the two comparisons made, 45 minutes after temperature shift. For those genes where a comparison with the Rpb1 experiment could be made, 16% showed a dependence on $TAF_{II}145$ that was similar to their dependence on Rpb1 (see Example 1, above). Interestingly, a large number of genes involved in functions associated with progression through the cell cycle are among the genes most likely to have a direct requirement for $TAF_{II}145$ function. The $TAF_{II}145$ ts mutant has a cell cycle phenotype: it arrests growth in G1-S after cells are shifted to the nonpermissive temperature. Previous studies showed that several G1-S cyclin genes are expressed at reduced levels in these cells, perhaps accounting for the cell cycle arrest phenotype $TAF_{II}145$. (Walker, S. S. et al., (1997) *Cell* 90, 607–14) A subset of the genes that have a direct requirement for $TAF_{II}145$ function and which are involved in functions associated with progression through the cell cycle are listed in Table 2. For example a significant decrease in mRNA levels was observed for Ctr9, which is required for expression of G1 cyclins Cln1 and Cln2. In addition, genes which are involved in DNA repair and DNA synthesis are dependent on $TAF_{II}145$ function. Thus, the G1/S arrest phenotype of $TAF_{II}145$ mutants may be due to multiple defects in cyclin and chromosome synthesis which occur during this period of the cell cycle.

Analysis of which genes depend on $TAF_{II}17$, a histone H3-like TAF which is shared by TFIID and SAGA complexes, for their expression was also carried out. RNA was isolated from a $TAF_{II}17$ temperature sensitive cell (TAF17-ts) and its wild type counterpart 45 minutes after a shift to the nonpermissive temperature and was hybridized to RDAs. Of the yeast genes identified in the $TAF_{II}17$ experiment and appropriate for comparison, 67% are as dependent on $TAF_{II}17$ function as they are on Rpb1, and are thus most likely to have a direct requirement for $TAF_{II}17$ function Example 1, above. This indicates that $TAF_{II}17$ is critical for the expression of a much larger portion of the transcriptome than $TAF_{II}145$. The presence of $TAF_{II}7$ in two different complexes may account for this observation.

Dependence on Gcn5 Subunit of SAGA

The recent discovery that certain TAFs are components of both the TFIID general transcription factor and the SAGA complex (Grant, P. A. et al., (1998) *Cell* 94, 45–53) makes it particularly interesting to compare the effects of a mutation in a component specific to each complex ($TAF_{II}145$ in the case of TFIID and Gcn5 in the case of SAGA) with those of a mutation in a component shared by the two complexes ($TAF_{II}17$). The expression profile of a GCN5 deletion mutant was compared with its isogenic counterpart (Example 1, above). Of the 4912 genes which were scored, 185 transcripts were reduced by 2-fold or more and 83 increased by 2-fold or more.

The Gcn5 results indicate that this component of SAFA is necessary for normal expression of no more than 5% of yeast genes. Expression of 16% of protein-coding genes depends on the $TAF_{II}145$ subunit of TFIID to the same extent they depend on Rpb1. In contrast, the expression of 67% of yeast genes depends on the function of the $TAF_{II}17$ subunit shared by SAGA and TFIID.

TABLE 1

Transcriptional Machinery

| Complex and Subunit | Features | Fraction of genes dependent on subunit function |
|---|---|---|
| RNA Polymerase II | | |
| Rpb1 | Largest subunit, mRNA catalysis, contains CTD | 100% |
| Srb/mediator (core) | | |
| Srb4 | Target of Gal4 activator | 93%* |
| Srb5 | Unknown function | 16% |
| Med6 | Role in activation of some genes | 10% |
| Srb CDK complex | | |
| Srb10 | CTD kinase, negative regulator | 3% |
| Swi/Snf | | |
| Swi2 | ATP-dependent chromatin remodeling | 6% |
| General Transcription Factors | | |
| TFIID ($TAF_{II}145$) | Large TBP-associate factor, histone acetylase | 16% |
| ($TAF_{II}17$) | Component of both TFIID and SAGA | 67% |
| TFIIE (Tfa1) | Promoter opening | 54% |
| TFIIH (Kin28) | CTD kinase | 87%* |
| SAGA | | |
| Gcn5 | Histone acetylase | 5% |
| $TAF_{II}17$ | Component of both TFIID and SAGA | 67% |

*Srb4 and Kin28 results were essentially identical to Rpb1, but because of the stringency applied by the fit algorithm, a minimal estimate is produced.

TABLE 2

Genes That Require Taf145 Function
Cell Cycle

| GENE | DESCRIPTION | FOLD REDUCTION |
|---|---|---|
| *DDCI | DNA damage checkpoint protein | 10 |
| YER066W | Similar to CDC4, which degrades G1 cyclins | 9 |
| SPO1 | Possible role in spindle pole body duplication | 8 |
| *LTE1 | GDP/GTP exchange factor | 8 |
| *MKK2 | Kinase involved in cell wall integrity | 8 |
| *BIM1 | Possible role in early spindle pole body assembly | 8 |
| *MDM1 | Involved in mitochondrial segregation | 7 |
| *CTR9 | Required for normal expression of G1 cyclins | 7 |
| *PAC1 | Possible role in spindle pole body orientation | 6 |
| *SCP160 | Involved in control of chromosome transmission | 6 |
| CDC13 | Telomere binding protein | 6 |
| *TOP3 | DNA topoisomerase III | 5 |
| *TRX1 | Thioredoxin I | 5 |
| ARD1 | N-acetyltransferase | 5 |
| *SCC2 | Required for sister chromatid cohesion | 5 |
| *CLB2 | G2/M cyclin | 5 |
| *KIP2 | Kinesin related protein | 5 |
| *MEC1 | Cell cycle checkpoint protein | 4 |
| RAD9 | DNA repair checkpoint protein | 4 |
| *SPC98 | Spindle pole body component | 4 |
| *BCK1 | Kinase involved in cell wall integrity | 4 |
| DNA Repair | | |
| *RAD3 | Involved in nucleotide excision repair | 8 |
| *YHR031C | Possible role in chromosome repair | 7 |

TABLE 2-continued

Genes That Require Taf145 Function
Cell Cycle

| GENE | DESCRIPTION | FOLD REDUCTION |
|---|---|---|
| *RAD5 | Involved in DNA repair | 6 |
| *HSM3 | Involved in mismatch repair | 6 |
| *RAD50 | Involved in recombinational repair | 5 |
| *EXO1 | Involved in mismatch repair | 5 |
| *MSH3 | Involved in mismatch repair | 5 |
| YER041W | Similar to DNA repair protein, Rad2 | 5 |
| REV1 | Involved in translesion DNA synthesis | 4 |
| HDF2 | Involved in DNA end-joining repair pathway | 4 |
| MSH6 | Involved in mismatch repair | 4 |
| DNA Synthesis | | |
| *MCM3 | Involved in replication initiation, MCM/P1 family | 13 |
| RLF2 | Chromatin assembly complex, subunit 2 | 9 |
| *MCM6 | Involved in replication initiation, MCM/P1 family | 9 |
| REV7 | DNA polymerase subunit zeta | 7 |
| *MIP1 | Mitochrondial DNA-directed DNA polymerase | 6 |
| *CDC47 | Involved in replication initiation, MCM/P1 family | 6 |
| *CDC5 | Kinase | 5 |
| *CDC46 | Involved in replication initiation, MCM/P1 family | 5 |
| *RFC1 | DNA replication protein RFC large subunit | 5 |
| *CAC2 | Chromatin assembly complex, subunit 1 | 5 |

*Gene exhibits equivalent dependence on Taf145 and Rbp1 for normal expression

While this invention has been particularly shown and described with reference to preferred embodiments thereof, it will be understood by those skilled in the art that various changes in form and details may be made therein without departing from the spirit and scope of the invention as described herein and/or as defined by the appended claims.

What is claimed is:

1. A method of identifying a gene as a member of a regulatory pathway of a component of general transcription machinery in a cell, comprising the steps of:
    (a) hybridizing a transcription indicator of a test cell to a set of nucleic acid probes;
    (b) hybridizing a transcription indicator of a control cell to the set of nucleic acid probes,
wherein the transcription indicators are selected from the group consisting of mRNA, cDNA and cRNA, wherein the test cell contains a mutant component of the general transcription machinery and the control cell is a wild-type isogenic counterpart of the test cell;
    (c) detecting amounts of the transcription indicators which hybridize to each of said set of nucleic acid probes; and
    (d) identifying a gene as a member of the regulatory pathway of the component of the general transcription machinery, if the amount of transcription indicator of the test cell which hybridizes to a nucleic acid probe comprising a portion of the gene is different from the amount of transcription indicator of the control cell which hybridizes to a nucleic acid probe comprising a portion of the gene.

2. The method of claim 1 wherein the difference between the amount of transcription indicator of the test cell which hybridizes to a nucleic acid probe comprising a portion of the gene, and the amount of transcription indicator of the control cell which hybridizes to a nucleic acid probe comprising a portion of the gene, is at least 2-fold.

3. The method of claim 1 wherein the difference between the amount of transcription indicator of the test cell which hybridizes to a nucleic acid probe comprising a portion of the gene, and the amount of transcription indicator of the control cell which hybridizes to a nucleic acid probe comprising a portion of the gene, is at least 3-fold.

4. The method of claim 1 wherein the difference between the amount of transcription indicator of the test cell which hybridizes to a nucleic acid probe comprising a portion of the gene, and the amount of transcription indicator of the control cell which hybridizes to a nucleic acid probe comprising a portion of the gene, is at least 5-fold.

5. The method of claim 1 wherein the difference between the amount of transcription indicator of the test cell which hybridizes to a nucleic acid probe comprising a portion of the gene, and the amount of transcription indicator of the control cell which hybridizes to a nucleic acid probe comprising a portion of the gene, is at least 10-fold.

6. The method of claim 1 wherein the mutant component of the general transcription machinery is a mutant general transcription factor.

7. The method of claim 1 wherein the mutant component of the general transcription machinery is a temperature sensitive mutant.

8. The method of claim 1 wherein the mutant component of the general transcription machinery is a point mutant.

9. The method of claim 1 wherein the mutant component of the general transcription machinery is a deletion mutant.

10. The method of claim 1 wherein the mutant component of the general transcription machinery is a component of RNA polymerase II holoenzyme.

11. The method of claim 1 wherein the mutant component of the general transcription machinery is necessary to reconstitute promoter-dependent transcription in vitro with core RNA polymerase II.

* * * * *